US012528764B2

(12) United States Patent
Lim et al.

(10) Patent No.: US 12,528,764 B2
(45) Date of Patent: Jan. 20, 2026

(54) COMPOUND, COATING COMPOSITION COMPRISING SAME, ORGANIC LIGHT-EMITTING DEVICE USING SAME, AND MANUFACTURING METHOD THEREFOR

(71) Applicant: LG Chem, Ltd., Seoul (KR)

(72) Inventors: Dowon Lim, Daejeon (KR); Jiyoung Lee, Daejeon (KR); Hyeonah Shin, Daejeon (KR); Doohwan Choi, Daejeon (KR); Min Suk Jung, Daejeon (KR); Jaesoon Bae, Daejeon (KR); Jaechol Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 867 days.

(21) Appl. No.: 17/791,339

(22) PCT Filed: Jan. 29, 2021

(86) PCT No.: PCT/KR2021/001227
§ 371 (c)(1),
(2) Date: Jul. 7, 2022

(87) PCT Pub. No.: WO2021/154041
PCT Pub. Date: Aug. 5, 2021

(65) Prior Publication Data
US 2023/0354697 A1 Nov. 2, 2023

(30) Foreign Application Priority Data
Jan. 31, 2020 (KR) ........................ 10-2020-0011751
Sep. 28, 2020 (KR) ........................ 10-2020-0125952

(51) Int. Cl.

| | |
|---|---|
| ***C07C 211/61*** | (2006.01) |
| ***C07D 305/06*** | (2006.01) |
| ***H10K 50/15*** | (2023.01) |
| ***H10K 85/60*** | (2023.01) |
| *H10K 50/17* | (2023.01) |

(52) U.S. Cl.
CPC .......... *C07C 211/61* (2013.01); *C07D 305/06* (2013.01); *H10K 50/15* (2023.02); *H10K 85/631* (2023.02); *H10K 50/17* (2023.02)

(58) Field of Classification Search
None
See application file for complete search history.

(56) References Cited

U.S. PATENT DOCUMENTS

| | | | | |
|---|---|---|---|---|
| 11,316,112 | B2 * | 4/2022 | Gorohmaru | C08L 65/02 |
| 2009/0200926 | A1 | 8/2009 | Lee et al. | |
| 2013/0234118 | A1 | 9/2013 | Kwon et al. | |
| 2019/0237669 | A1 | 8/2019 | Kang et al. | |
| 2019/0264053 | A1 * | 8/2019 | Kim | C09D 11/52 |
| 2019/0338140 | A1 * | 11/2019 | Shin | C08F 212/26 |
| 2020/0239610 | A1 * | 7/2020 | Seo | C08F 212/24 |
| 2022/0085292 | A1 * | 3/2022 | Lim | H10K 85/111 |
| 2022/0216415 | A1 * | 7/2022 | Kamo | H10K 85/10 |
| 2023/0309369 | A1 * | 9/2023 | Lee | H10K 50/15 |

FOREIGN PATENT DOCUMENTS

| | | | | |
|---|---|---|---|---|
| EP | 4180416 | A1 | 5/2023 | |
| KR | 20090058063 | A | 6/2009 | |
| KR | 20130101830 | A | 9/2013 | |
| KR | 20130106255 | A | 9/2013 | |
| KR | 20130125575 | A | 11/2013 | |
| KR | 20180092270 | A | 8/2018 | |
| KR | 20190035513 | A | 4/2019 | |
| WO | WO-2018097654 | A2 * | 5/2018 | C07D 307/91 |

OTHER PUBLICATIONS

Machine translation of WO-2018097654, translation generated Jul. 2025, 29 pages. (Year: 2025).*
International Search Report for PCT/KR2021/001227 dated May 31, 2021. 3 pgs.
Extended European Search Report including Written Opinion for Application No. 21748165.4 dated Jun. 14, 2023, pp. 1-5.

* cited by examiner

*Primary Examiner* — Robert S Loewe
(74) *Attorney, Agent, or Firm* — Lerner David LLP

(57) ABSTRACT

The present specification relates to a compound of Formula 1, a coating composition comprising the same, an organic light emitting device formed by using the same, and a method for manufacturing the same,

[Formula 1]

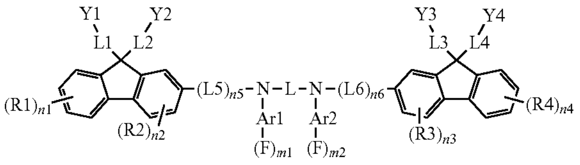

wherein all the variables are described herein.

14 Claims, 1 Drawing Sheet

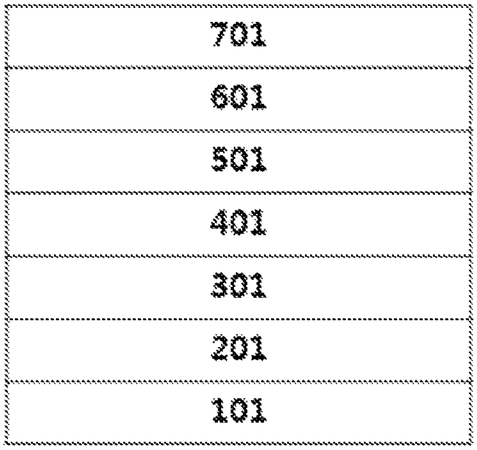
701
601
501
401
301
201
101

COMPOUND, COATING COMPOSITION COMPRISING SAME, ORGANIC LIGHT-EMITTING DEVICE USING SAME, AND MANUFACTURING METHOD THEREFOR

CROSS-REFERENCE TO RELATED APPLICATION

The present application is a national stage entry under 35 U.S.C. § 371 of International Application No. PCT/KR2021/001227 filed on Jan. 29, 2021, which claims priority from Korean Patent Application No. 10-2020-0011751 filed on Jan. 31, 2020, and Korean Patent Application No. 10-2020-0125952 filed on Sep. 28, 2020, all the disclosures of which are incorporated herein by reference.

TECHNICAL FIELD

The present specification relates to a compound, a coating composition including the compound, an organic light emitting device formed by using the coating composition, and a method of manufacturing the same.

BACKGROUND

An organic light emission phenomenon is one of the examples in which an electric current is converted into visible rays through an internal process of a specific organic molecule. The principle of the organic light emission phenomenon is as follows. When an organic material layer is disposed between an anode and a cathode and an electric current is applied between the two electrodes, electrons and holes are injected into the organic material layer from the cathode and the anode, respectively. The electrons and the holes which are injected into the organic material layer are recombined to form an exciton, and the exciton falls down again to the ground state to emit light. An organic light emitting device using this principle can be generally composed of a cathode, an anode, and an organic material layer disposed therebetween, for example, an organic material layer including a hole injection layer, a hole transport layer, a light emitting layer, and an electron transport layer.

In order to manufacture an organic light emitting device in the related art, a deposition process has been usually used. However, when an organic light emitting device is manufactured by a deposition process, there is a problem in that the loss of materials frequently occurs, so that in order to solve the problem, a technology of manufacturing a device by a solution process capable of increasing the production efficiency due to the low loss of materials has been developed, and there is a need for developing a material that can be used during the solution process.

A material used in an organic light emitting device for a solution process needs to have properties described below.

First, the material used in the organic light emitting device needs to be able to form a storable homogenous solution. Since a commercialized material for a deposition process has good crystallinity so that the material is not dissolved well in a solution or the crystals thereof are easily formed even though the material forms a solution, it is highly likely that according to the storage period, the concentration gradient of the solution varies or a defective device is formed.

Second, a material used for a solution process needs to be excellent in coatability such that during the formation of a thin film, a thin film having a uniform thickness can be formed without the occurrence of holes or an aggregation phenomenon.

Third, layers in which the solution process is performed needs to be resistant to the solvents and materials used in a process of forming other layers, and are required to have excellent current efficiency and excellent service life characteristics when an organic light emitting device is manufactured.

Therefore, there is a need for developing a new organic material in the art.

[Prior Art Document] (Patent Document 1) Korean Patent Application Laid-Open No. 2013-106255

BRIEF DESCRIPTION

Technical Problem

An object of the present specification is to provide a compound, which can be used in an organic light emitting device for a solution process, and an organic light emitting device including the same.

Technical Solution

Provided is a compound of the following Formula 1.

[Formula 1]

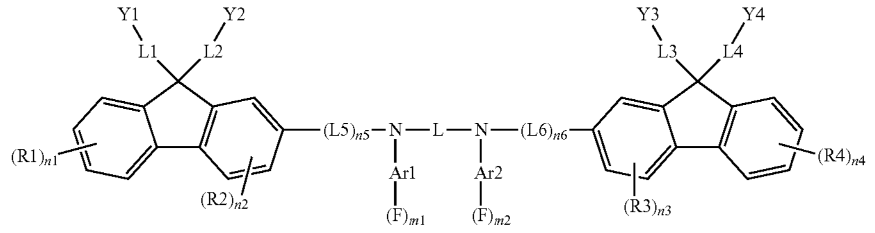

wherein, in Formula 1:

L and L1 to L4 are the same as or different from each other, and are each independently a substituted or unsubstituted arylene group, L5 and L6 are the same as or different from each other, and are each independently a direct bond; or a substituted or unsubstituted arylene group, Ar1 and Ar2 are the same as or different from each other, and are each independently a substituted or unsubstituted aryl group; or a substituted or unsubstituted heteroaryl group, R1 to R4 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group, Y1 to Y4 are the same as or different from each other, and are each independently —(R101)s; or —X-A, and two or more of Y1 to Y4 are —X-A, R101 is hydrogen; deuterium; a halogen group; a substituted or unsubstituted alkyl group; a substituted or unsubstituted alkoxy group; a substituted or unsubstituted aryl group; or a substituted or unsubstituted aryloxy group, s is an integer from 0 to 5, and when s is 2 or higher, each occurrence of R101 is the same as or different from each other, X is O or S, A is a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, m1 and m2 are each an integer from 1 to 5, n5 and n6 are each an integer from 0 to 2, n1 and n4 are each an integer from 0 to 4, n2 and n3 are each an integer from 0 to 3, when n5 and n6 are each 2, substituents in the parenthesis are the same as or different from each other, and when n1 to n4 are each 2 or higher, substituents in the parenthesis are the same as or different from each other.

The present specification provides a coating composition including the compound.

The present specification also provides an organic light emitting device including: a first electrode; a second electrode; and an organic material layer having one or more layers provided between the first electrode and the second electrode, in which one or more layers of the organic material layer include the above-described coating composition or a cured product thereof.

Finally, the present specification provides a method for manufacturing an organic light emitting device, the method including: preparing a substrate; forming a first electrode on the substrate; forming an organic material layer having one or more layers on the first electrode; and forming a second electrode on the organic material layer, in which the forming of the organic material layer includes forming the organic material layer having one or more layers by using the coating composition.

Advantageous Effects

A compound according to an exemplary embodiment of the present invention can be subjected to a solution process, can achieve a large area of a device, can be used as a material for an organic material layer of an organic light emitting device, and can provide low driving voltage, high light emitting efficiency, and high service life characteristics.

Further, the compound of the present invention deepens the highest occupied molecular orbital (HOMO) of a molecule due to a strong electron withdrawing effect by substituting a bonded substituent of an amine group with a fluoro group (—F), and when the compound of the present invention having a deep HOMO is used for an organic light emitting device, for example, a hole injection layer, the hole mobility is increased as a whole due to a reduced difference in energy level from a hole transport layer, thereby having an effect of improving the service life of the organic light emitting device.

DESCRIPTION OF DRAWINGS

The FIGURE illustrates an example of an organic light emitting device according to an exemplary embodiment of the present specification.

EXPLANATION OF REFERENCE NUMERALS AND SYMBOLS

101: Substrate
201: Anode
301: Hole injection layer
401: Hole transport layer
501: Light emitting layer
601: Layer which simultaneously transports and injects electrons
701: Cathode

DETAILED DESCRIPTION

Hereinafter, the present specification will be described in detail.

An exemplary embodiment of the present specification provides a compound of the following Formula 1.

[Formula 1]

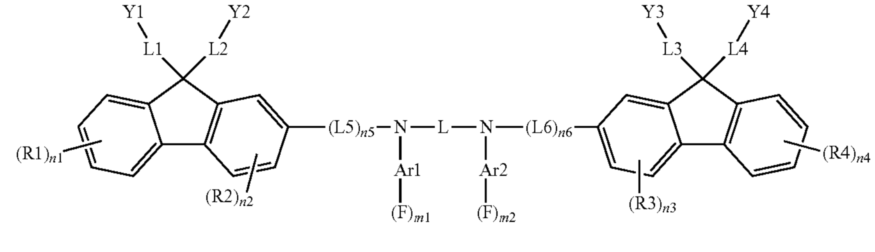

wherein, in Formula 1,

L and L1 to L4 are the same as or different from each other, and are each independently a substituted or unsubstituted arylene group, L5 and L6 are the same as or different from each other, and are each independently a direct bond; or a substituted or unsubstituted arylene group, Ar1 and Ar2 are the same as or different from each other, and are each independently a substituted or unsubstituted aryl group; or a substituted or unsubstituted heteroaryl group, R1 to R4 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group, Y1 to Y4 are the same as or different from each other, and are each independently —(R101)s; or —X-A, and two or more of Y1 to Y4 are —X-A, R101 is hydrogen; deuterium; a halogen group; a substituted or unsubstituted alkyl group; a substituted or unsubstituted alkoxy group; a substituted or unsubstituted aryl group; or a substituted or unsubstituted aryloxy group, s is an integer from 0 to 5, and when s is 2 or higher, each occurrence of R101 is the same as or different from each other, X is O or S, A is a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, m1 and m2 are each an integer from 1 to 5, n5 and n6 are each an integer from 0 to 2, n1 and n4 are each an integer from 0 to 4, n2 and n3 are each an integer from 0 to 3, when n5 and n6 are each 2, substituents in the parenthesis are the same as or different from each other, and when n1 to n4 are each 2 or higher, substituents in the parenthesis are the same as or different from each other.

In Formula 1, F means a fluoro group.

A compound according to an exemplary embodiment of the present invention forms a stable thin film completely cured by heat treatment or light treatment by including oxygen (O) or sulfur (S) atoms in the compound. Specifically, the above-described compound of the present invention has solvent selectivity due to a high affinity with hydrocarbon-based and/or ether-based solvents, and is resistant to a solvent to be used when other layers in addition to an organic material layer including the compound are formed by the solution process, so that it is possible to prevent the compound from moving to other layers.

Further, the compound of the present invention can provide a device having excellent service life characteristics by including a fluoro group as a substituent.

In addition, the compound of the present invention can provide excellent coatability, low driving voltage, high light emitting efficiency, and long service life characteristics.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element can be further included.

In an exemplary embodiment of the present specification, the compound of Formula 1 is preferably compounds having solubility to a suitable organic solvent.

Furthermore, in the case of a compound according to an exemplary embodiment of the present specification, an organic light emitting device can be manufactured by a solution application method, thereby enabling a large area of the device to be implemented.

In the present specification, "a cross-linkable functional group by heat or light" can mean a reactive substituent which cross-links compounds by being exposed to heat and/or light. The cross-linkage can be produced while radicals produced by decomposing carbon-carbon multiple bonds or cyclic structures by means of a heat treatment or light irradiation are linked to each other.

Hereinafter, the substituents of the present specification will be described in detail.

In the present specification,

means a moiety bonded to another substituent or a bonding portion.

In the present specification, the term "substitution" means that a hydrogen atom bonded to a carbon atom of a compound is changed into another substituent, and a position to be substituted is not limited as long as the position is a position at which the hydrogen atom is substituted, that is, a position at which the substituent can be substituted, and when two or more substituents are substituted, the two or more substituents can be the same as or different from each other.

In the present specification, the term "substituted or unsubstituted" means being substituted with one or more substituents selected from the group consisting of deuterium; a halogen group; a nitrile group; an alkyl group; a cycloalkyl group; an alkoxy group; an aryloxy group; an aryl group; and a heterocyclic group, and being substituted with a substituent to which two or more substituents among the substituents exemplified above are linked, or unsubstituted. For example, "the substituent to which two or more substituents are linked" can be a biphenyl group. That is, the biphenyl group can also be an aryl group, and can be interpreted as a substituent to which two phenyl groups are linked.

In the present specification, a halogen group is a fluoro group (—F), a chloro group (—Cl), a bromo group (—Br), or an iodo group (—I).

In the present specification, an alkyl group can be straight-chained or branched, and the number of carbon atoms thereof is not particularly limited, but can be 1 to 60, and according to an exemplary embodiment, the number of carbon atoms of the alkyl group can be 1 to 30. According to another exemplary embodiment, the number of carbon atoms of the alkyl group is 1 to 10. Specific examples of the alkyl group include a methyl group, an ethyl group, a propyl group, an isopropyl group, an n-butyl group, an isobutyl group, a tert-butyl group, an n-pentyl group, an n-hexyl group, an n-heptyl group, and the like, but are not limited thereto.

In the present specification, an alkenyl group is not particularly limited, but the number of carbon atoms thereof can be 2 to 20.

In the present specification, a cycloalkyl group is not particularly limited, but can have 3 to 60 carbon atoms, and according to an exemplary embodiment, the number of carbon atoms of the cycloalkyl group is 3 to 40. According to another exemplary embodiment, the number of carbon atoms of the cycloalkyl group is 3 to 20. Specific examples of the cycloalkyl group include a cyclopropyl group, a cyclobutyl group, a cyclopentyl group, a cyclohexyl group, a cycloheptyl group, a cyclooctyl group, and the like, but are not limited thereto.

In the present specification, a heterocycloalkyl group means a cycloalkyl group including one or more heteroatoms, and the number of carbon atoms thereof is not particularly limited, but can be 2 to 60, 2 to 30, and 2 to 20.

In the present specification, an alkoxy group means an alkyl group to which an oxygen radical is attached, and can be straight-chained or branched. The number of carbon atoms of the alkoxy group is not particularly limited, but can be 1 to 20. Specific examples of the alkoxy group include a methoxy group, an ethoxy group, an n-propoxy group, an n-butoxy group, a tert-butoxy group, an n-pentyloxy group, an n-hexyloxy group, an n-octyloxy group, an n-nonyloxy group, an n-decyloxy group, and the like, but are not limited thereto.

In the present specification, an alkeneoxy group means an alkenyl group to which an oxygen radical is attached, and the number of carbon atoms thereof can be 2 to 20, but is not limited thereto.

In the present specification, an aryl group is not particularly limited, but can have preferably 6 to 60 carbon atoms, and can be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthrenyl group, a pyrenyl group, a perylenyl group, a triphenyl group, a chrysenyl group, a fluorenyl group, and the like, but are not limited thereto.

In the present specification, a fluorenyl group can be substituted, and two substituents can be bonded to each other to form a spiro structure.

In the present specification, a fluorenyl group can be substituted, and two substituents can be bonded to each other to form a spiro structure.

When the fluorenyl group is substituted, the substituent can be a spirofluorenyl group such as

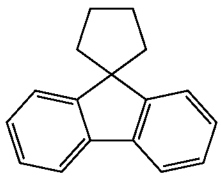 and 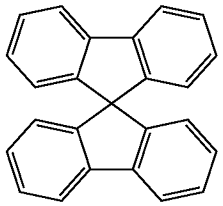, and a substituted fluorenyl group such as

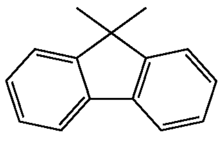

(a 9,9-dimethylfluorenyl group) and

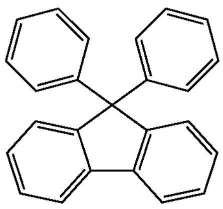 [SMILES: c1ccc(C2(c3ccccc3)c3ccccc3-c3ccccc32)cc1]

(a 9,9-diphenylfluorenyl group). However, the substituent is not limited thereto.

In the present specification, a heterocyclic group is a heterocyclic group including one or more of N, O, P, S, Si, or Se as a heteroatom, and the number of carbon atoms thereof is not particularly limited, but can be 2 to 60. According to an exemplary embodiment, the number of carbon atoms of the heterocyclic group is 2 to 30. According to another exemplary embodiment, the number of carbon atoms of the heterocyclic group is 2 to 20. Examples of the heterocyclic group include a pyridyl group, a pyrrole group, a pyrimidyl group, a pyridazinyl group, a furanyl group, a thiophene group, a benzothiophene group, a benzofuran group, a dibenzothiophene group, a dibenzofuran group, and the like, but are not limited thereto. In addition, the heterocyclic group can include a form in which a hetero ring and a hydrocarbon ring are fused.

In the present specification, the above-described description on the heterocyclic group can be applied to a heteroaryl group except for an aromatic heteroaryl group.

In the present specification, the hydrocarbon ring group can be an aromatic, aliphatic or aromatic-aliphatic fused ring. The above-described description on the cycloalkyl group can be applied to the aliphatic hydrocarbon ring group, the above-described description on the aryl group can be applied to the aromatic hydrocarbon ring group, and examples of the aromatic and aliphatic fused ring include a structure in which benzene and cyclobutane are fused as described below.

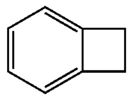

In the present specification, the above-described description on the aryl group is applied to an arylene group except for a divalent arylene group.

In the present specification, the above-described description on the aryl group is applied to an aryl group in an aryloxy group.

According to an exemplary embodiment of the present specification, Y1 to Y4 are the same as or different from each other, and are each independently —(R101)s; or —X-A, and two or more of Y1 to Y4 are —X-A.

According to another exemplary embodiment, Y1 to Y4 are the same as or different from each other, and are each independently —(R101)s; or —X-A, and two of Y1 to Y4 are —X-A.

According to still another exemplary embodiment, Y1 and Y4 are the same as or different from each other, and are each independently —X-A, and Y2 and Y3 are the same as or different from each other, and are each independently —(R101) s.

In another exemplary embodiment, Y1 and Y2 are the same as or different from each other, and are each independently —X-A, Y3 and Y4 are the same as or different from each other, and are each independently —(R101)s.

According to yet another exemplary embodiment, Y1, Y2, and Y4 are the same as or different from each other, and are each independently —X-A, and Y3 is —(R101)s.

In still another exemplary embodiment, Y1 to Y4 are the same as or different from each other, and are each independently —X-A.

According to an exemplary embodiment of the present specification, Formula 1 is the following Formula 2.

[Formula 2]

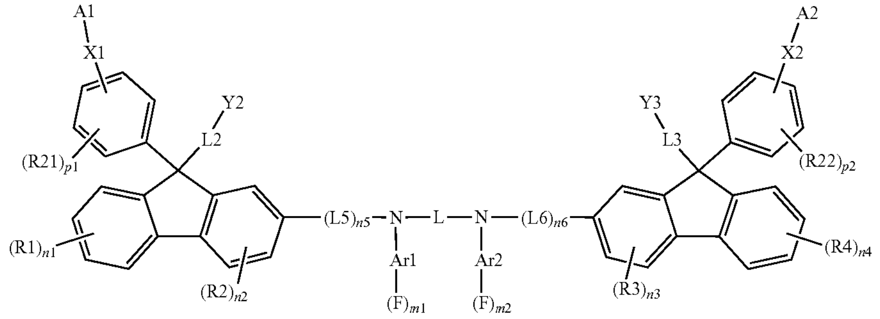

Wherein, in Formula 2,

R1 to R4, L2, L3, L5, L6, n1 to n6, Ar1, Ar2, L, Y2, Y3, m1, and m2 are the same as those defined in Formula 1, X1 and X2 are the same as or different from each other, and are each independently O or S, A1 and A2 are the same as or different from each other, and are each independently a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, R21 and R22 are the same as or different from each other, and are each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group, p1 and p2 are each an integer from 0 to 4, and when p1 and p2 are each 2 or higher, substituents in the parenthesis are the same as or different from each other.

According to an exemplary embodiment of the present specification, L1 to L4 are the same as or different from each other, and are each independently a substituted or unsubstituted arylene group having 6 to 60 carbon atoms.

According to another exemplary embodiment, L1 to L4 are the same as or different from each other, and are each independently a substituted or unsubstituted arylene group having 6 to 30 carbon atoms.

According to still another exemplary embodiment, L1 to L4 are the same as or different from each other, and are each independently a substituted or unsubstituted phenylene group; or a substituted or unsubstituted naphthylene group.

According to an exemplary embodiment of the present specification, Formula 1 is the following Formula 3 or 4.

[Formula 3]

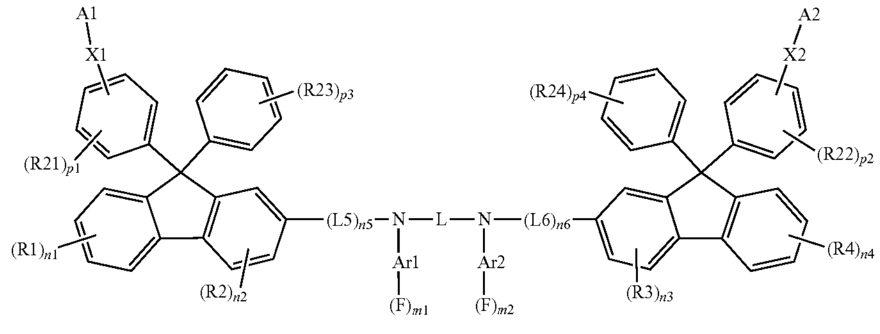

-continued

[Formula 4]

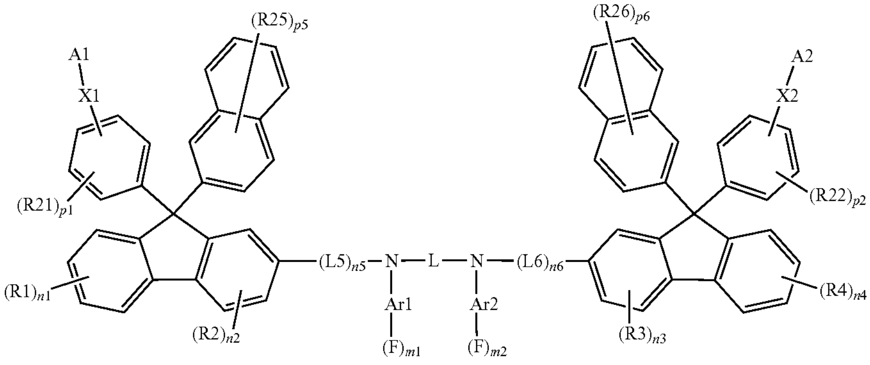

wherein, in Formulae 3 and 4,

R1 to R4, L5, L6, n1 to n6, Ar1, Ar2, L, m1, and m2 are the same as those defined in Formula 1, X1 and X2 are the same as or different from each other, and are each independently O or S, A1 and A2 are the same as or different from each other, and are each independently a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, R21 to R26 are the same as or different from each other, and are each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group, p1 and p2 are each an integer from 0 to 4, p3 and p4 are each an integer from 0 to 5, p5 and p6 are each an integer from 0 to 7, and when p1 to p6 are each 2 or higher, substituents in the parenthesis are the same as or different from each other.

According to an exemplary embodiment of the present specification, Formula 1 any one of the following Formulae 5 to 8.

[Formula 5]

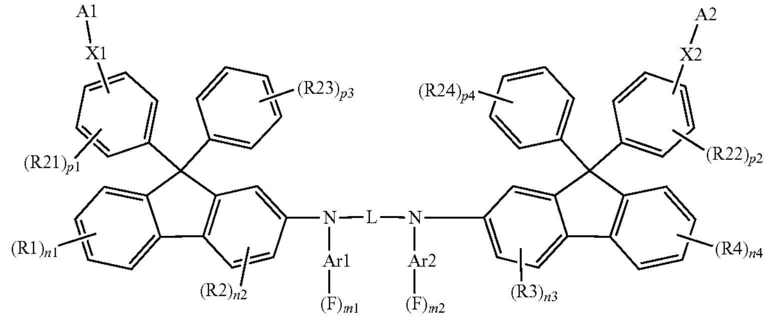

[Formula 6]

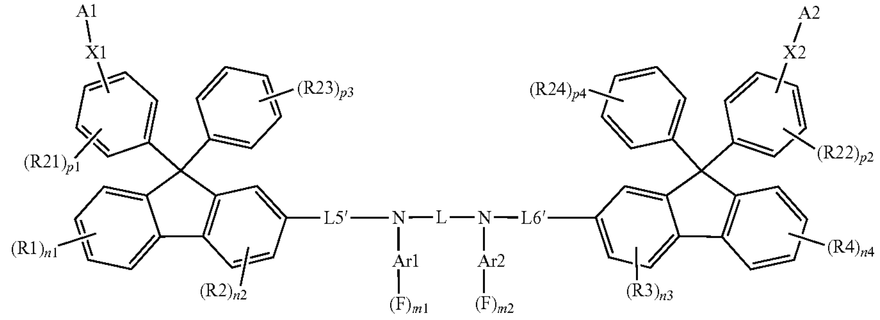

-continued

[Formula 7]

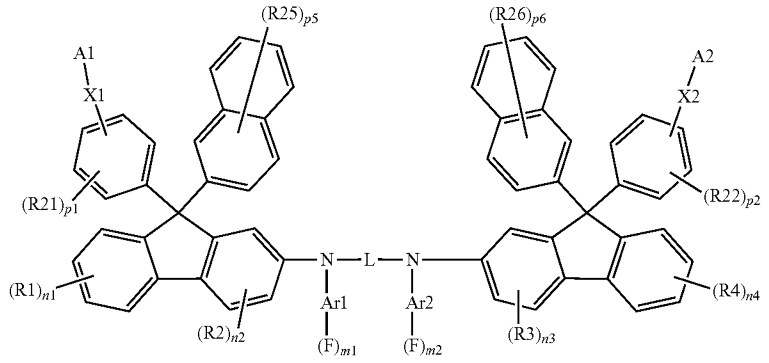

[Formula 8]

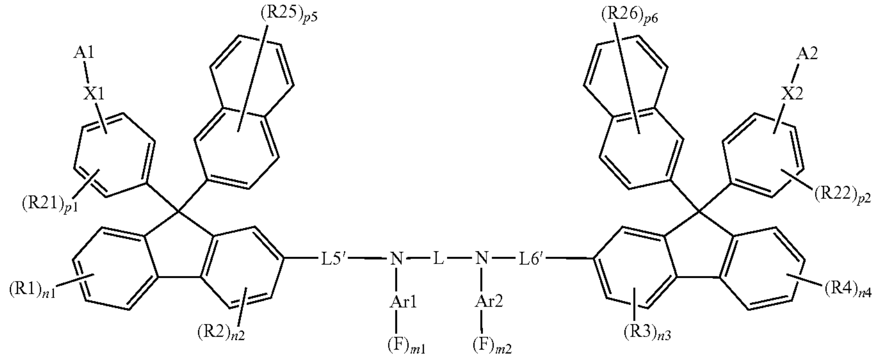

wherein, in Formulae 5 to 8,

R1 to R4, n1 to n4, Ar1, Ar2, L, m1, and m2 are the same as those defined in Formula 1, X1 and X2 are the same as or different from each other, and are each independently O or S, A1 and A2 are the same as or different from each other, and are each independently a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, L5' and L6' are the same as or different from each other, and are each independently a substituted or unsubstituted arylene group, R21 to R26 are the same as or different from each other, and are each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group, p1 and p2 are each an integer from 0 to 4, p3 and p4 are each an integer from 0 to 5, p5 and p6 are each an integer from 0 to 7, and when p1 to p6 are each 2 or higher, substituents in the parenthesis are the same as or different from each other.

In an exemplary embodiment of the present specification, L5' and L6' are the same as or different from each other, and are each independently a substituted or unsubstituted arylene group having 6 to 30 carbon atoms.

According to an exemplary embodiment of the present specification, X is O.

According to an exemplary embodiment of the present specification, X is S.

According to an exemplary embodiment of the present specification, X1 and X2 are each 0.

According to an exemplary embodiment of the present specification, X1 and X2 are each S.

In an exemplary embodiment of the present specification, A is a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group.

According to another exemplary embodiment, A is a substituted or unsubstituted alkyl group having 1 to 20 carbon atoms; a substituted or unsubstituted alkenyl group having 2 to 20 carbon atoms; a substituted or unsubstituted heterocycloalkyl group having 2 to 30 carbon atoms; a substituted or unsubstituted alkeneoxy group having 2 to 20 carbon atoms; a substituted or unsubstituted hydrocarbon ring group having 3 to 30 carbon atoms; or a substituted or unsubstituted heterocyclic group having 2 to 30 carbon atoms. The groups can be unsubstituted or substituted with one or more substituents selected from the group consisting of a halogen group; an alkyl group; an alkenyl group; a silyloxy group; a heterocycloalkyl group; and a hydrocarbon ring group, or can be unsubstituted or substituted with a substituent to which two or more substituents among the substituents exemplified above are linked.

In another exemplary embodiment, A is a substituted or unsubstituted methyl group; a substituted or unsubstituted butyl group; a substituted or unsubstituted ethenyl group; a substituted or unsubstituted oxiranyl group; a substituted or unsubstituted oxetanyl group; a substituted or unsubstituted vinyloxy group; a substituted or unsubstituted phenyl group; or a substituted or unsubstituted benzoxazinyl group. The groups can be unsubstituted or substituted with one or more substituents selected from the group consisting of a halogen group; an alkyl group; an alkenyl group; a silyloxy group; a heterocycloalkyl group; and a hydrocarbon ring group, or can be unsubstituted or substituted with a substituent to which two or more substituents among the substituents exemplified above are linked.

In an exemplary embodiment of the present specification, A1 and A2 are the same as or different from each other, and are each independently a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group.

According to still another exemplary embodiment, A1 and A2 are the same as or different from each other, and are each independently a substituted or unsubstituted alkyl group having 1 to 20 carbon atoms; a substituted or unsubstituted alkenyl group having 2 to 20 carbon atoms; a substituted or unsubstituted heterocycloalkyl group having 2 to 30 carbon atoms; a substituted or unsubstituted alkeneoxy group having 2 to 20 carbon atoms; a substituted or unsubstituted hydrocarbon ring group having 3 to 30 carbon atoms; or a substituted or unsubstituted heterocyclic group having 2 to 30 carbon atoms. The groups can be unsubstituted or substituted with one or more substituents selected from the group consisting of a halogen group; an alkyl group; an alkenyl group; a silyloxy group; a heterocycloalkyl group; and a hydrocarbon ring group, or can be unsubstituted or substituted with a substituent to which two or more substituents among the substituents exemplified above are linked.

In another exemplary embodiment, A1 and A2 are the same as or different from each other, and are each independently a substituted or unsubstituted methyl group; a substituted or unsubstituted butyl group; a substituted or unsubstituted ethenyl group; a substituted or unsubstituted oxiranyl group; a substituted or unsubstituted oxetanyl group; a substituted or unsubstituted vinyloxy group; a substituted or unsubstituted phenyl group; or a substituted or unsubstituted benzoxazinyl group. The groups can be unsubstituted or substituted with one or more substituents selected from the group consisting of a halogen group; an alkyl group; an alkenyl group; a silyloxy group; a heterocycloalkyl group; and a hydrocarbon ring group, or can be unsubstituted or substituted with a substituent to which two or more substituents among the substituents exemplified above are linked.

According to an exemplary embodiment of the present specification, A, A1, and A2 can be 'a cross-linkable functional group by heat or light'.

A is any one of the following structures.

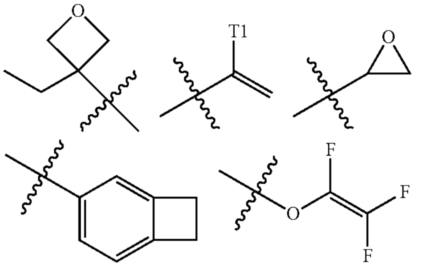

-continued

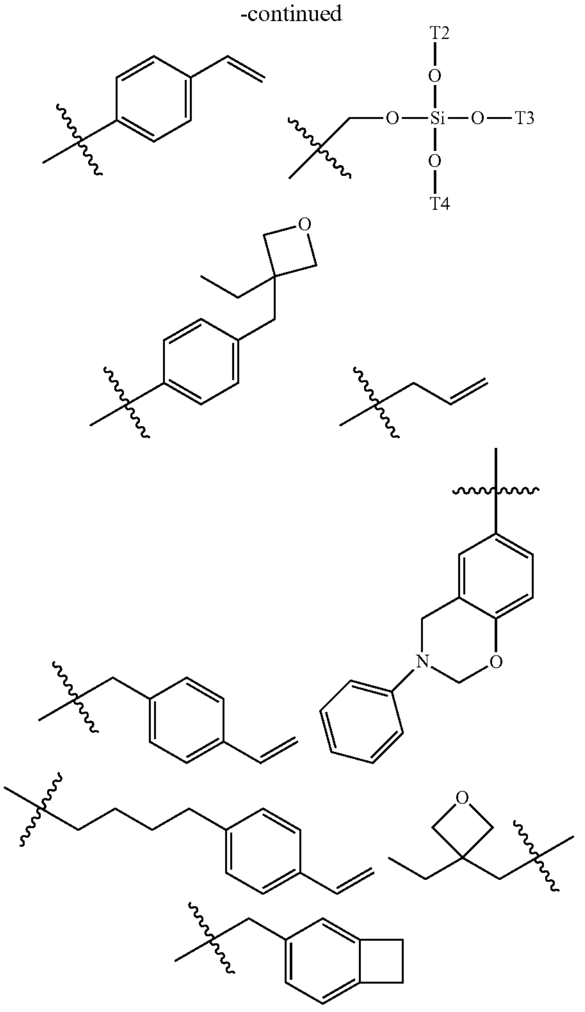

In the structures,

T1 is hydrogen; or a substituted or unsubstituted alkyl group having 1 to 6 carbon atoms, and T2 to T4 are the same as or different from each other, and are each independently a substituted or unsubstituted alkyl group having 1 to 6 carbon atoms.

In an exemplary embodiment of the present specification, T1 is hydrogen; a substituted or unsubstituted methyl group; a substituted or unsubstituted ethyl group; a substituted or unsubstituted propyl group; or a substituted or unsubstituted butyl group.

In another exemplary embodiment, T1 is hydrogen; a methyl group; an ethyl group; a propyl group; or a butyl group.

According to an exemplary embodiment of the present specification, T2 to T4 are the same as or different from each other, and are each independently a substituted or unsubstituted methyl group; a substituted or unsubstituted ethyl group; a substituted or unsubstituted propyl group; or a substituted or unsubstituted butyl group.

In still another exemplary embodiment, T2 to T4 are the same as or different from each other, and are each independently a methyl group; an ethyl group; a propyl group; or a butyl group.

According to an exemplary embodiment of the present specification, s is an integer from 0 to 2, and when s is 2, each occurrence of R101 is the same as or different from each other.

According to an exemplary embodiment of the present specification, R101 is hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted aryloxy group having 6 to 30 carbon atoms.

According to another exemplary embodiment, R101 is hydrogen; deuterium; or a substituted or unsubstituted alkyl group having 1 to 20 carbon atoms.

According to still another exemplary embodiment, R101 is hydrogen; deuterium; a substituted or unsubstituted methyl group; a substituted or unsubstituted ethyl group; a substituted or unsubstituted propyl group; or a substituted or unsubstituted butyl group.

According to yet another exemplary embodiment, R101 is hydrogen; deuterium; a methyl group; an ethyl group; a propyl group; or a butyl group.

According to an exemplary embodiment of the present specification, R21 to R26 are the same as or different from each other, and are each independently hydrogen; deuterium; a halogen group; a substituted or unsubstituted alkyl group having 1 to 20 carbon atoms; a substituted or unsubstituted alkoxy group having 1 to 20 carbon atoms; a substituted or unsubstituted aryloxy group having 6 to 30 carbon atoms; a substituted or unsubstituted aryl group having 6 to 30 carbon atoms; or a substituted or unsubstituted heteroaryl group having 2 to 30 carbon atoms.

According to an exemplary embodiment of the present specification, R21 and R22 are the same as or different from each other, and are each independently hydrogen; deuterium; or a substituted or unsubstituted alkyl group having 1 to 20 carbon atoms.

According to another exemplary embodiment, R21 and R22 are each hydrogen.

In an exemplary embodiment of the present specification, R23 to R26 are the same as or different from each other, and are each independently hydrogen; deuterium; a substituted or unsubstituted alkyl group having 1 to 20 carbon atoms; or a substituted or unsubstituted alkoxy group having 1 to 20 carbon atoms.

According to still another exemplary embodiment, R23 to R26 are the same as or different from each other, and are each independently hydrogen; deuterium; a substituted or unsubstituted methyl group; a substituted or unsubstituted ethyl group; a substituted or unsubstituted propyl group; a substituted or unsubstituted butyl group; or a substituted or unsubstituted ethoxy group.

According to yet another exemplary embodiment, R23 to R26 are the same as or different from each other, and are each independently hydrogen; deuterium; a methyl group; an ethyl group; a propyl group; a butyl group; or an ethoxy group substituted with an ethoxy group.

According to an exemplary embodiment of the present specification, p1 is an integer from 0 to 4, and when p1 is 2 or higher, each occurrence of R21 is the same as or different from each other.

According to an exemplary embodiment of the present specification, p1 is 0 or 1.

According to an exemplary embodiment of the present specification, p2 is an integer from 0 to 4, and when p2 is 2 or higher, each occurrence of R22 is the same as or different from each other.

According to an exemplary embodiment of the present specification, p2 is 0 or 1.

According to an exemplary embodiment of the present specification, p3 is an integer from 0 to 5, and when p3 is 2 or higher, each occurrence of R23 is the same as or different from each other.

According to an exemplary embodiment of the present specification, p3 is an integer from 0 to 2, and when p3 is 2, two R23's are the same as or different from each other.

According to an exemplary embodiment of the present specification, p4 is an integer from 0 to 5, and when p4 is 2 or higher, each occurrence of R24 is the same as or different from each other.

According to an exemplary embodiment of the present specification, p4 is an integer from 0 to 2, and when p4 is 2, two R24's are the same as or different from each other.

According to an exemplary embodiment of the present specification, p5 is an integer from 0 to 7, and when p5 is 2 or higher, each occurrence of R25 is the same as or different from each other.

According to an exemplary embodiment of the present specification, p5 is an integer from 0 to 2, and when p5 is 2, two R25's are the same as or different from each other.

According to an exemplary embodiment of the present specification, p6 is an integer from 0 to 7, and when p6 is 2 or higher, each occurrence of R26 is the same as or different from each other.

According to an exemplary embodiment of the present specification, p6 is an integer from 0 to 2, and when p6 is 2, two R26's are the same as or different from each other.

According to an exemplary embodiment of the present specification, L is a substituted or unsubstituted arylene group having 6 to 60 carbon atoms.

According to another exemplary embodiment, L is a substituted or unsubstituted phenylene group; a substituted or unsubstituted biphenylylene group; or a substituted or unsubstituted spirobifluorenylene group.

According to still another exemplary embodiment, L is any one of the following Formulae 1-A to 1-C.

[Formula 1-A]

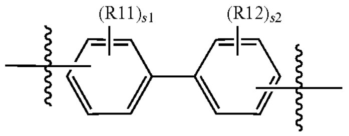

[Formula 1-B]

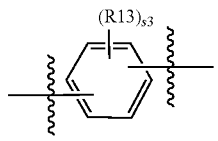

[Formula 1-C]

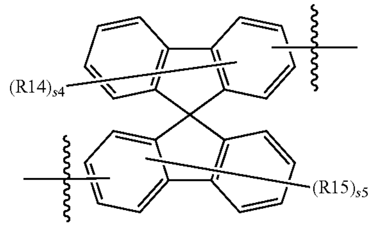

wherein, in Formulae 1-A to 1-C,

R11 to R15 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group, s1 to s3 are each an integer from 0 to 4, s4 and s5 are each an integer from 0 to 7, and when s1 to s5 are each 2 or higher, substituents in the parenthesis are the same as or different from each other.

According to an exemplary embodiment of the present specification, L is Formula 1-A.

According to an exemplary embodiment of the present specification, R11 to R15 are the same as or different from each other, and are each independently hydrogen; deuterium; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms.

According to an exemplary embodiment of the present specification, R11 to R15 are the same as or different from each other, and are each independently hydrogen; or deuterium.

According to an exemplary embodiment of the present specification, s1 is an integer from 0 to 4, and when s1 is 2 or higher, each occurrence of R11 is the same as or different from each other.

According to another exemplary embodiment, s1 is 0 or 1.

According to an exemplary embodiment of the present specification, s2 is an integer from 0 to 4, and when s2 is 2 or higher, each occurrence of R12 is the same as or different from each other.

According to another exemplary embodiment, s2 is 0 or 1.

According to an exemplary embodiment of the present specification, s3 is an integer from 0 to 4, and when s3 is 2 or higher, each occurrence of R13 is the same as or different from each other.

According to another exemplary embodiment, s3 is 0 or 1.

According to an exemplary embodiment of the present specification, s4 is an integer from 0 to 7, and when s4 is 2 or higher, each occurrence of R14 is the same as or different from each other.

According to another exemplary embodiment, s4 is 0 or 1.

According to an exemplary embodiment of the present specification, s5 is an integer from 0 to 7, and when s5 is 2 or higher, each occurrence of R15 is the same as or different from each other.

According to another exemplary embodiment, s5 is 0 or 1.

According to an exemplary embodiment of the present specification, L5 and L6 are the same as or different from each other, and are each independently a direct bond; or a substituted or unsubstituted arylene group having 6 to 60 carbon atoms.

According to another exemplary embodiment, L5 and L6 are the same as or different from each other, and are each independently a direct bond; or a substituted or unsubstituted phenylene group.

According to an exemplary embodiment of the present specification, L5 and L6 are the same as or different from each other, and are each independently a direct bond; or a phenylene group.

According to another exemplary embodiment, L5 and L6 are each a direct bond.

According to still another exemplary embodiment, L5 and L6 are each a phenylene group.

According to an exemplary embodiment of the present specification, n5 is an integer from 0 to 2, and when n5 is 2, two L5's are the same as or different from each other.

According to an exemplary embodiment of the present specification, n6 is an integer from 0 to 2, and when n6 is 2, two L6's are the same as or different from each other.

According to an exemplary embodiment of the present specification, R1 to R4 are the same as or different from each other, and are each independently hydrogen; deuterium; a substituted or unsubstituted alkyl group having 1 to 20 carbon atoms; a substituted or unsubstituted alkoxy group having 1 to 20 carbon atoms; a substituted or unsubstituted aryl group having 6 to 30 carbon atoms; or a substituted or unsubstituted heteroaryl group having 2 to 30 carbon atoms.

According to an exemplary embodiment of the present specification, R1 to R4 are the same as or different from each other, and are each independently hydrogen; deuterium; a substituted or unsubstituted alkyl group having 1 to 20 carbon atoms; or a substituted or unsubstituted aryl group having 6 to 30 carbon atoms.

According to an exemplary embodiment of the present specification, n1 is an integer from 0 to 4, and when n1 is 2 or higher, each occurrence of R1 is the same as or different from each other.

In another exemplary embodiment, n1 is 0 or 1.

According to an exemplary embodiment of the present specification, n2 is an integer from 0 to 3, and when n2 is 2 or higher, each occurrence of R2 is the same as or different from each other.

In still another exemplary embodiment, n2 is 0 or 1.

According to an exemplary embodiment of the present specification, n3 is an integer from 0 to 3, and when n3 is 2 or higher, each occurrence of R3 is the same as or different from each other.

In yet another exemplary embodiment, n3 is 0 or 1.

According to an exemplary embodiment of the present specification, n4 is an integer from 0 to 4, and when n4 is 2 or higher, each occurrence of R4 is the same as or different from each other.

In still yet another exemplary embodiment, n4 is 0 or 1.

According to an exemplary embodiment of the present specification, Ar1 and Ar2 are the same as or different from each other, and are each independently a substituted or unsubstituted aryl group having 6 to 60 carbon atoms; or a substituted or unsubstituted heteroaryl group having 2 to 60 carbon atoms.

According to another exemplary embodiment, Ar1 and Ar2 are the same as or different from each other, and are each independently an aryl group having 6 to 60 carbon atoms, which is unsubstituted or substituted with an alkyl group having 1 to 20 carbon atoms.

According to still another exemplary embodiment, Ar1 and Ar2 are the same as or different from each other, and are each independently a phenyl group which is unsubstituted or substituted with an alkyl group having 1 to 20 carbon atoms; a biphenyl group which is unsubstituted or substituted with an alkyl group having 1 to 20 carbon atoms; or a terphenyl group which is unsubstituted or substituted with an alkyl group having 1 to 20 carbon atoms.

According to yet another exemplary embodiment, Ar1 and Ar2 are the same as or different from each other, and are each independently a phenyl group which is unsubstituted or substituted with one or more substituents of a methyl group, an ethyl group, a propyl group, or a butyl group; a biphenyl group which is unsubstituted or substituted with one or more substituents of a methyl group, an ethyl group, a propyl group, or a butyl group; or a terphenyl group which is unsubstituted or substituted with an alkyl group having 1 to 20 carbon atoms, which is unsubstituted or substituted with one or more substituents of a methyl group, an ethyl group, a propyl group, or a butyl group.

According to an exemplary embodiment of the present specification, m1 is an integer from 1 to 3.

According to an exemplary embodiment of the present specification, m1 is 1 or 2.

According to an exemplary embodiment of the present specification, m2 is an integer from 1 to 3.

According to an exemplary embodiment of the present specification, m2 is 1 or 2.

According to another exemplary embodiment, —Ar1-$(F)_{m1}$ and —Ar2-$(F)_{m2}$ are the same as or different from each other, and are each independently any one of the following Formulae 101 to 103.

[Formula 101]

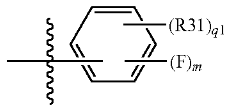

[Formula 102]

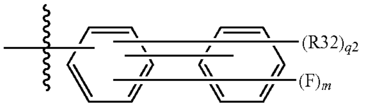

[Formula 103]

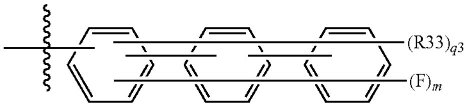

wherein, in Formulae 101 to 103,

R31 tp R33 are the same as or different from each other, and are each independently hydrogen; or a substituted or unsubstituted alkyl group, m is an integer from 1 to 5, q1 is an integer from 0 to 4, and when q1 is 2 or higher, each occurrence of R31 is the same as or different from each other, q2 is an integer from 0 to 8, and when q2 is 2 or higher, each occurrence of R32 is the same as or different from each other, and q3 is an integer from 0 to 12, and when q3 is 2 or higher, each occurrence of R33 is the same as or different from each other.

According to an exemplary embodiment of the present specification, R31 to R33 are the same as or different from each other, and are each independently hydrogen; or a substituted or unsubstituted alkyl group having 1 to 20 carbon atoms.

According to another exemplary embodiment, R31 to R33 are the same as or different from each other, and are each independently hydrogen; a substituted or unsubstituted methyl group; a substituted or unsubstituted ethyl group; a substituted or unsubstituted propyl group; or a substituted or unsubstituted butyl group.

According to still another exemplary embodiment, R31 to R33 are the same as or different from each other, and are each independently hydrogen; a methyl group; an ethyl group; a propyl group; or a butyl group.

According to an exemplary embodiment of the present specification, m is 1 or 2.

According to an exemplary embodiment of the present specification, q1 is an integer from 0 to 2.

According to an exemplary embodiment of the present specification, q1 is 0 or 1.

According to an exemplary embodiment of the present specification, q2 is an integer from 0 to 2.

According to an exemplary embodiment of the present specification, q2 is 0 or 1.

According to an exemplary embodiment of the present specification, q3 is an integer from 0 to 2.

According to an exemplary embodiment of the present specification, q3 is 0 or 1.

In an exemplary embodiment of the present specification, Formula 1 can be any one of the following compounds.

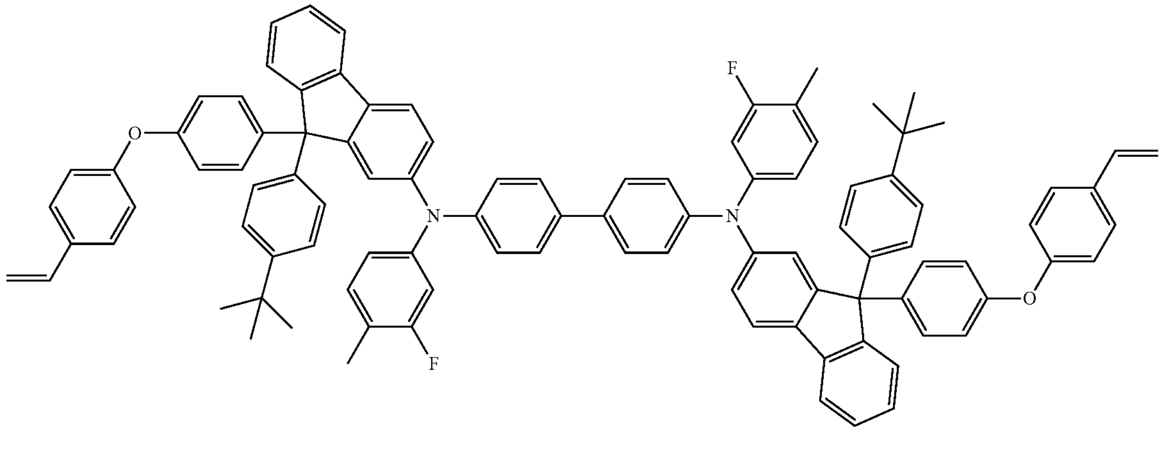

-continued
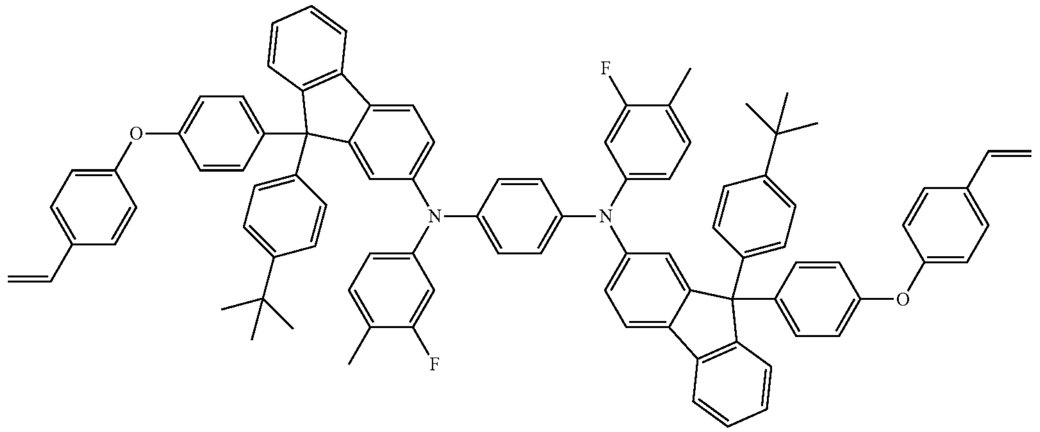
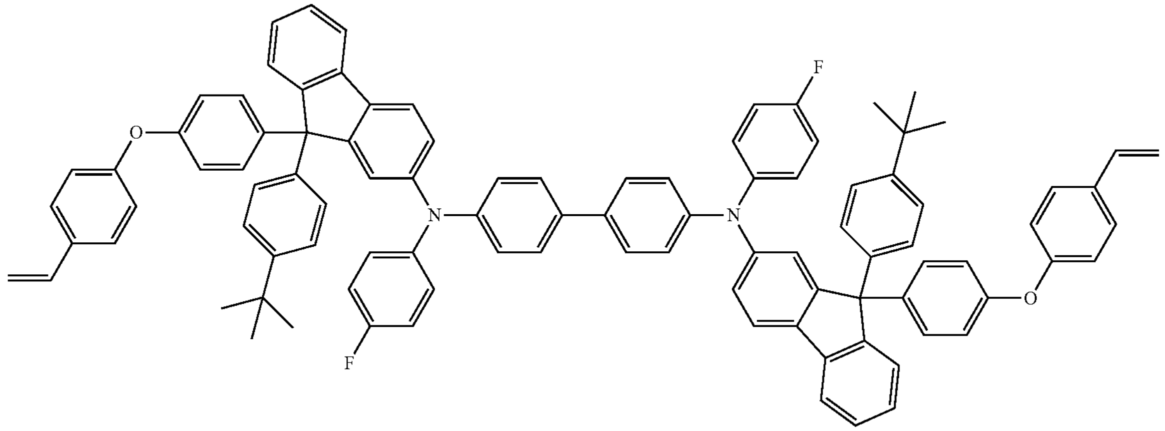
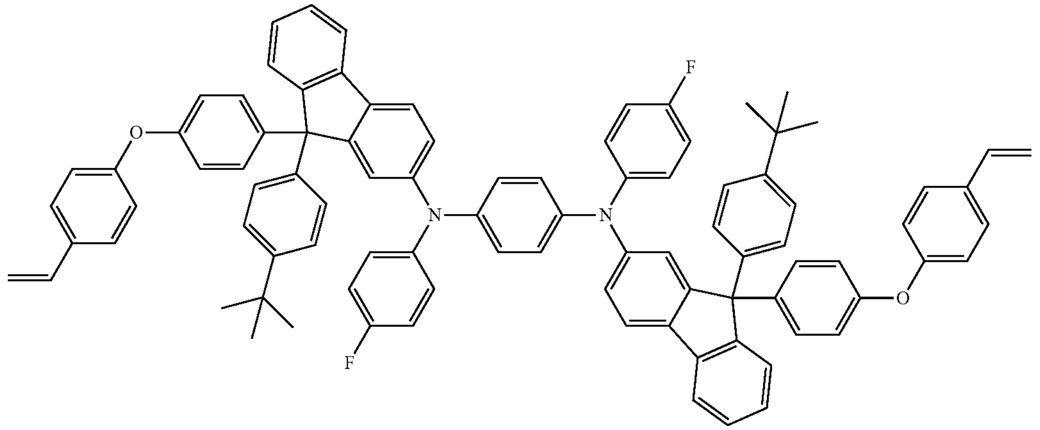
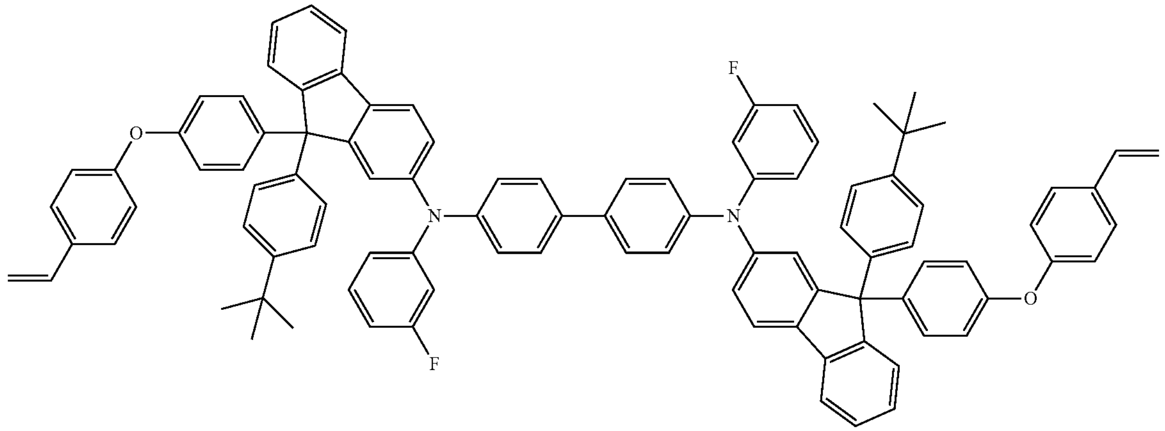

-continued
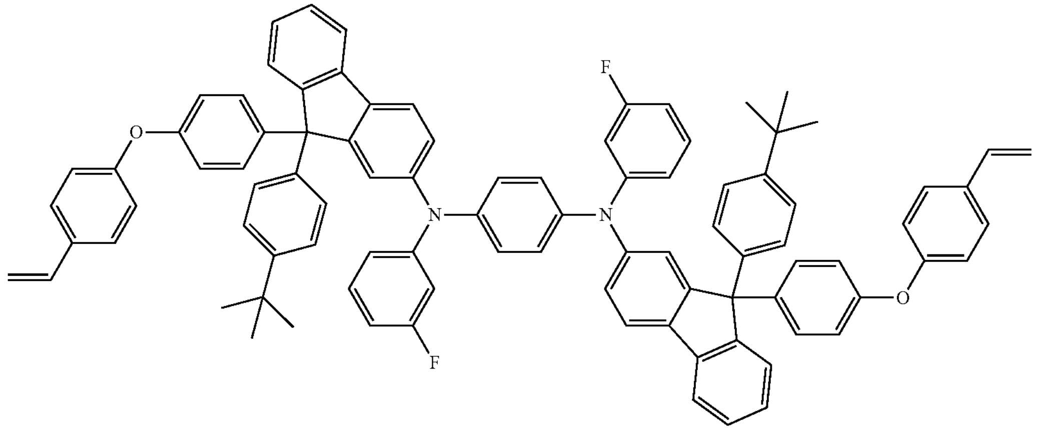
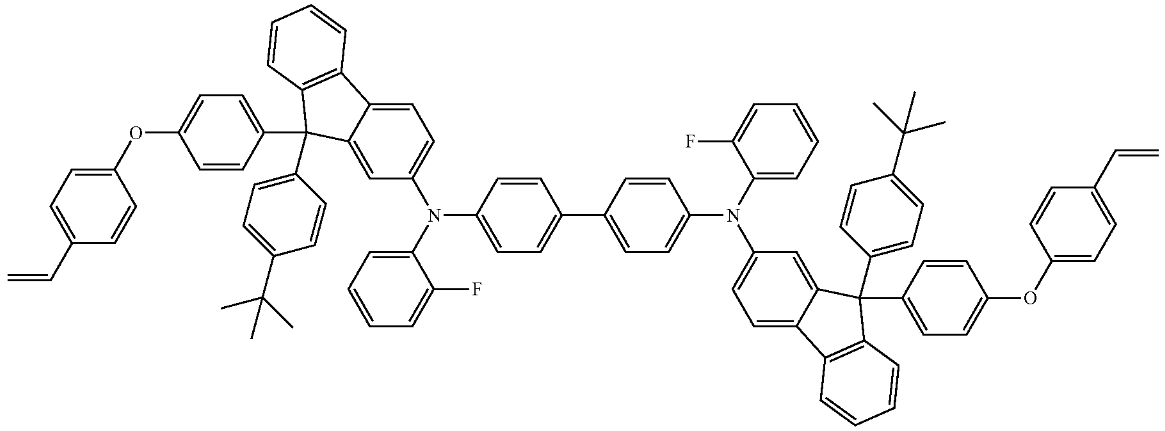
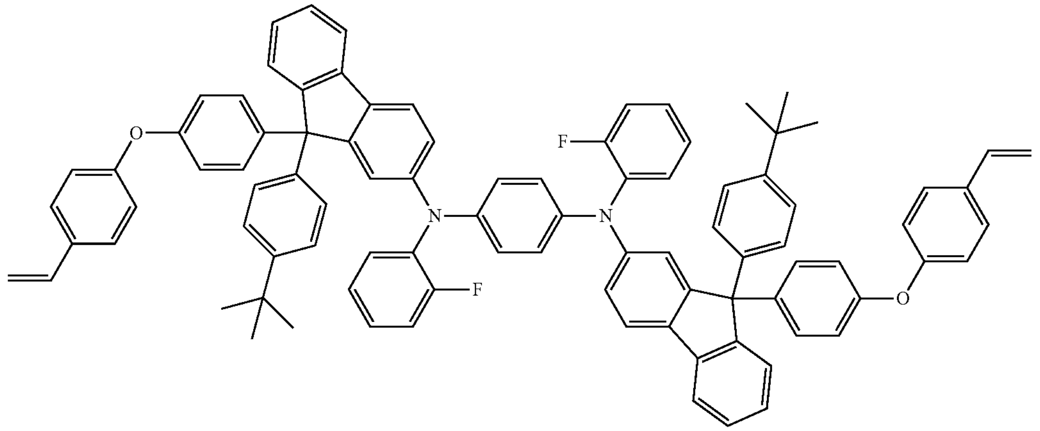
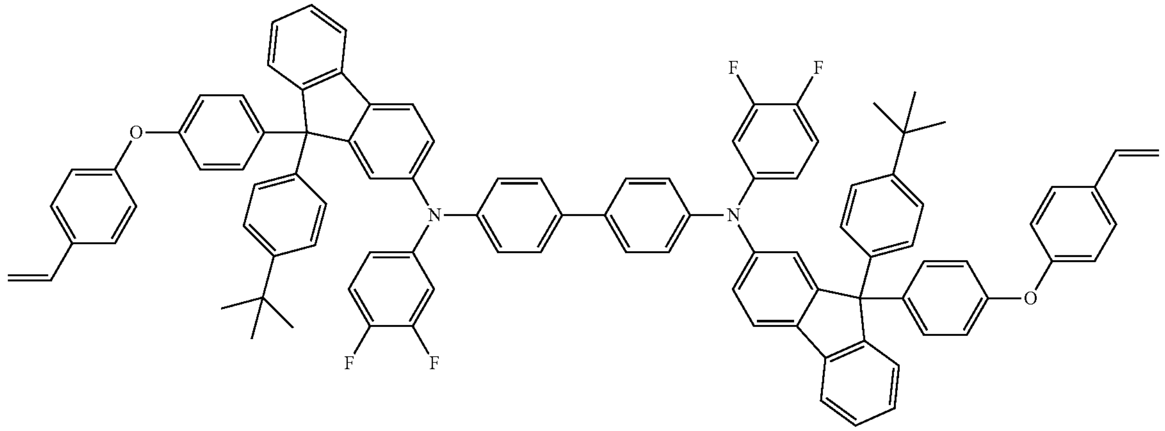

-continued
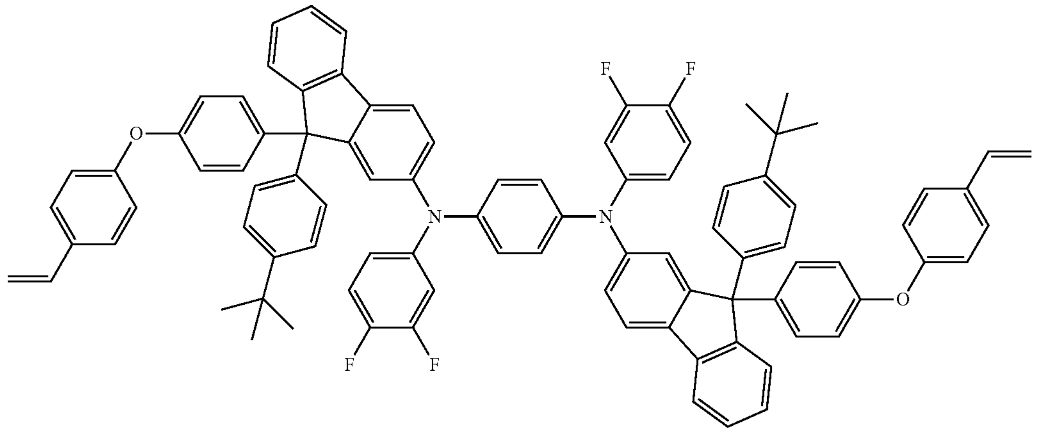
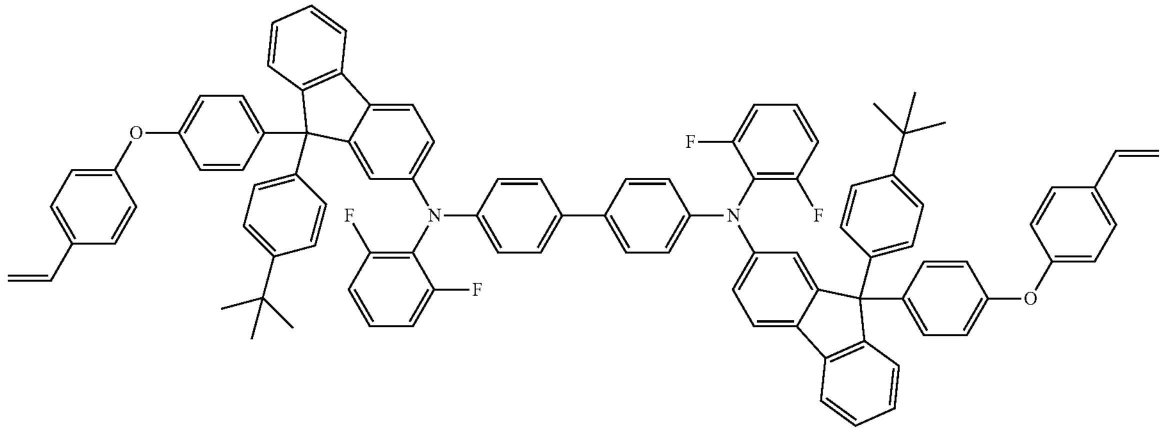
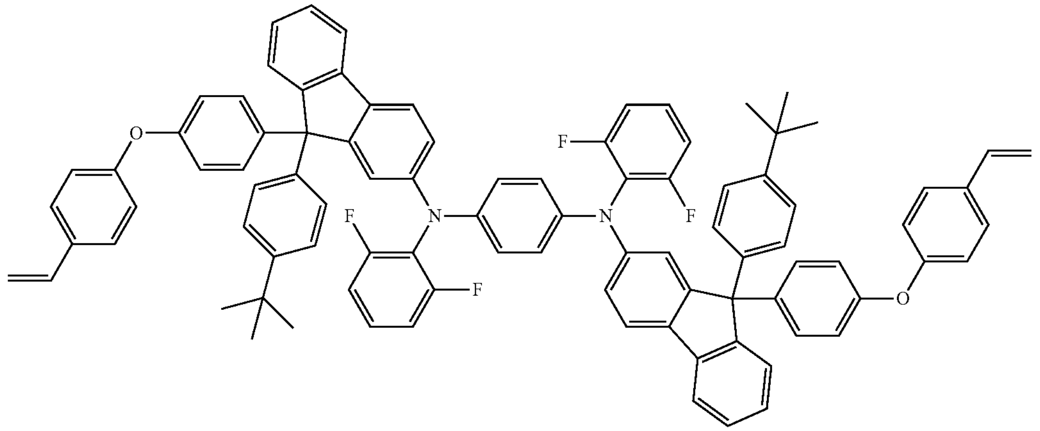
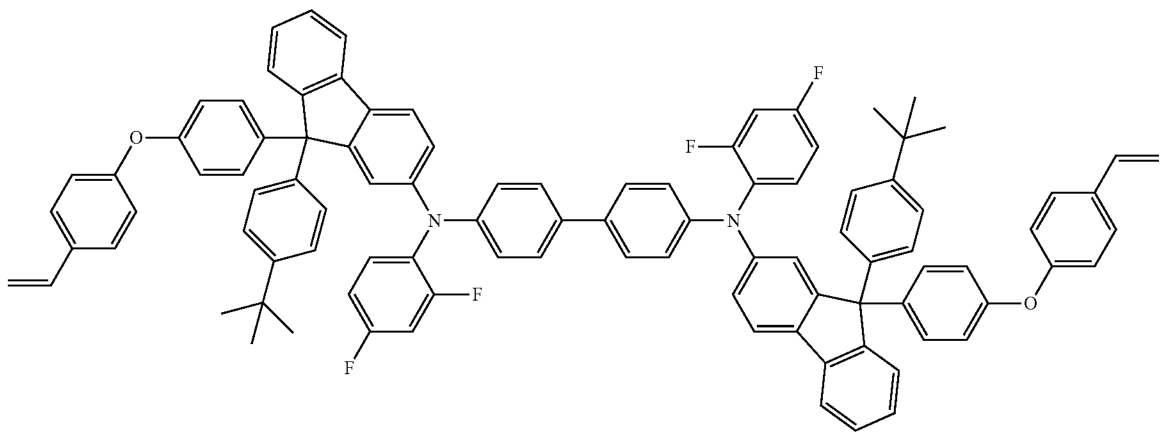

-continued
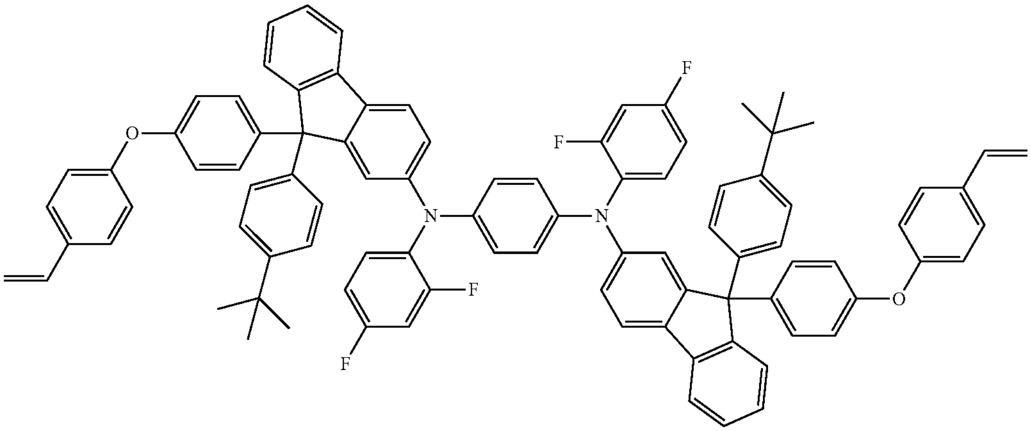
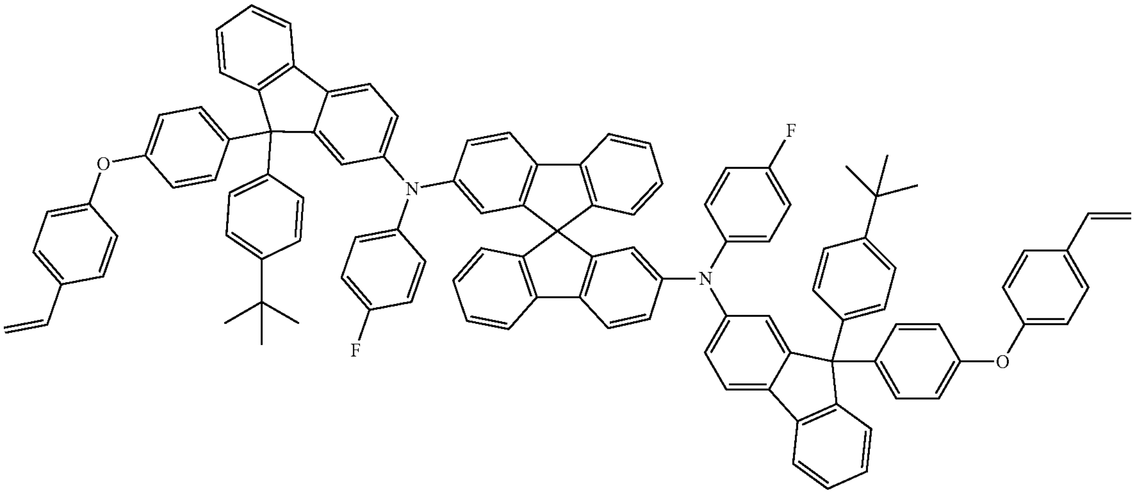
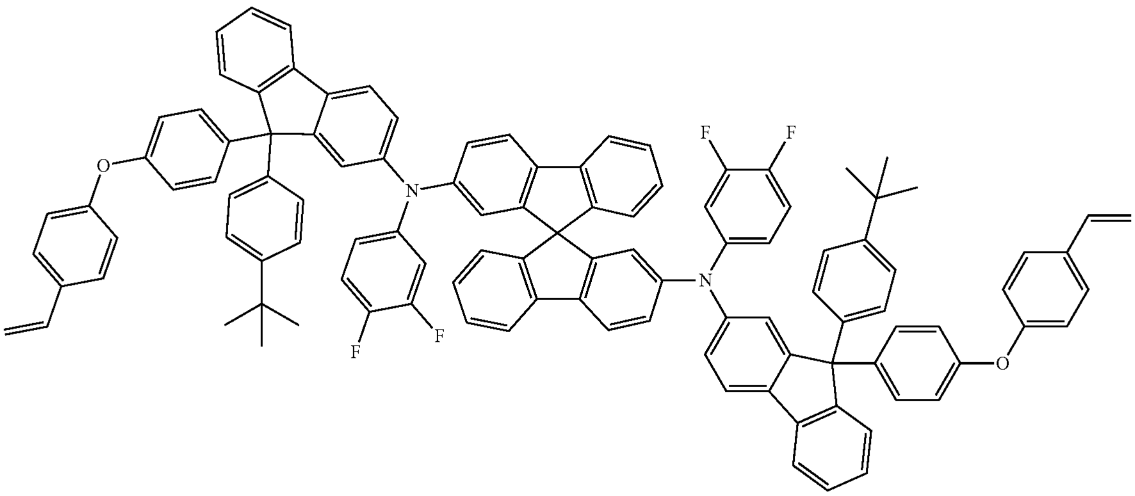

-continued
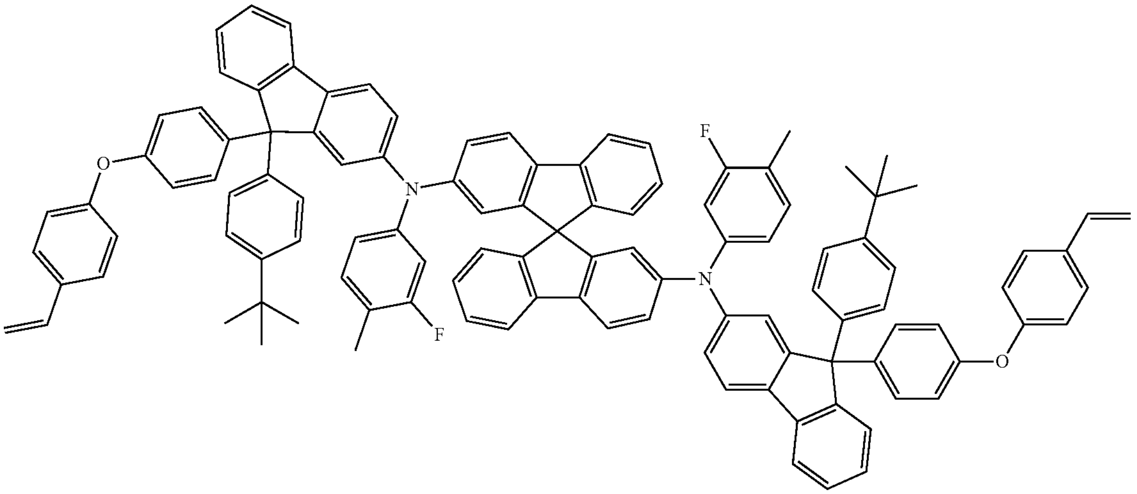
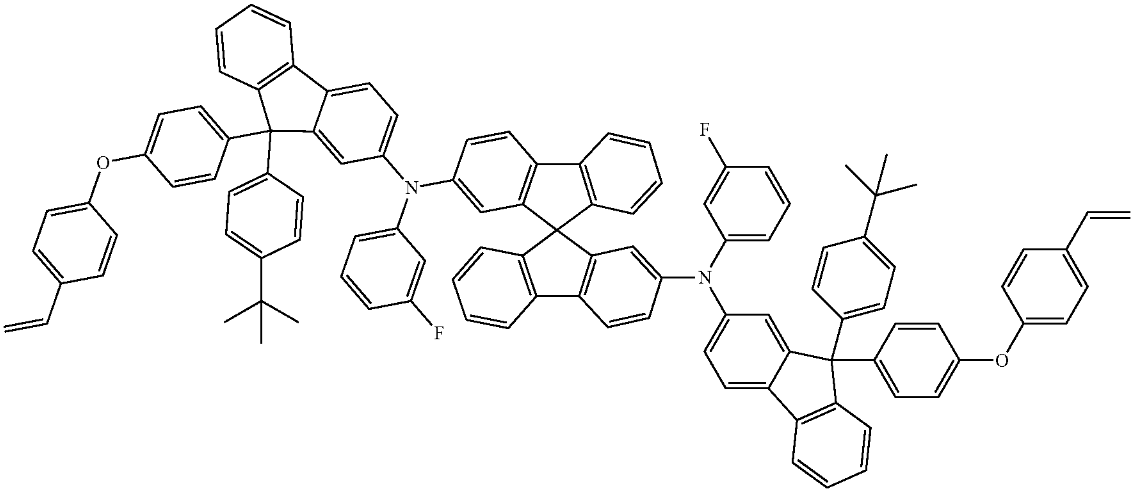
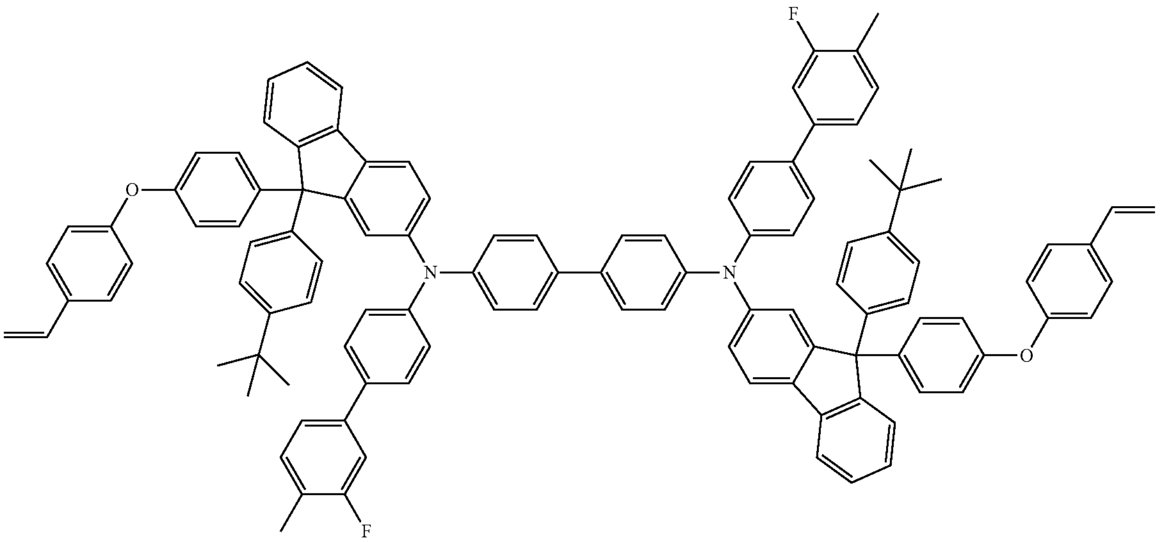

-continued
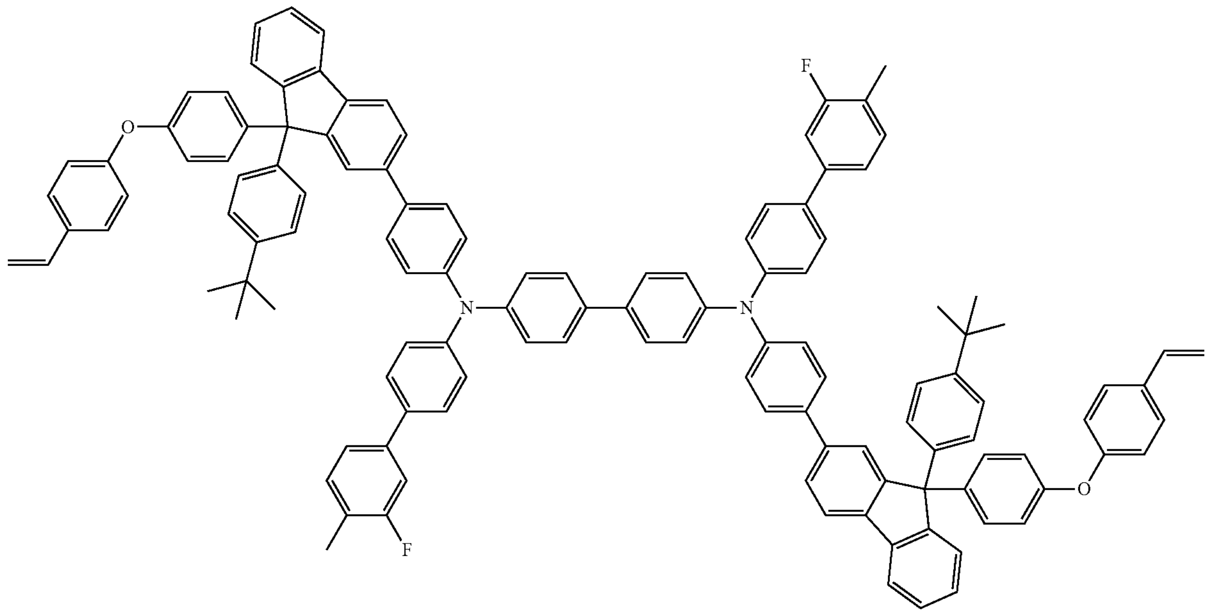
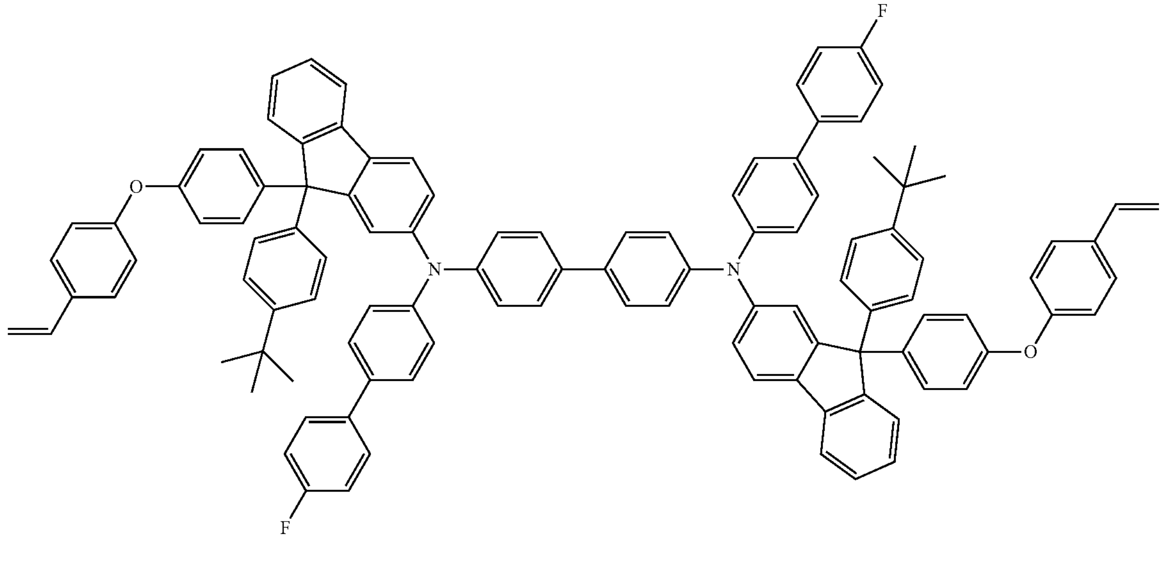

-continued
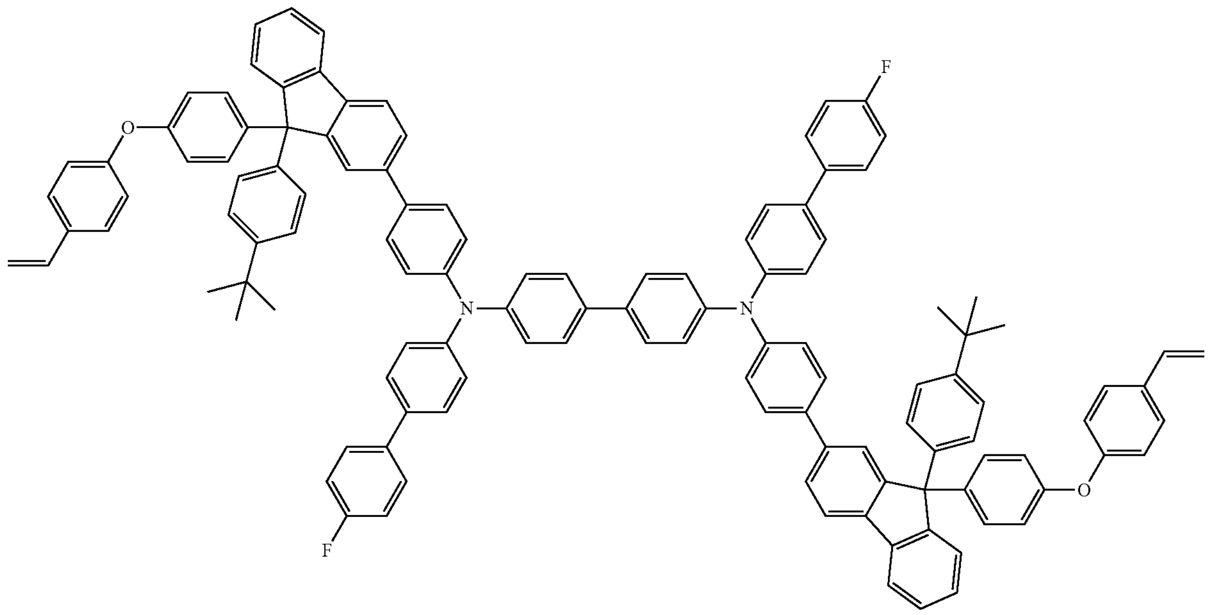
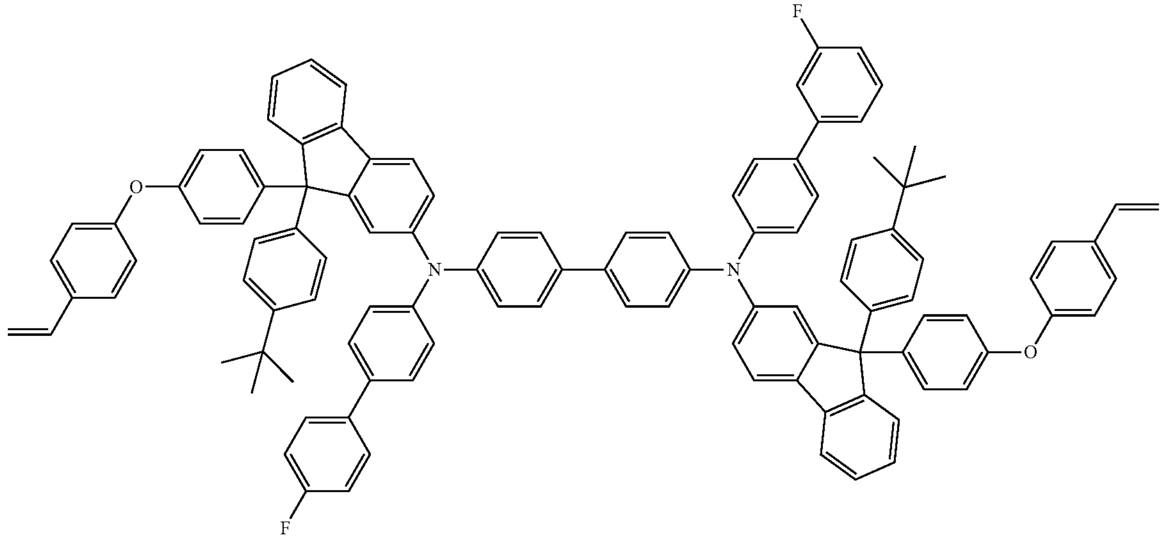

-continued
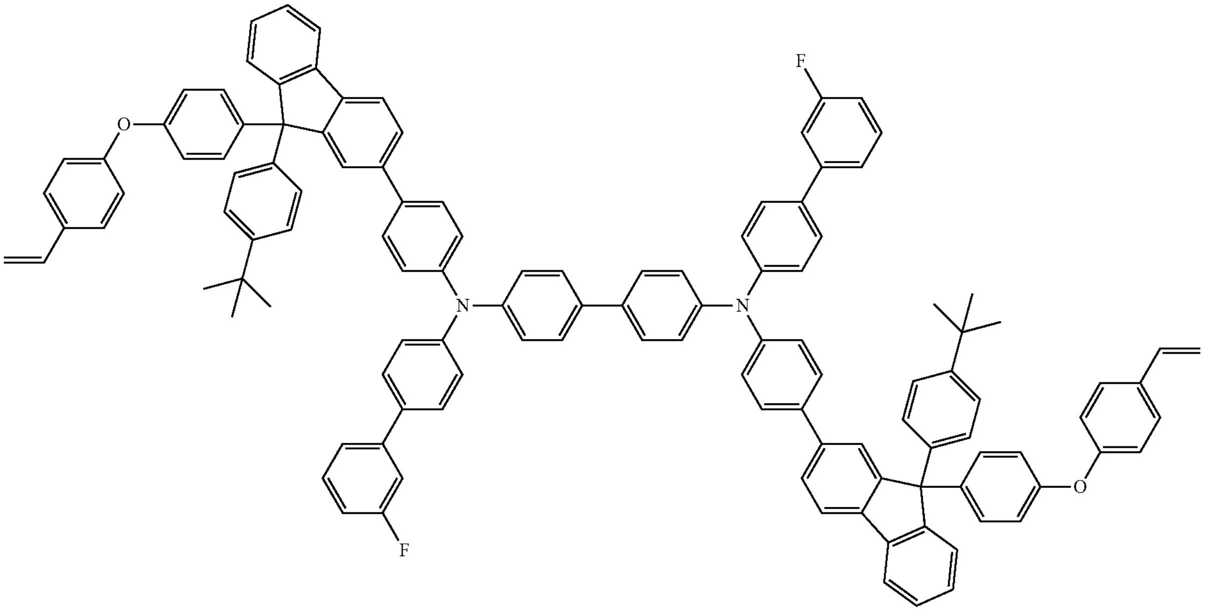
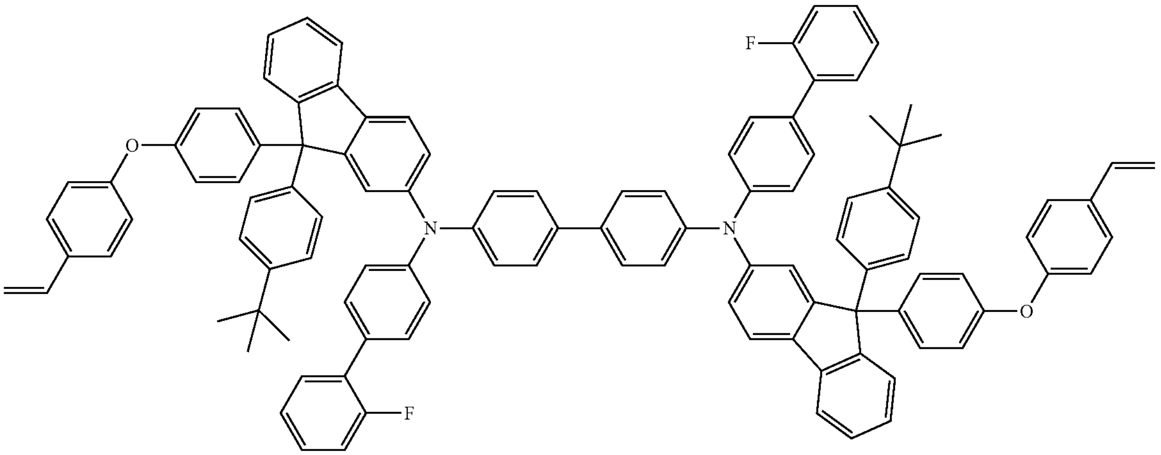
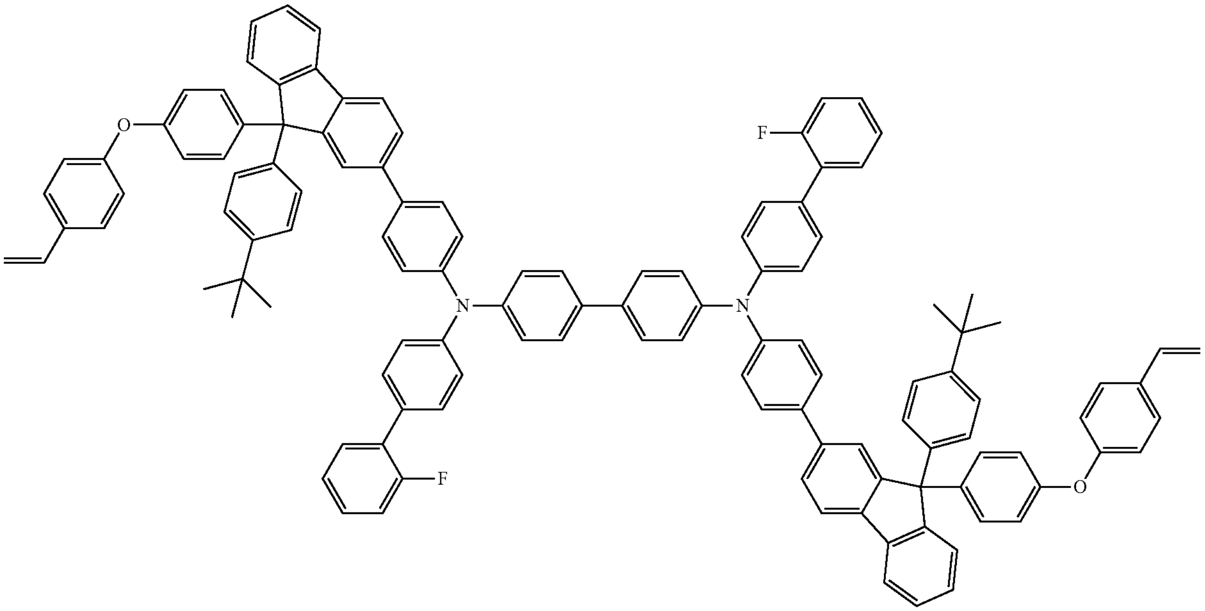

-continued
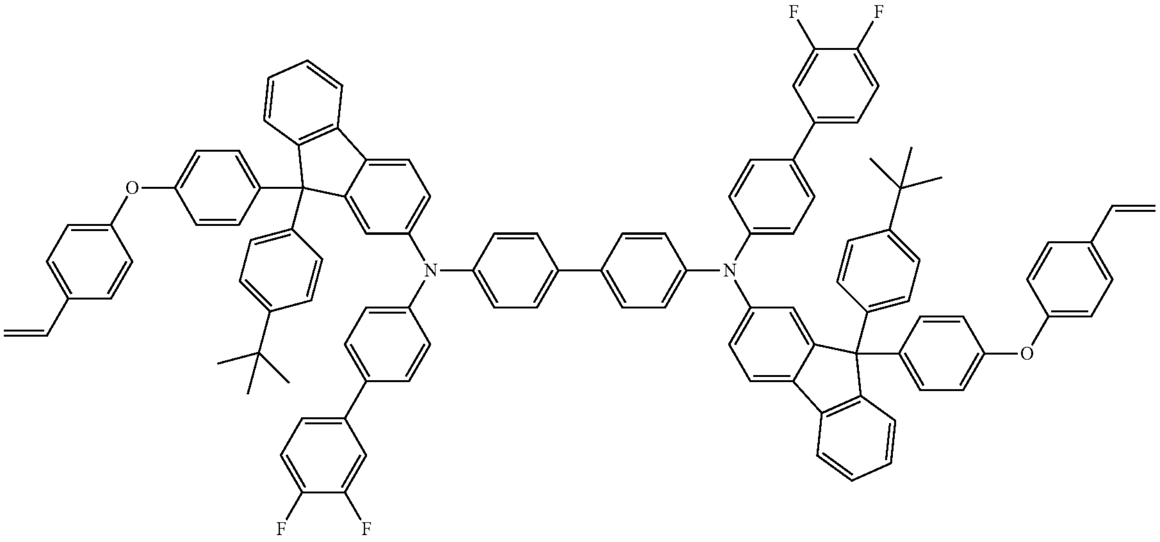
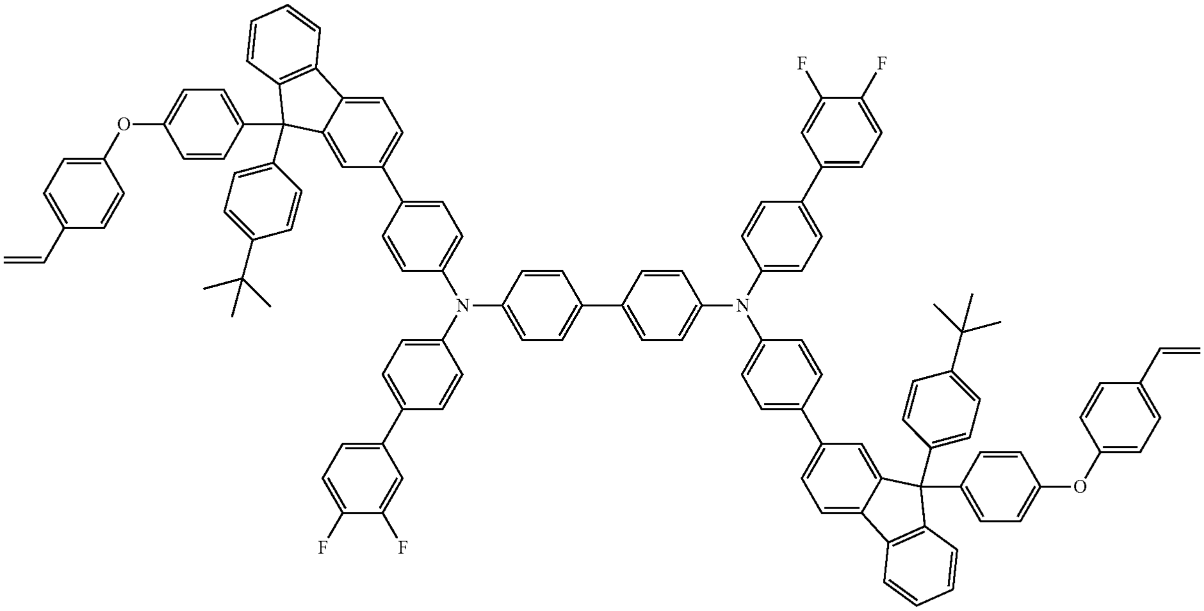
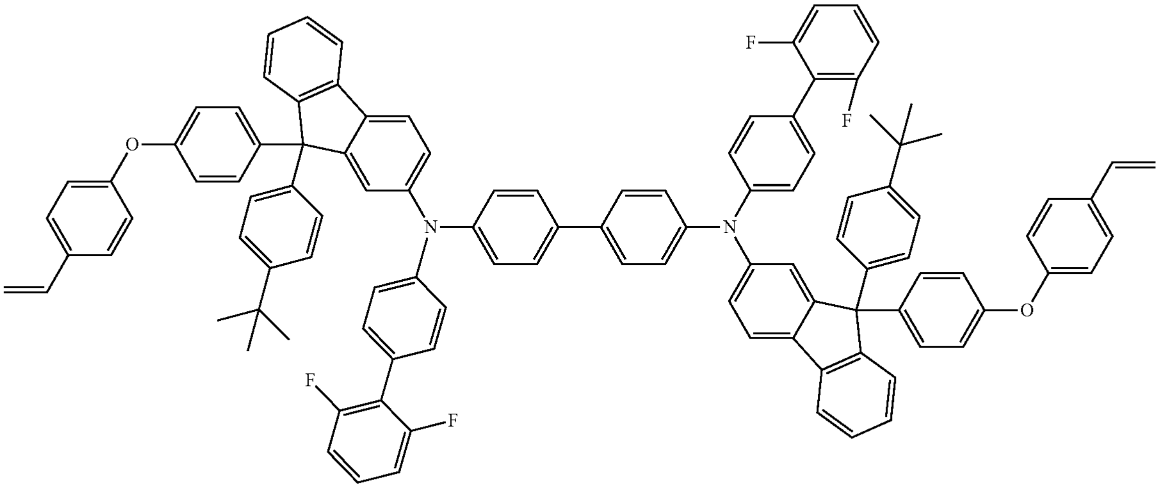

-continued
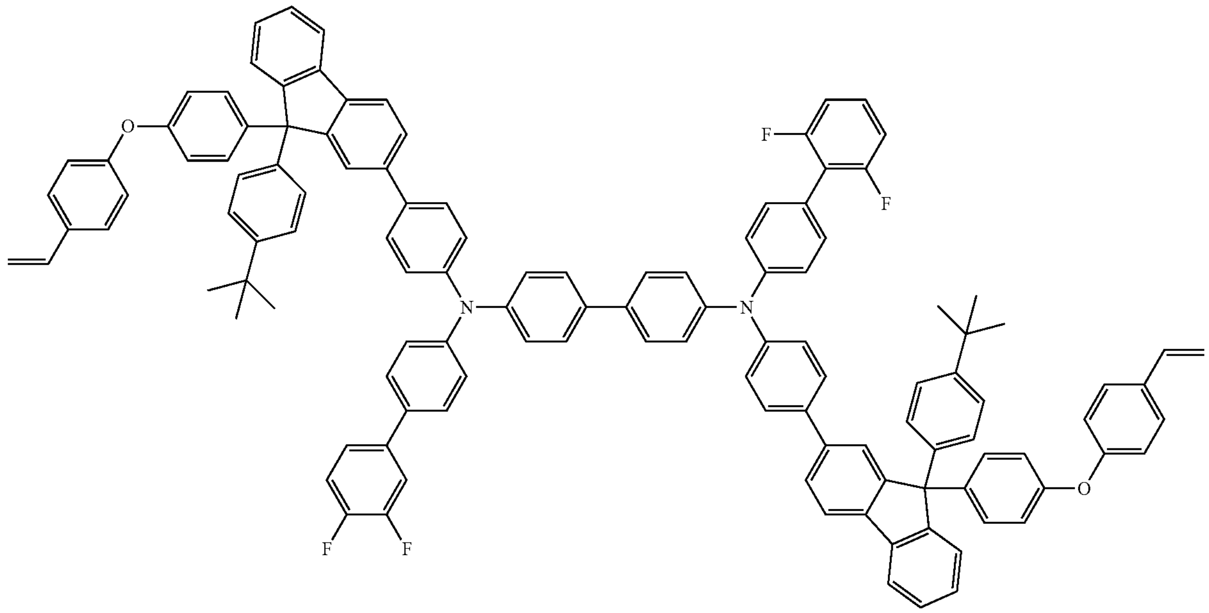
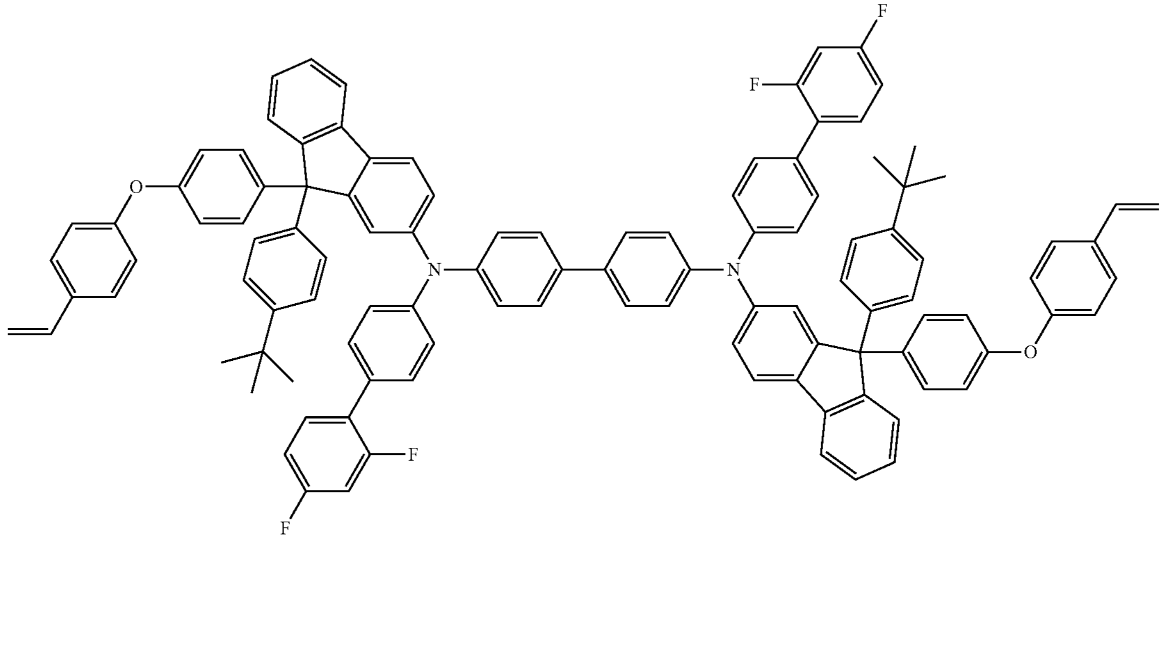

-continued
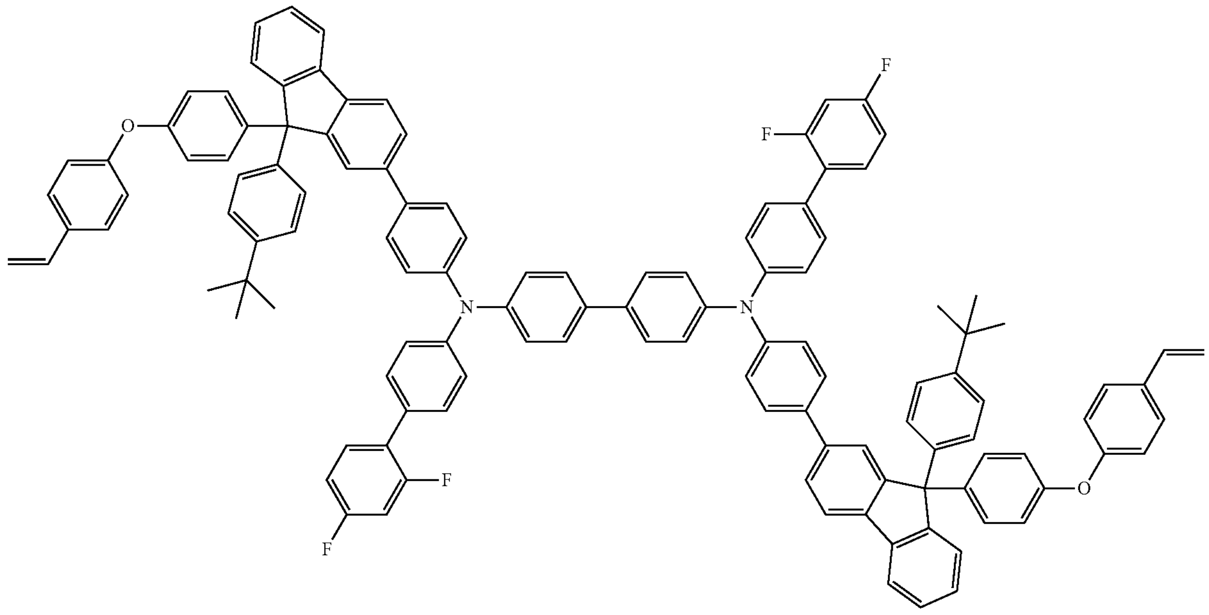
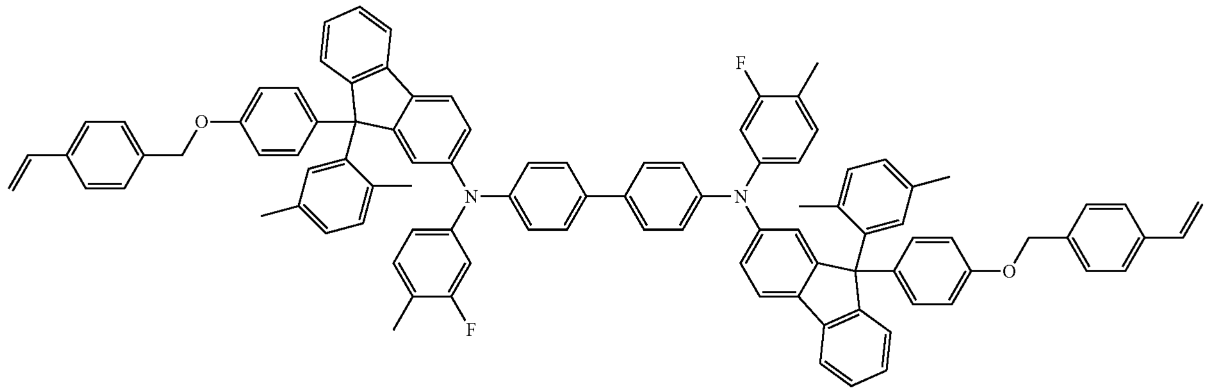
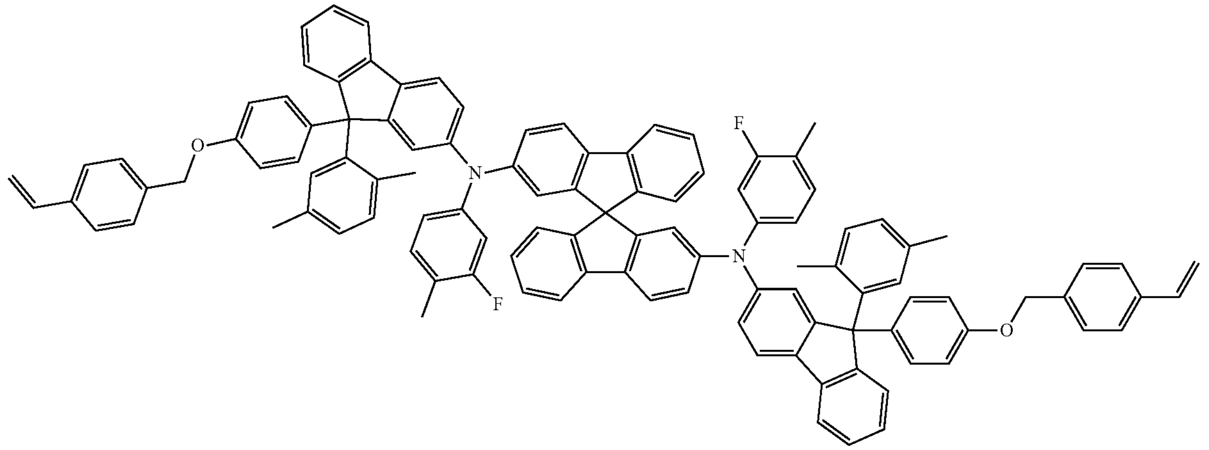

-continued
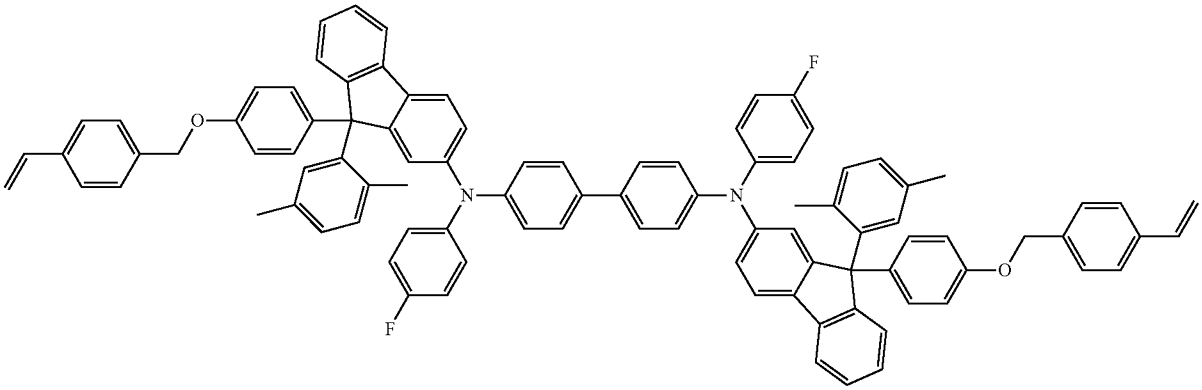
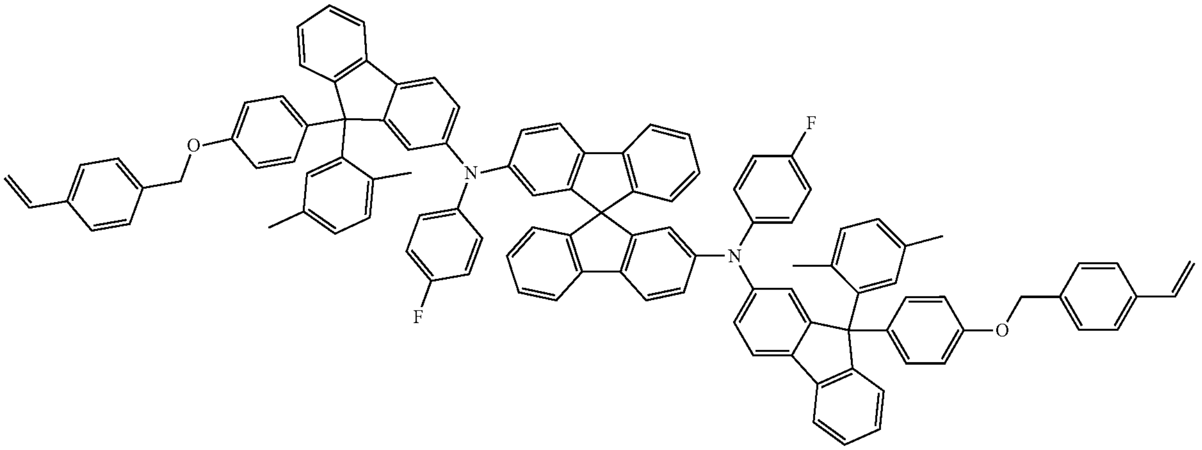
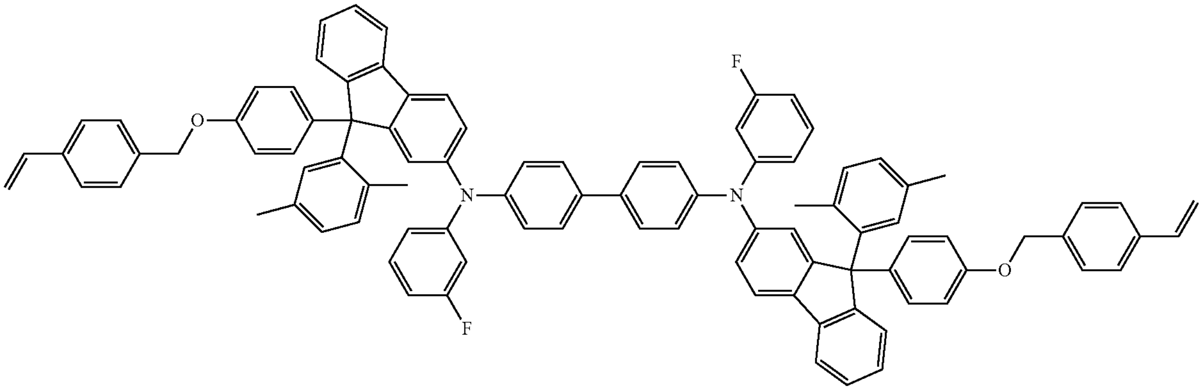
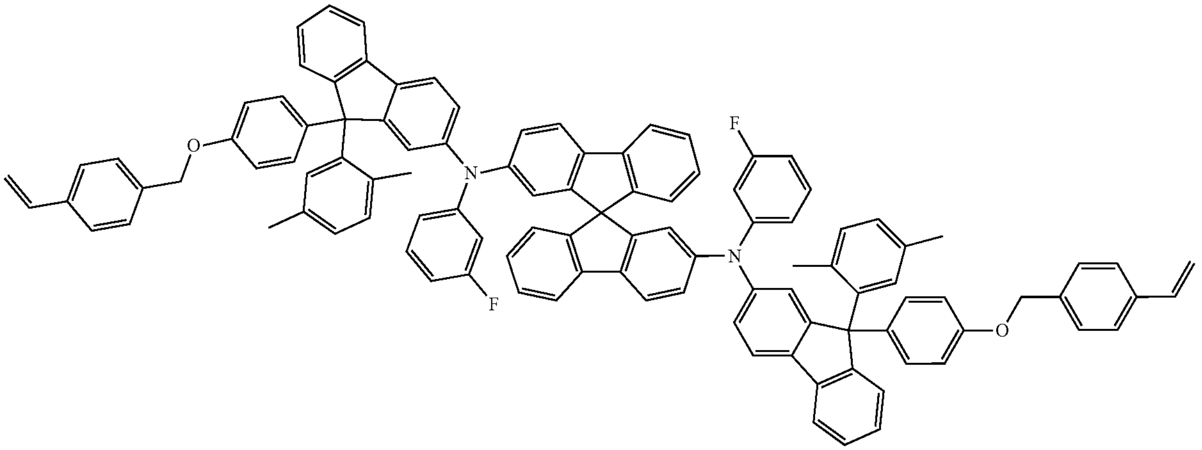

-continued
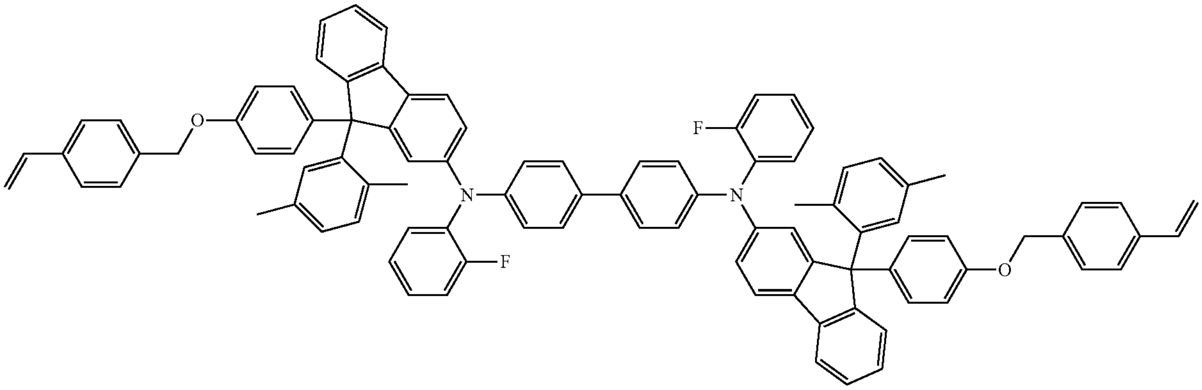
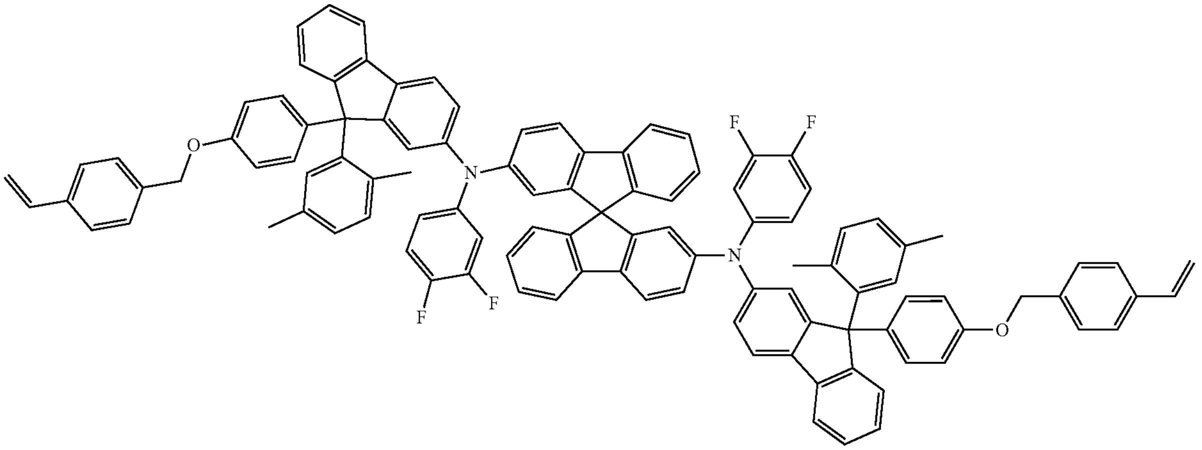
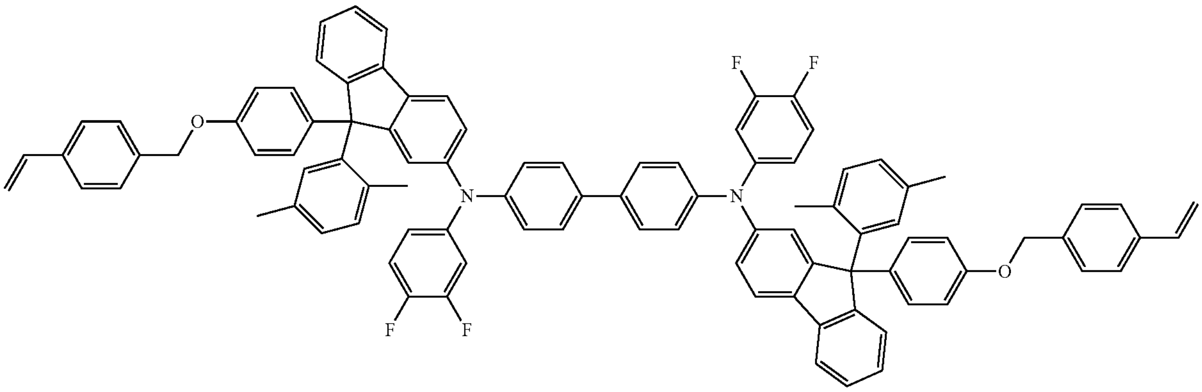
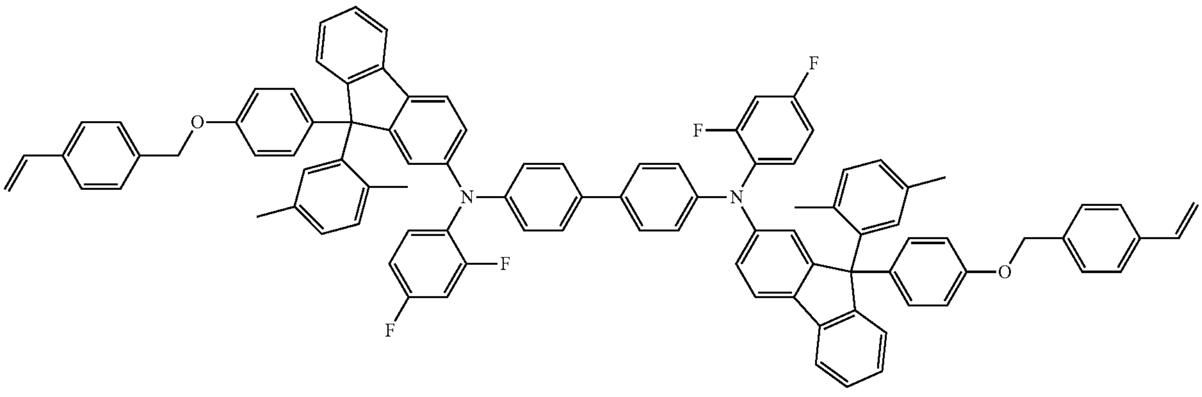

-continued
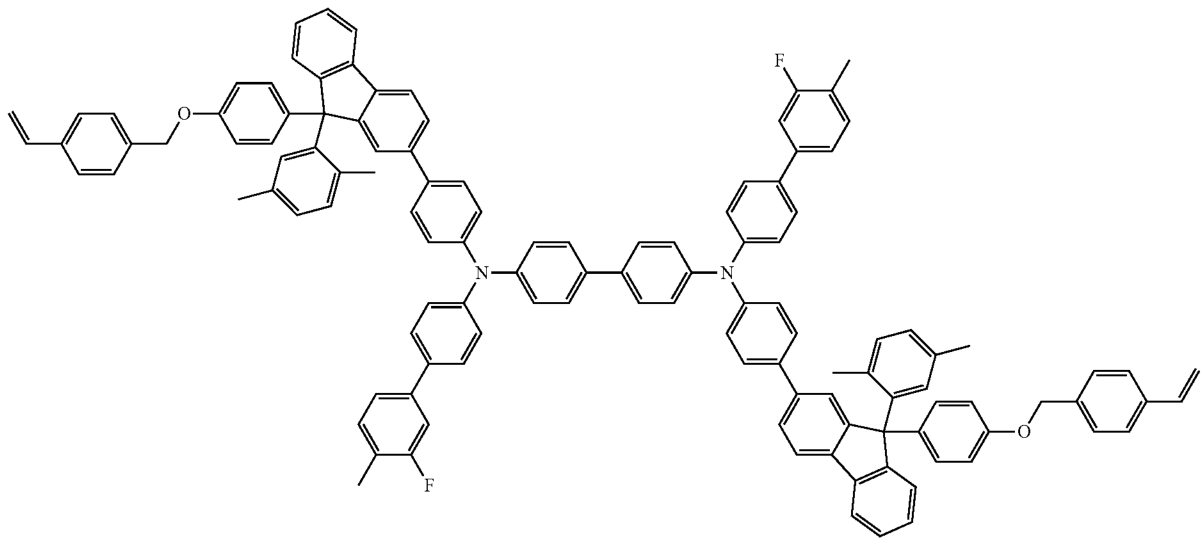
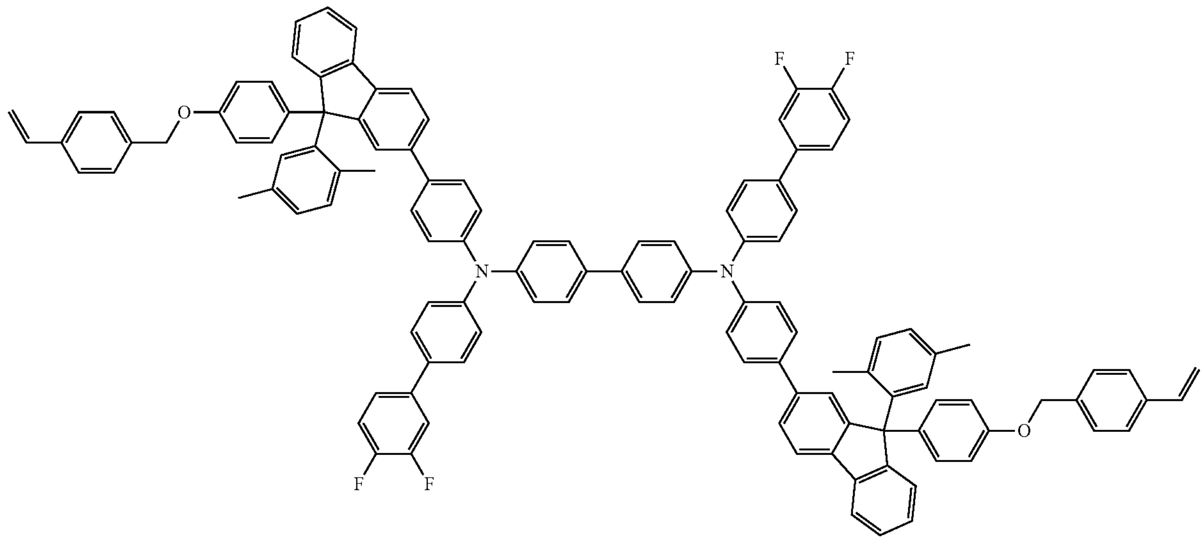
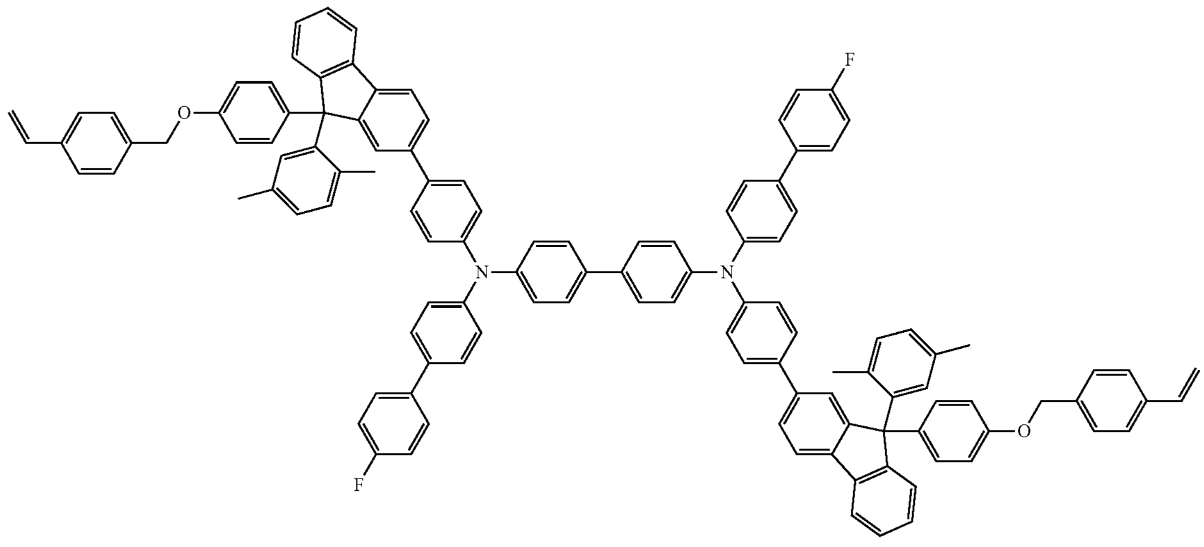

-continued
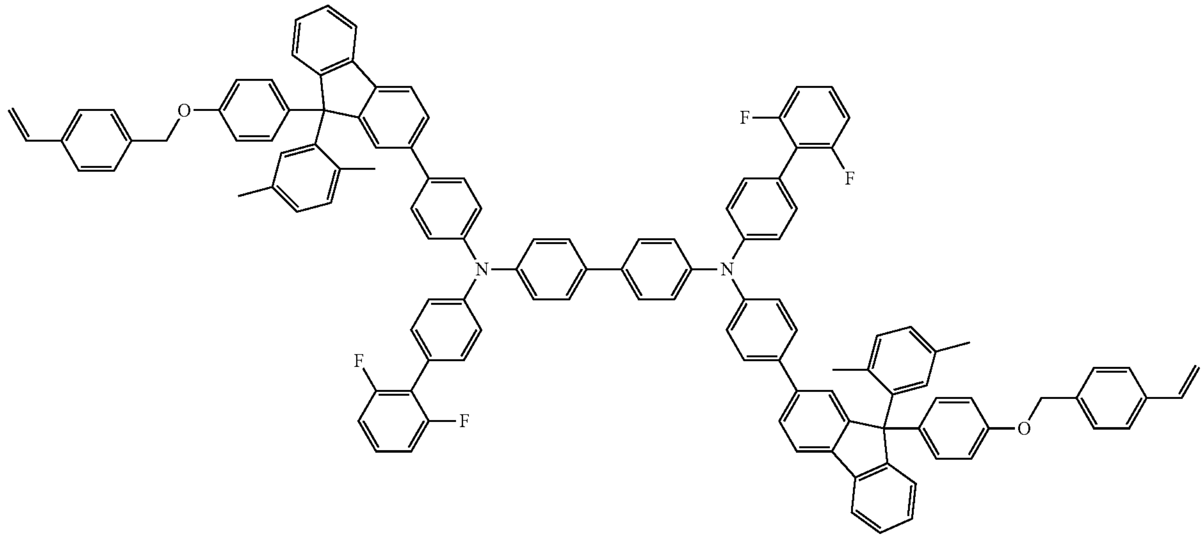
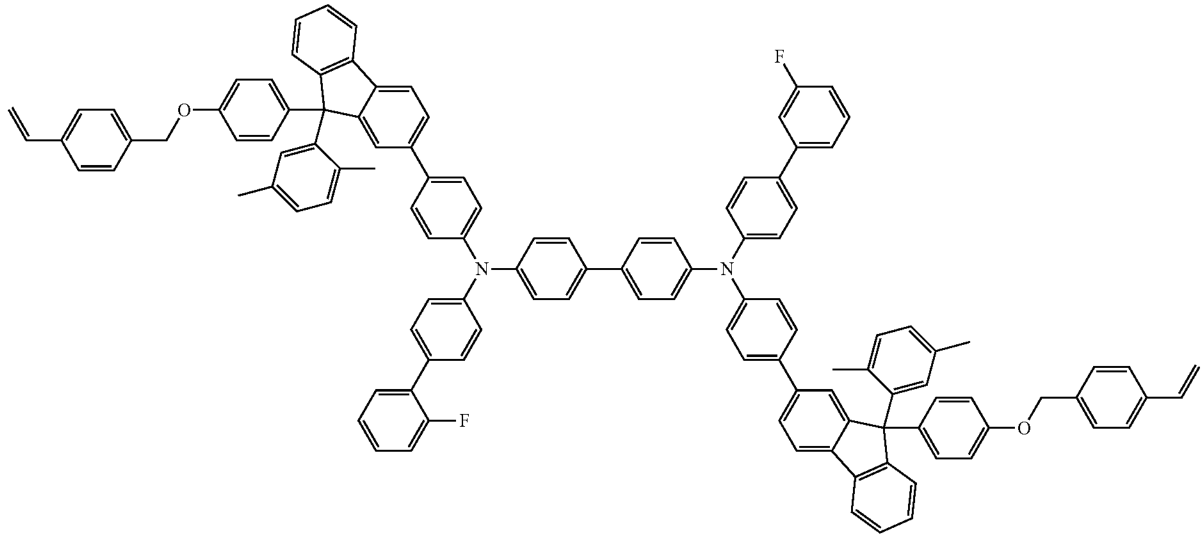
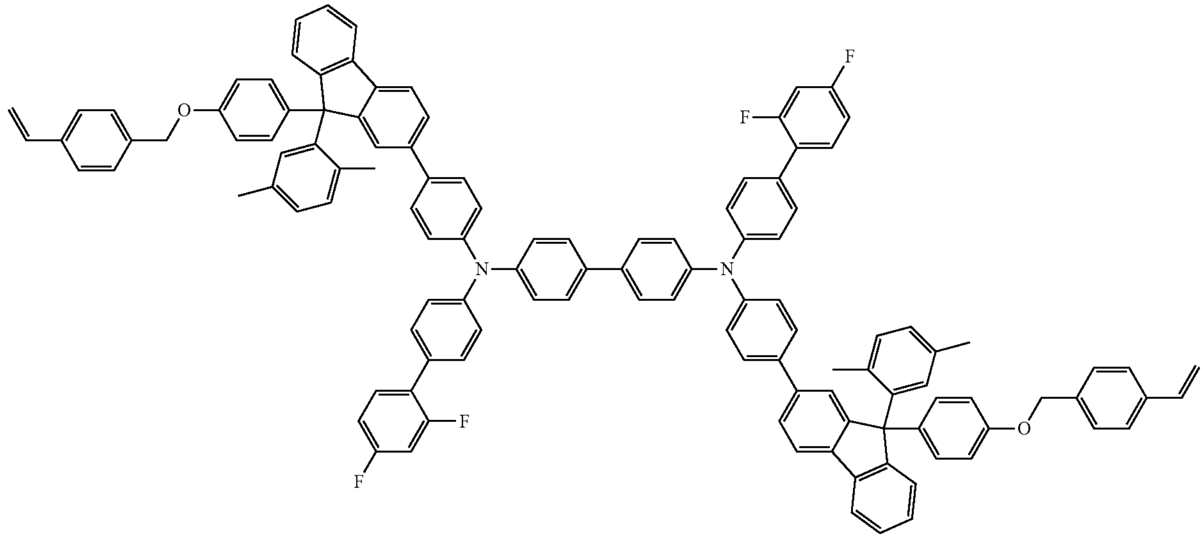

-continued
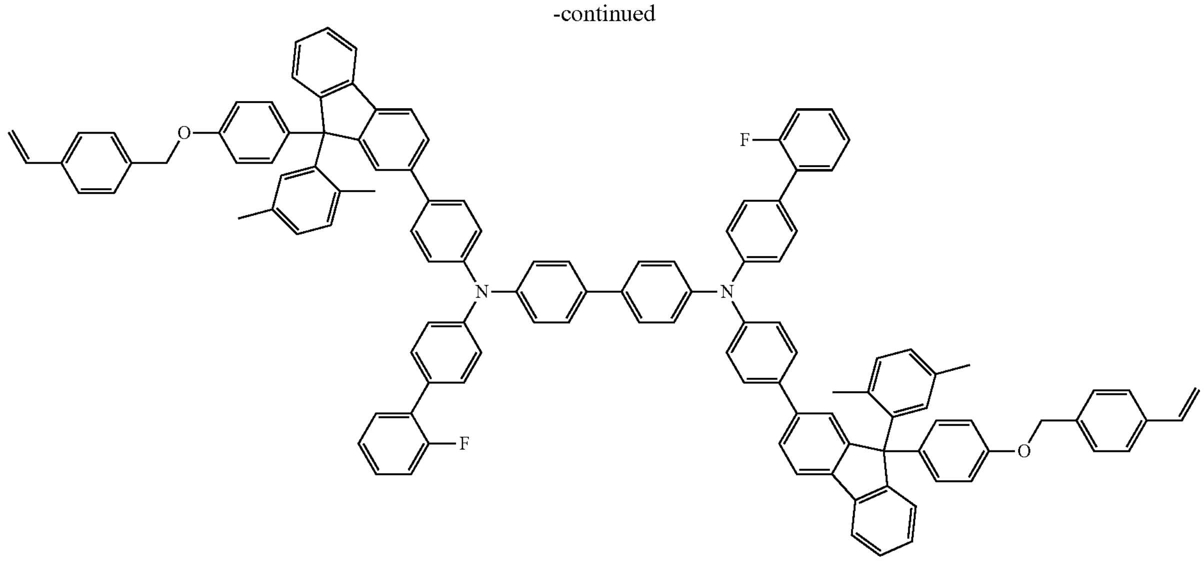
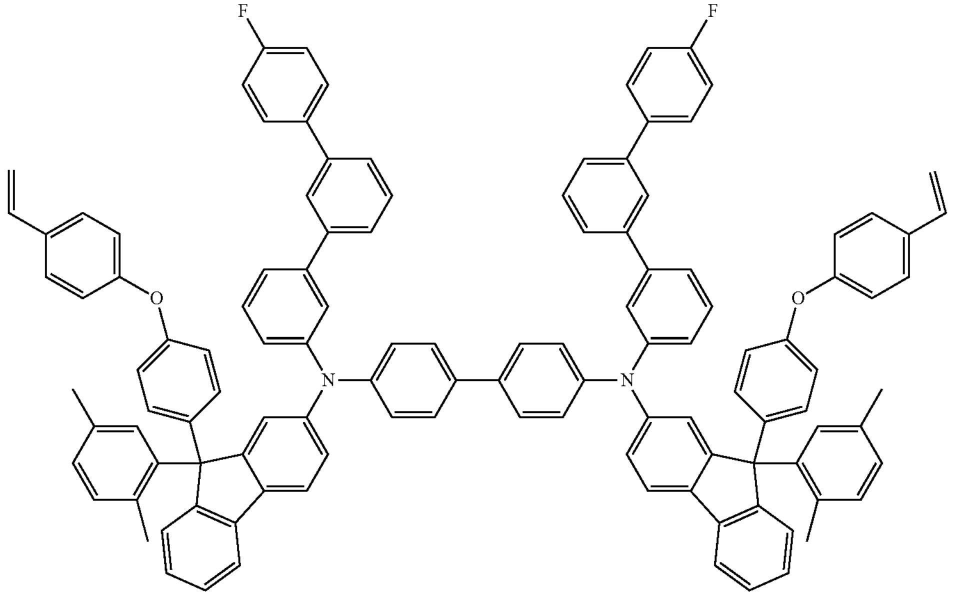
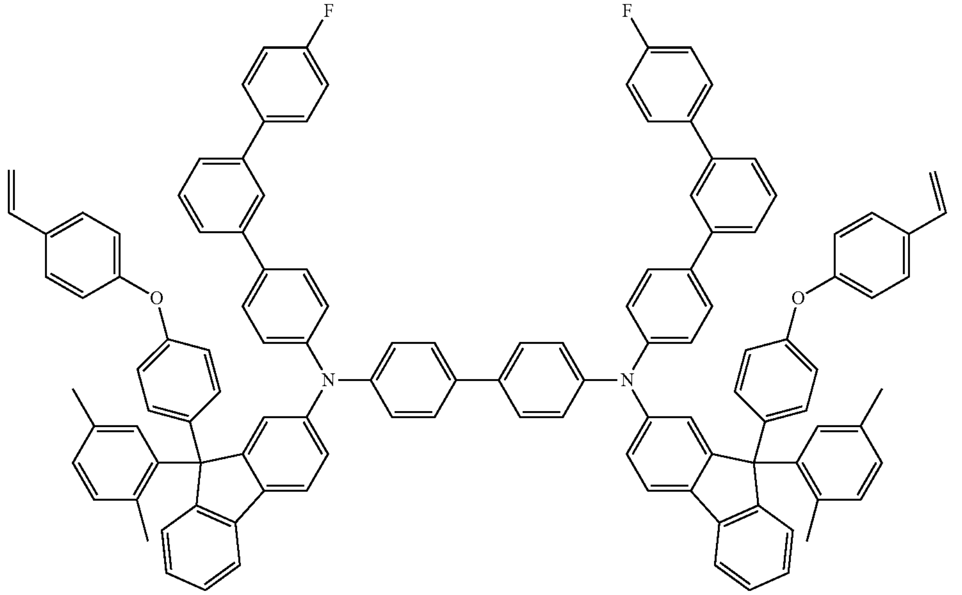

-continued
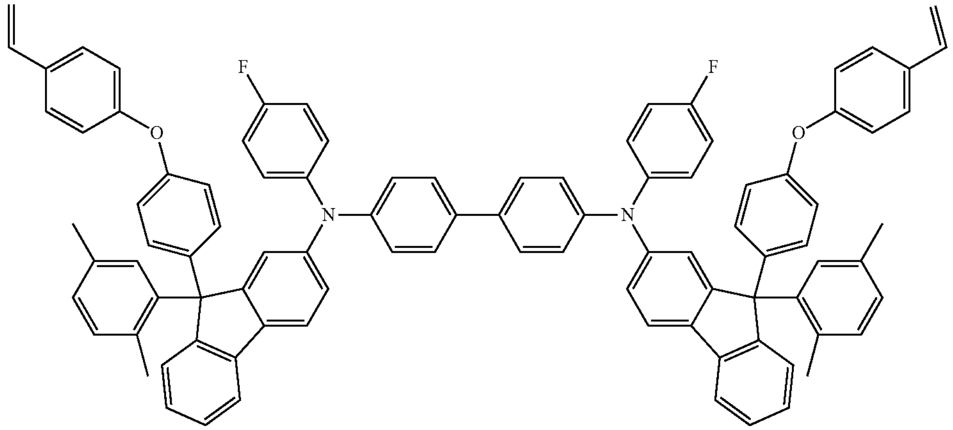
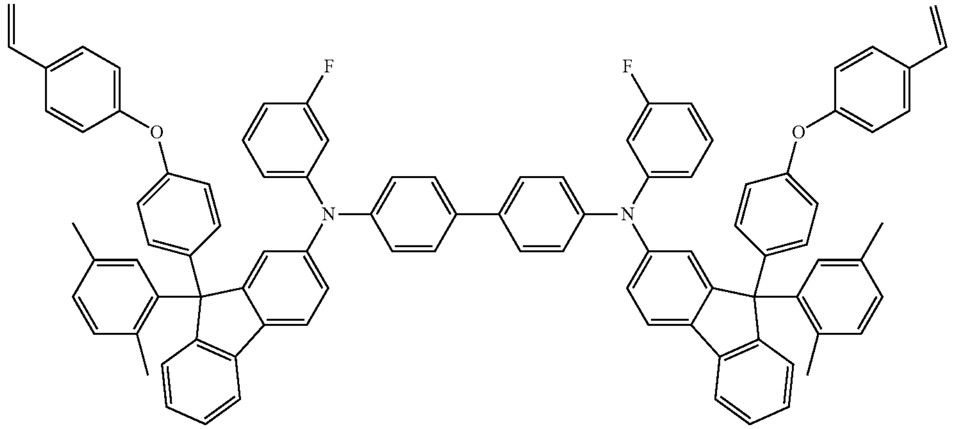
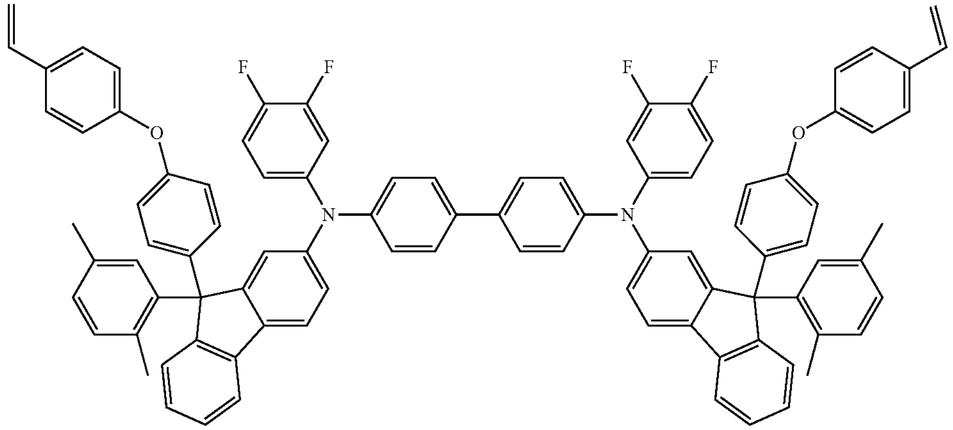
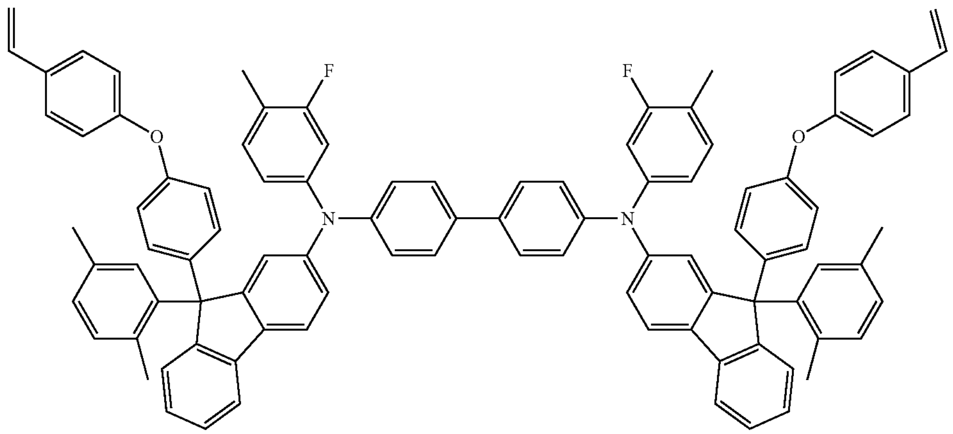

-continued
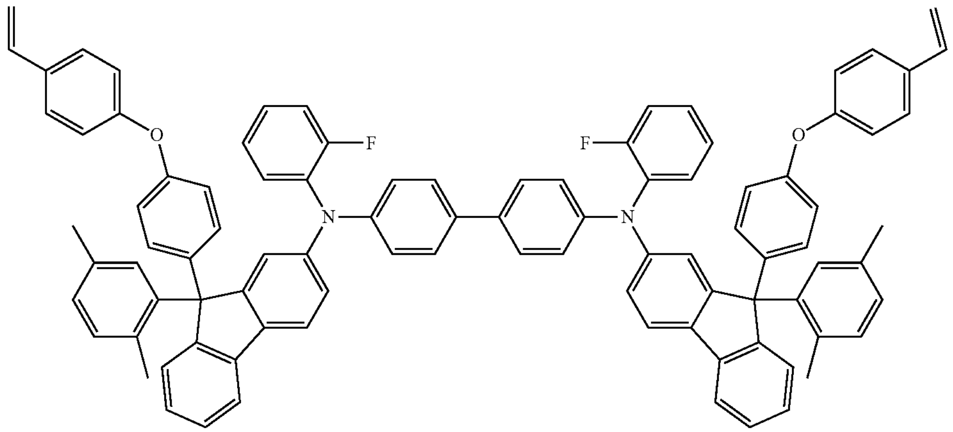
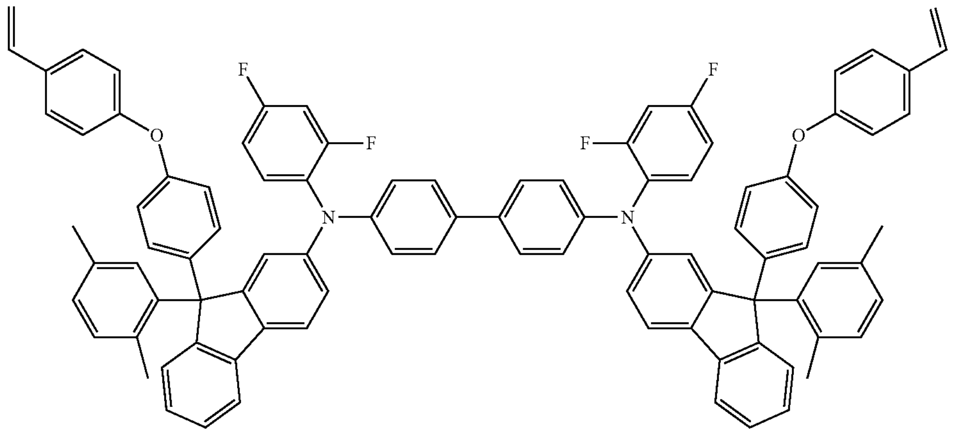
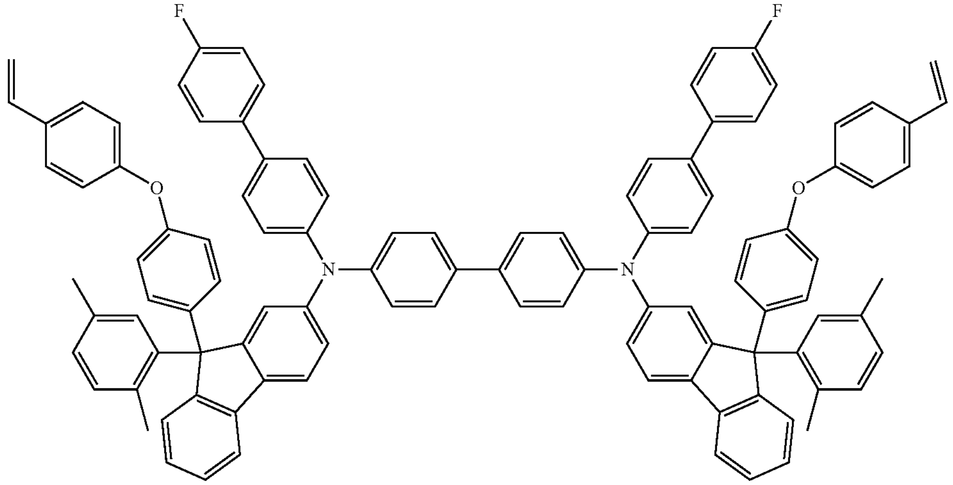

-continued
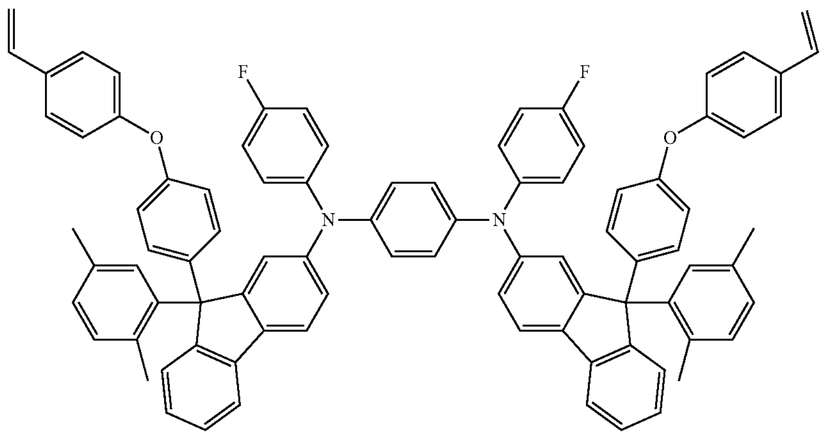
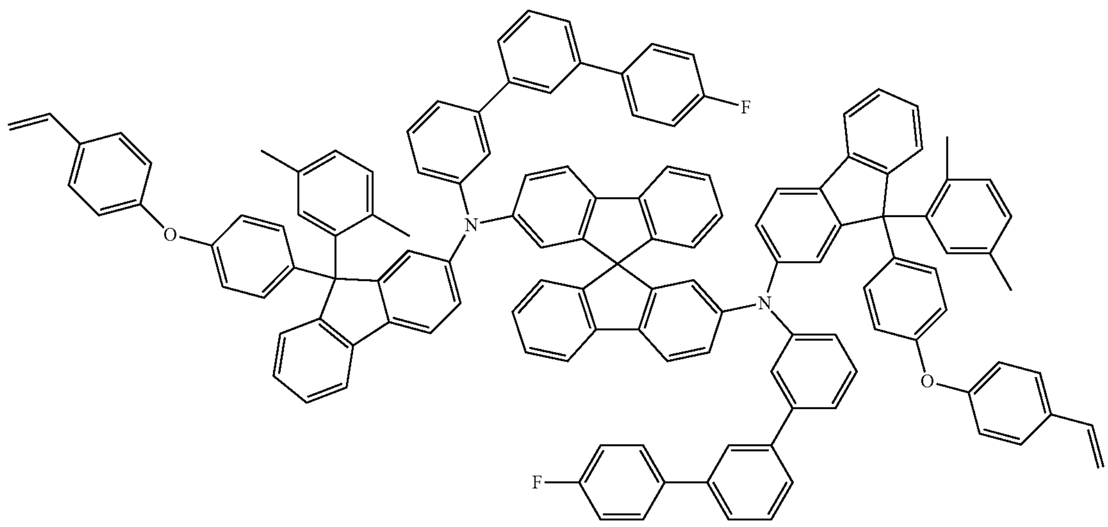

-continued
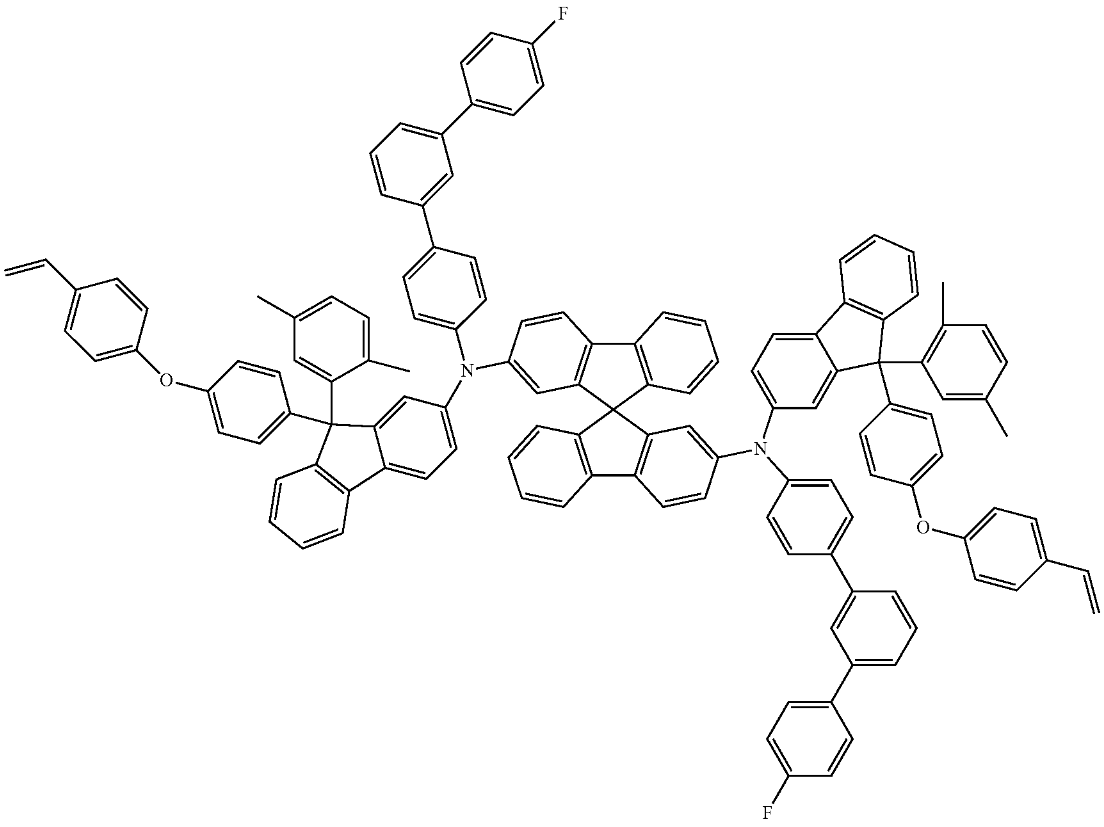
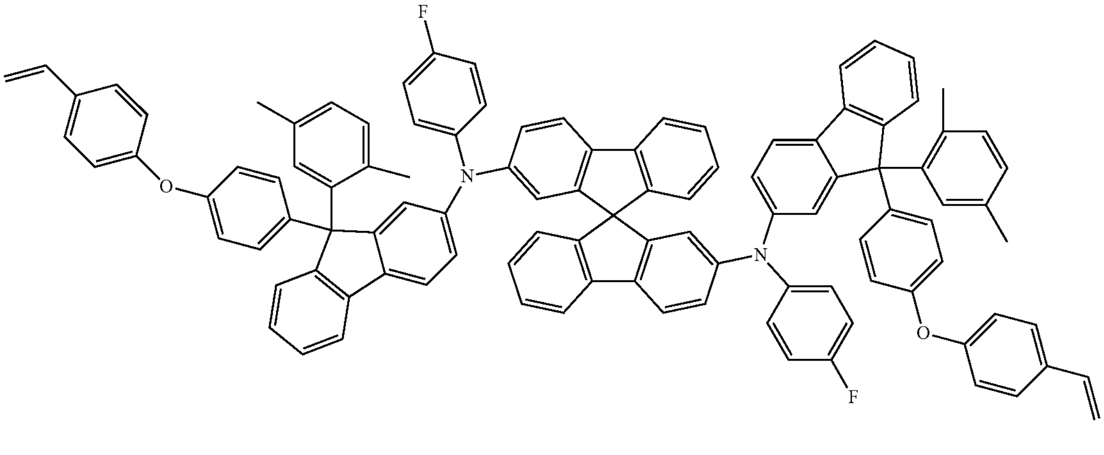
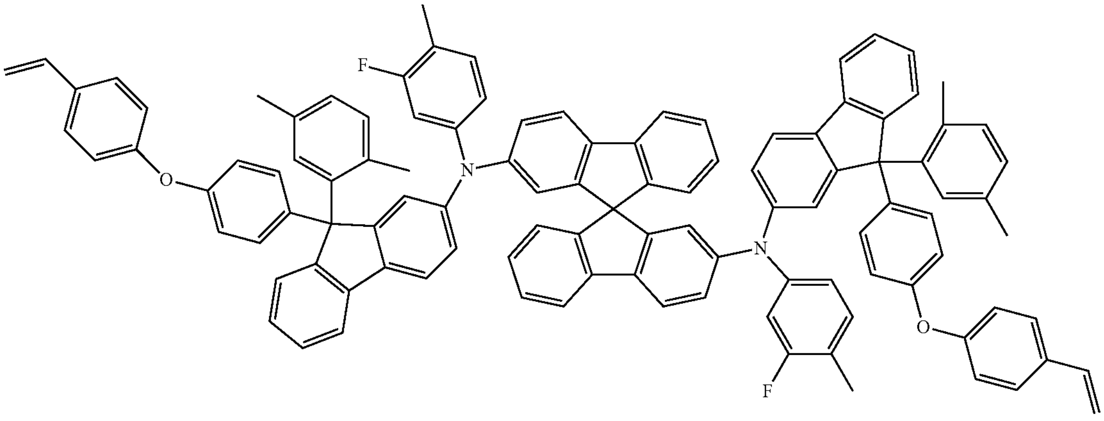

-continued
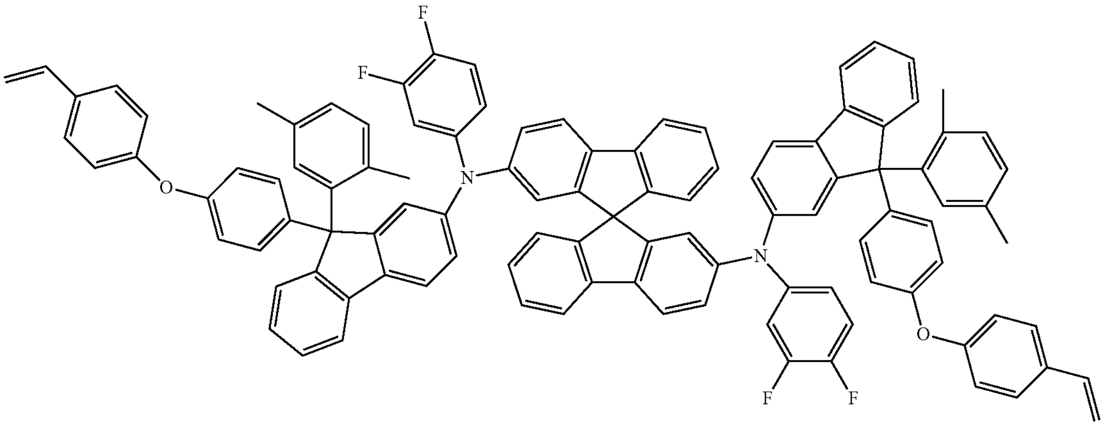
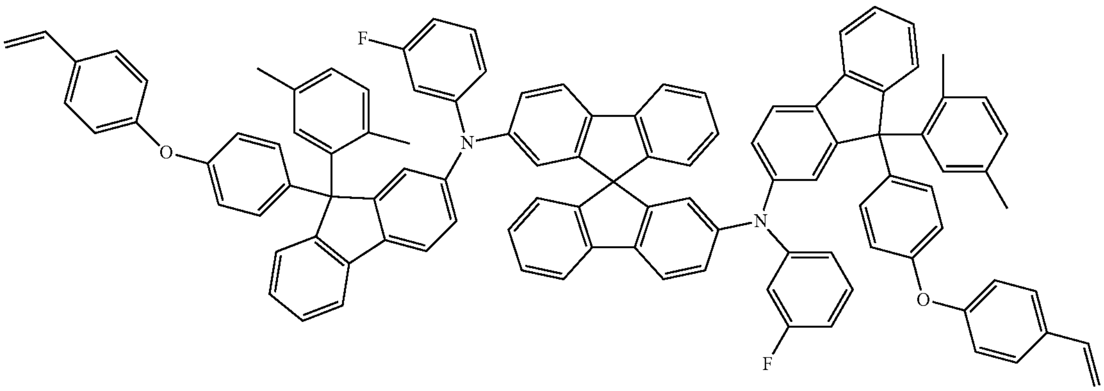
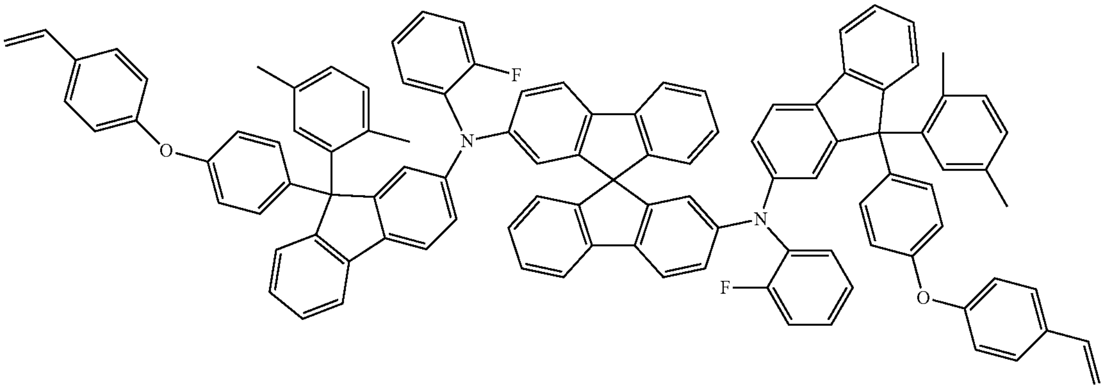
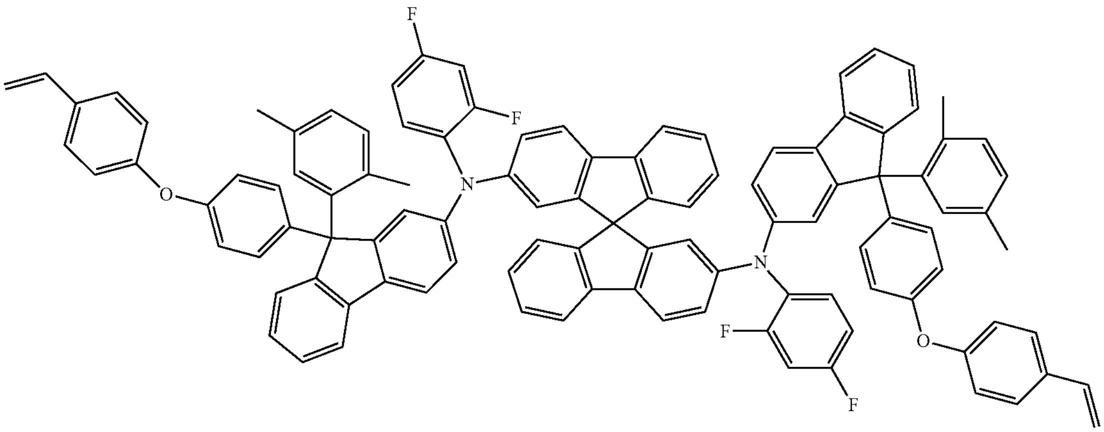

-continued
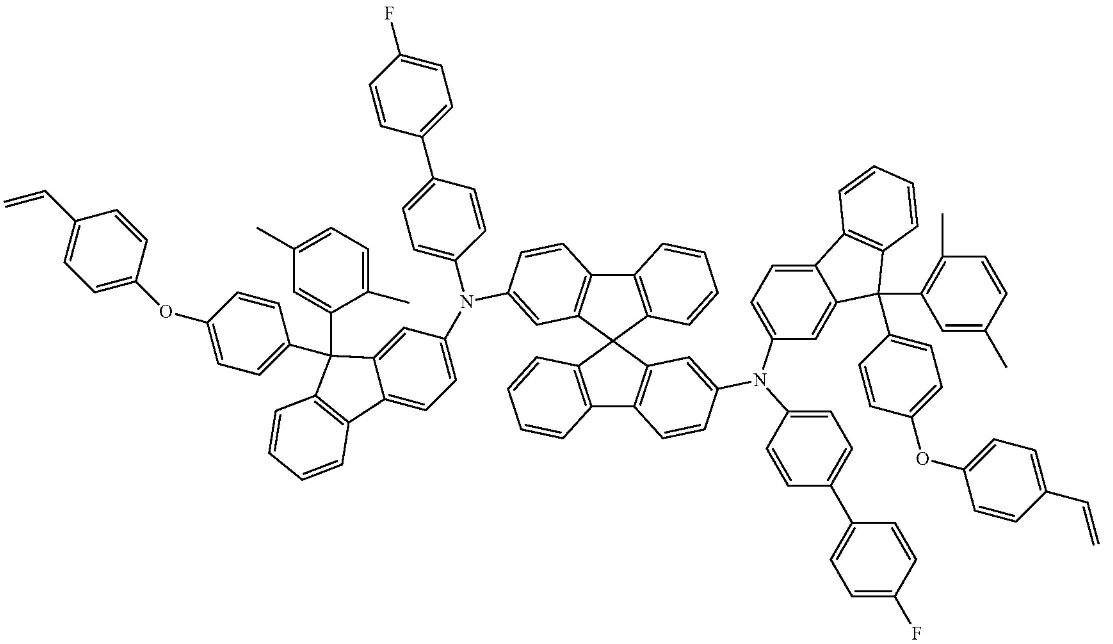
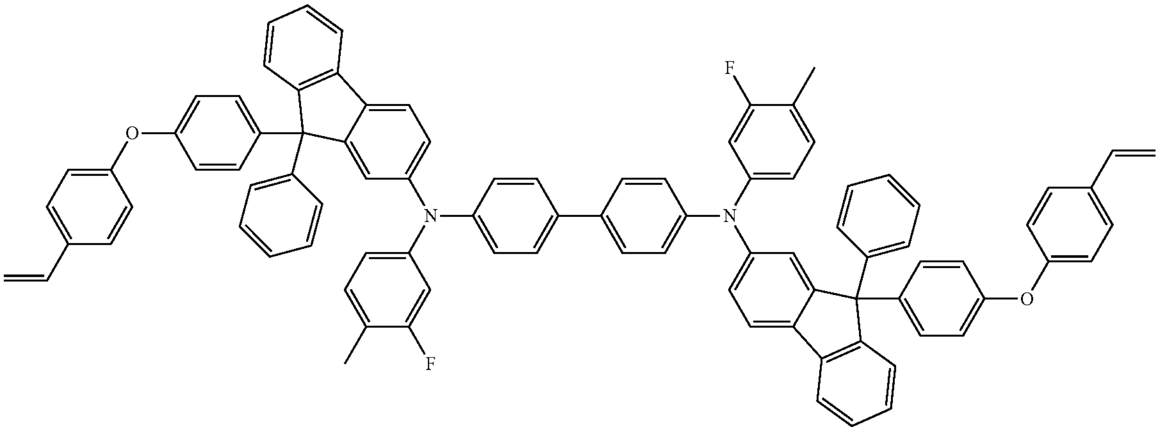
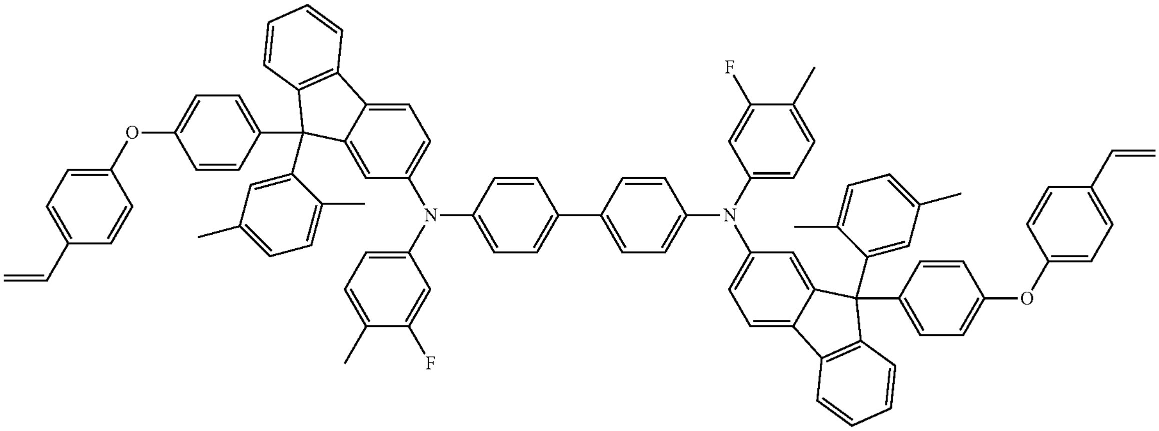

-continued
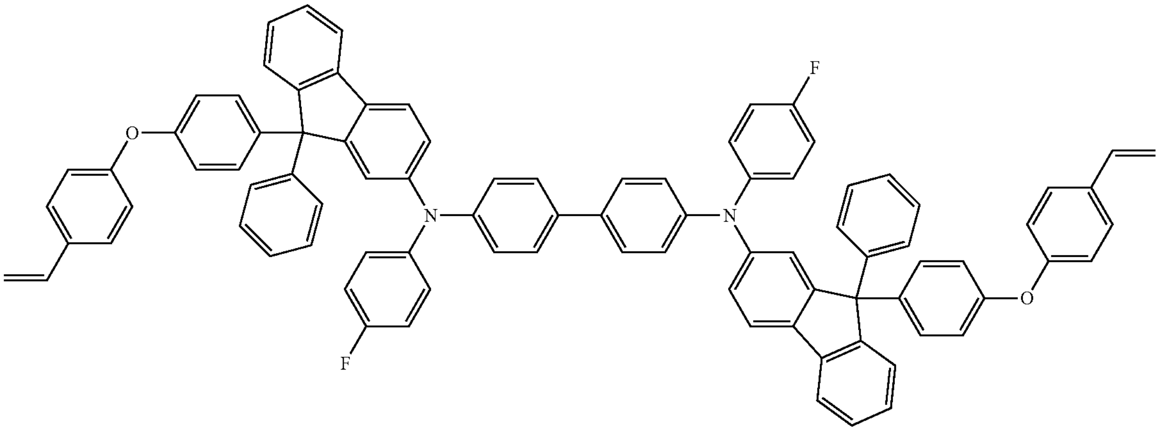
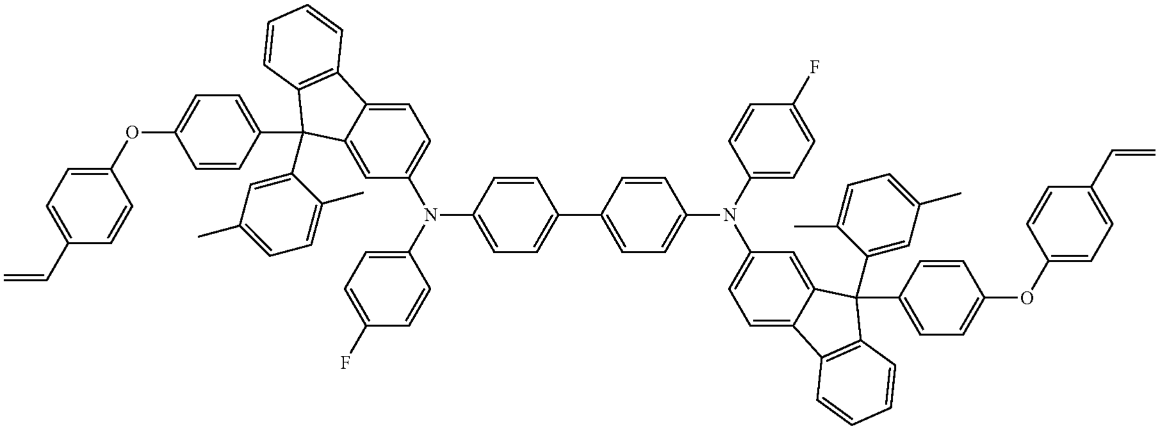
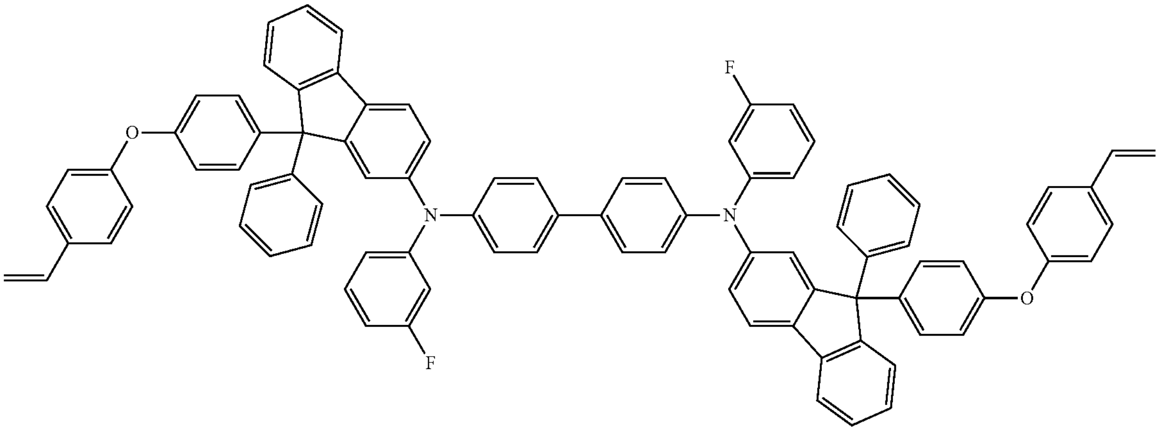
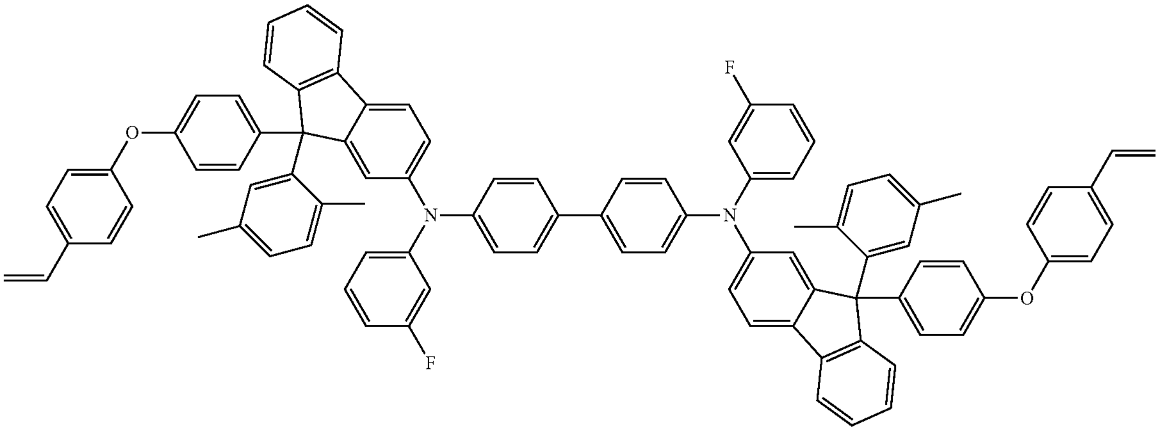

-continued
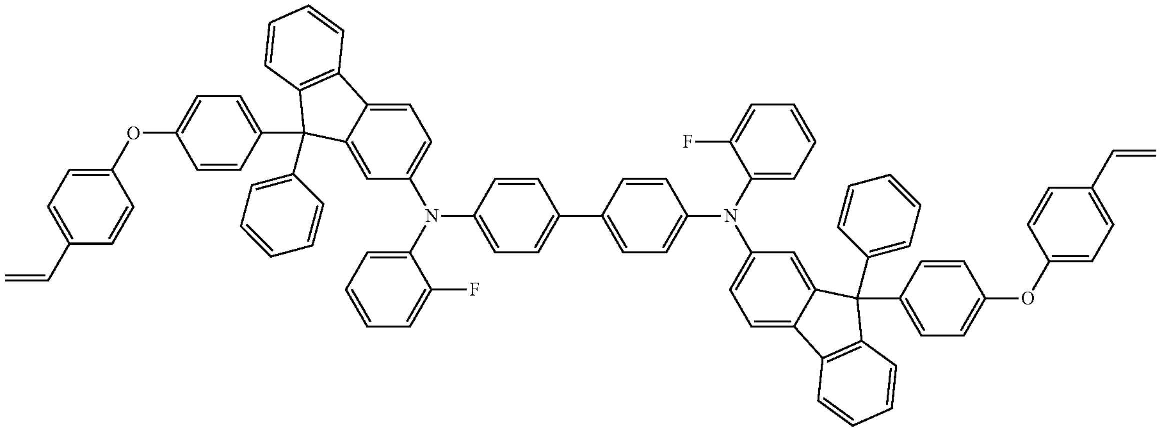
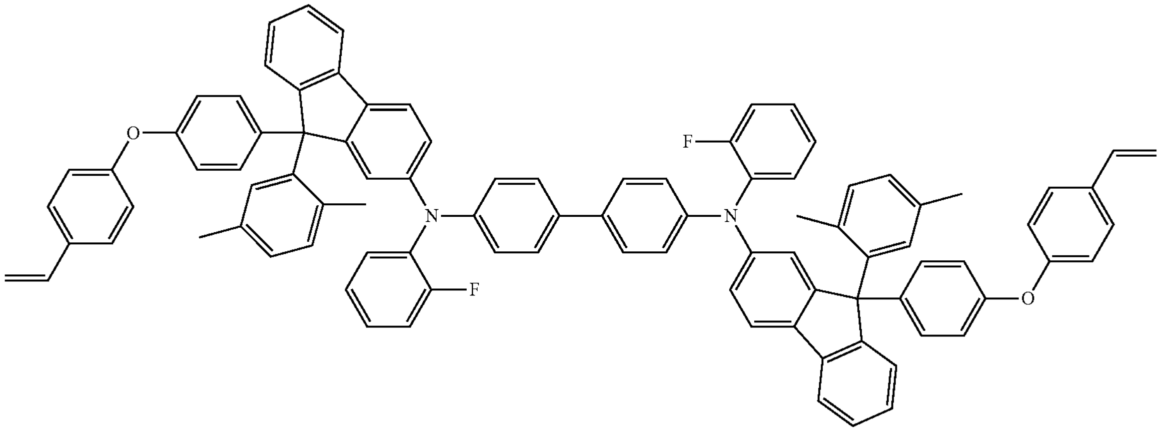
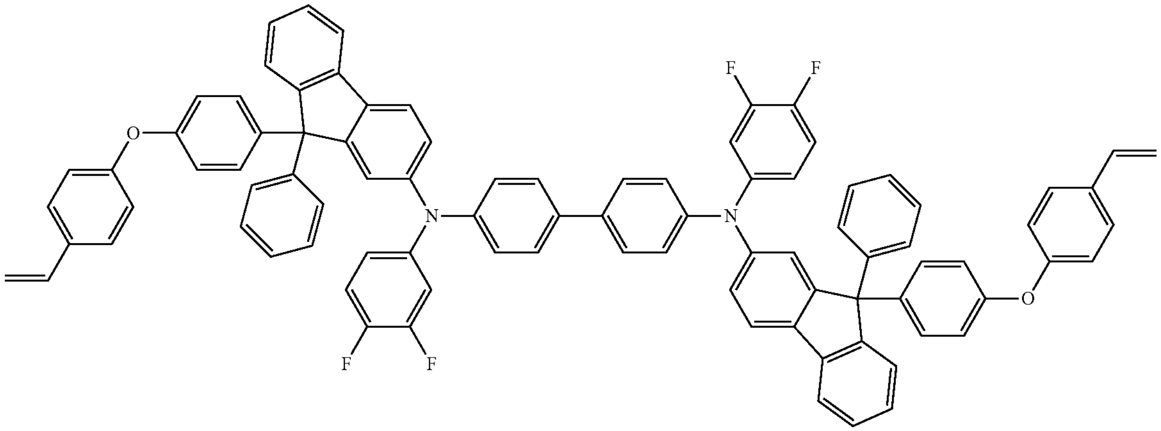
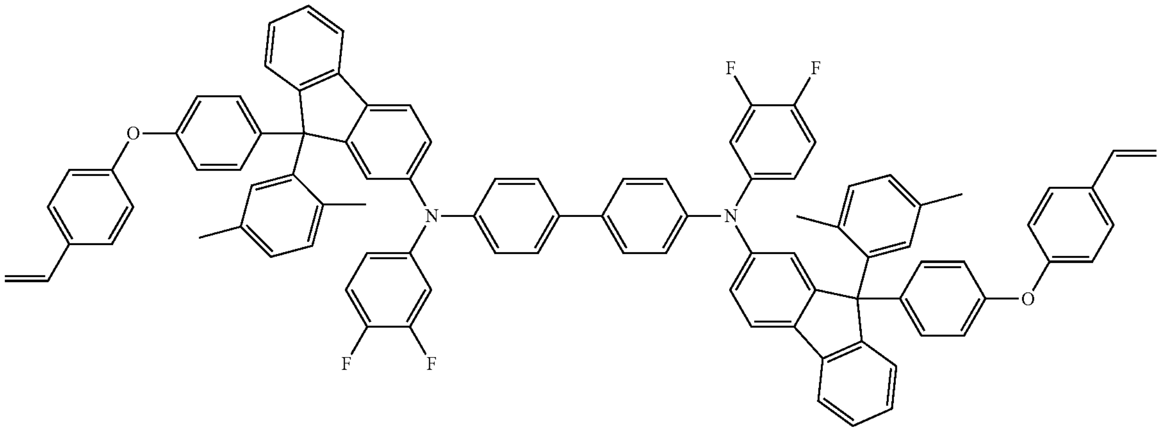

-continued
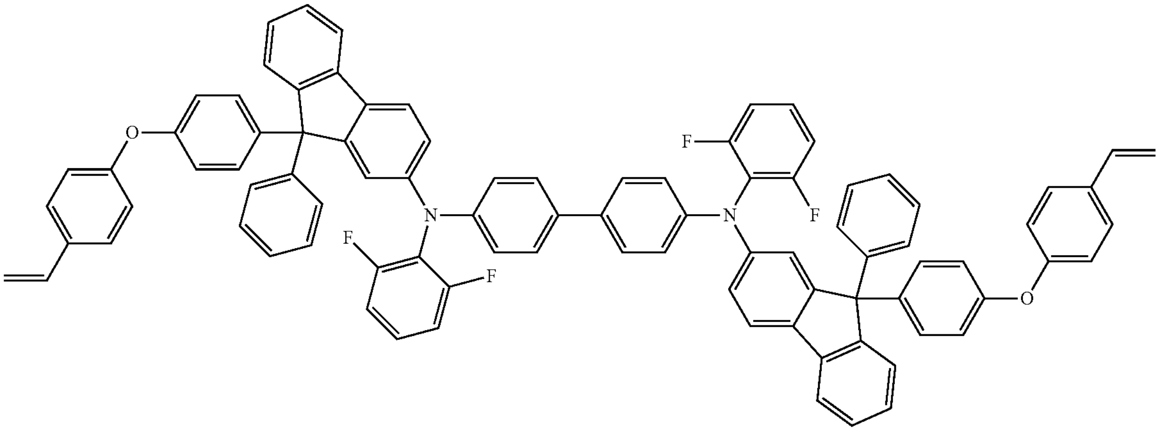
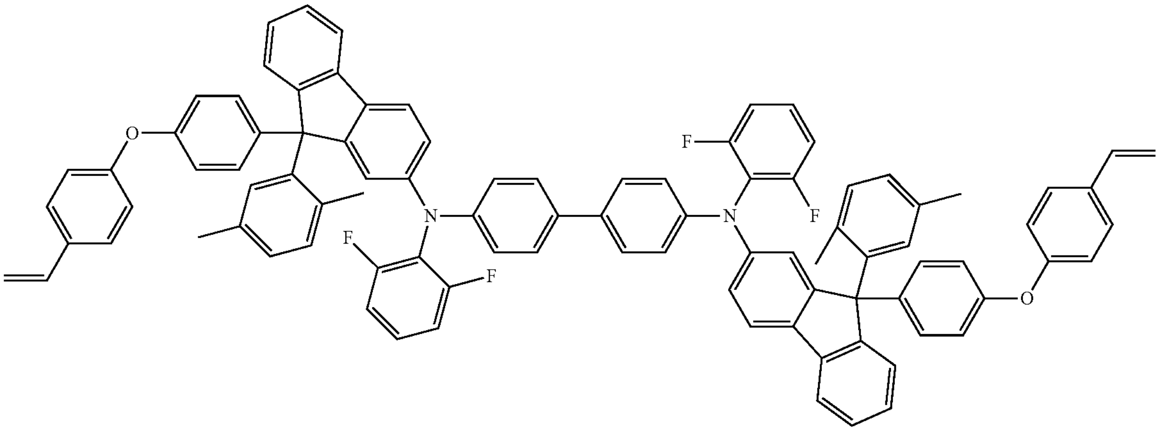
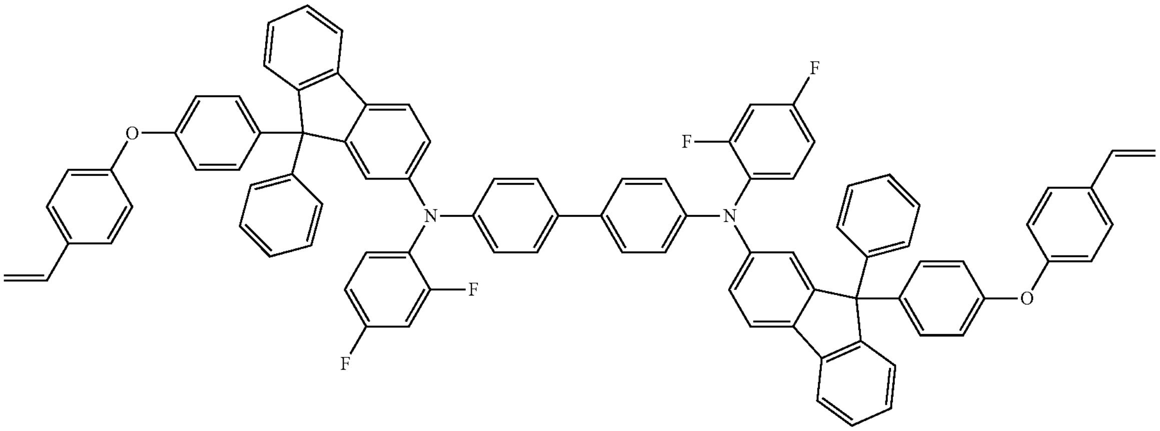
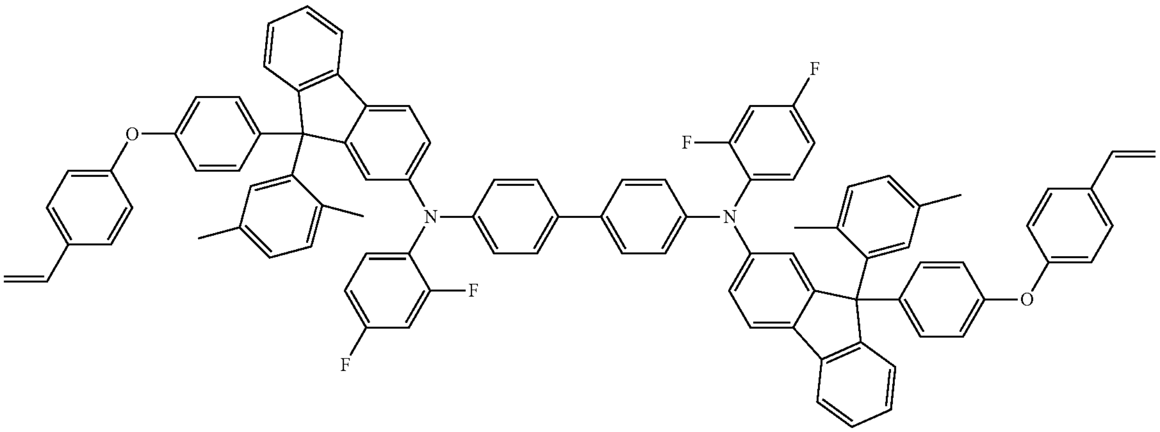

-continued
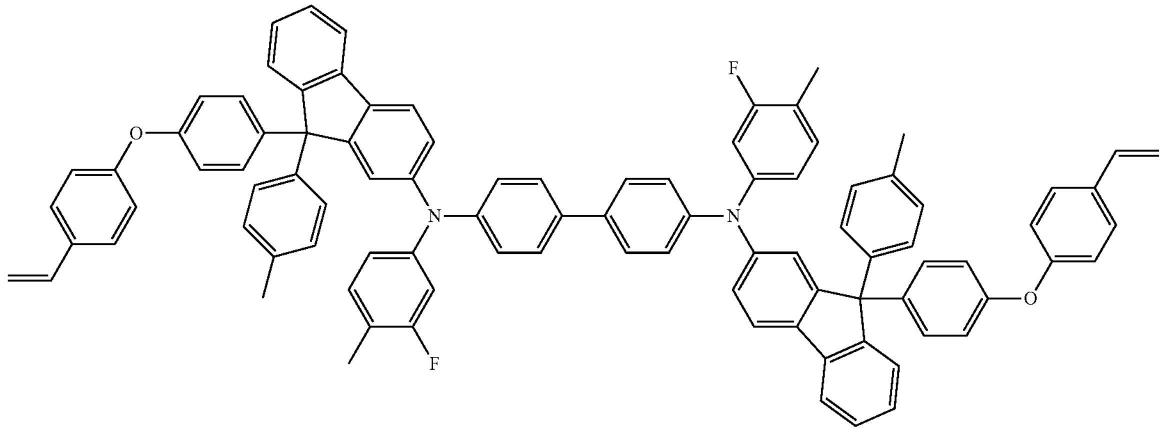
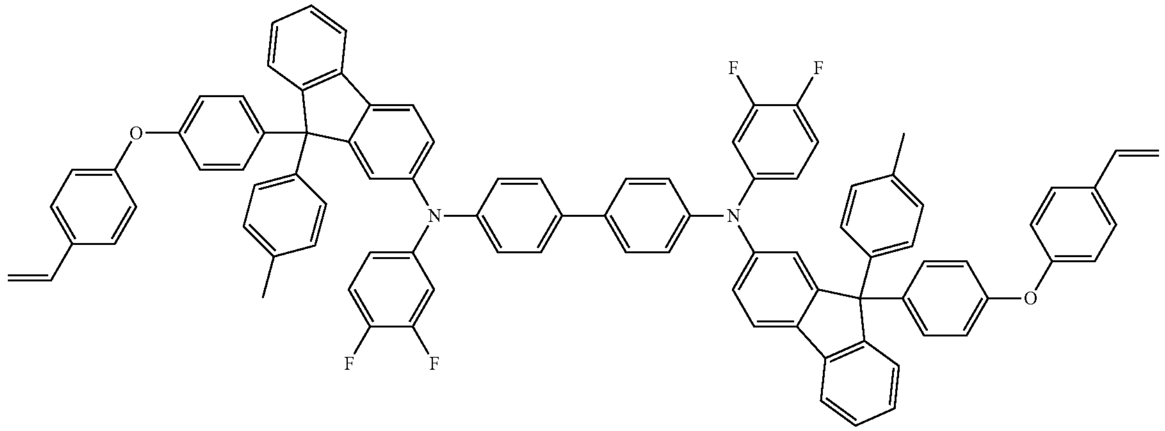
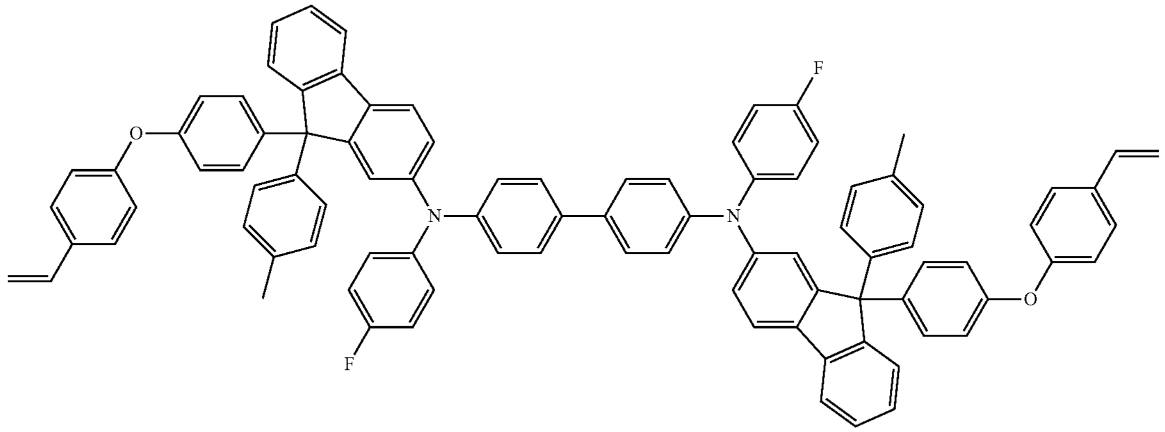
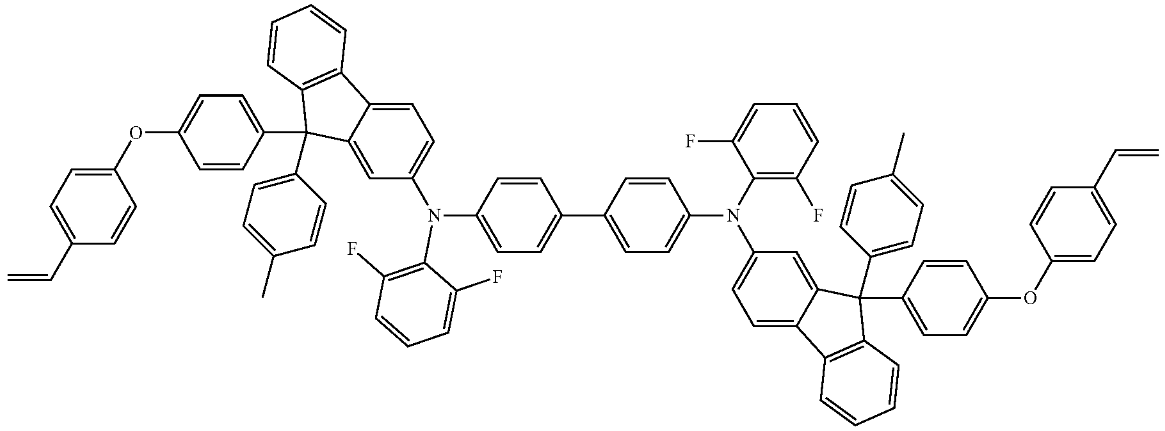

-continued
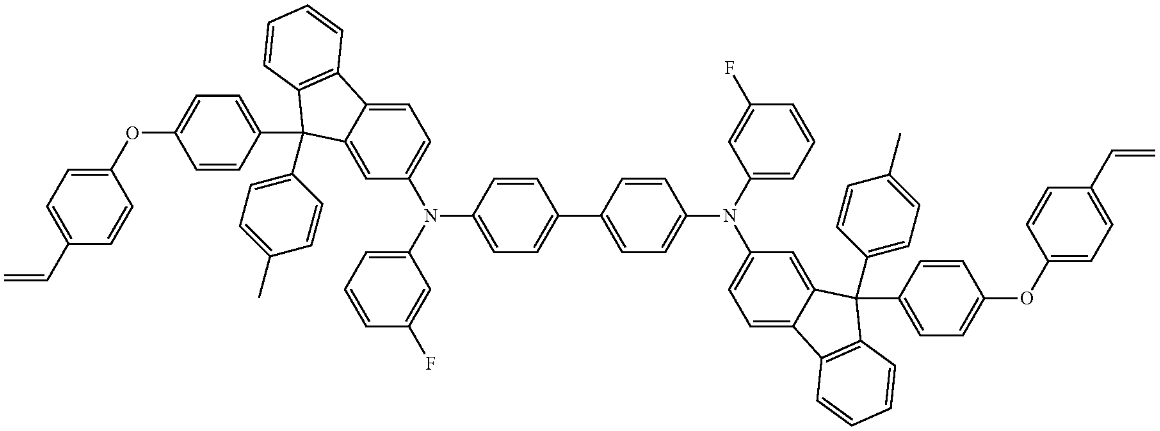
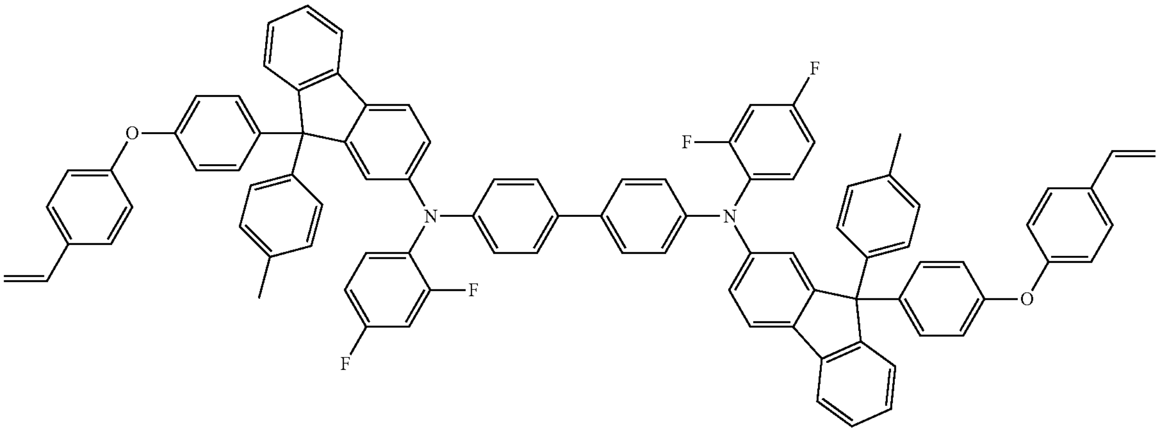
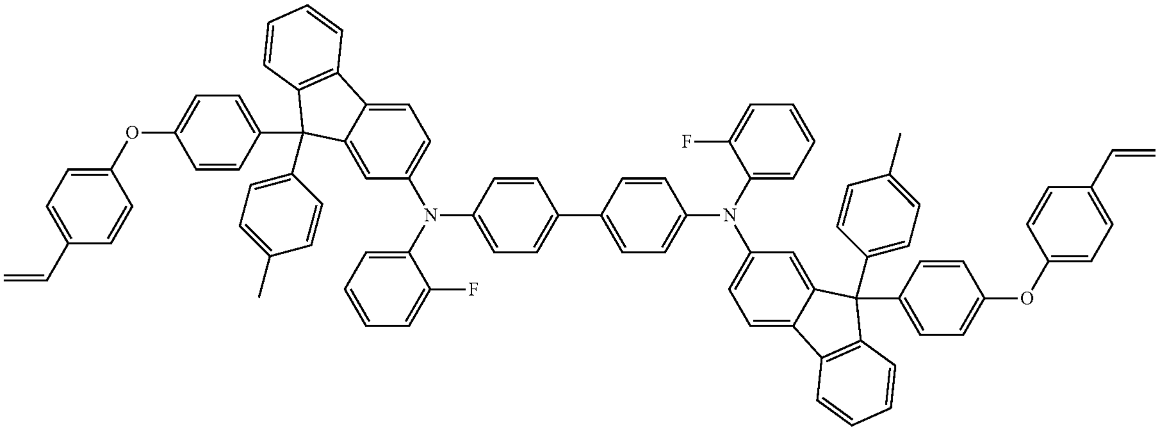

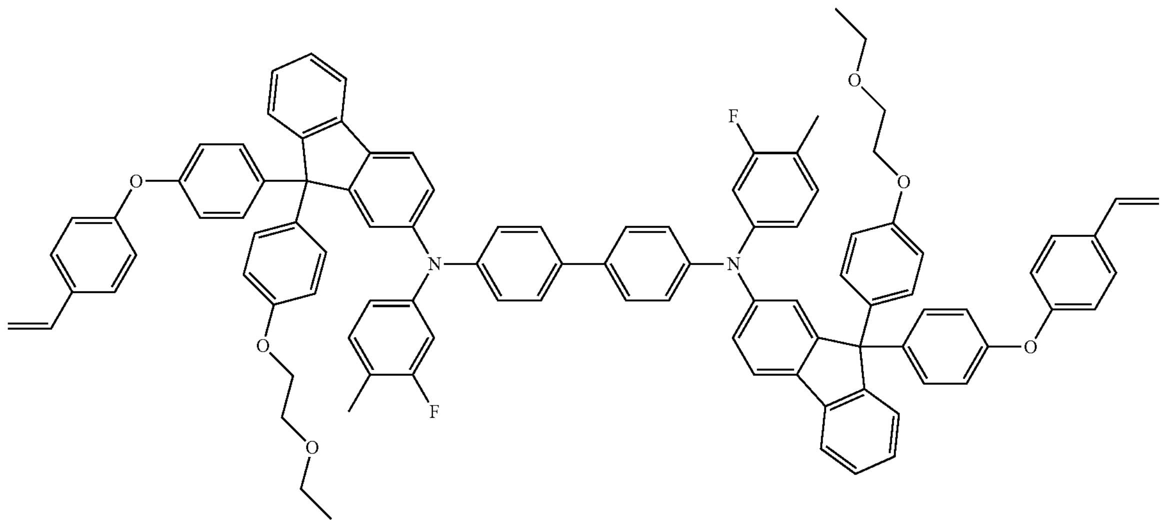
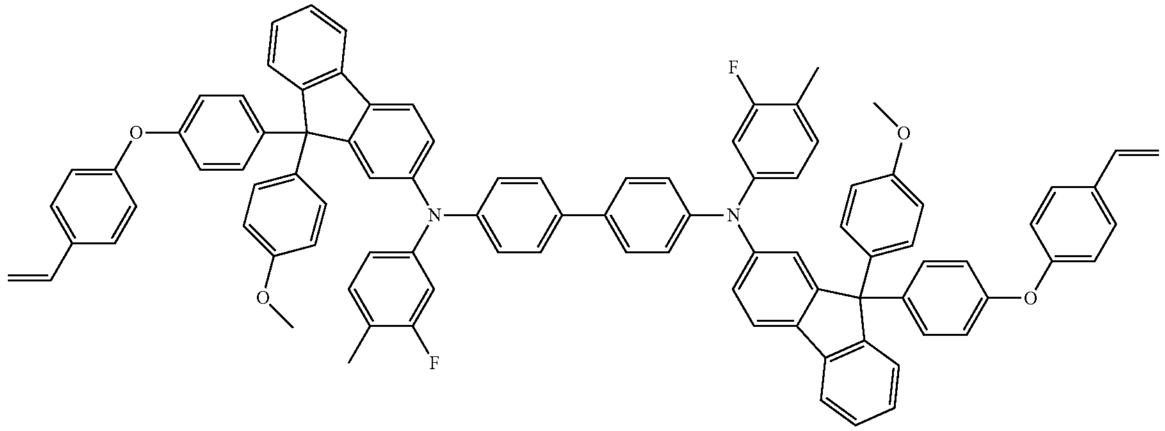
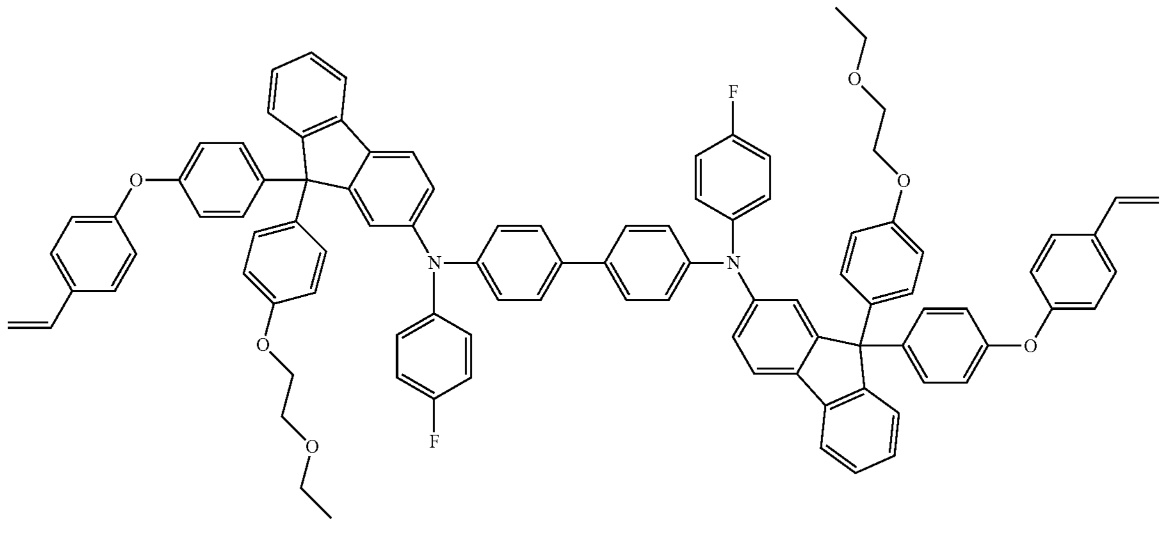

-continued
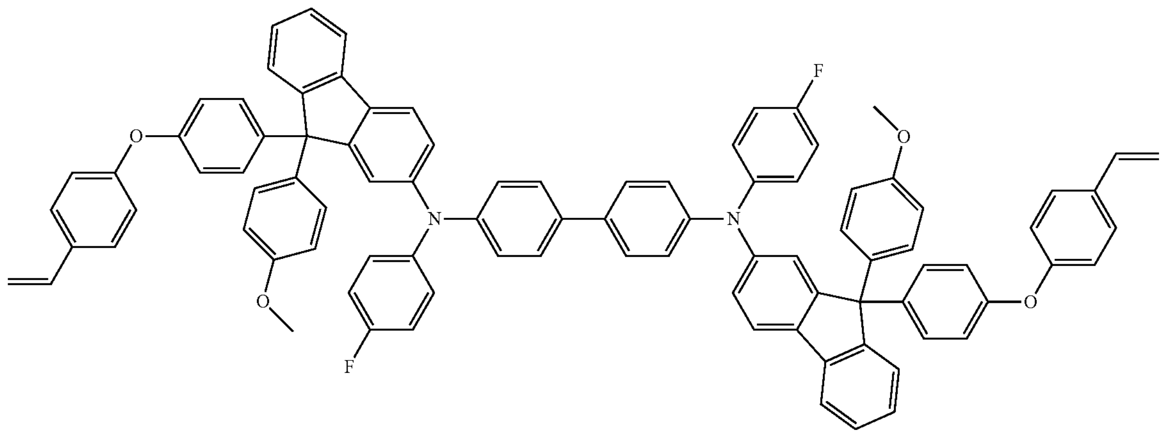
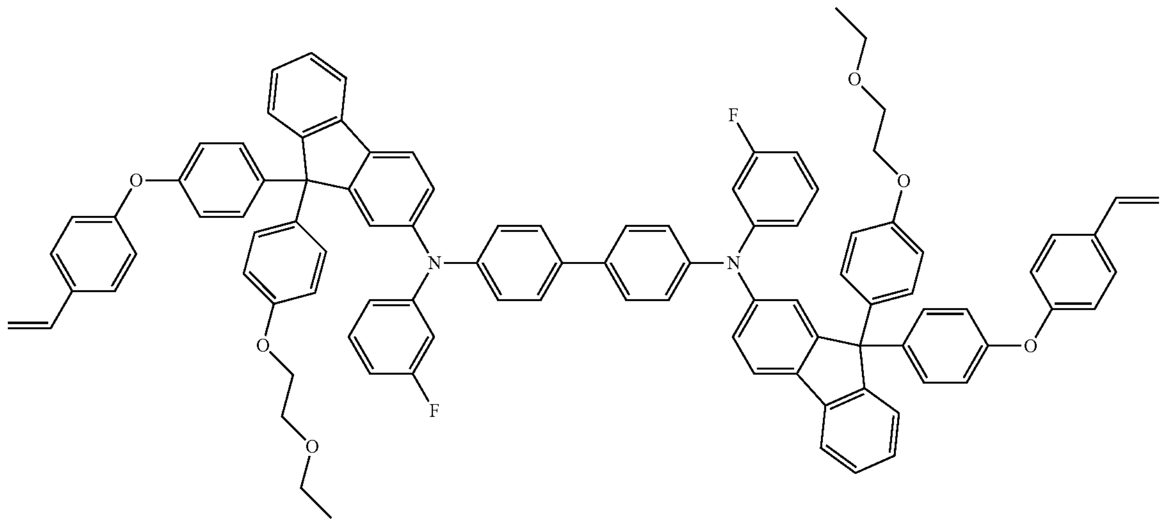
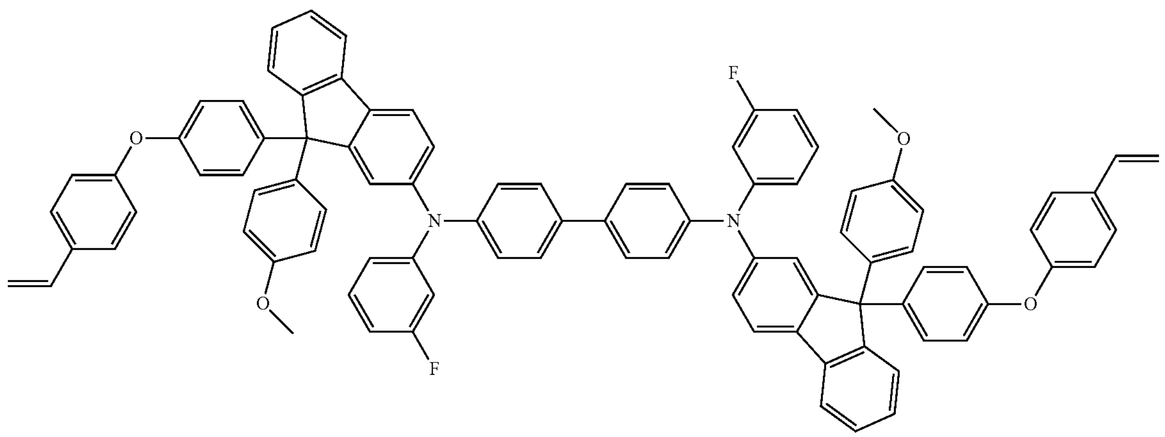

-continued
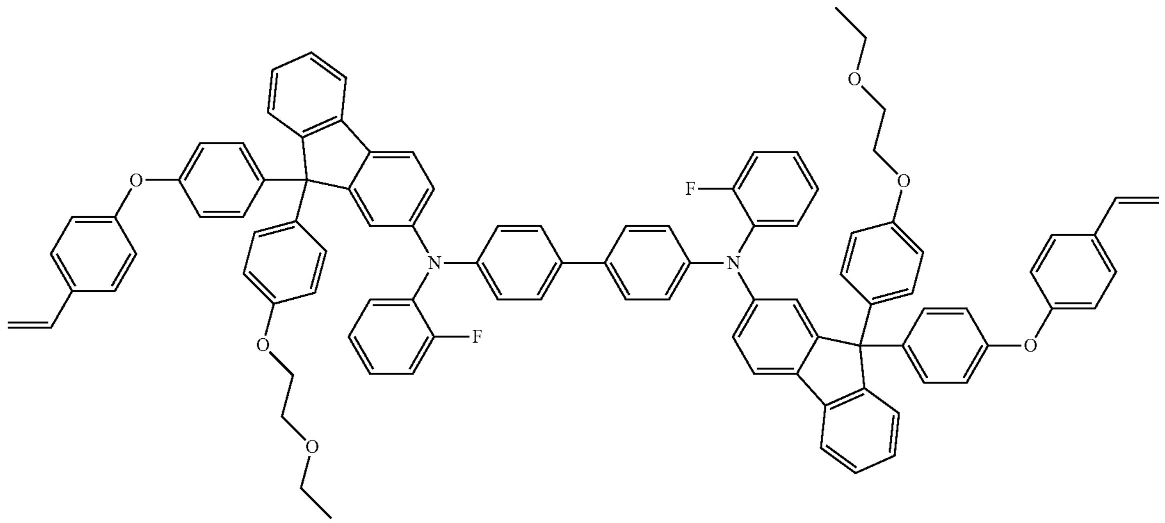
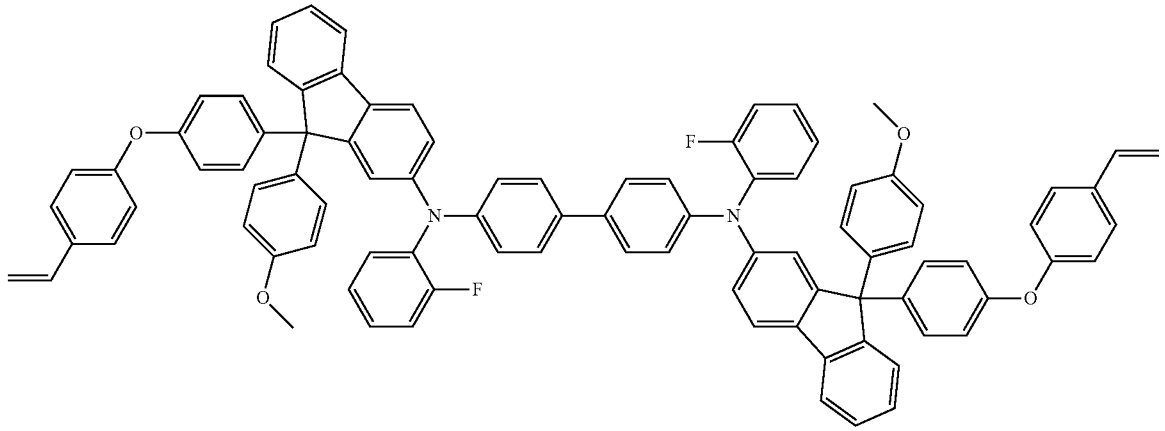
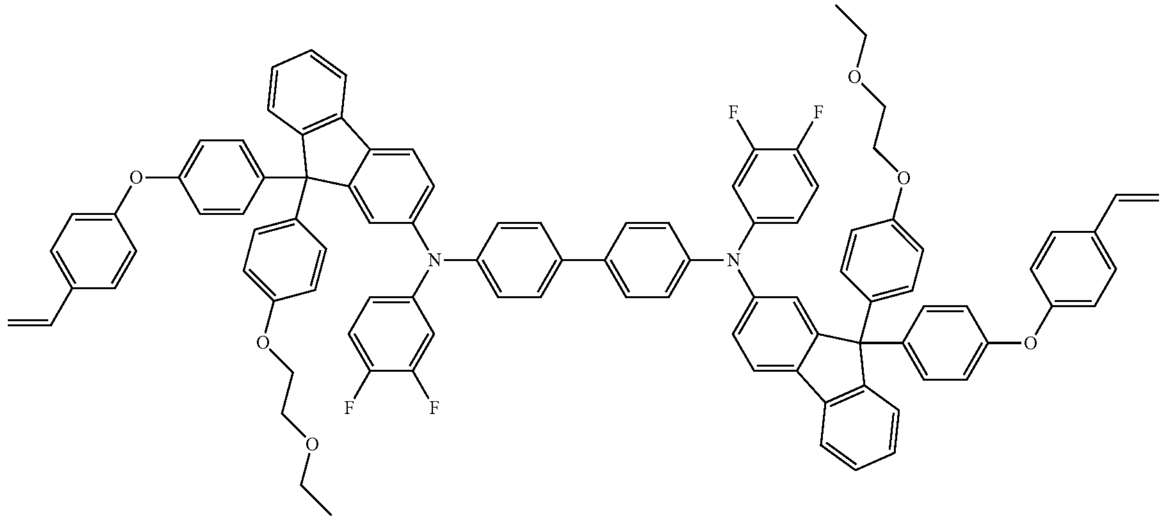

-continued
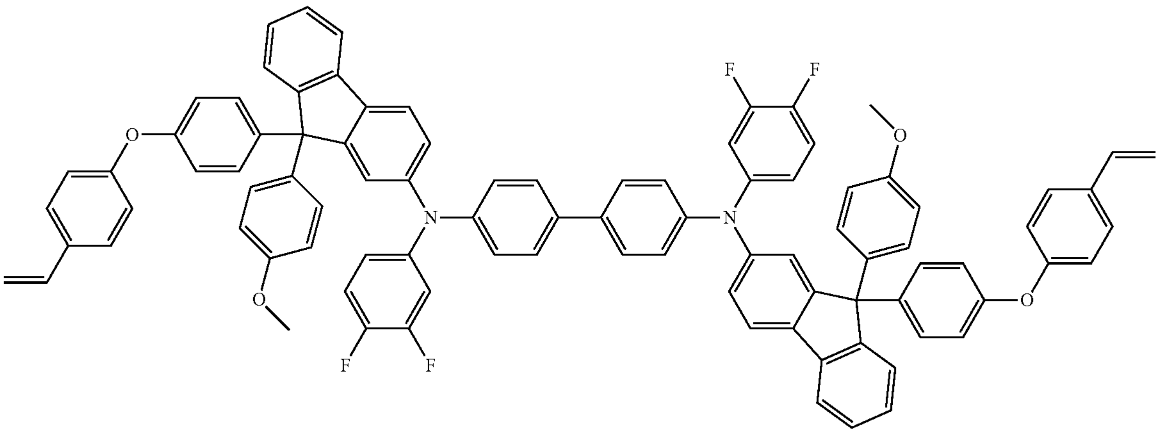
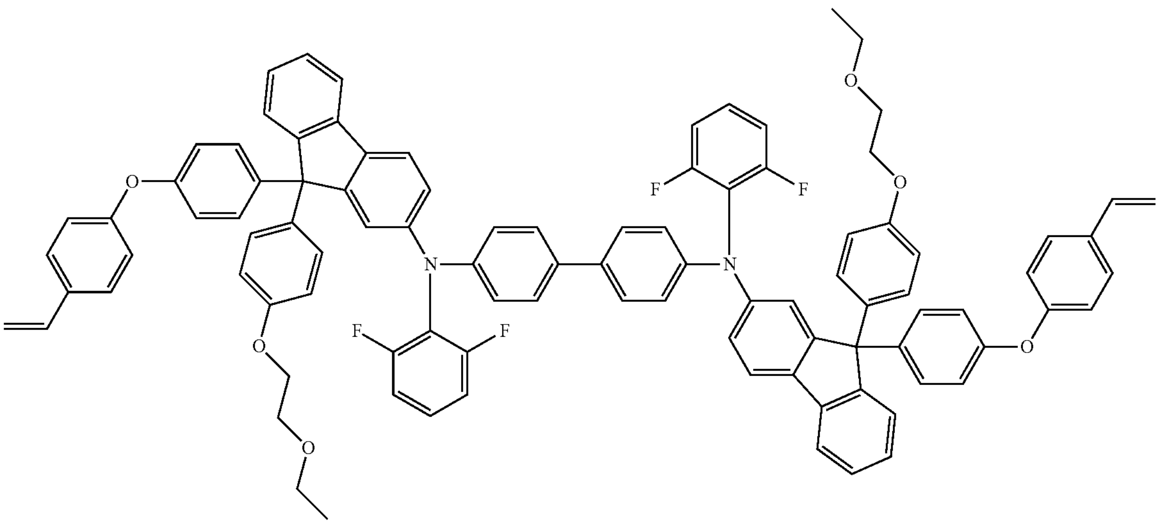
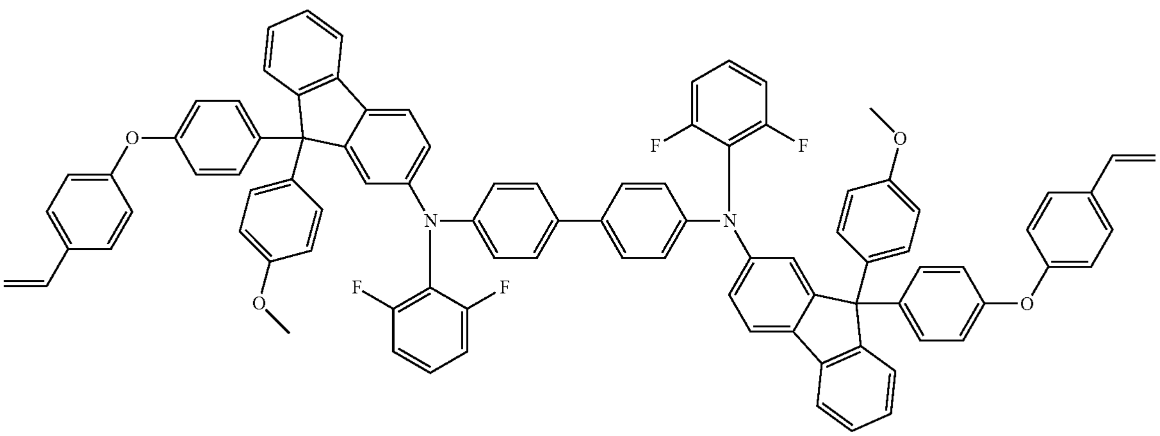

-continued
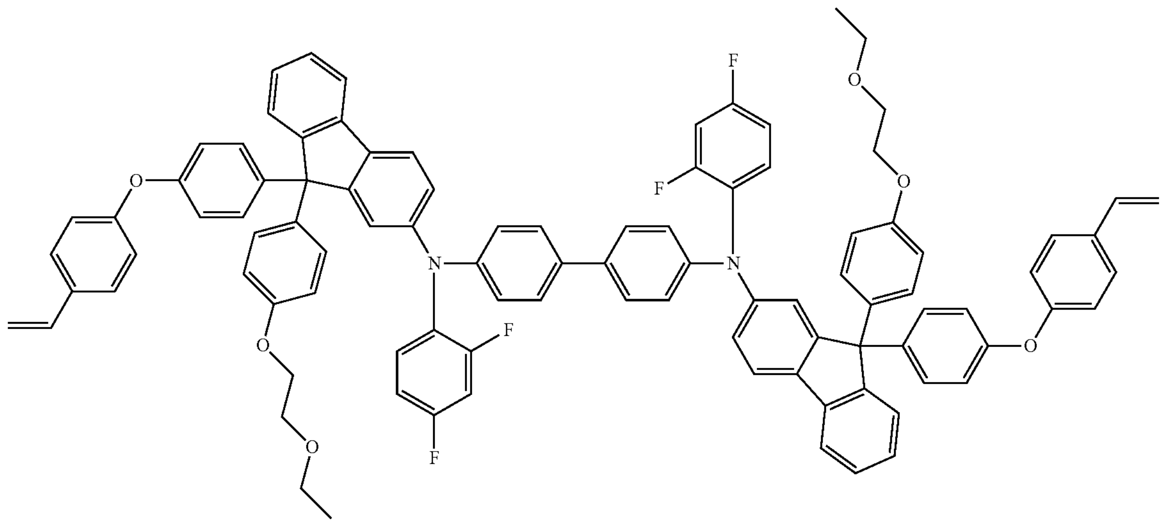
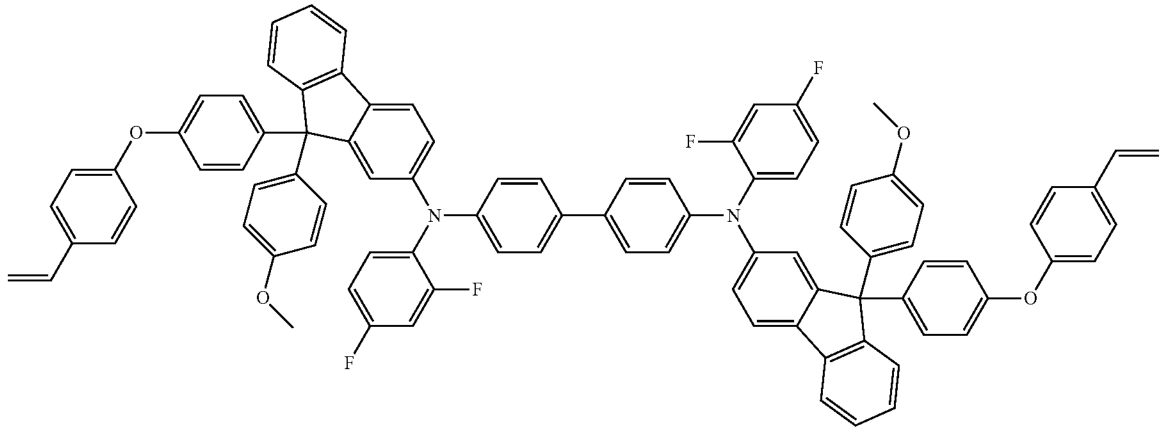
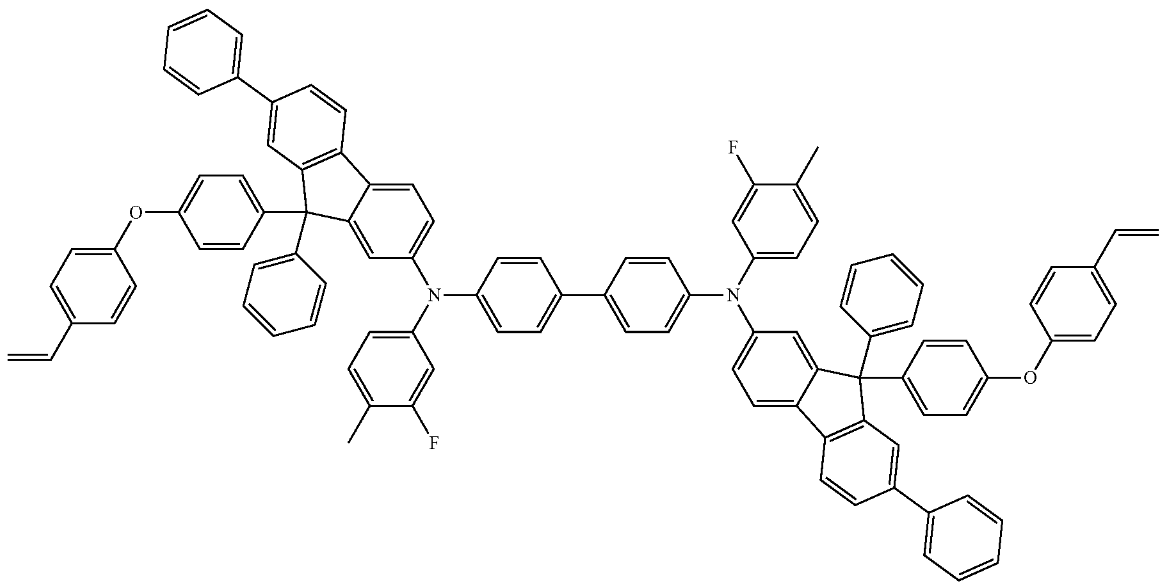

-continued
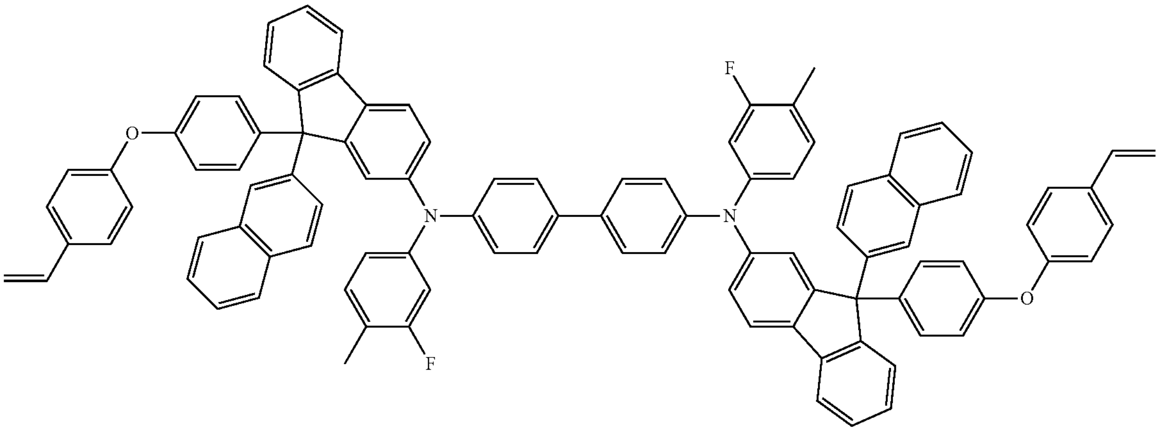
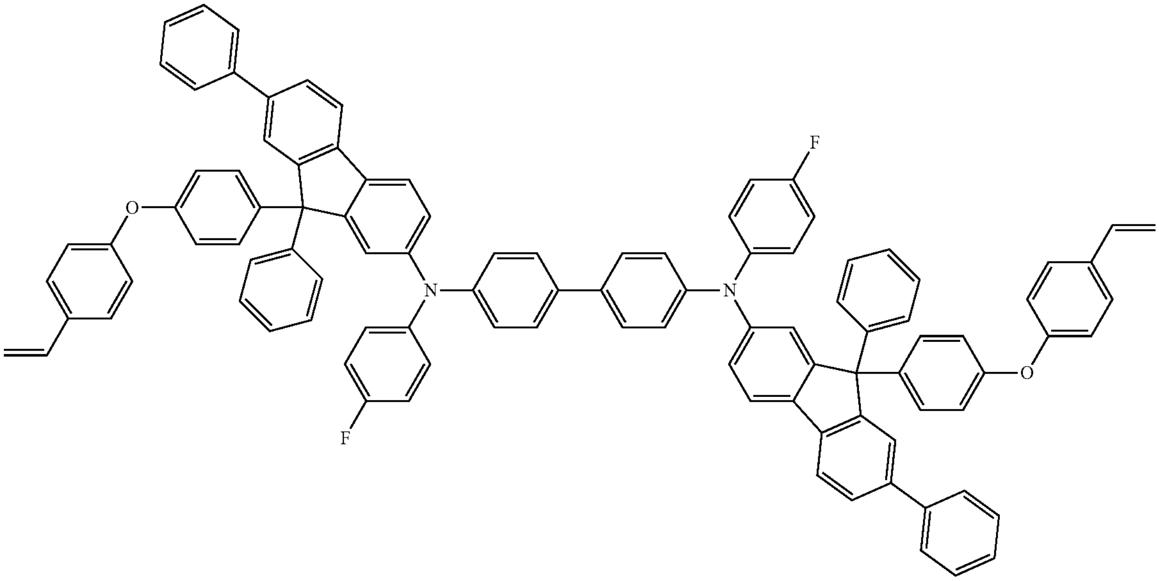
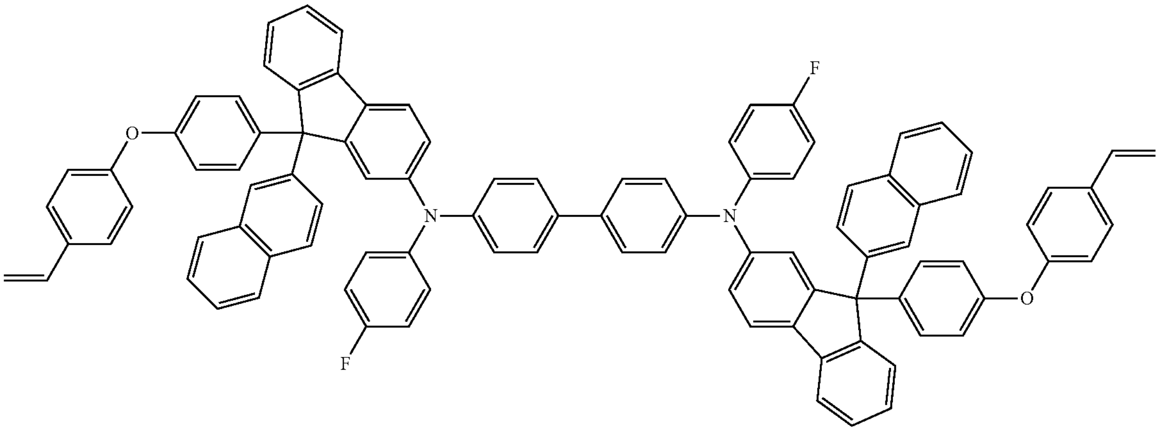

-continued
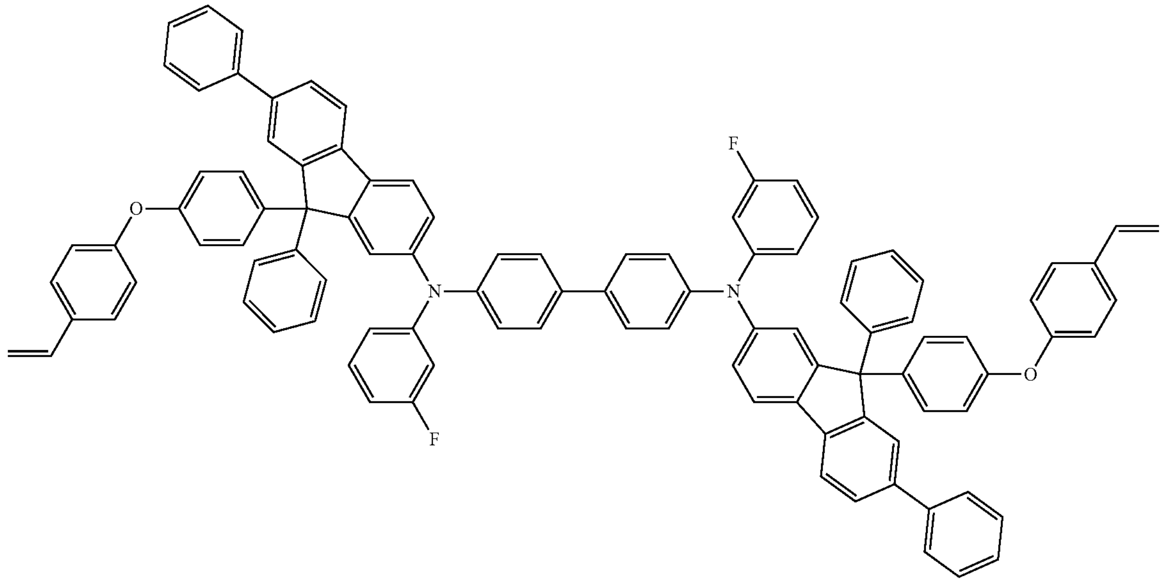
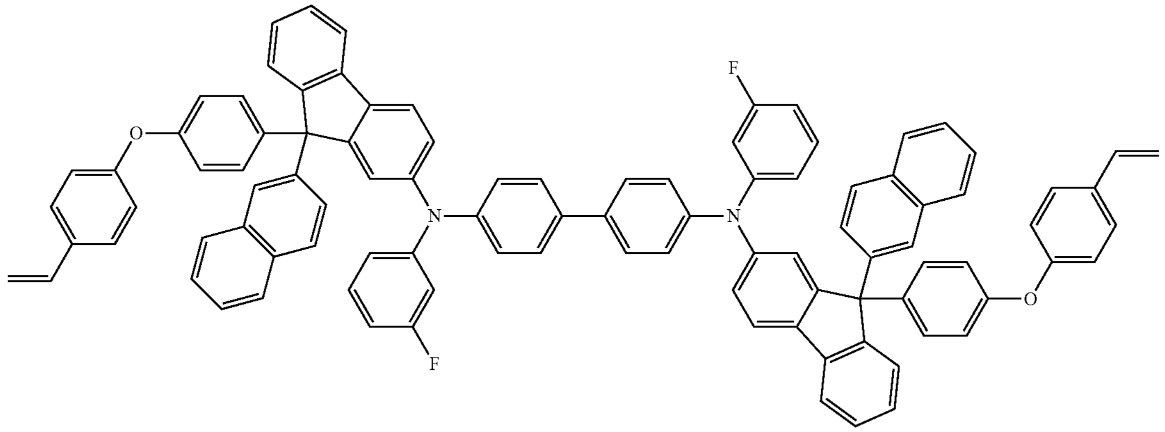
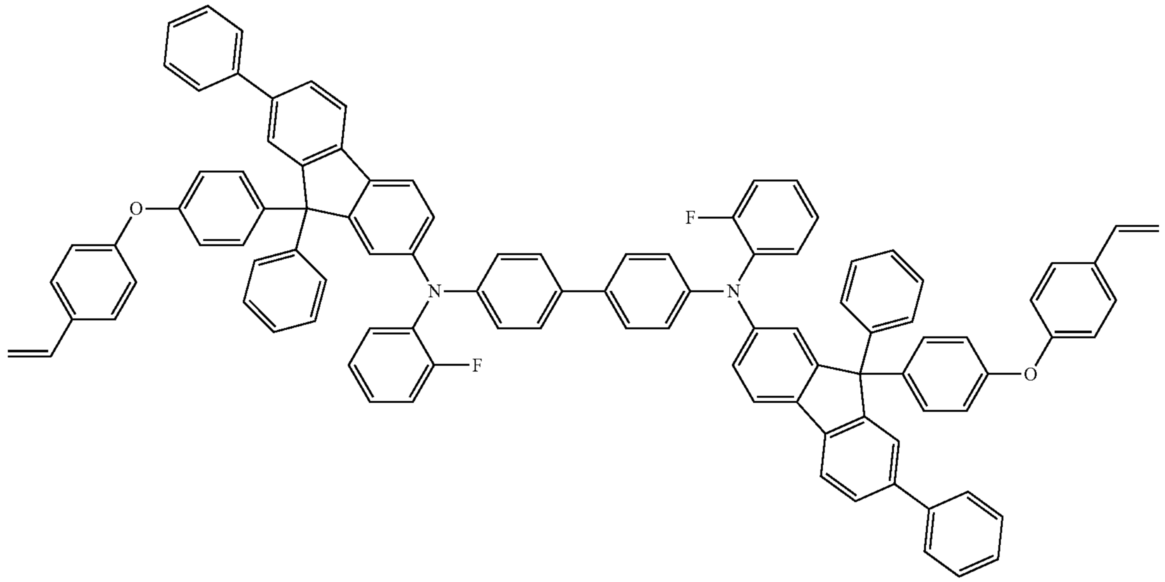

-continued
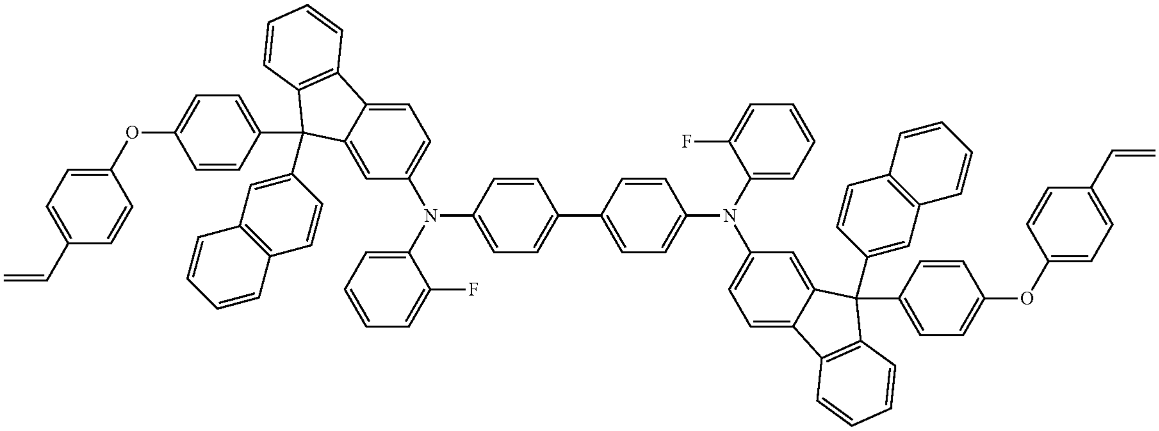
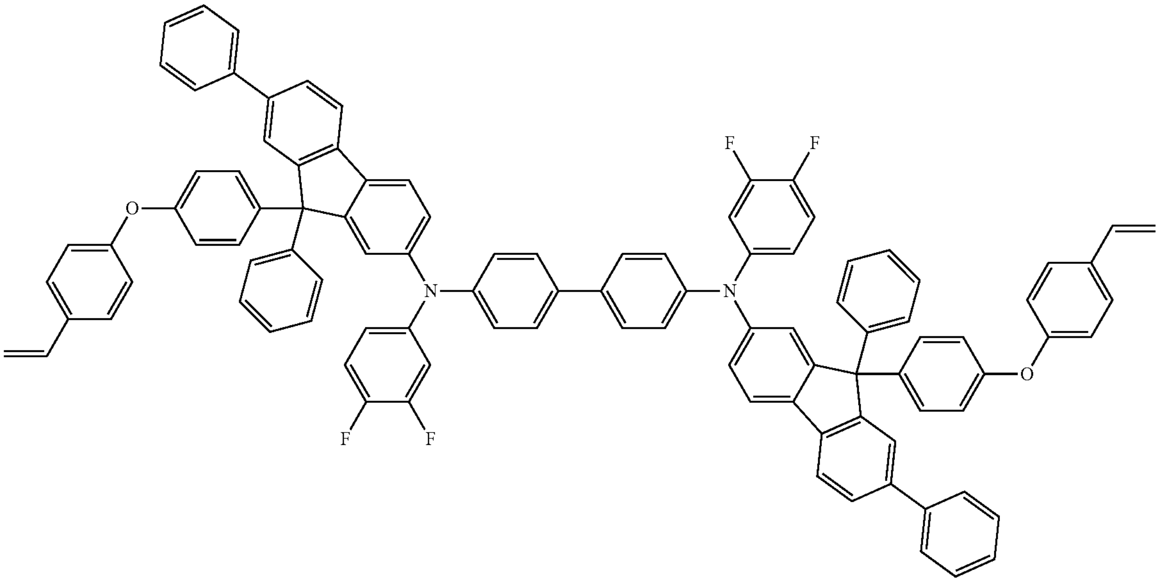
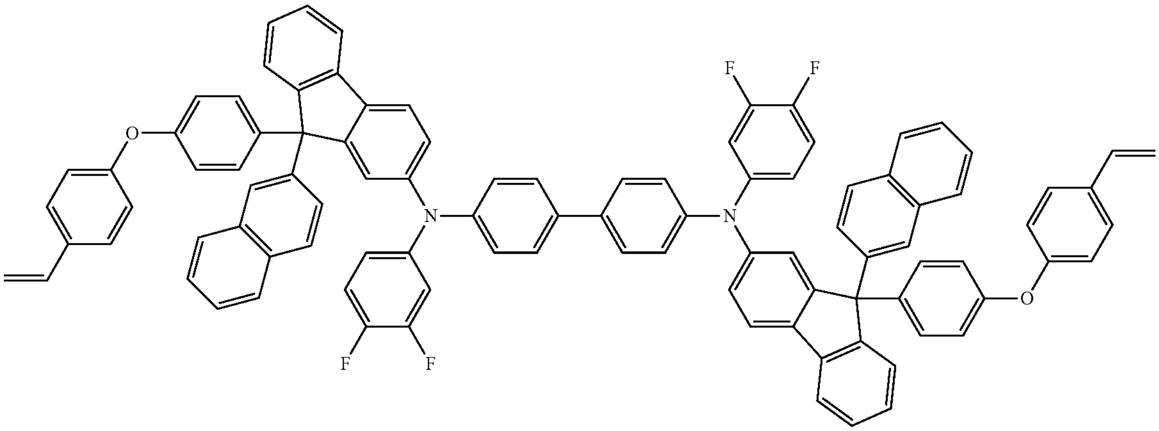

-continued
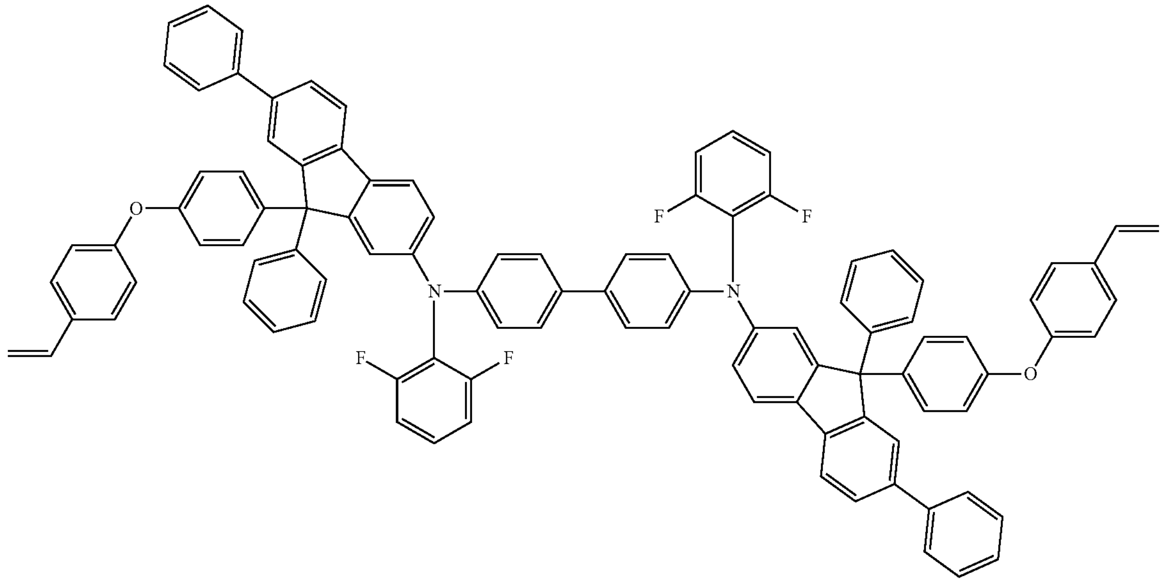
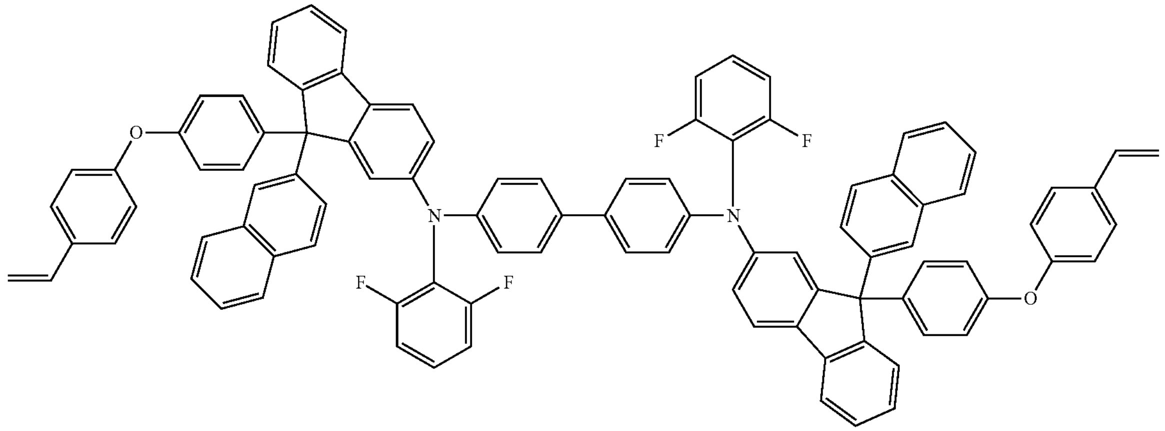
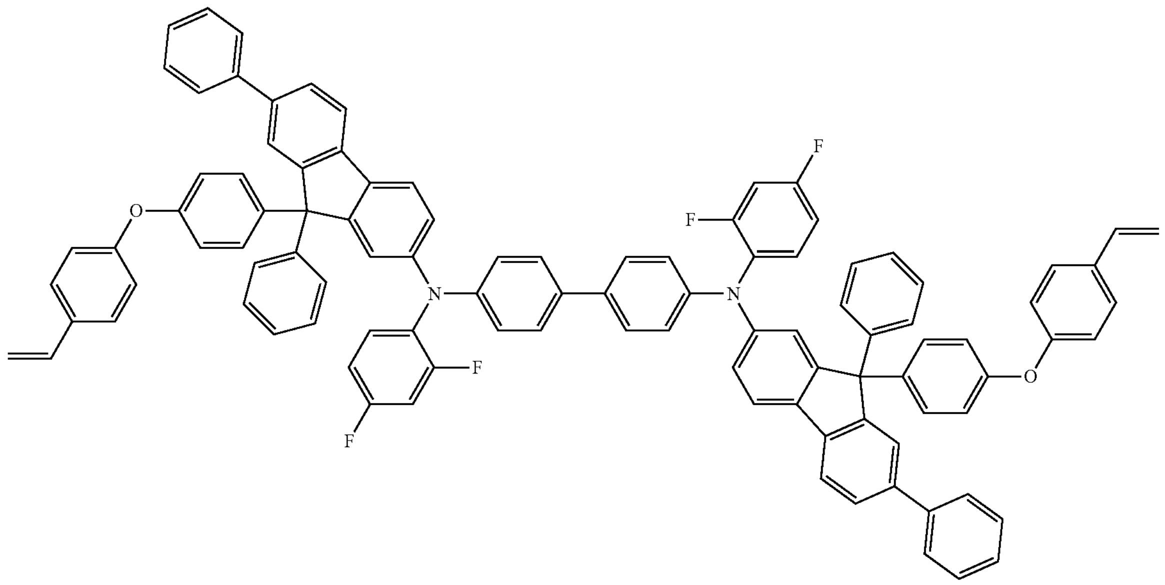

-continued
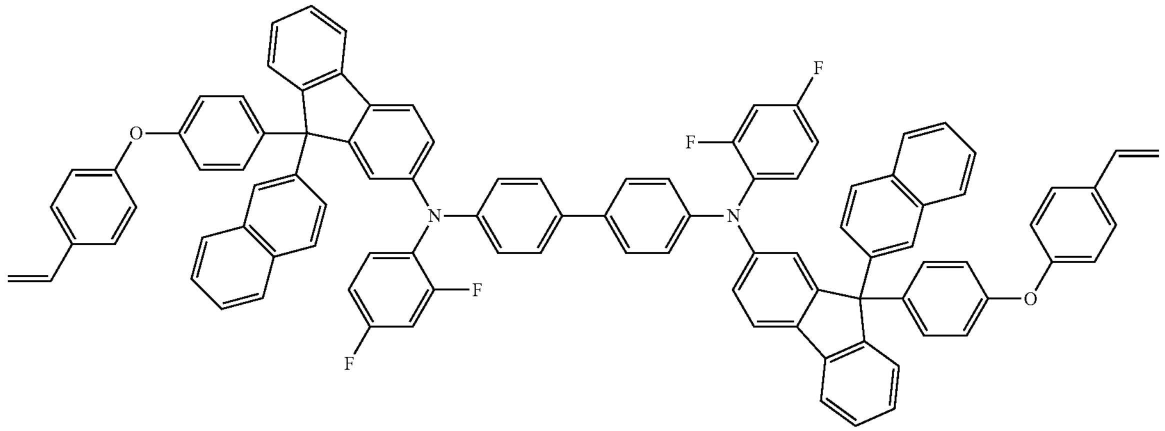
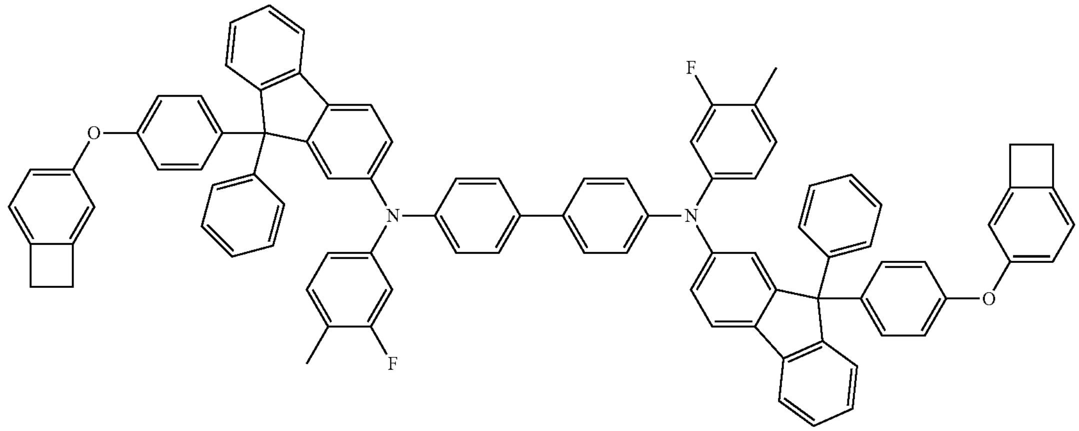
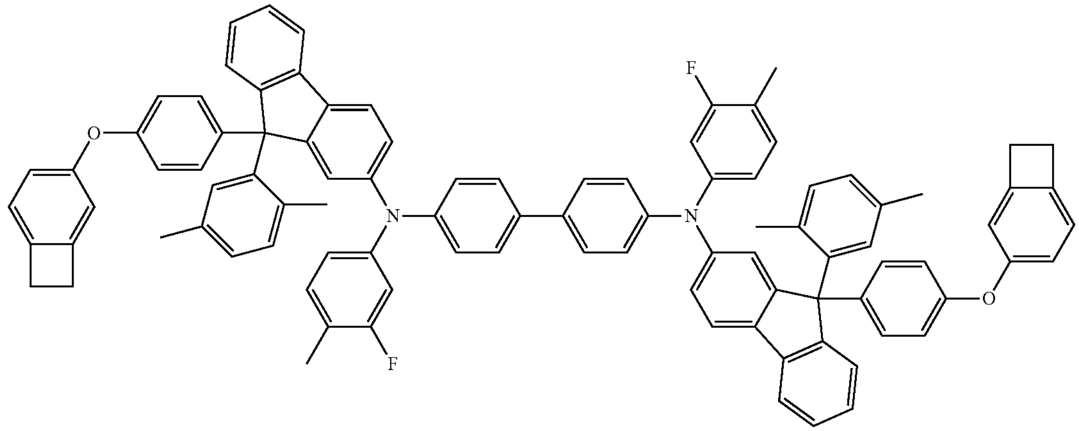
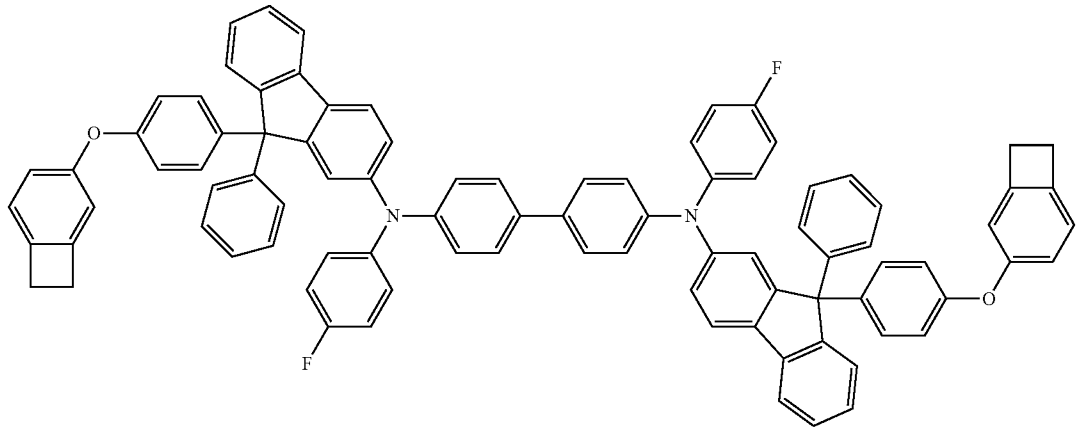

-continued
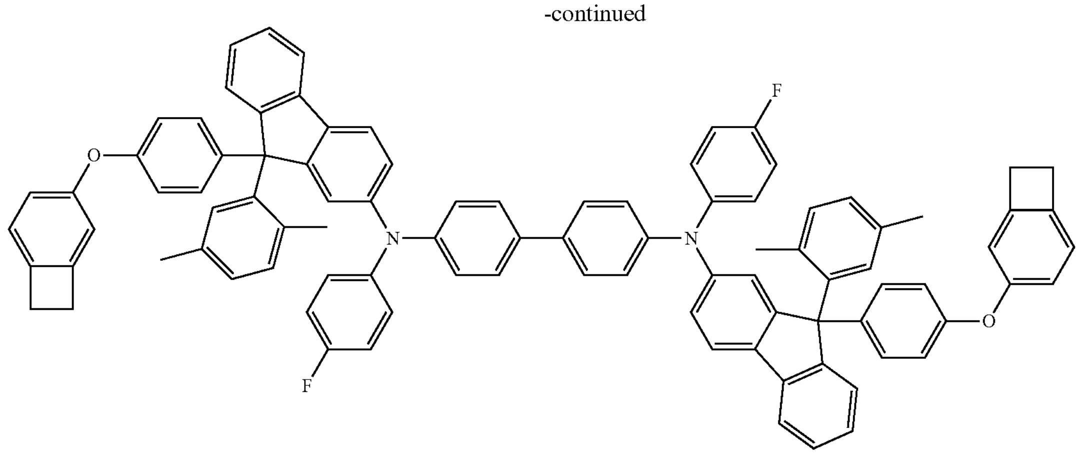
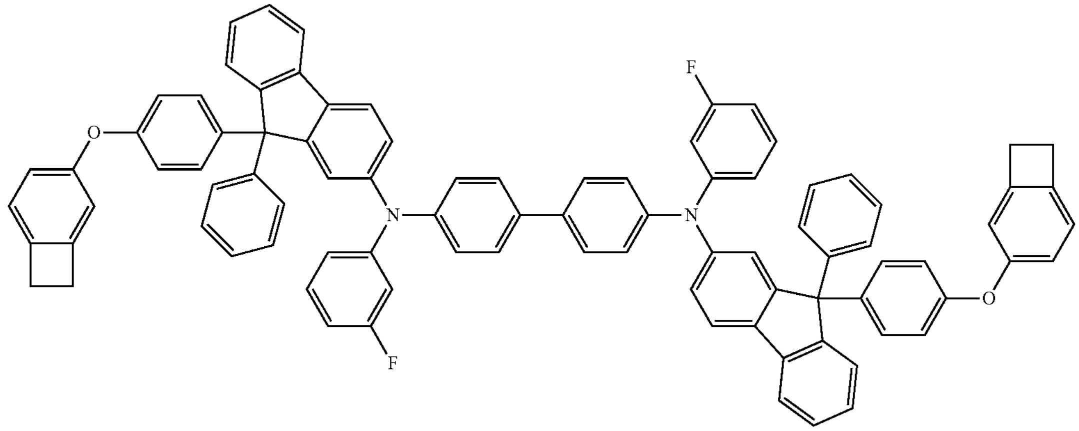
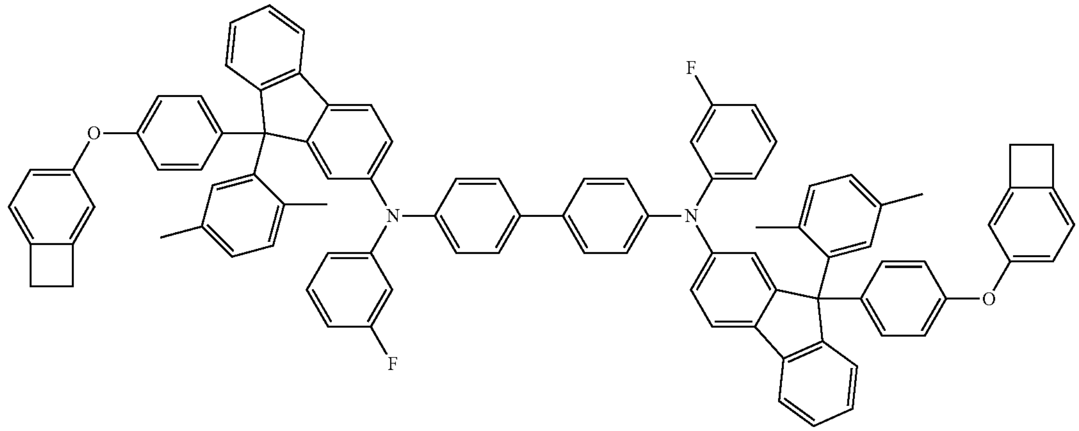
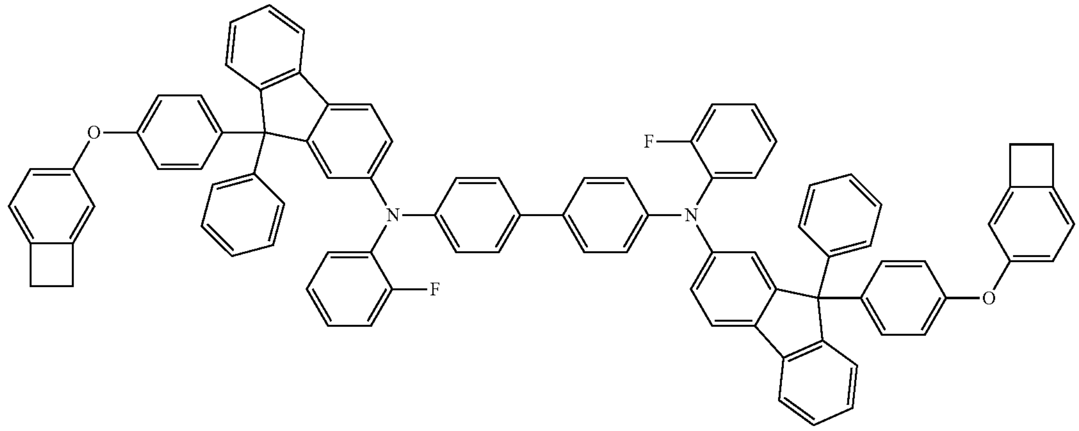

-continued
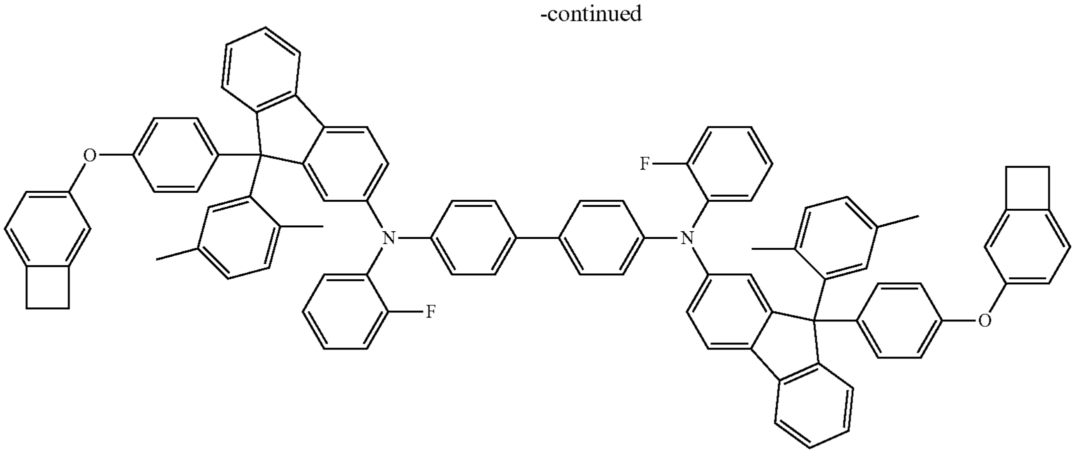
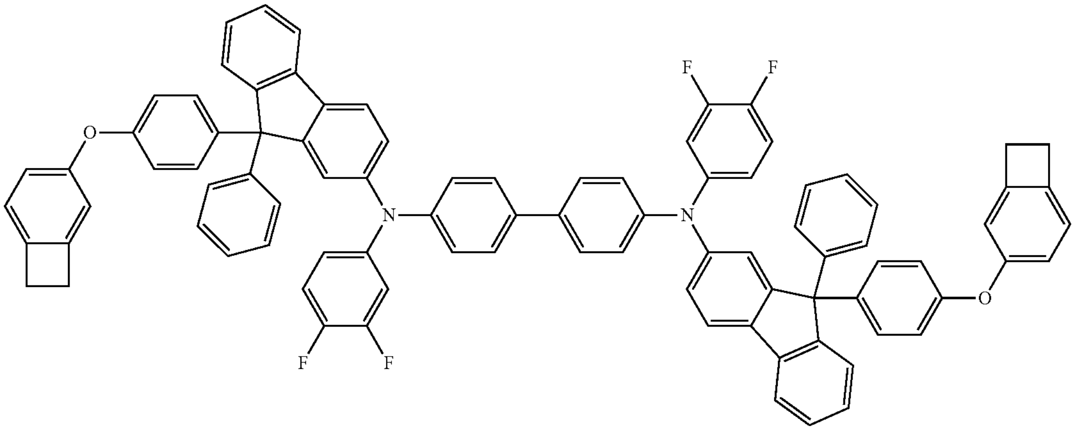
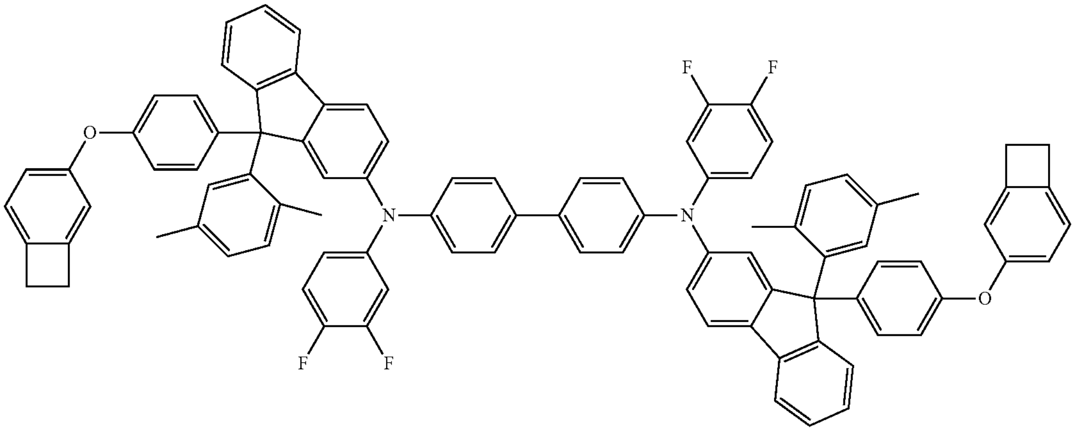
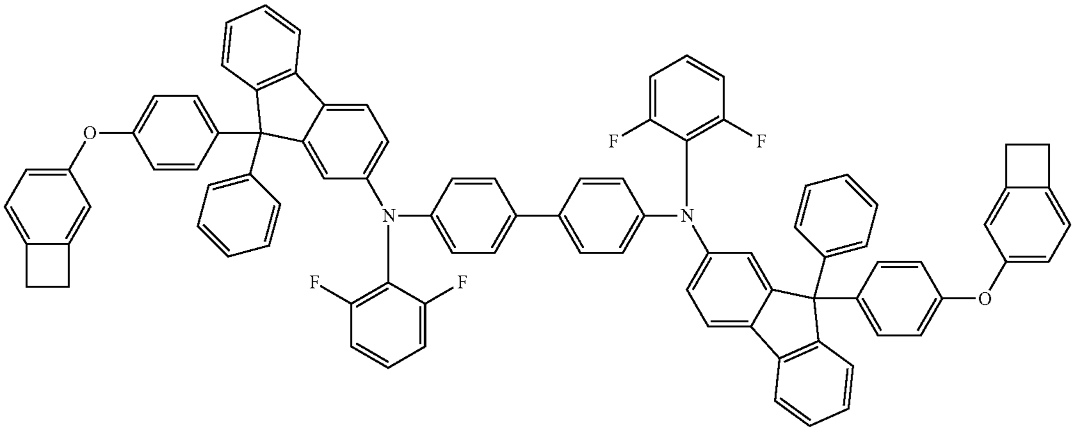

-continued
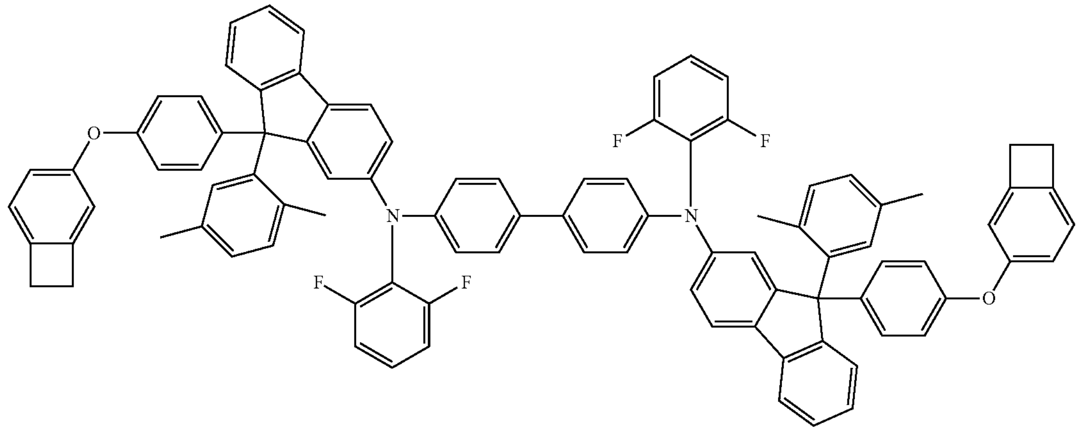
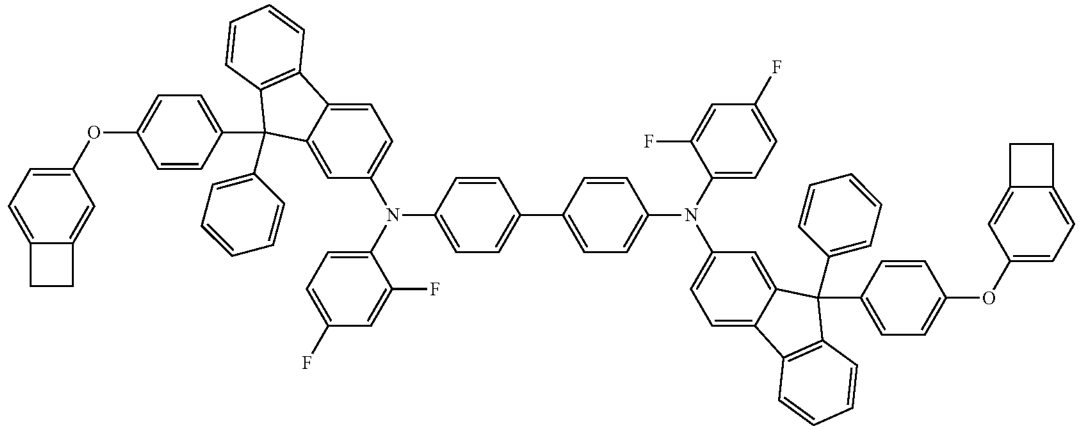
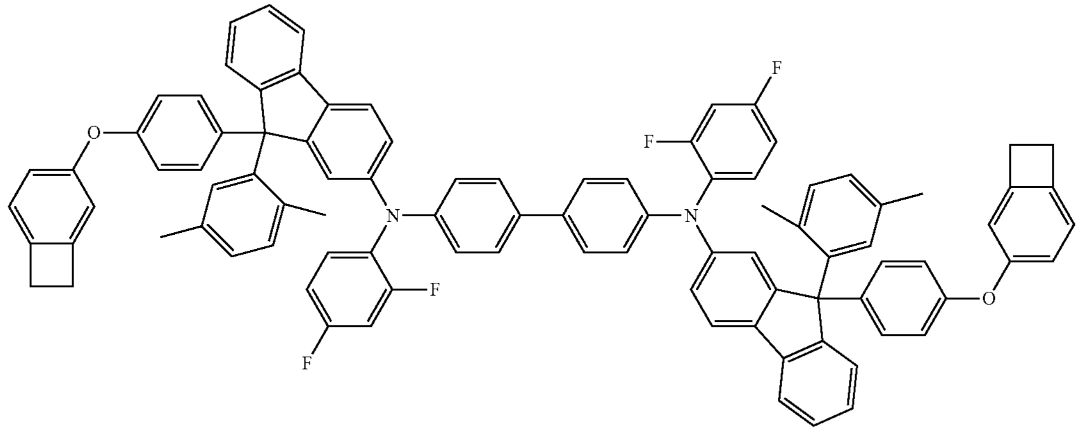
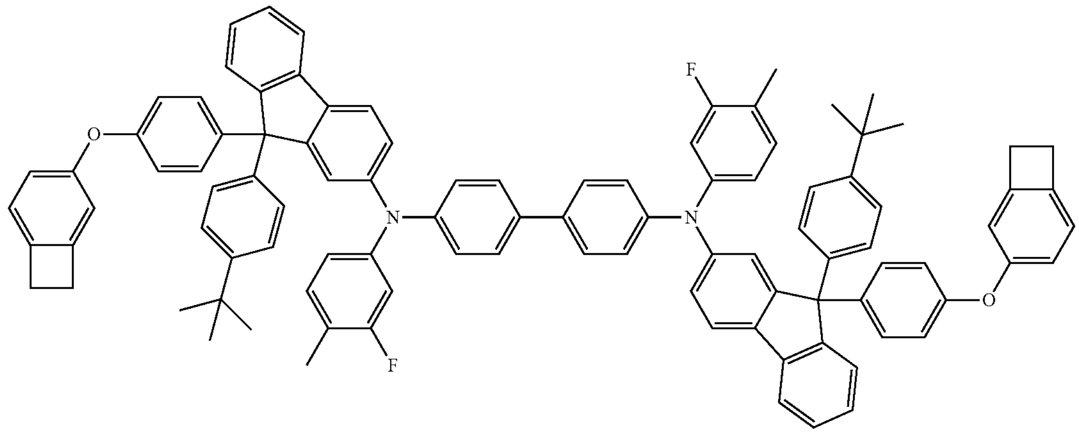

-continued
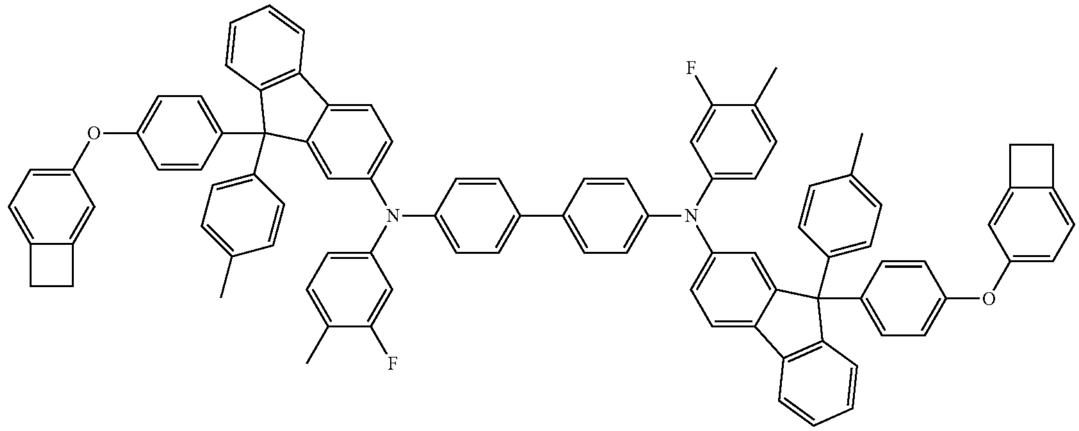
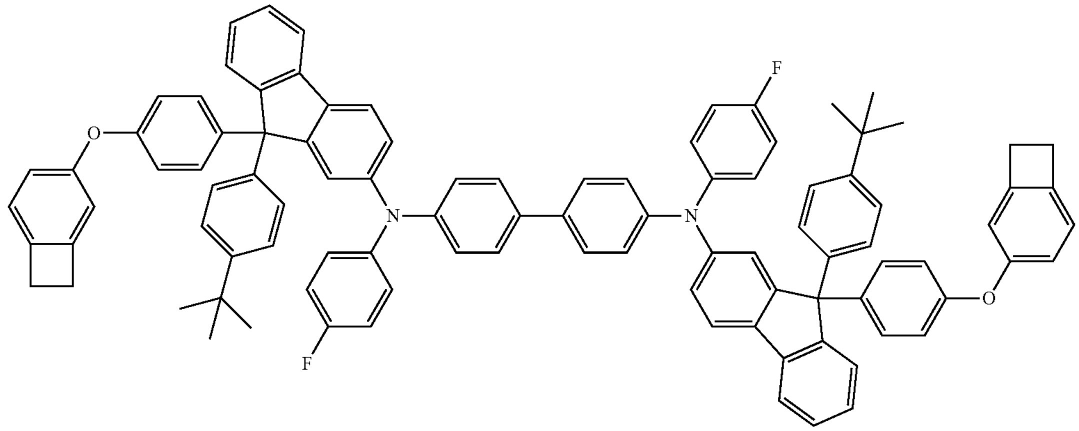
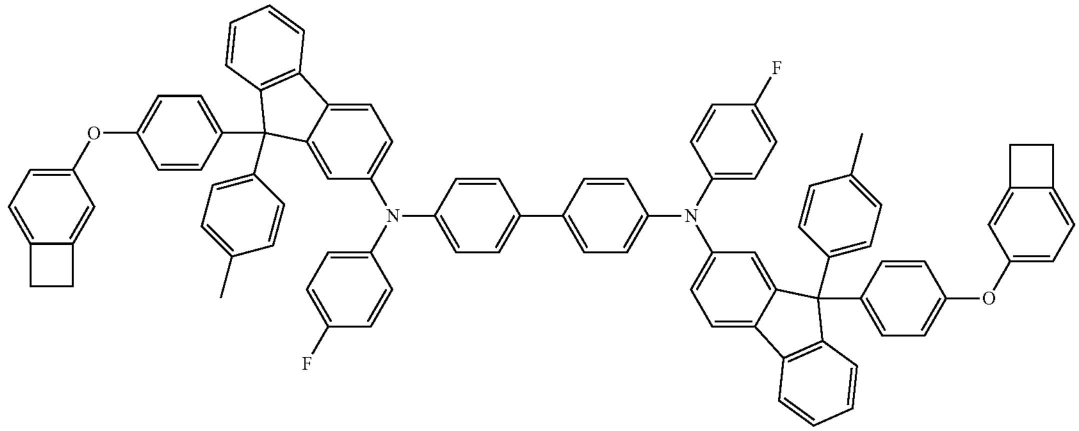
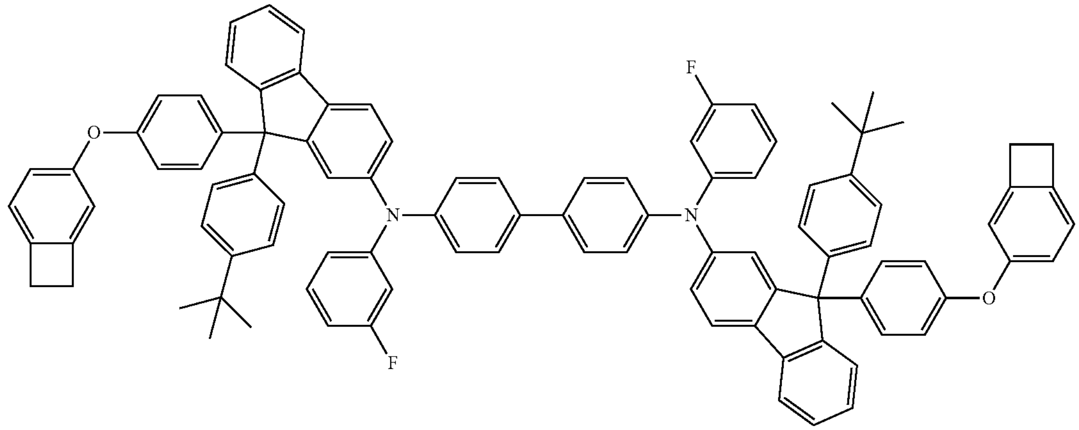

-continued
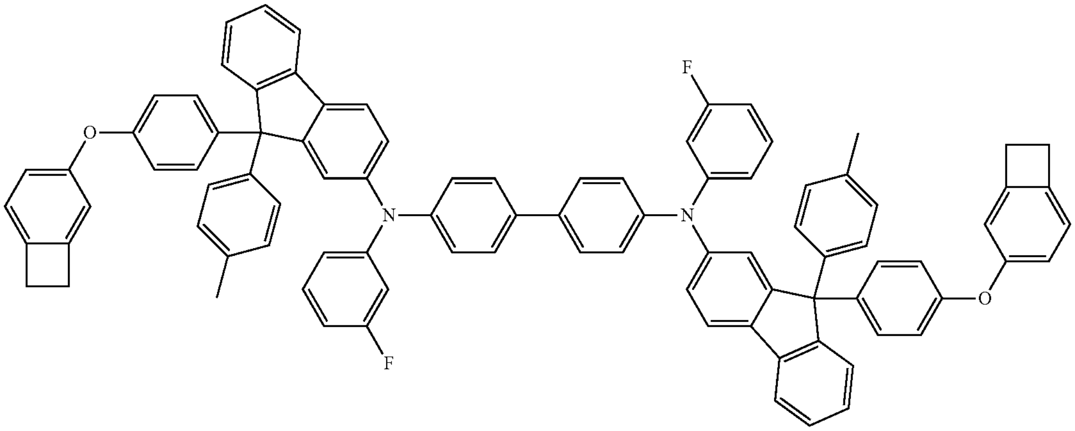
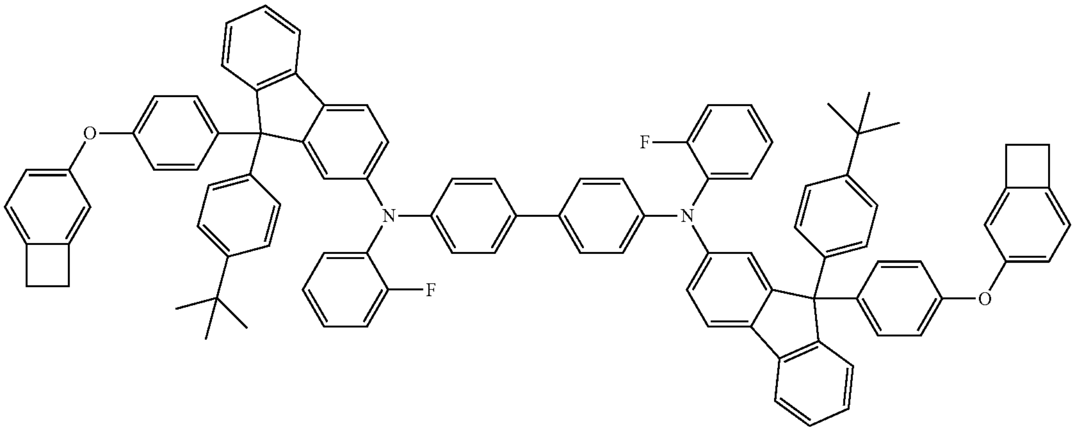
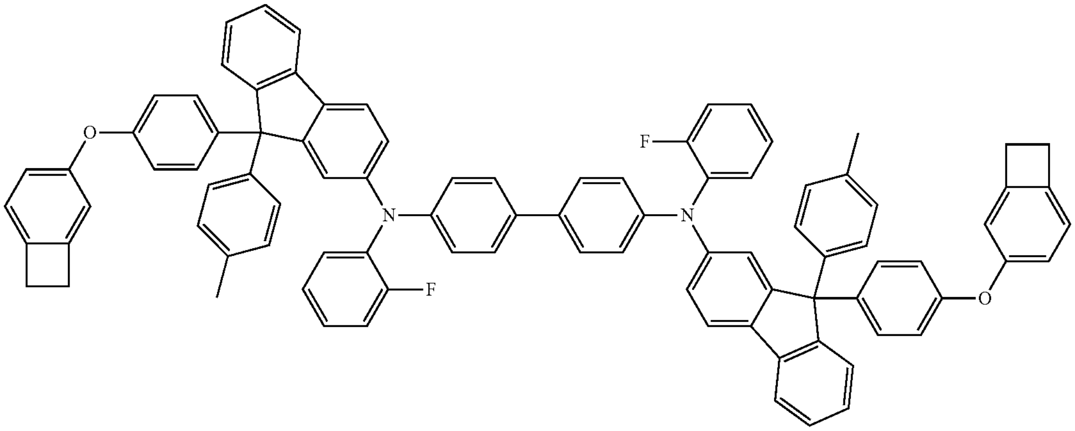
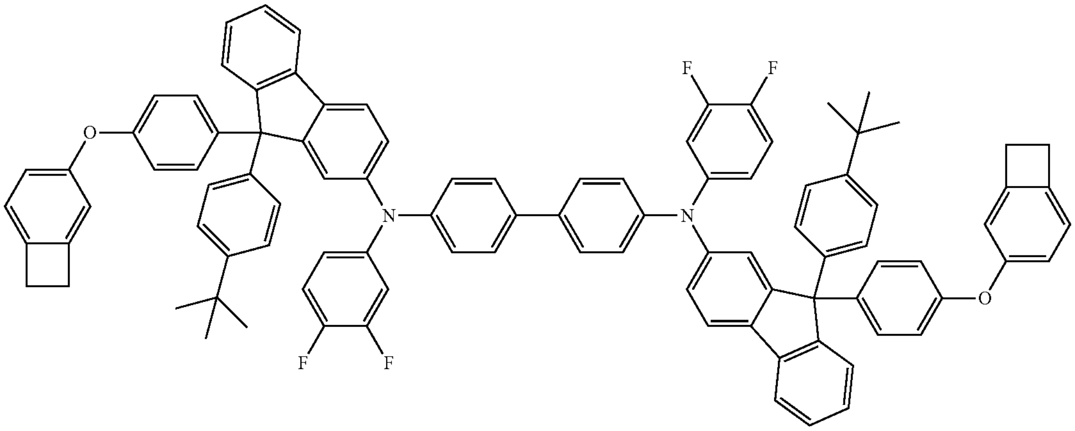

-continued
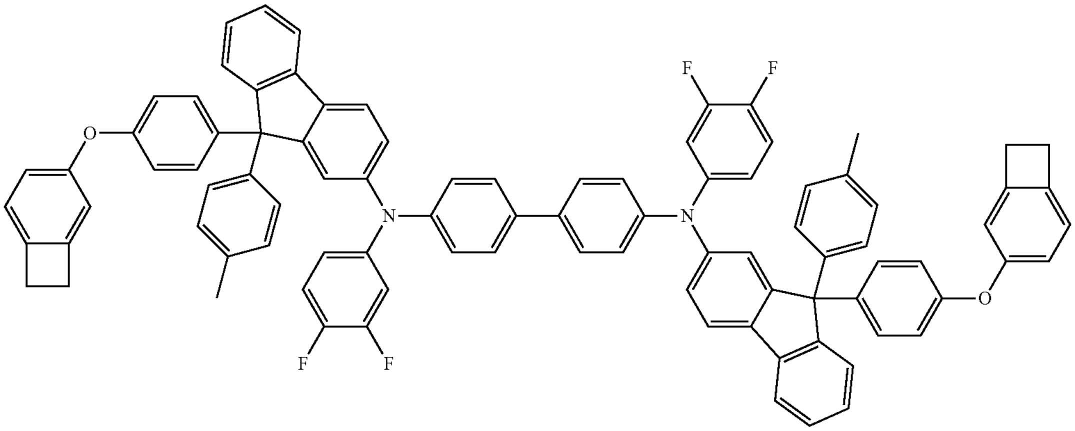
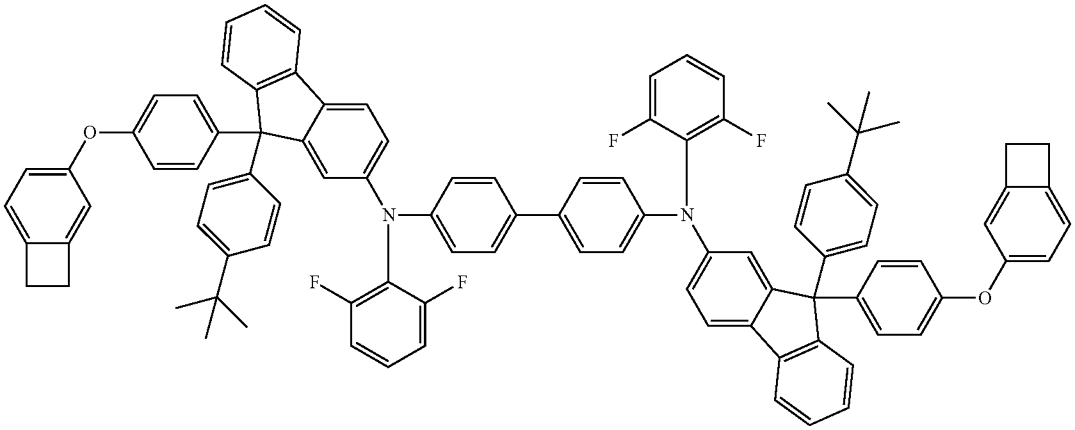
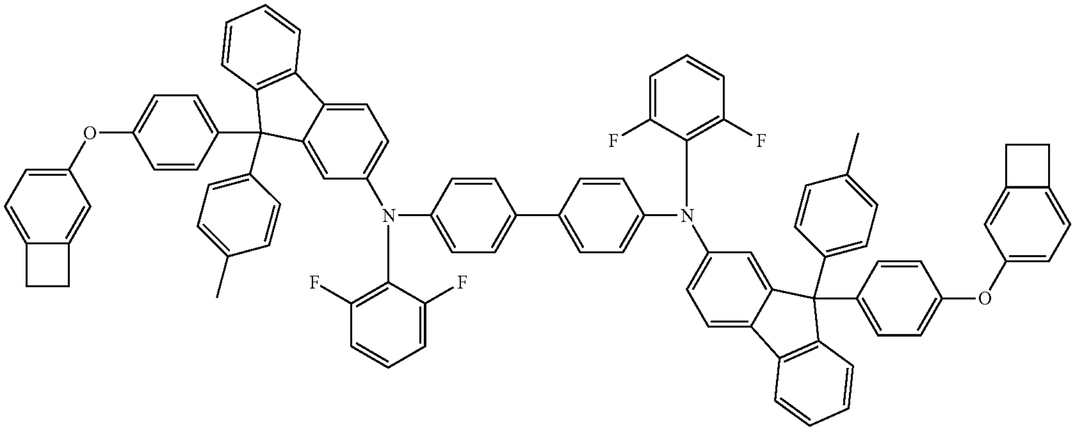
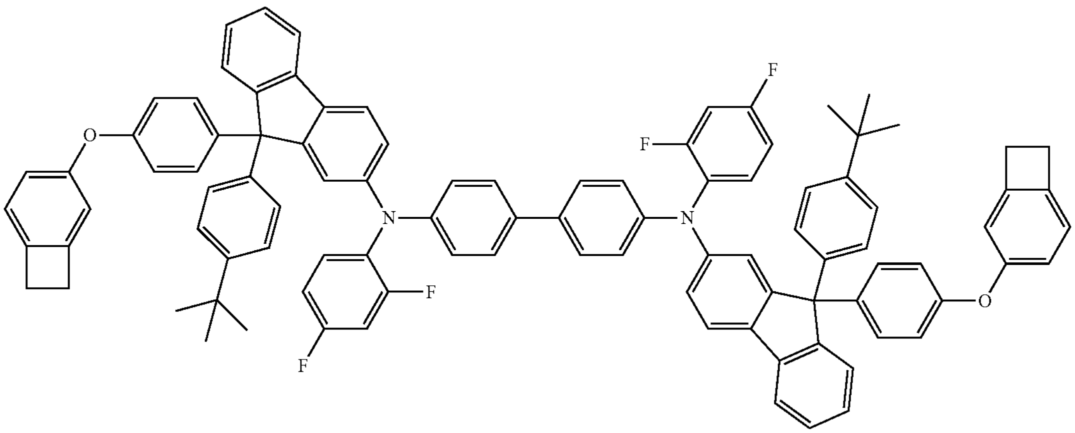

-continued
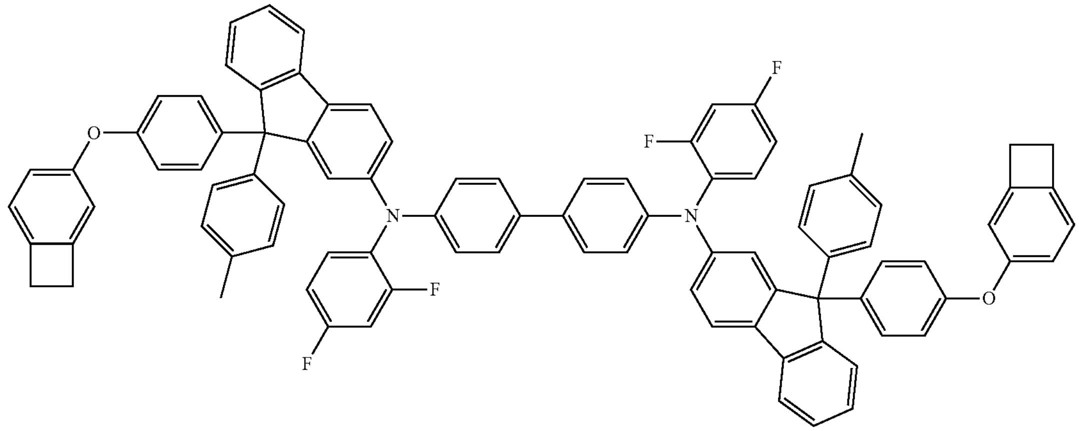
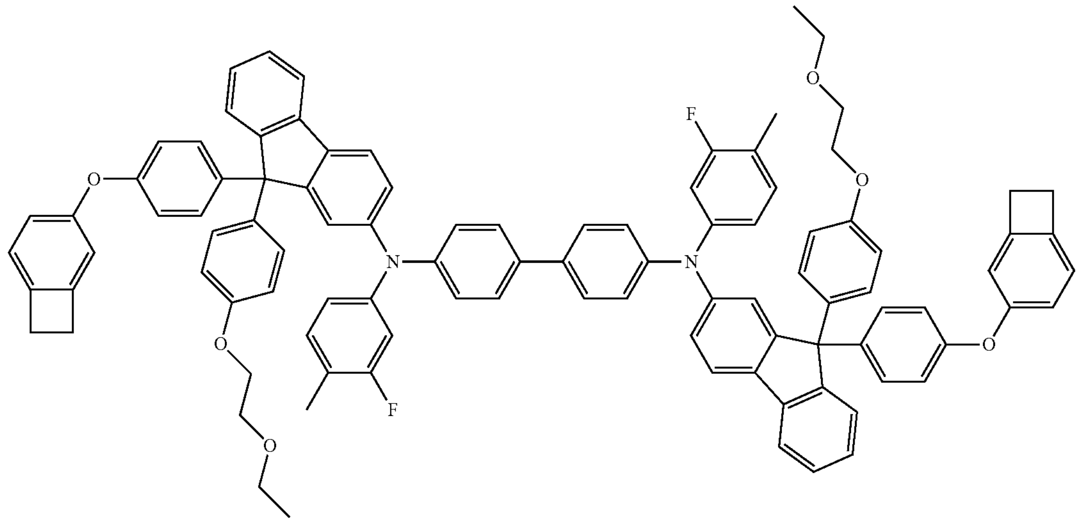
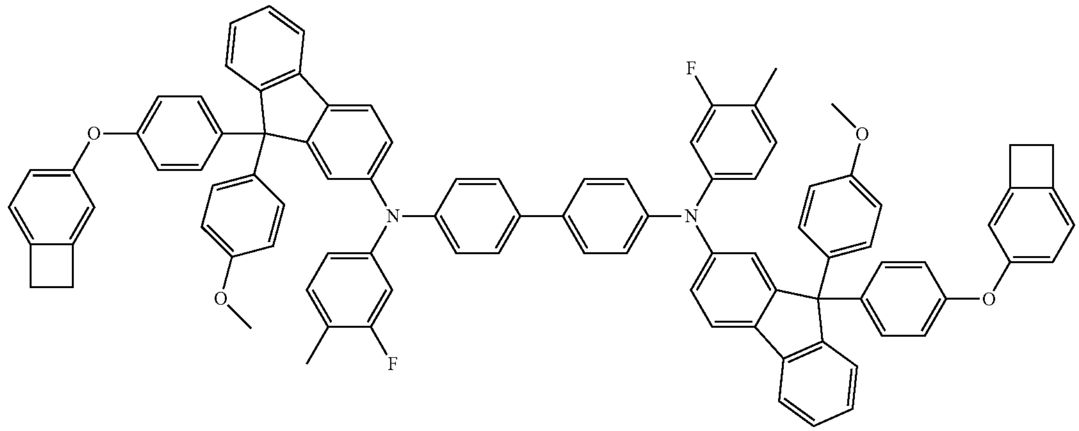

-continued
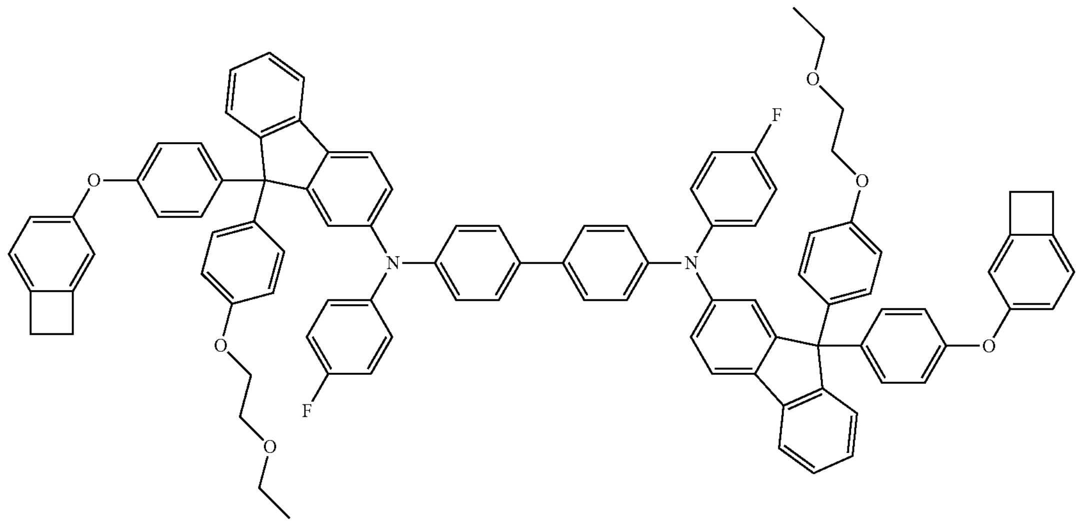
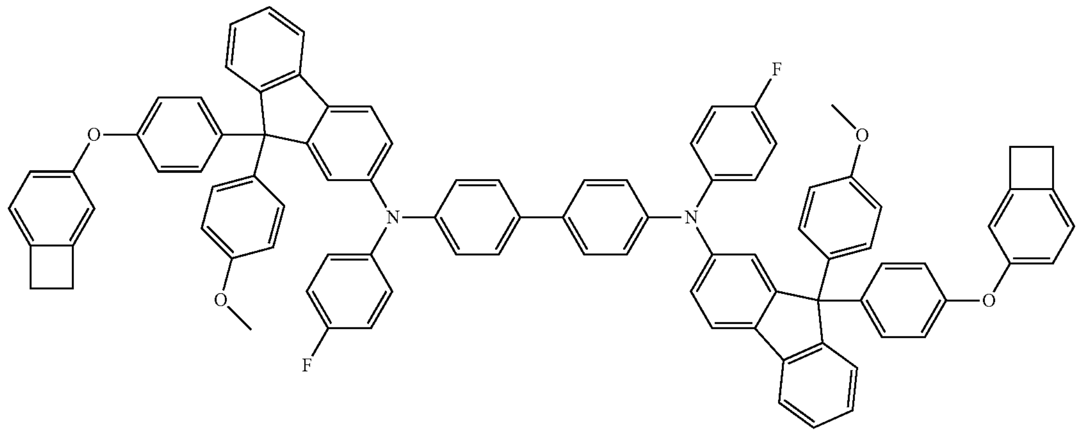
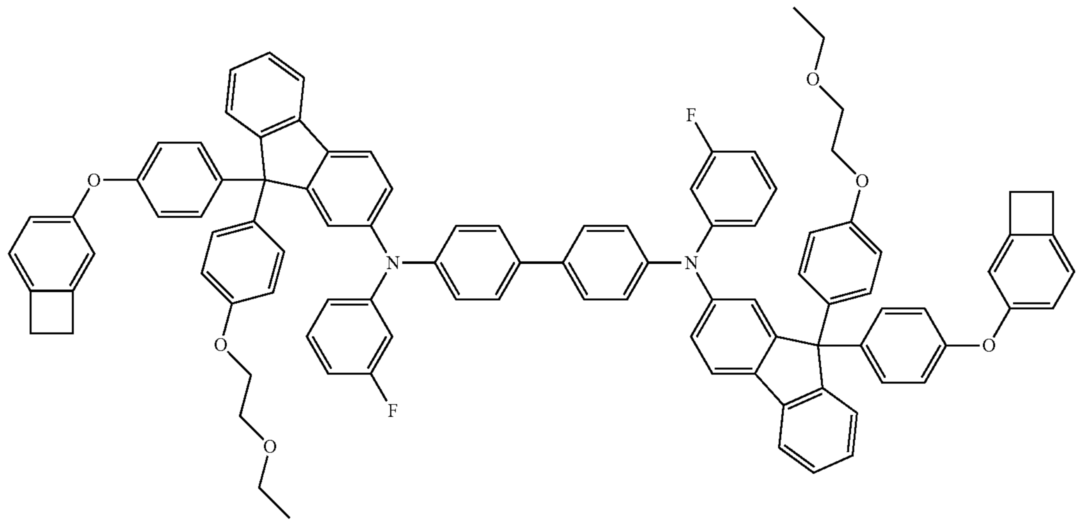

-continued
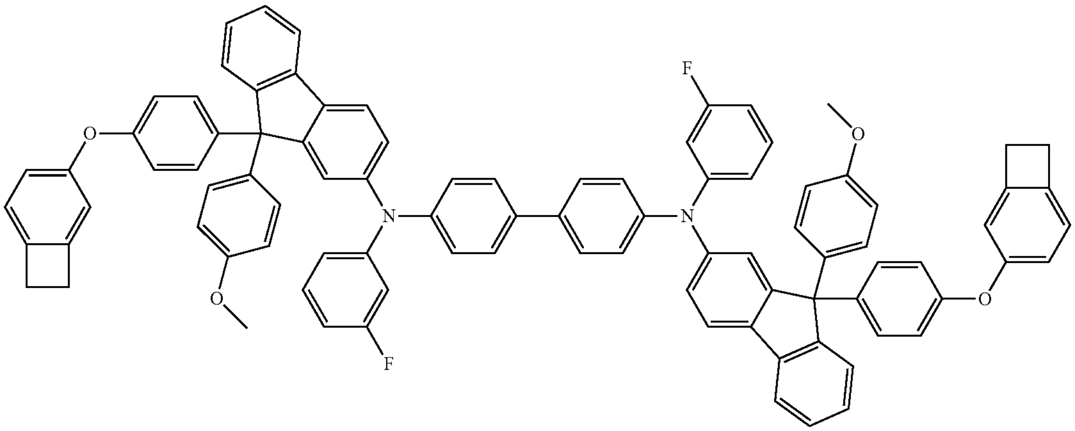
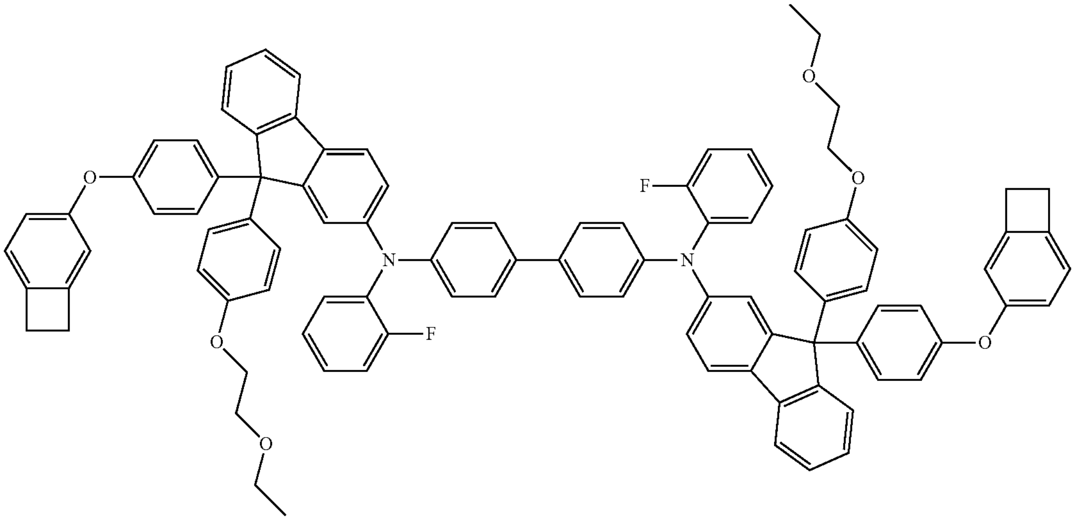
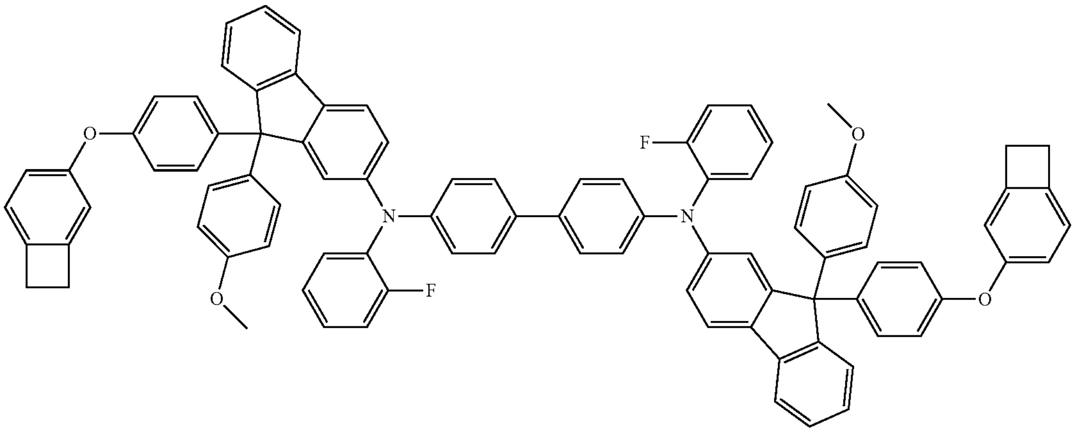

-continued
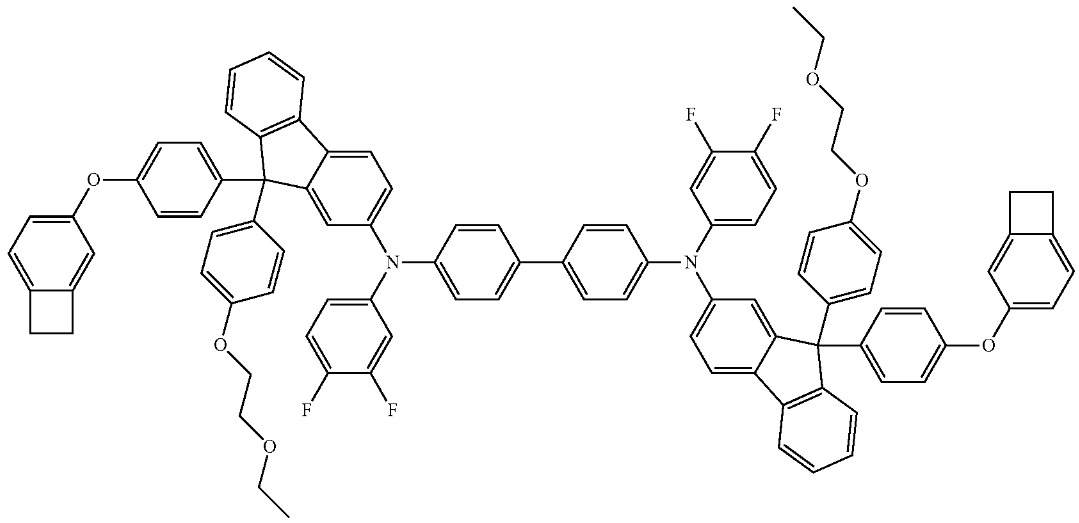
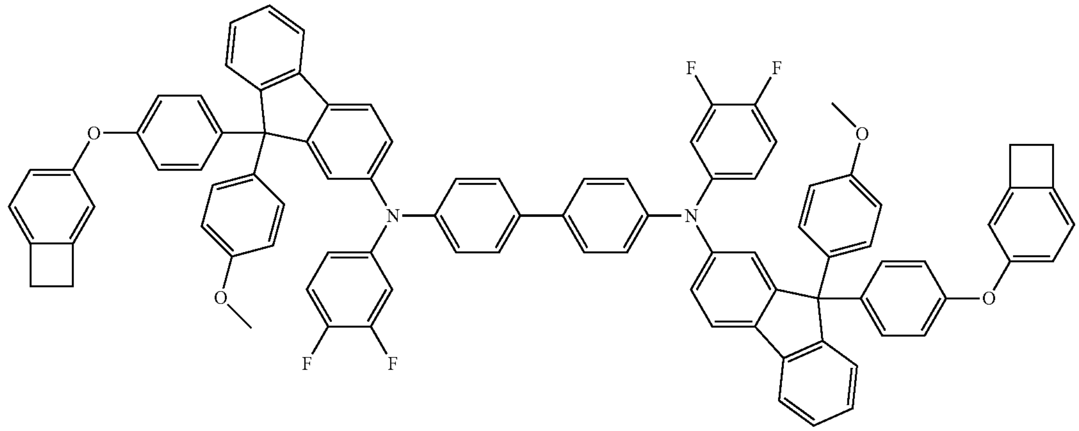
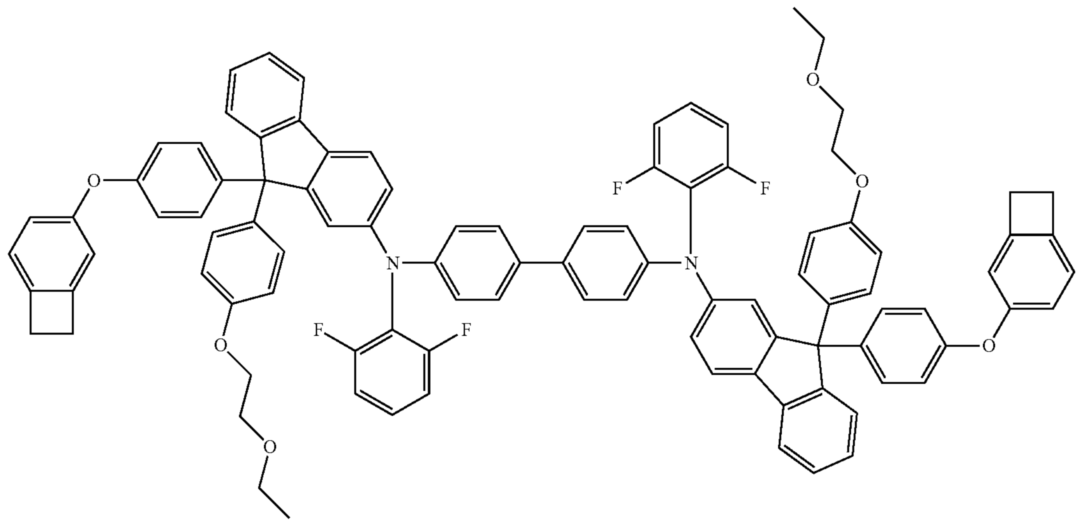

-continued
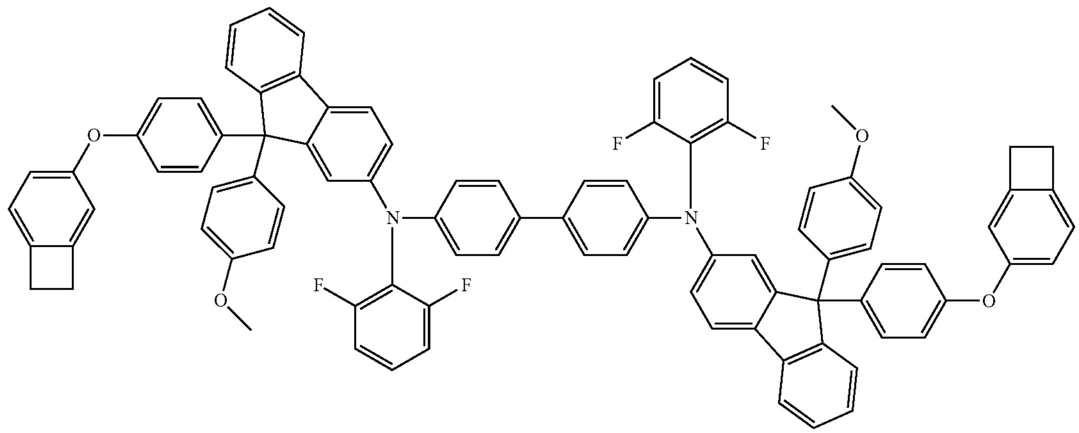
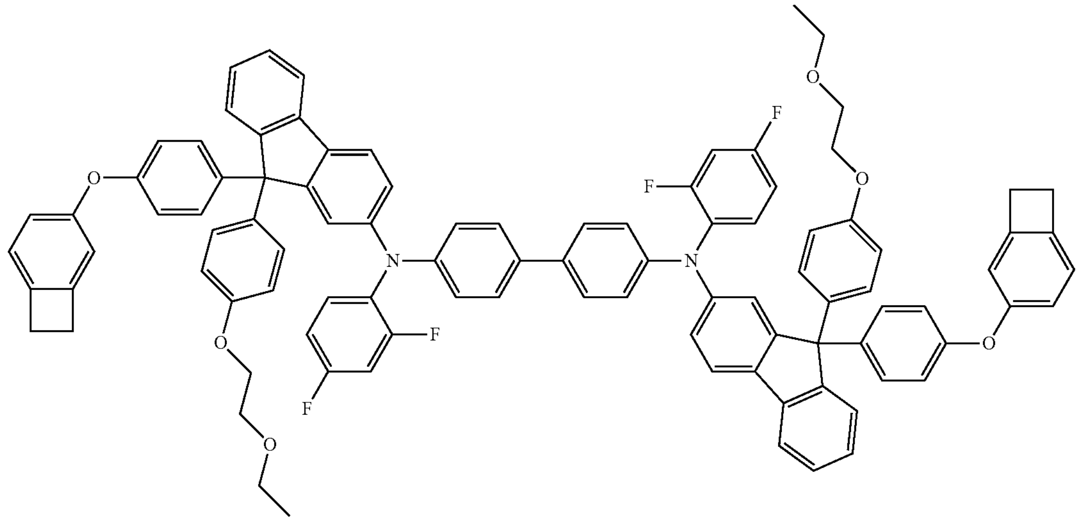
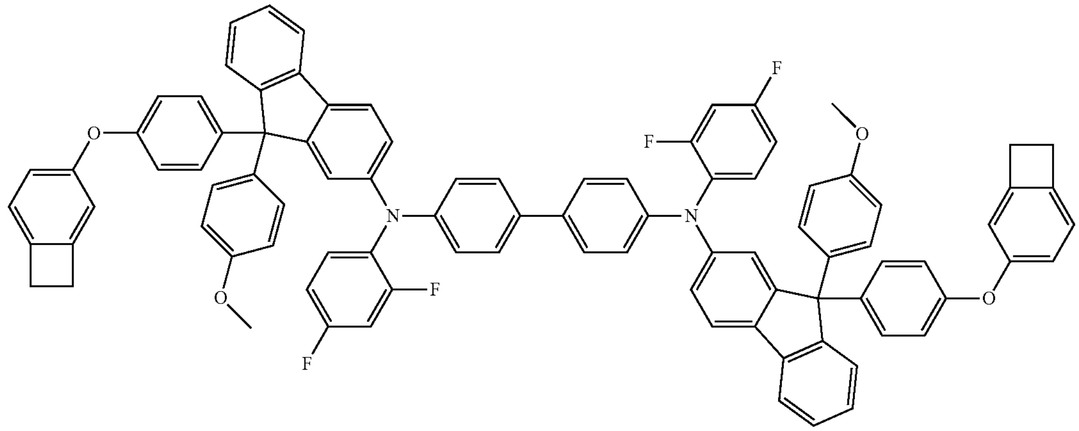

-continued
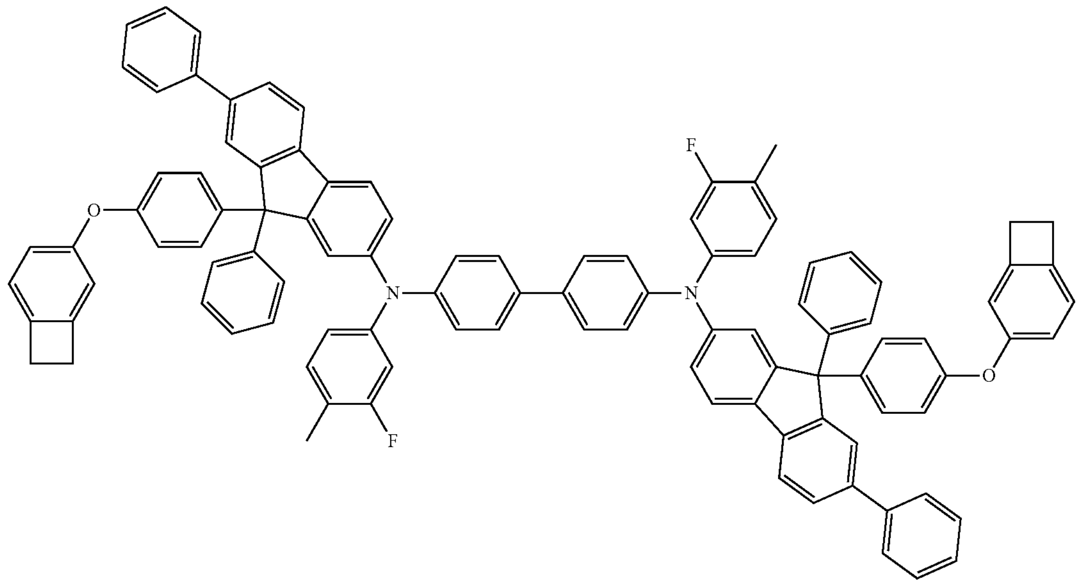
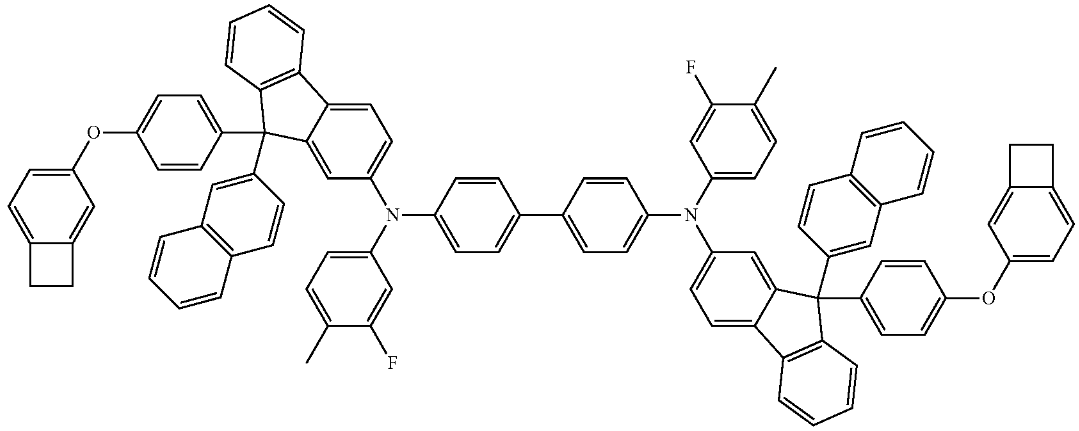
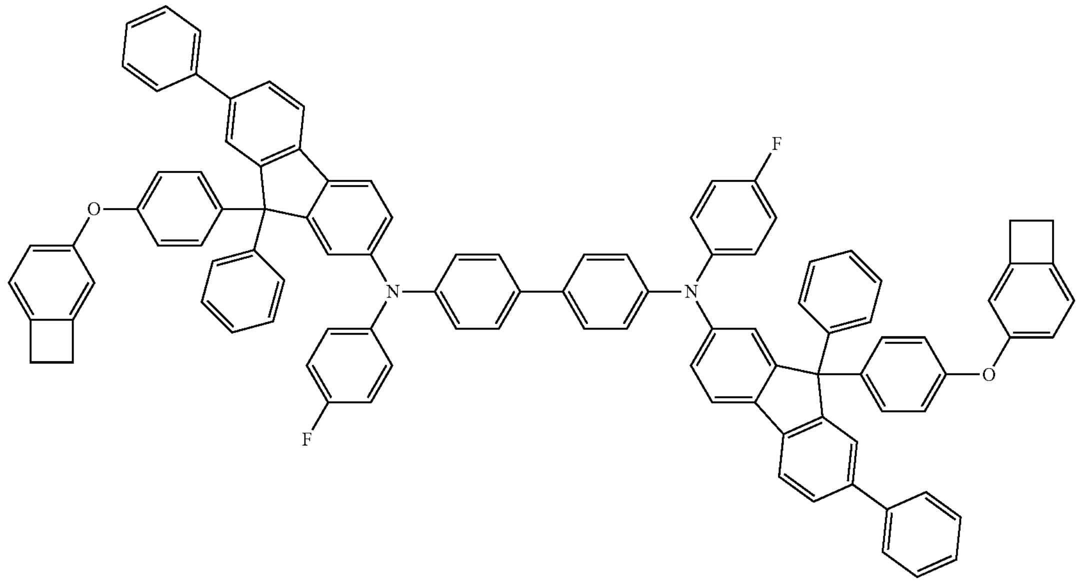

-continued
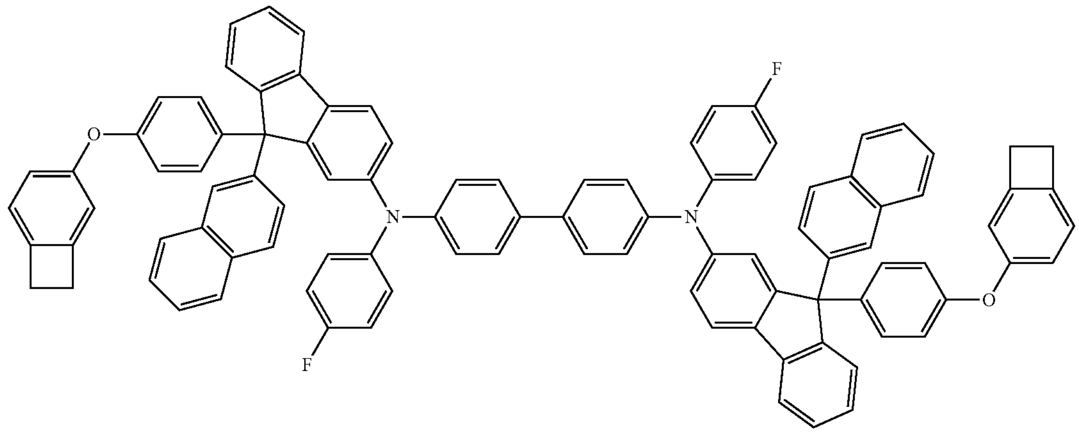
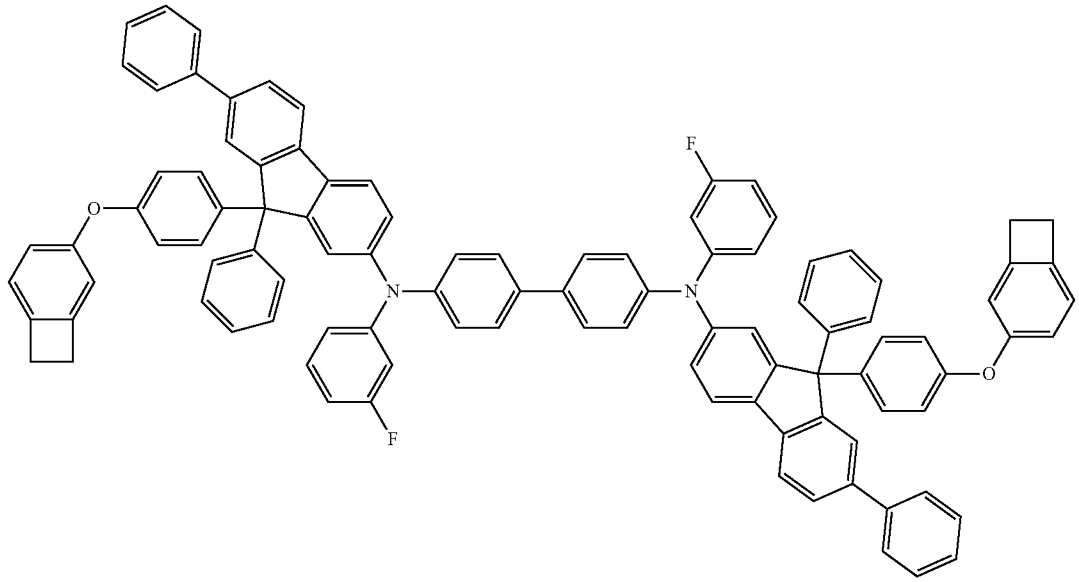
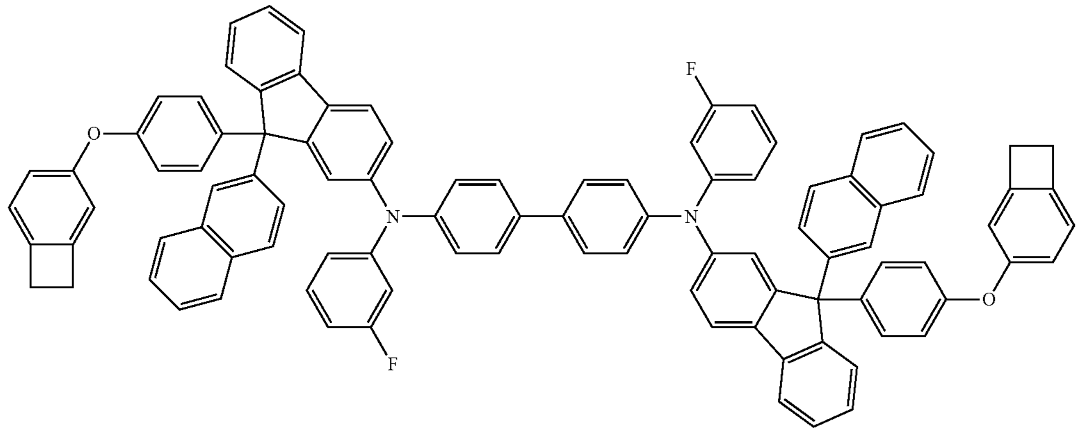

-continued
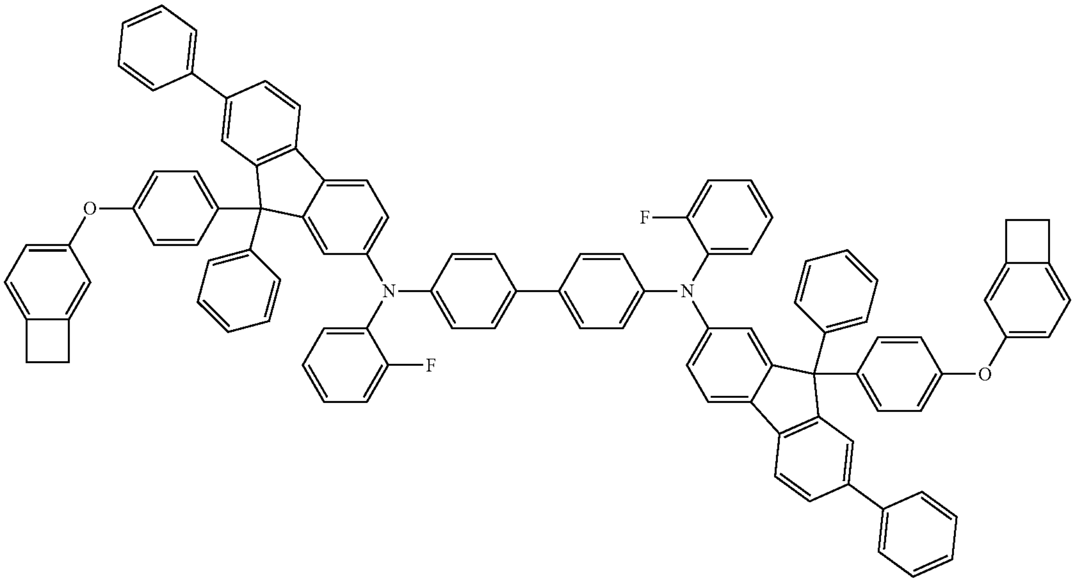
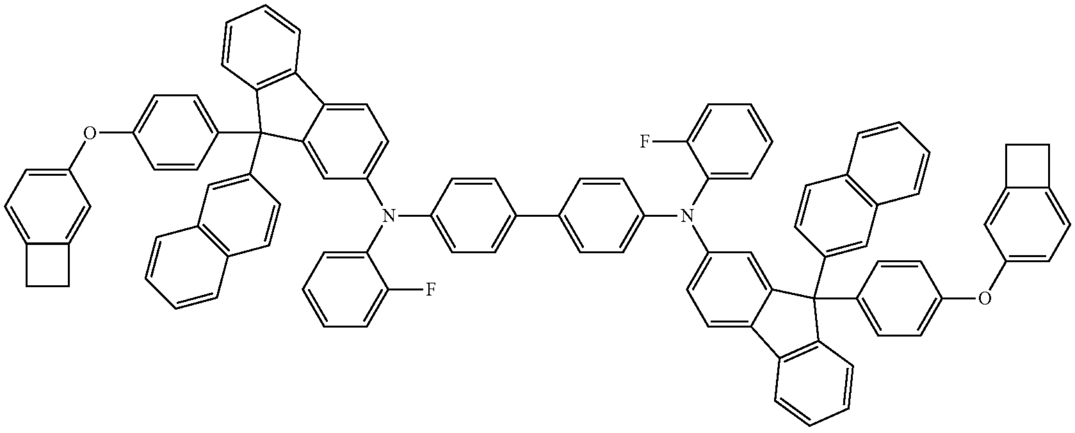
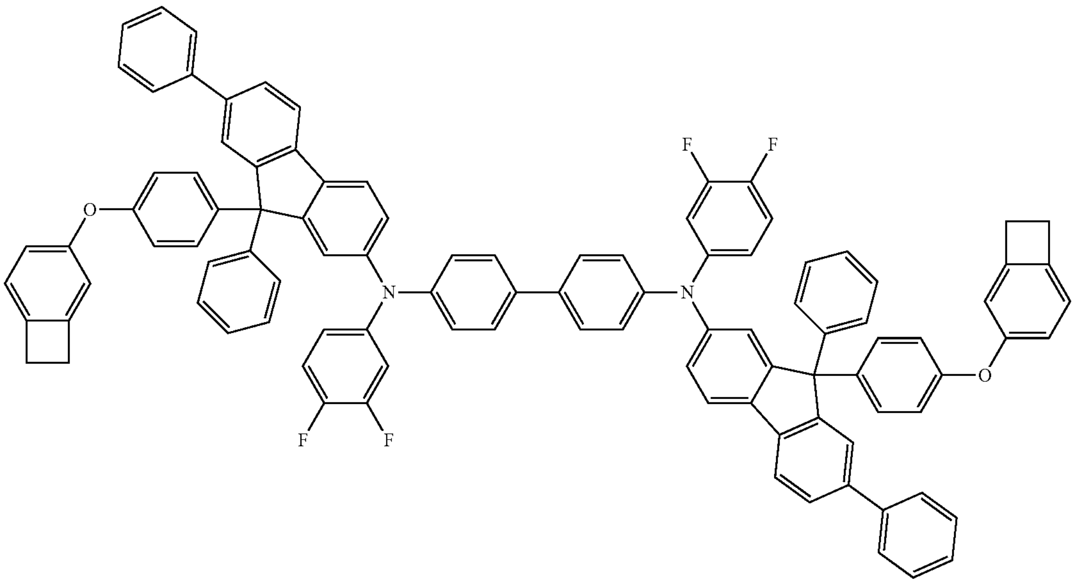

-continued
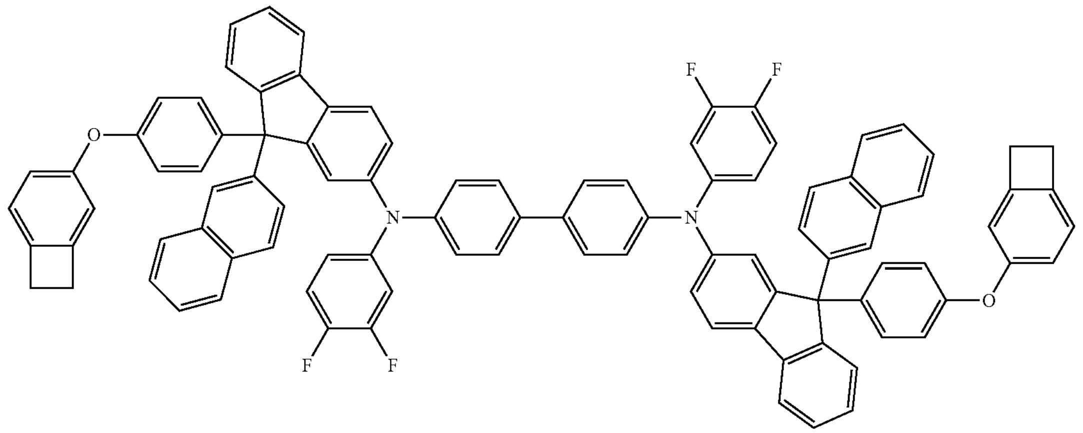
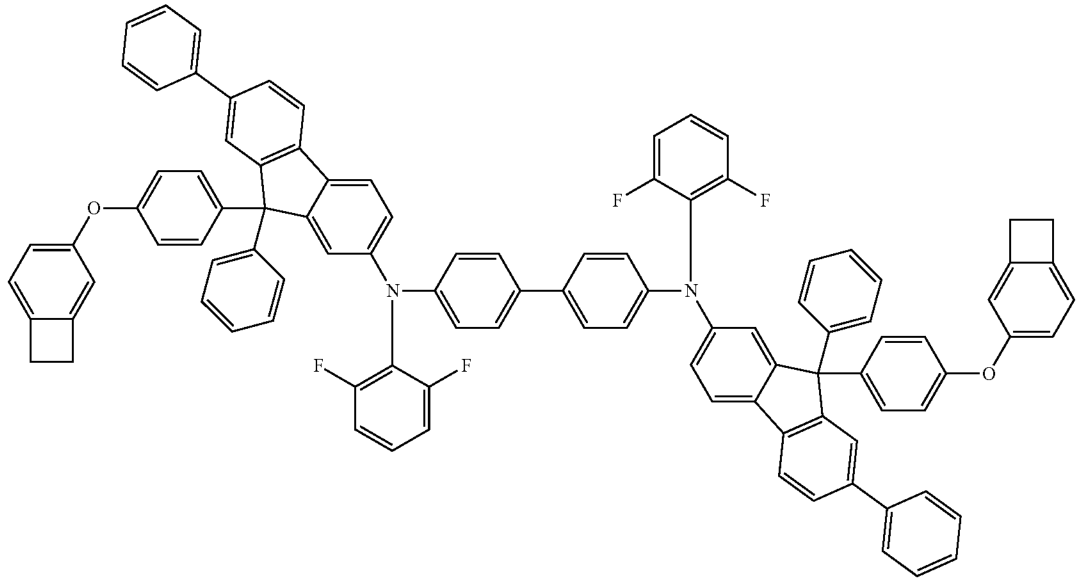
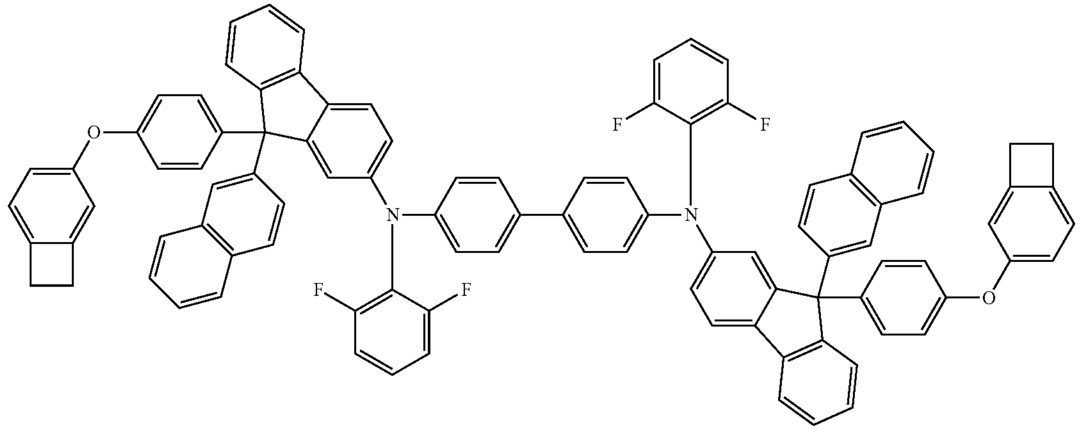

-continued
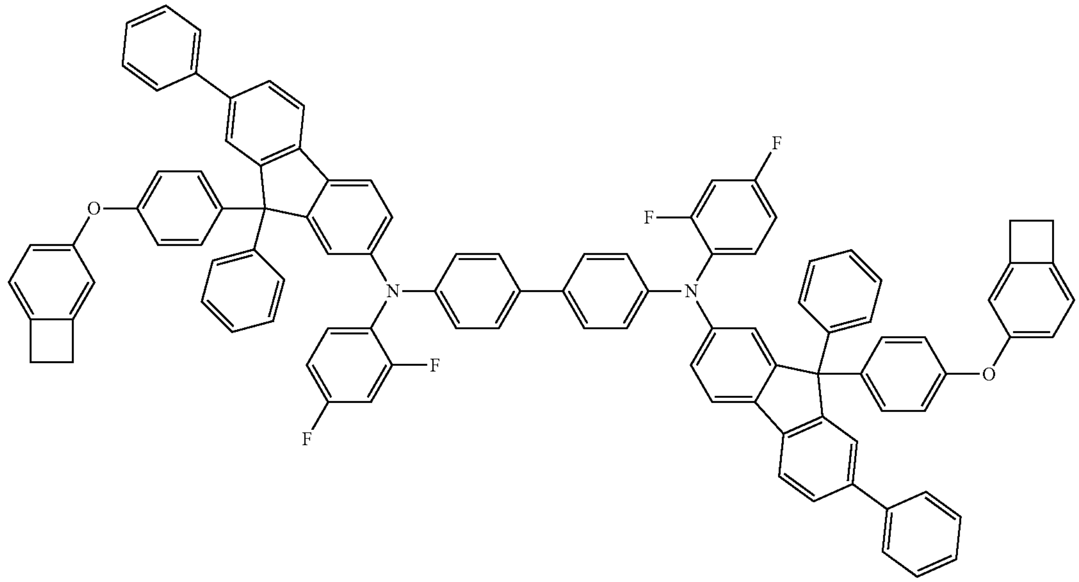
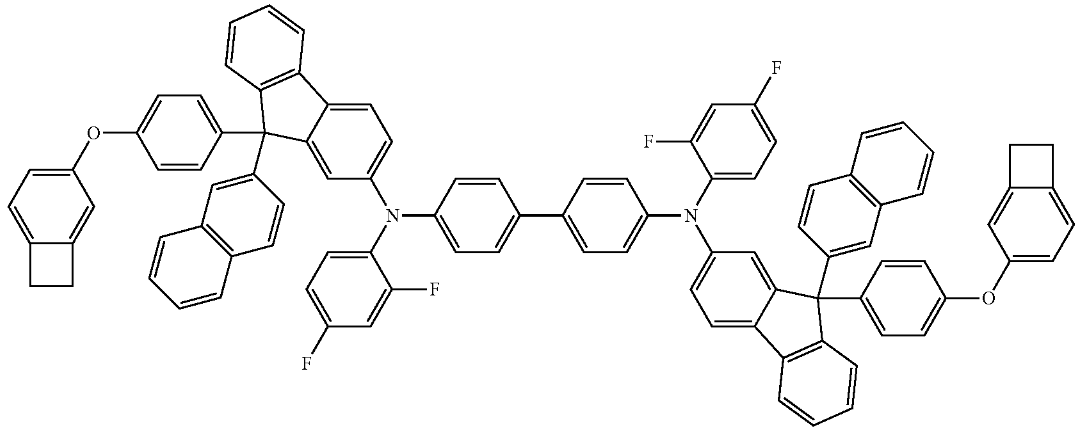
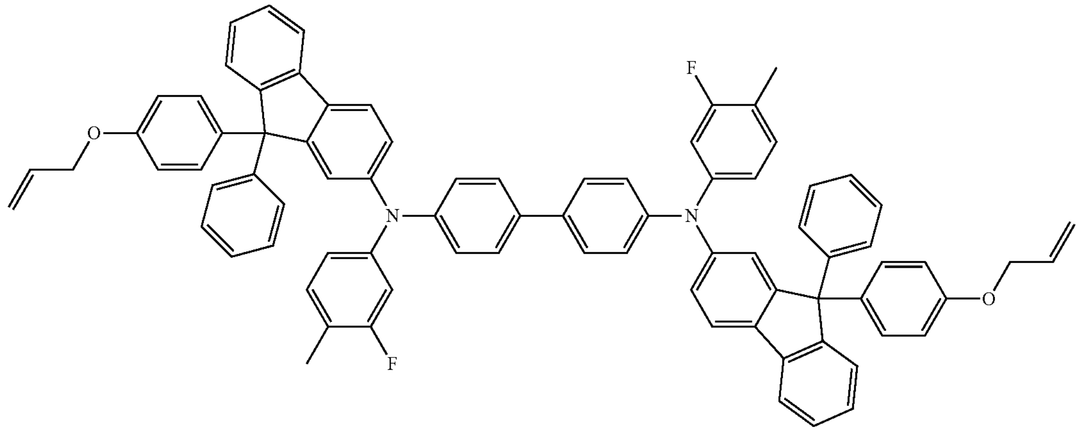

-continued
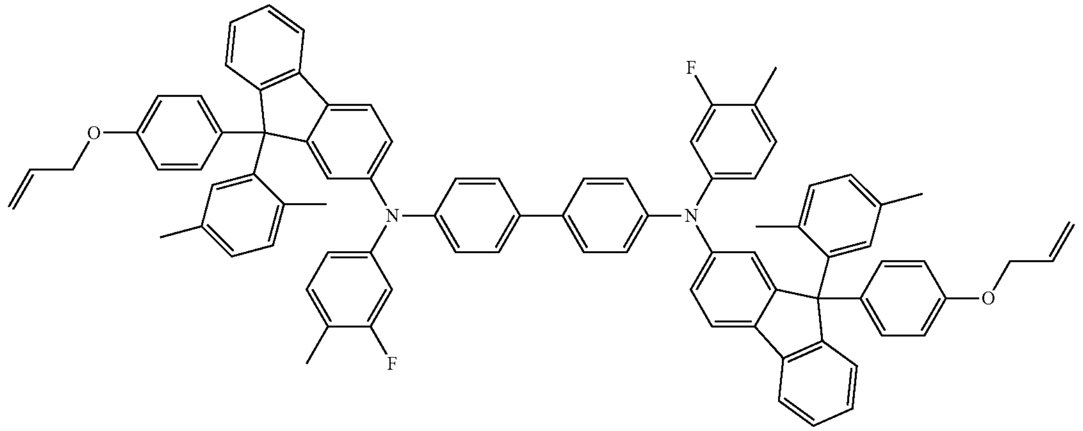
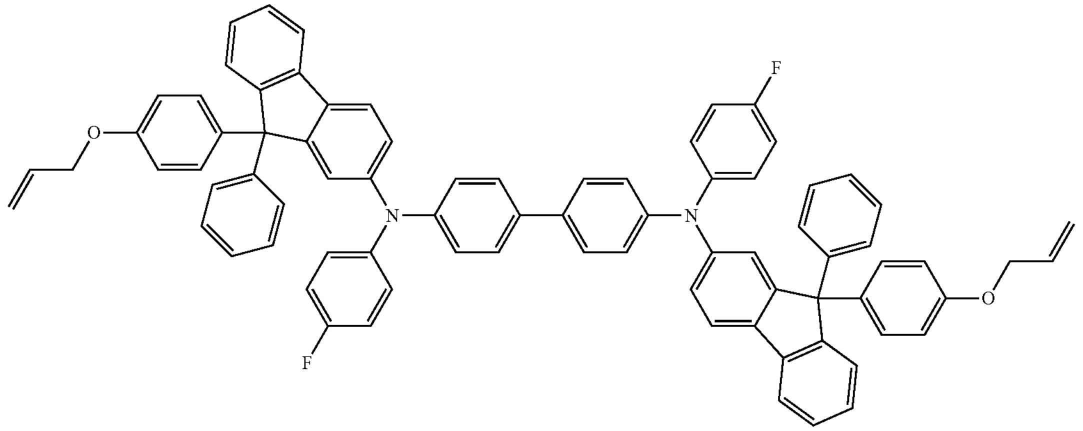
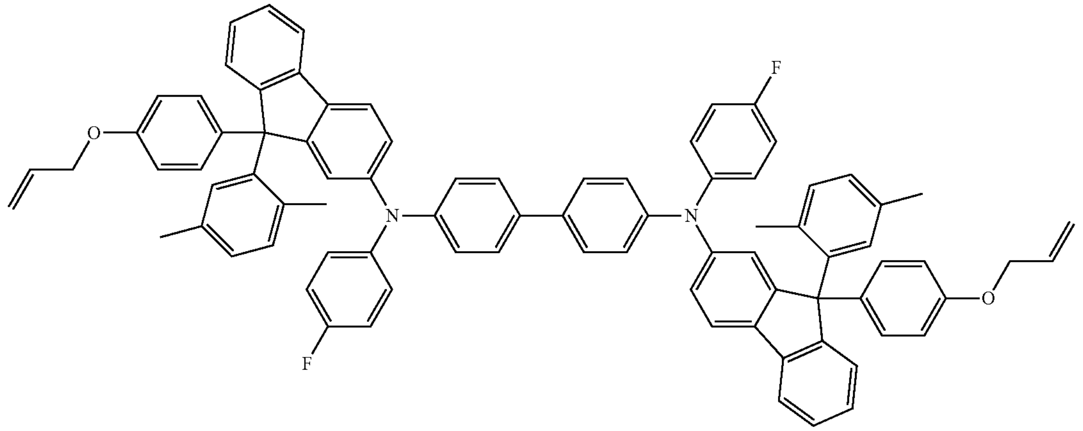
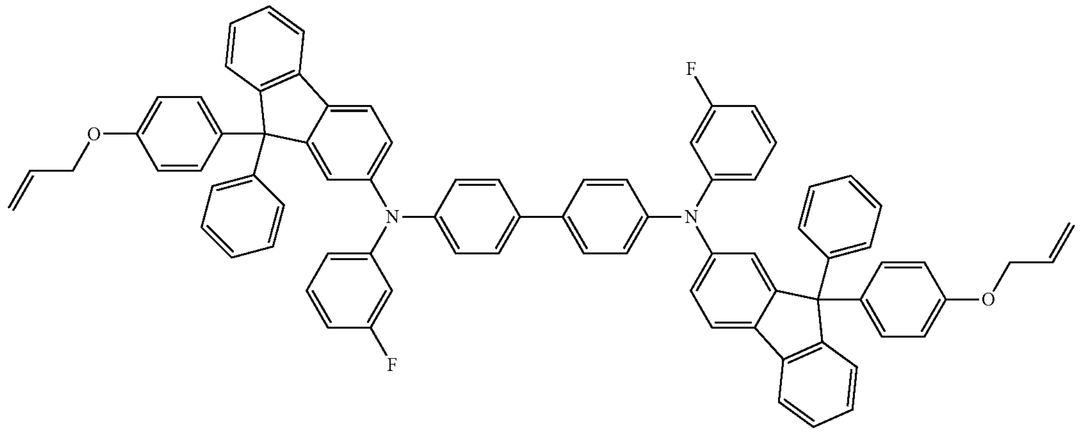

-continued
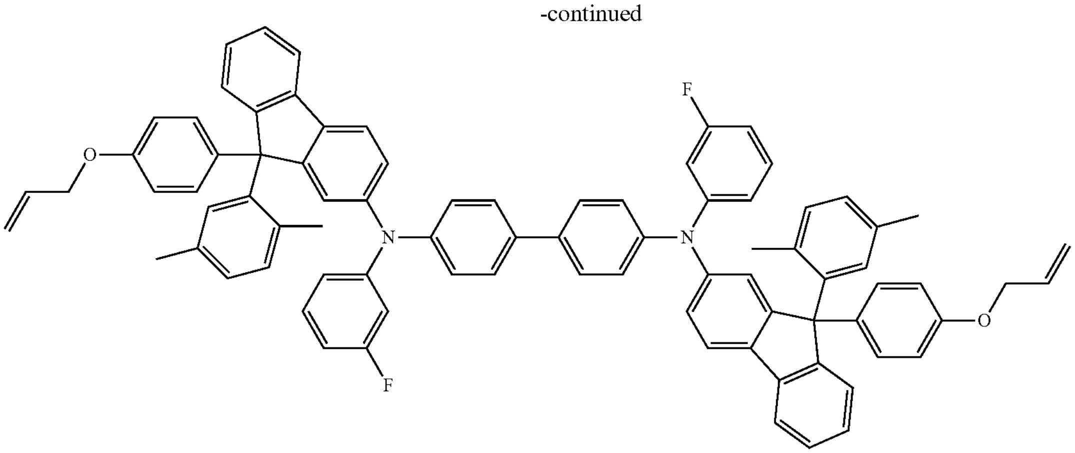
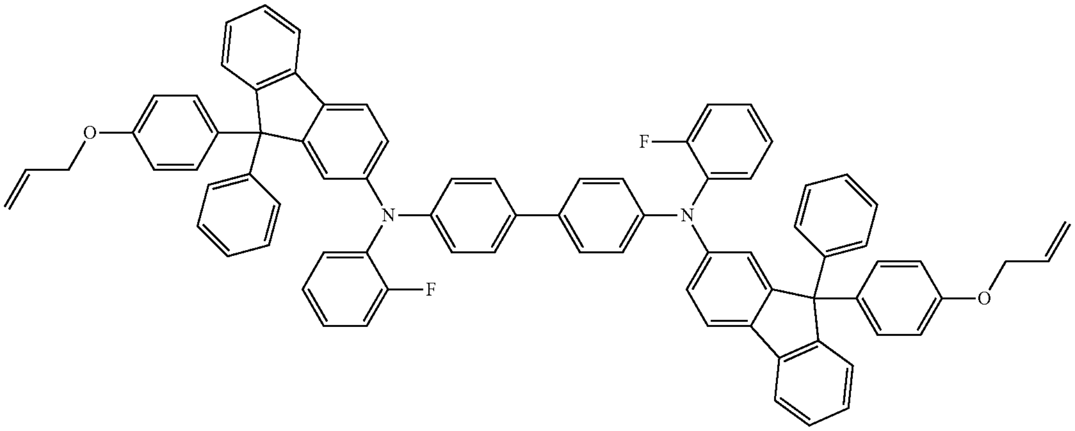
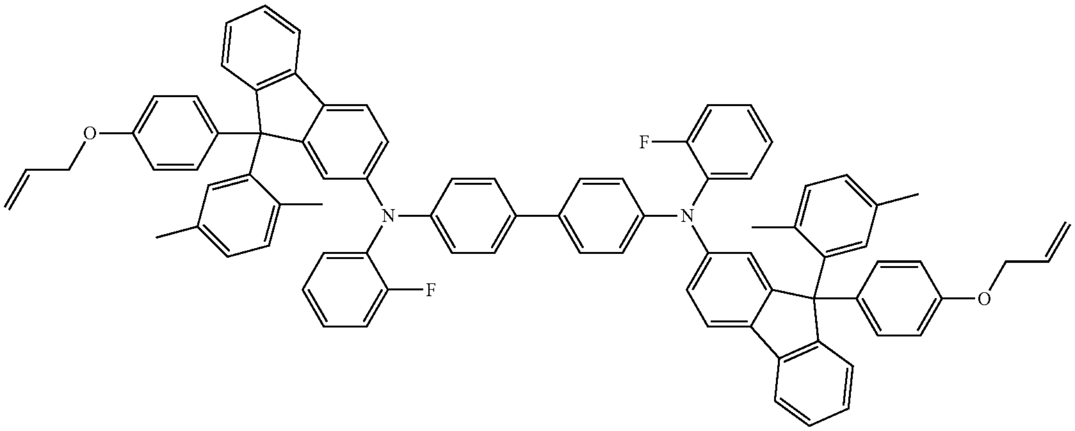
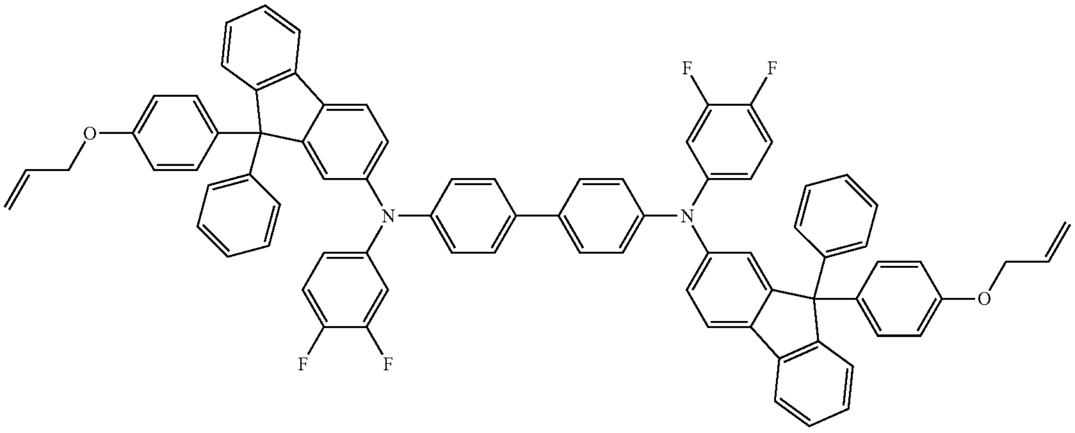

-continued
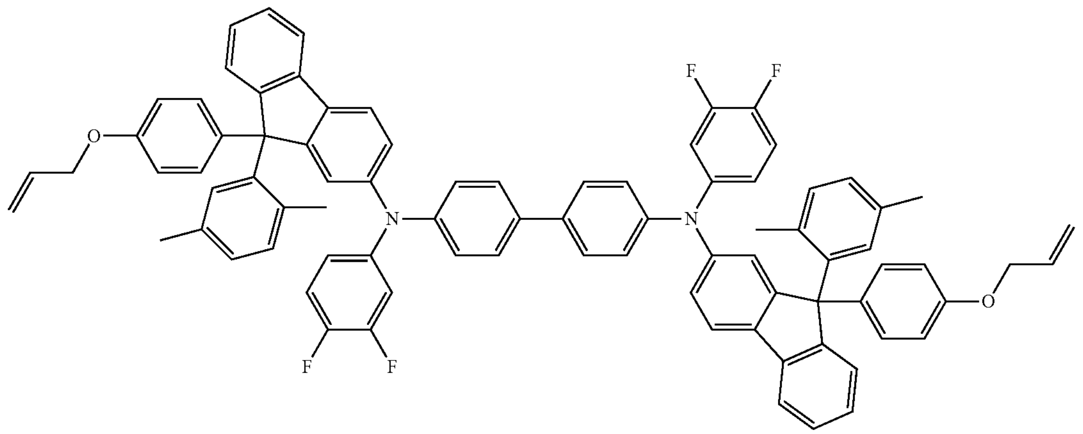
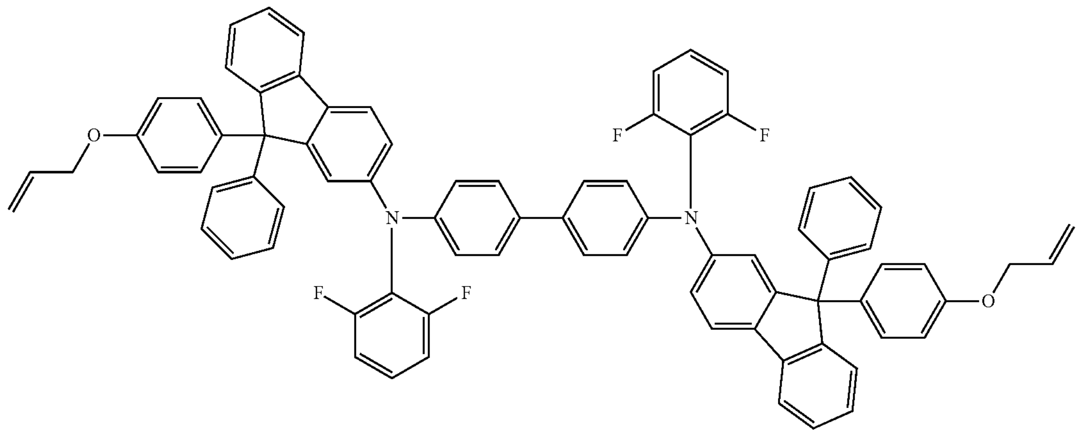
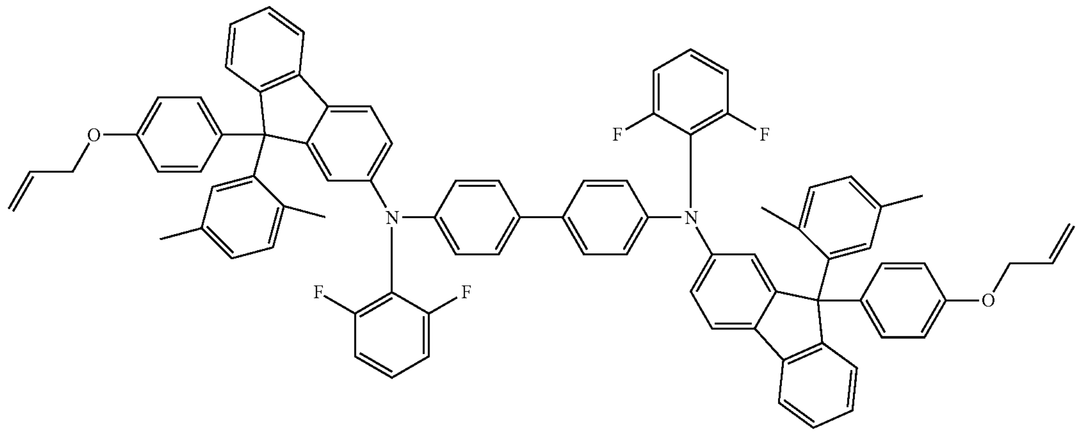

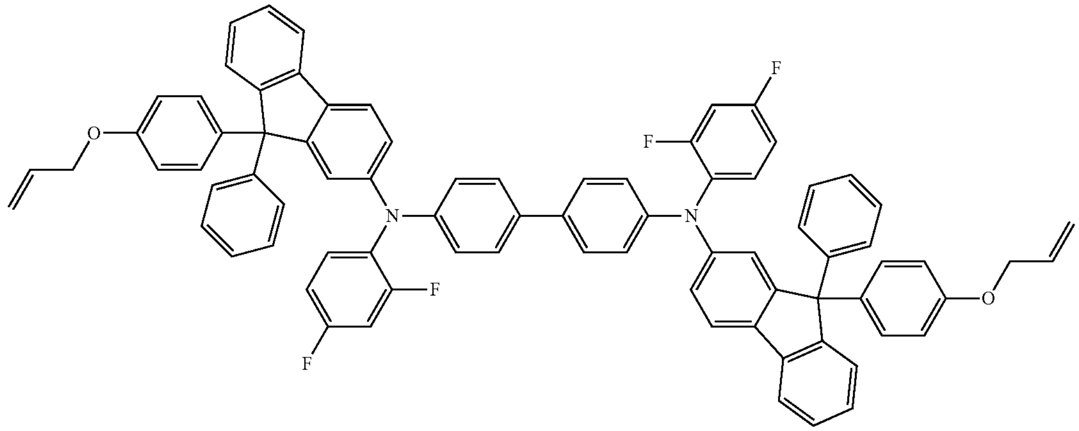
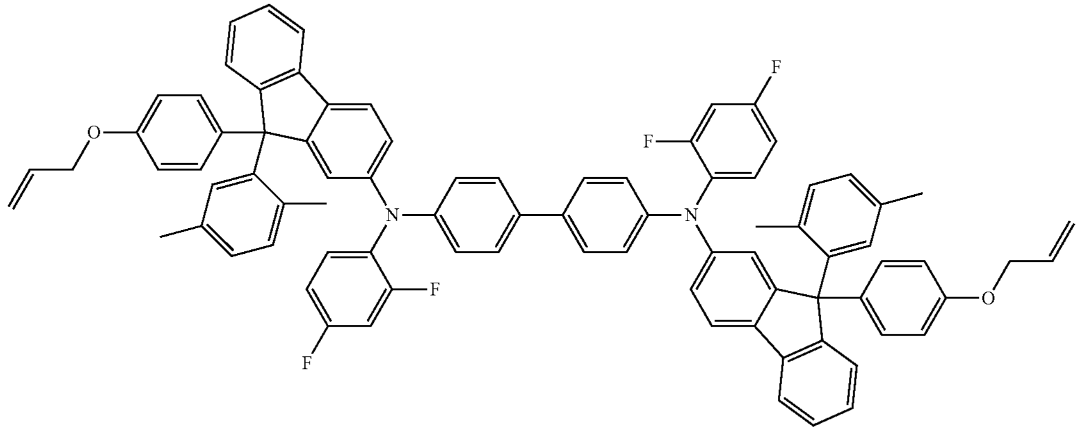
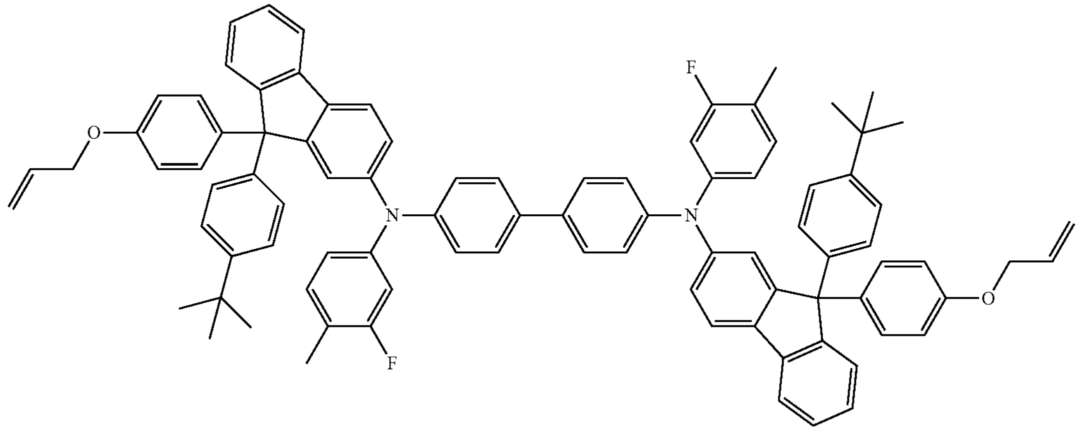
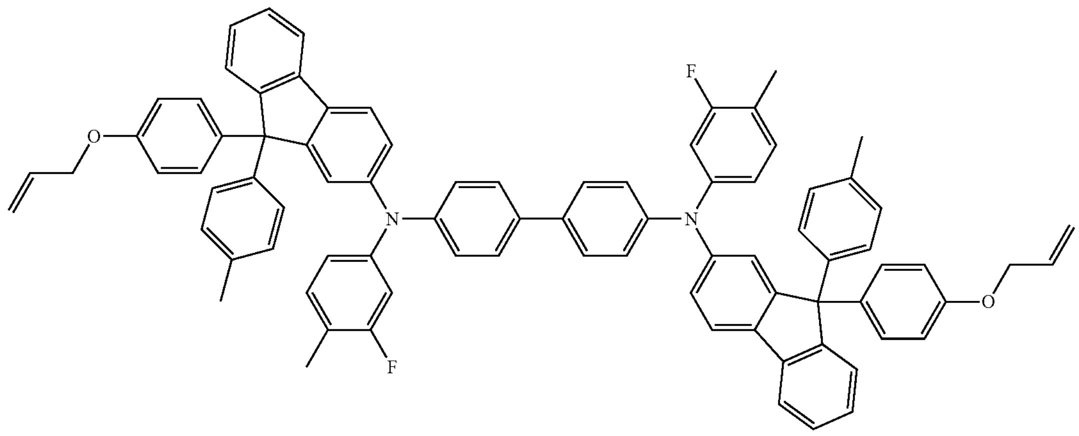

-continued
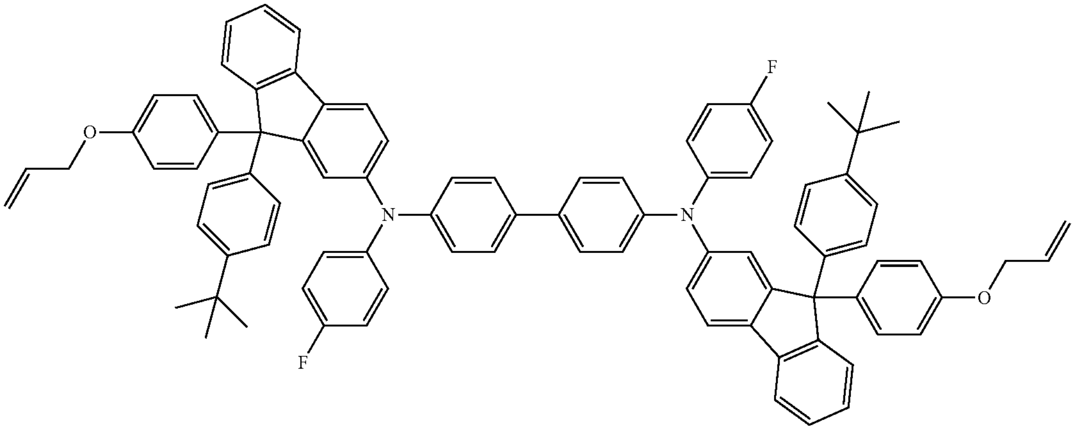
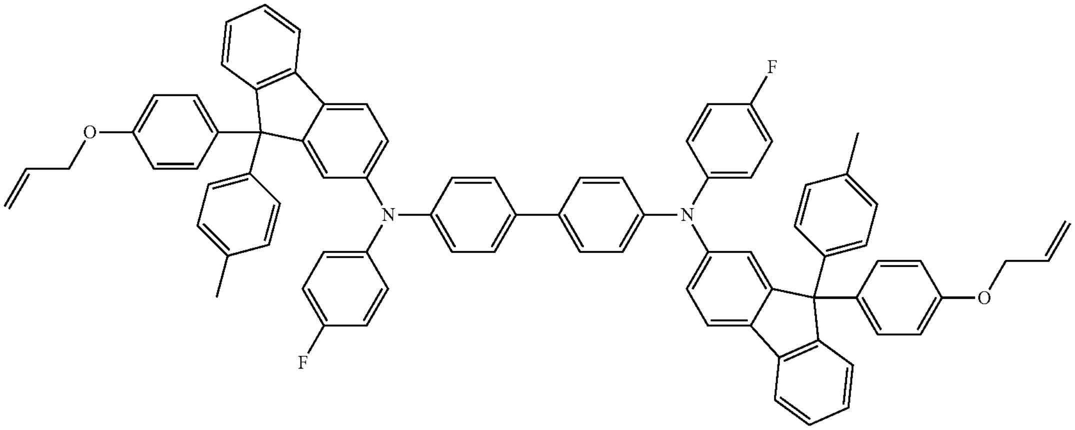
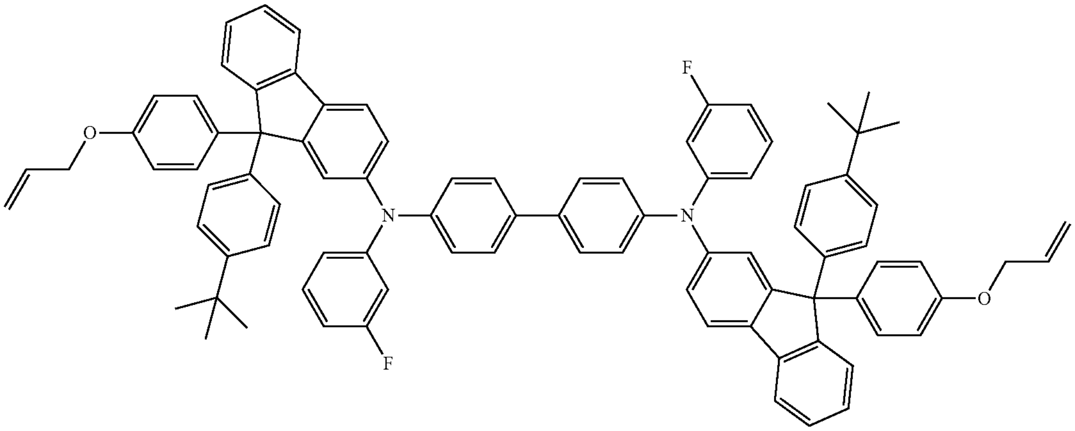
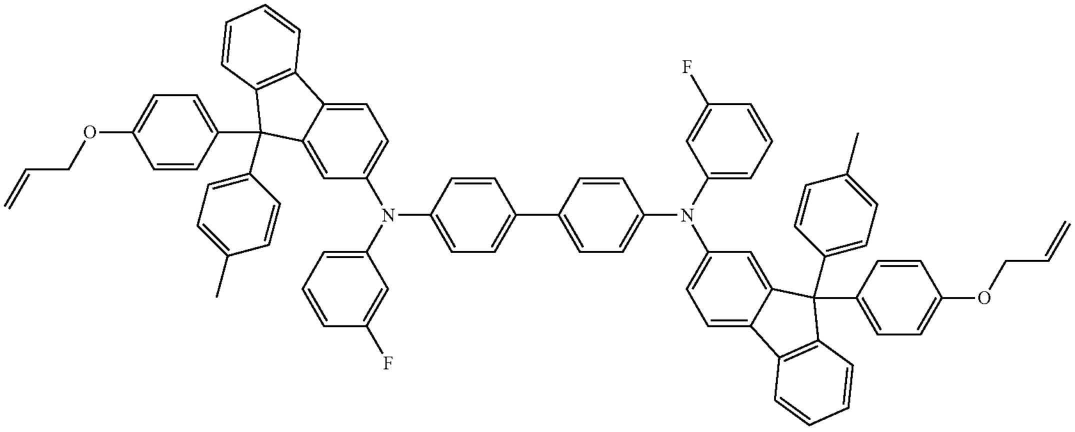

-continued
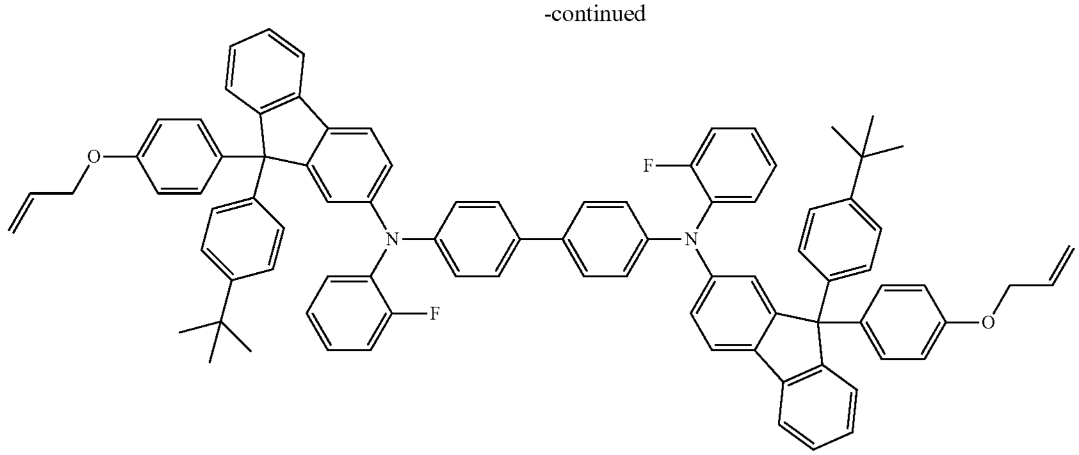
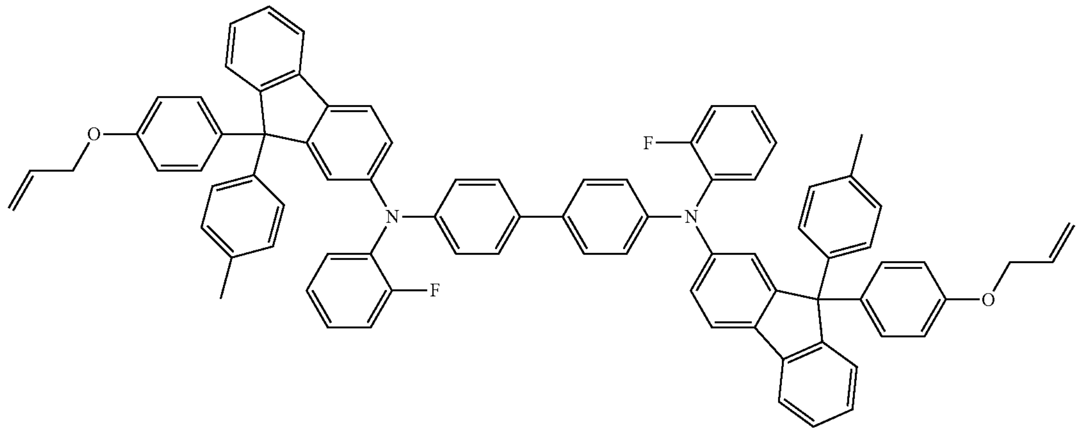
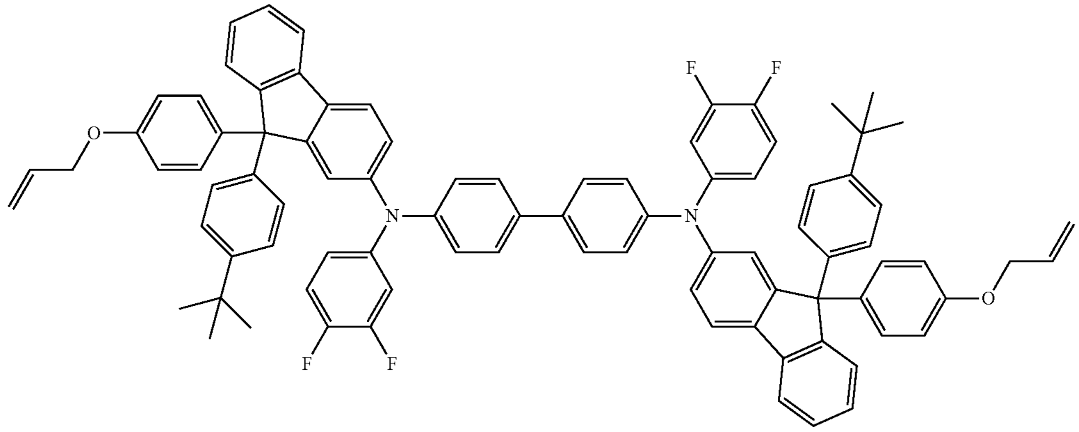
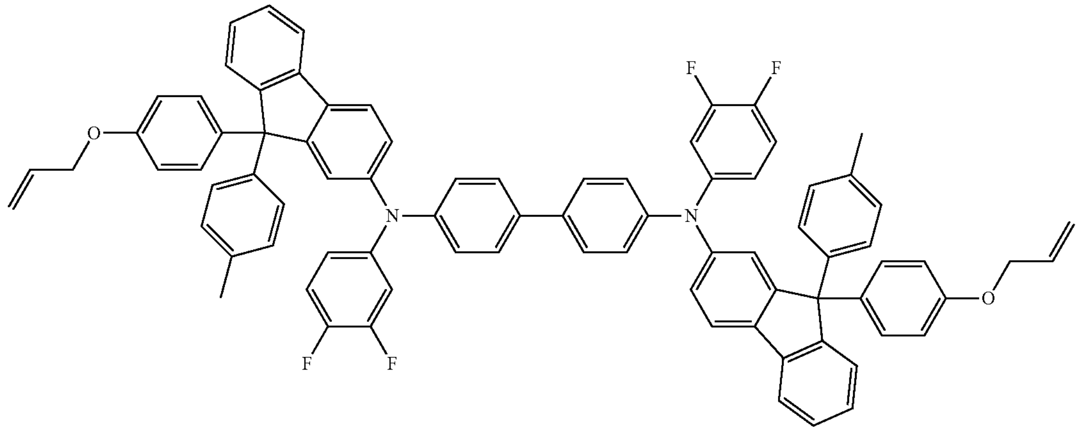

-continued
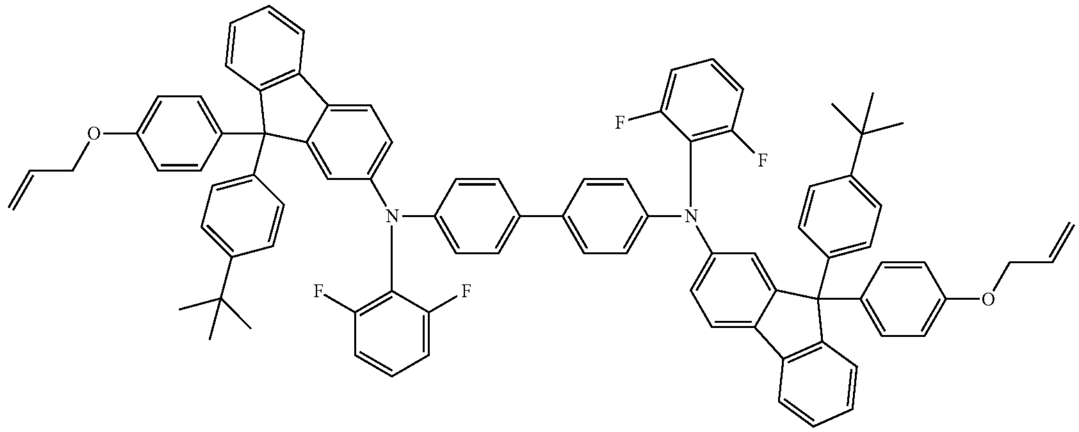
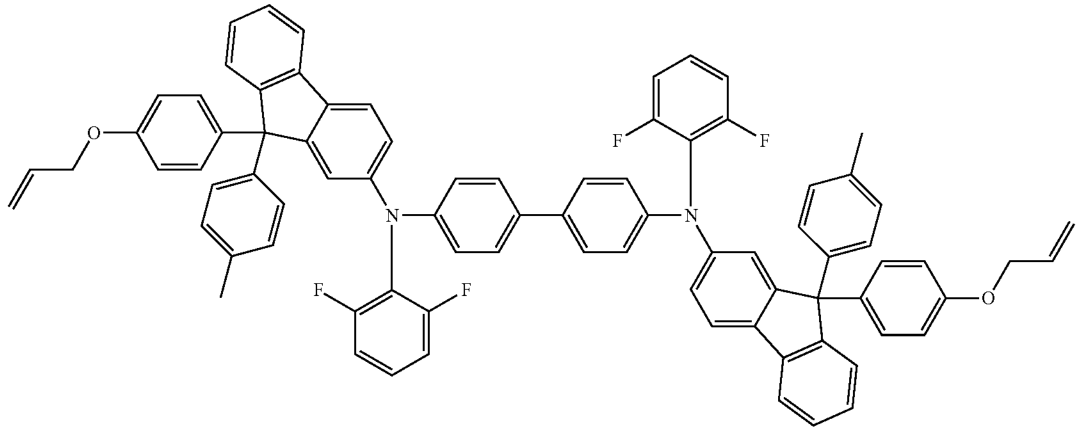
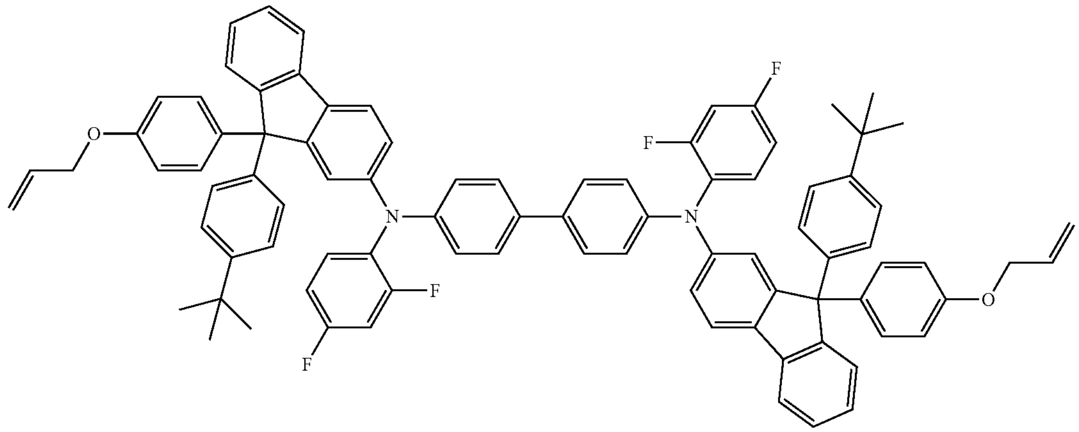
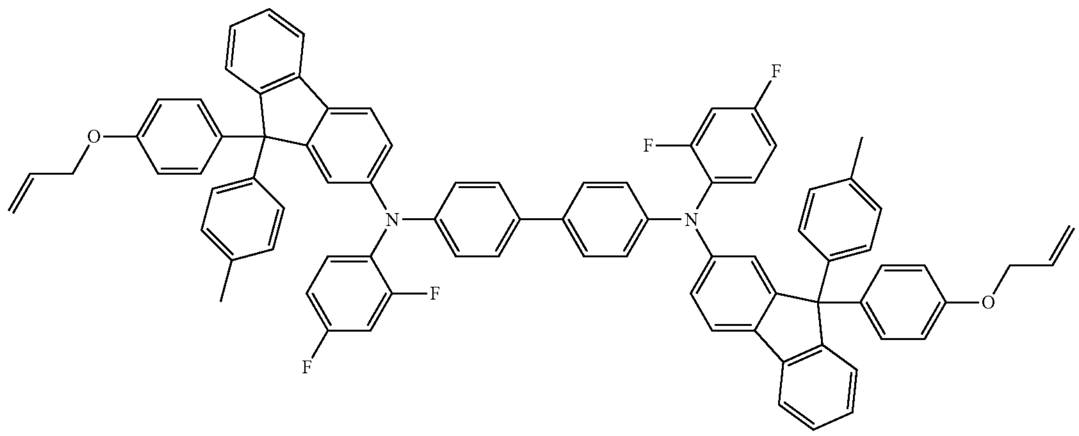

-continued
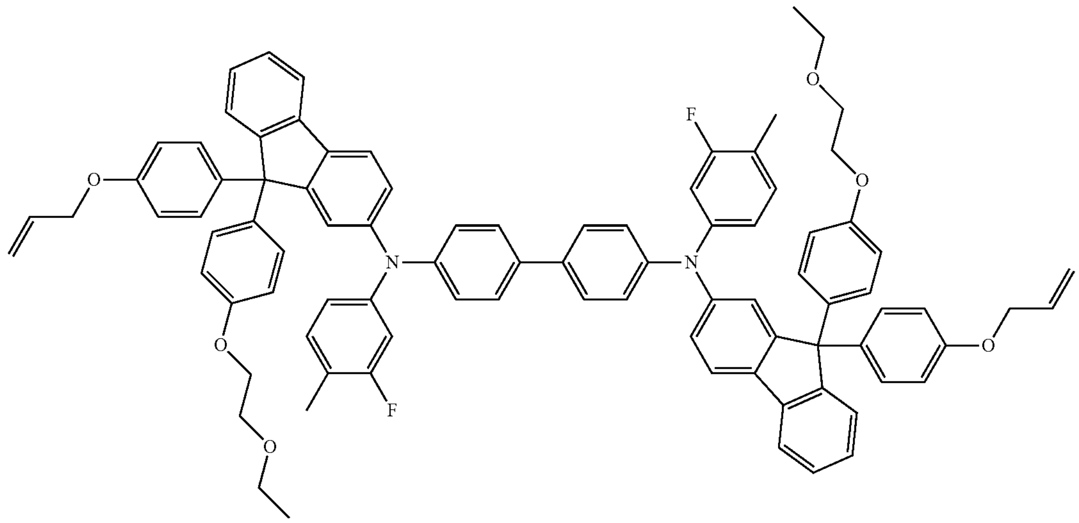
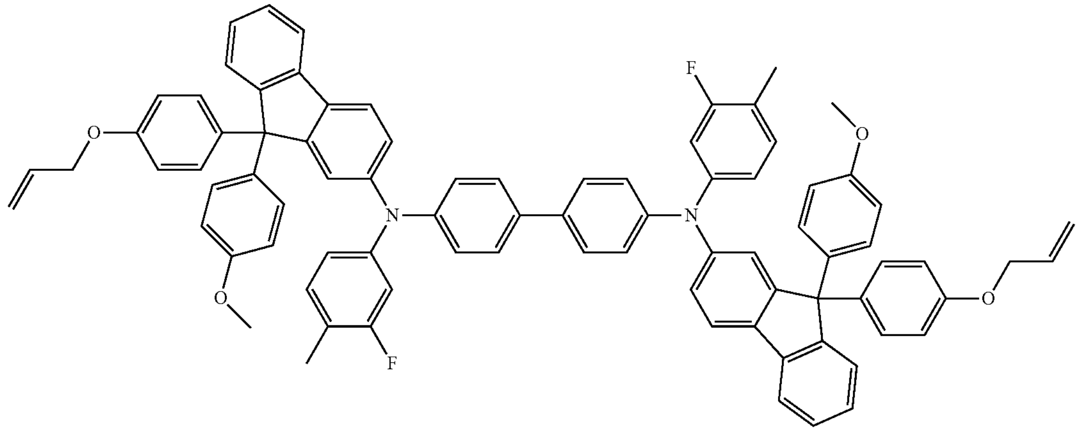
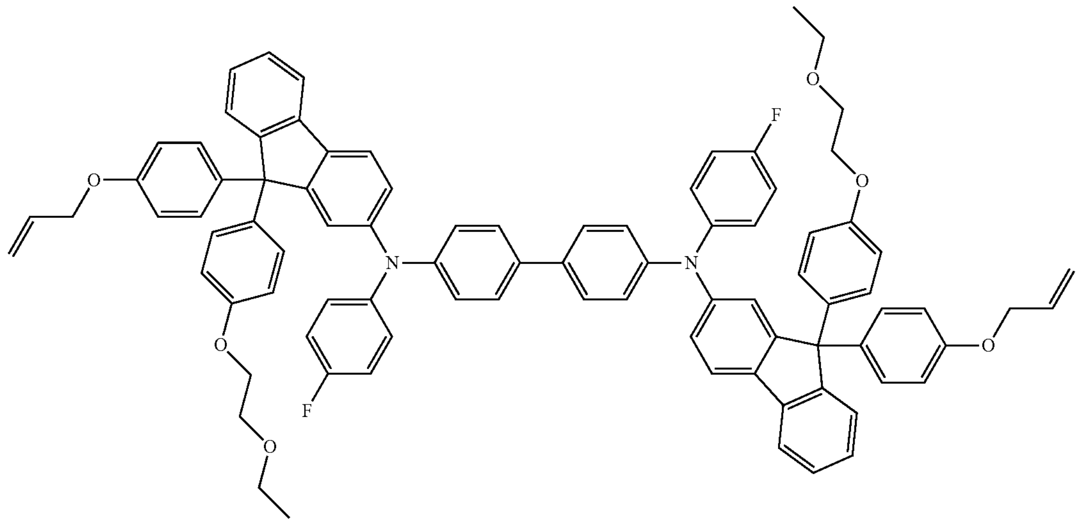

-continued
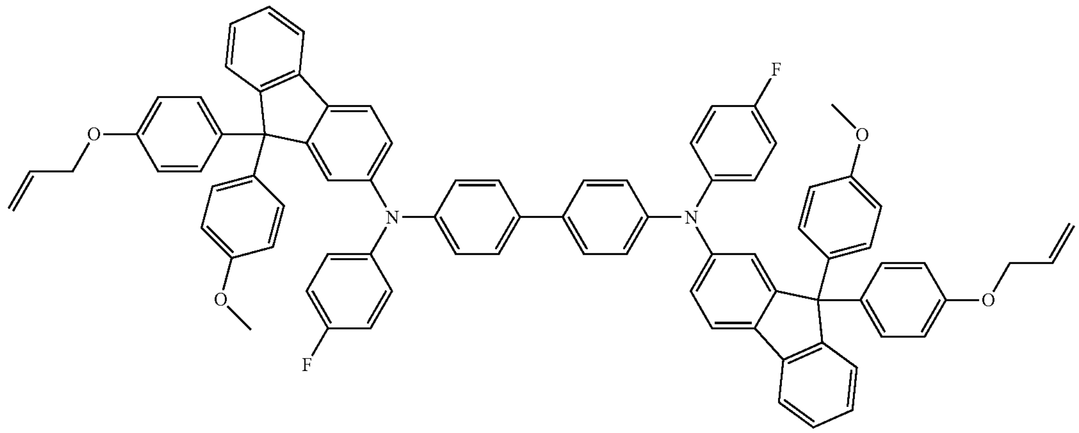
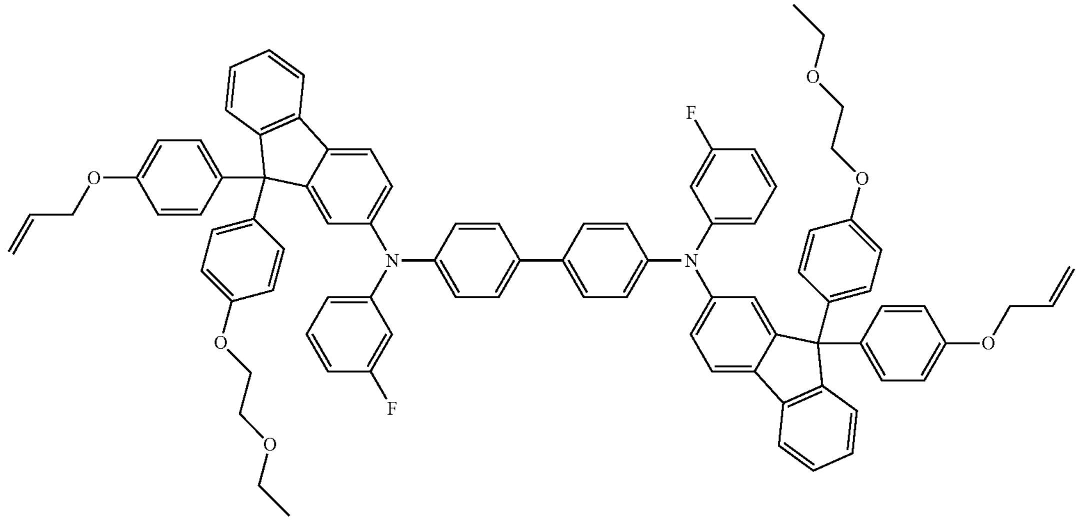
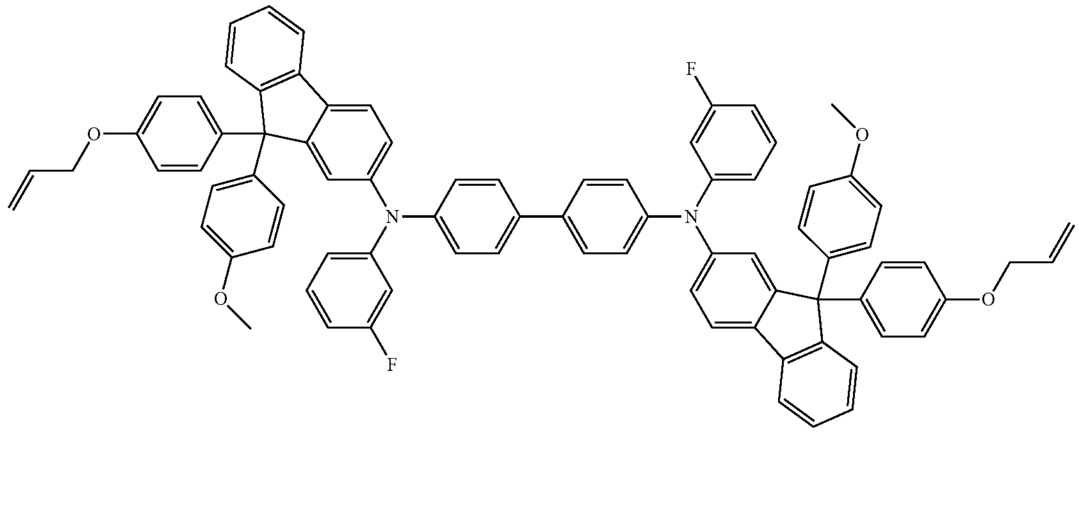

-continued
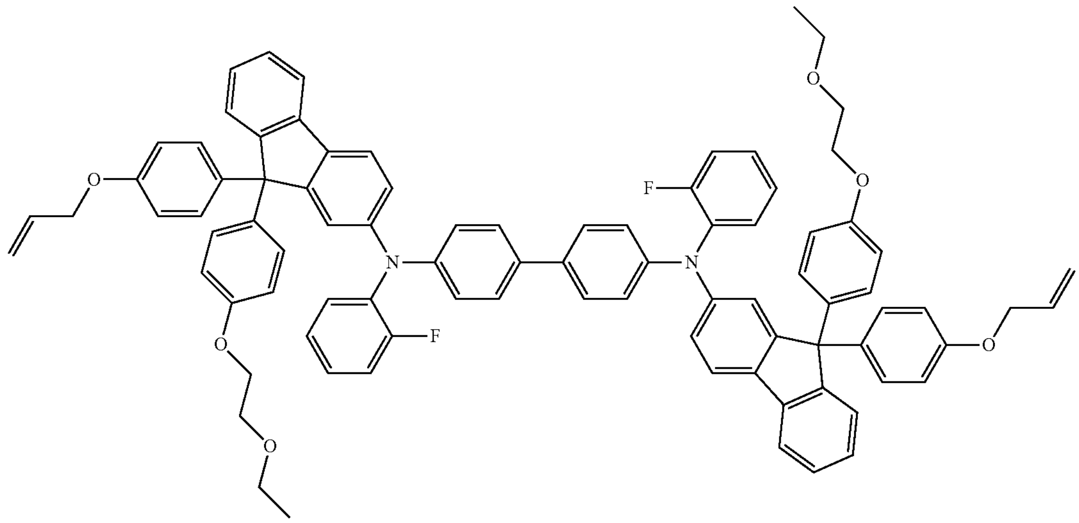
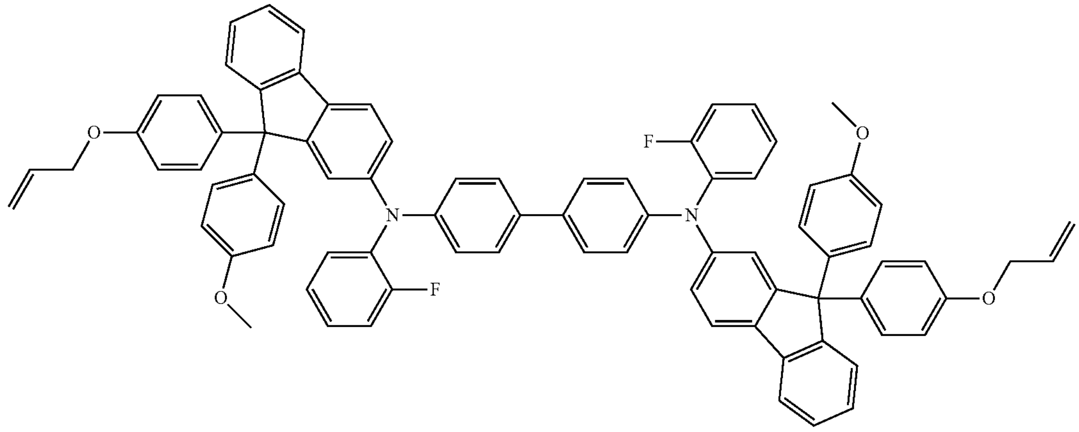
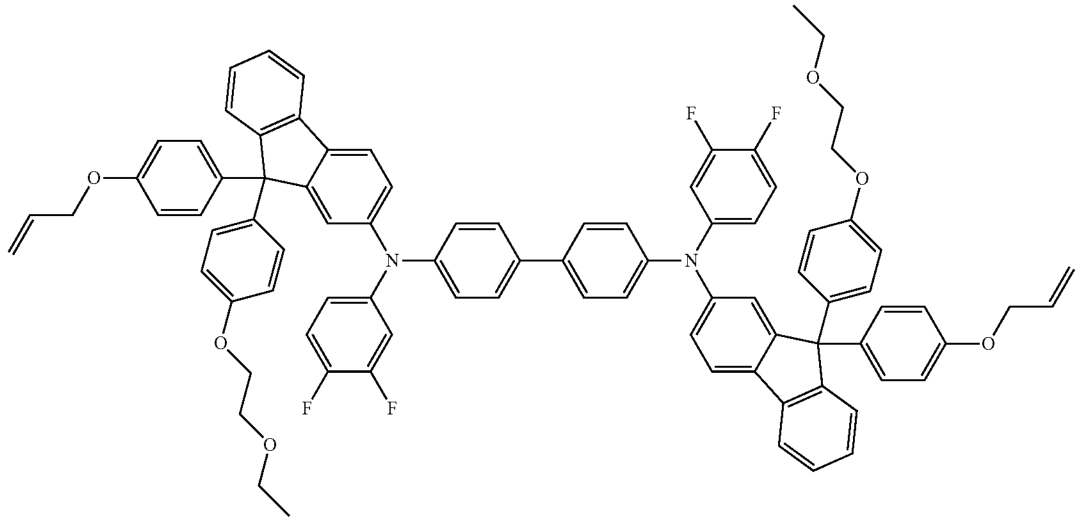

-continued
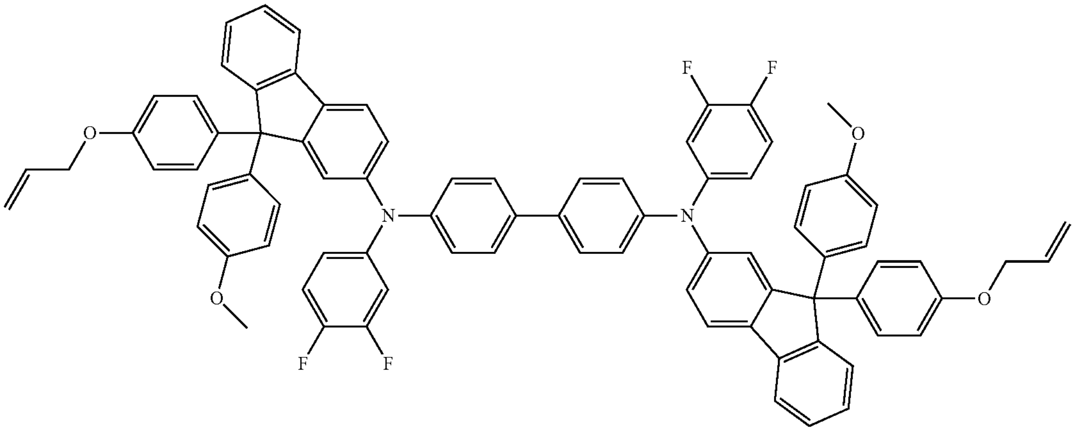
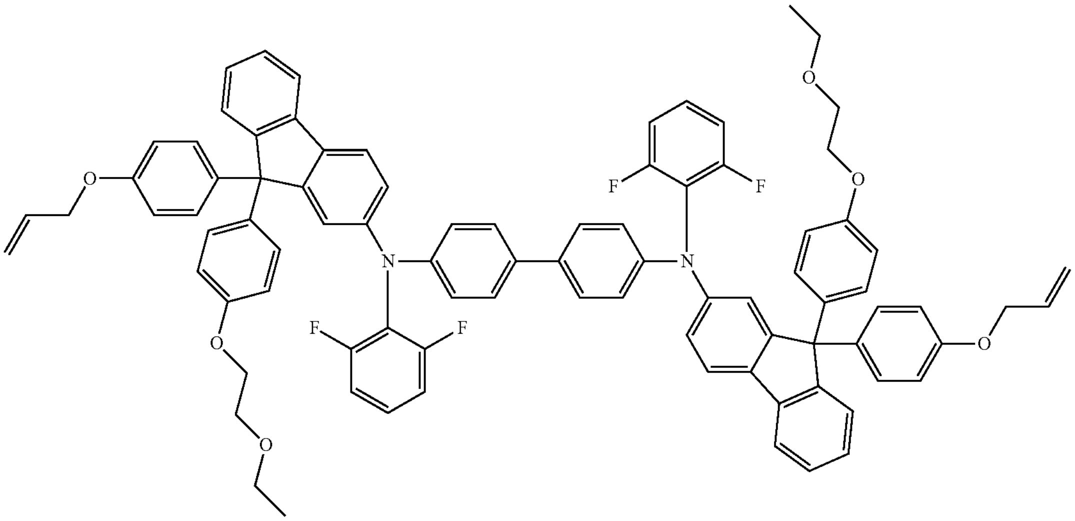
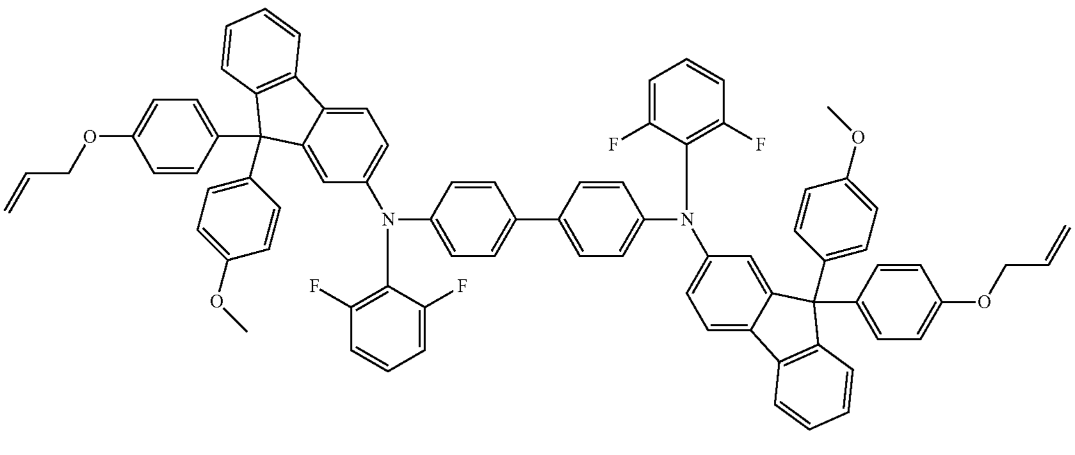

-continued
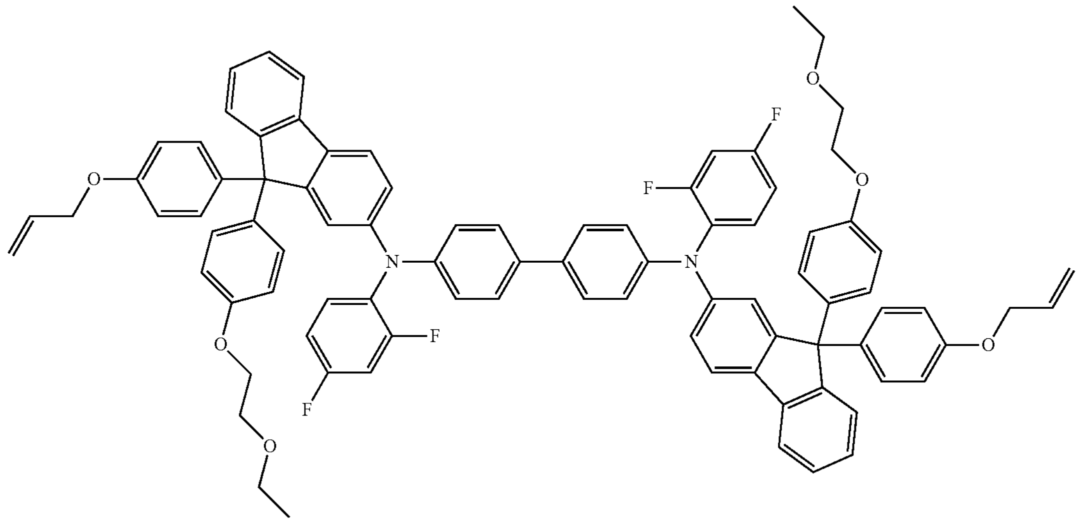
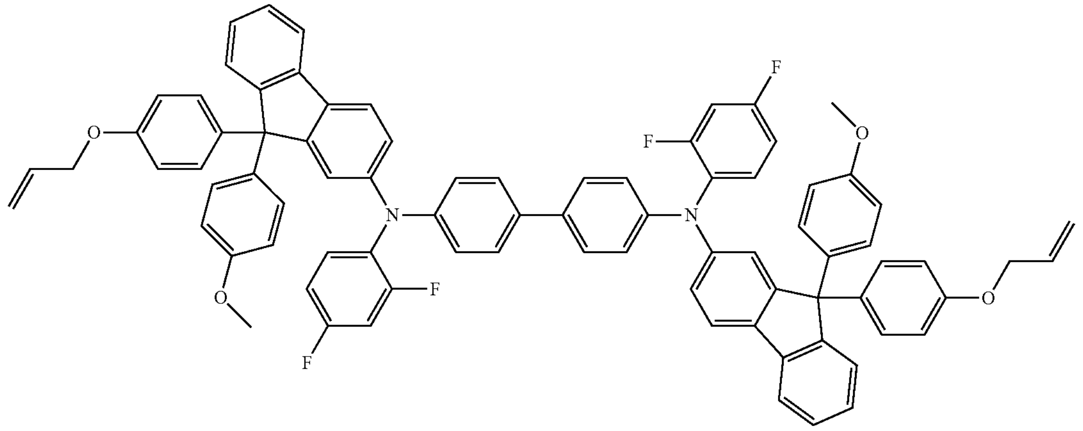
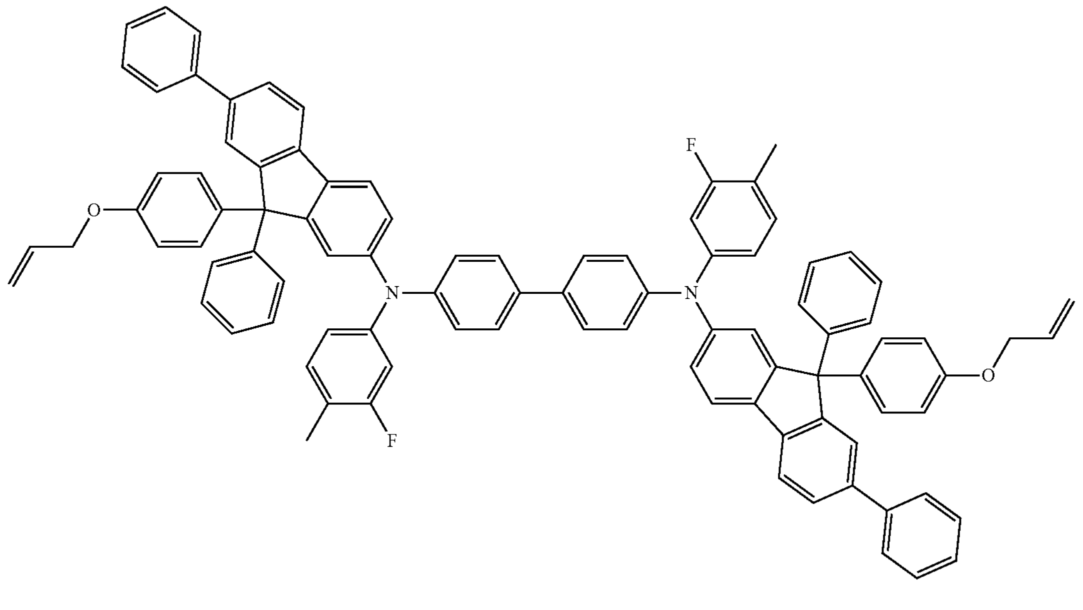

-continued
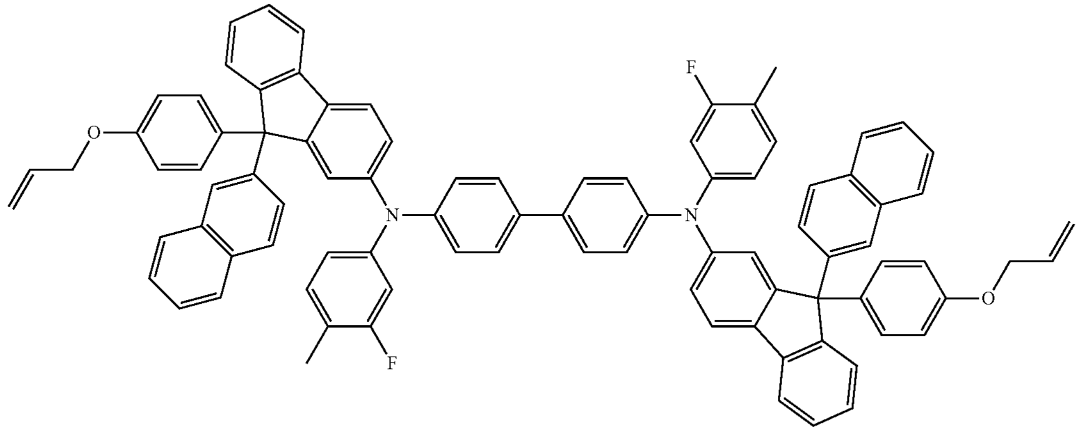
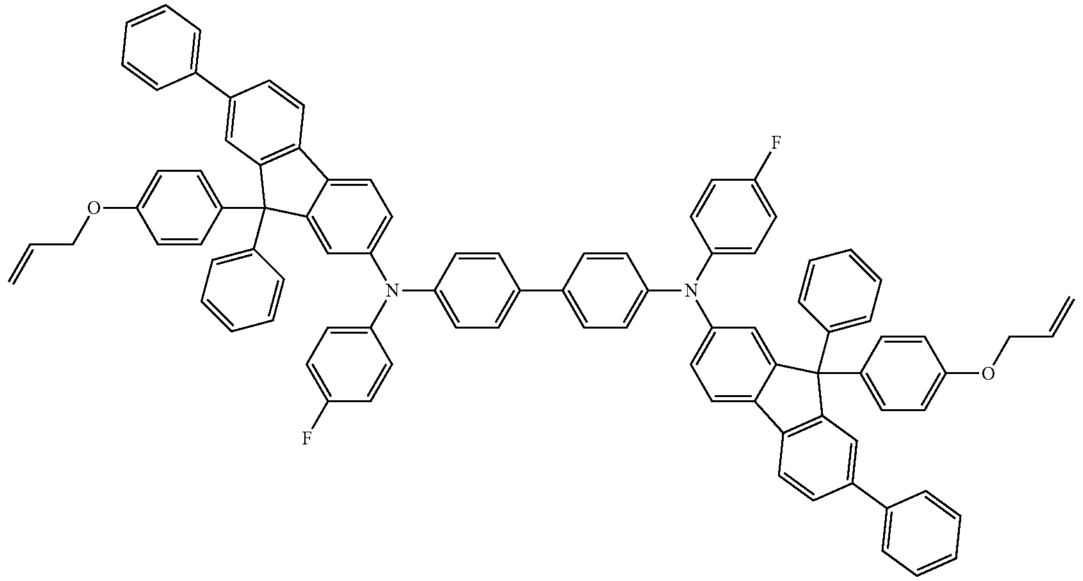
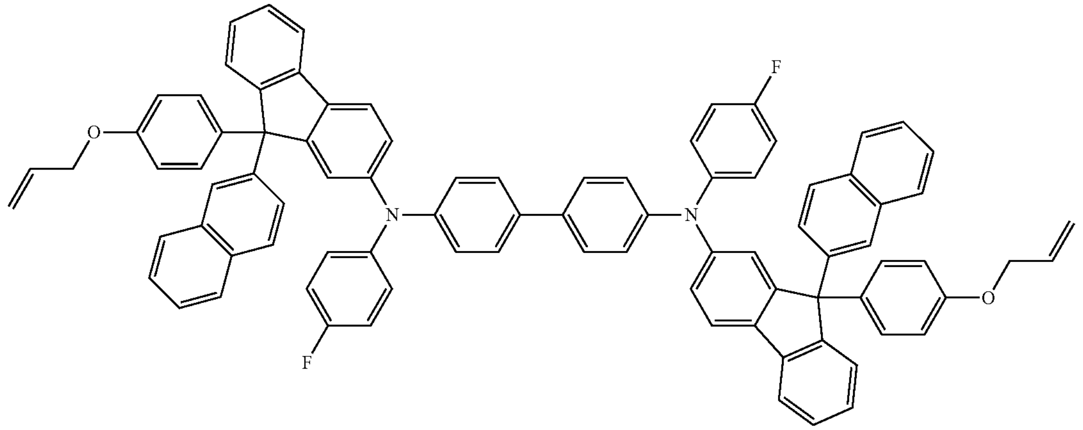

-continued
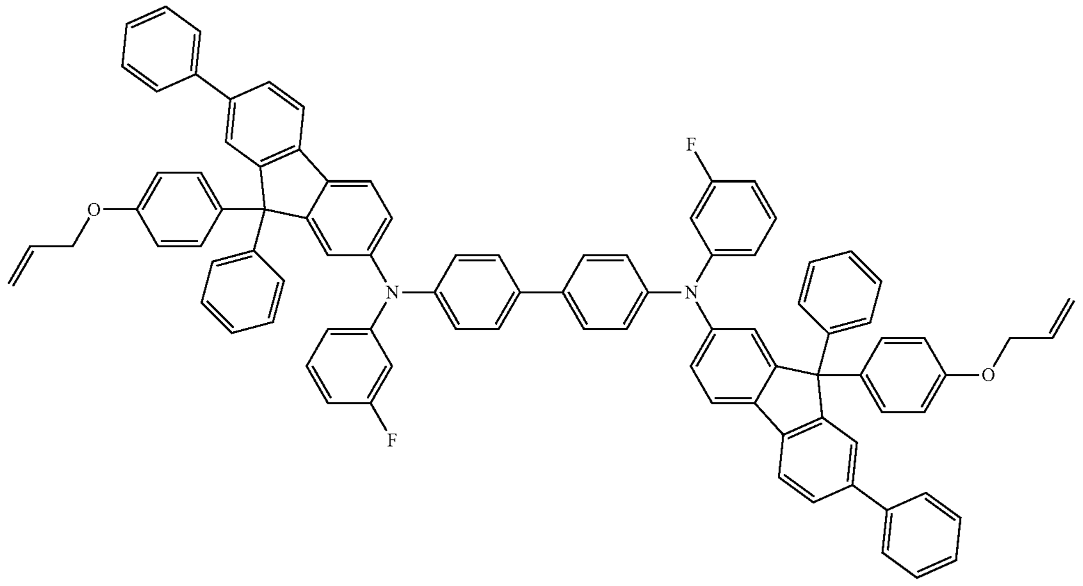
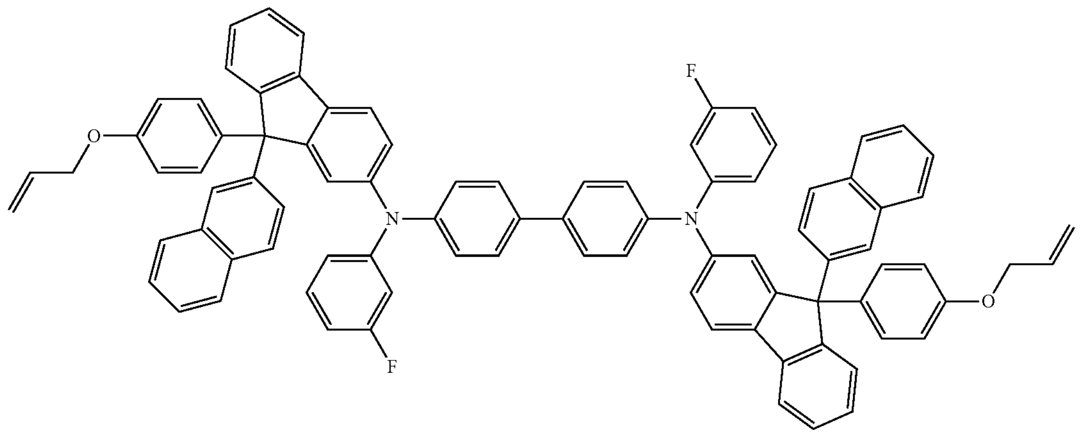
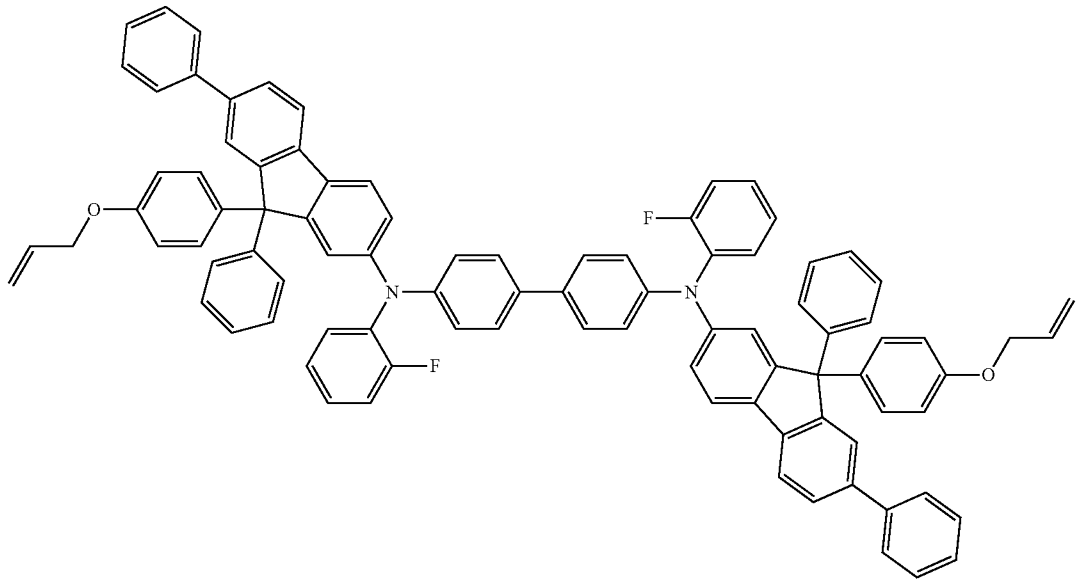

-continued
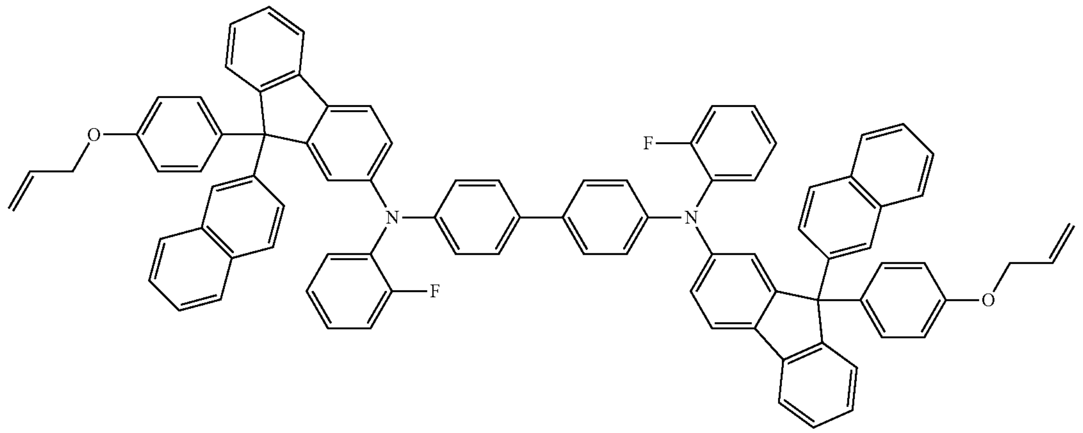
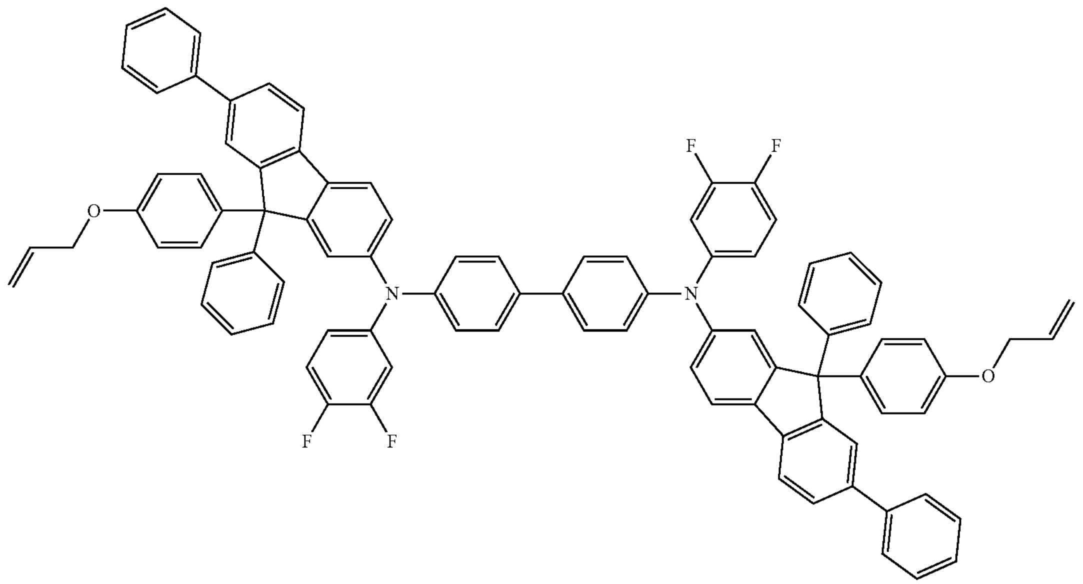
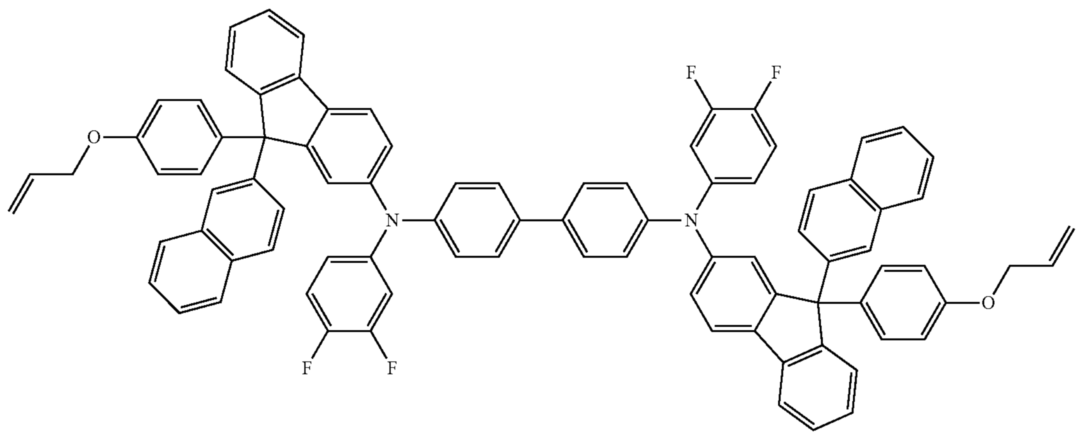

-continued
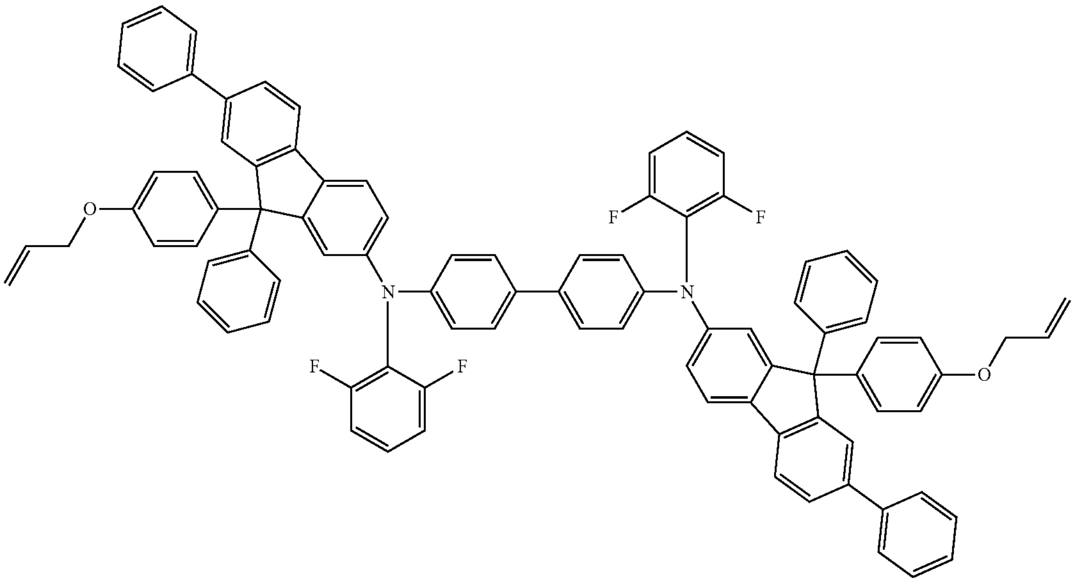
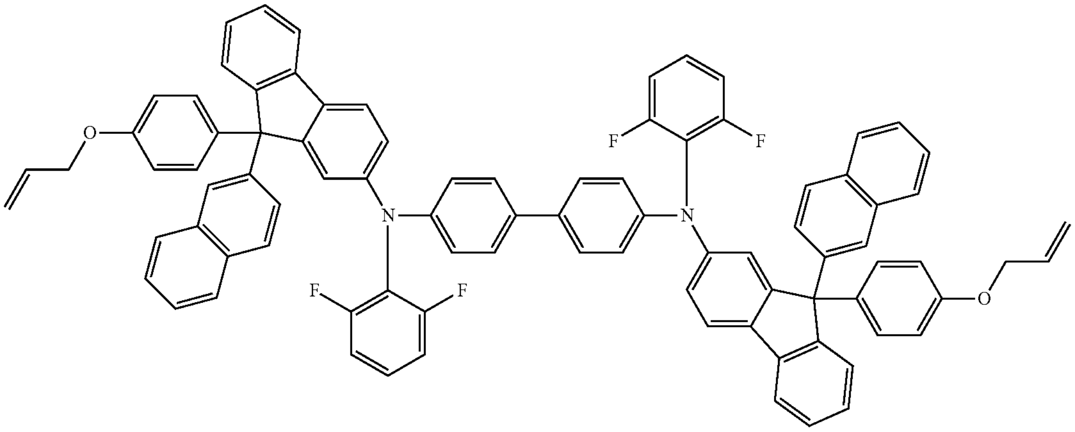
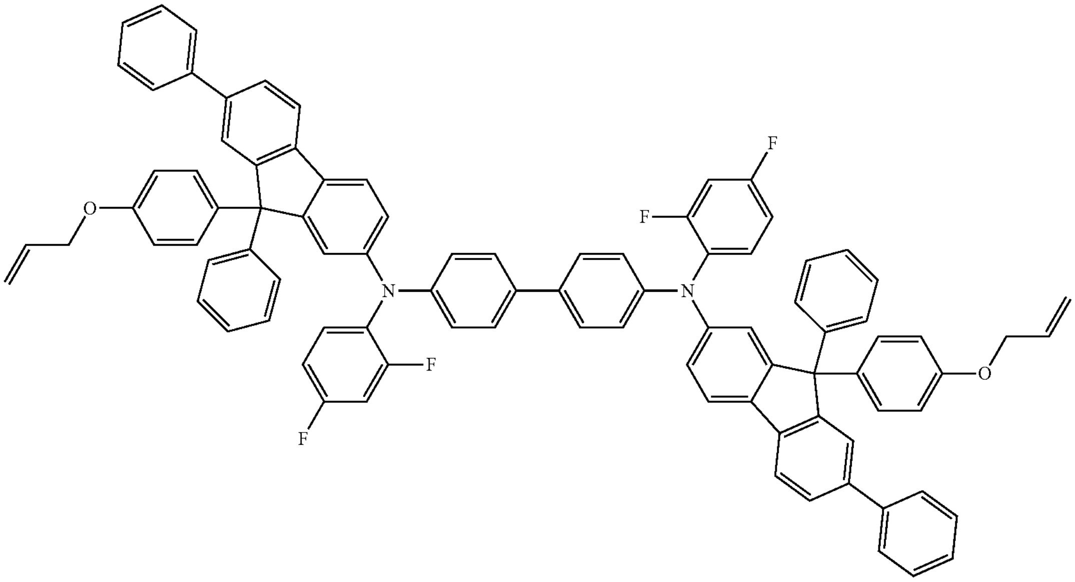

-continued
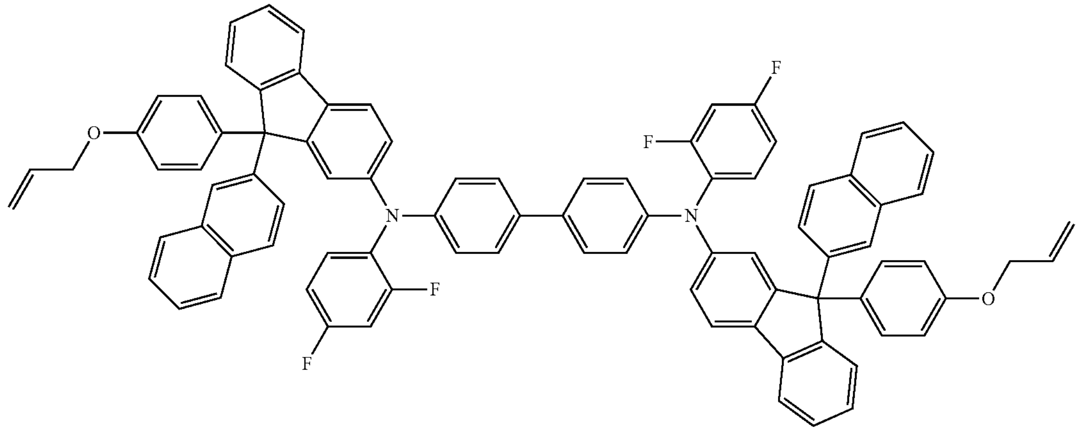
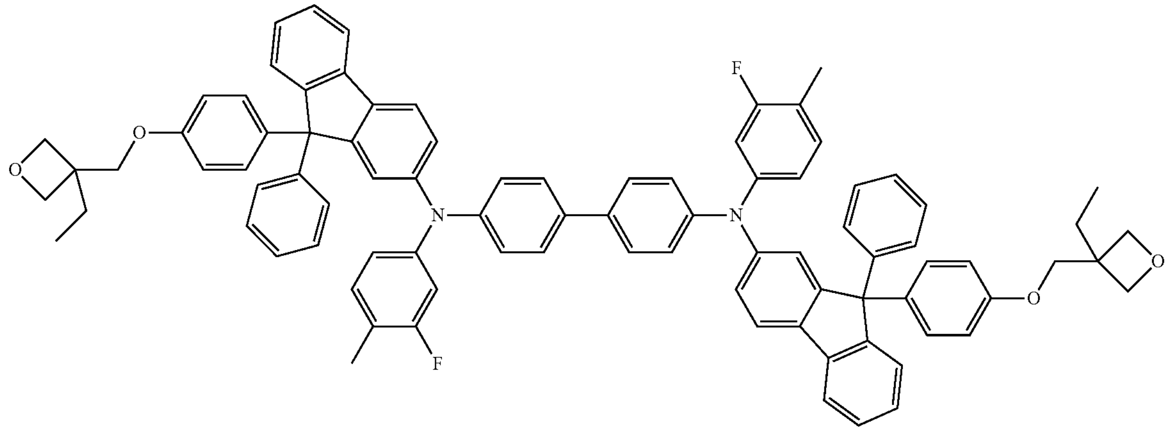
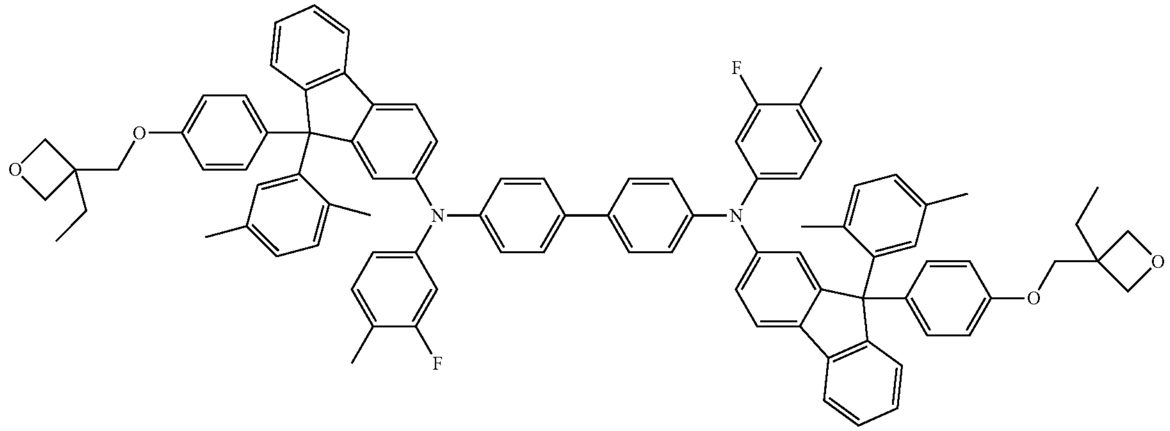
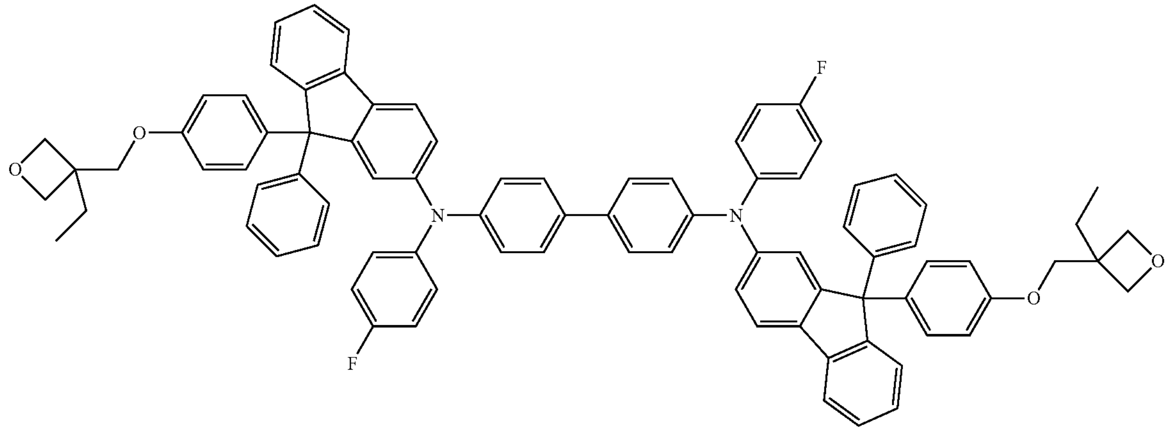

-continued
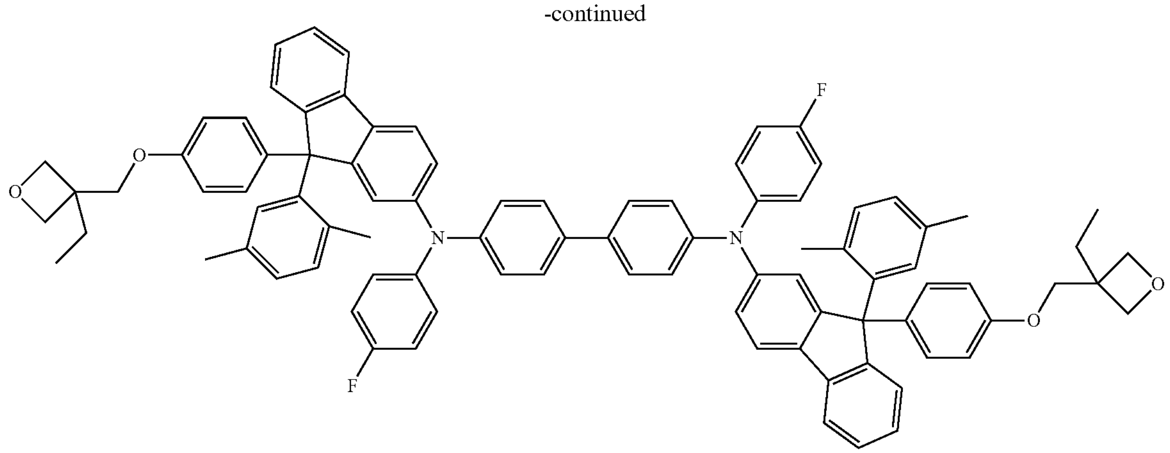
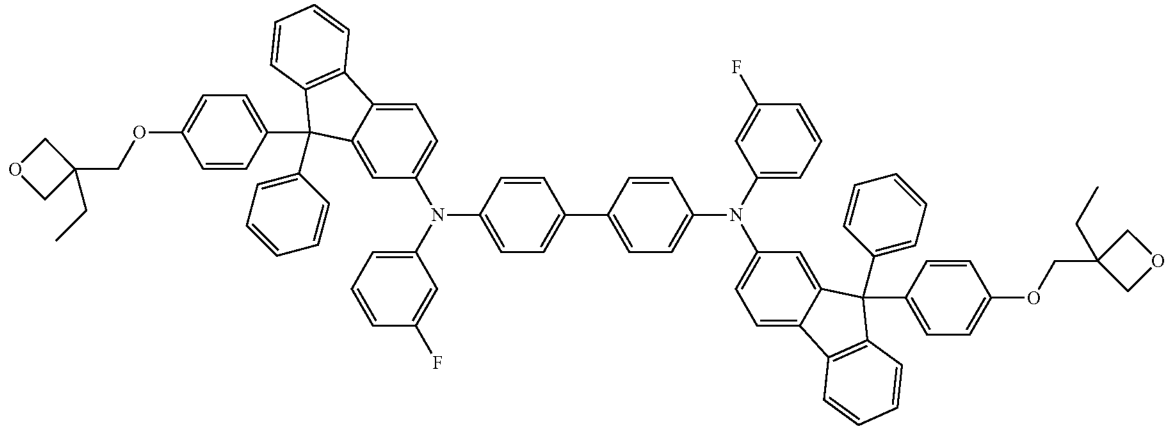
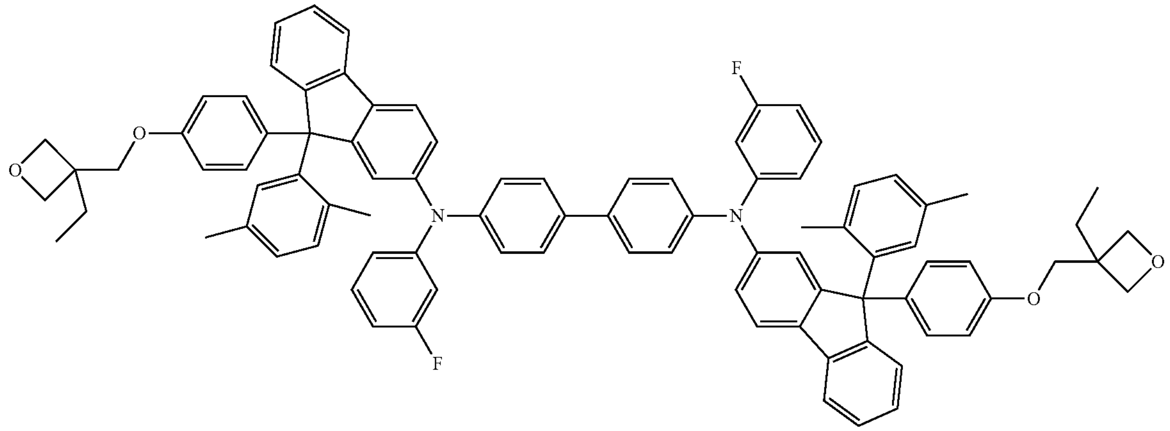
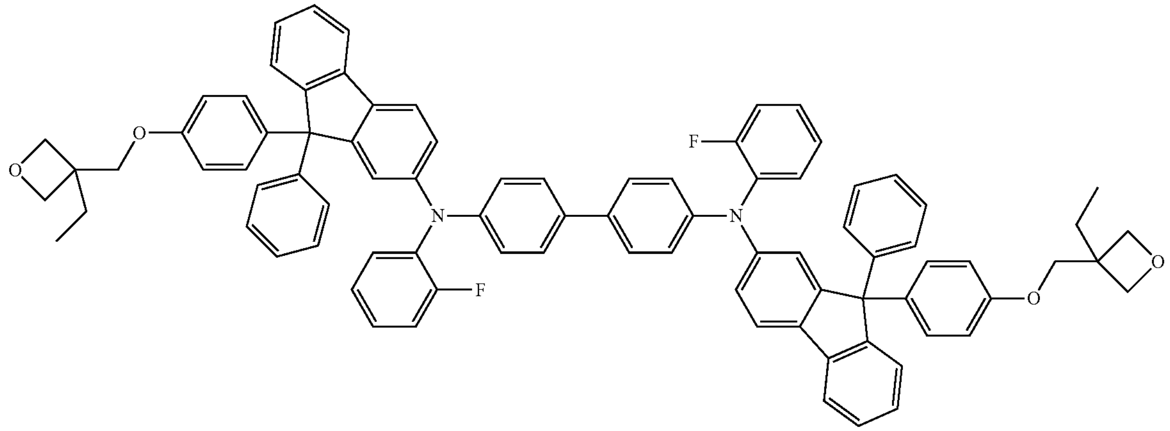

-continued
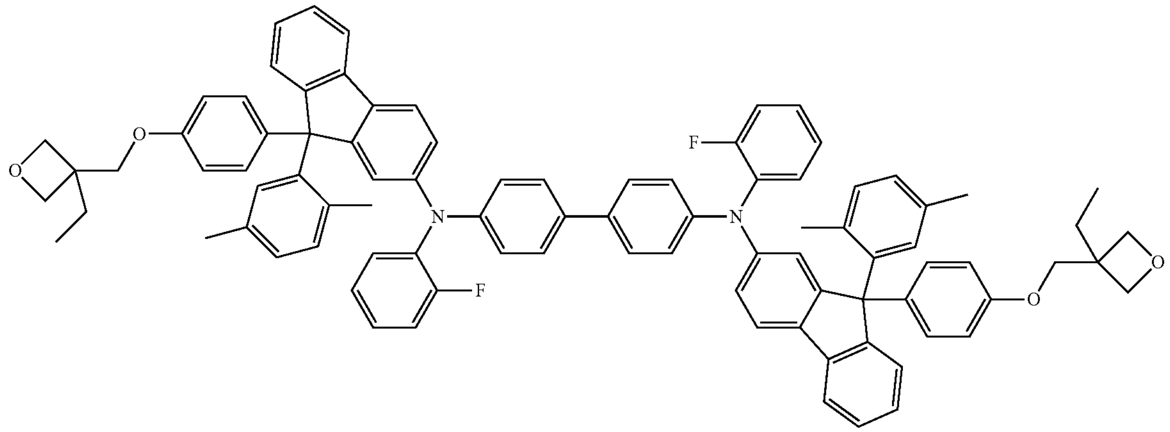
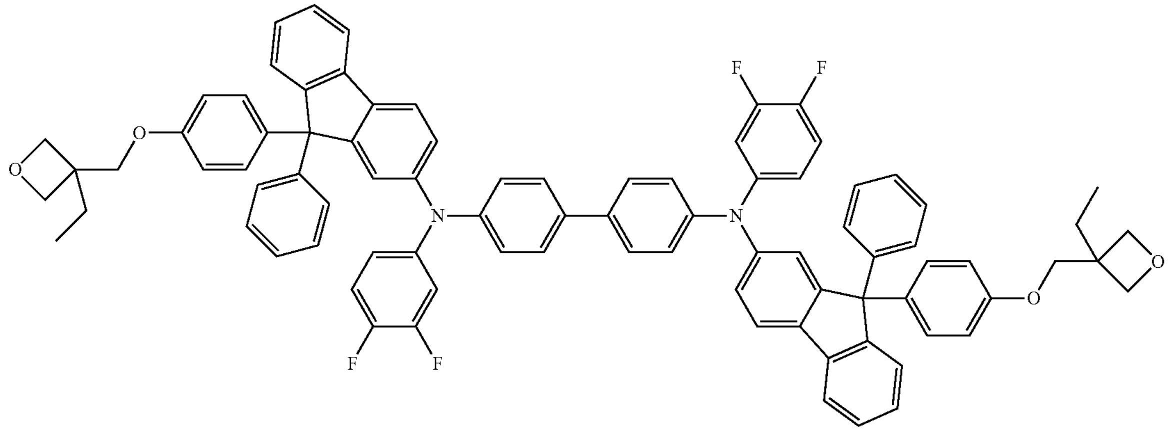
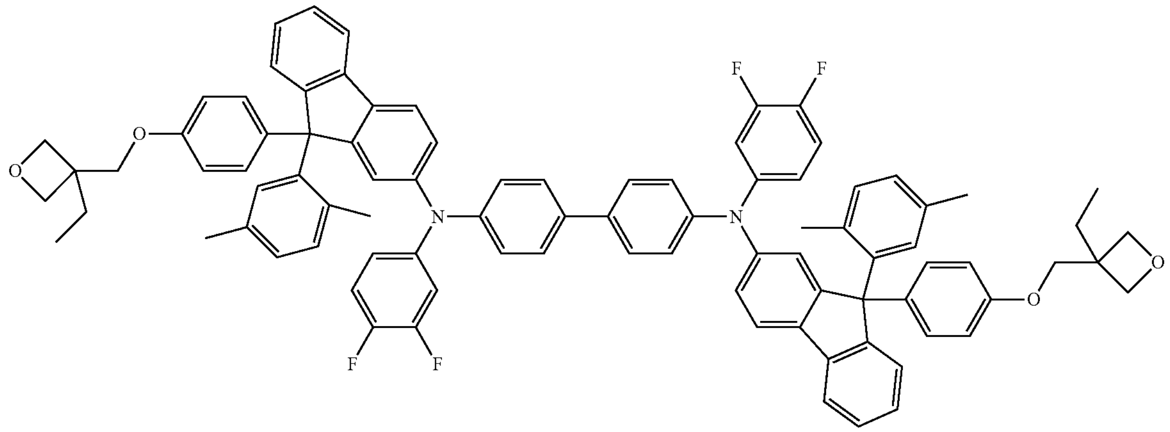
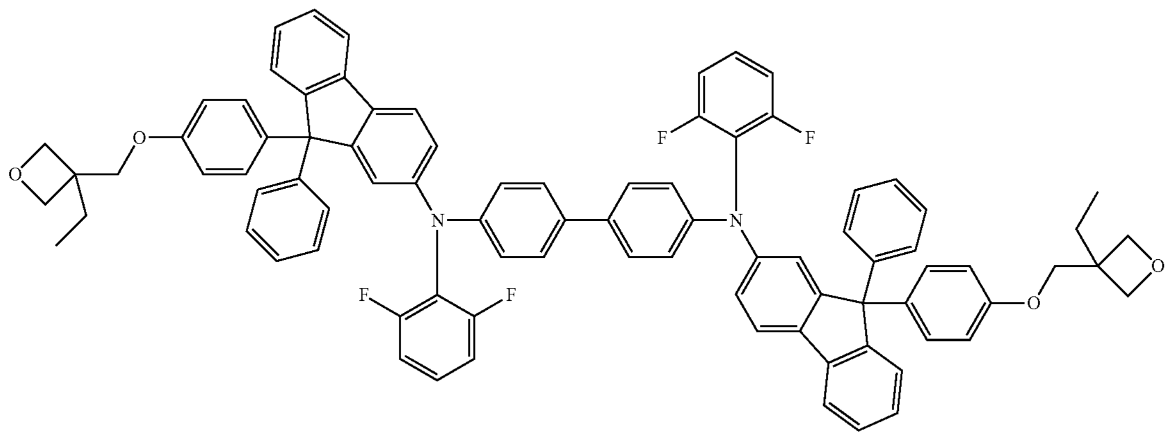

-continued
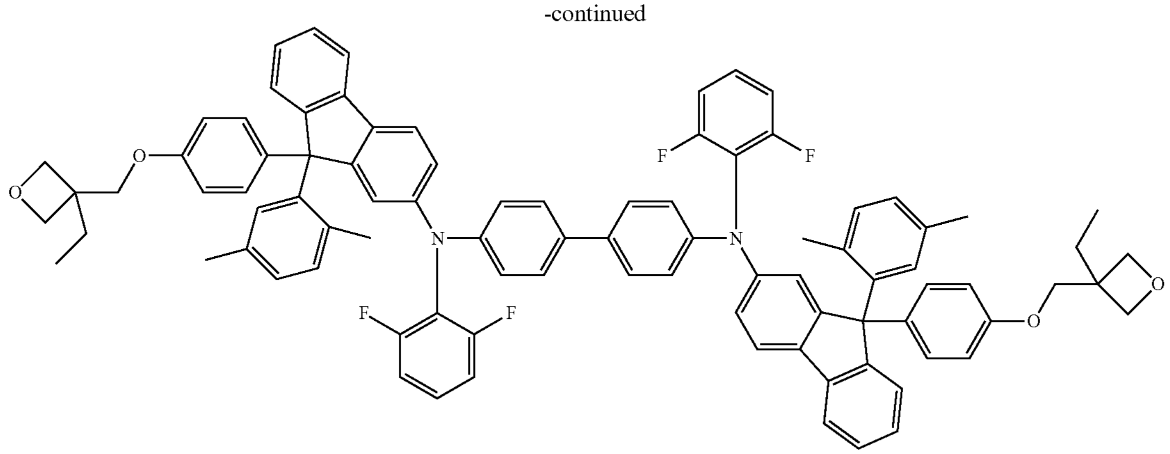
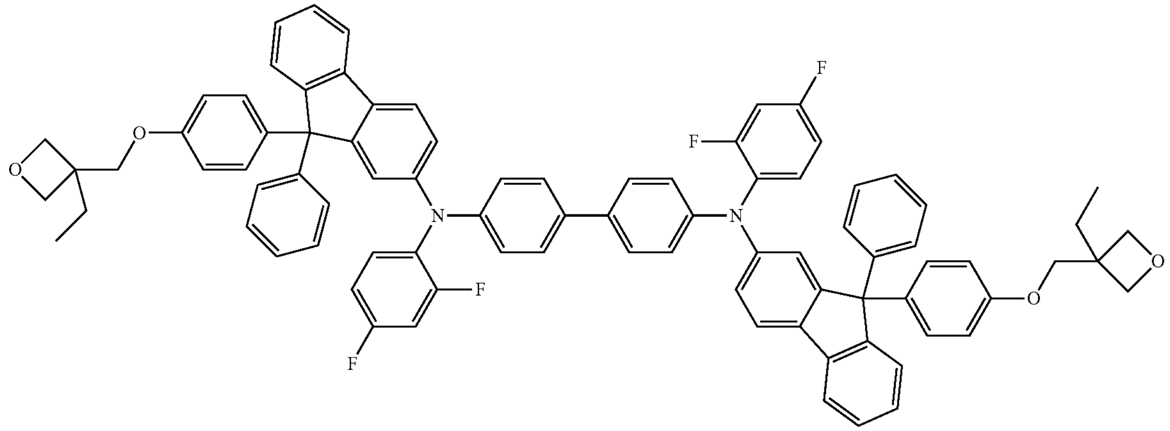
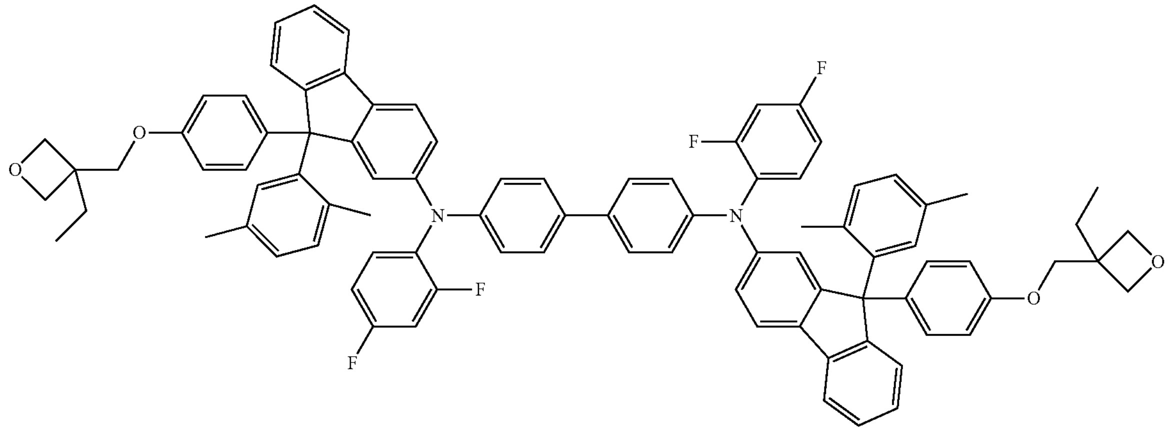
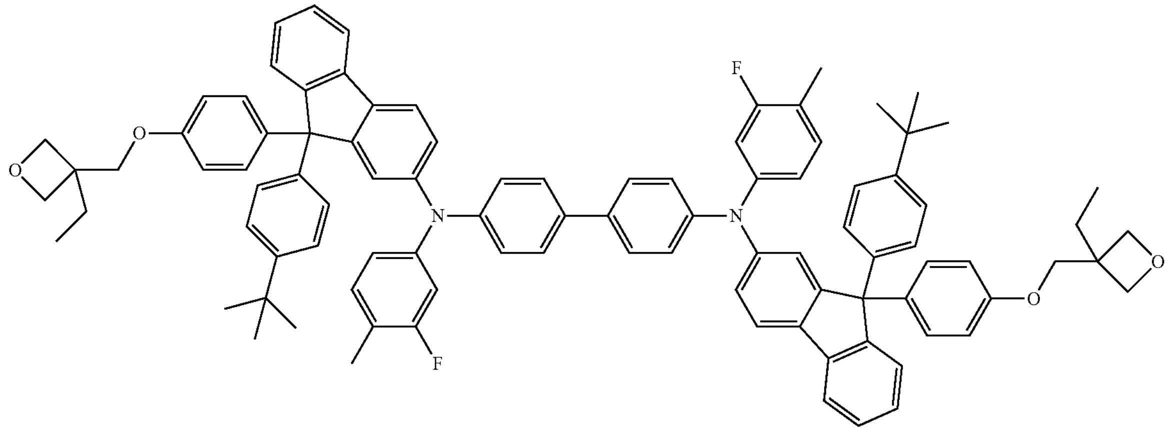

-continued
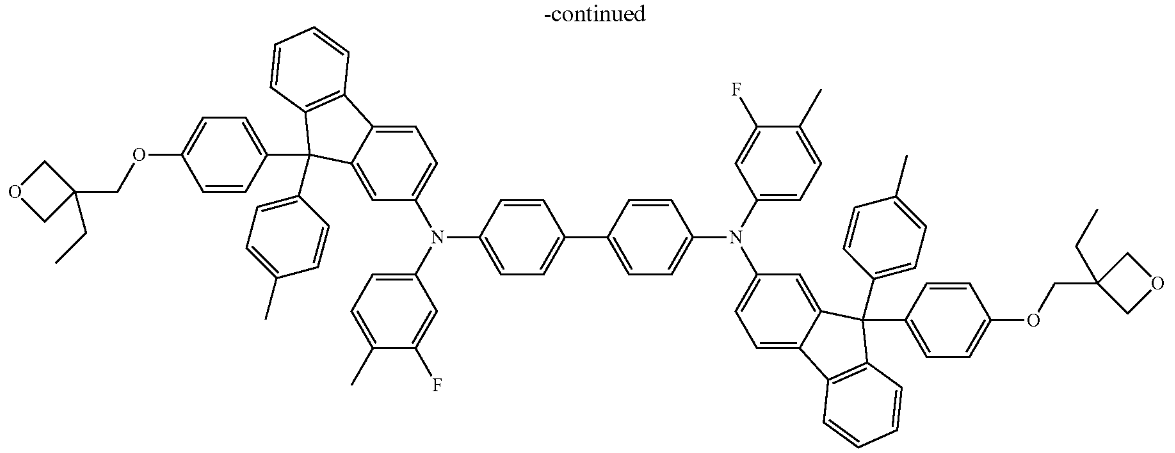
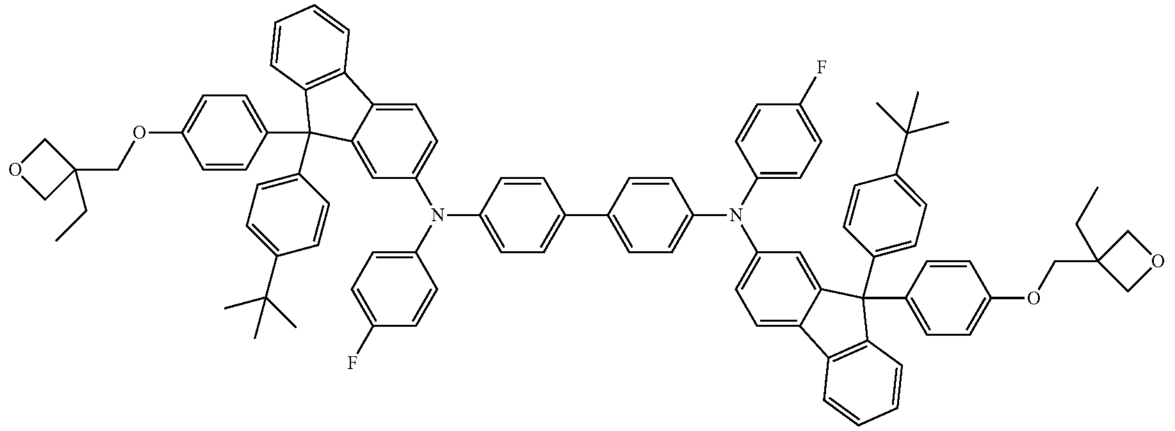
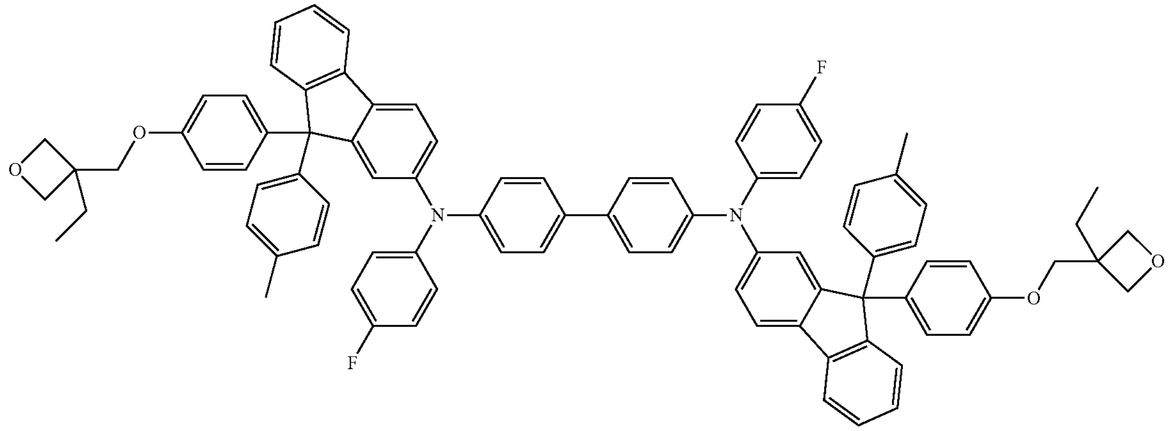
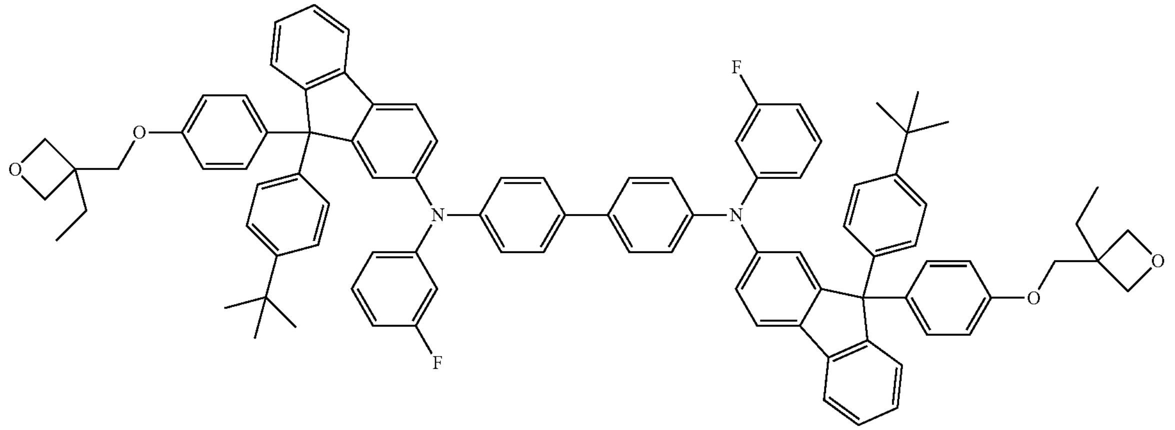

-continued
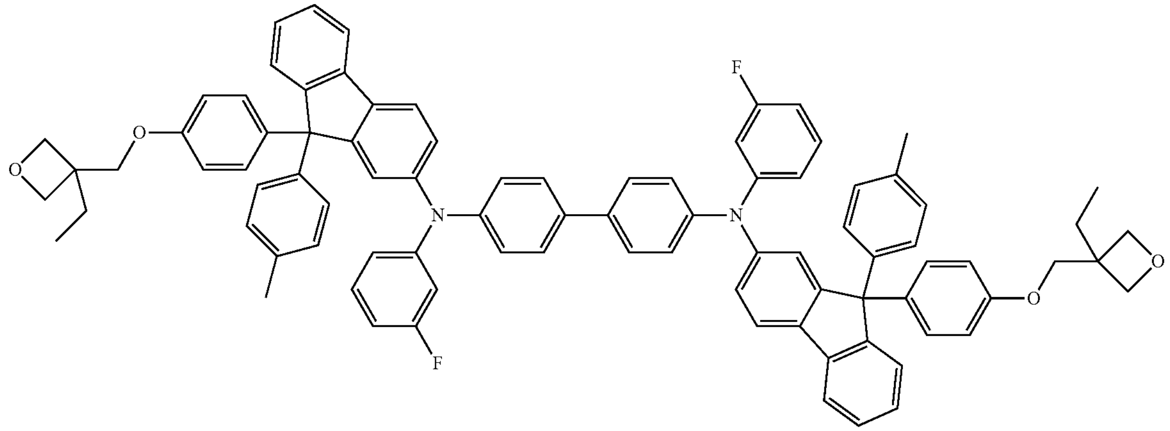
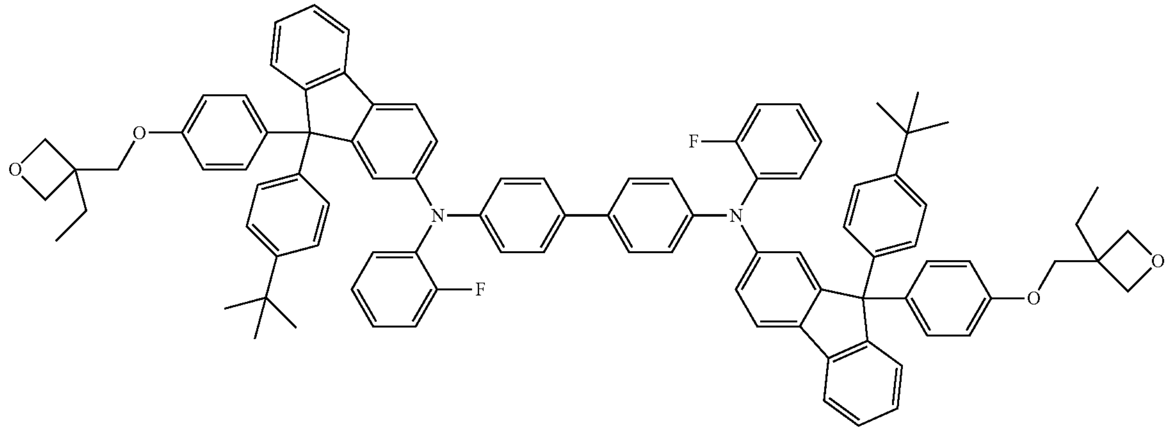
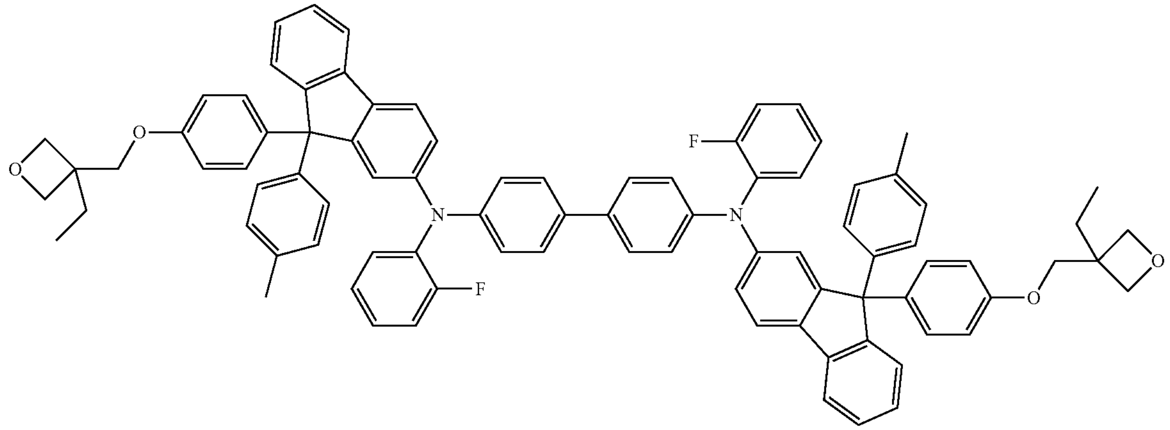
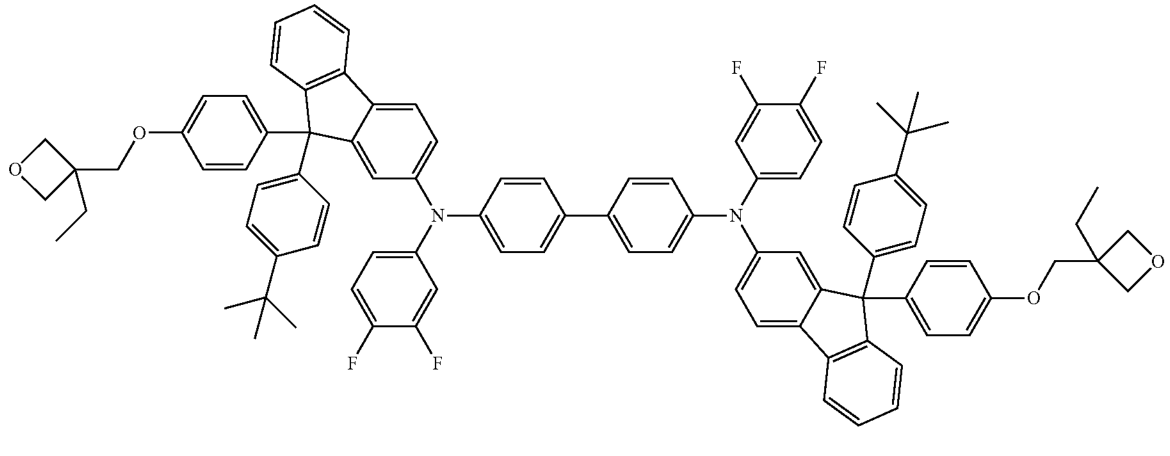

-continued
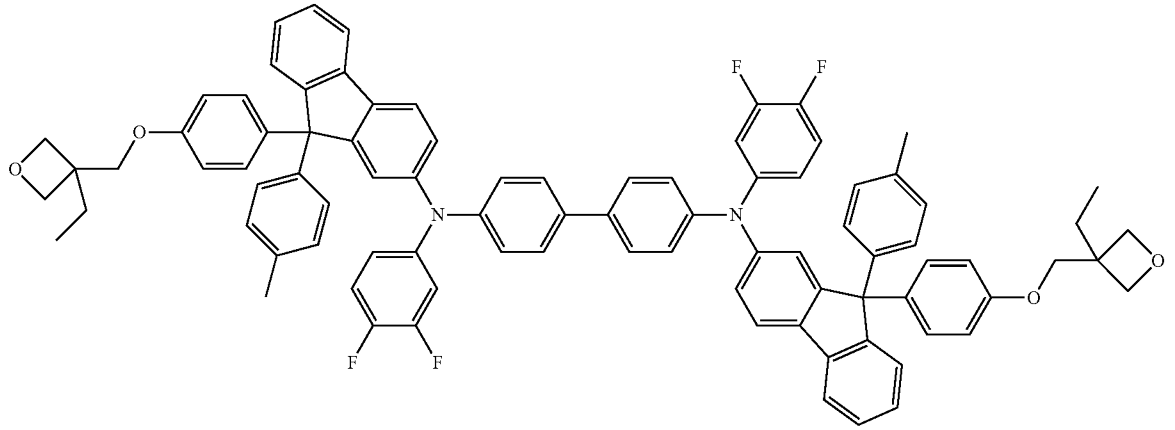
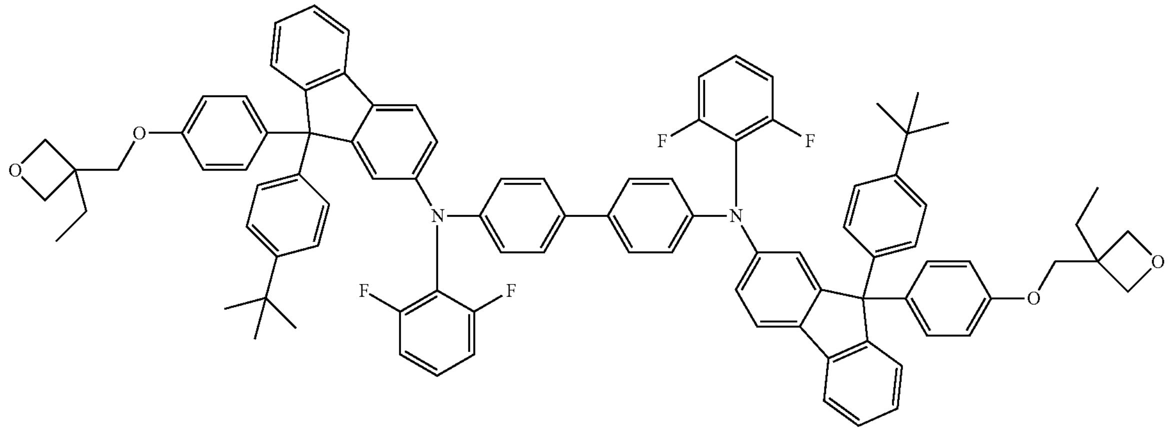
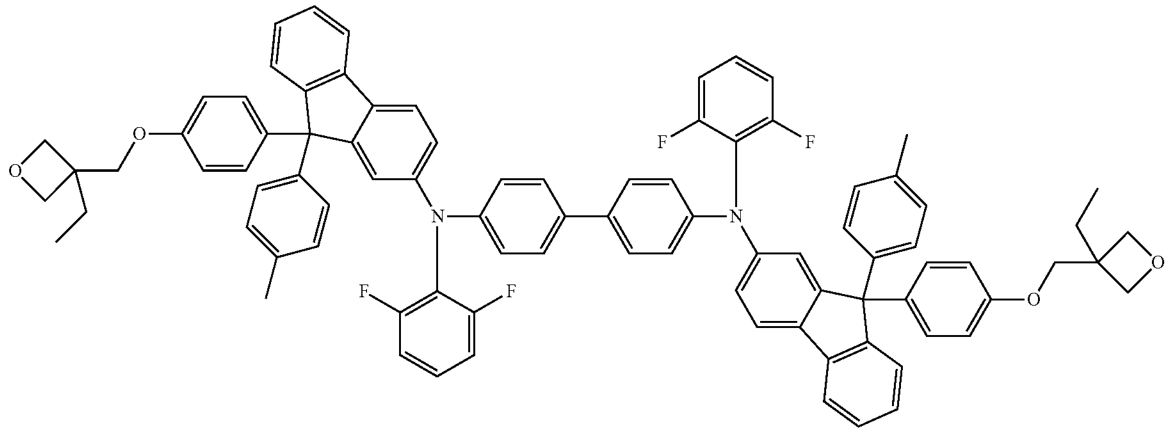
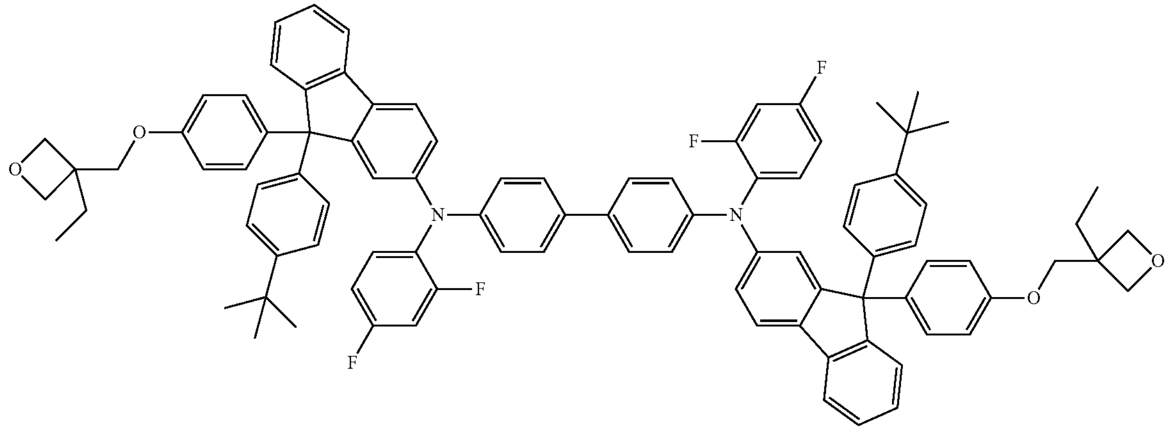

-continued
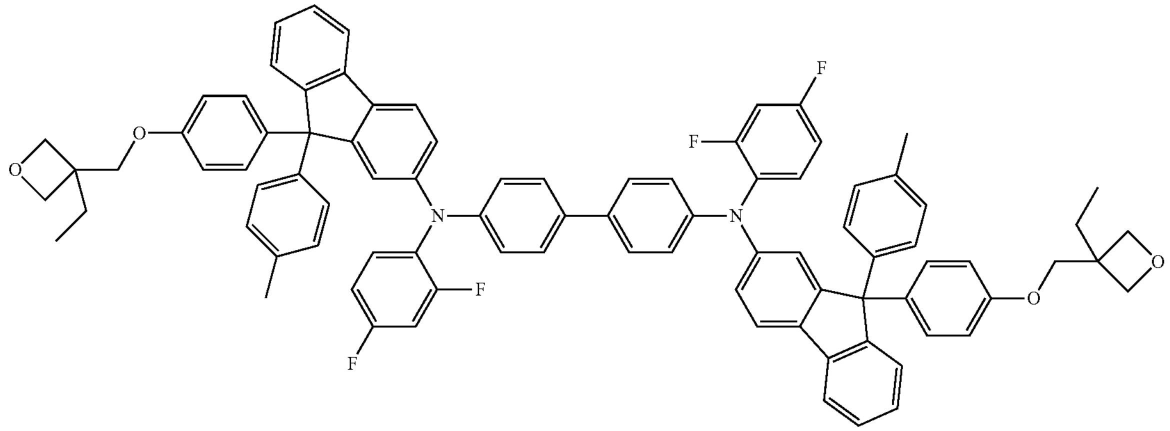
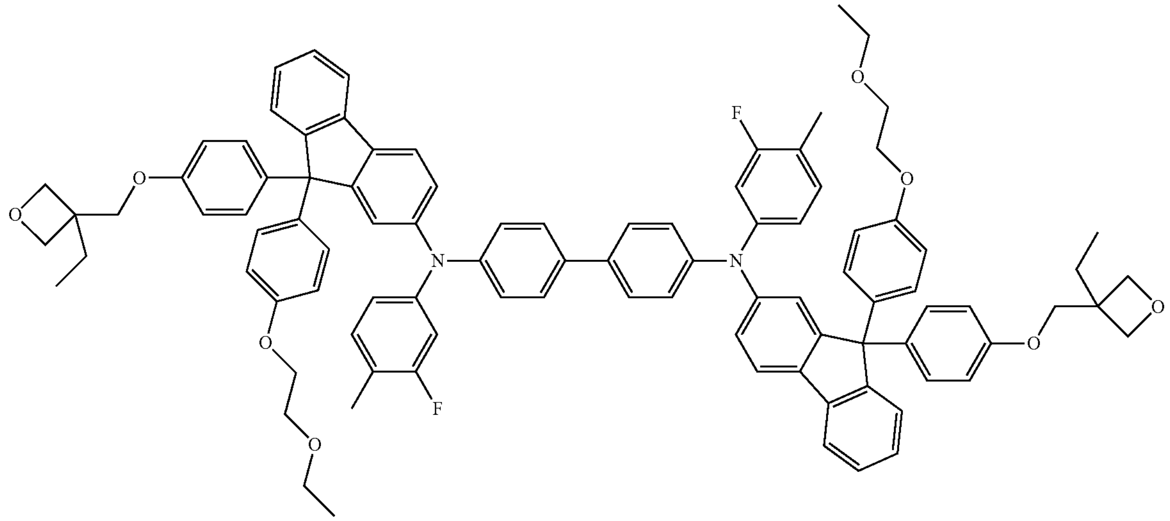
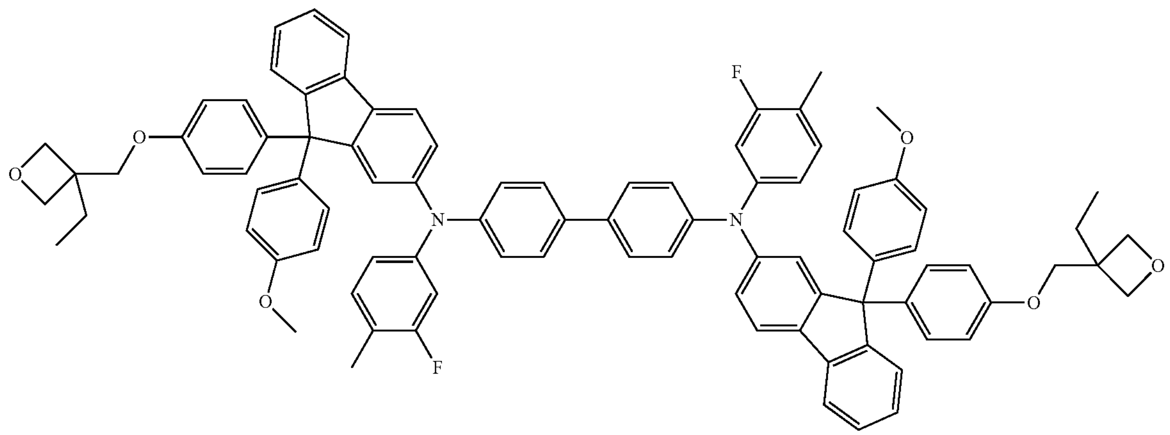

-continued
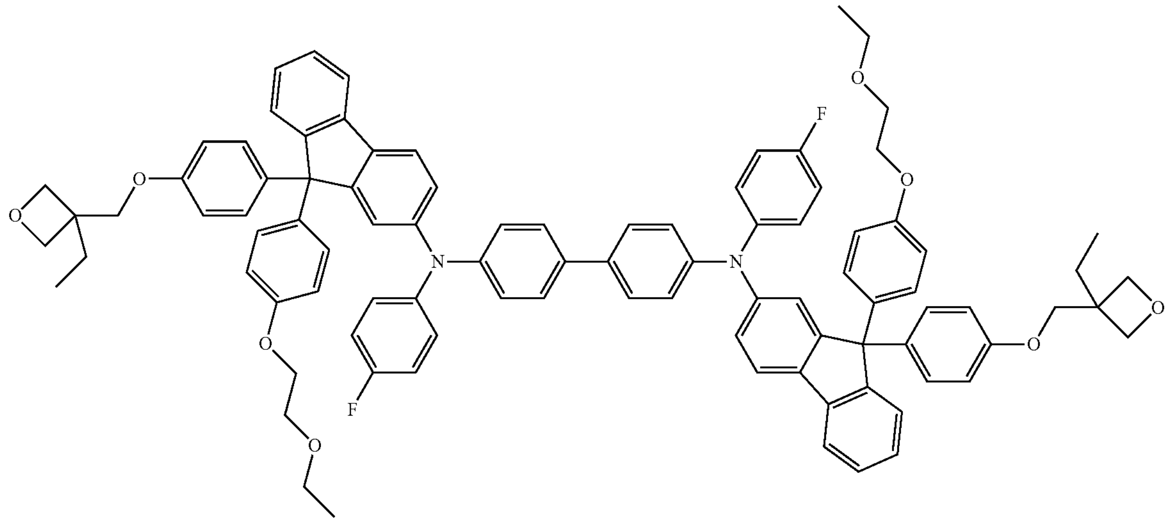
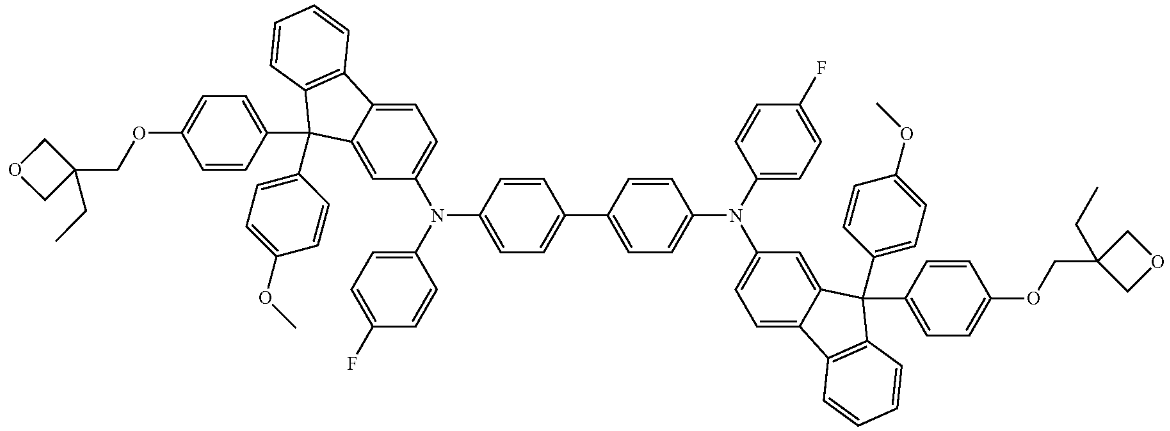
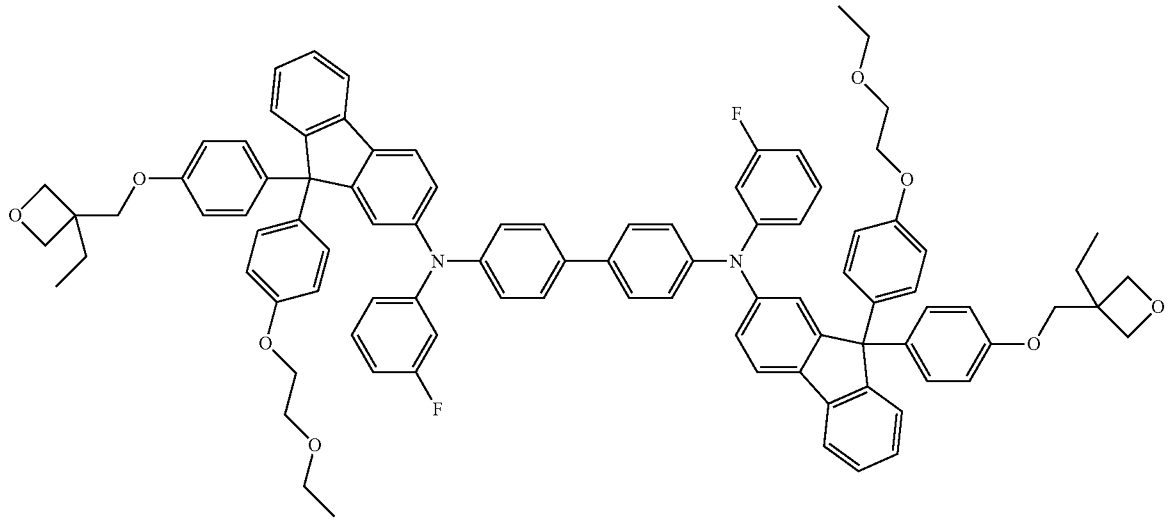

-continued
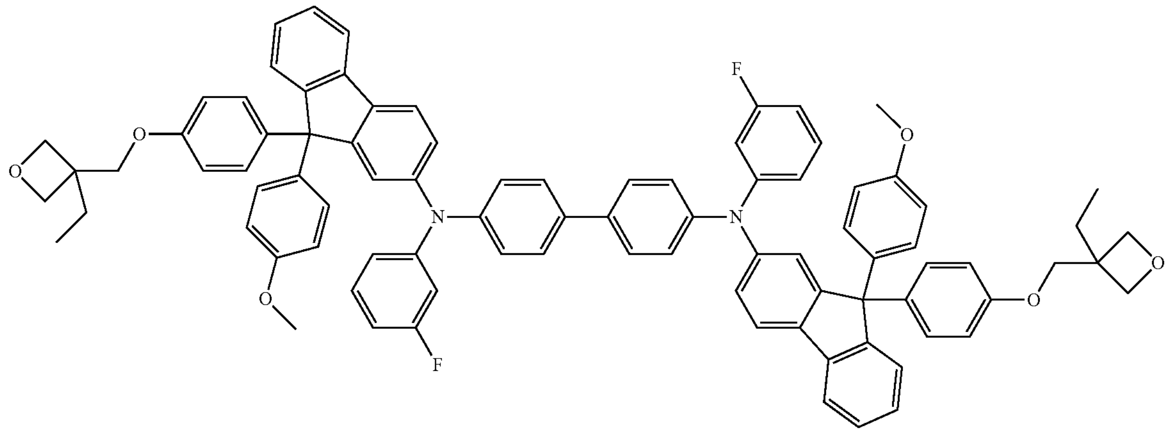
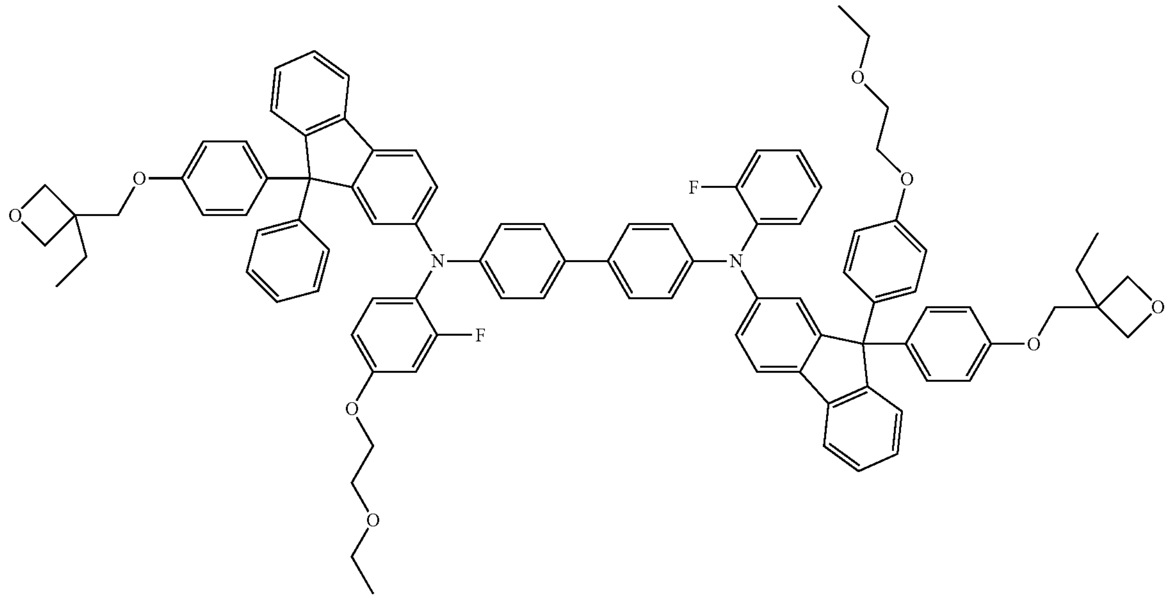
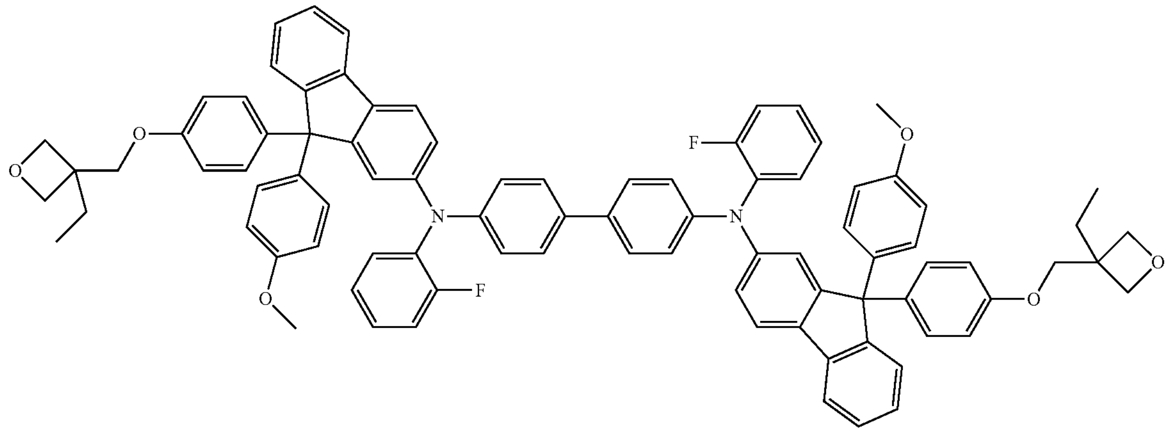

-continued
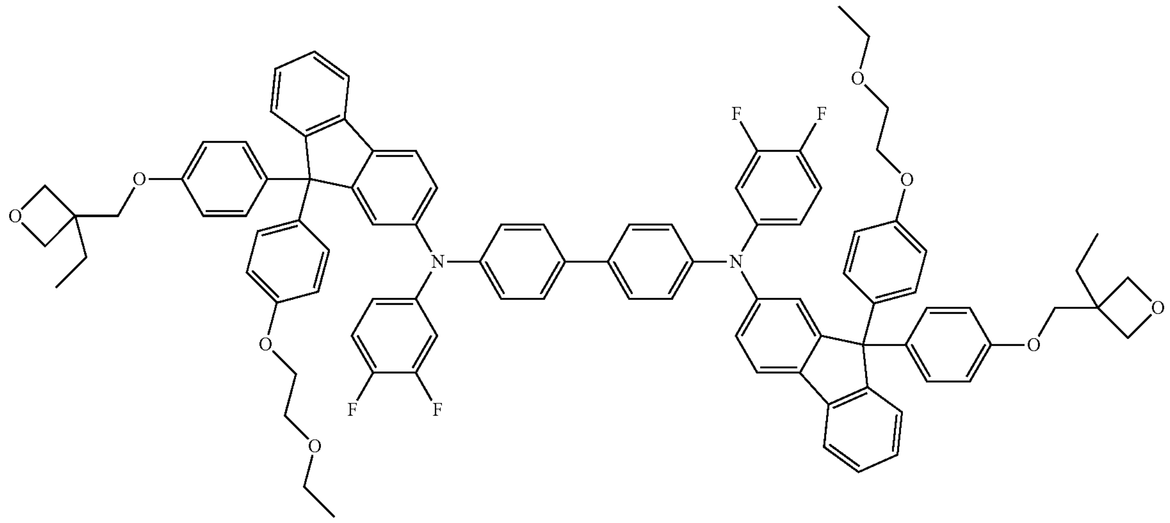
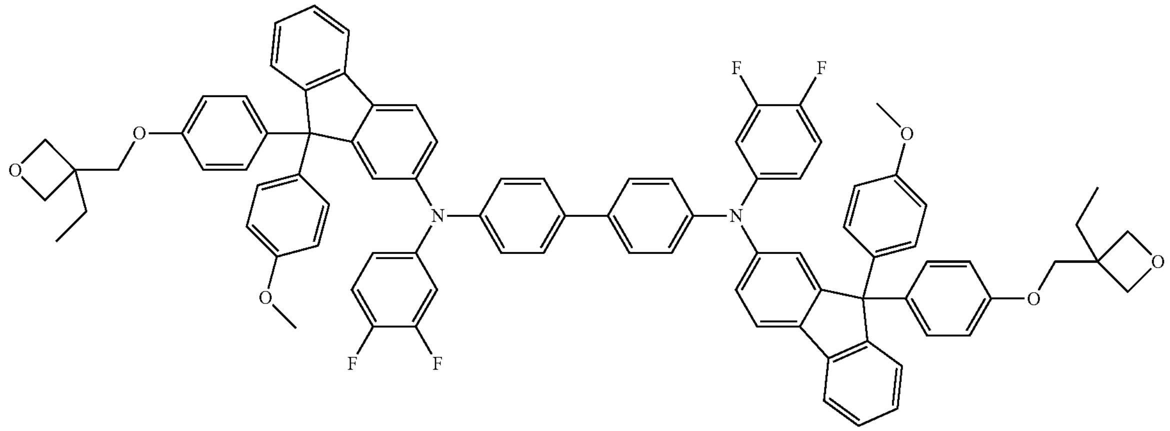
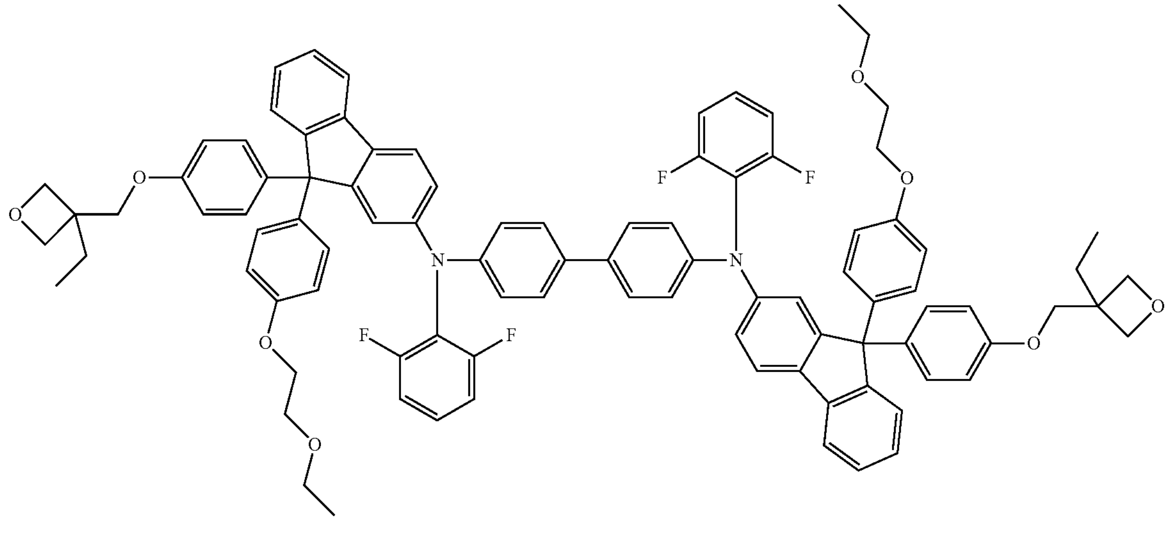

-continued
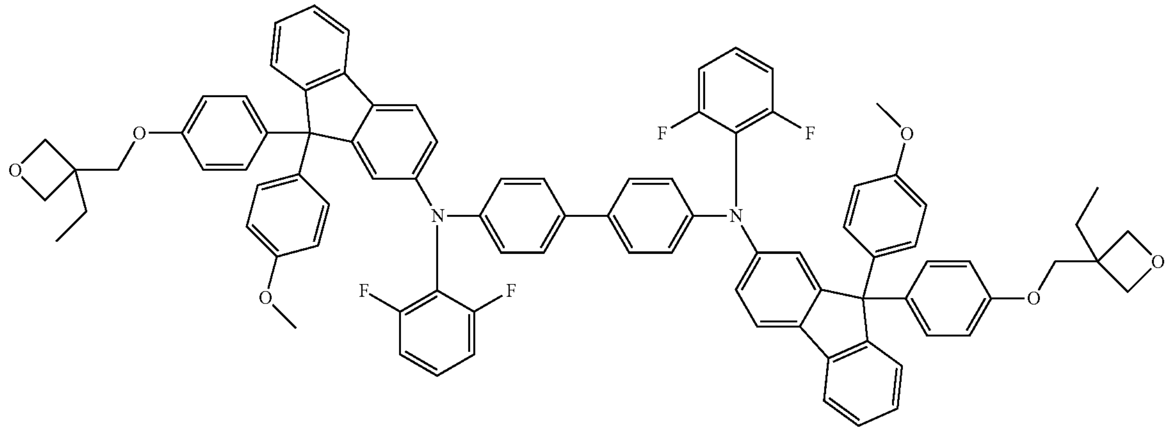
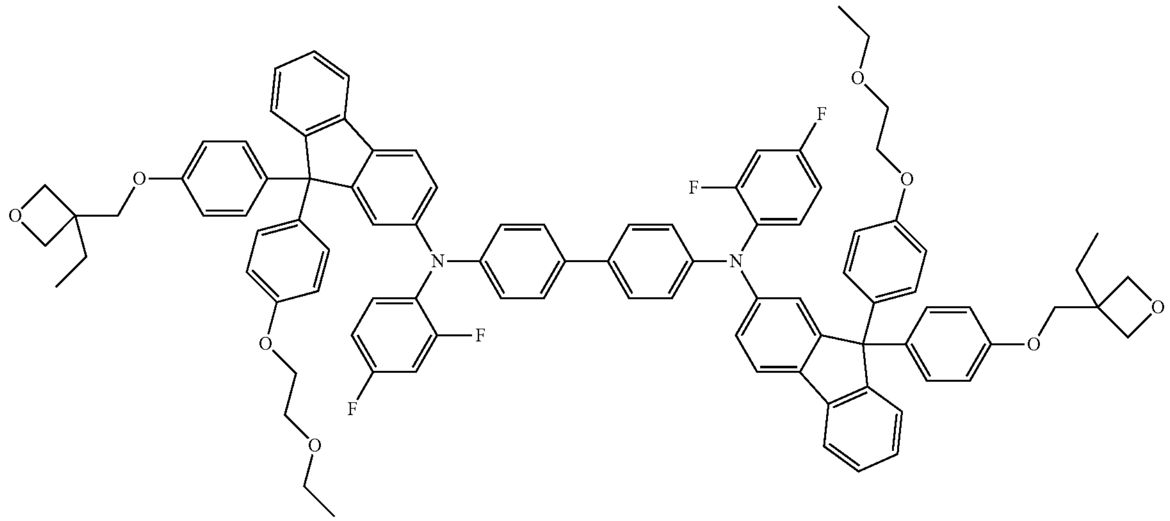
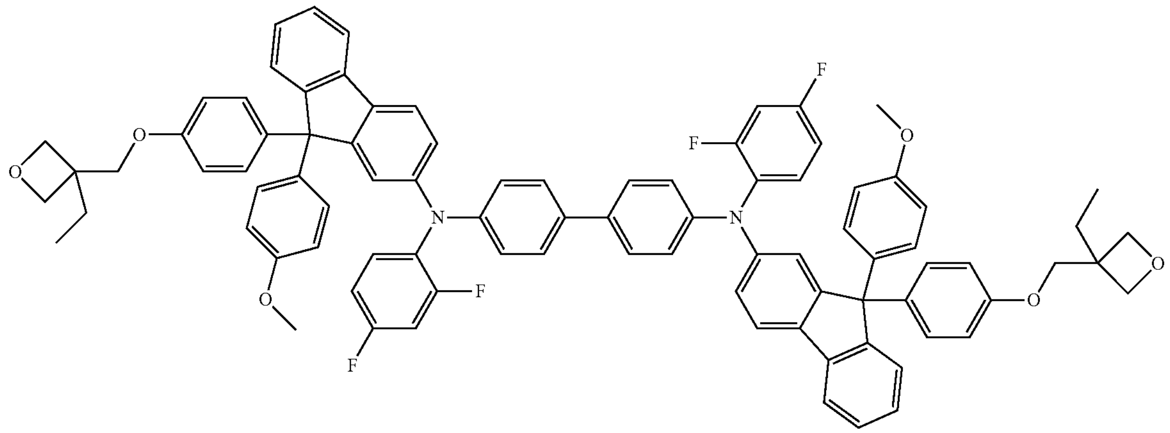

-continued
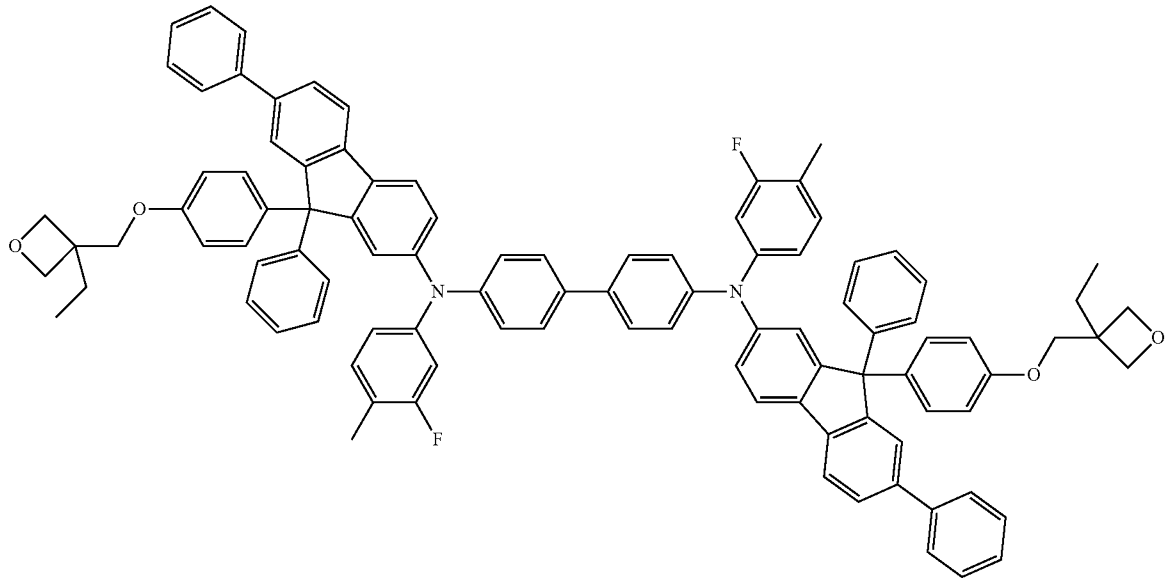
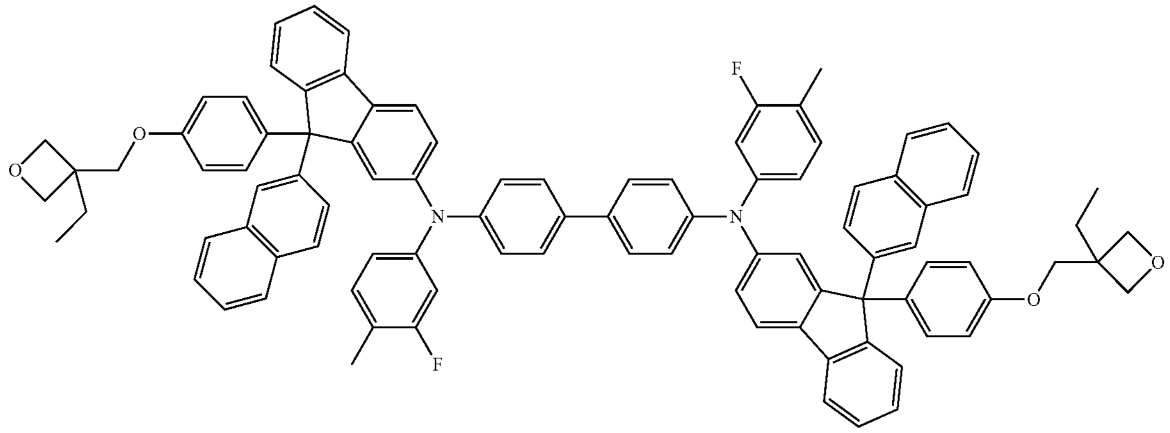
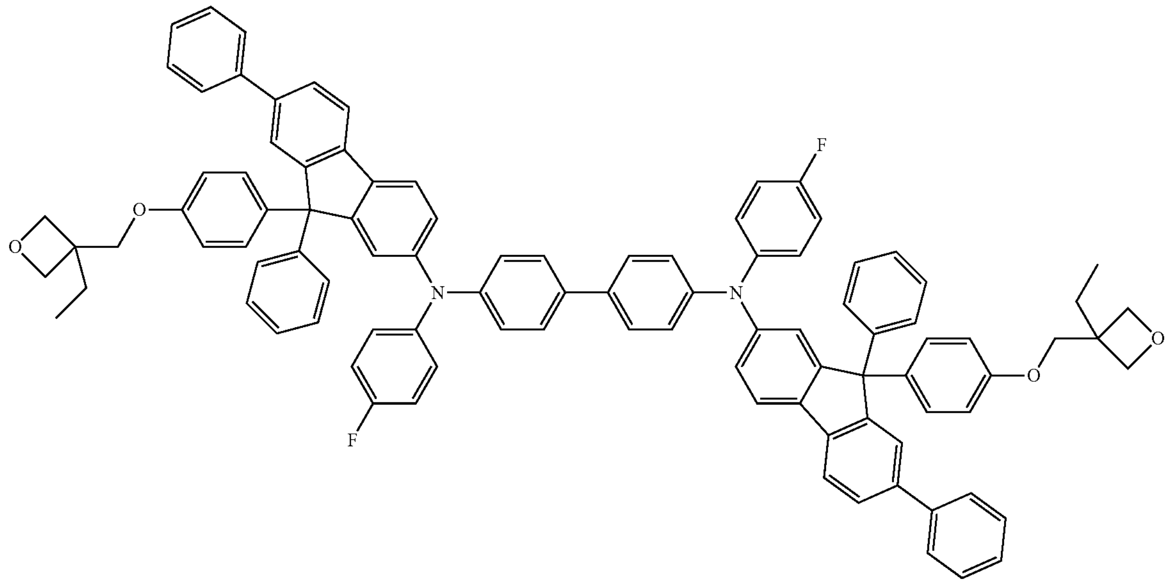

-continued
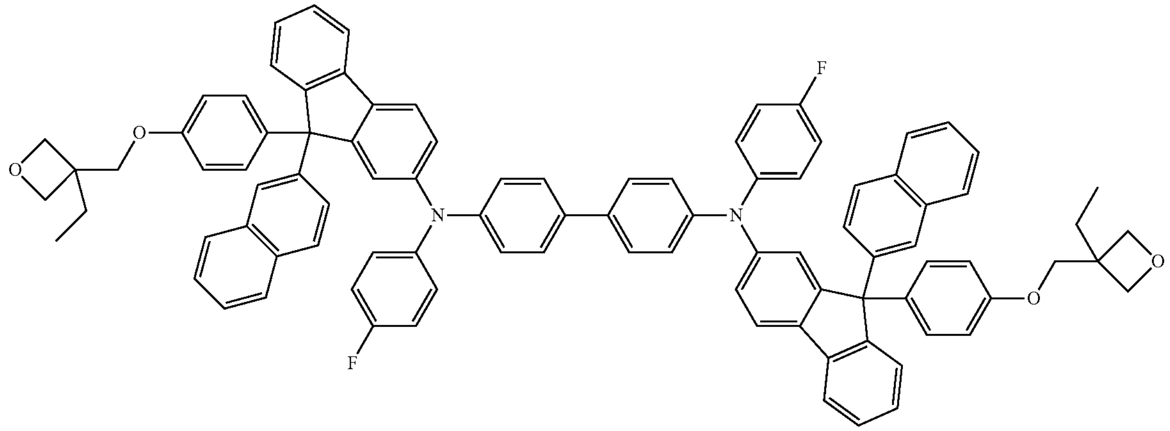
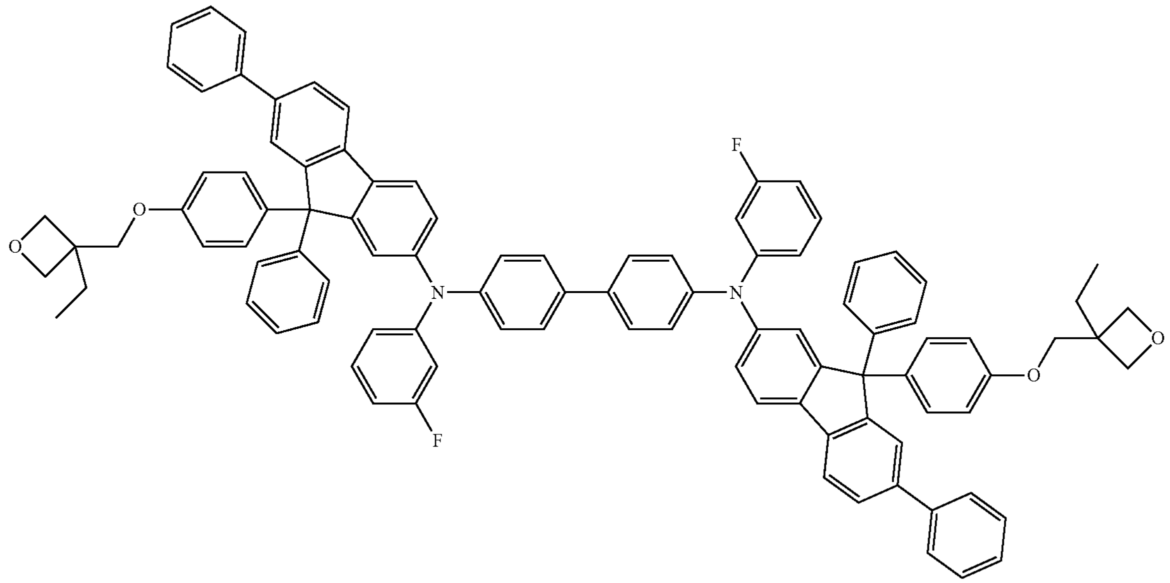
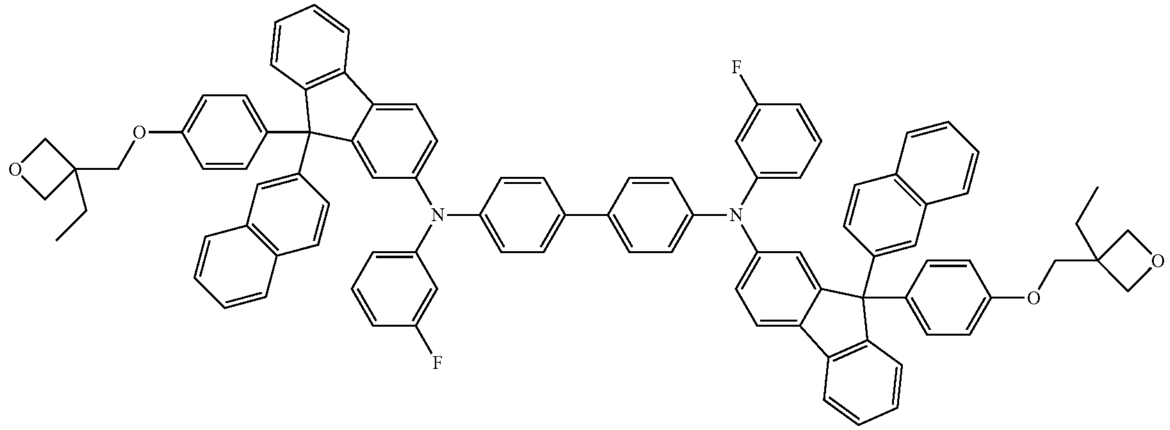

-continued
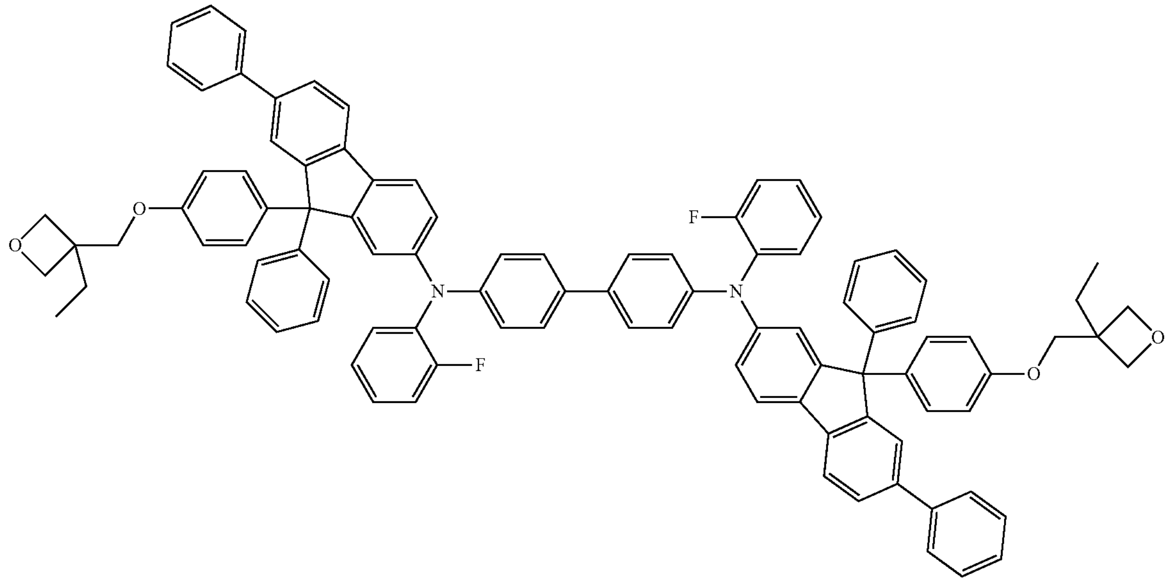
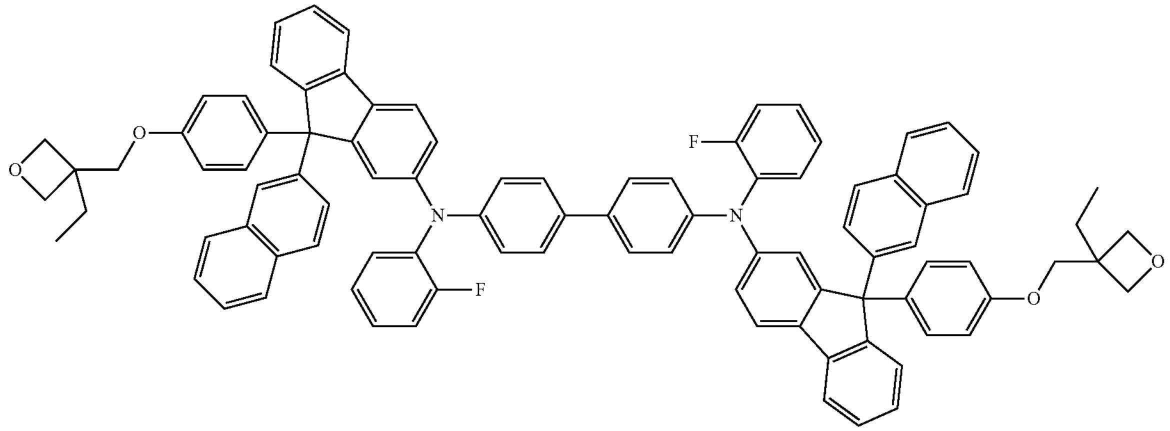
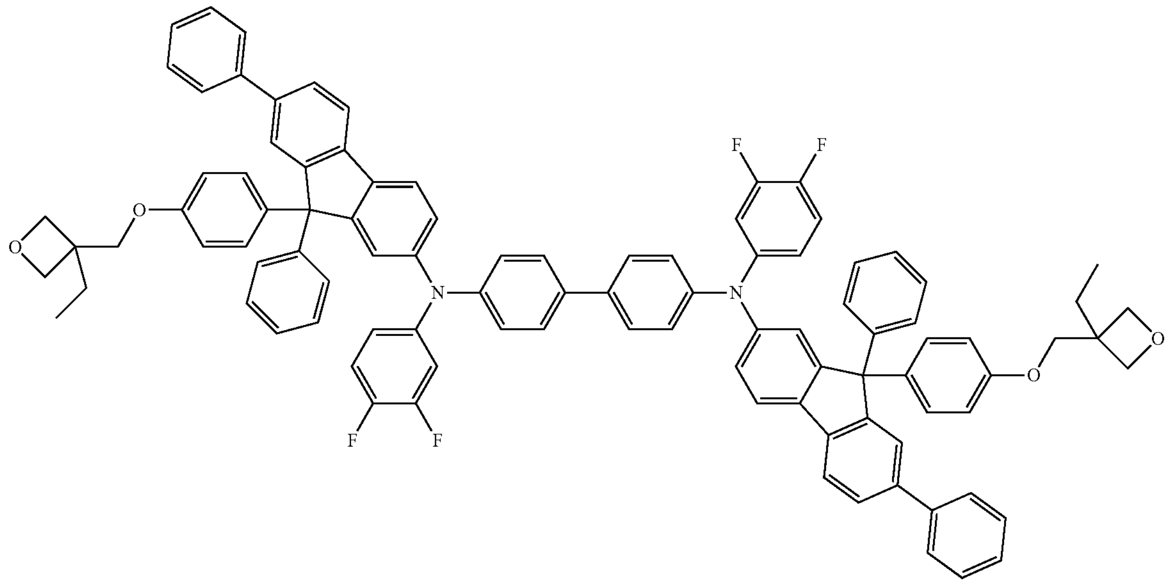

-continued
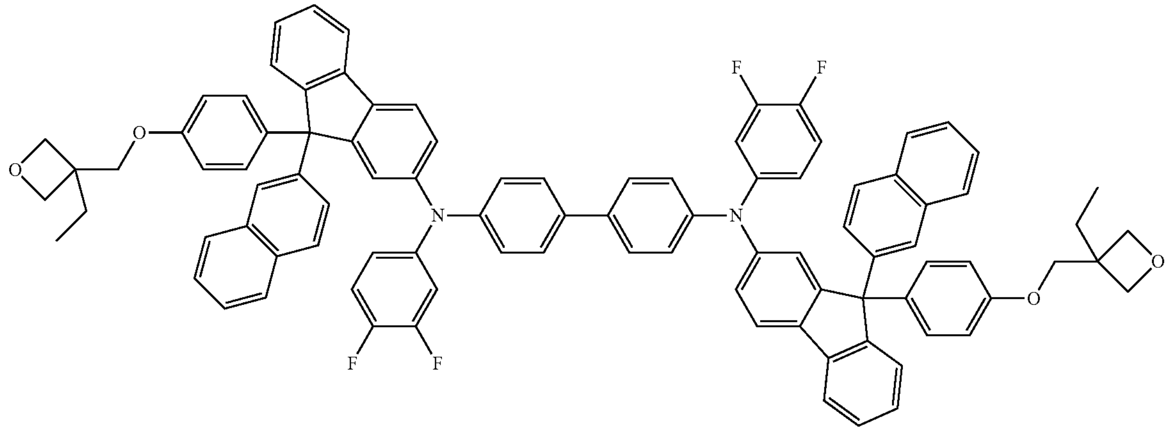
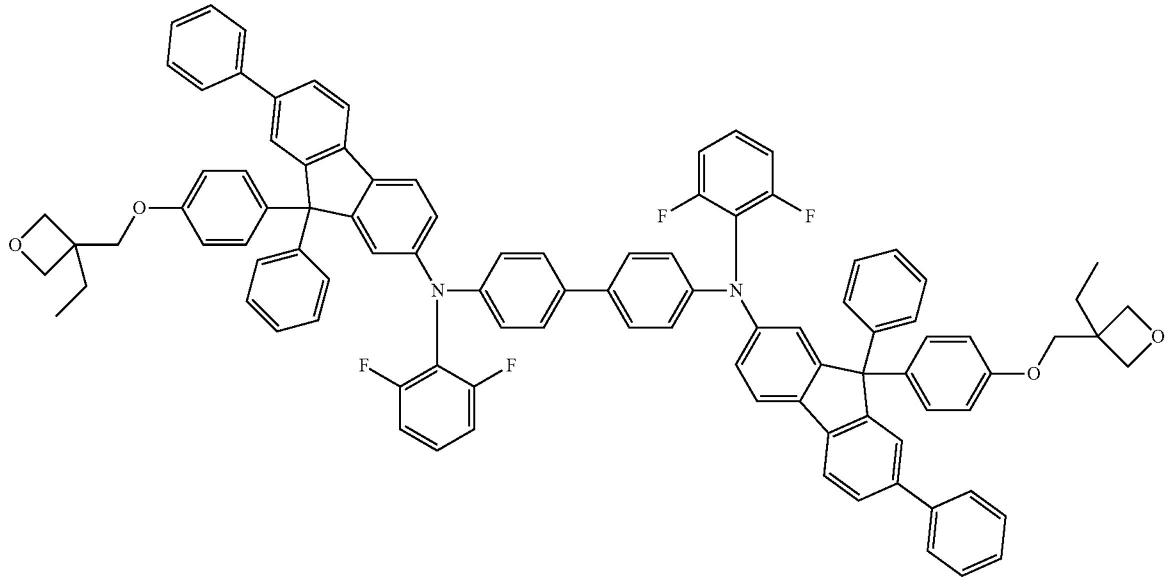
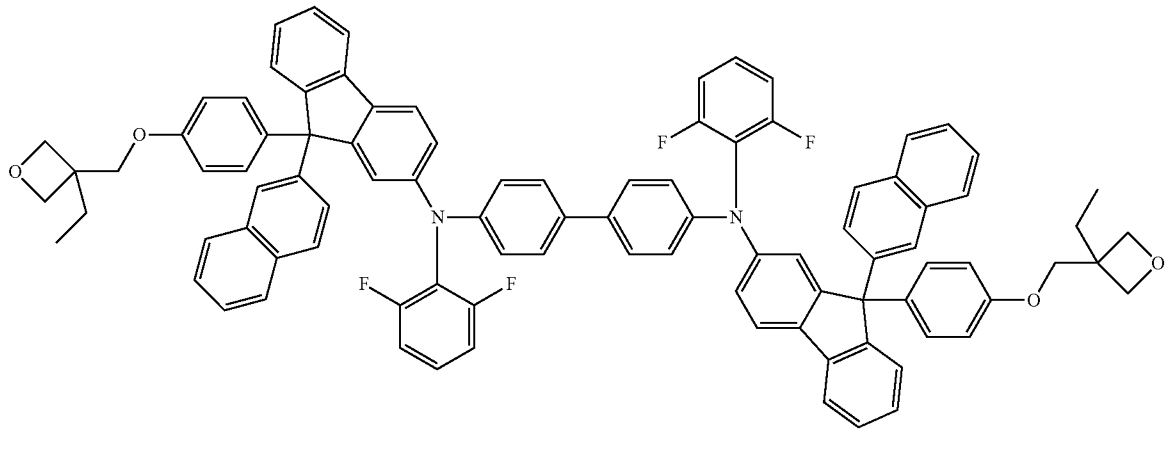

-continued

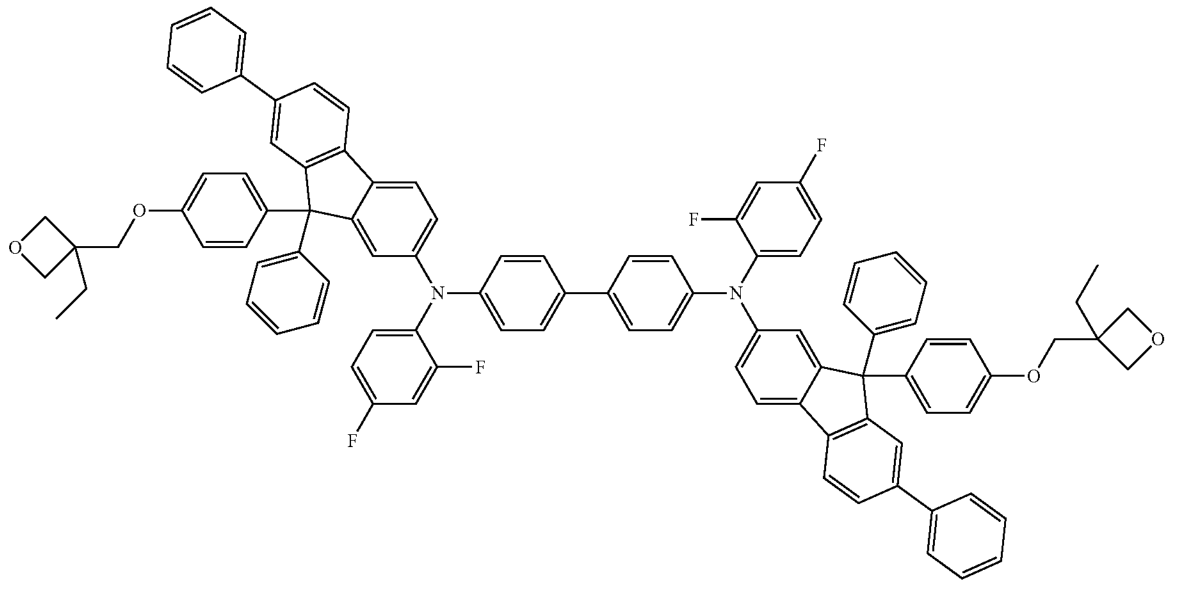

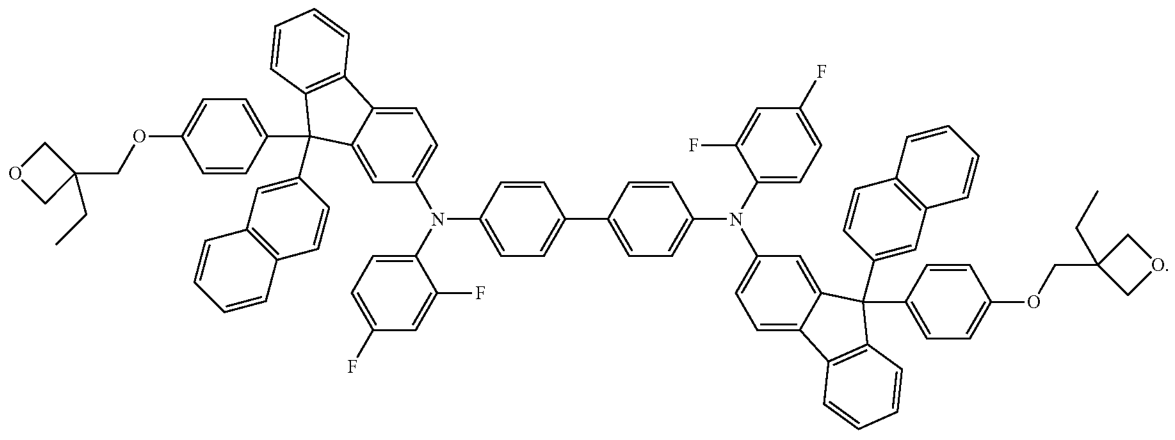 [SMILES: CCC1(COc2ccc(C3(c4ccc5ccccc5c4)c4ccccc4-c4ccc(N(c5ccc(-c6ccc(N(c7ccc8c(c7)C(c7ccc(OCC9(CC)COC9)cc7)(c7ccc9ccccc9c7)c7ccccc7-8)c7ccc(F)cc7F)cc6)cc5)c5ccc(F)cc5F)cc43)cc2)COC1]

A core structure can be prepared as in the following Reaction Scheme 1 in the compound according to an exemplary embodiment of the present specification. Further, the substituent can be bonded by a method known in the art, and the type and position of the substituent or the number of substituents can be changed according to the technology known in the art.

<Reaction Scheme 1>

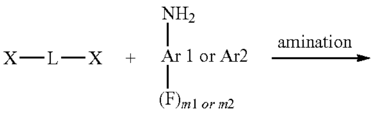

-continued

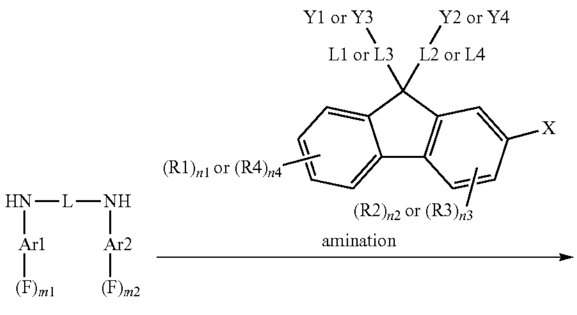

-continued

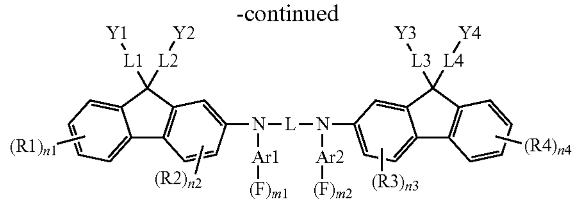

X: halide

In Reaction Scheme 1, the substituent is the same as the definition of the substituent in Formula 1.

An exemplary embodiment of the present specification provides a coating composition including the above-described compound of Formula 1.

In an exemplary embodiment of the present specification, the coating composition includes the compound of Formula 1 and a solvent.

In an exemplary embodiment of the present specification, the coating composition can be in a liquid phase. The "liquid phase" means that the composition is in a liquid state at room temperature under atmospheric pressure.

In an exemplary embodiment of the present specification, the solvent is exemplified as, for example, a chlorine-based solvent such as chloroform, methylene chloride, 1,2-dichloroethane, 1,1,2-trichloroethane, chlorobenzene, and o-dichlorobenzene; an ether-based solvent such as tetrahydrofuran and dioxane; an aromatic hydrocarbon-based solvent such as toluene, xylene, trimethylbenzene, and mesitylene; an aliphatic hydrocarbon-based solvent such as cyclohexane, methylcyclohexane, n-pentane, n-hexane, n-heptane, n-octane, n-nonane, and n-decane; a ketone-based solvent such as acetone, methyl ethyl ketone, cyclohexanone, isophorone, tetralone, decalone, and acetylacetone; an ester-based solvent such as ethyl acetate, butyl acetate, and ethyl cellosolve acetate; a polyhydric alcohol such as ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, and 1,2-hexanediol, and derivatives thereof; an alcohol-based solvent such as methanol, ethanol, propanol, isopropanol, and cyclohexanol; a sulfoxide-based solvent such as dimethyl sulfoxide; an amide-based solvent such as N-methyl-2-pyrrolidone and N,N-dimethylformamide; and a solvent such as tetralin, but the solvent is sufficient as long as the solvent can dissolve or disperse the compound of Formula 1 according to an exemplary embodiment of the present invention, and is not limited thereto.

In another exemplary embodiment, the solvents can be used either alone or in a mixture of two or more solvents.

In an exemplary embodiment of the present specification, the coating composition does not further include a p-doping material.

In an exemplary embodiment of the present specification, the coating composition further includes a p-doping material.

In the present specification, the p-doping material means a material which allows a host material to have p-semiconductor characteristics. The p-semiconductor characteristics mean characteristics of injecting or transporting holes at the highest occupied molecular orbital (HOMO) energy level, that is, characteristics of a material having large hole conductivity.

In an exemplary embodiment of the present specification, the p-doping material can be any one of the following Formulae A to H, but is not limited thereto.

[Formula A]

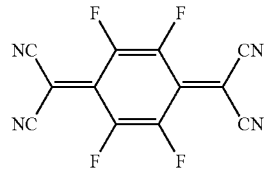

[Formula B]

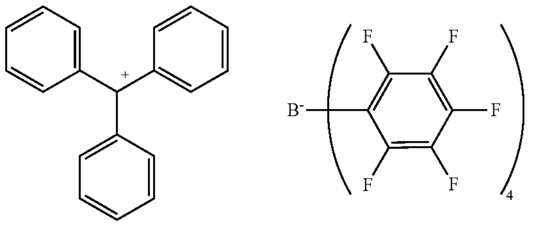

[Formula C]

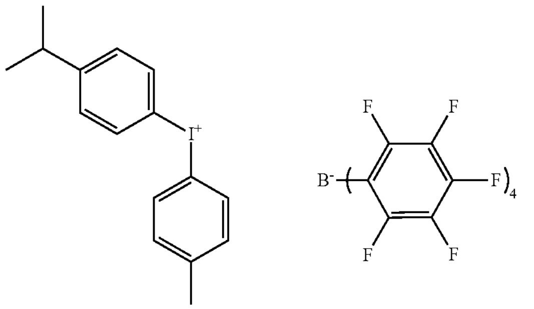

[Formula D]

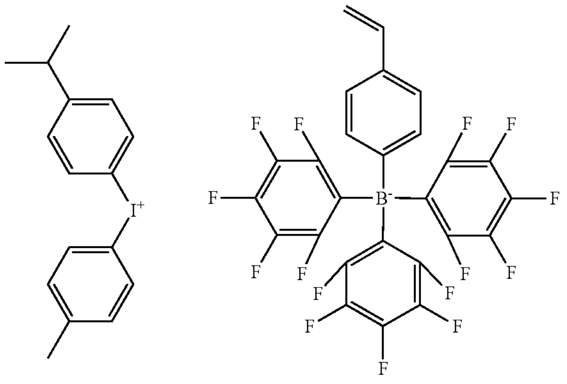

[Formula E]

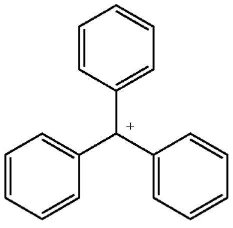

-continued

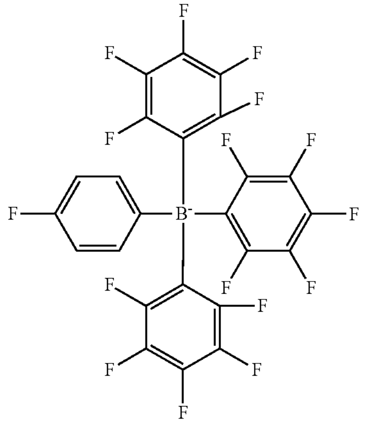

[Formula F]

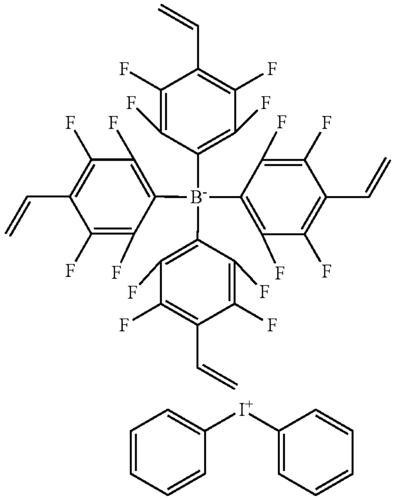

[Formula G]

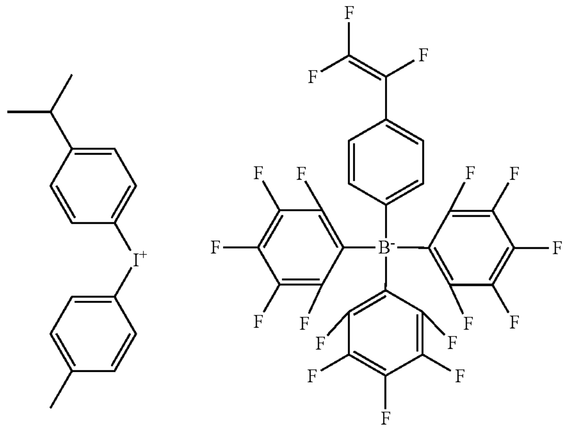

[Formula H]

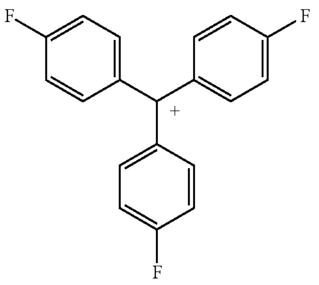

-continued

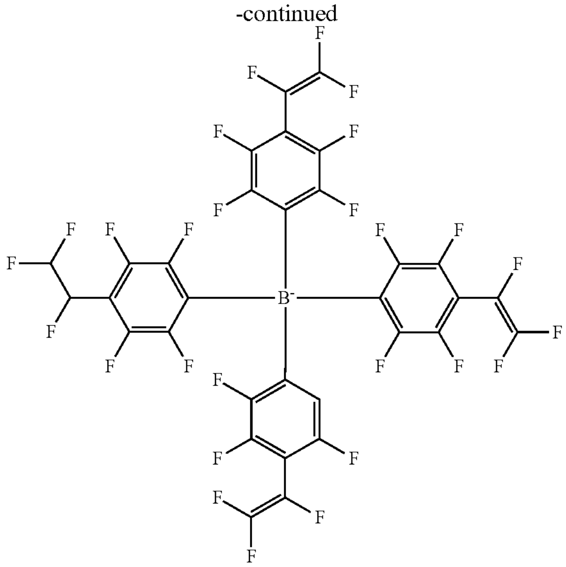

In the present specification, the p-doping material is sufficient as long as the material is a material which is allowed to have p-semiconductor characteristics, one or two or more thereof can be used, and the type thereof is not limited.

In an exemplary embodiment of the present specification, the content of the p-doping material is 0 wt % to 50 wt % based on the compound of Formula 1.

In an exemplary embodiment of the present specification, the content of the p-doping material is 0 to 30 wt % based on the total solid content of the coating composition. In an exemplary embodiment of the present specification, it is preferred that the content of the p-doping material is 1 to 30 wt % based on the total solid content of the coating composition, and in another exemplary embodiment, it is more preferred that the content of the p-doping material is 10 to 30 wt % based on the total solid content of the coating composition.

In another exemplary embodiment, the coating composition can further include: a single molecule including a cross-linkable functional group by heat or light; or a single molecule including an end group capable of forming a polymer by heat. As described above, the single molecule including a single molecule including a cross-linkable functional group by heat or light; or the single molecule including an end group capable of forming a polymer by heat can be a compound having a molecular weight of 3,000 g/mol or less.

In an exemplary embodiment of the present specification, the coating composition further includes: a single molecule having a molecular weight of 2,000 g/mol or less and including a cross-linkable functional group by heat or light; or a single molecule including an end group capable of forming a polymer by heat.

The single molecule including a cross-linkable functional group by heat or light; or the single molecule including an end group capable of forming a polymer by heat can mean a single molecule in which a cross-linkable functional group by heat or light or an end group capable of forming a polymer by heat is substituted with an aryl such as phenyl, biphenyl, fluorene, and naphthalene; arylamine; or fluorene.

In another exemplary embodiment, the coating composition has a viscosity of 2 cP to 15 cP at room temperature.

When the above viscosity is satisfied, a device is easily manufactured.

The present specification also provides an organic light emitting device formed by using the coating composition.

In an exemplary embodiment of the present specification, the organic light emitting device includes: a first electrode; a second electrode; and an organic material layer having one or more layers provided between the first electrode and the second electrode, in which one or more layers of the organic material layer include the coating composition or a cured product thereof, and the cured product of the coating composition is in a state where the coating composition is cured by a heat treatment or a light treatment.

In an exemplary embodiment of the present specification, the organic material layer including the coating composition or the cured product thereof is a hole transport layer or a hole injection layer.

In an exemplary embodiment of the present specification, the organic material layer including the coating composition or the cured product thereof is an electron transport layer or an electron injection layer.

In another exemplary embodiment, the organic material layer including the coating composition or the cured product thereof is a light emitting layer.

In another exemplary embodiment, the organic material layer including the coating composition or the cured product thereof is a light emitting layer, and the light emitting layer includes the compound of Formula 1 as a host of the light emitting layer.

In still another exemplary embodiment, the organic material layer including the coating composition or the cured product thereof is a light emitting layer, and the light emitting layer includes the compound of Formula 1 as a dopant of the light emitting layer.

In an exemplary embodiment of the present specification, the organic light emitting device further includes one or two or more layers selected from the group consisting of a hole injection layer, a hole transport layer, an electron transport layer, an electron injection layer, an electron blocking layer, a hole blocking layer, a layer which simultaneously transports and injects holes, and a layer which simultaneously transports and injects electrons.

In an exemplary embodiment of the present specification, the first electrode is an anode, and the second electrode is a cathode.

According to another exemplary embodiment, the first electrode is a cathode, and the second electrode is an anode.

In another exemplary embodiment, the organic light emitting device can be a normal type organic light emitting device in which an anode, an organic material layer having one or more layers, and a cathode are sequentially stacked on a substrate.

In still another exemplary embodiment, the organic light emitting device can be an inverted type organic light emitting device in which a cathode, an organic material layer having one or more layers, and an anode are sequentially stacked on a substrate.

The organic material layer of the organic light emitting device of the present specification can also be composed of a single-layered structure, but can be composed of a multi-layered structure in which an organic material layer having two or more layers is stacked. For example, the organic light emitting device of the present invention can have a structure including a hole injection layer, a hole transport layer, a light emitting layer, an electron transport layer, an electron injection layer, a layer which simultaneously transports and injects holes, a layer which simultaneously transports and injects electrons, and the like as an organic material layer. However, the structure of the organic light emitting device is not limited thereto, and can include a fewer number of organic layers.

For example, the structure of the organic light emitting device according to an exemplary embodiment of the present specification is exemplified in the FIGURE.

The FIGURE exemplifies a structure of an organic light emitting device in which an anode 201, a hole injection layer 301, a hole transport layer 401, a light emitting layer 501, a layer 601 which simultaneously transports and injects electrons, and a cathode 701 are sequentially stacked on a substrate 101.

The FIGURE exemplifies an organic light emitting device, and the organic light emitting device is not limited thereto.

When the organic light emitting device includes a plurality of organic material layers, the organic material layers can be formed of the same material or different materials.

The organic light emitting device of the present specification can be manufactured by the materials and methods known in the art, except that one or more layers of the organic material layer are formed by using the coating composition including the compound of Formula 1.

For example, the organic light emitting device of the present specification can be manufactured by sequentially stacking an anode, an organic material layer, and a cathode on a substrate. In this case, the organic light emitting device can be manufactured by depositing a metal or a metal oxide having conductivity, or an alloy thereof on a substrate to form an anode, forming an organic material layer including a hole injection layer, a hole transport layer, a light emitting layer, and a layer which simultaneously transports and injects electrons thereon through a solution process, a deposition process, and the like, and then depositing a material, which can be used as a cathode, thereon, by using a physical vapor deposition (PVD) method such as sputtering or e-beam evaporation. In addition to the method described above, an organic light emitting device can be made by sequentially depositing a cathode material, an organic material layer, and an anode material on a substrate.

The present specification also provides a method for manufacturing an organic light emitting device formed by using the coating composition.

Specifically, in an exemplary embodiment of the present specification, the method includes: preparing a substrate; forming a first electrode on the substrate; forming an organic material layer having one or more layers on the first electrode; and forming a second electrode on the organic material layer, in which the forming of the organic material layer includes forming an organic material layer having one or more layers by using the coating composition.

In an exemplary embodiment of the present specification, the forming of the organic material layer having one or more layers by using the coating composition uses a spin coating method.

In another exemplary embodiment, the forming of the organic material layer having one or more layers by using the coating composition uses a printing method.

In an exemplary embodiment state of the present specification, examples of the printing method include inkjet printing, nozzle printing, offset printing, transfer printing or screen printing, and the like, but are not limited thereto.

A solution process is suitable for the coating composition according to an exemplary embodiment of the present specification due to the structural characteristics thereof, so that the organic material layer can be formed by a printing method, and as a result, there is an economic effect in terms of time and costs when a device is manufactured.

In an exemplary embodiment of the present specification, the forming of the organic material layer having one or more layers by using the coating composition includes: coating the first electrode or the organic material layer having one or more layers with the coating composition; and heat-treating or light-treating the coated coating composition.

In an exemplary embodiment of the present specification, the heat-treating of the coated coating composition can be performed through a heat treatment, and the heat treatment temperature in the heat-treating of the coated coating composition can be 85° C. to 250° C., can be 100° C. to 250° C. according to an exemplary embodiment, and can be 150° C. to 250° C. in another exemplary embodiment.

In another exemplary embodiment, the heat treatment time in the heat-treating of the coated coating composition can be 1 minute to 2 hours, can be 1 minute to 1 hour according to an exemplary embodiment, and can be 30 minutes to 1 hour in another exemplary embodiment.

When the forming of the organic material layer formed by using the coating composition includes the heat-treating or light-treating of the coated coating composition, a plurality of the compounds included in the coating composition can form a cross-linkage, thereby providing an organic material layer including a thin-filmed structure. In this case, it is possible to prevent the organic material layer from being dissolved, morphologically affected or decomposed by a solvent when another layer is stacked on the surface of the organic material layer formed by using the coating composition.

Therefore, when the organic material layer formed by using the coating composition is formed by a method including the heat-treating or light-treating of the coated coating composition, resistance to a solvent is increased, so that a plurality of layers can be formed by repeatedly performing solution deposition and cross-linking methods, and stability is increased, so that the service life characteristic of the device can be increased.

As the anode material, materials having a high work function are usually preferred so as to facilitate the injection of holes into an organic material layer. Specific examples of the anode material which can be used in the present invention include: a metal such as vanadium, chromium, copper, zinc, and gold, or an alloy thereof; a metal oxide such as zinc oxide, indium oxide, indium tin oxide (ITO), and indium zinc oxide (IZO); a combination of a metal and an oxide, such as ZnO:Al or $SnO_2$:Sb; a conductive polymer such as poly(3-methylthiophene), poly[3,4-(ethylene-1,2-dioxy)thiophene] (PEDOT), polypyrrole, and polyaniline; and the like, but are not limited thereto.

As the cathode material, materials having a low work function are usually preferred so as to facilitate the injection of electrons into an organic material layer. Specific examples of the cathode material include: a metal such as barium, magnesium, calcium, sodium, potassium, titanium, indium, yttrium, lithium, gadolinium, aluminum, silver, tin, and lead, or an alloy thereof; a multi-layer structured material, such as LiF/Al or $LiO_2$/Al; and the like, but are not limited thereto.

The hole injection layer is a layer which injects holes from an electrode, and a hole injection material is preferably a compound which has a capability of transporting holes, and thus has an effect of injecting holes at an anode and an excellent effect of injecting holes into a light emitting layer or a light emitting material, prevents excitons produced from the light emitting layer from moving to an electron injection layer or an electron injection material, and is also excellent in the ability to form a thin film. The highest occupied molecular orbital (HOMO) of the hole injection material is preferably a value between the work function of the anode material and the HOMO of the neighboring organic material layer. Specific examples of the hole injection material include the above-described compound of Formula 1, metal porphyrin, oligothiophene, arylamine-based organic materials, hexanitrile hexaazatriphenylene-based organic materials, quinacridone-based organic materials, perylene-based organic materials, anthraquinone, polyaniline-based and polythiophene-based electrically conductive polymers, and the like, but are not limited thereto.

The hole transport layer is a layer which accepts holes from a hole injection layer and transports the holes to a light emitting layer, and a hole transport material is suitably a material having high hole mobility which can accept holes from an anode or a hole injection layer and transfer the holes to a light emitting layer. Specific examples thereof include arylamine-based organic materials, conductive polymers, block copolymers having both conjugated portions and non-conjugated portions, and the like, but are not limited thereto.

The layer which simultaneously transports and injects holes can include materials for the hole transport layer and the hole injection layer described above.

The light emitting material is a material which can accept holes and electrons from a hole transport layer and an electron transport layer, respectively, and combine the holes and the electrons to emit light in a visible ray region, and is preferably a material having high quantum efficiency for fluorescence or phosphorescence. Specific examples thereof include: 8-hydroxy-quinoline aluminum complexes ($Alq_3$); carbazole-based compounds; dimerized styryl compounds; BAlq; 10-hydroxybenzoquinoline-metal compounds; benzoxazole-based, benzthiazole-based and benzimidazole-based compounds; poly(p-phenylenevinylene) (PPV)-based polymers; spiro compounds; polyfluorene, lubrene, and the like, but are not limited thereto.

The light emitting layer can include a host material and a dopant material. Examples of the host material include a fused aromatic ring derivative, or a hetero ring-containing compound, and the like. Specifically, examples of the fused aromatic ring derivatives include anthracene derivatives, pyrene derivatives, naphthalene derivatives, pentacene derivatives, phenanthrene compounds, fluoranthene compounds, and the like, and examples of the hetero ring-containing compounds include carbazole derivatives, dibenzofuran derivatives, ladder-type furan compounds, pyrimidine derivatives, and the like, but the examples thereof are not limited thereto.

Examples of the dopant material include aromatic amine derivatives, styrylamine compounds, boron complexes, fluoranthene compounds, metal complexes, and the like. Specifically, the aromatic amine derivative is a fused aromatic ring derivative having a substituted or unsubstituted arylamino group, and examples thereof include pyrene, anthracene, chrysene, periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group is or are substituted or unsubstituted. Specific examples thereof include styrylamine, styryldiamine, styryltriamine, styryltetramine, and the like, but are not limited thereto. Further, examples of the metal complex include iridium complexes, platinum complexes, and the like, but are not limited thereto.

The electron transport layer is a layer which accepts electrons from an electron injection layer and transports the electrons to a light emitting layer, and an electron transport material is suitably a material having high electron mobility which can proficiently accept electrons from a cathode and transfer the electrons to a light emitting layer. Specific examples thereof include: Al complexes of 8-hydroxyquinoline; complexes including $Alq_3$; organic radical compounds; hydroxyflavone-metal complexes, and the like, but are not limited thereto. The electron transport layer can be used with any desired cathode material, as used according to the related art. In particular, examples of an appropriate cathode material include a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and an electron injection material is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, metal complex compounds, nitrogen-containing 5-membered ring derivatives, and the like, but are not limited thereto.

The layer which simultaneously transports and injects electrons can include materials for the electron transport layer and the electron injection layer described above.

Examples of the metal complex compounds include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The hole blocking layer is a layer which blocks holes from reaching a cathode, and can be generally formed under the same conditions as those of the hole injection layer. Specific examples thereof include oxadiazole derivatives or triazole derivatives, phenanthroline derivatives, BCP, aluminum complexes, and the like, but are not limited thereto.

The electron blocking layer is a layer which blocks electrons from reaching an anode, and materials known in the art can be used.

The organic light emitting device according to the present specification can be a top emission type, a bottom emission type, or a dual emission type according to the materials to be used.

Hereinafter, the present specification will be described in detail with reference to Examples for specifically describing the present specification. However, the Examples according to the present specification can be modified into various forms, and it is not to be interpreted that the scope of the present specification is limited to the Examples described below in detail. The Examples of the present specification are provided to describe the present specification more completely to a person with ordinary skill in the art.

PREPARATION EXAMPLES

Preparation Example 1. Preparation of Compound A

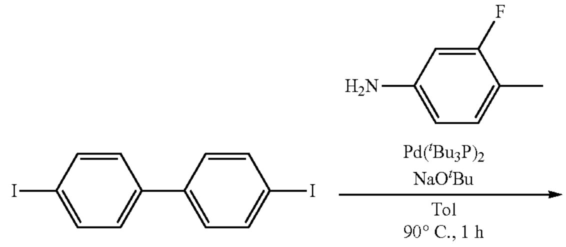

-continued

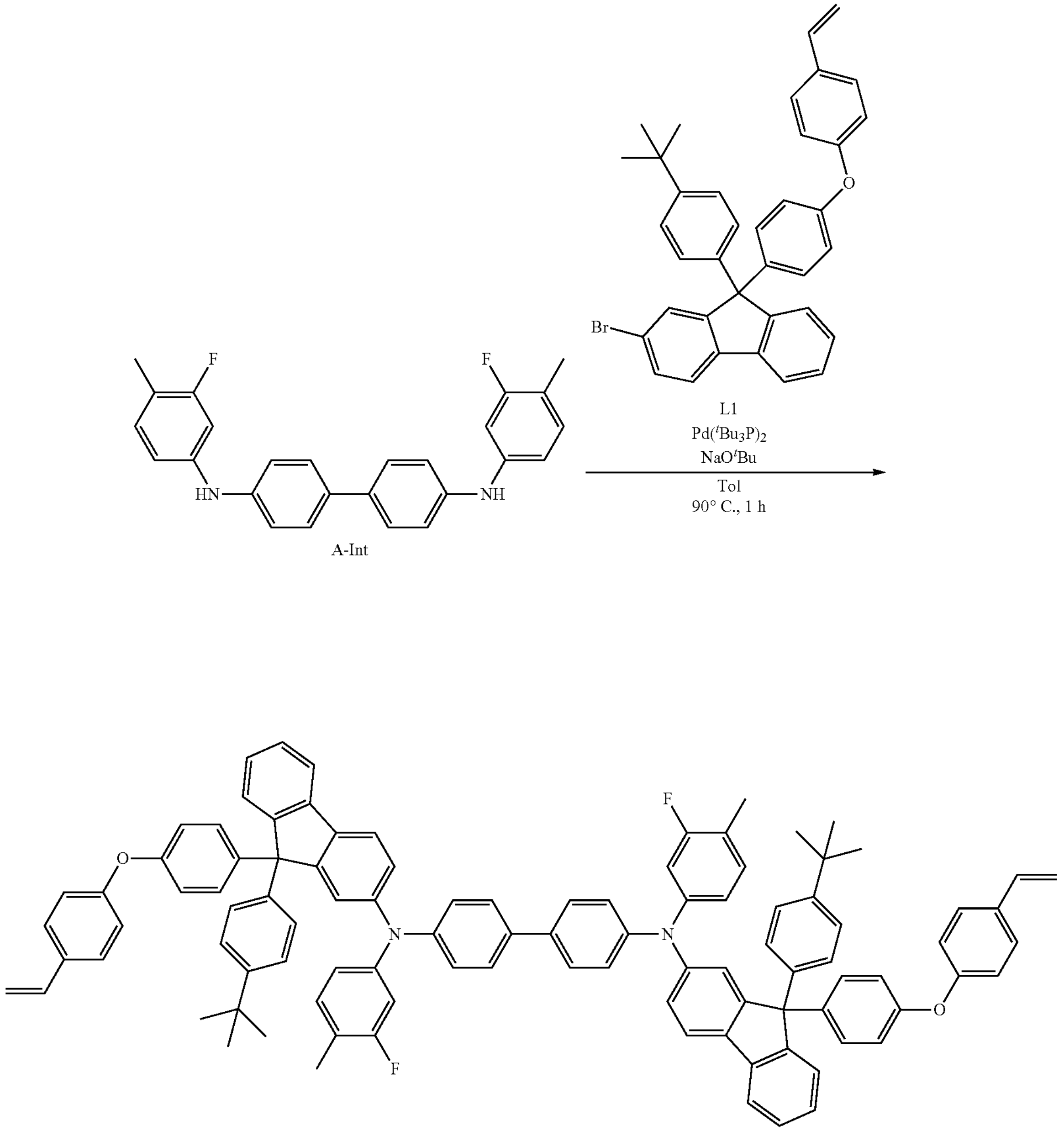

A-Int

A

Synthesis of A-Int: diiodobiphenyl (10.0 g, 24.6 mmol), 3-fluoro-4-methylaniline (6.20 mL, 54.2 mmol), and NaOtBu (7.10 g, 73.9 mmol) were put into a round bottom flask (RBF), and then toluene (120 mL) was introduced therein. After Pd($^tBu_3P)_2$ (0.629 g, 1.23 mmol) was introduced therein, the resulting mixture was stirred at 90° C. for 1 hour. Thereafter, water was added thereto, an organic layer was extracted with ethyl acetate (EA), and then dried over $MgSO_4$, dichloromethane (DCM) was put thereinto, and the resulting mixture was filtered to obtain A-Int (6.00 g).

Synthesis of A: A-Int (1.50 g, 3.75 mmol), L1 (4.50 g, 7.87 mmol), and NaOtBu (1.08 g, 11.2 mmol) were put into a round bottom flask (RBF), and then toluene (30 mL) was introduced therein. After the resulting mixture was warmed to 90° C., Pd($^tBu_3P)_2$ (0.134 g, 0.262 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound A (3.61 g). $[M+H]^+=1382$ $^1H$ NMR: δ 7.72-7.70 (m, 2H), 7.66-7.64 (m, 2H), 7.41-7.33 (m, 12H), 7.26-7.20 (m, 8H), 7.12-7.02 (m, 16H), 6.94-6.92 (m, 4H), 6.85-6.83 (m, 4H), 6.78-6.75 (m, 4H), 6.67-6.61 (dd, 2H), 5.64-5.60 (d, 2H), 5.14-5.12 (d, 2H), 2.22 (br s, 6H), 1.27 (m, 18H)

Preparation Example 2. Preparation of Compound B

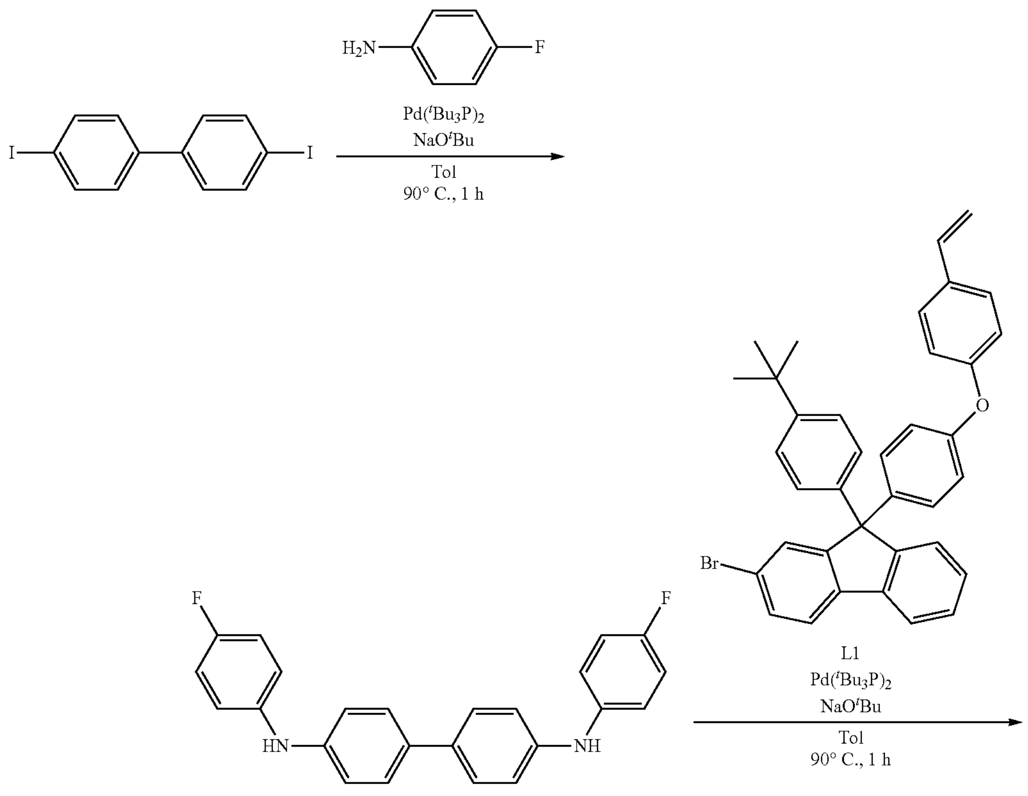

B-Int

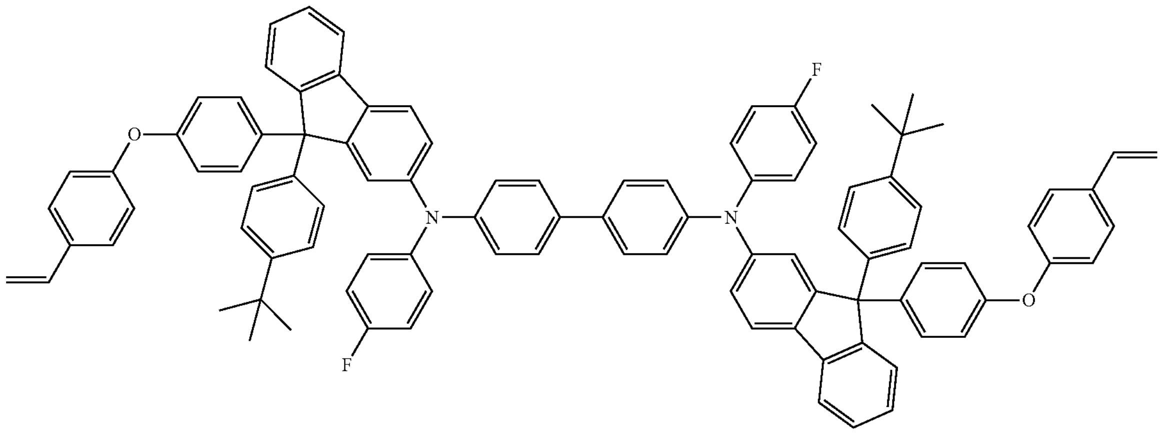

B

Synthesis of B-Int: diiodobiphenyl (10.0 g, 24.6 mmol), 4-fluoroaniline (5.12 mL, 54.2 mmol), and NaOtBu (7.10 g, 73.9 mmol) were put into a round bottom flask (RBF), and then toluene (120 mL) was introduced therein. After Pd($^t$Bu$_3$P)$_2$ (0.629 g, 1.23 mmol) was introduced therein, the resulting mixture was stirred at 90° C. for 1 hour. Thereafter, water was added thereto, an organic layer was extracted with ethyl acetate (EA), and then dried over $MgSO_4$, dichloromethane (DCM) was put thereinto, and the resulting mixture was filtered to obtain B-Int (6.10 g).

Synthesis of B: B-Int (1.50 g, 4.03 mmol), L1 (4.83 g, 8.46 mmol), and NaOtBu (1.16 g, 12.1 mmol) were put into a round bottom flask (RBF), and then toluene (30 mL) was introduced therein. After the resulting mixture was warmed to 90° C., Pd($^t$Bu$_3$P)$_2$ (0.144 g, 0.282 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound B (3.43 g). $[M+H]^+=1354$ $^1$H NMR: δ 7.71-7.69 (d, 2H), 7.65-7.63 (d, 2H), 7.39-7.33 (m, 12H), 7.26-7.22 (m, 6H), 7.18 (m, 2H), 7.11-7.02 (m, 18H), 6.98-6.92 (m, 8H), 6.85-6.83 (m, 4H), 6.67-6.61 (dd, 2H), 5.64-5.60 (d, 2H), 5.15-5.12 (d, 2H), 1.27 (m, 18H)

Preparation Example 3. Preparation of Compound C

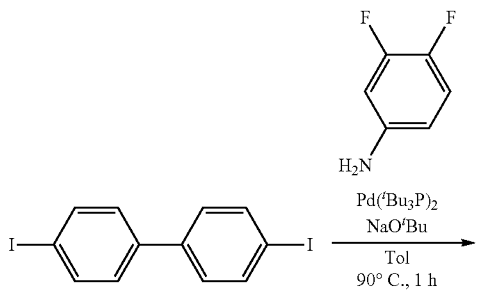

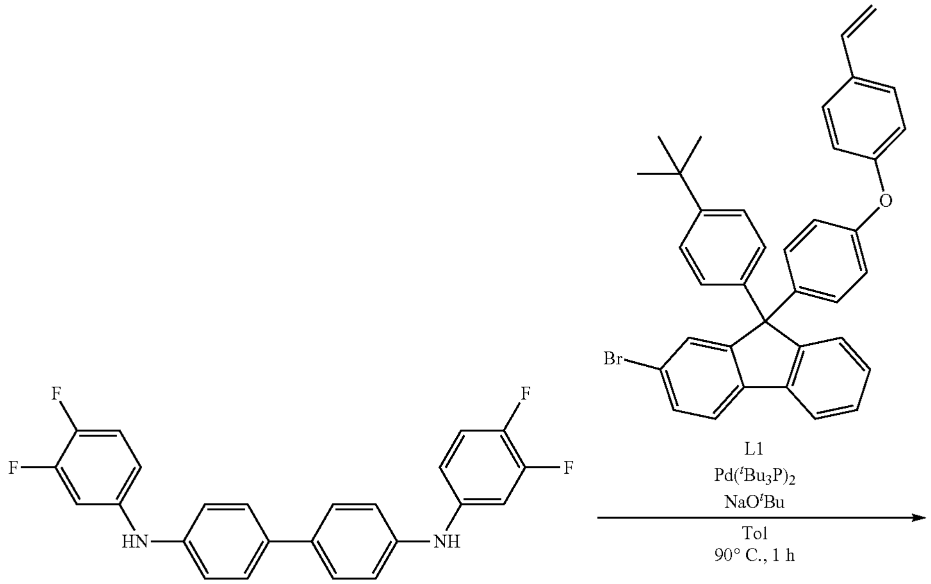

C-Int

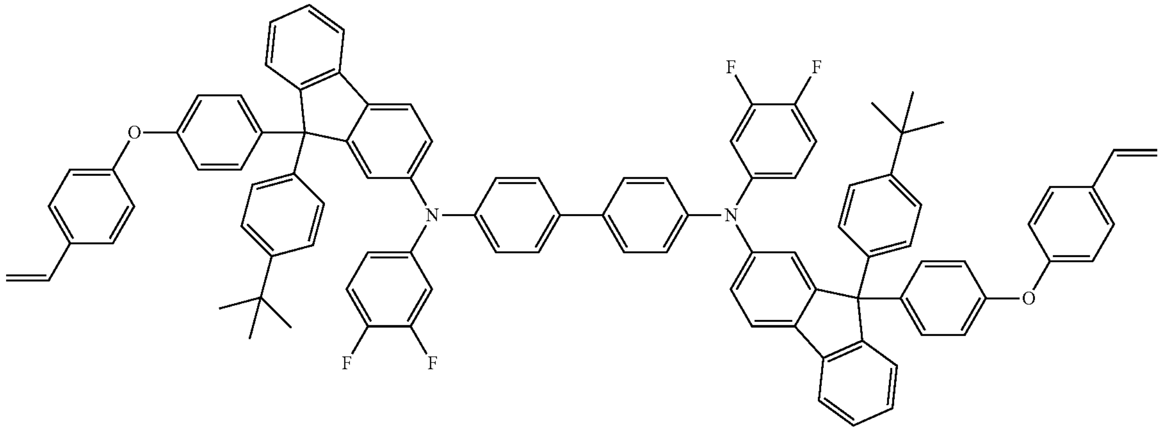

C

Synthesis of C-Int: diiodobiphenyl (12.0 g, 29.6 mmol), 3,4-difluoroaniline (6.45 mL, 65.0 mmol), and NaOtBu (8.52 g, 88.7 mmol) were put into a round bottom flask (RBF), and then toluene (150 mL) was introduced therein. After $Pd(^tBu_3P)_2$ (0.755 g, 1.48 mmol) was introduced therein, the resulting mixture was stirred at 90° C. for 1 hour. Thereafter, water was added thereto, an organic layer was extracted with ethyl acetate (EA), and then dried over $MgSO_4$, dichloromethane (DCM) was put thereinto, and the resulting mixture was filtered to obtain C-Int (9.56 g).

Synthesis of C: C-Int (0.600 g, 1.47 mmol), L1 (1.70 g, 2.98 mmol), and NaOtBu (0.424 g, 4.41 mmol) were put into a round bottom flask (RBF), and then toluene (20 mL) was introduced therein. After the resulting mixture was warmed to 90° C., $Pd(^tBu_3P)_2$ (0.0526 g, 0.103 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound C (1.17 g). $[M+H]^+$=1390

$^1H$ NMR: δ 7.73-7.71 (d, 2H), 7.68-7.66 (d, 2H), 7.43-7.41 (m, 4H), 7.38-7.33 (m, 8H), 7.27-7.23 (m, 6H), 7.19 (m, 2H), 7.11-7.00 (m, 16H), 6.94-6.92 (m, 6H), 6.86-6.80 (m, 6H), 6.67-6.61 (dd, 2H), 5.64-5.61 (d, 2H), 5.15-5.13 (d, 2H), 1.26 (m, 18H)

Preparation Example 4. Preparation of Compound D

Synthesis of D-Int: diiodobiphenyl (6.00 g, 14.8 mmol), 2,6-difluoroaniline (3.50 mL, 32.5 mmol), and NaOtBu (4.26 g, 44.3 mmol) were put into a round bottom flask (RBF), and then toluene (80 mL) was introduced therein.

After $Pd(^tBu_3P)_2$ (0.854 g, 0.739 mmol) was introduced therein, the resulting mixture was stirred at 90° C. for 1 hour. Thereafter, water was added thereto, an organic layer was extracted with ethyl acetate (EA), and then dried over $MgSO_4$, dichloromethane (DCM) was put thereinto, and the resulting mixture was filtered to obtain D-Int (5.50 g).

Synthesis of D: D-Int (2.00 g, 4.90 mmol), L1 (5.74 g, 10.0 mmol), and NaOtBu (1.41 g, 14.7 mmol) were put into a round bottom flask (RBF), and then toluene (48 mL) was

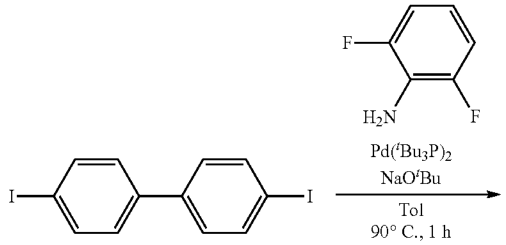

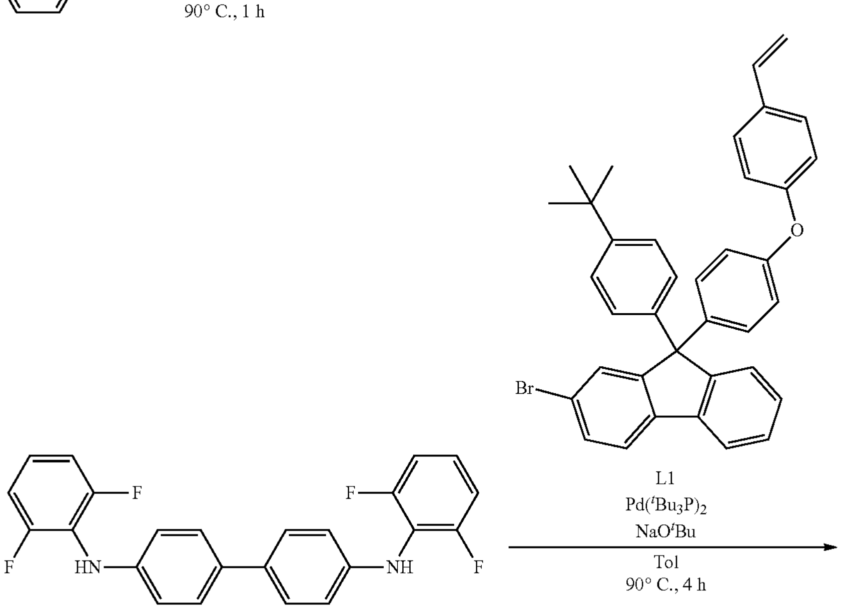

D-Int

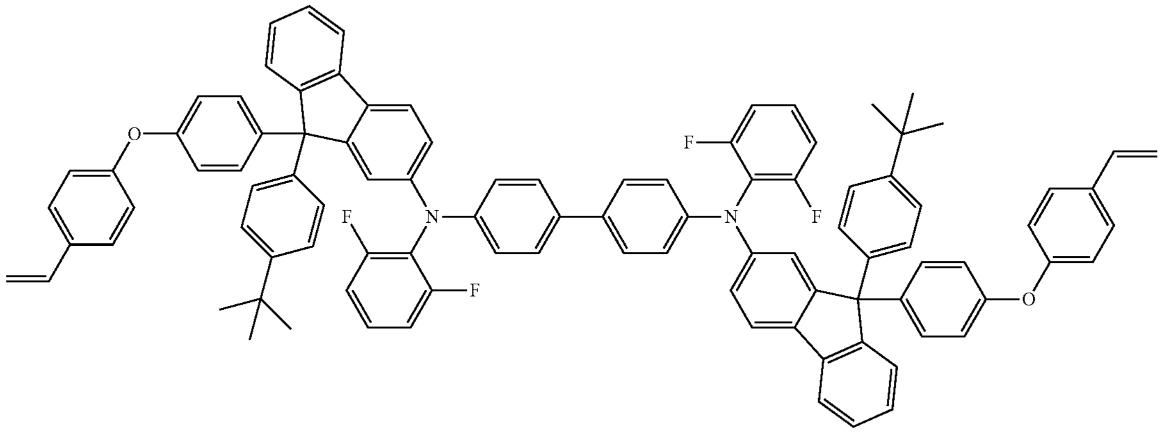

D introduced therein. After the resulting mixture was warmed to 90° C., Pd($^t$Bu$_3$P)$_2$ (0.175 g, 0.343 mmol) was introduced therein, and the resulting mixture was stirred for 4 hours. Water was added thereto, and an organic layer was extracted with dichloromethane (DCM), and then dried over $MgSO_4$, and column purified with dichloromethane/hexane to obtain high-purity Compound D (1.20 g). $[M+H]^+$=1390

$^1$H NMR: δ 7.71-7.70 (d, 2H), 7.66-7.65 (d, 2H), 7.38-7.33 (m, 12H), 7.27-7.22 (m, 8H), 7.17 (m, 2H), 7.11-7.06 (m, 8H), 7.01-6.91 (m, 14H), 6.85-6.83 (m, 4H), 6.66-6.60 (dd, 2H), 5.63-5.60 (d, 2H), 5.14-5.12 (d, 2H), 1.27 (m, 18H)

Preparation Example 5: Preparation of Compound E

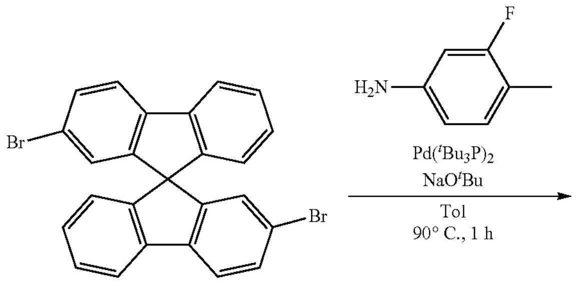

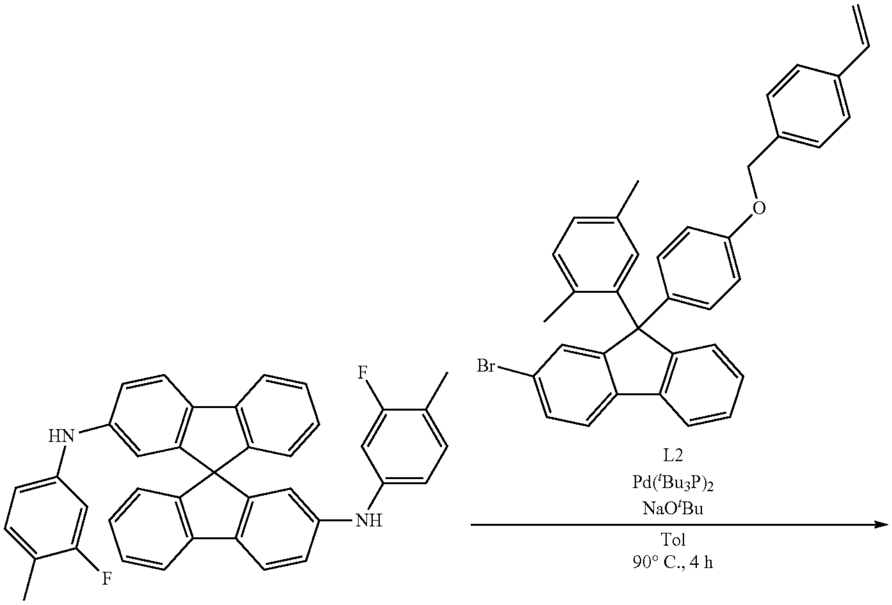

E-Int

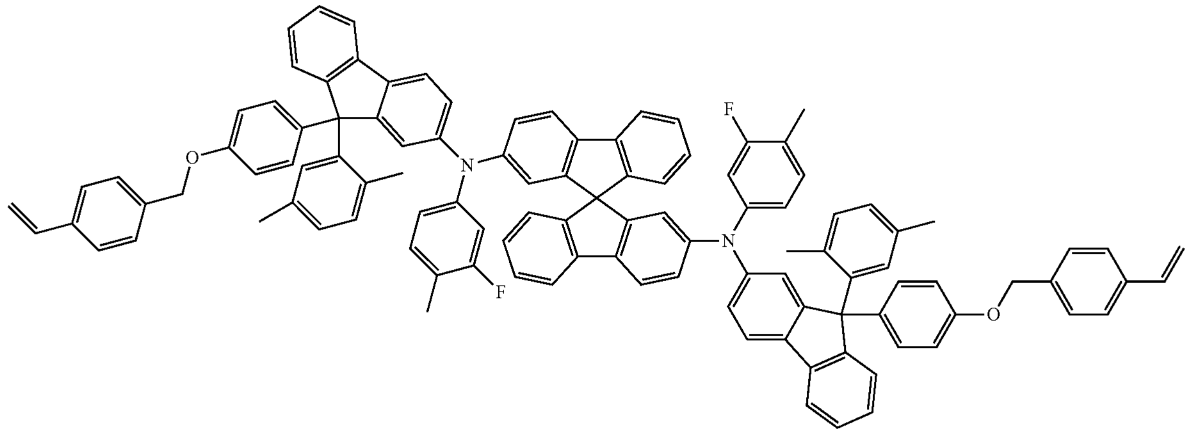

E

Synthesis of E-Int: 2,2'-dibromo-9,9'-spirobifluorene (8.00 g, 16.9 mmol), 3-fluoro-4-methylaniline (4.25 mL, 37.1 mmol), and NaOtBu (4.86 g, 50.6 mmol) were put into a round bottom flask (RBF), and then toluene (160 mL) was introduced therein. After Pd($^t$Bu$_3$P)$_2$ (0.431 g, 0.844 mmol) was introduced therein, the resulting mixture was stirred at 90° C. for 1 hour. Thereafter, water was added thereto, an organic layer was extracted with ethyl acetate (EA), and then dried over $MgSO_4$, dichloromethane (DCM) was put thereinto, and the resulting mixture was filtered to obtain E-Int (6.64 g).

Synthesis of E: E-Int (2.00 g, 3.56 mmol), L2 (4.16 g, 7.47 mmol), and NaOtBu (1.02 g, 10.7 mmol) were put into a round bottom flask (RBF), and then toluene (70 mL) was introduced therein. After the resulting mixture was warmed to 90° C., Pd($^t$Bu$_3$P)$_2$ (0.127 g, 0.249 mmol) was introduced therein, and the resulting mixture was stirred for 4 hours. Water was added thereto, and an organic layer was extracted with dichloromethane (DCM), and then dried over $MgSO_4$, and column purified with dichloromethane/hexane to obtain high-purity Compound E (2.69 g). $[M+H]^+$=1516

$^1$H NMR: δ 7.71-7.70 (m, 4H), 7.65-7.63 (m, 4H), 7.40-7.34 (m, 12H), 7.27-7.21 (m, 8H), 7.11-7.03 (m, 16H), 6.95-6.91 (m, 4H), 6.84-6.82 (m, 4H), 6.79-6.76 (m, 4H), 6.68-6.62 (dd, 2H), 5.64-5.60 (d, 2H), 5.14-5.12 (d, 2H), 4.81 (s, 4H), 2.22 (br s, 6H), 2.18 (m, 12H)

Preparation Example 6: Preparation of Compound F

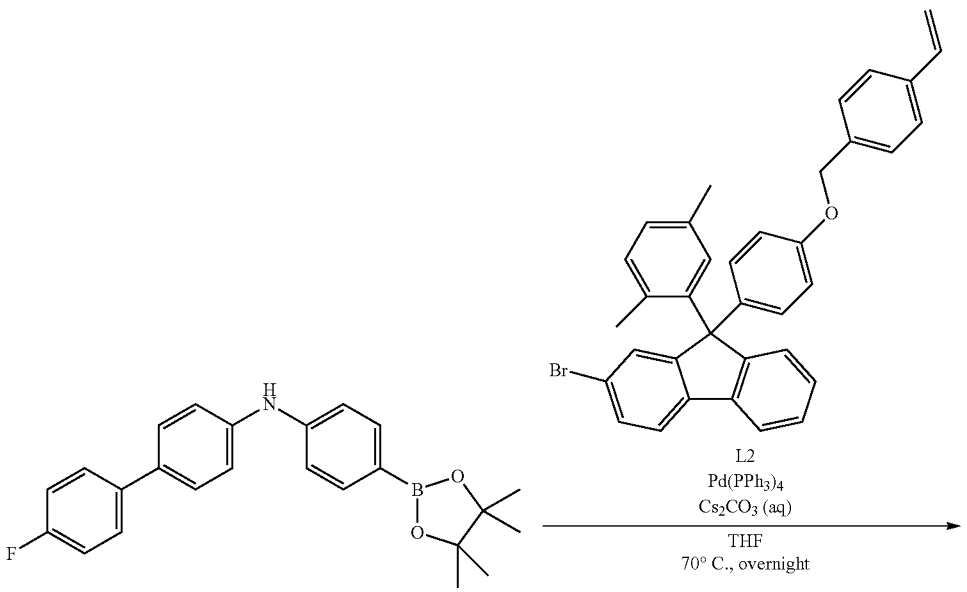

F-Int-1

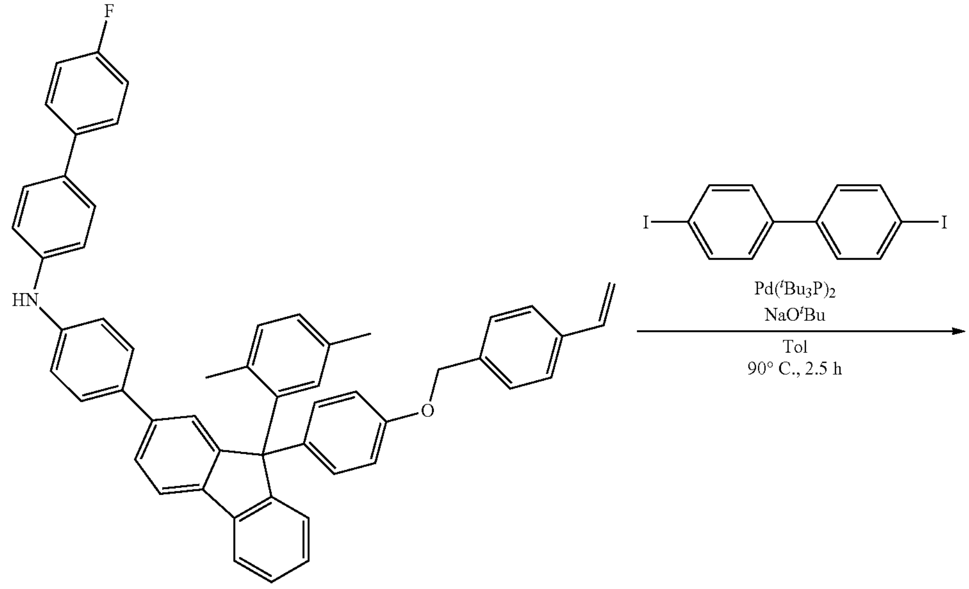

F-Int-2

-continued

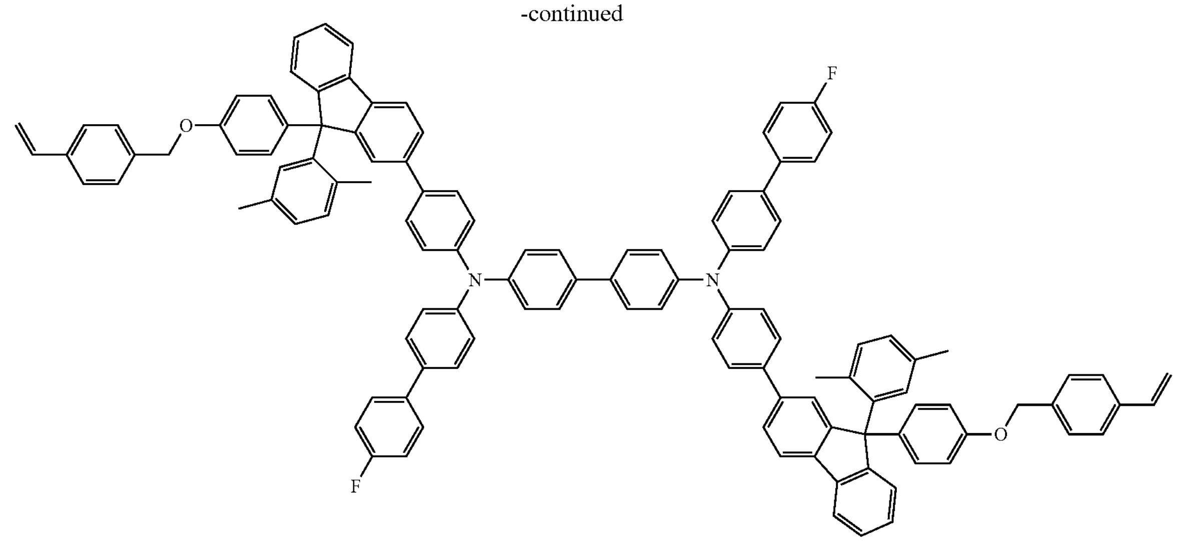

F

Synthesis of F-Int-2: F-Int-1 (4.00 g, 10.3 mmol) and L2 (11.7 g, 21.1 mmol) were put into a round bottom flask (RBF), and then tetrahydrofuran (THF) (100 mL) was introduced therein. $Cs_2CO_3$ (10.0 g, 30.8 mmol) and $Pd(PPh_3)_4$ (0.831 g, 0.719 mmol) dissolved in 25 mL of water were introduced therein in this order, and then the resulting mixture was stirred at 70° C. overnight. Water was added thereto, and an organic layer was extracted with dichloromethane (DCM), and then dried over $MgSO_4$, and column purified with dichloromethane/hexane to obtain Compound F-Int-2 (5.32 g).

Synthesis of F: diiodobiphenyl (1.20 g, 2.96 mmol), F-Int-2 (4.59 g, 6.21 mmol), and NaOtBu (0.852 g, 8.87 mmol) were put into a round bottom flask (RBF), and then toluene (60 mL) was introduced therein. After the resulting mixture was warmed to 90° C., $Pd(^tBu_3P)_2$ (0.106 g, 0.207 mmol) was introduced therein, and the resulting mixture was stirred for 2.5 hours. Water was added thereto, and an organic layer was extracted with dichloromethane (DCM), and then dried over $MgSO_4$, and column purified with dichloromethane/hexane to obtain high-purity Compound F (2.41 g). $[M+H]^+=1630$ $^1H$ NMR: δ 7.74-7.72 (m, 2H), 7.65-7.63 (m, 2H), 7.40-7.32 (m, 12H), 7.30-7.28 (m, 16H), 7.26-7.23 (m, 6H), 7.20 (m, 2H), 7.15-7.05 (m, 18H), 6.98-6.92 (m, 6H), 6.87-6.84 (m, 4H), 6.66-6.60 (dd, 2H), 5.65-5.61 (d, 2H), 5.15-5.12 (d, 2H), 4.80 (s, 4H), 2.17 (m, 12H)

Preparation Example 7: Preparation of Compound G

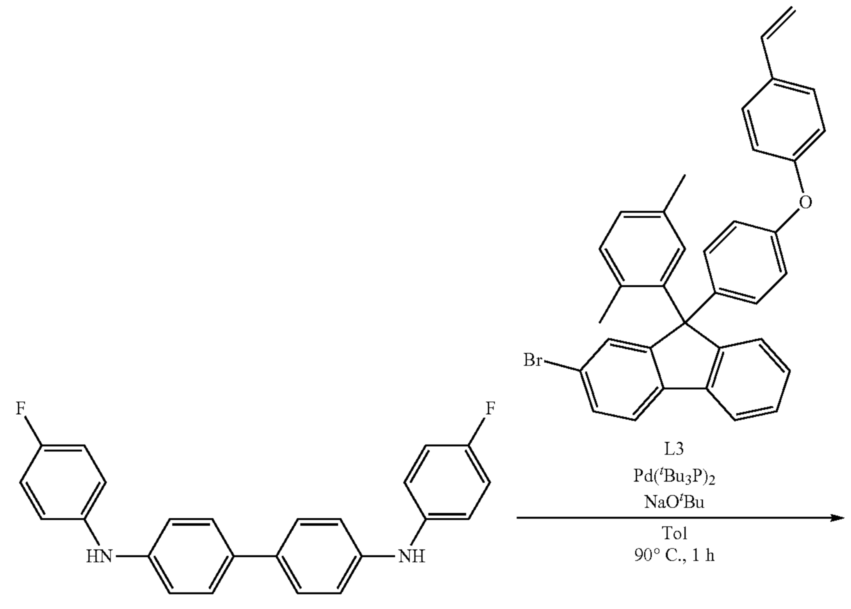

B-Int

-continued

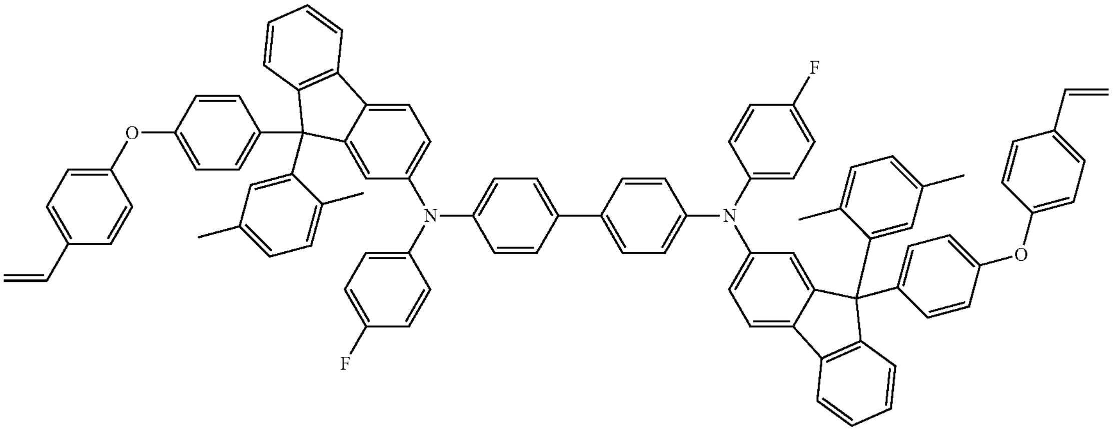

G

Synthesis of G: B-Int (1.50 g, 4.03 mmol), L3 (4.60 g, 8.46 mmol), and NaOtBu (1.16 g, 12.1 mmol) were put into a round bottom flask (RBF), and then toluene (80 mL) was introduced therein. After the resulting mixture was warmed to 90° C., $Pd(^tBu_3P)_2$ (0.103 g, 0.201 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound G (2.61 g). $[M+H]^+=1298$ $^1H$ NMR: δ 7.71-7.69 (d, 2H), 7.65-7.63 (d, 2H), 7.38-7.31 (m, 12H), 7.26-7.22 (m, 6H), 7.15 (m, 2H), 7.13-7.02 (m, 16H), 6.97-6.92 (m, 8H), 6.85-6.82 (m, 4H), 6.66-6.60 (dd, 2H), 5.63-5.60 (d, 2H), 5.15-5.12 (d, 2H), 2.25 (m, 12H)

Preparation Example 8: Preparation of Compound H

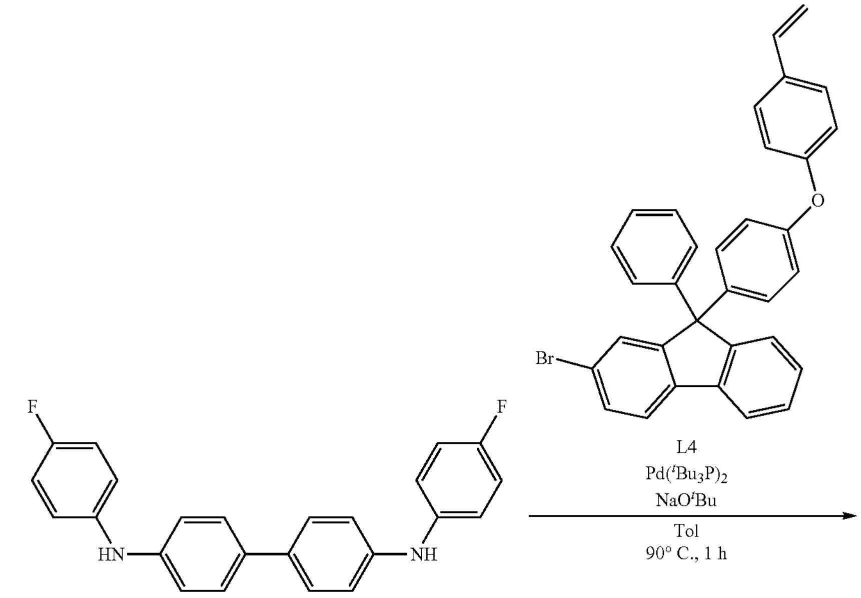

B-Int

-continued

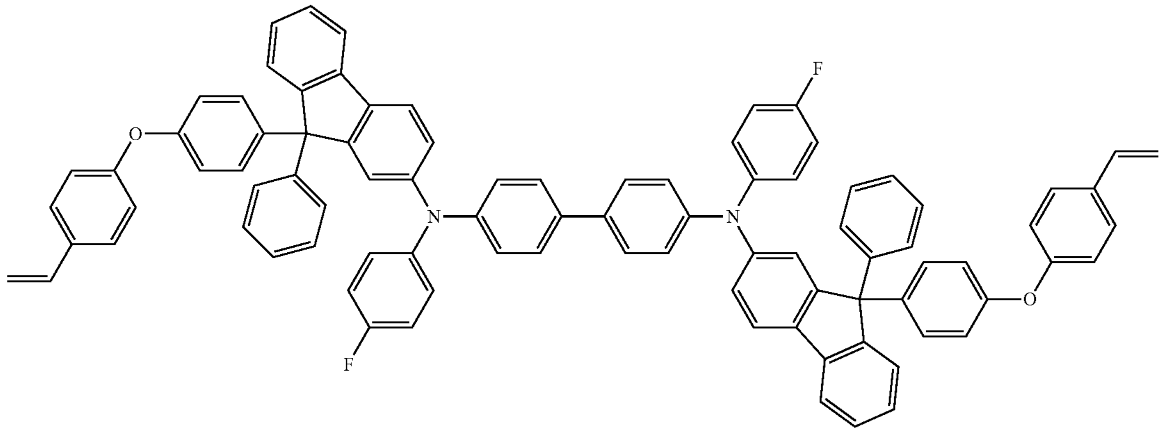

H

Synthesis of H: B-Int (1.60 g, 4.30 mmol), L4 (4.65 g, 9.02 mmol), and NaOtBu (1.24 g, 12.9 mmol) were put into a round bottom flask (RBF), and then toluene (80 mL) was introduced therein. After the resulting mixture was warmed to 90° C., Pd($^t$Bu$_3$P)$_2$ (0.110 g, 0.215 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound H (2.67 g). $[M+H]^+=1241$ $^1$H NMR: δ 7.71-7.69 (d, 2H), 7.65-7.63 (d, 2H), 7.37-7.31 (m, 12H), 7.25-7.22 (m, 6H), 7.16 (m, 2H), 7.12-7.01 (m, 20H), 6.98-6.91 (m, 8H), 6.86-6.82 (m, 4H), 6.66-6.61 (dd, 2H), 5.64-5.60 (d, 2H), 5.15-5.12 (d, 2H)

Preparation Example 9: Preparation of Compound I

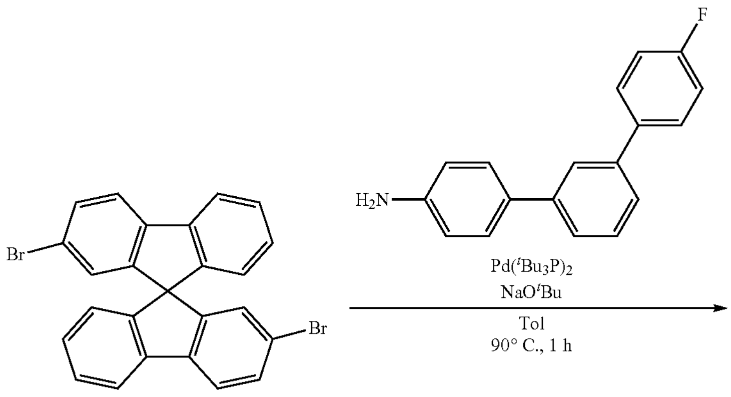

-continued

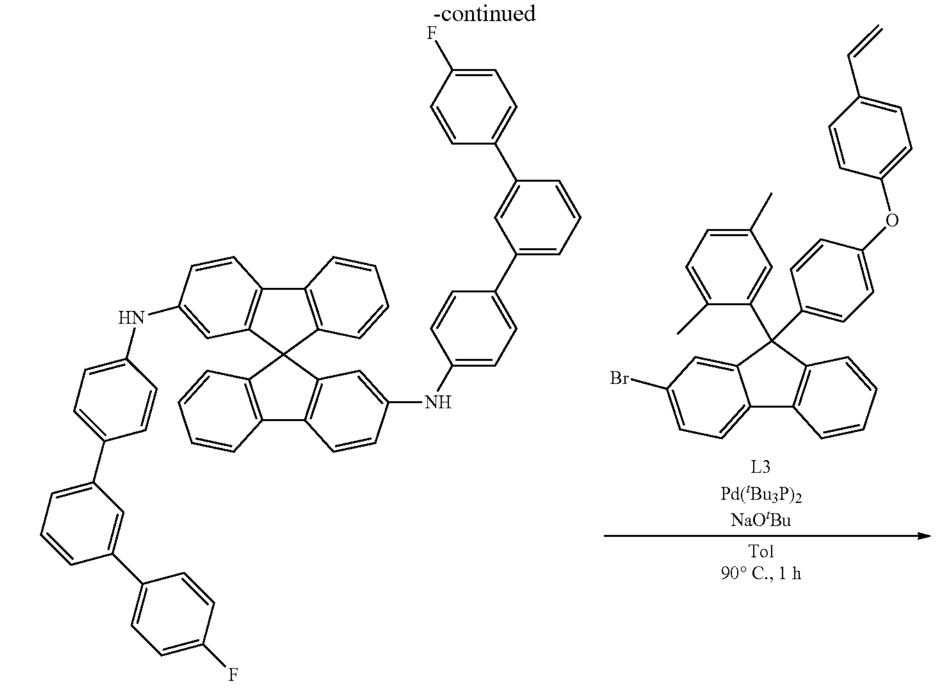

I-Int

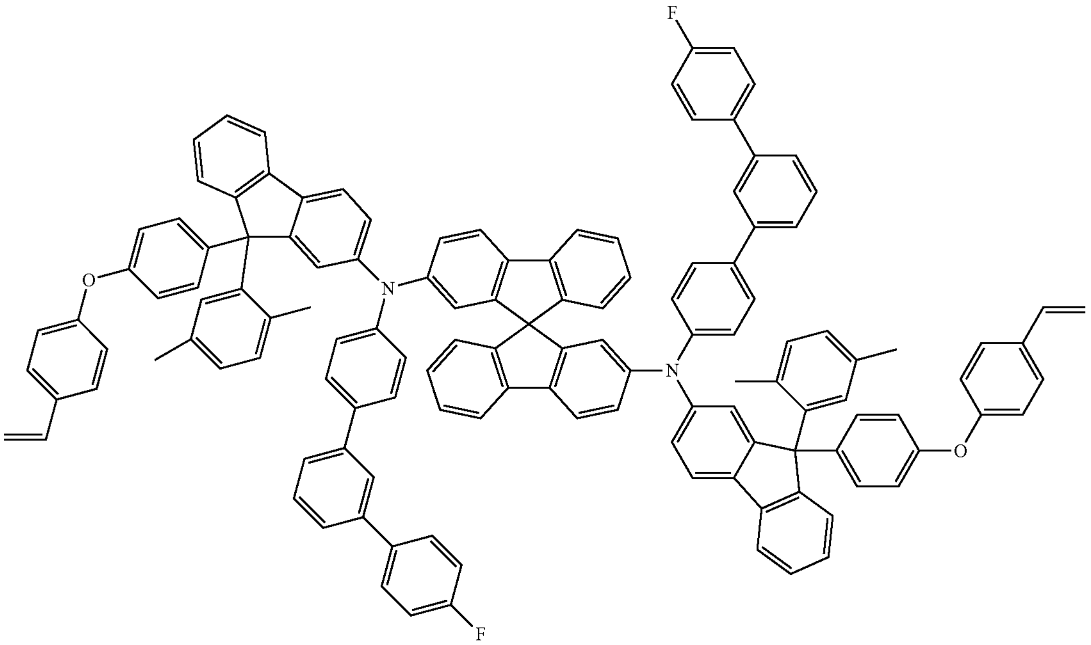

I

Synthesis of I-Int: 2,2'-dibromo-9,9'-spirobifluorene (5.00 g, 10.5 mmol), 4"-fluoro-[1,1':3',1"-terphenyl]-4-amine (6.11 g, 23.2 mmol), and NaOtBu (3.04 g, 31.6 mmol) were put into a round bottom flask (RBF), and then toluene (150 mL) was introduced therein. After $Pd(^tBu_3P)_2$ (0.269 g, 0.527 mmol) was introduced therein, the resulting mixture was stirred at 90° C. for 1 hour. Thereafter, water was added thereto, an organic layer was extracted with ethyl acetate (EA), and then dried over $MgSO_4$, dichloromethane (DCM) was put thereinto, and the resulting mixture was filtered to obtain I-Int (6.19 g).

Synthesis of I: I-Int (1.60 g, 1.91 mmol), L3 (2.18 g, 2.10 mmol), and NaOtBu (0.550 g, 5.72 mmol) were put into a round bottom flask (RBF), and then toluene (38 mL) was introduced therein. After the resulting mixture was warmed to 90° C., $Pd(^tBu_3P)_2$ (0.0487 g, 0.095 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound I (1.68 g). $[M+H]^+$=1764

$^1H$ NMR: δ 7.73-7.69 (m, 4H), 7.66-7.61 (m, 4H), 7.58-7.50 (m, 8H), 7.42-7.34 (m, 8H), 7.27-7.22 (m, 12H), 7.18-7.14 (m, 6H), 7.11-7.01 (m, 16H), 6.97-6.89 (m, 8H), 6.84-6.81 (m, 4H), 6.77-6.74 (m, 4H), 6.68-6.62 (dd, 2H), 5.64-5.60 (d, 2H), 5.14-5.12 (d, 2H), 2.18 (m, 12H)

Preparation Example 10: Preparation of Compound J

Synthesis of J: B-Int (2.00 g, 5.37 mmol), L5 (6.38 g, 11.3 mmol), and NaOtBu (1.55 g, 16.1 mmol) were put into a round bottom flask (RBF), and then toluene (100 mL) was introduced therein. After the resulting mixture was warmed to 90° C., $Pd(^tBu_3P)_2$ (0.137 g, 0.269 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound J (3.60 g). $[M+H]^+$=1342

$^1H$ NMR: δ 7.70-7.68 (d, 2H), 7.64-7.62 (d, 2H), 7.50-7.47 (m, 2H), 7.35-7.30 (m, 12H), 7.26-7.22 (m, 6H), 7.16 (m, 2H), 7.13-7.03 (m, 20H), 6.97-6.91 (m, 8H), 6.84-6.79 (m, 4H), 6.64-6.59 (dd, 2H), 5.64-5.61 (d, 2H), 5.14-5.09 (d, 2H)

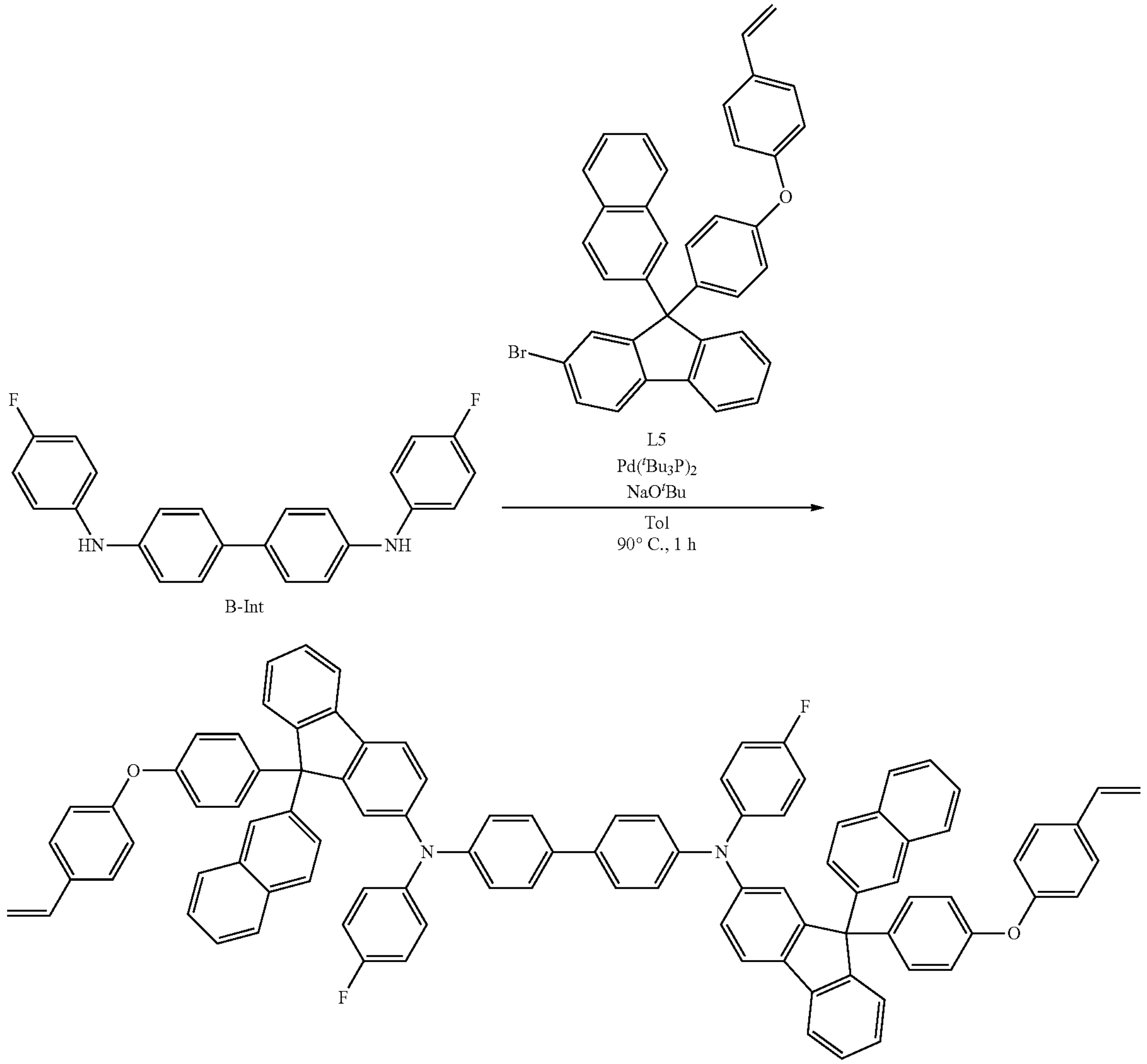

J

Preparation Example 11: Preparation of Compound K

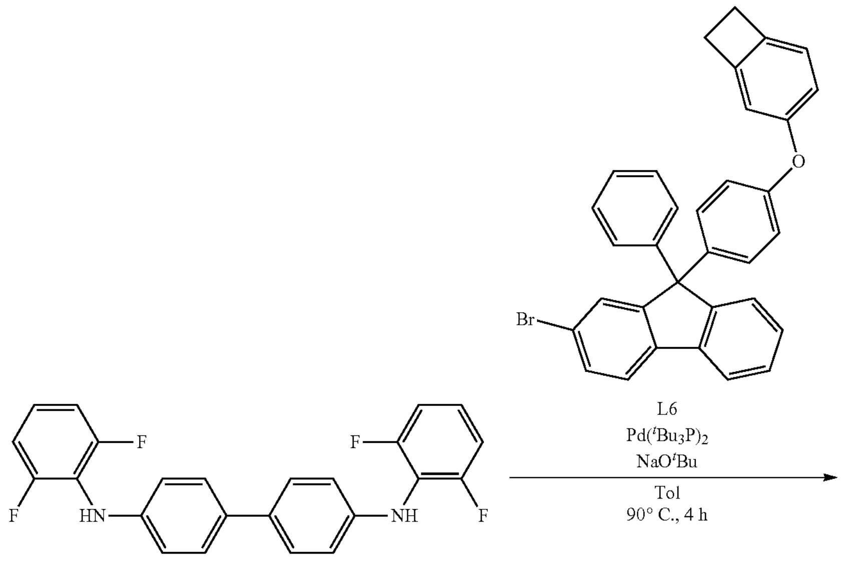

D-Int

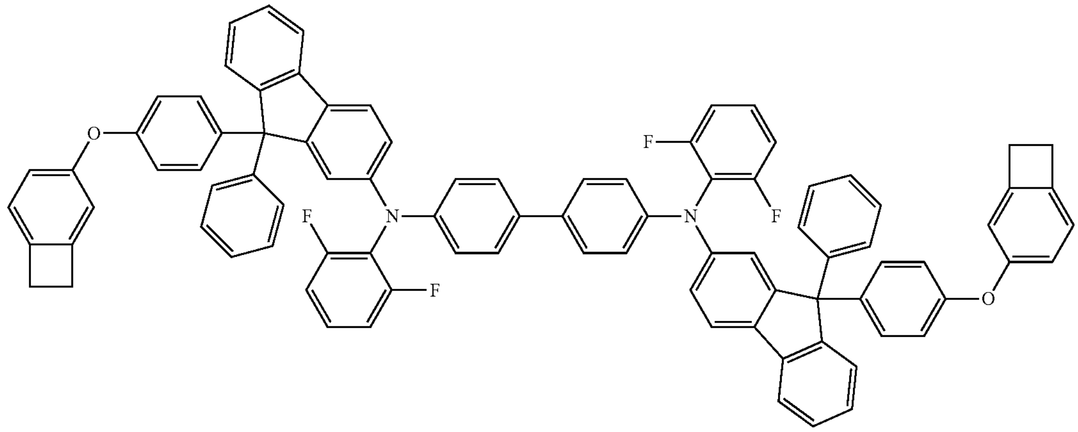

K

Synthesis of K: D-Int (1.50 g, 3.67 mmol), L6 (3.98 g, 7.71 mmol), and NaOtBu (1.06 g, 11.0 mmol) were put into a round bottom flask (RBF), and then toluene (70 mL) was introduced therein. After the resulting mixture was warmed to 90° C., Pd($^t$Bu$_3$P)$_2$ (0.0939 g, 0.184 mmol) was introduced therein, and the resulting mixture was stirred for 4 hours. Water was added thereto, and an organic layer was extracted with dichloromethane (DCM), and then dried over $MgSO_4$, and column purified with dichloromethane/hexane to obtain high-purity Compound K (2.35 g). $[M+H]^+=1277$ $^1$H NMR: δ 7.74-7.72 (d, 2H), 7.69-7.66 (d, 2H), 7.58-7.52 (m, 4H), 7.42-7.32 (m, 8H), 7.26-7.20 (m, 8H), 7.16 (m, 2H), 7.11-7.08 (m, 4H), 7.03-7.01 (m, 4H), 6.99-6.87 (m, 14H), 6.84-6.79 (m, 4H), 2.82 (m, 8H)

Preparation Example 12: Preparation of Compound L

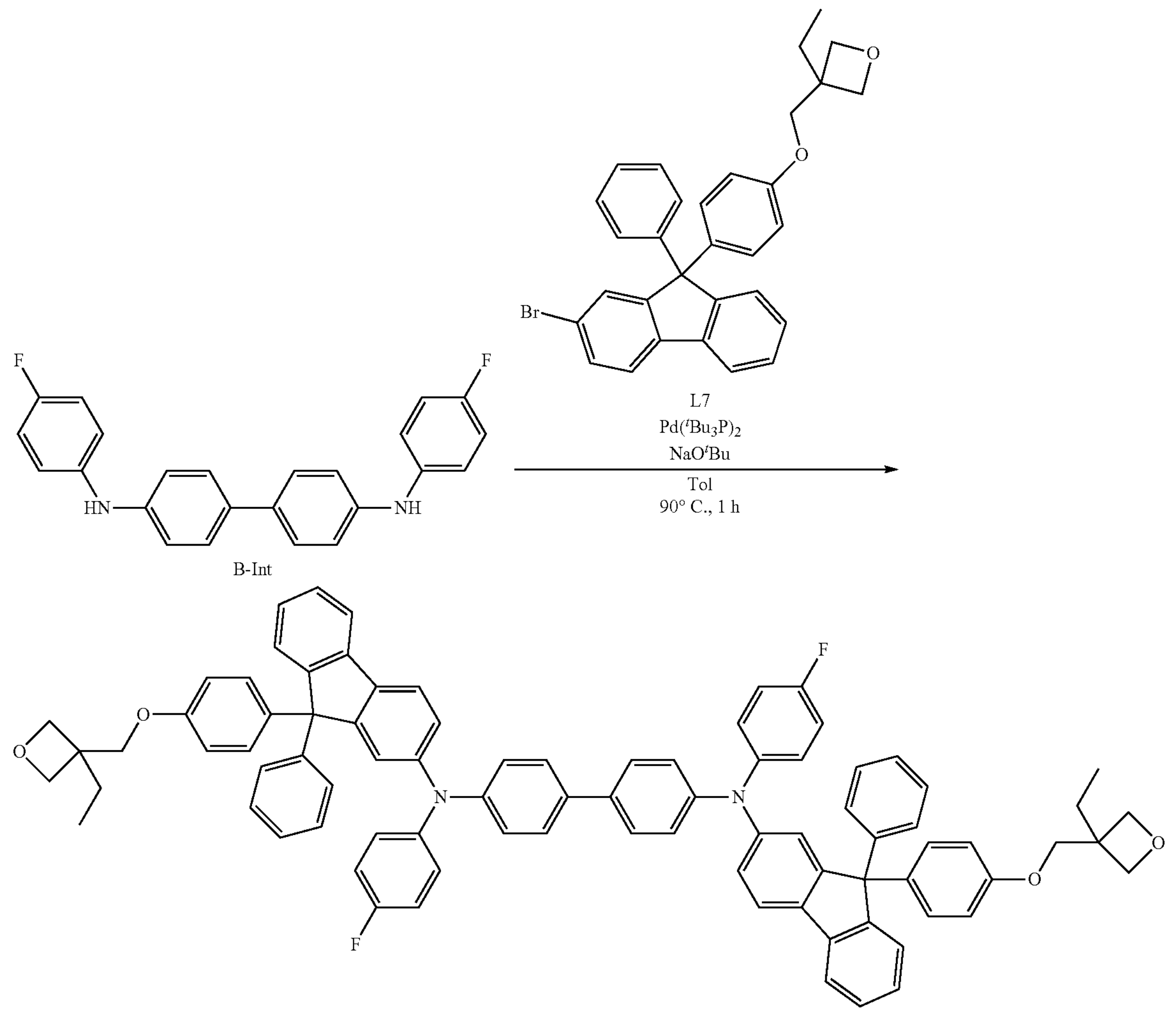

L

Synthesis of L: B-Int (2.00 g, 5.37 mmol), L7 (5.77 g, 11.3 mmol), and NaOtBu (1.55 g, 16.1 mmol) were put into a round bottom flask (RBF), and then toluene (100 mL) was introduced therein. After the resulting mixture was warmed to 90° C., Pd($^t$Bu$_3$P)$_2$ (0.137 g, 0.269 mmol) was introduced therein, and the resulting mixture was stirred for 1 hour. Water was added thereto, and an organic layer was extracted with dichloromethane (DCM), and then dried over $MgSO_4$, and column purified with dichloromethane/hexane to obtain high-purity Compound L (3.31 g). $[M+H]^+=1234$ $^1$H NMR: δ 7.73-7.71 (d, 2H), 7.59-7.56 (d, 2H), 7.40-7.31 (m, 12H), 7.24-7.20 (m, 6H), 7.09-7.01 (m, 16H), 6.95-6.91 (m, 6H), 6.84-6.81 (m, 4H), 4.38-4.36 (m, 4H), 4.23-4.21 (m, 4H), 3.75 (s, 4H), 1.80 (m, 4H), 1.29 (m, 6H)

EXAMPLES

Example 1

A glass substrate thinly coated with indium tin oxide (ITO) to have a thickness of 1,500 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing with distilled water was completed, the substrate was ultrasonically washed with isopropyl alcohol and acetone solvents, and dried, and then the substrate was cleaned for 5 minutes, and the substrate was transported to a glovebox.

On the ITO transparent electrode prepared above, a 1.5 wt % cyclohexanone ink including Compound A previously prepared in Preparation Example 1 and the following Compound P at a weight ratio (Compound A:Compound P) of 8:2 was spin-coated onto the ITO surface, and heat-treated (cured) at 220° C. for 30 minutes, thereby forming a hole injection layer having a thickness of 30 nm. A 2 wt % toluene ink of the following α-NPD Compound was spin-coated onto the hole injection layer, thereby forming a hole transport layer having a thickness of 40 nm. Thereafter, the ITO transparent electrode was transferred to a vacuum deposition machine, and then the following ADN compound and the following DPAVBi compound were vacuum-deposited to have a thickness of 20 nm at a weight ratio (ADN: DPAVBi) of 20:1 on the hole transport layer, thereby forming a light emitting layer. The following BCP compound was vacuum-deposited to have a thickness of 35 nm on the light emitting layer, thereby forming a layer which simultaneously transports and injects electrons. LiF and aluminum were sequentially deposited on the layer which simultaneously injects and transports electrons to have a thickness of 1 nm and 100 nm, respectively, thereby forming a cathode.

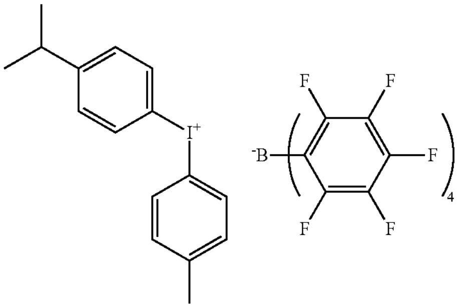

P

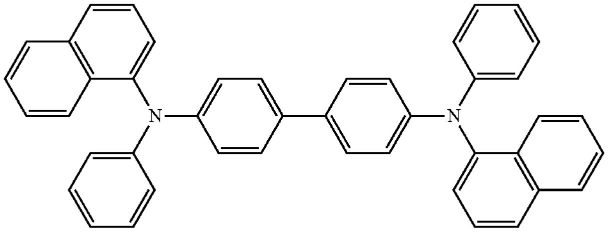

a-NPD

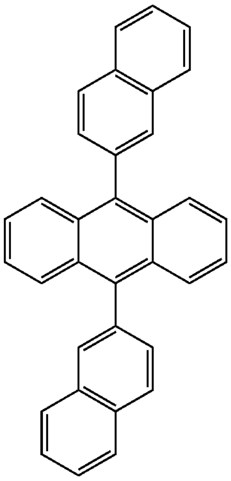

ADN

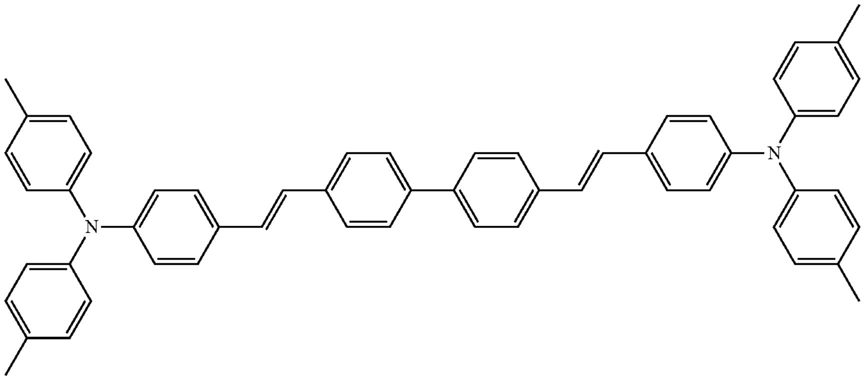

DPAVBi

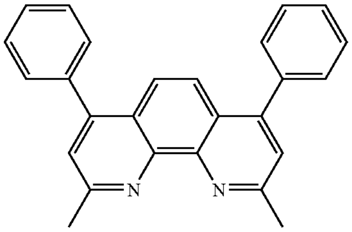

BCP

In the aforementioned procedure, the deposition rate of the organic material was maintained at 0.4 to 0.7 Å/sec, the deposition rates of lithium fluoride and aluminum of the cathode were maintained at 0.3 Å/sec and at 2 Å/sec, respectively, and the degree of vacuum during the deposition was maintained at $2\times10^{-7}$ to $5\times10^{-6}$ torr.

Example 2

An organic light emitting device was manufactured in the same manner as in Example 1, except that Compound B was used instead of Compound A.

Example 3

An organic light emitting device was manufactured in the same manner as in Example 1, except that Compound C was used instead of Compound A.

Example 4

An organic light emitting device was manufactured in the same manner as in Example 1, except that Compound D was used instead of Compound A.

Example 5

An organic light emitting device was manufactured in the same manner as in Example 1, except that Compound E was used instead of Compound A.

Example 6

An organic light emitting device was manufactured in the same manner as in Example 1, except that Compound F was used instead of Compound A.

Example 7

An organic light emitting device was manufactured in the same manner as in Example 1, except that the following Compound G was used instead of Compound A.

Example 8

An organic light emitting device was manufactured in the same manner as in Example 1, except that the following Compound H was used instead of Compound A.

Example 9

An organic light emitting device was manufactured in the same manner as in Example 1, except that the following Compound I was used instead of Compound A.

Example 10

An organic light emitting device was manufactured in the same manner as in Example 1, except that the following Compound J was used instead of Compound A.

Example 11

An organic light emitting device was manufactured in the same manner as in Example 1, except that the following Compound K was used instead of Compound A.

Example 12

An organic light emitting device was manufactured in the same manner as in Example 1, except that the following Compound L was used instead of Compound A.

Comparative Example 1

An organic light emitting device was manufactured in the same manner as in Example 1, except that the following compound was used instead of Compound A.

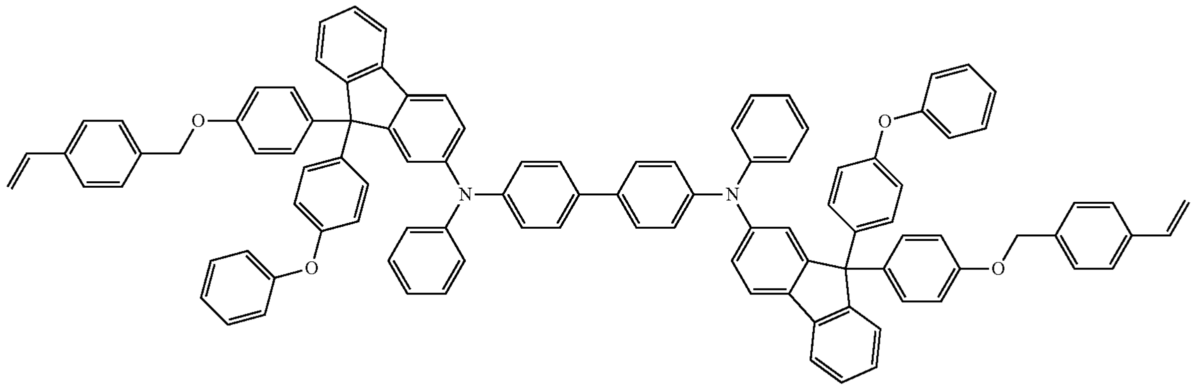 [SMILES: C=Cc1ccc(COc2ccc(C3(c4ccc(Oc5ccccc5)cc4)c4ccccc4-c4ccc(N(c5ccccc5)c5ccc(-c6ccc(N(c7ccccc7)c7ccc8c(c7)C(c7ccc(OCc9ccc(C=C)cc9)cc7)(c7ccc(Oc9ccccc9)cc7)c7ccccc7-8)cc6)cc5)cc43)cc2)cc1]

Comparative Example 2
An organic light emitting device was manufactured in the same manner as in Example 1, except that the following compound was used instead of Compound A.
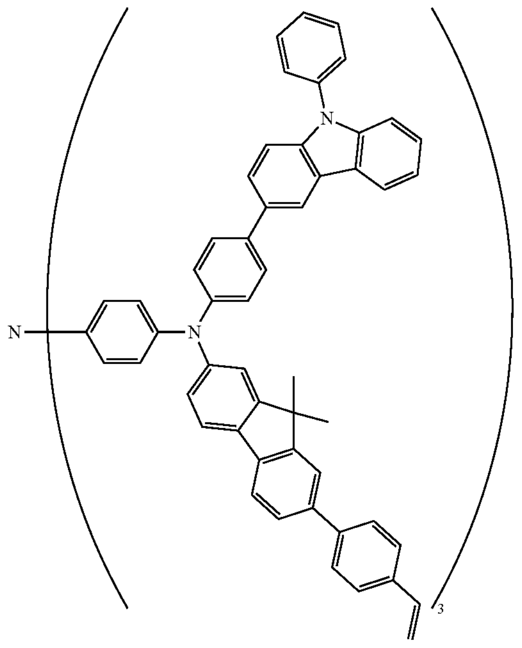
Comparative Example 3
An organic light emitting device was manufactured in the same manner as in Example 1, except that the following compound was used instead of Compound A.
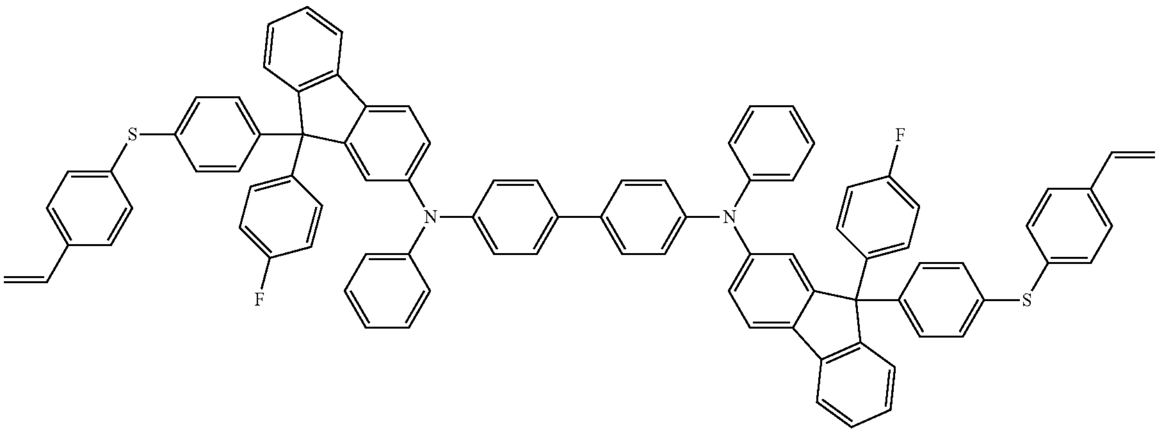 [SMILES: C=Cc1ccc(Sc2ccc(C3(c4ccc(F)cc4)c4ccccc4-c4ccc(N(c5ccccc5)c5ccc(-c6ccc(N(c7ccccc7)c7ccc8c(c7)C(c7ccc(F)cc7)(c7ccc(Sc9ccc(C=C)cc9)cc7)c7ccccc7-8)cc6)cc5)cc43)cc2)cc1]

Comparative Example 4

An organic light emitting device was manufactured in the same manner as in Example 1, except that the following compound was used instead of Compound A.

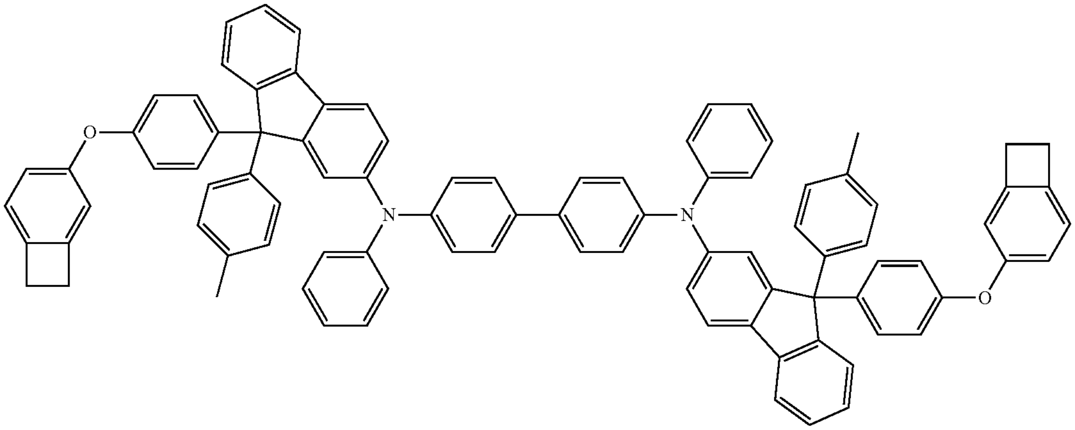 [SMILES: Cc1ccc(C2(c3ccc(Oc4ccc5c(c4)CC5)cc3)c3ccccc3-c3ccc(N(c4ccccc4)c4ccc(-c5ccc(N(c6ccccc6)c6ccc7c(c6)C(c6ccc(C)cc6)(c6ccc(Oc8ccc9c(c8)CC9)cc6)c6ccccc6-7)cc5)cc4)cc32)cc1]

Comparative Example 5

An organic light emitting device was manufactured in the same manner as in Example 1, except that the following compound was used instead of Compound A.

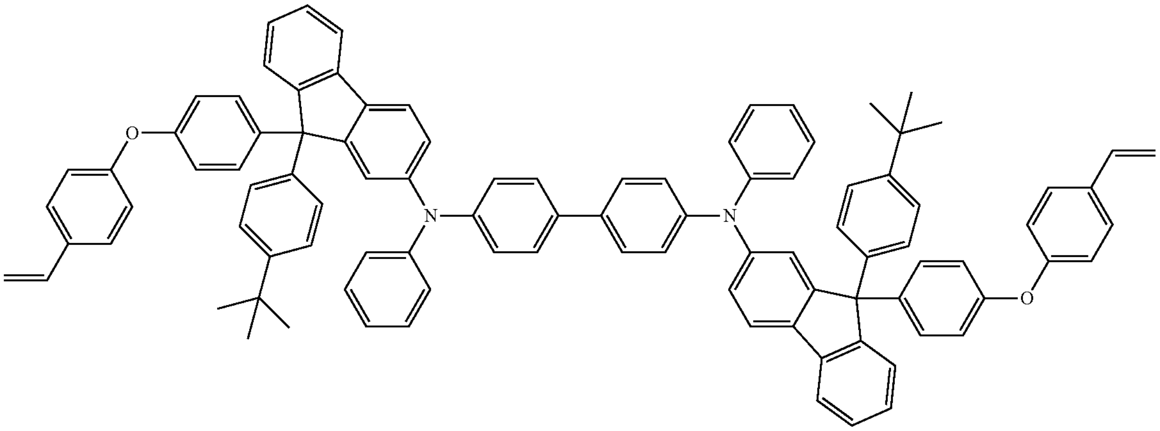 [SMILES: C=Cc1ccc(Oc2ccc(C3(c4ccc(C(C)(C)C)cc4)c4ccccc4-c4ccc(N(c5ccccc5)c5ccc(-c6ccc(N(c7ccccc7)c7ccc8c(c7)C(c7ccc(Oc9ccc(C=C)cc9)cc7)(c7ccc(C(C)(C)C)cc7)c7ccccc7-8)cc6)cc5)cc43)cc2)cc1]

For the organic light emitting devices manufactured in Examples 1 to 12 and Comparative Examples 1 to 5, the driving voltage, current efficiency, quantum efficiency (QE), and luminance values were measured at an electric current of 10 mA/cm$^2$, and time (T95) taken for the luminance to become 95% of the initial luminance (1000 nit) was measured. The results are shown in the following Table 1.

TABLE 1

| Device | Driving voltage (V) | Current efficiency (cd/A) | QE (%) | Luminance (Cd/m$^2$) | Service life T95 (h) |
|---|---|---|---|---|---|
| Example 1 | 4.10 | 5.25 | 6.31 | 501.3 | 114 |
| Example 2 | 4.02 | 5.19 | 6.25 | 495.1 | 122 |
| Example 3 | 4.45 | 5.23 | 6.22 | 483.6 | 167 |
| Example 4 | 4.46 | 5.21 | 6.12 | 485.3 | 154 |

TABLE 1-continued

| Device | Driving voltage (V) | Current efficiency (cd/A) | QE (%) | Luminance (Cd/m$^2$) | Service life T95 (h) |
|---|---|---|---|---|---|
| Example 5 | 4.33 | 5.26 | 6.24 | 495.2 | 124 |
| Example 6 | 4.28 | 5.27 | 6.27 | 493.6 | 126 |
| Example 7 | 4.20 | 5.26 | 6.32 | 501.6 | 158 |
| Example 8 | 4.22 | 5.19 | 6.25 | 493.1 | 143 |
| Example 9 | 4.43 | 5.28 | 6.28 | 501.2 | 157 |
| Example 10 | 4.21 | 5.18 | 6.24 | 496.5 | 142 |
| Example 11 | 4.19 | 5.26 | 6.25 | 495.3 | 123 |
| Example 12 | 4.25 | 5.27 | 6.28 | 500.2 | 121 |
| Comparative Example 1 | 4.95 | 4.88 | 5.33 | 447.0 | 69 |
| Comparative Example 2 | 5.15 | 4.32 | 4.85 | 421.5 | 58 |

TABLE 1-continued

| Device | Driving voltage (V) | Current efficiency (cd/A) | QE (%) | Luminance ($Cd/m^2$) | Service life T95 (h) |
|---|---|---|---|---|---|
| Comparative Example 3 | 4.75 | 4.76 | 5.32 | 448.5 | 67 |
| Comparative Example 4 | 5.22 | 4.21 | 4.77 | 410.8 | 49 |
| Comparative Example 5 | 4.72 | 4.69 | 5.28 | 445.2 | 54 |

From the results in Table 1, it can be confirmed that the devices of Examples 1 to 12, including an organic material layer formed by using a coating composition including the compound of the present invention have low driving voltages, and excellent current efficiency, quantum efficiency, and service life values compared to the devices of Comparative Examples 1 to 5. Specifically, it can be confirmed that Examples 1 to 12 using the compound of the present invention have better device characteristics than Comparative Examples 1, 4, and 5 using compounds having a structure similar to that of the compound of the present invention, but does not include a fluoro group; Comparative Example 2 using a compound that has different bonding positions of a cross-linkable functional group by heat or light from the compound of the present invention and has three amine groups bonded to one nitrogen atoms; and Comparative Example 3 using a compound that has different bonding positions of a fluoro group from the compound of the present invention.

The invention claimed is:

1. A compound of the following Formula 1:

[Formula 1]

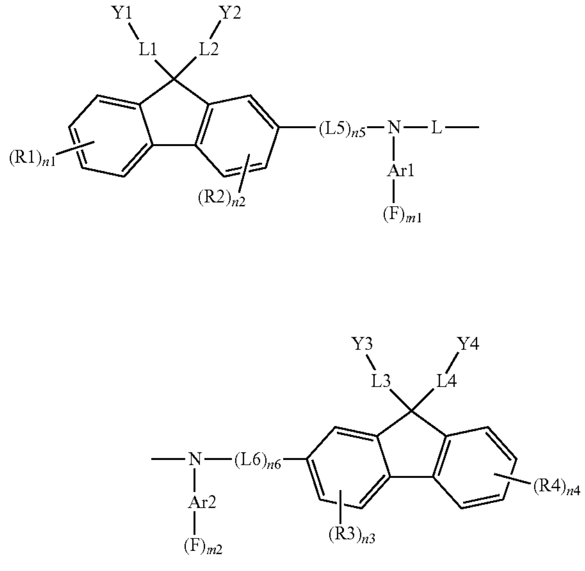

wherein, in Formula 1,

L and L1 to L4 are the same as or different from each other, and are each independently a substituted or unsubstituted arylene group, L5 and L6 are the same as or different from each other, and are each independently a direct bond; or a substituted or unsubstituted arylene group, Ar1 and Ar2 are the same as or different from each other, and are each independently a substituted or unsubstituted aryl group; or a substituted or unsubstituted heteroaryl group, R1 to R4 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group, Y1 to Y4 are the same as or different from each other, and are each independently —(R101) s; or —X-A, and two or more of Y1 to Y4 are —X-A, R101 is hydrogen; deuterium; a halogen group; a substituted or unsubstituted alkyl group; a substituted or unsubstituted alkoxy group; a substituted or unsubstituted aryl group; or a substituted or unsubstituted aryloxy group, s is an integer from 0 to 5, and when s is 2 or higher, each occurrence of R101 is the same as or different from each other, X is O or S, A is a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, m1 and m2 are each an integer from 1 to 5, n5 and n6 are each an integer from 0 to 2, n1 and n4 are each an integer from 0 to 4, n2 and n3 are each an integer from 0 to 3, when n5 and n6 are each 2, each occurrence of L5 and L6 is the same as or different from each other, respectively, and when n1 to n4 are each 2 or higher, each occurrence of R1 to R4 is the same as or different from each other, respectively.

2. The compound of claim 1, wherein A is any one of the following structures:

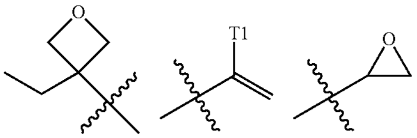

-continued

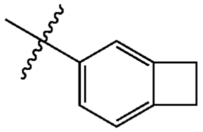

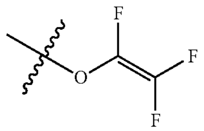

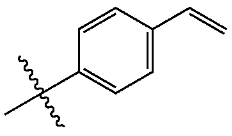

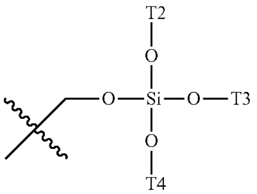

-continued

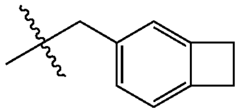

wherein, in the structures,

T1 is hydrogen; or a substituted or unsubstituted alkyl group having 1 to 6 carbon atoms, and T2 to T4 are the same as or different from each other, and are each independently a substituted or unsubstituted alkyl group having 1 to 6 carbon atoms.

3. The compound of claim 1, wherein Formula 1 is the following Formula 2:

[Formula 2]

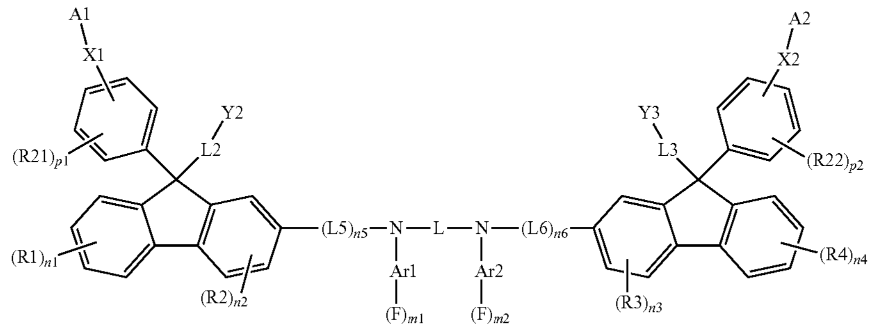

-continued

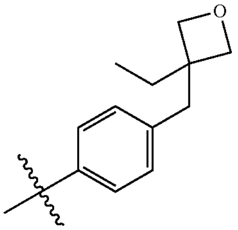

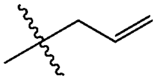

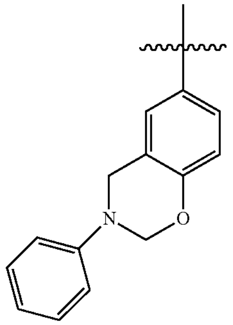

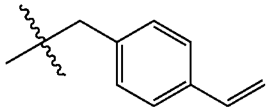

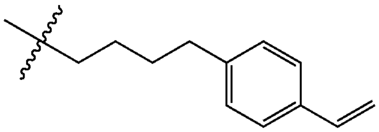

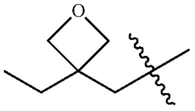

wherein, in Formula 2,

R1 to R4, L2, L3, L5, L6, n1 to n6, Ar1, Ar2, L, Y2, Y3, m1, and m2 are the same as those defined in Formula 1, X1 and X2 are the same as or different from each other, and are each independently O or S, A1 and A2 are the same as or different from each other, and are each independently a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, R21 and R22 are the same as or different from each other, and are each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group, p1 and p2 are each an integer from 0 to 4, and when p1 and p2 are each 2 or higher, each occurrence of R21 and R22 is the same as or different from each other, respectively.

4. The compound of claim 1, wherein Formula 1 is the following Formula 3 or 4:

[Formula 3]

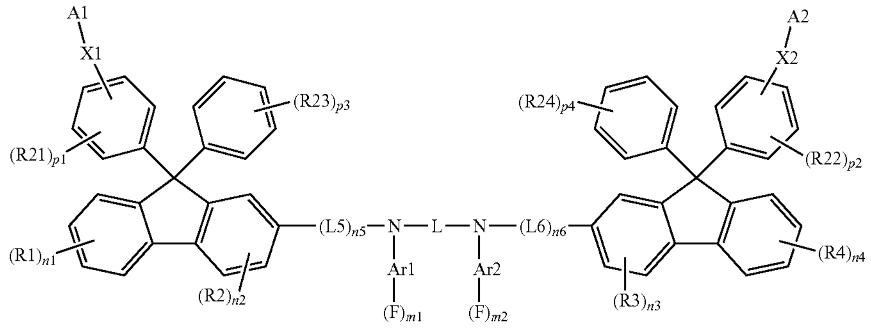

[Formula 4]

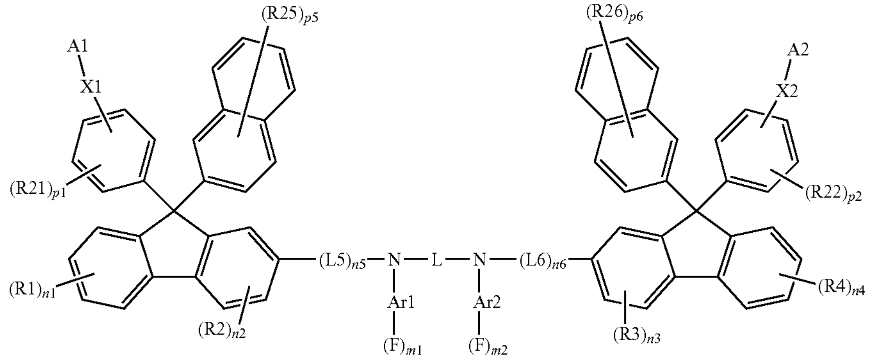

wherein, in Formulae 3 and 4,

R1 to R4, L5, L6, n1 to n6, Ar1, Ar2, L, m1, and m2 are the same as those defined in Formula 1, X1 and X2 are the same as or different from each other, and are each independently O or S, A1 and A2 are the same as or different from each other, and are each independently a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, R21 to R26 are the same as or different from each other, and are each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group, p1 and p2 are each an integer from 0 to 4, p3 and p4 are each an integer from 0 to 5, p5 and p6 are each an integer from 0 to 7, and when p1 to p6 are each 2 or higher, each occurrence of R21 to R26 is the same as or different from each other, respectively.

5. The compound of claim 1, wherein Formula 1 is any one of the following Formulae 5 to 8:

[Formula 5]

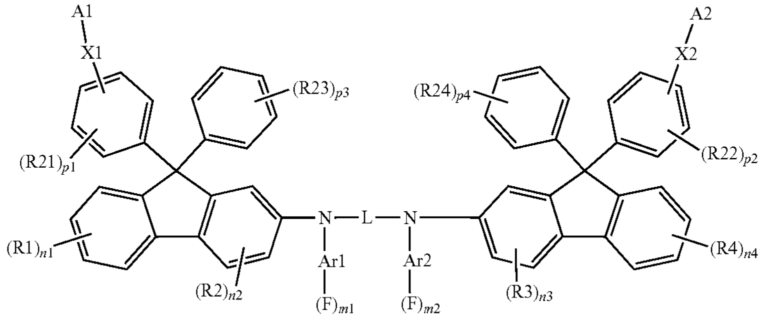

-continued

[Formula 6]

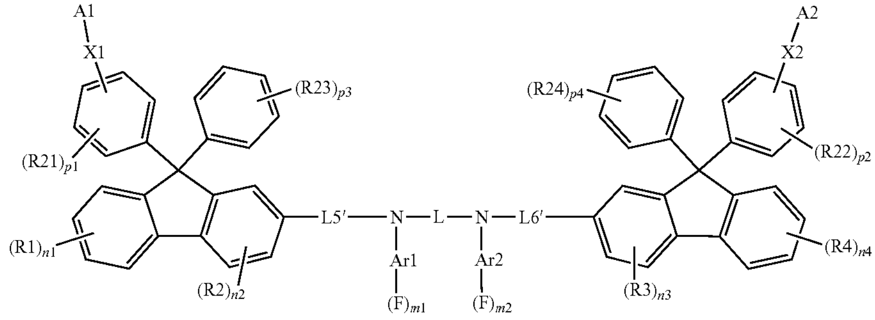

[Formula 7]

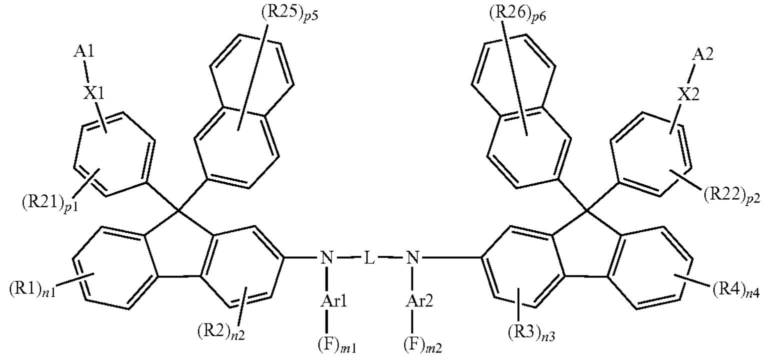

[Formula 8]

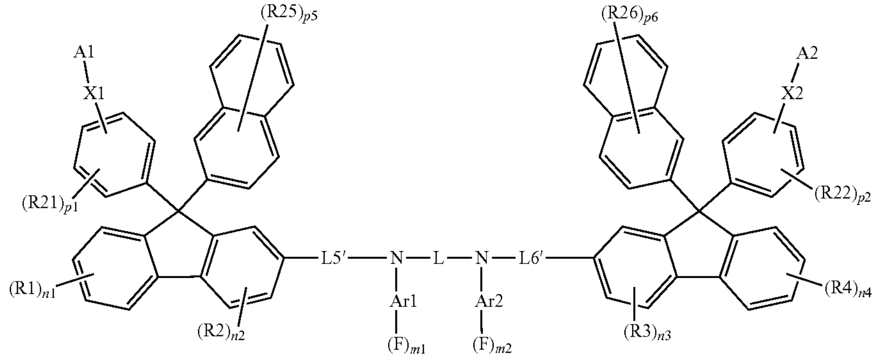

wherein, in Formulae 5 to 8,

R1 to R4, n1 to n4, Ar1, Ar2, L, m1, and m2 are the same as those defined in Formula 1, X1 and X2 are the same as or different from each other, and are each independently O or S, A1 and A2 are the same as or different from each other, and are each independently a substituted or unsubstituted alkyl group; a substituted or unsubstituted alkenyl group; a substituted or unsubstituted heterocycloalkyl group; a substituted or unsubstituted alkeneoxy group; a substituted or unsubstituted hydrocarbon ring group; or a substituted or unsubstituted heterocyclic group, L5' and L6' are the same as or different from each other, and are each independently a substituted or unsubstituted arylene group, R21 to R26 are the same as or different from each other, and are each independently hydrogen; deuterium; a halogen group; a substituted or unsubstituted alkyl group; a substituted or unsubstituted alkoxy group; a substituted or unsubstituted aryloxy group; a substituted or unsubstituted aryl group; or a substituted or unsubstituted heteroaryl group, p1 and p2 are each an integer from 0 to 4, p3 and p4 are each an integer from 0 to 5, p5 and p6 are each an integer from 0 to 7, and when p1 to p6 are each 2 or higher, each occurrence of R21 to R26 is the same as or different from each other, respectively.

6. The compound of claim 1, wherein L is any one of the following Formulae 1-A to 1-C:

[Formula 1-A]

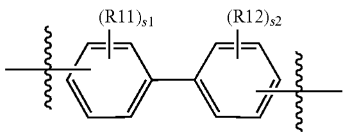

[Formula 1-B]

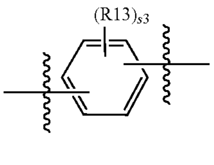

-continued

[Formula 1-C]

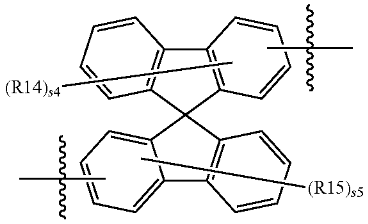

wherein, in Formulae 1-A to 1-C,

R11 to R15 are the same as or different from each other, and are each independently hydrogen; deuterium; a substituted or unsubstituted alkyl group; a substituted or unsubstituted alkoxy group; a substituted or unsubstituted aryl group; or a substituted or unsubstituted heteroaryl group, s1 to s3 are each an integer from 0 to 4, s4 and s5 are each an integer from 0 to 7, and when s1 to s5 are each 2 or higher, each occurrence of R11 to R15 is the same as or different from each other, respectively.

7. The compound of claim 1, wherein Formula 1 is any one of the following compounds:

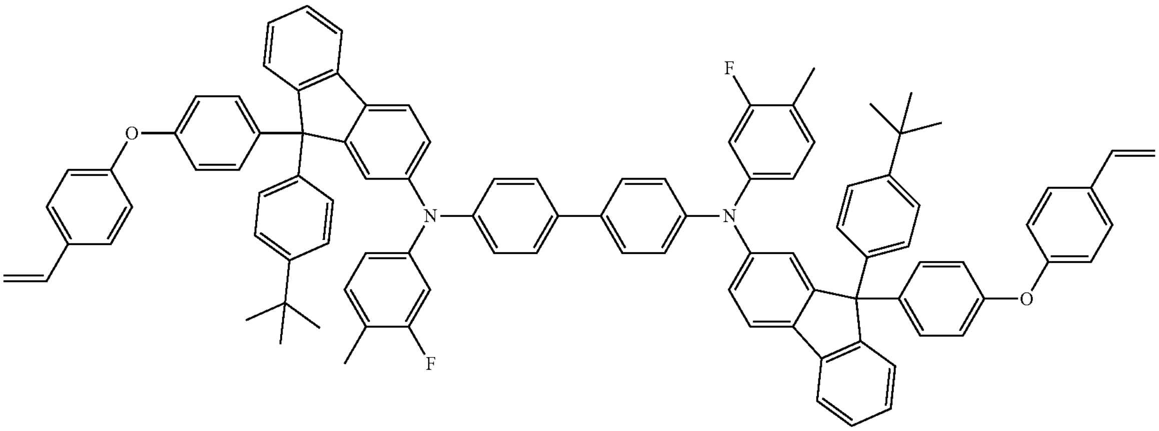

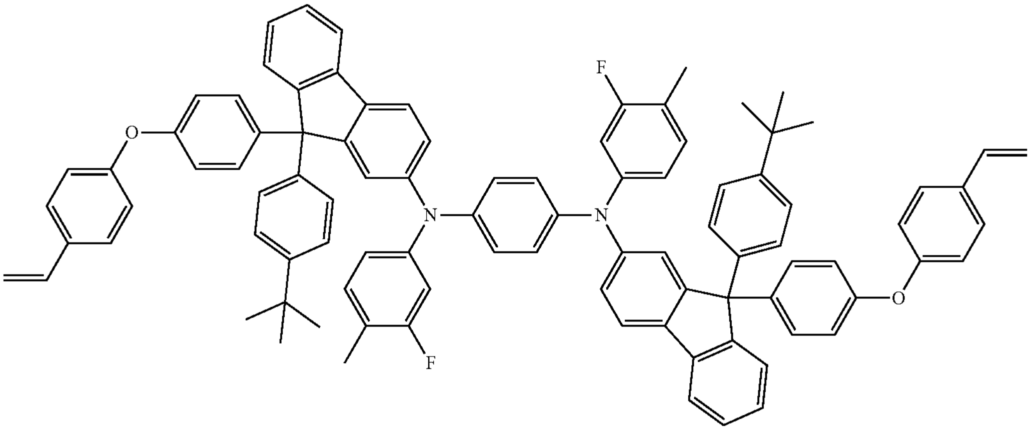

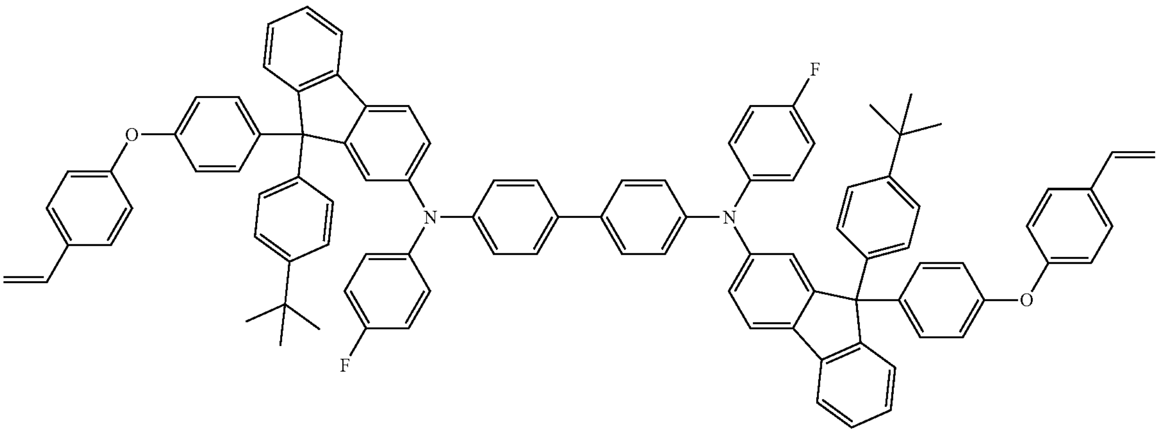

-continued
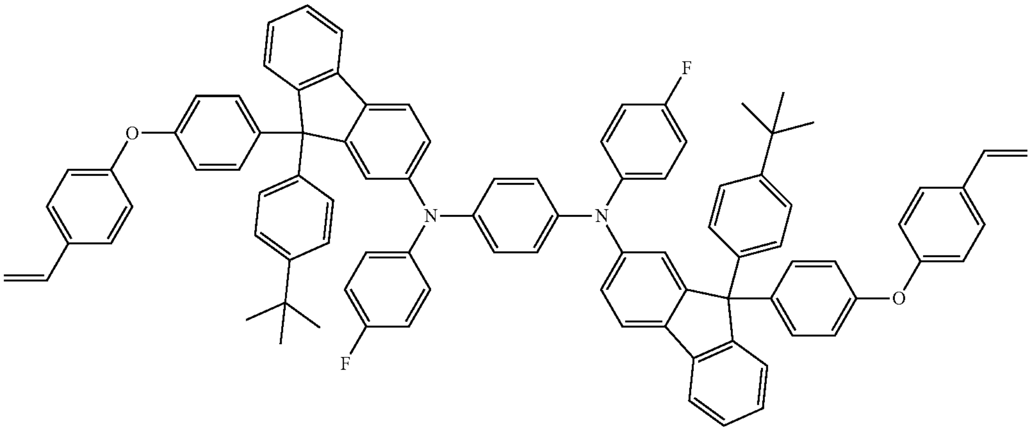
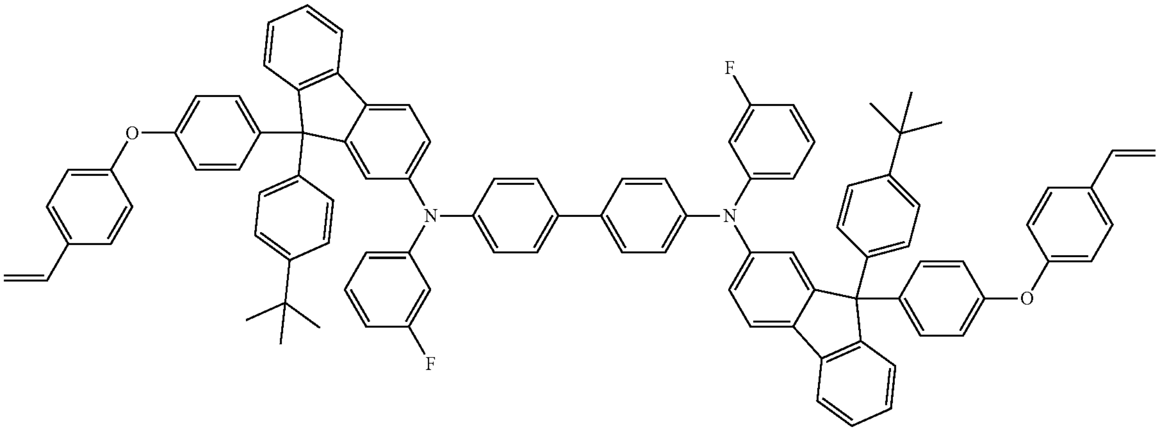
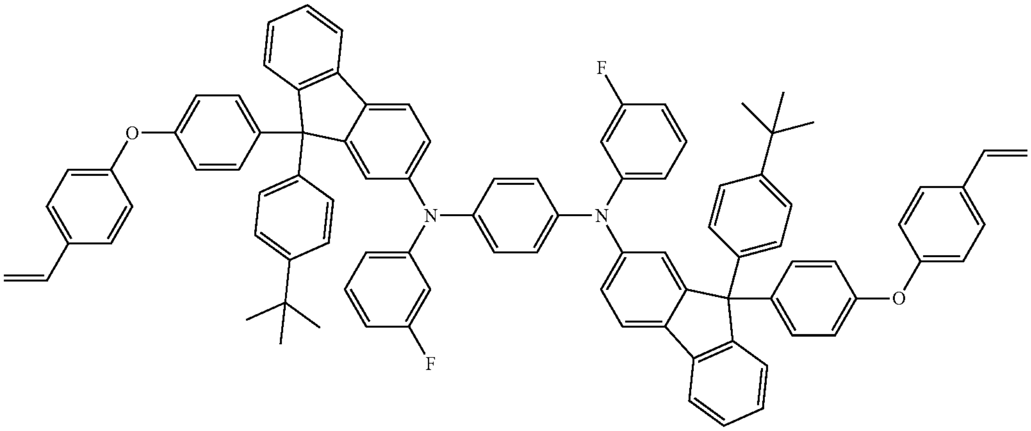
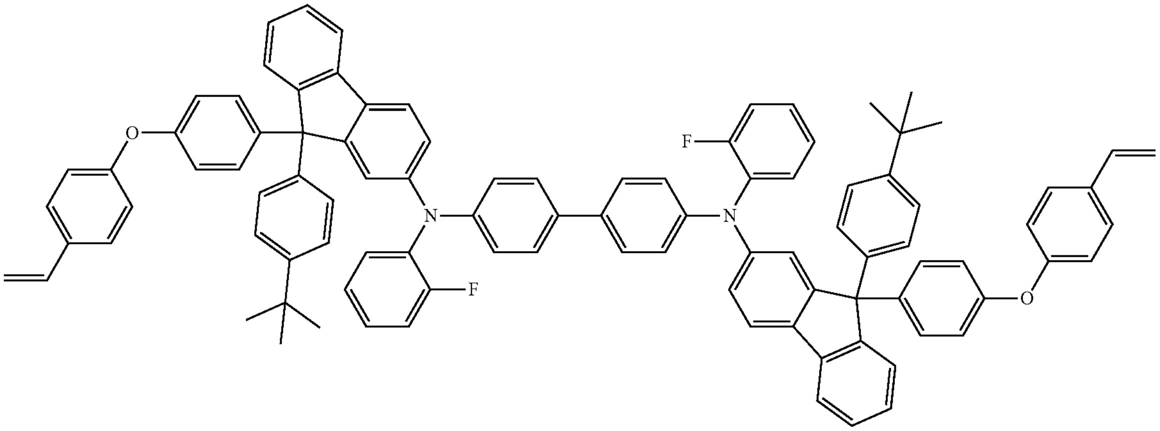

-continued
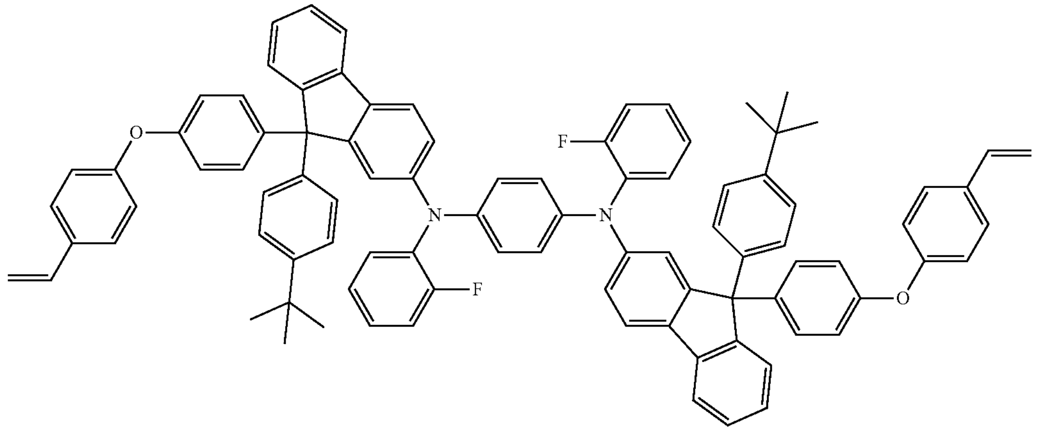
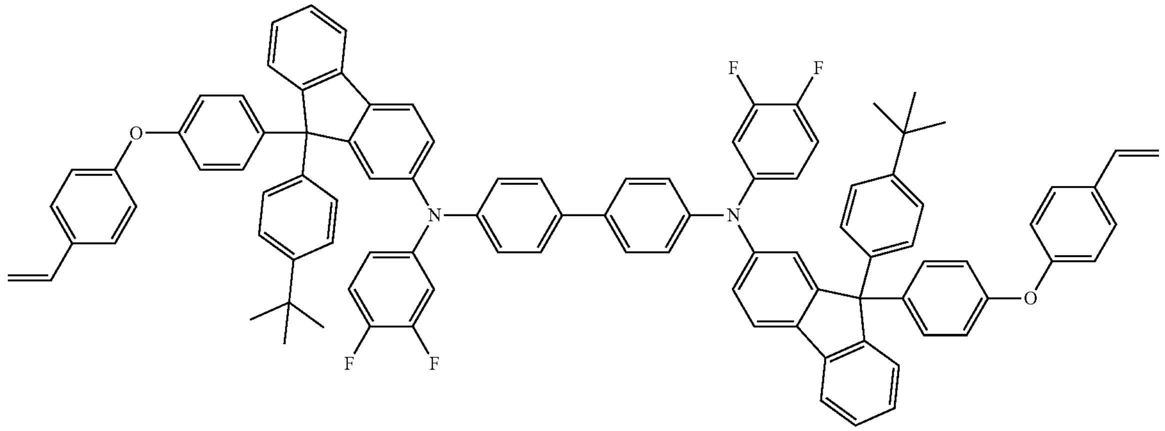
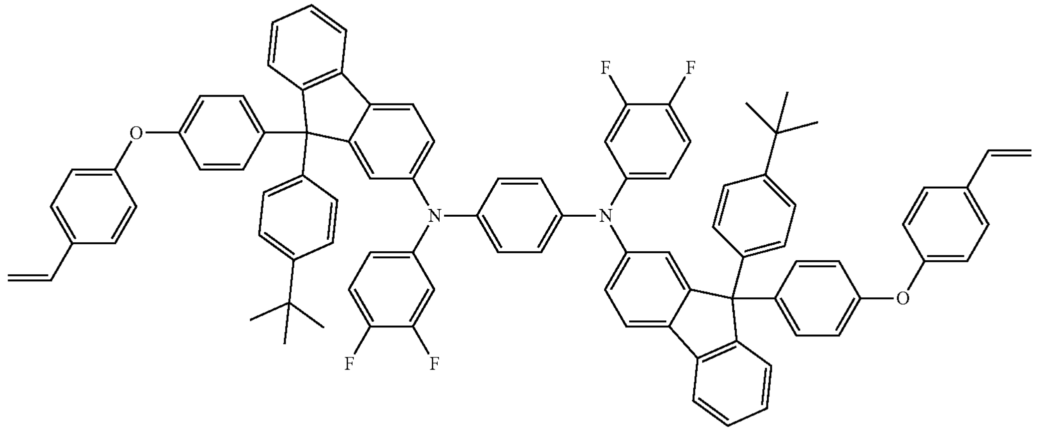
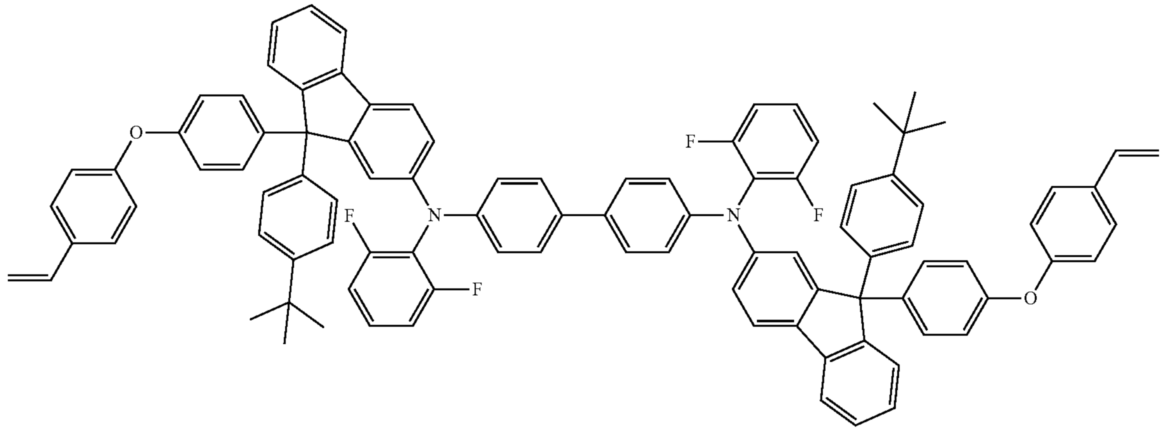

-continued
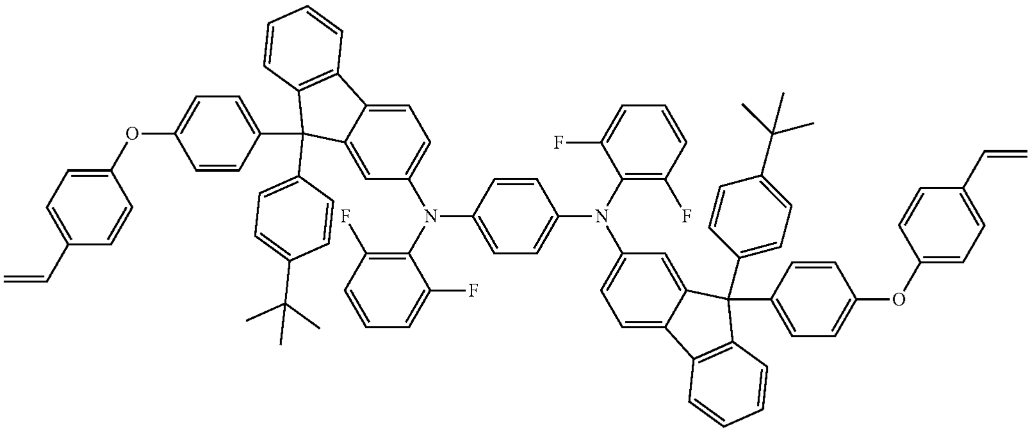
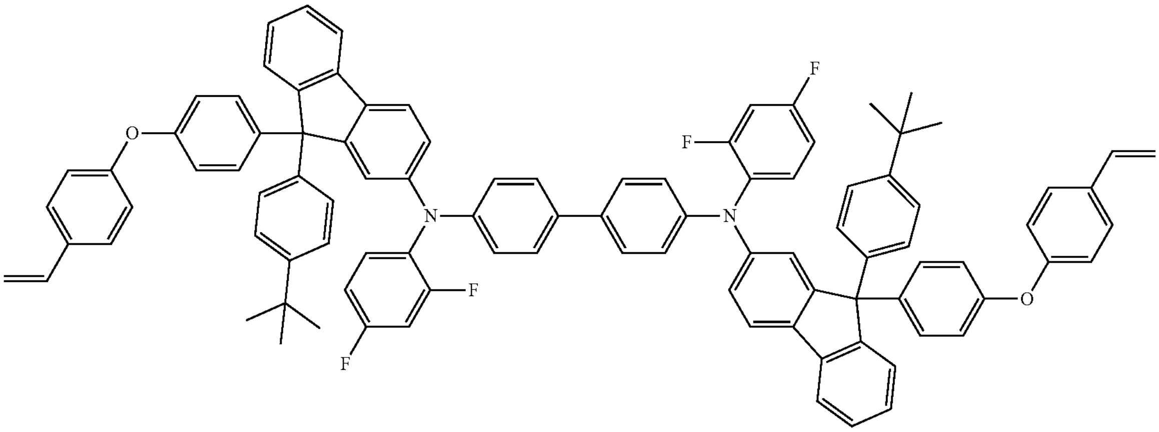
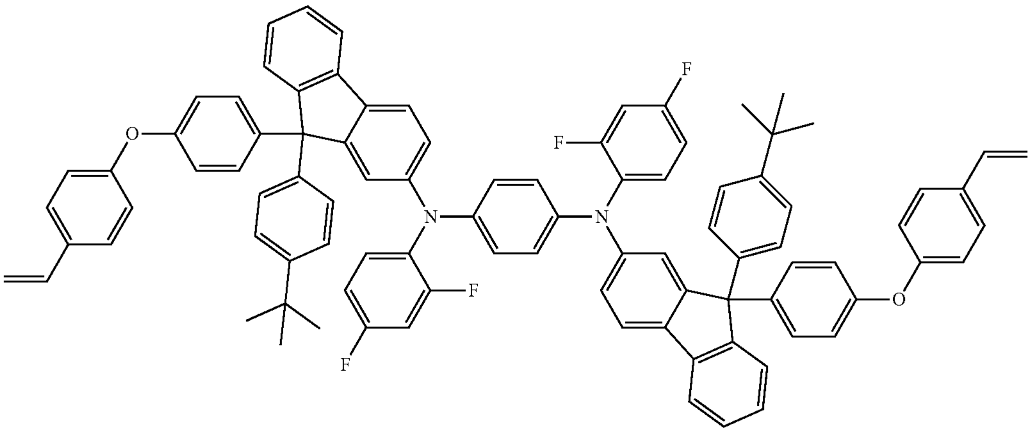

-continued
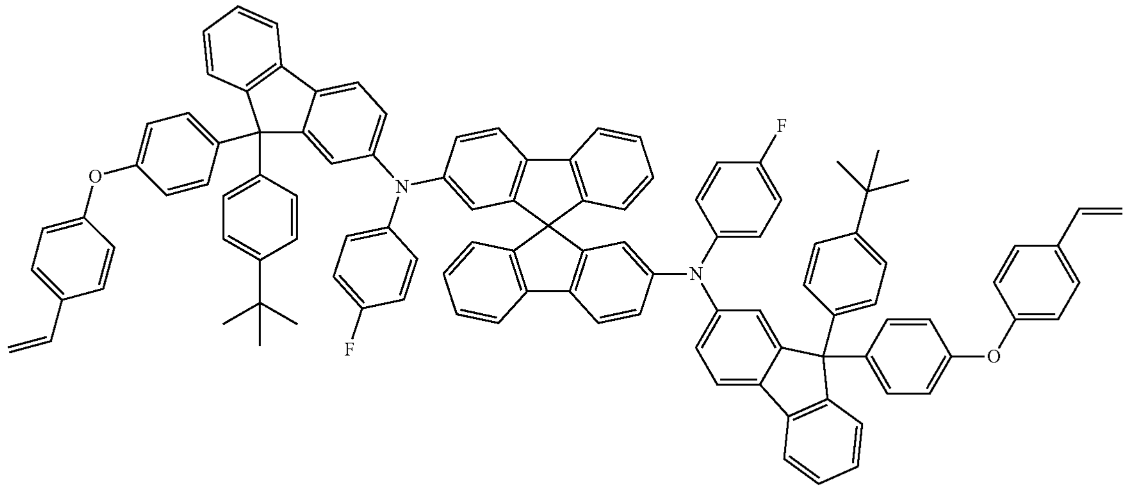
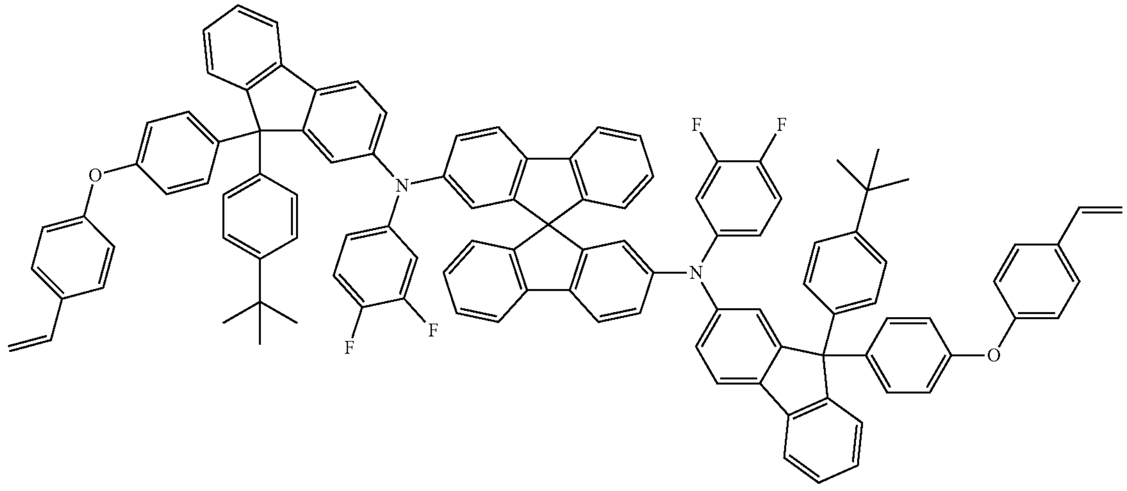
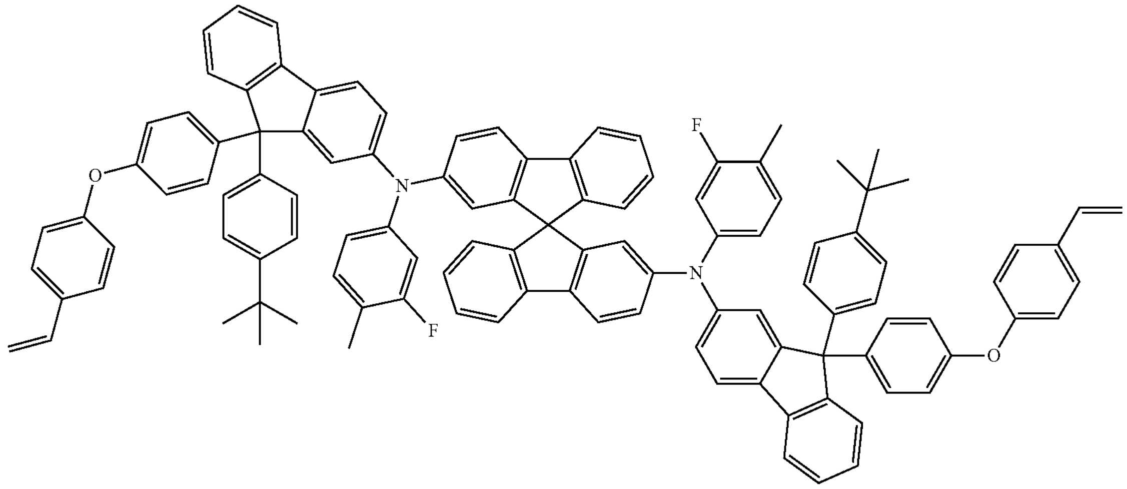

-continued
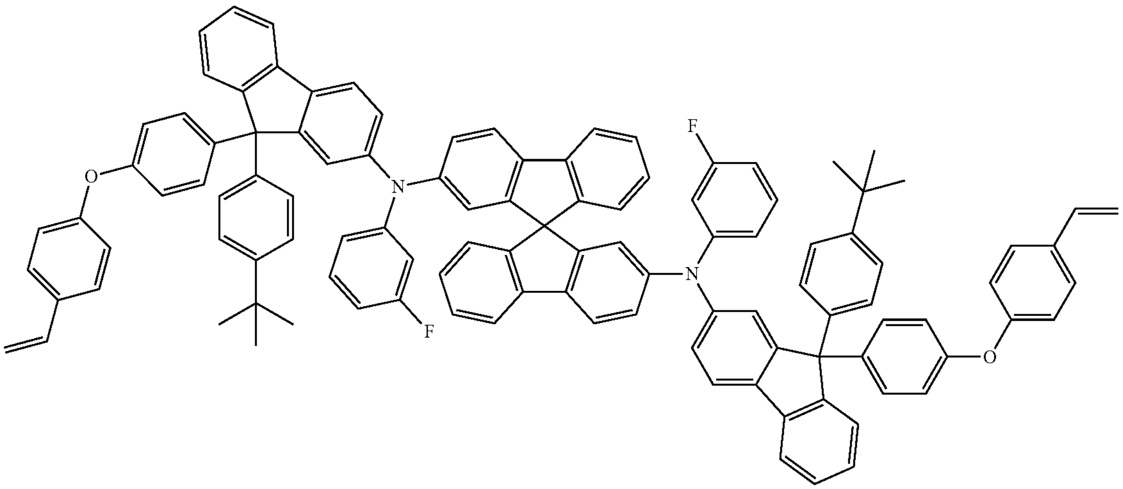
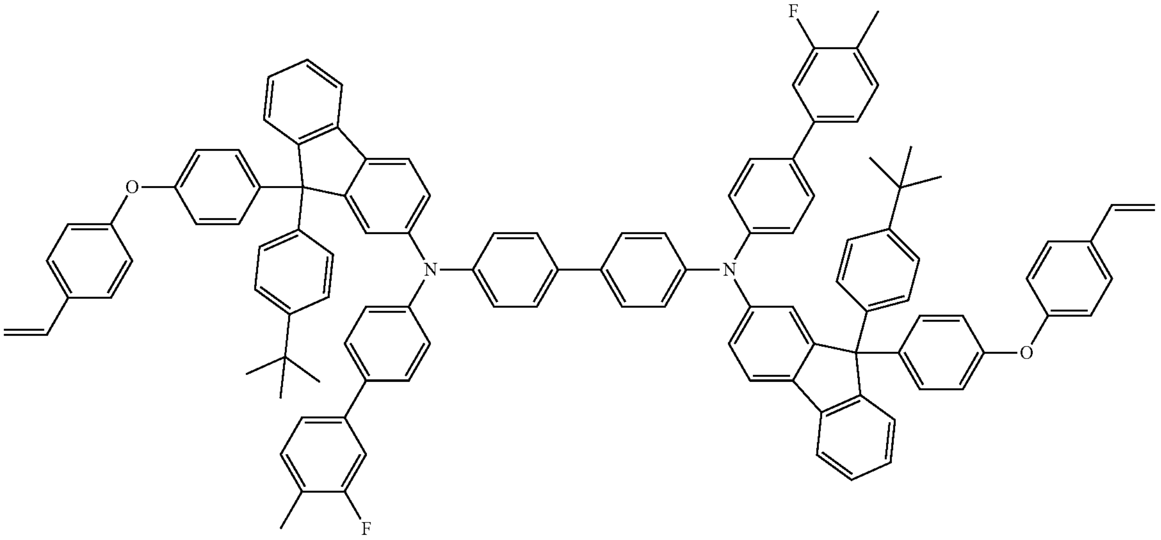
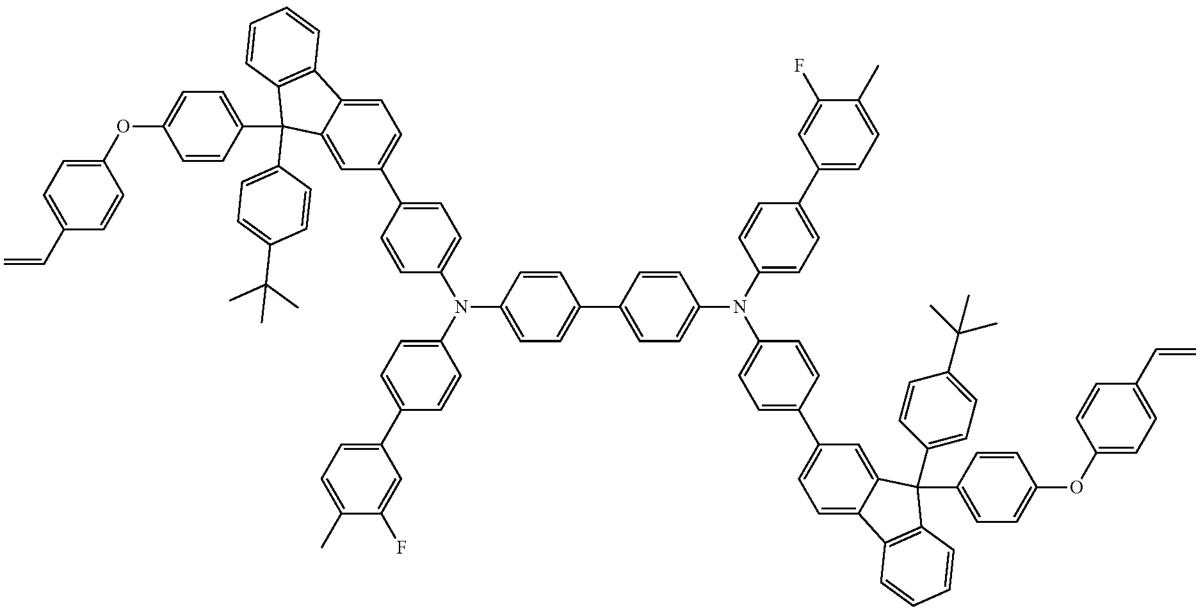

-continued
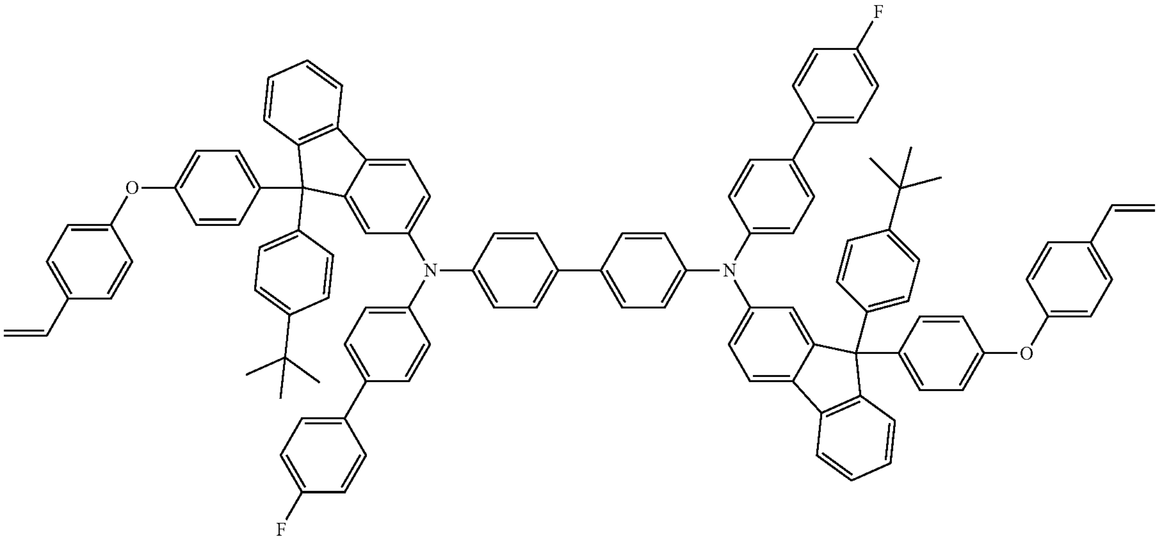
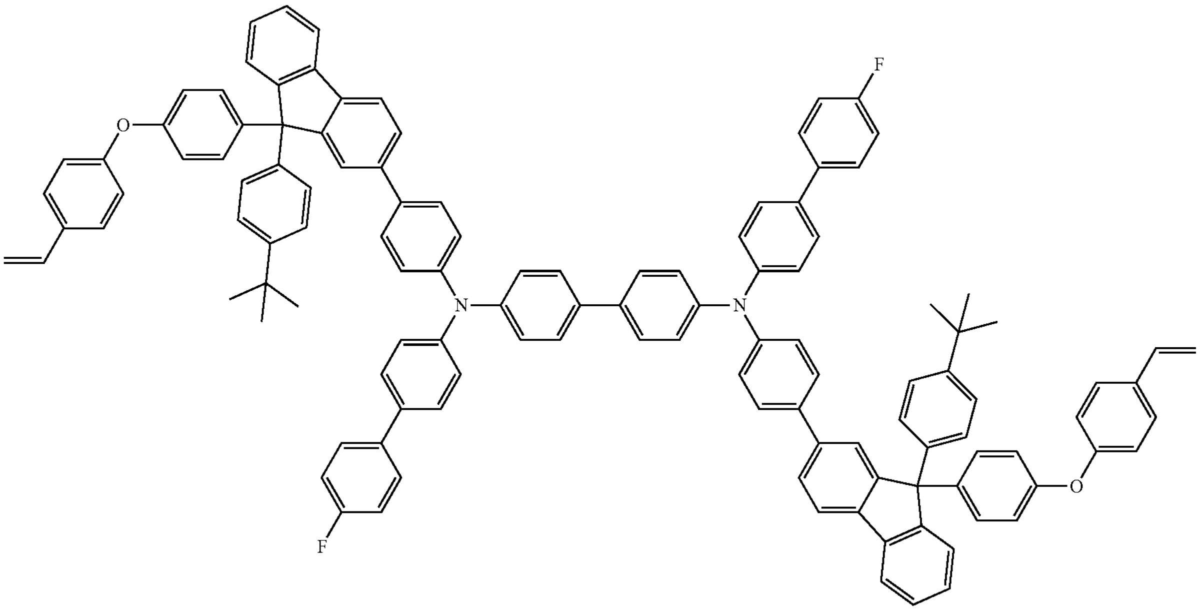
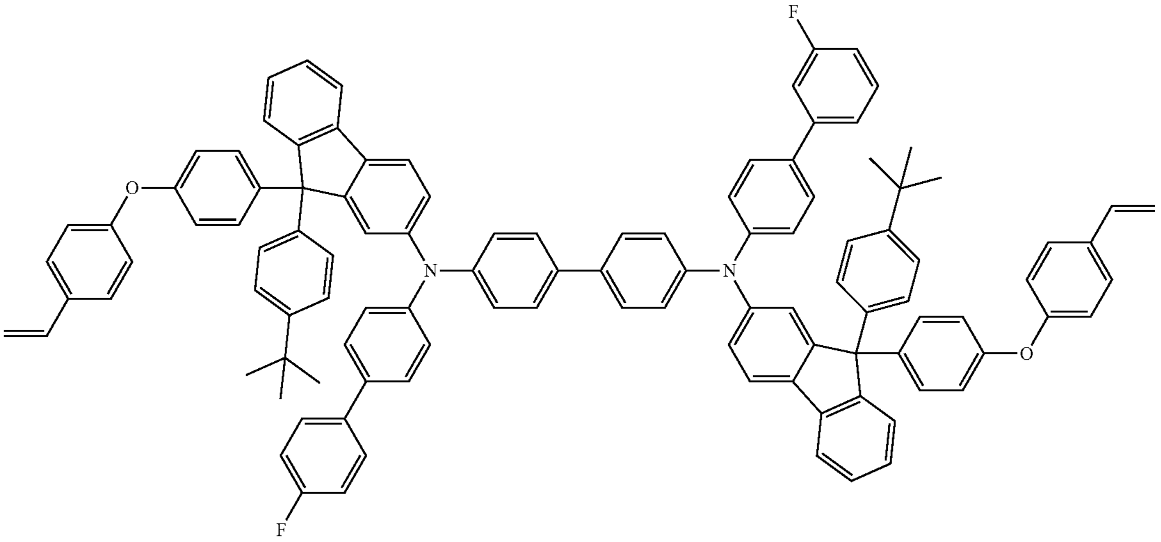

-continued
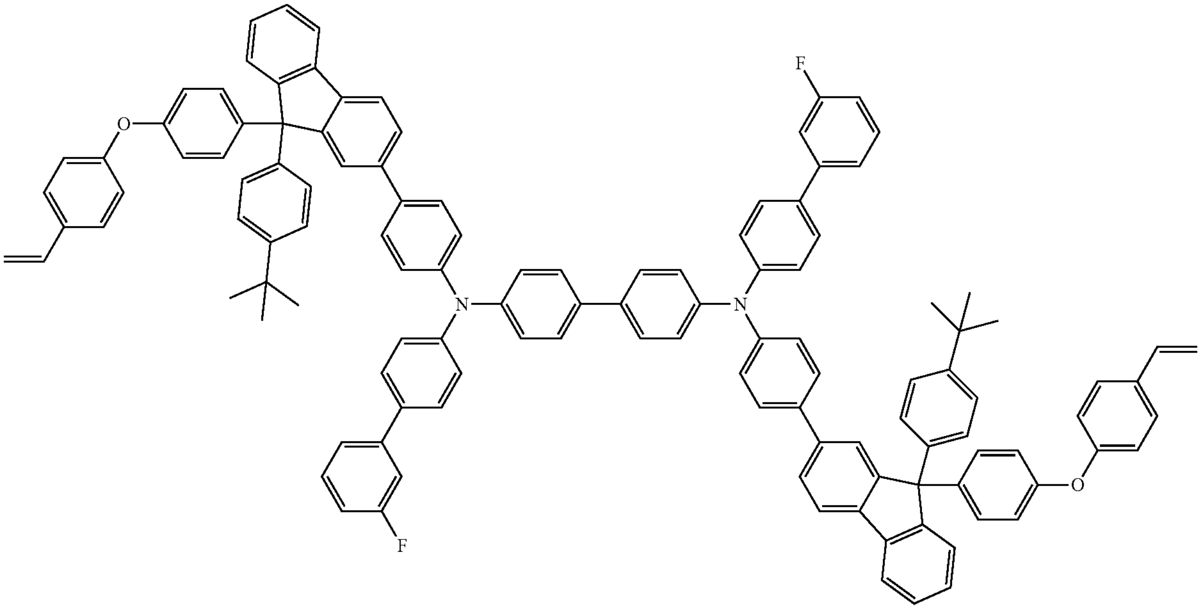
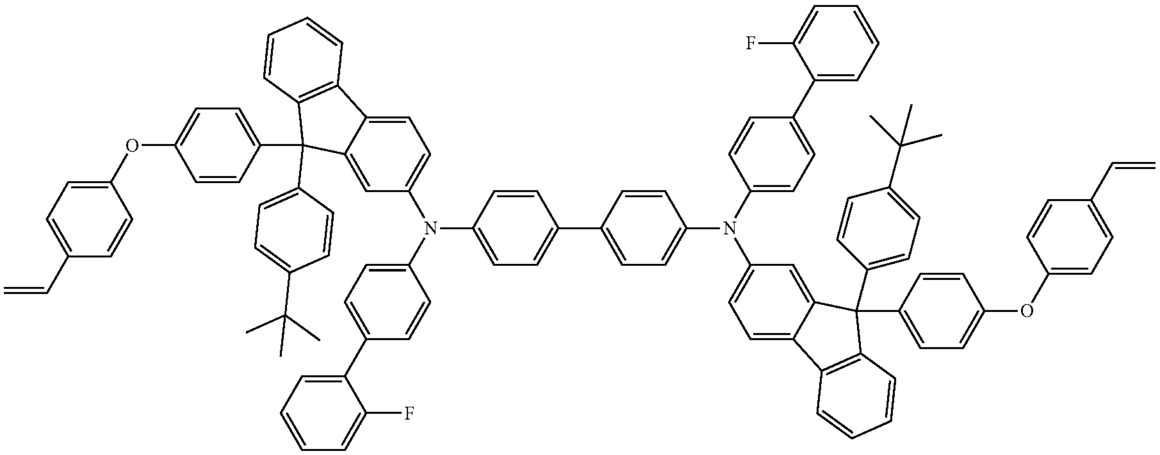
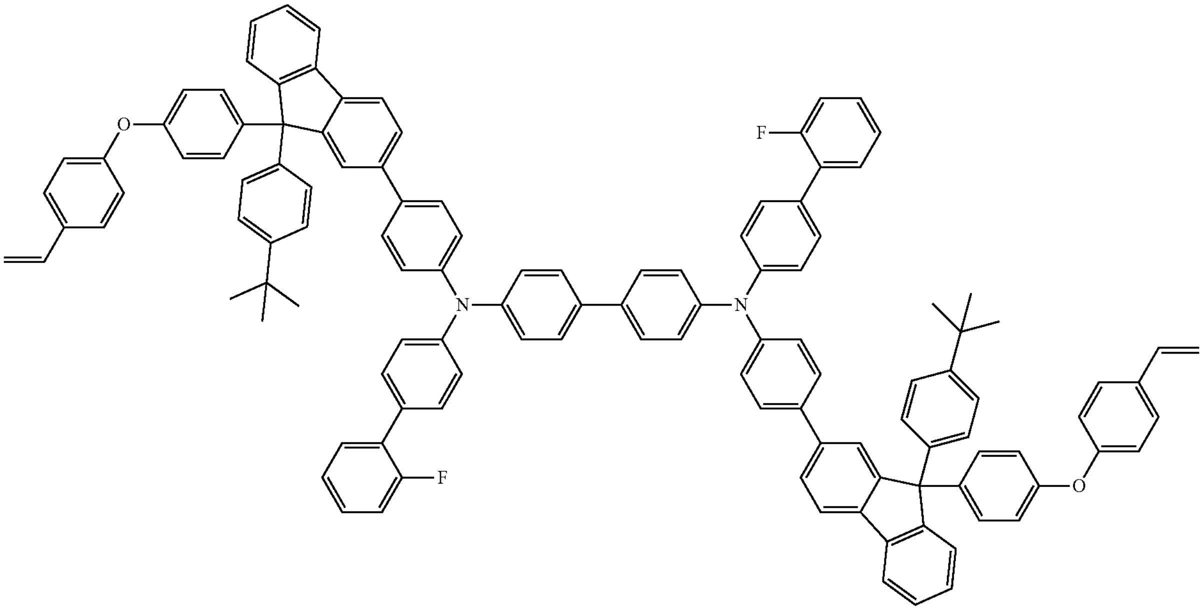

-continued
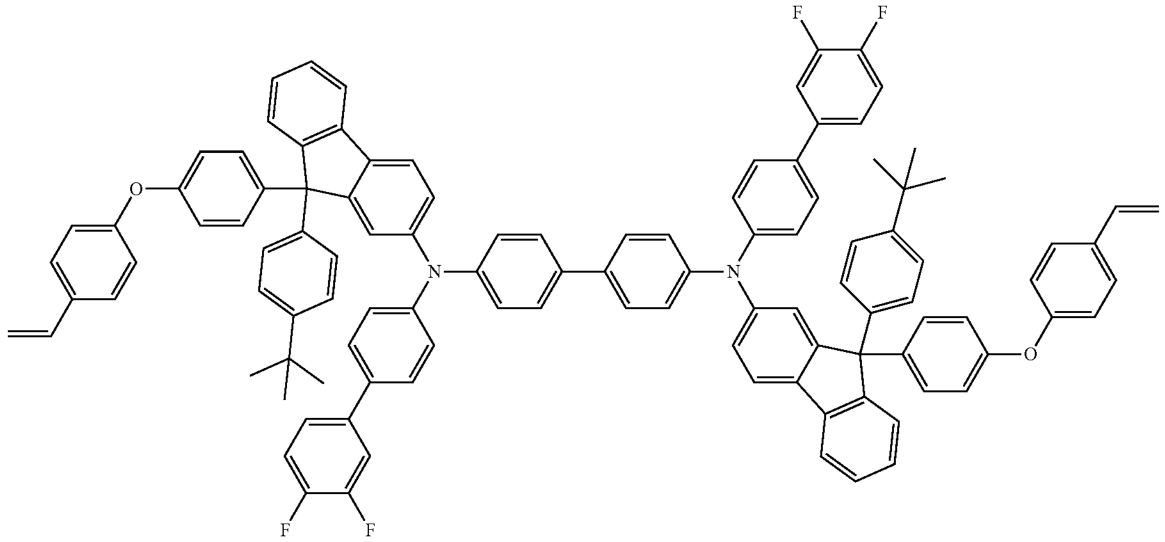
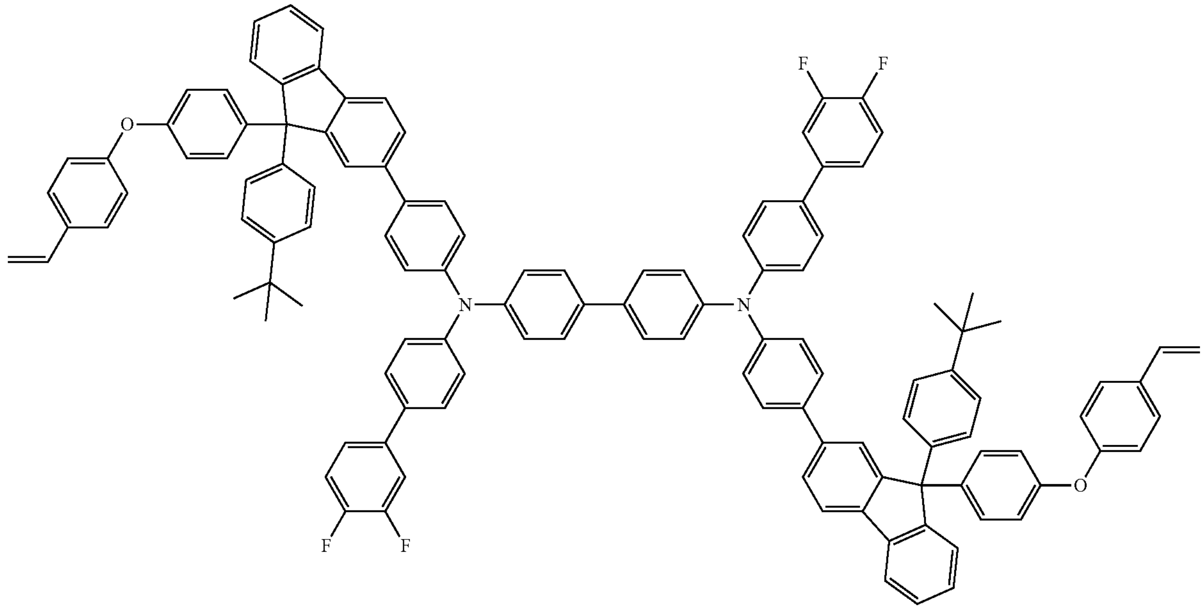
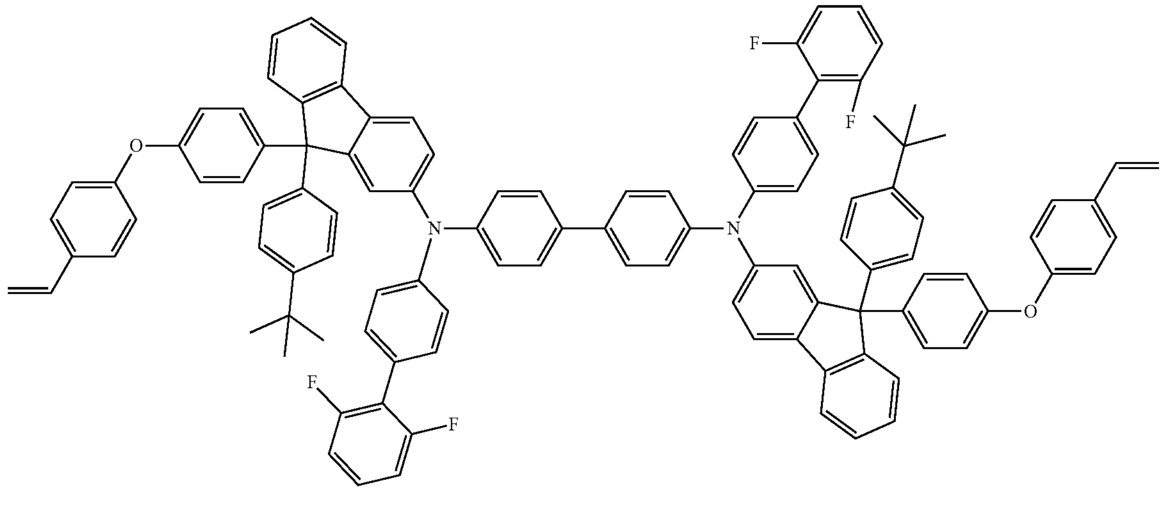

-continued
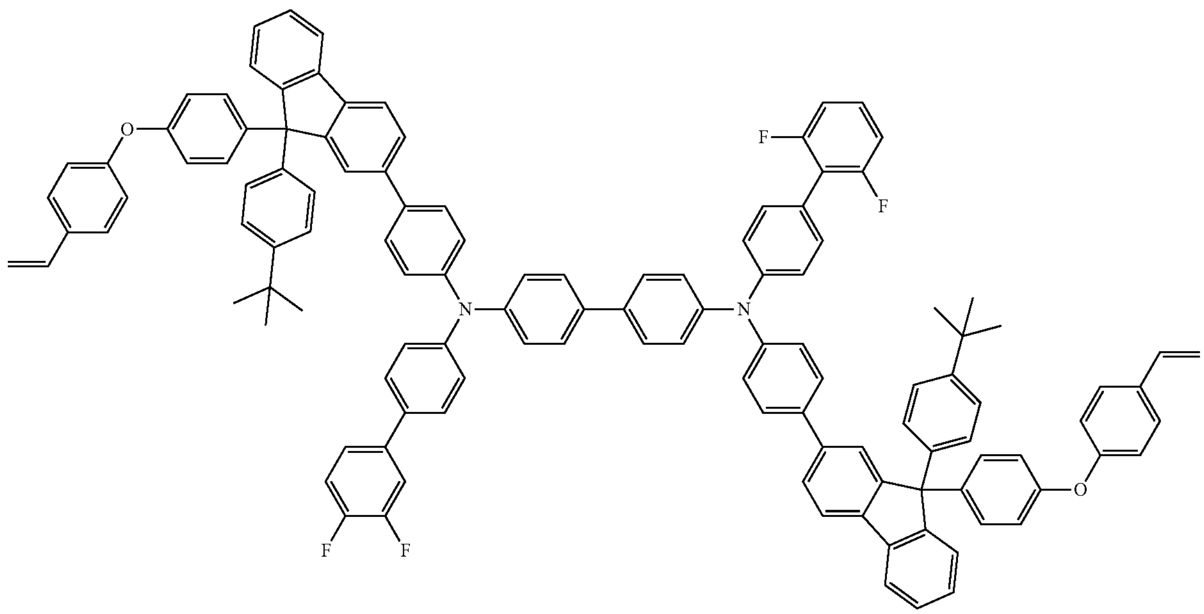
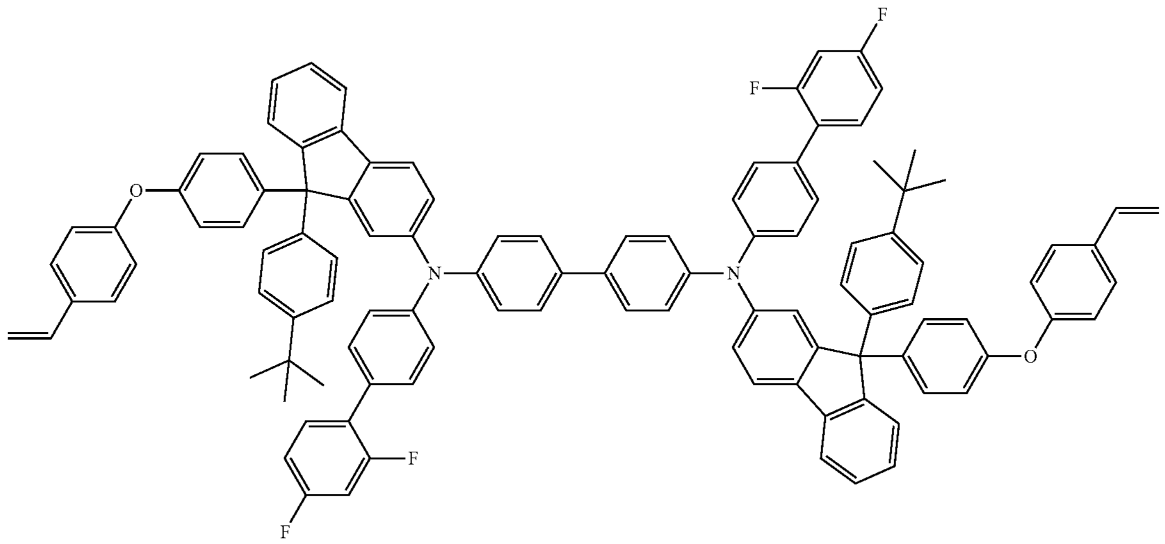

-continued
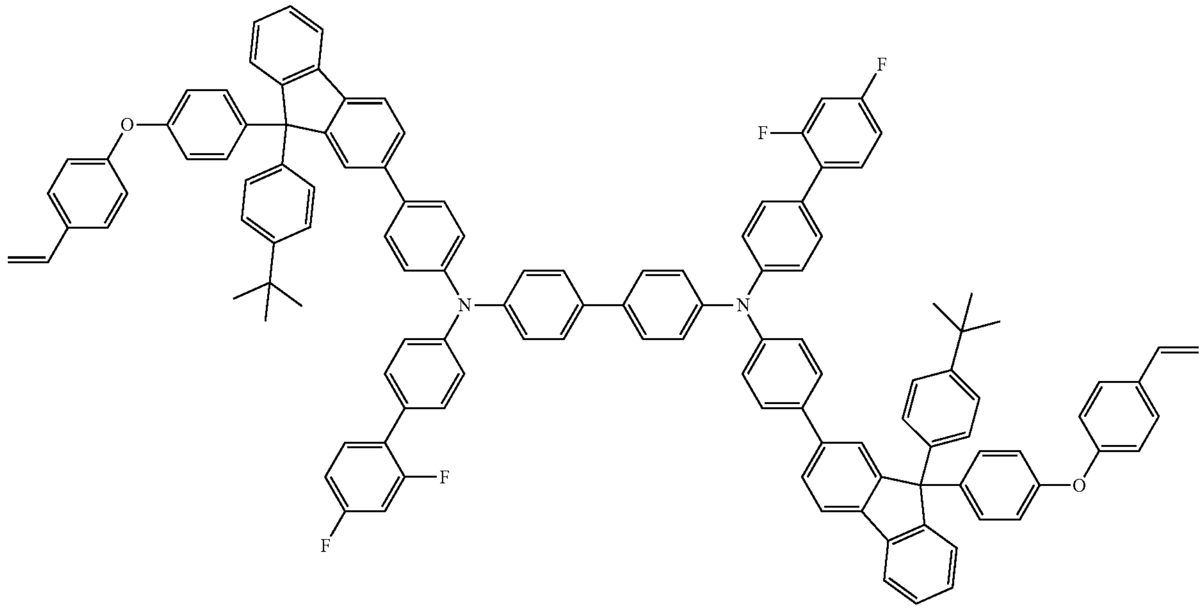
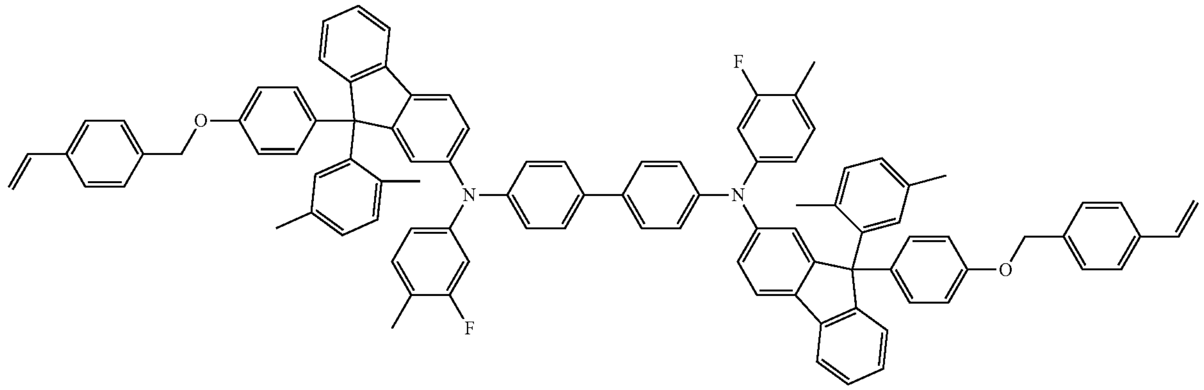
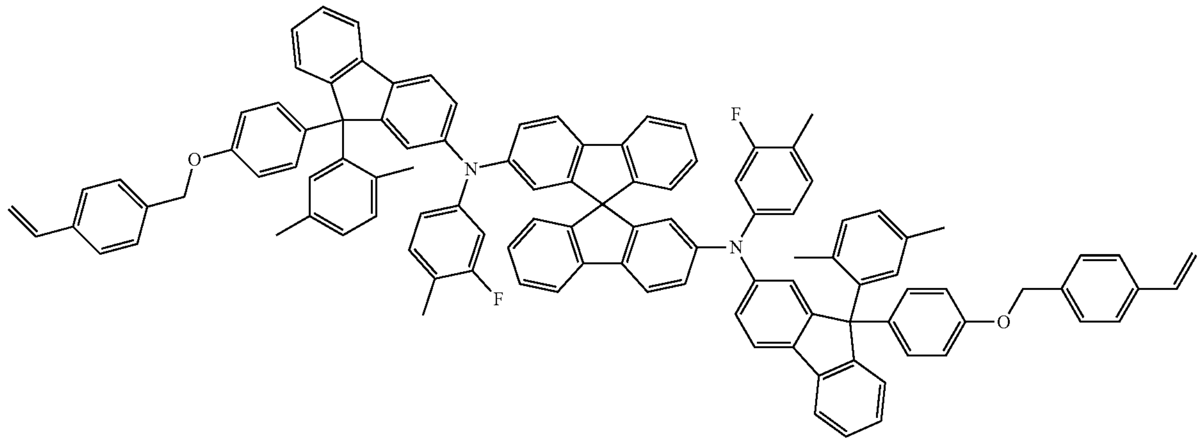

-continued
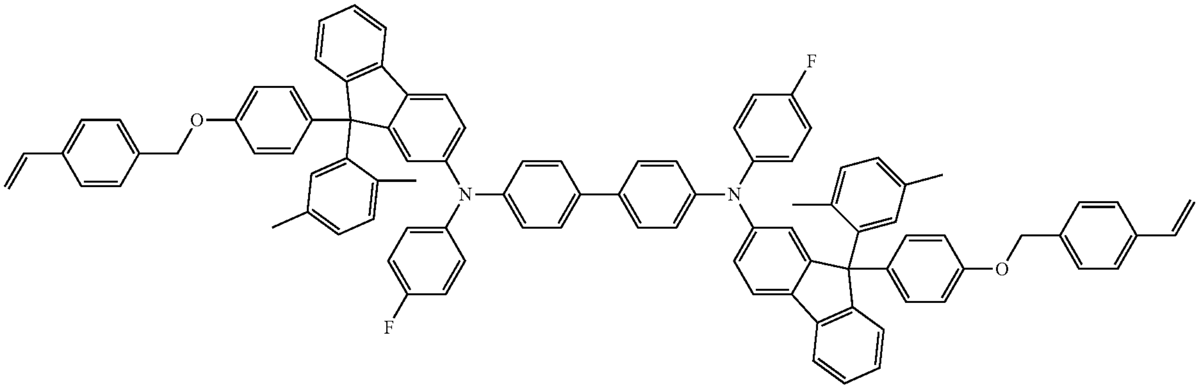
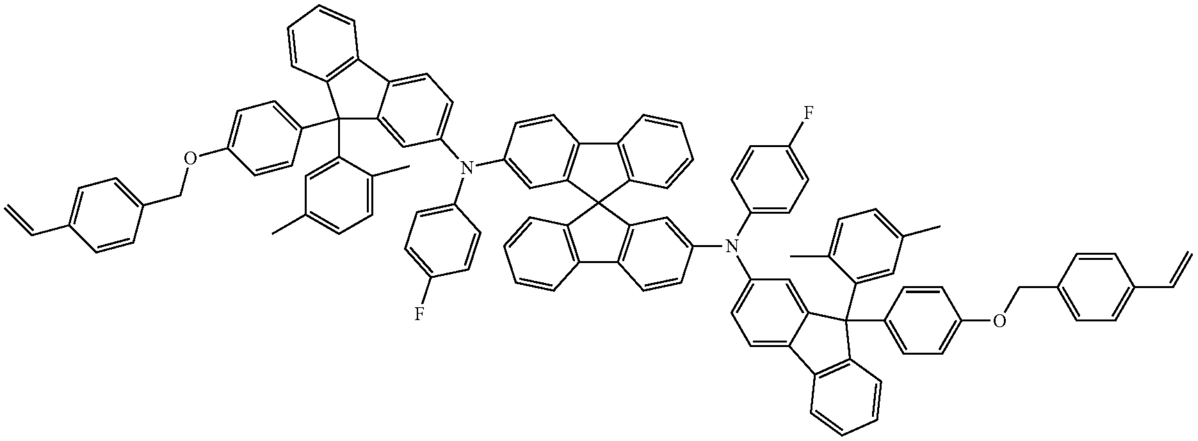
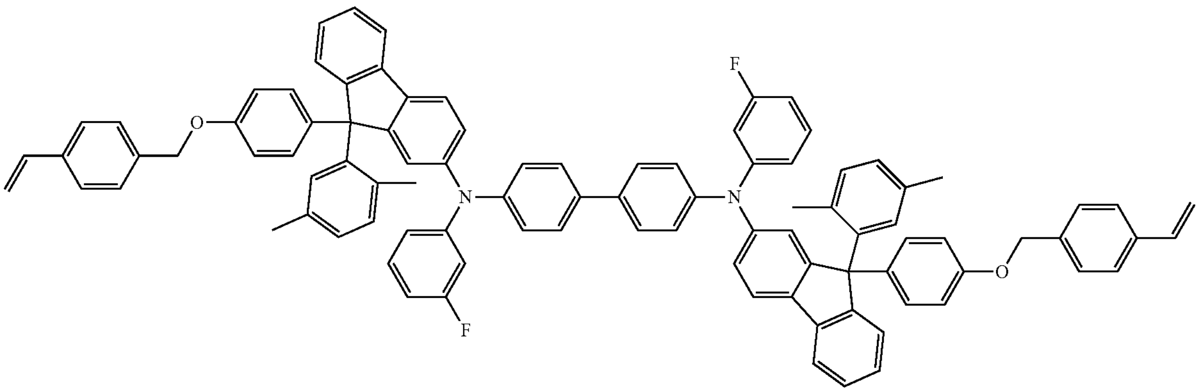
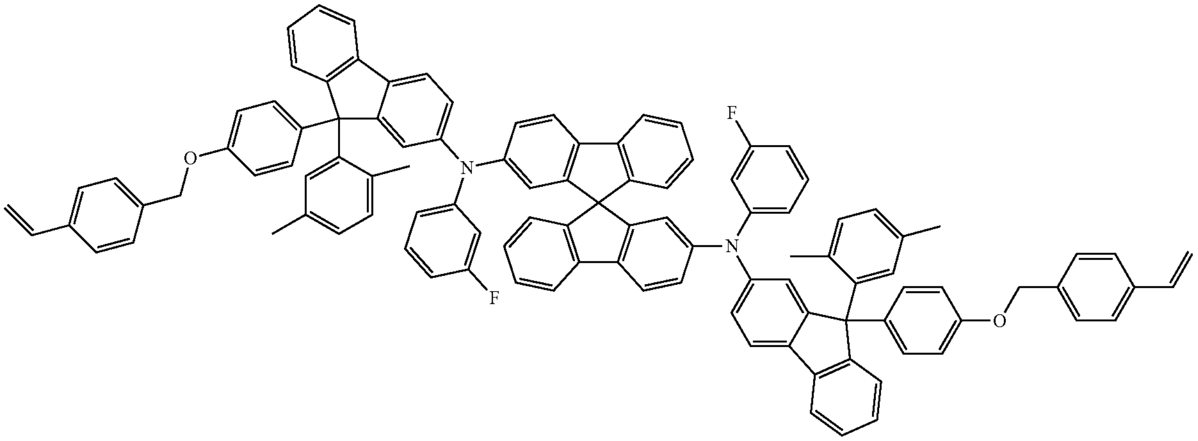

-continued
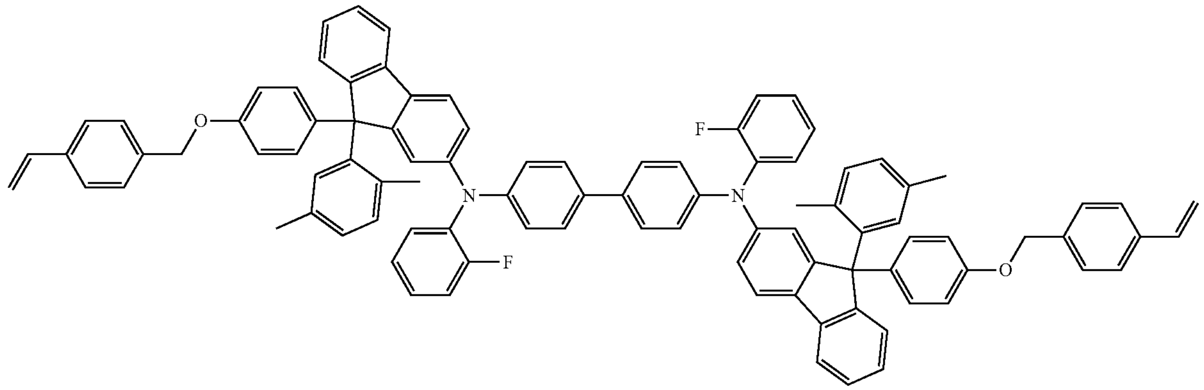
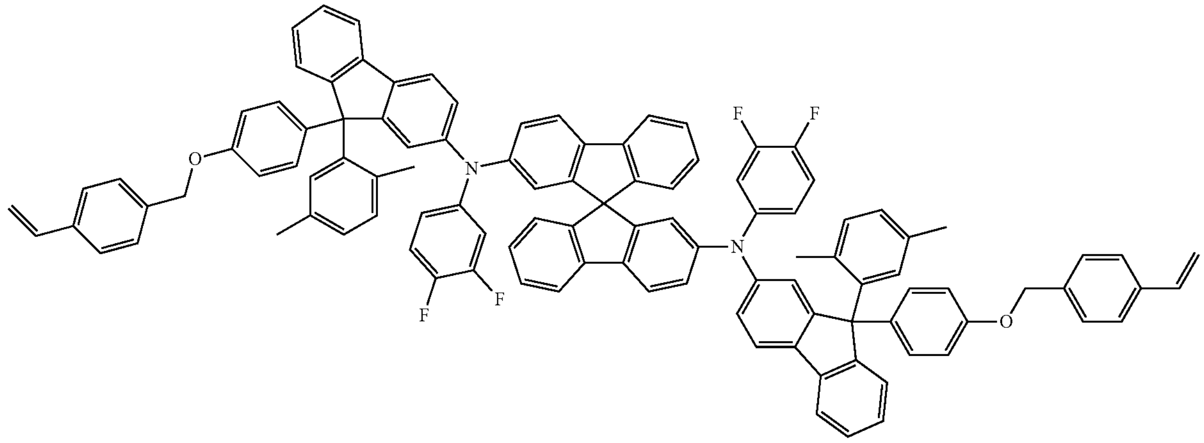
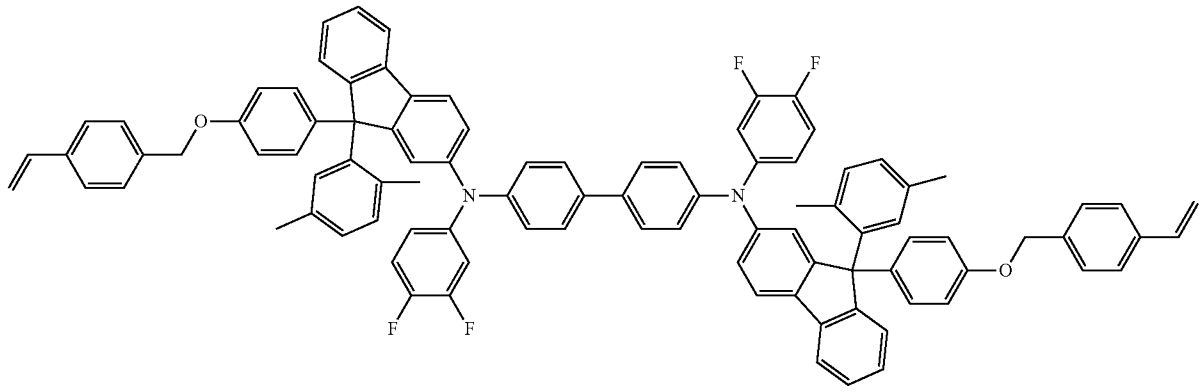
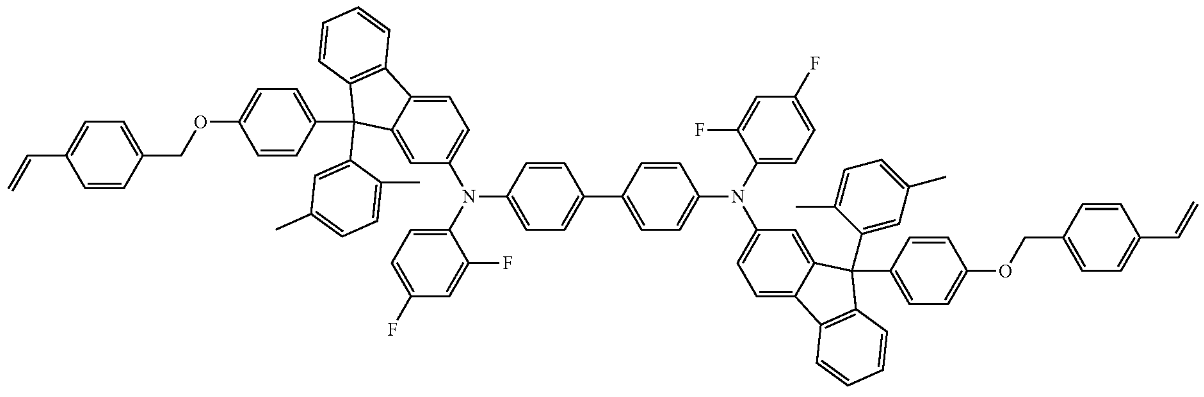

-continued
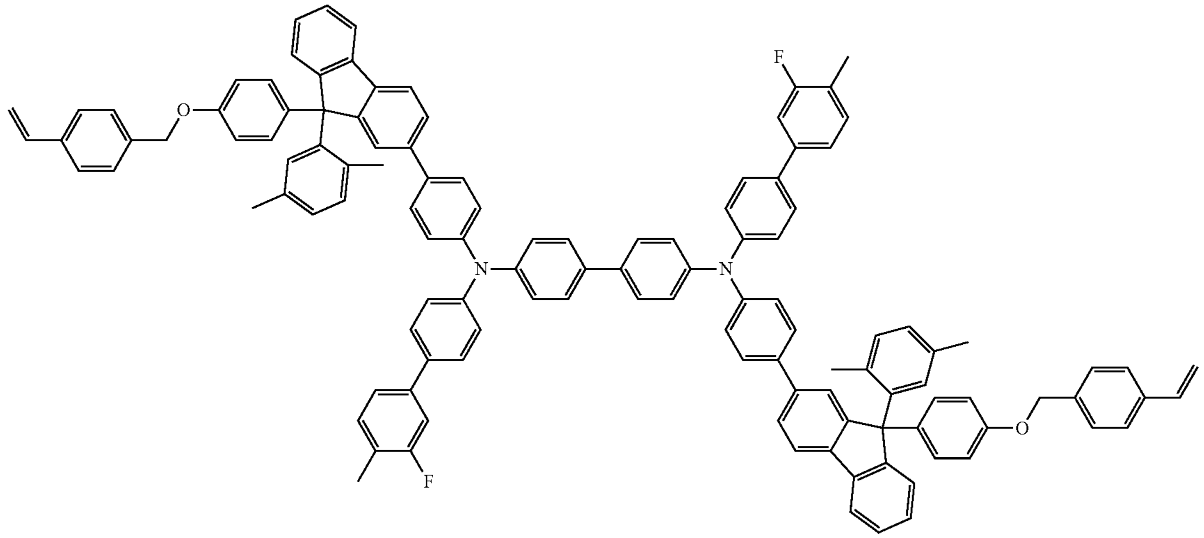
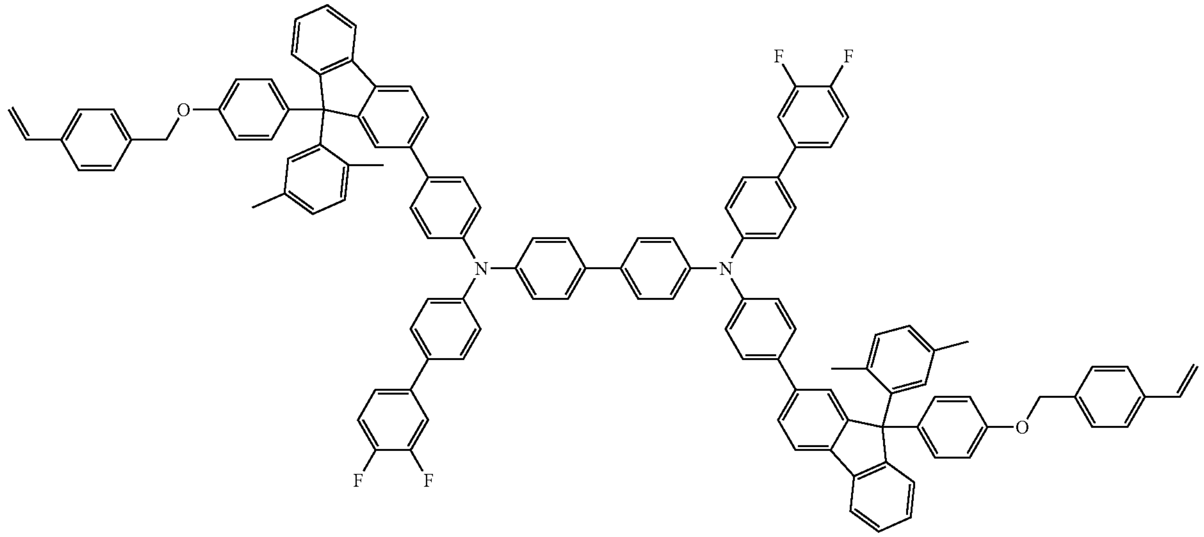
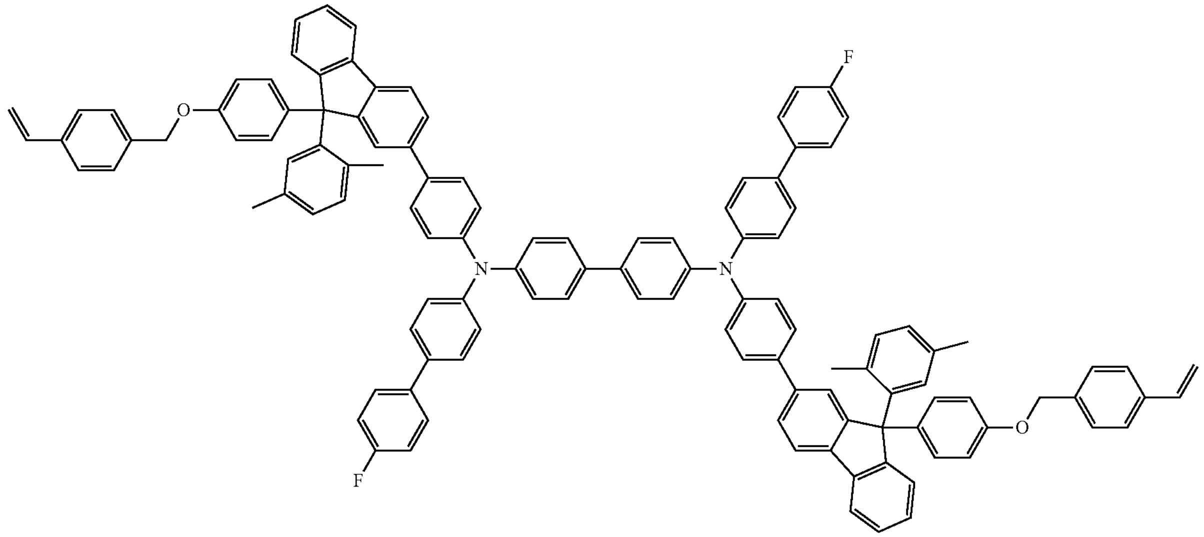

-continued
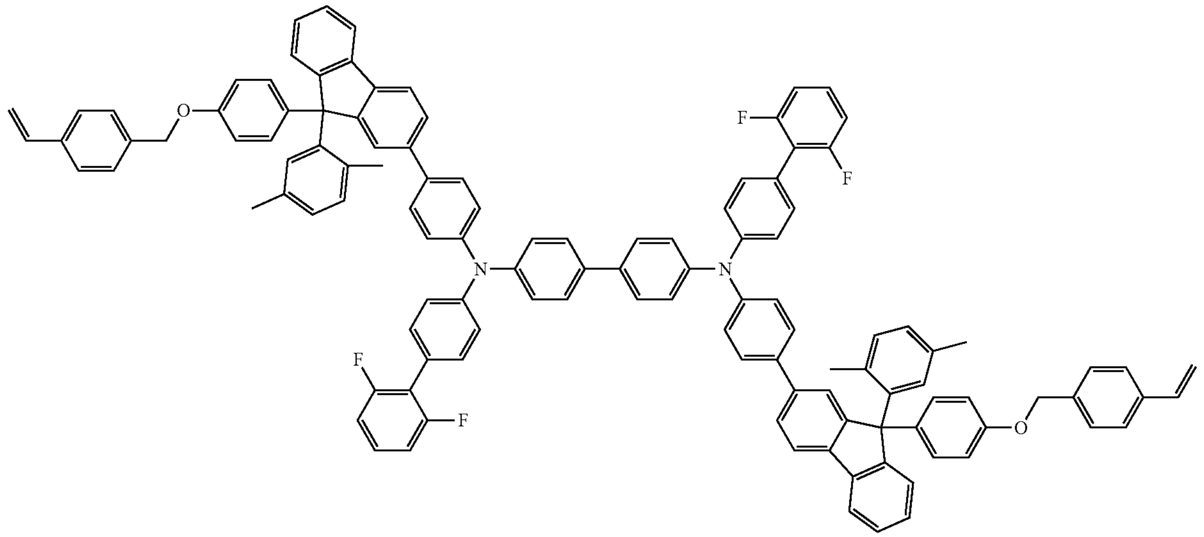
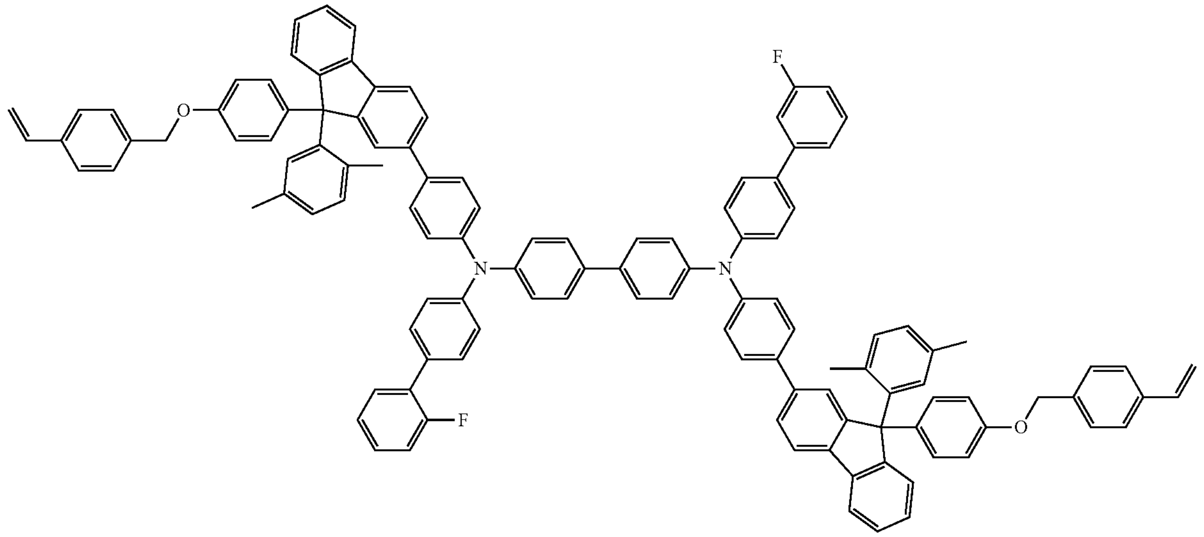
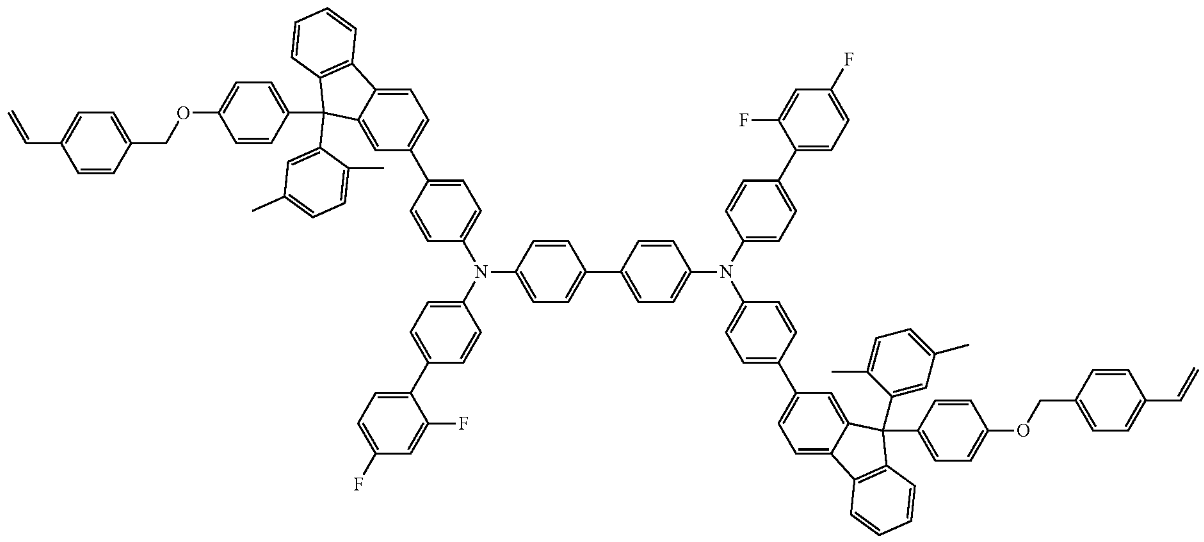

-continued
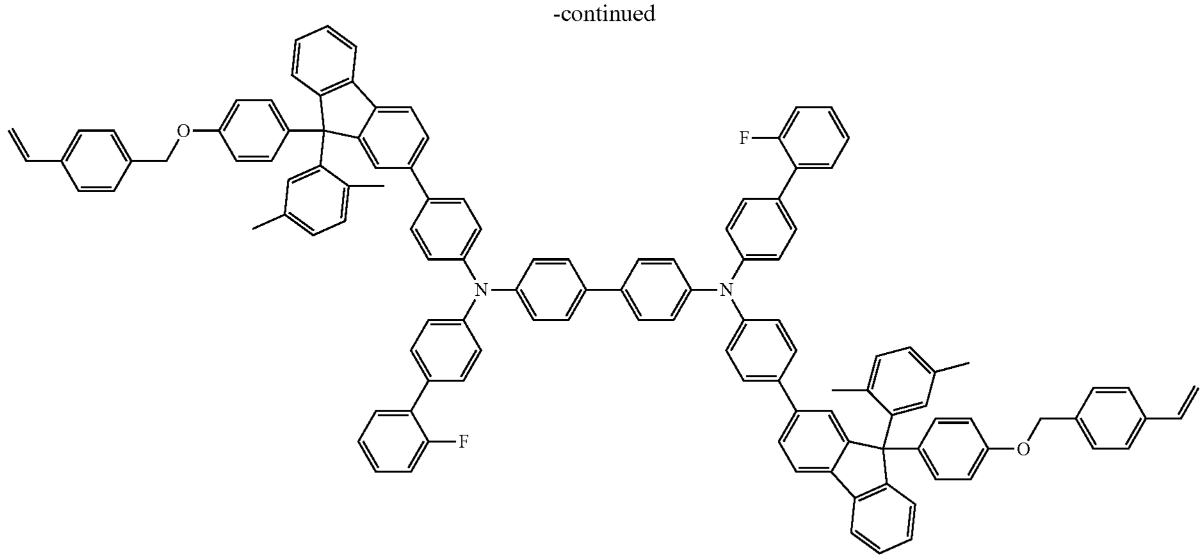
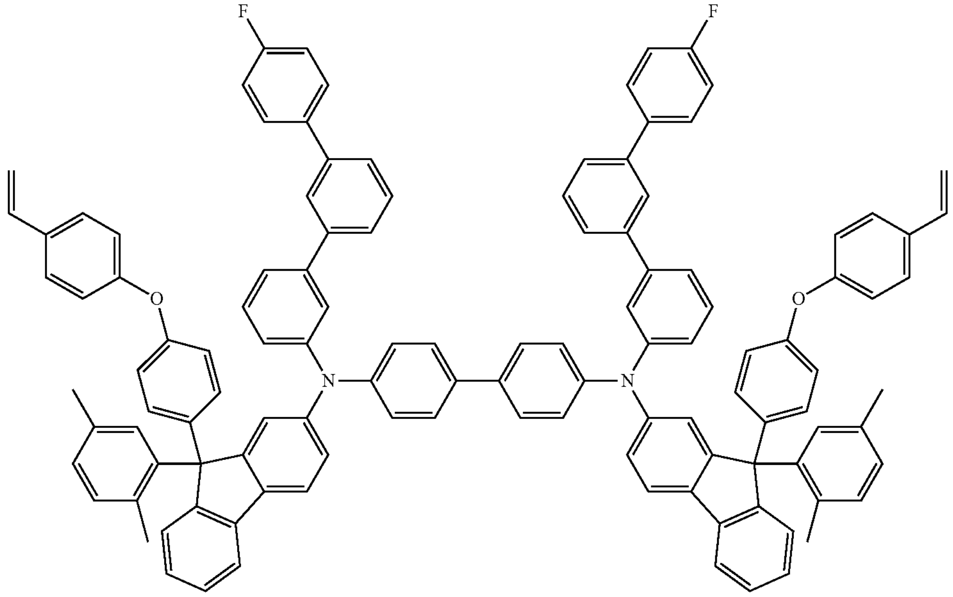
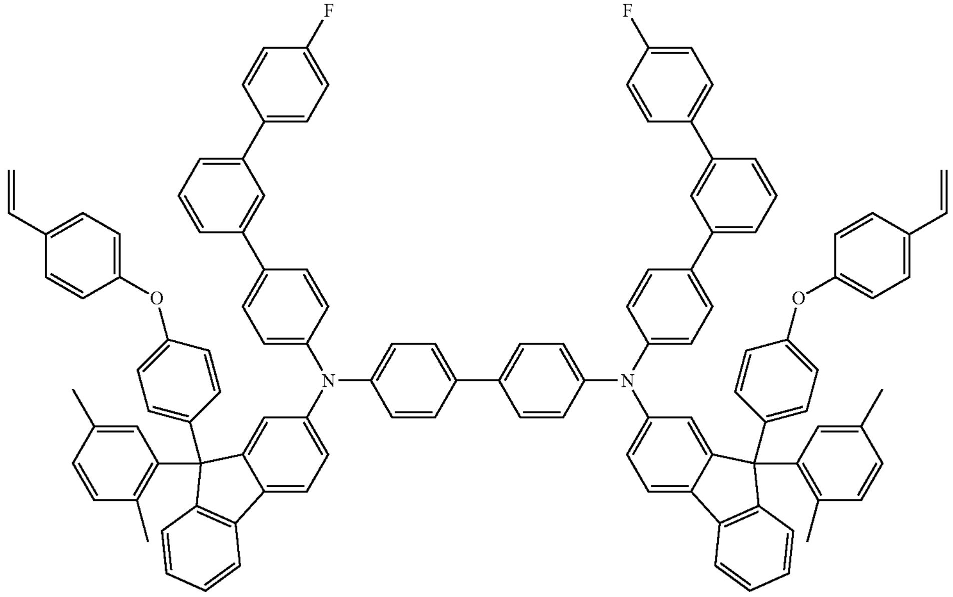

-continued
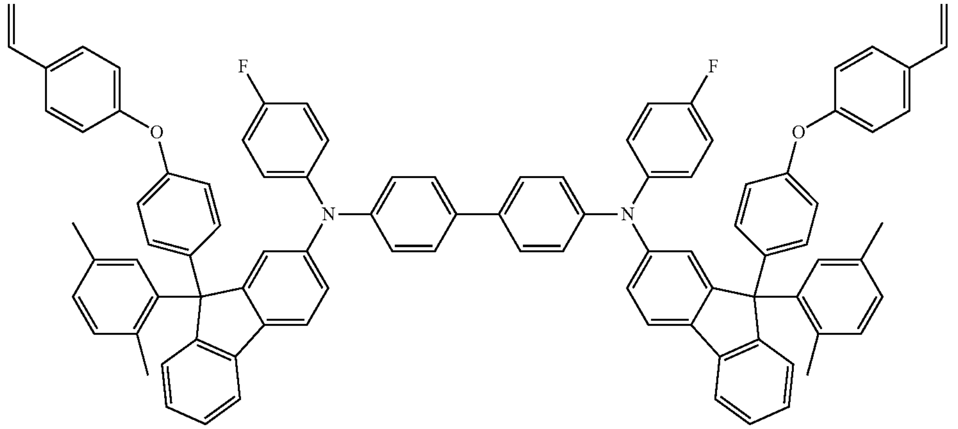
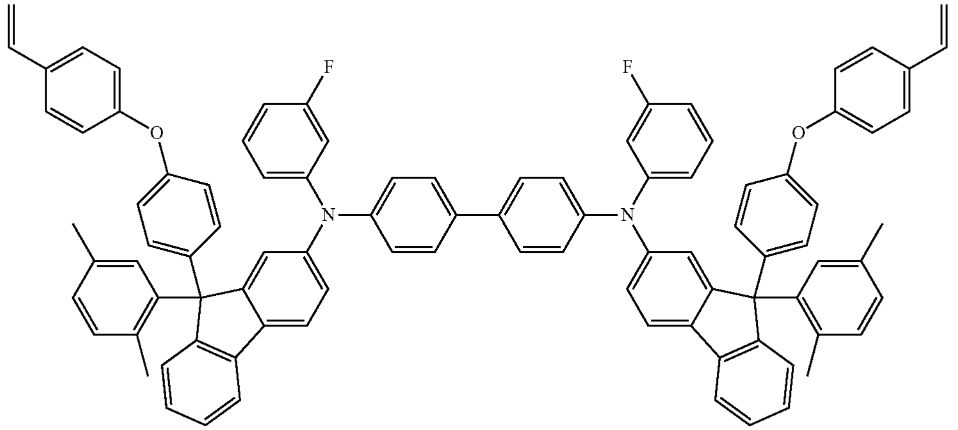
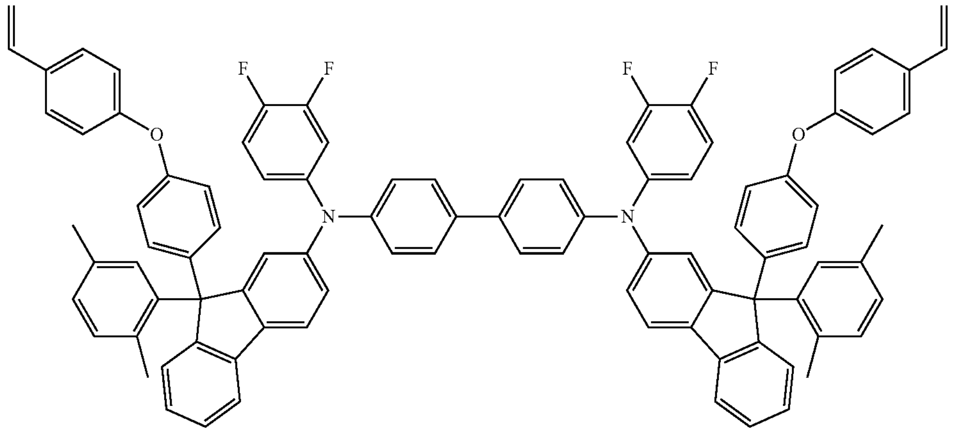
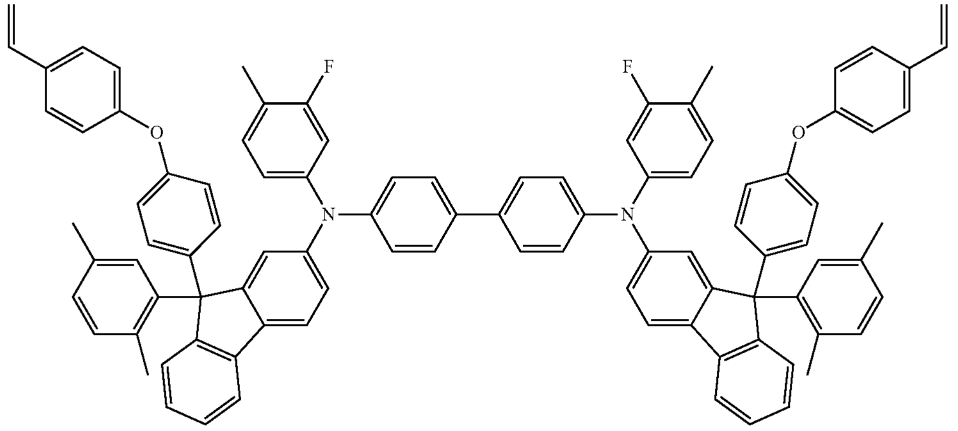

-continued
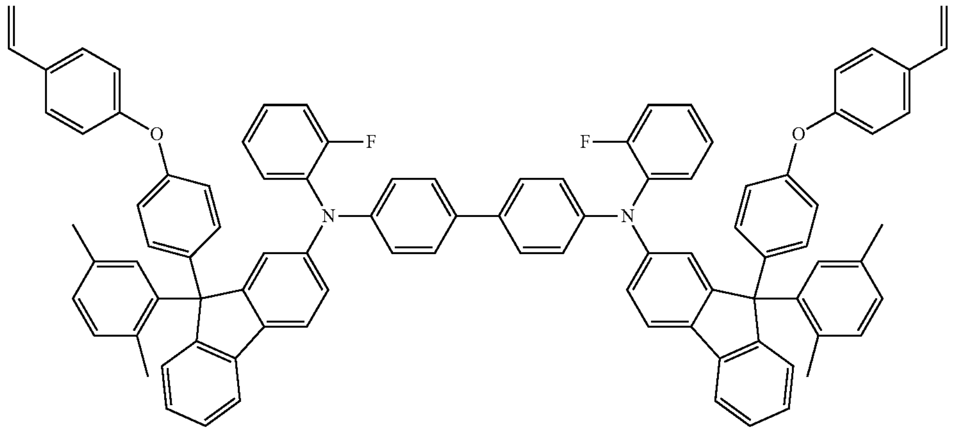
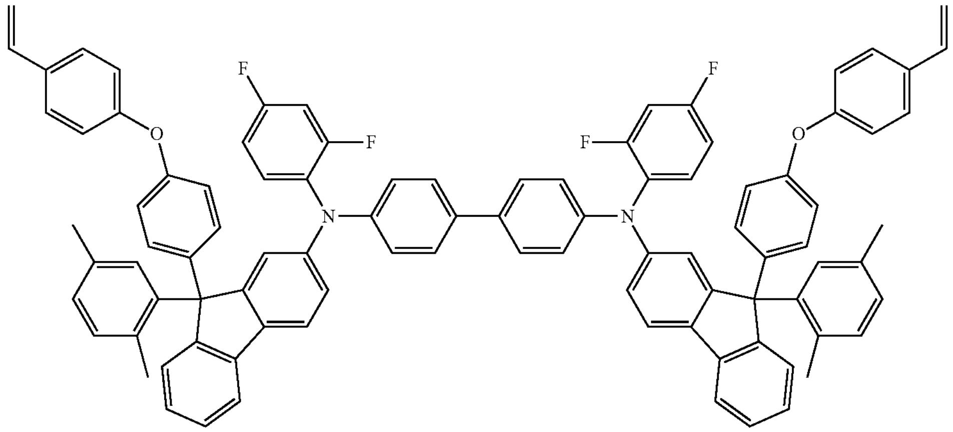
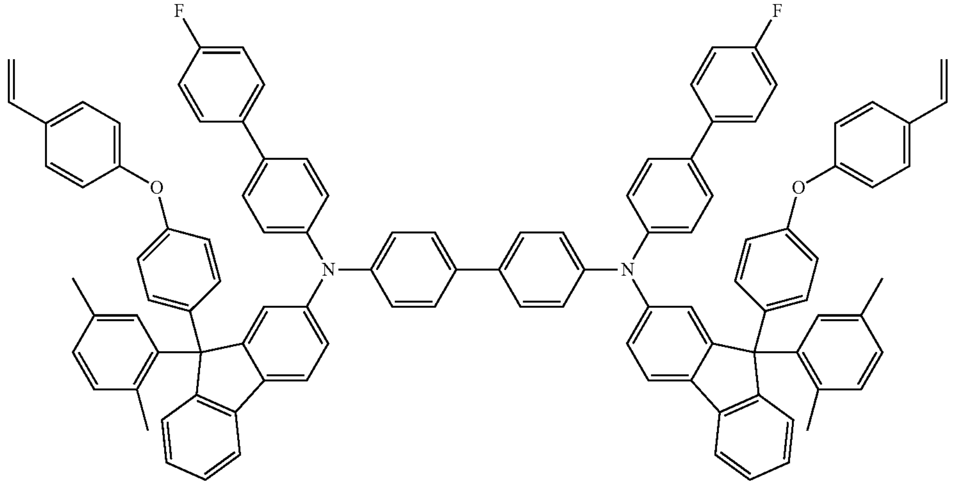

-continued
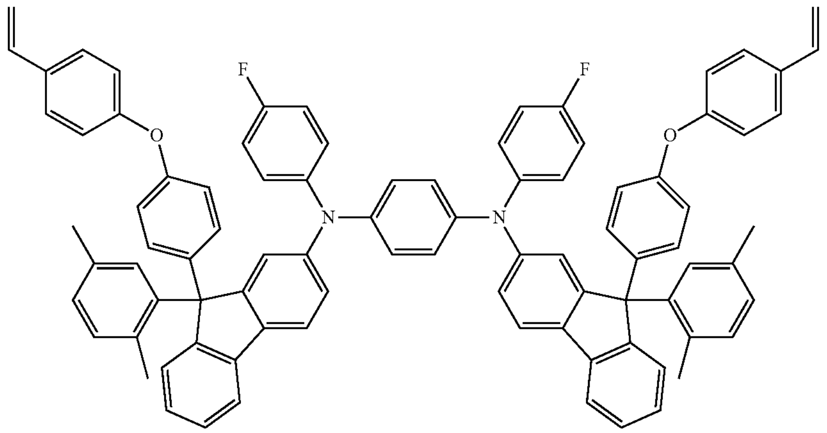
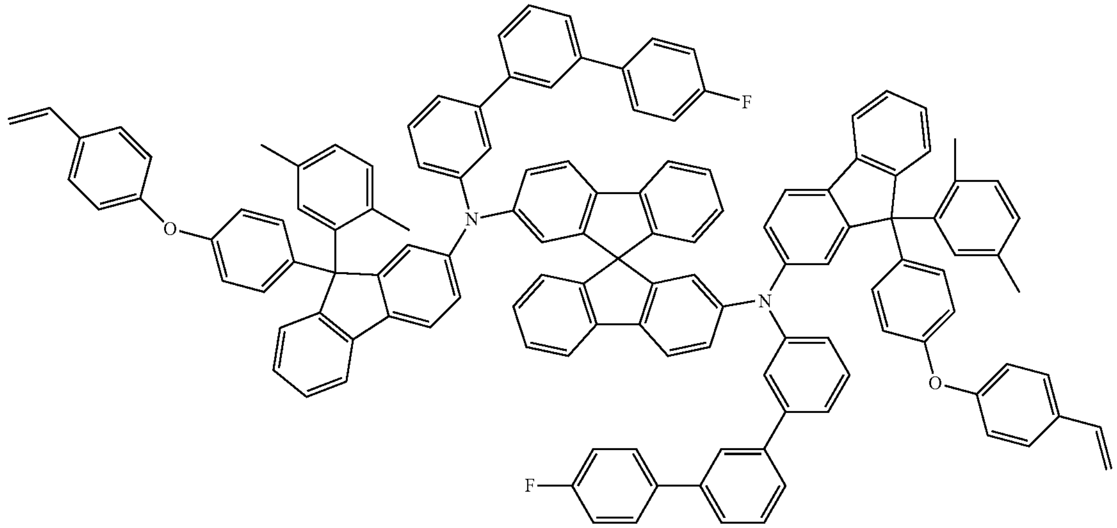

-continued
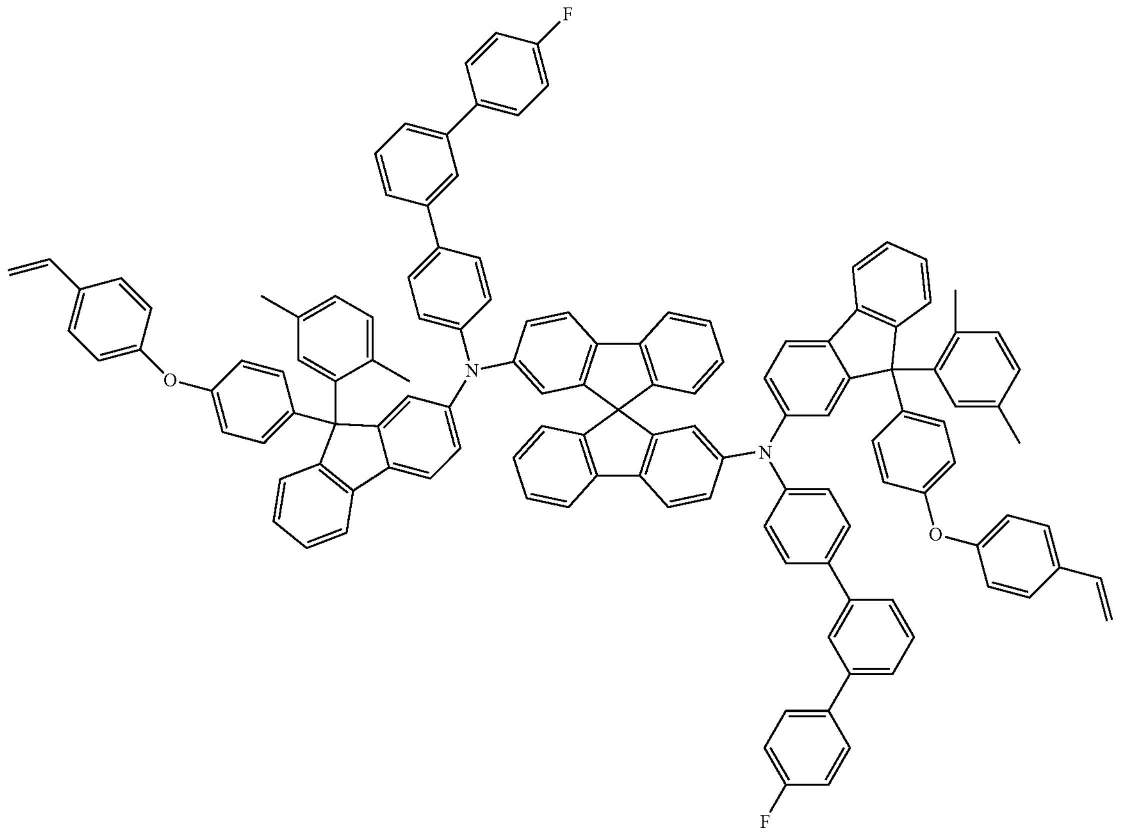
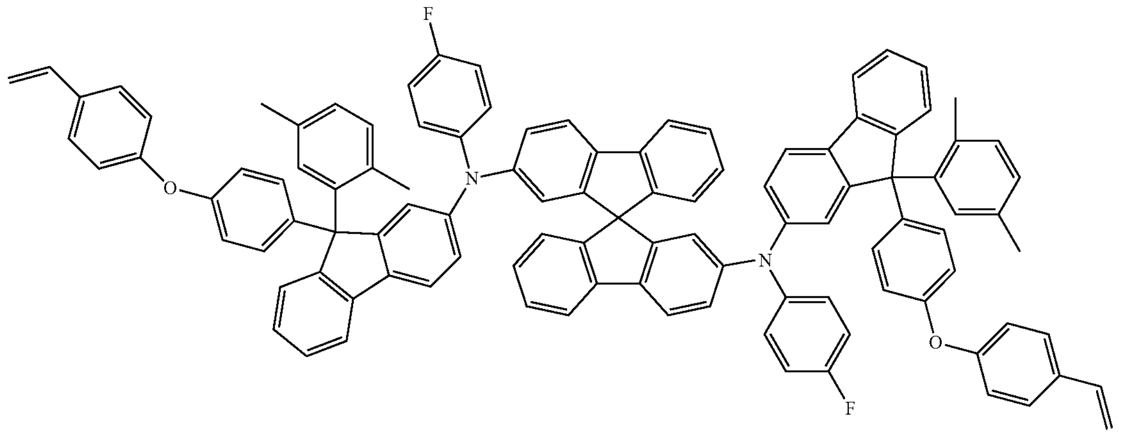
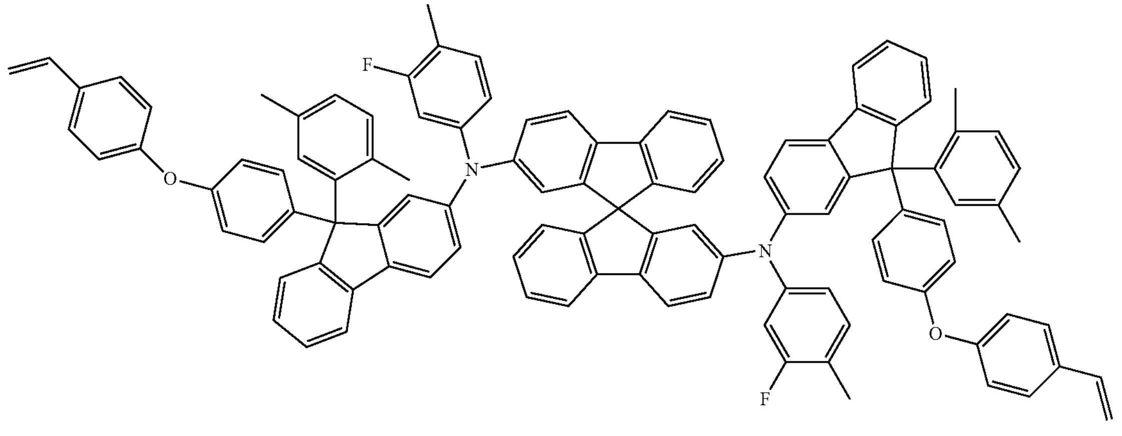

-continued
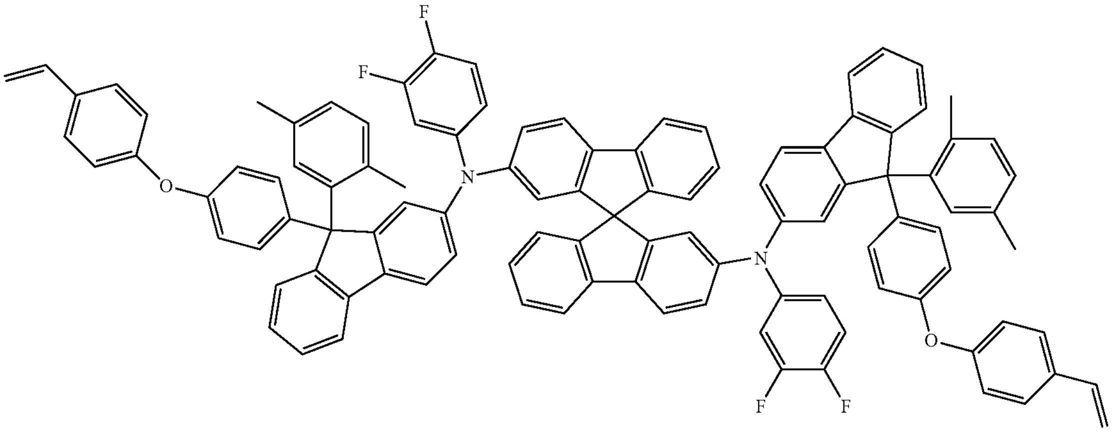
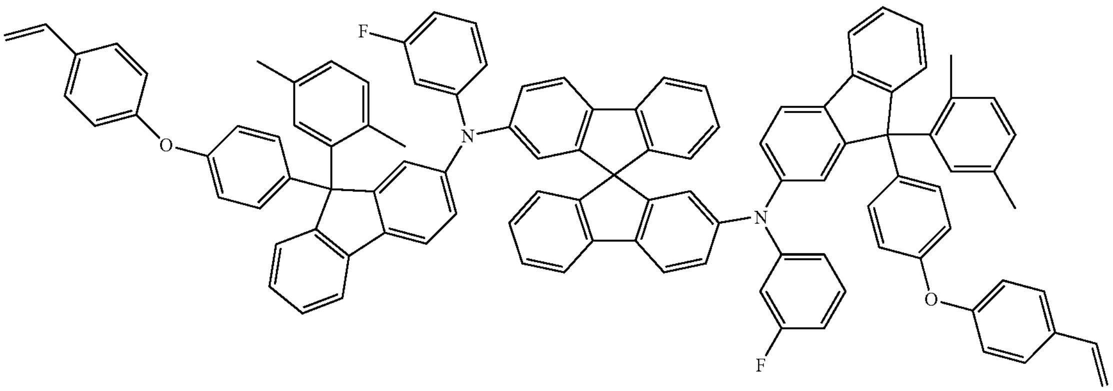
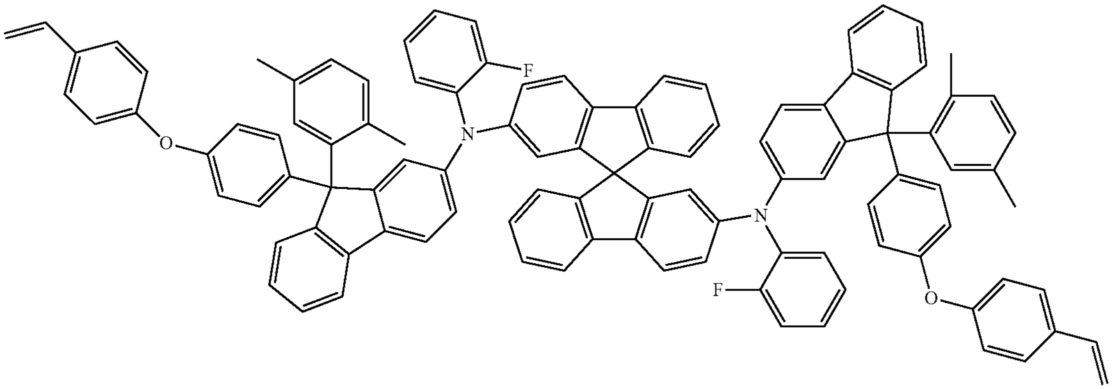
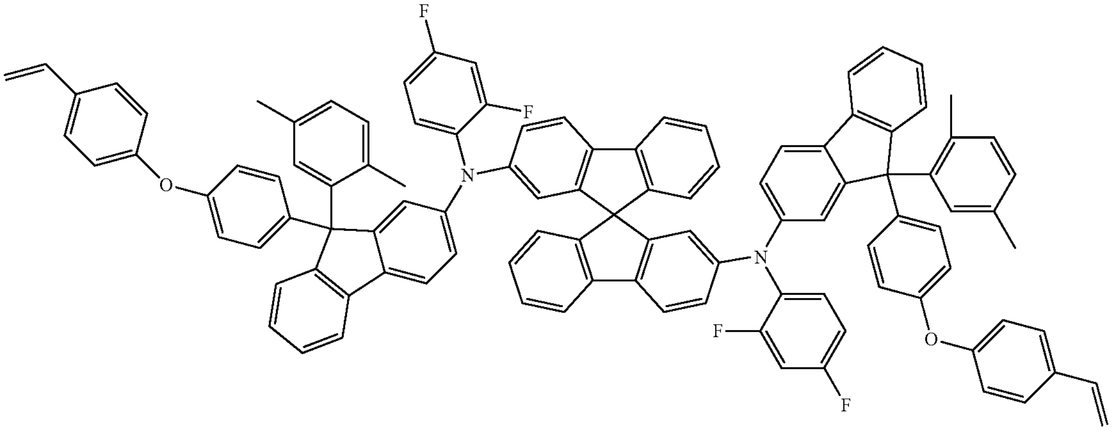

-continued
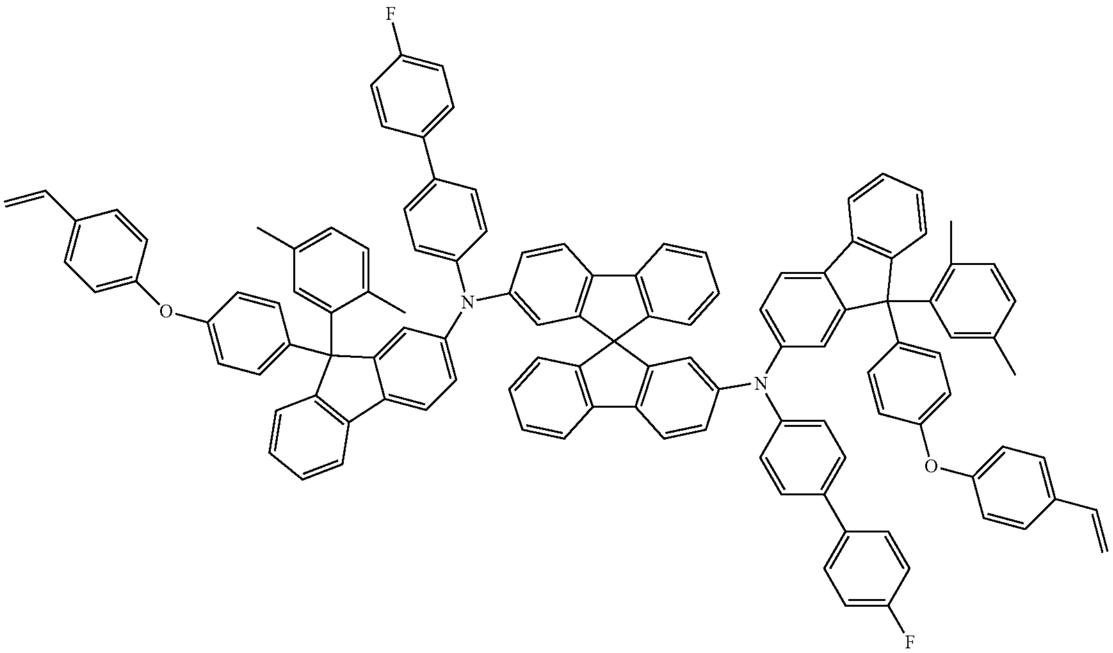
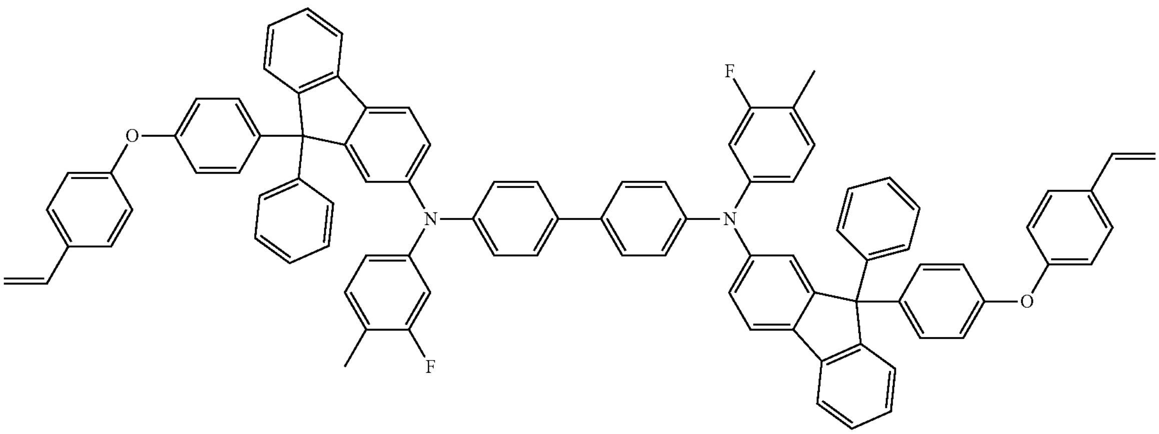
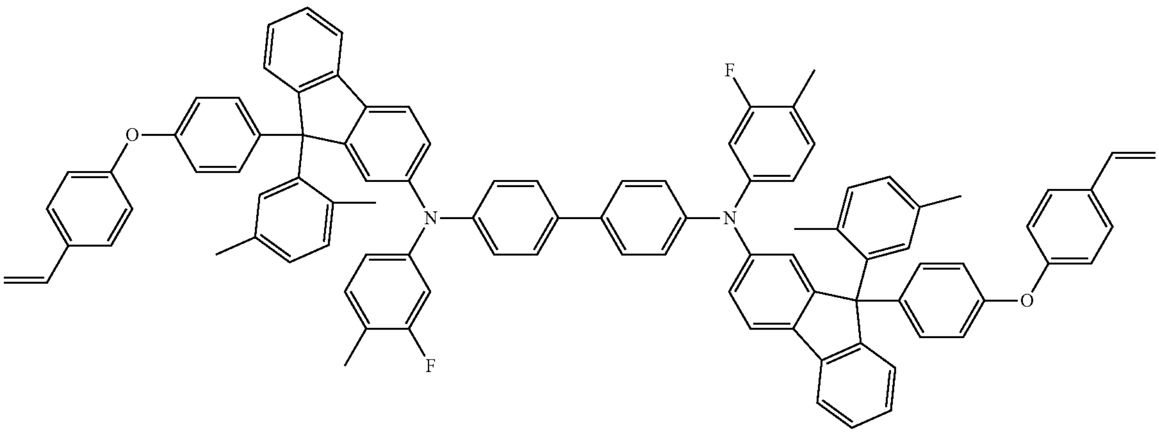

-continued
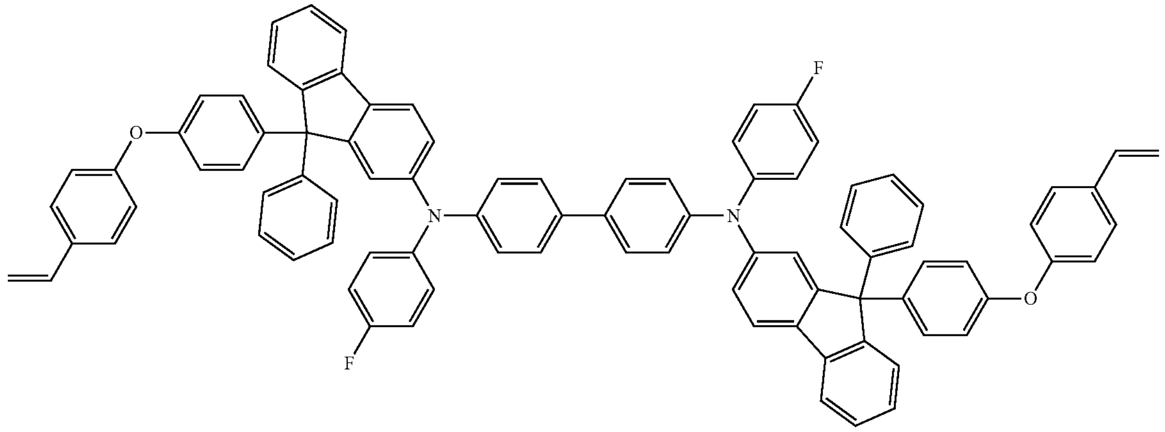
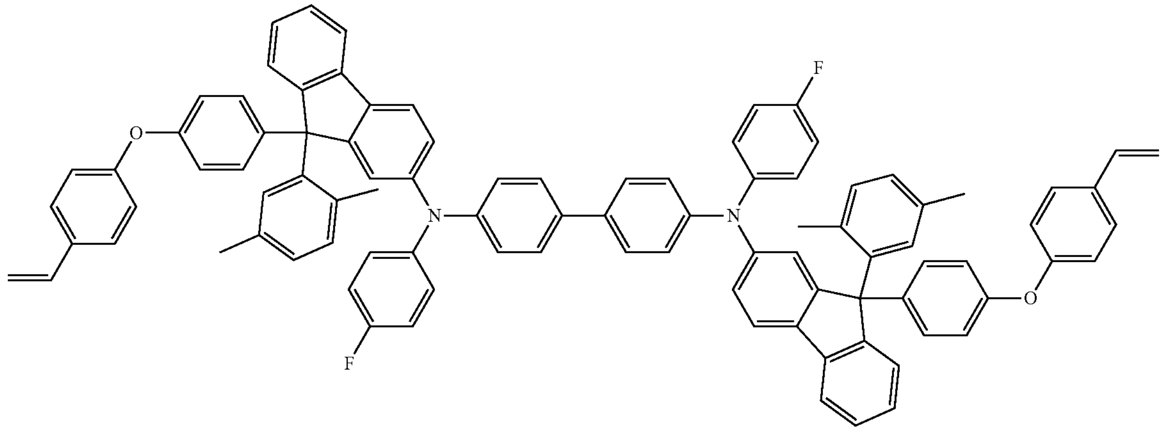
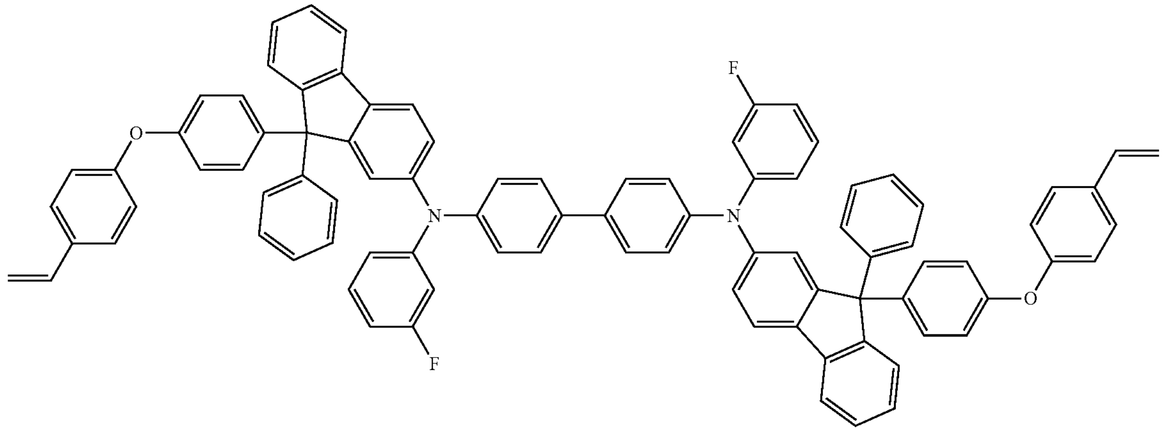
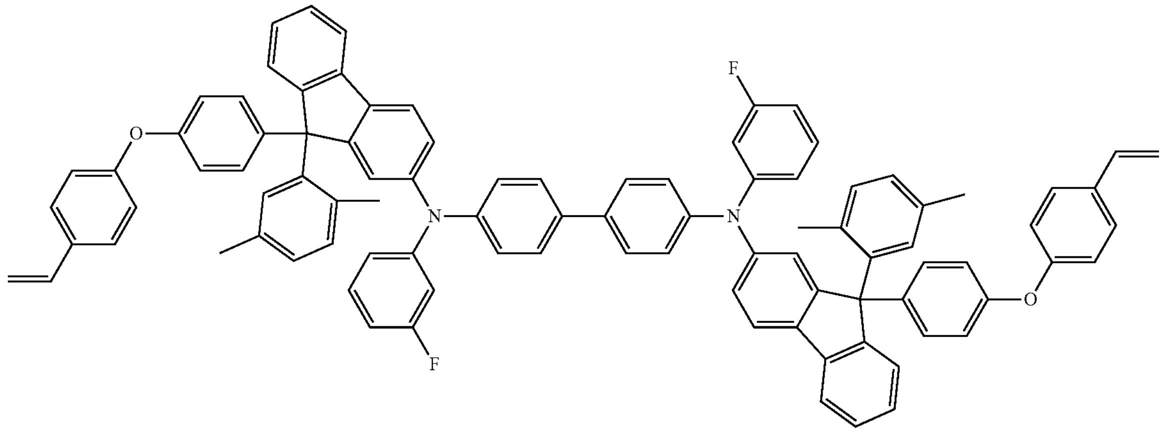

-continued
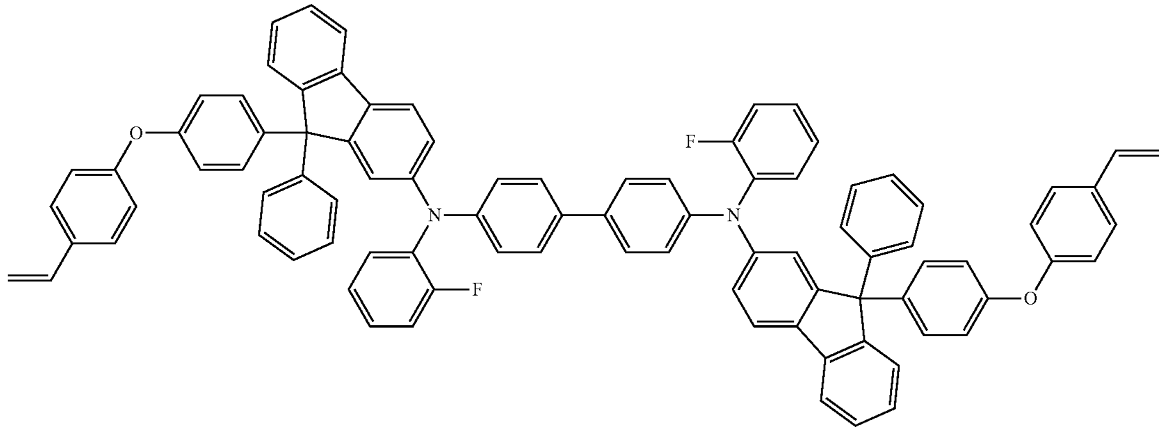
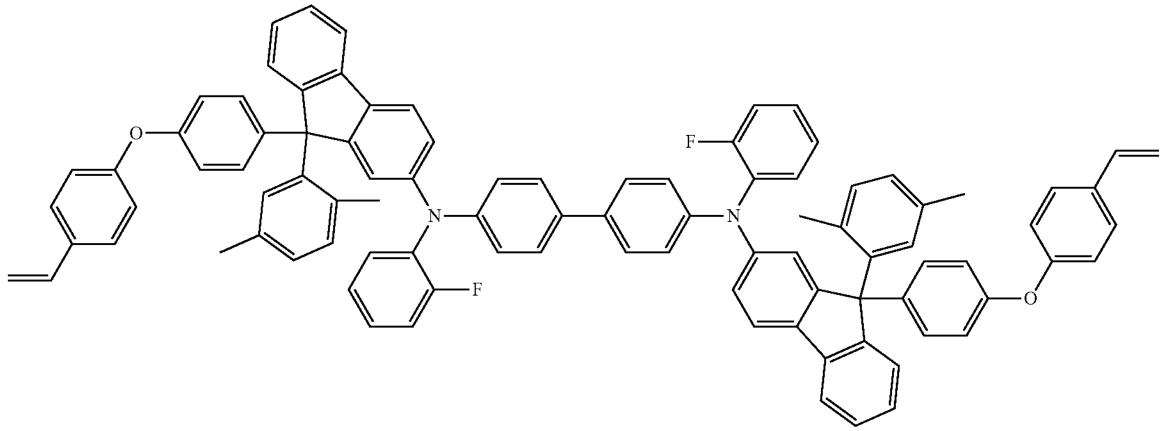
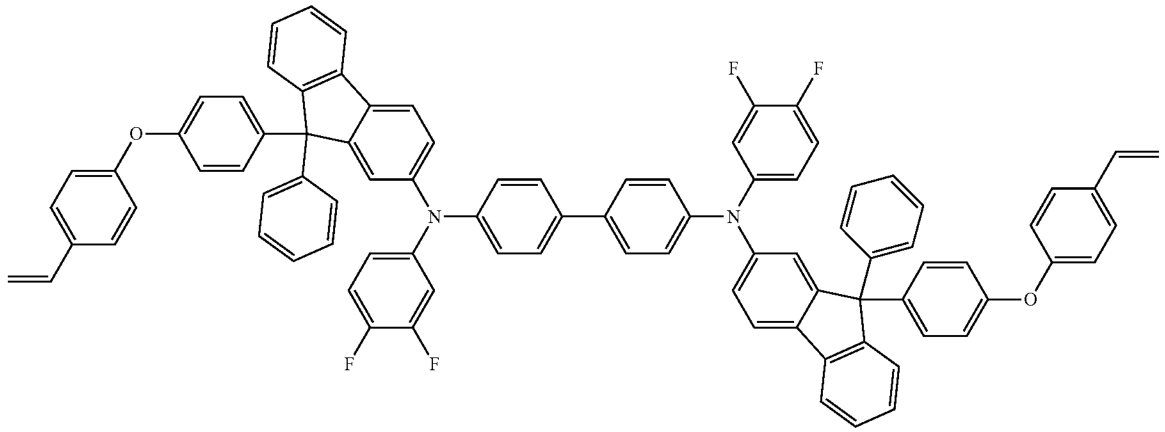
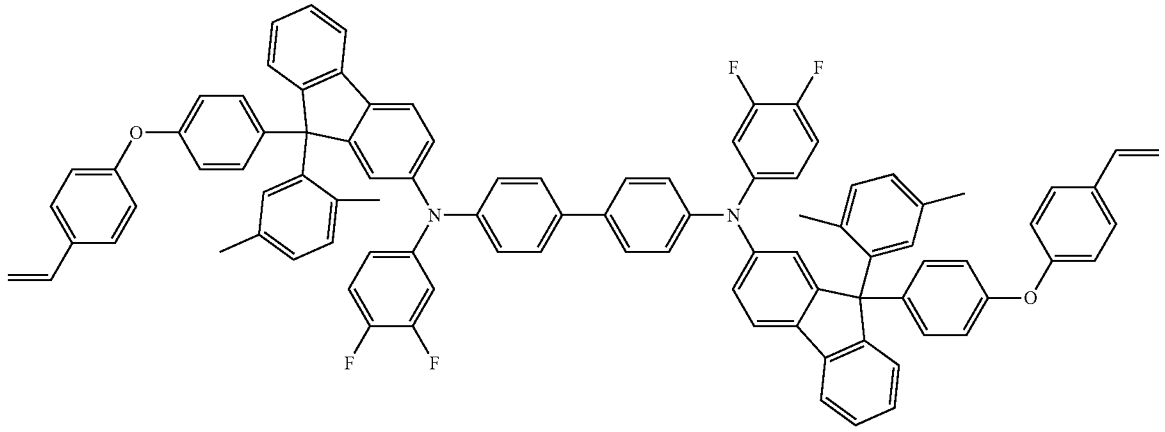

-continued
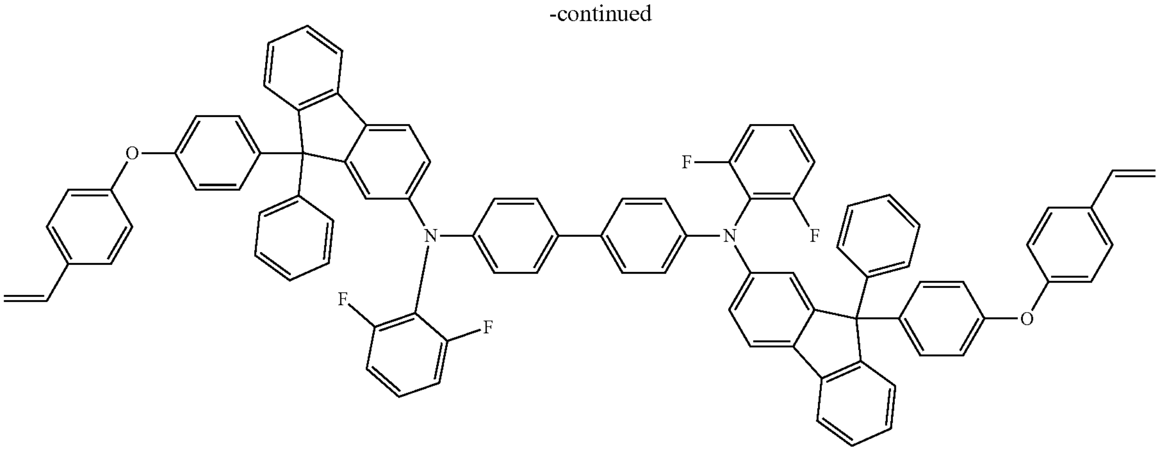
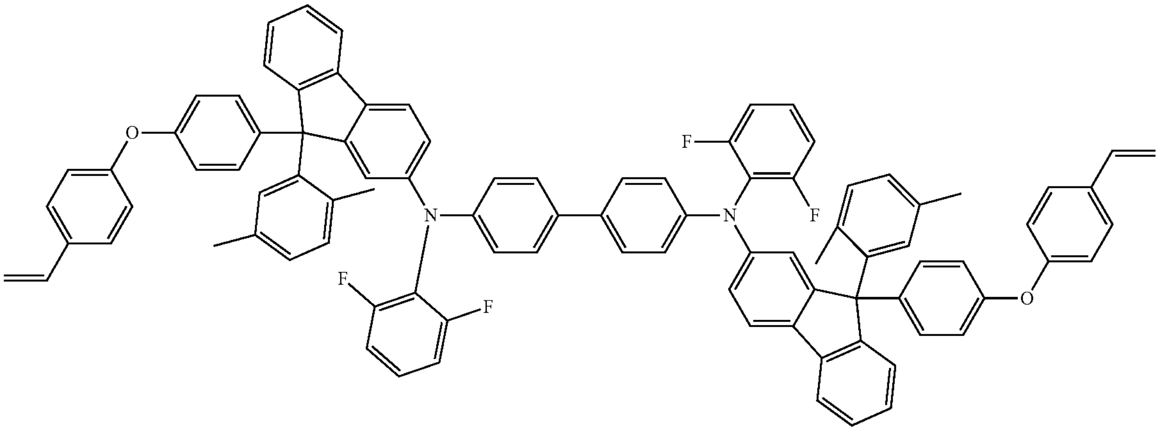 [SMILES: C=Cc1ccc(Oc2ccc(C3(c4cc(C)ccc4C)c4ccccc4-c4ccc(N(c5ccc(-c6ccc(N(c7ccc8c(c7)C(c7ccc(Oc9ccc(C=C)cc9)cc7)(c7cc(C)ccc7C)c7ccccc7-8)c7c(F)cccc7F)cc6)cc5)c5c(F)cccc5F)cc43)cc2)cc1]
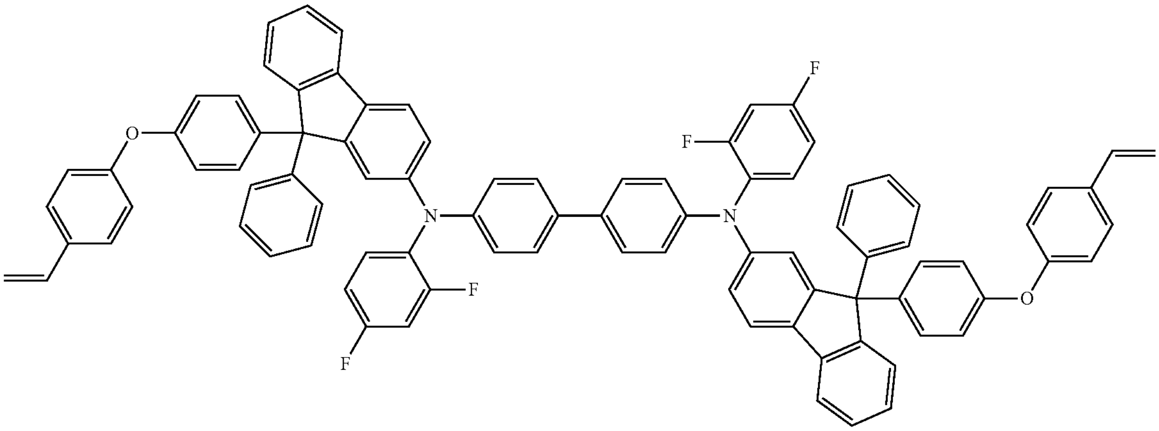

-continued
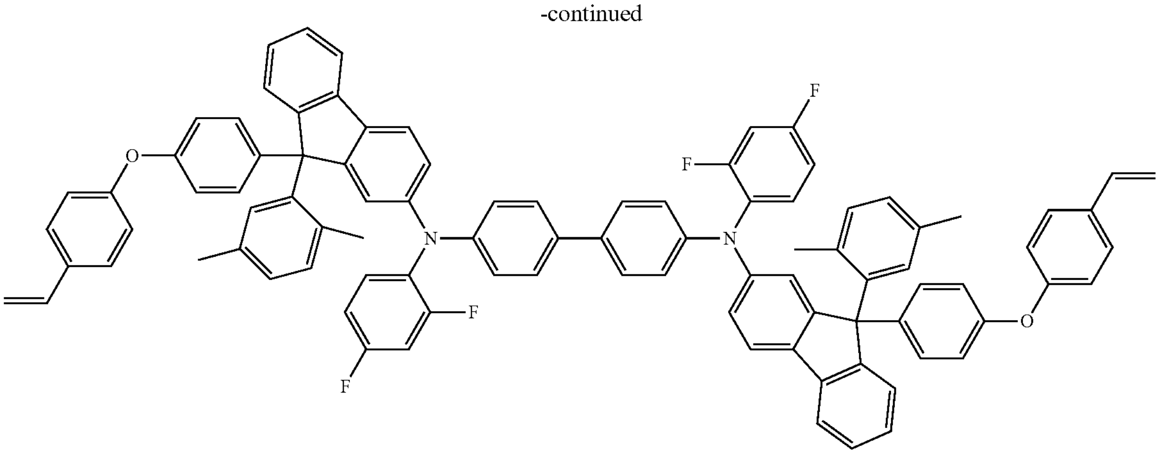
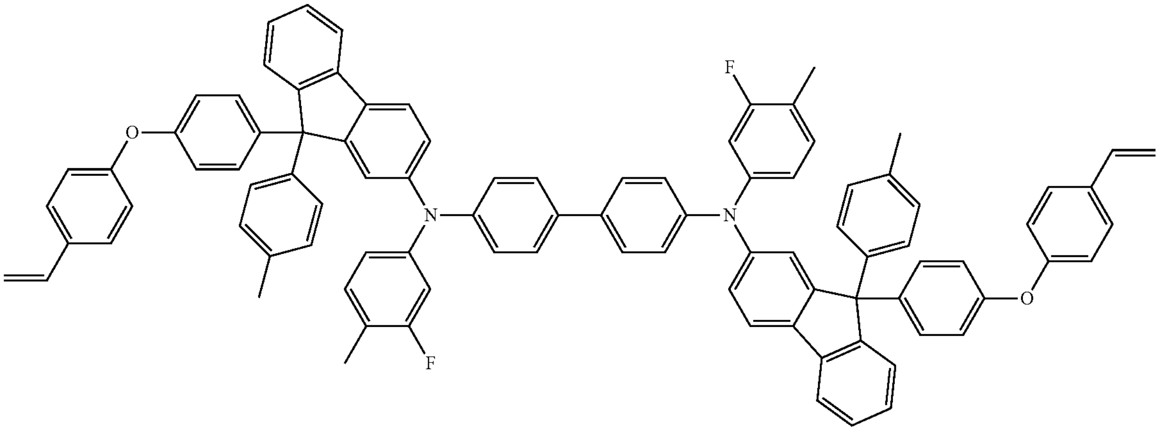
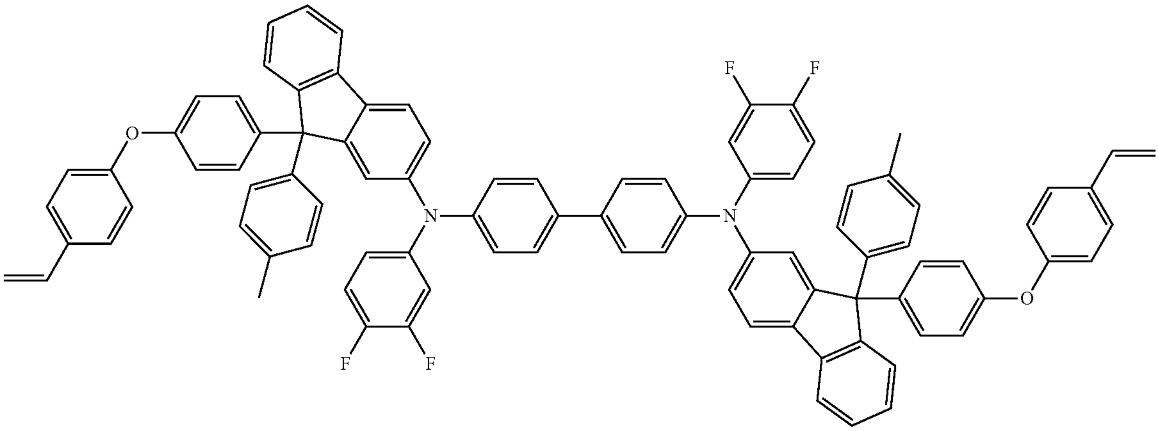
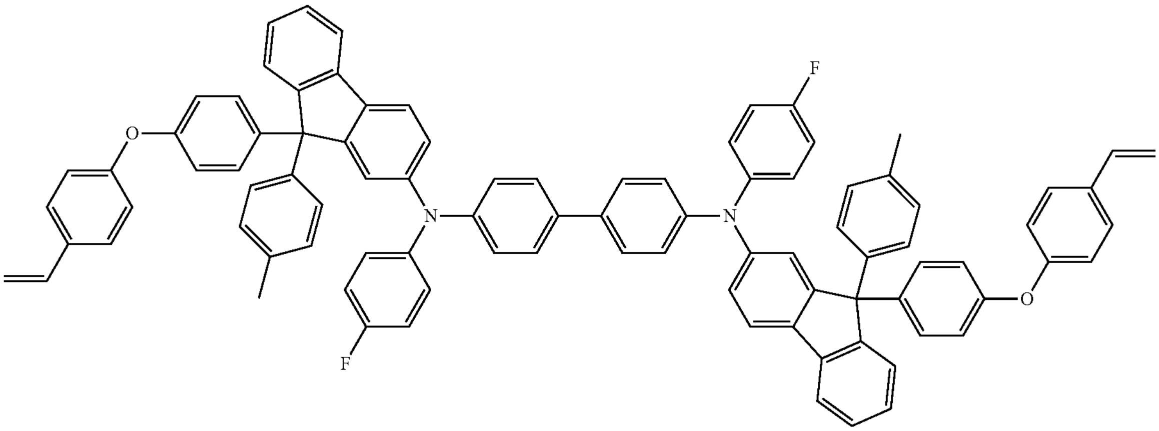

-continued
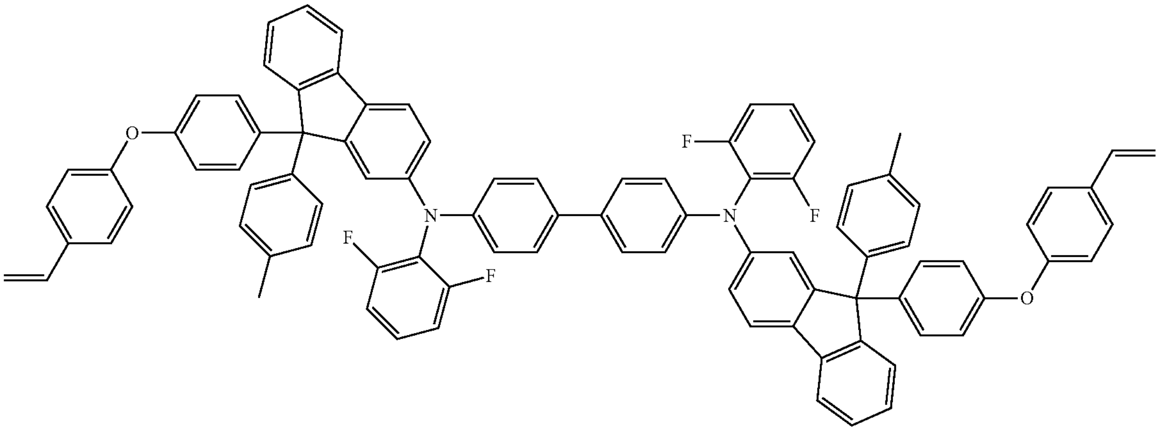
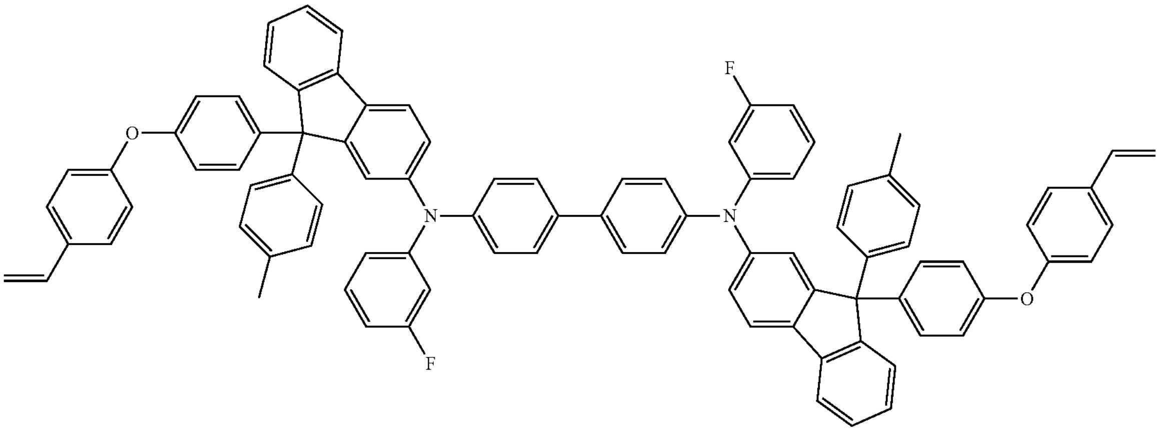
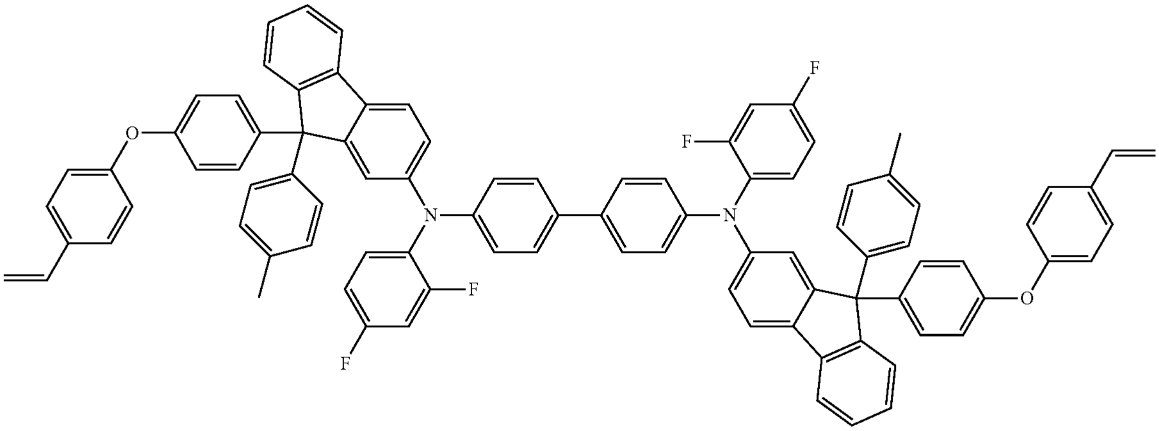
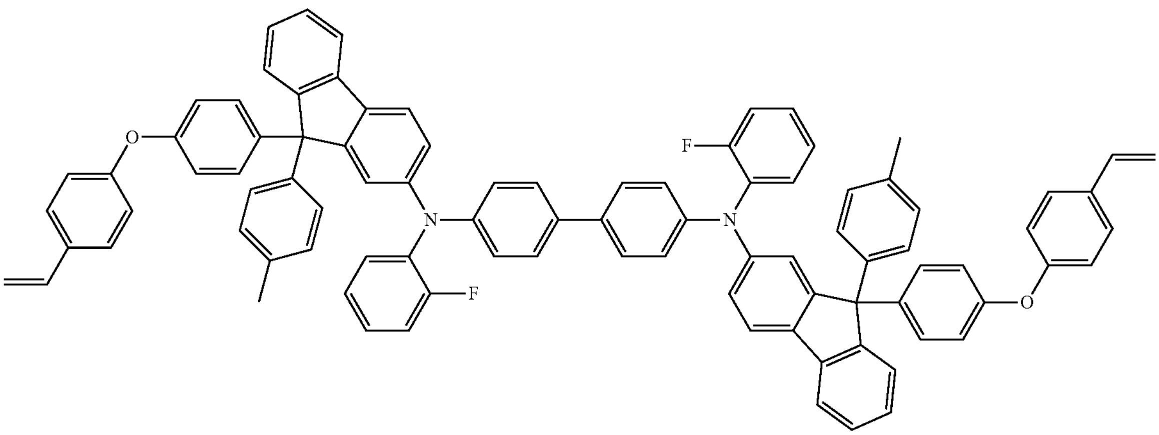

-continued
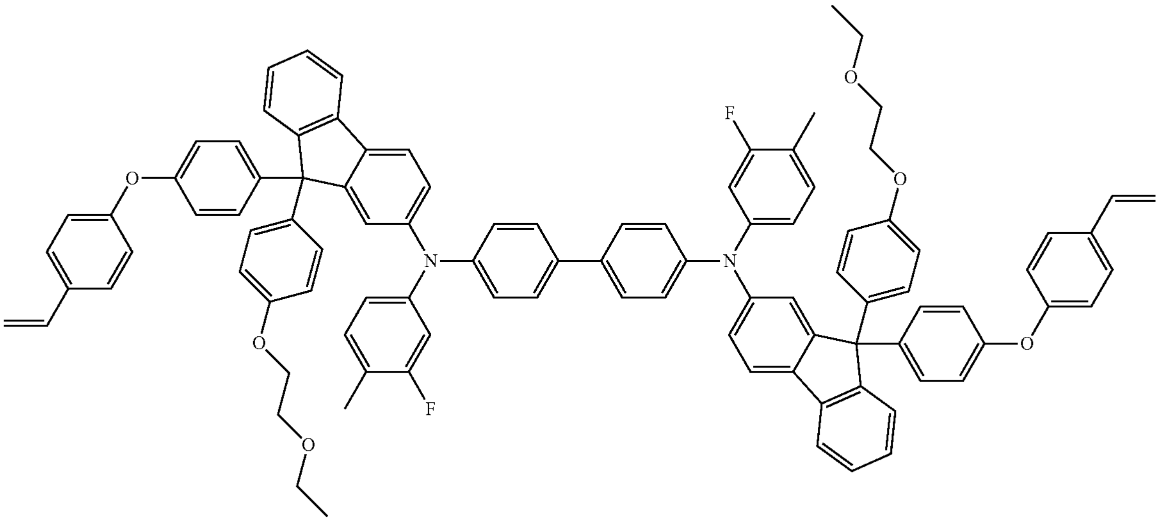
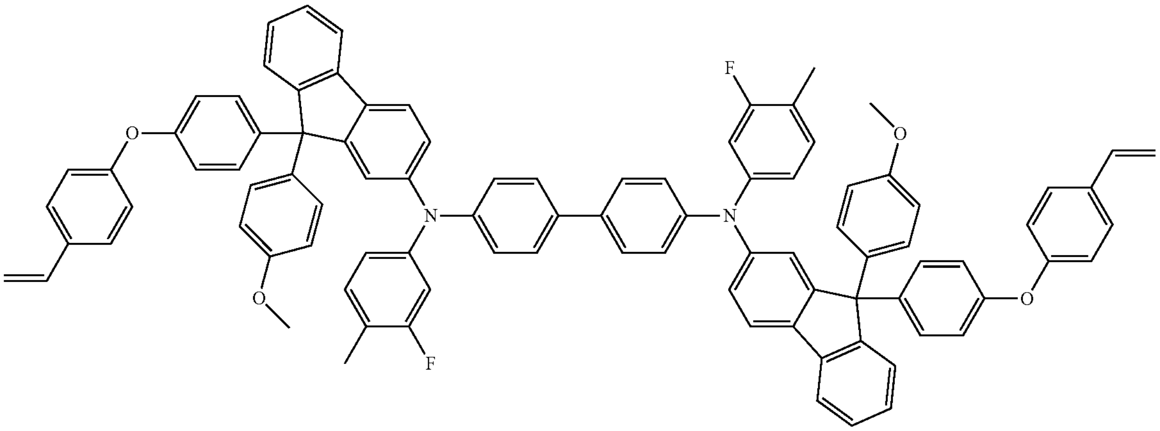
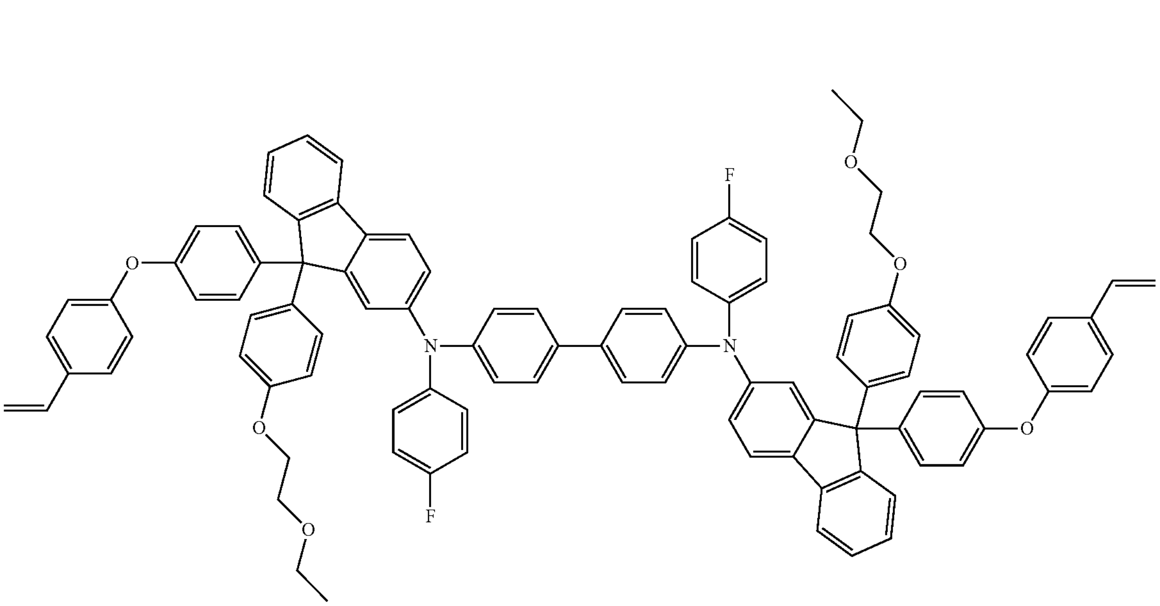

-continued
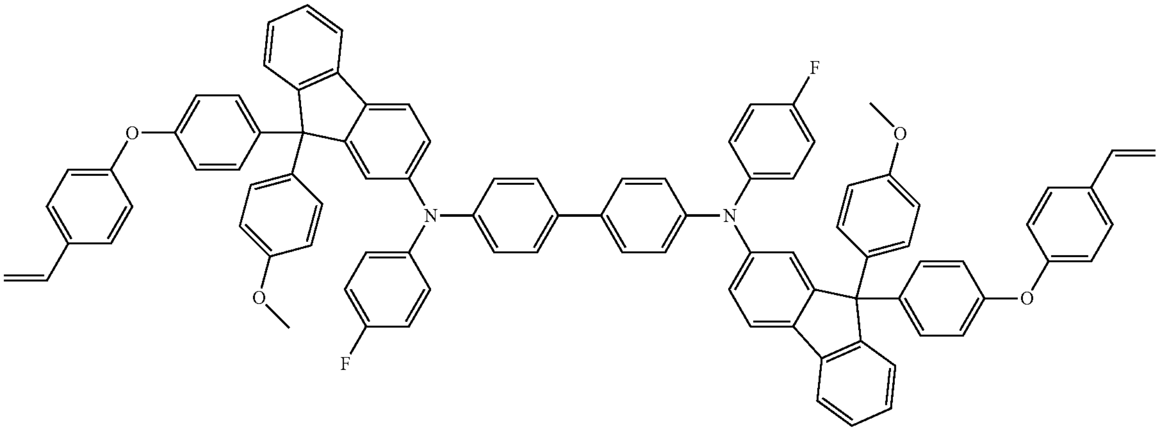
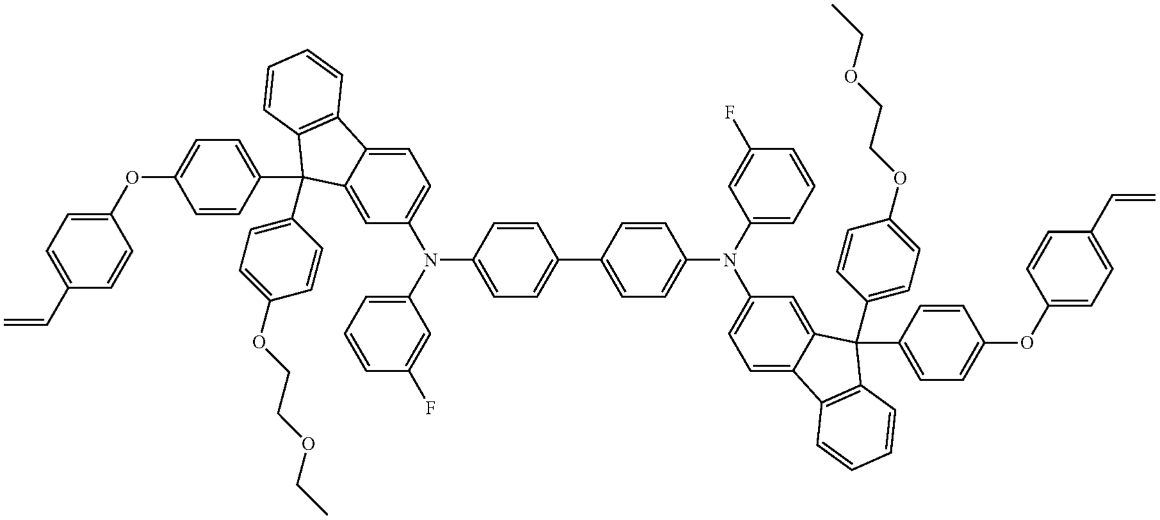
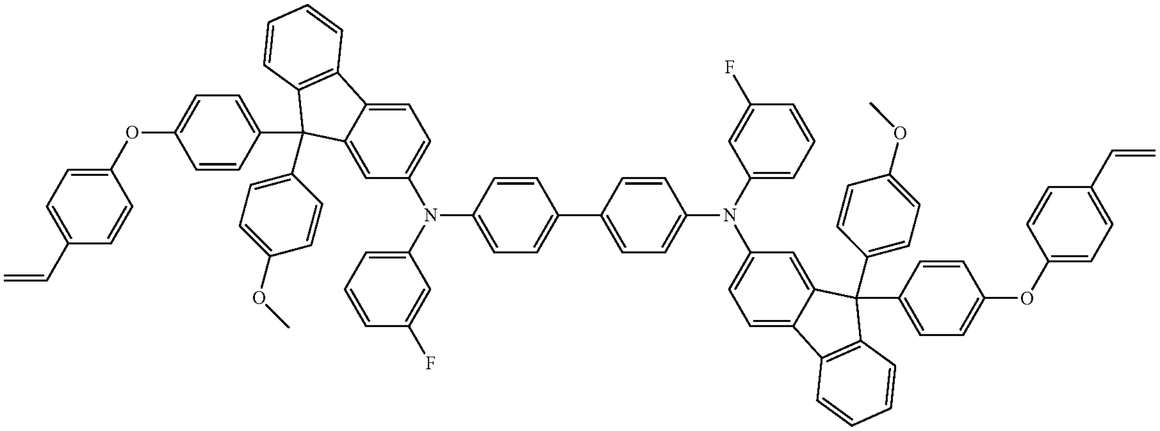

-continued
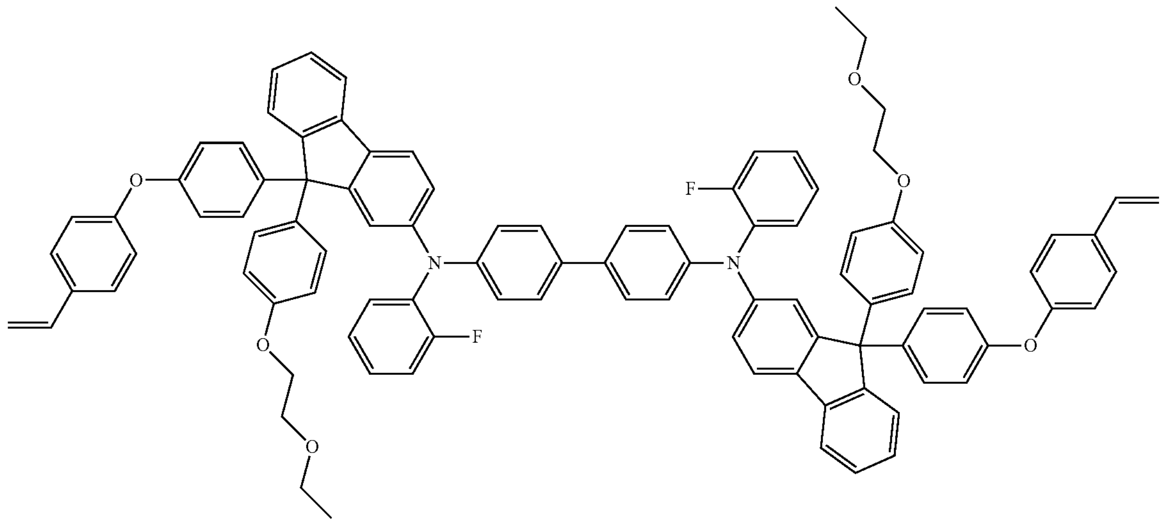
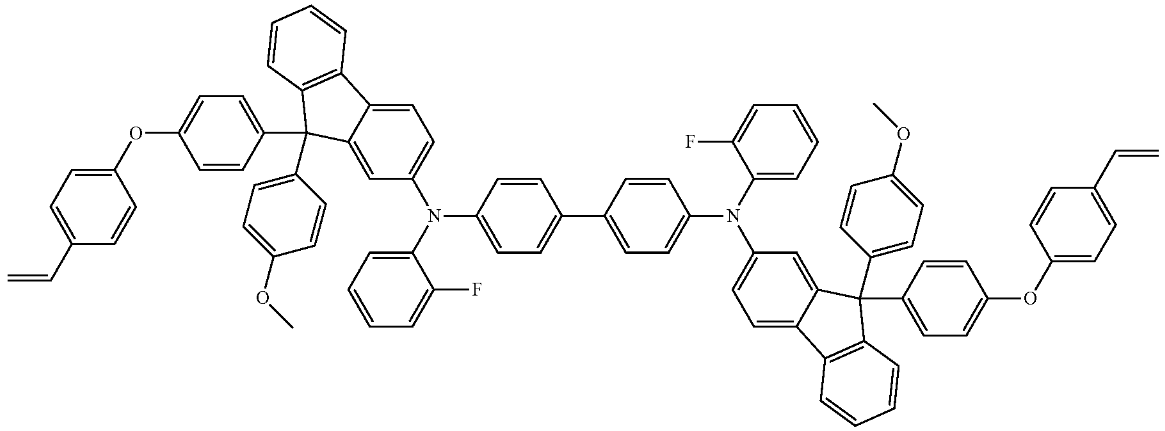
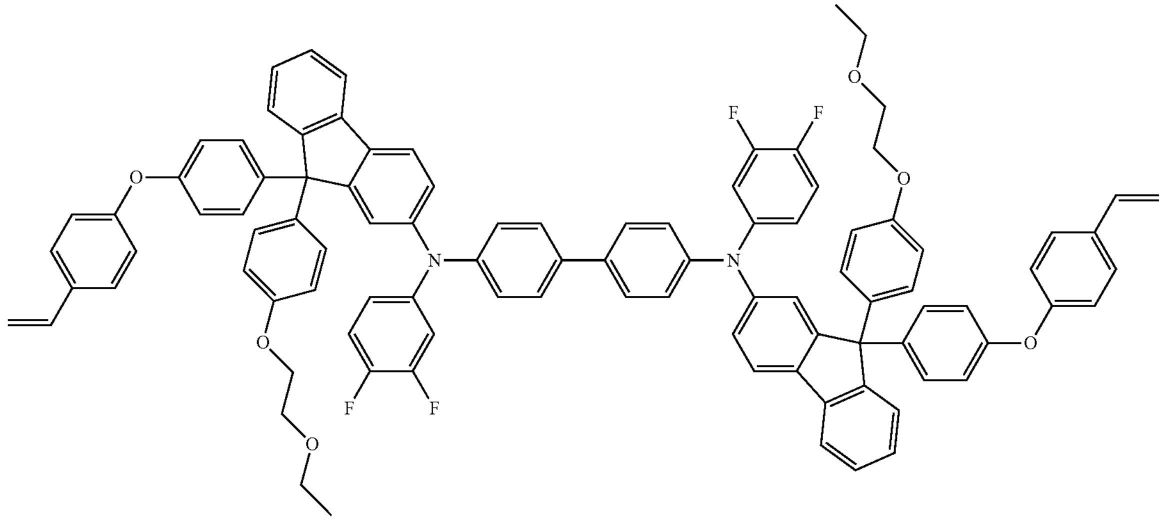

-continued
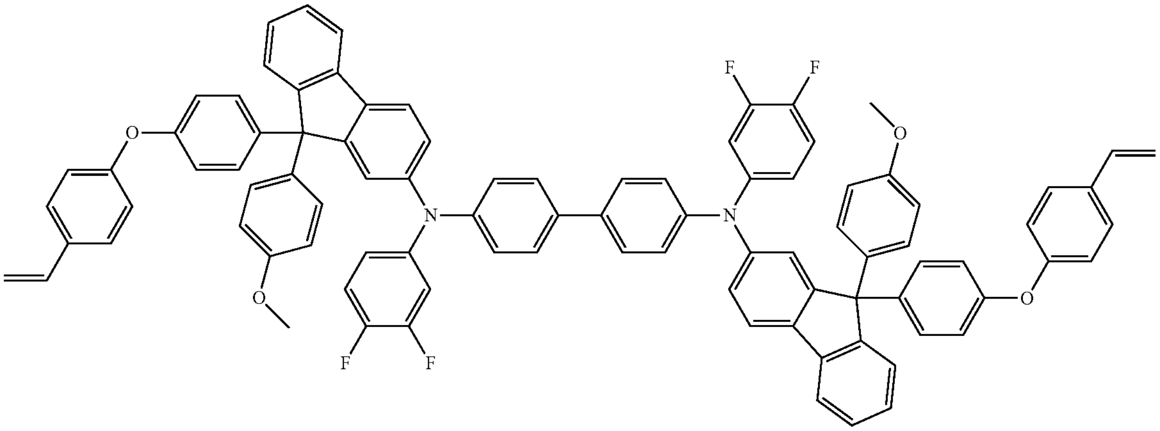
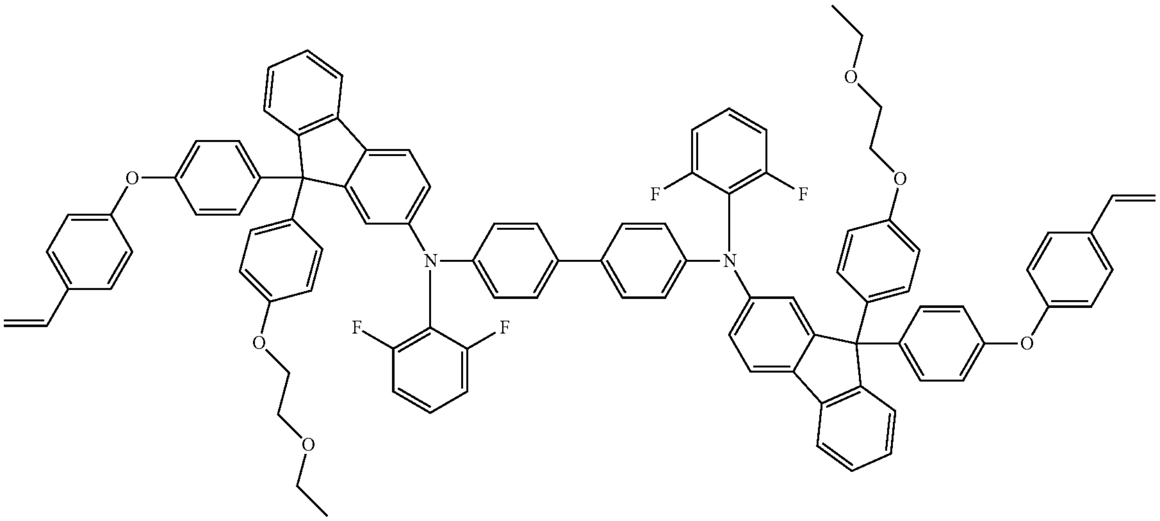
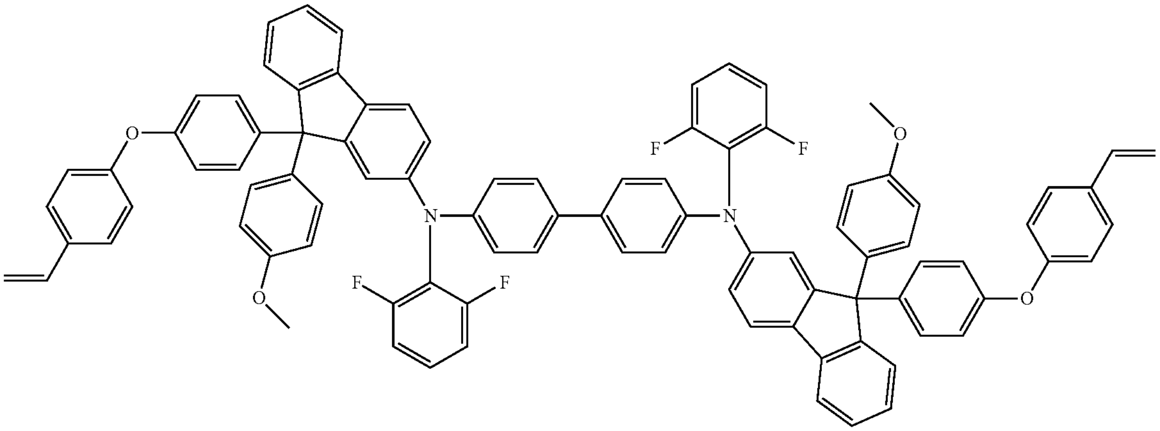

-continued
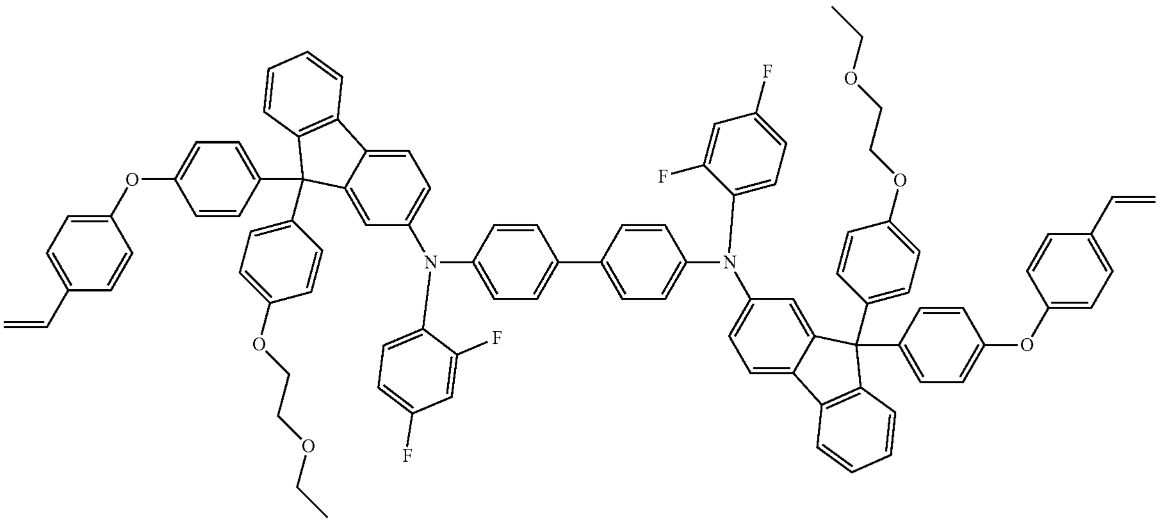
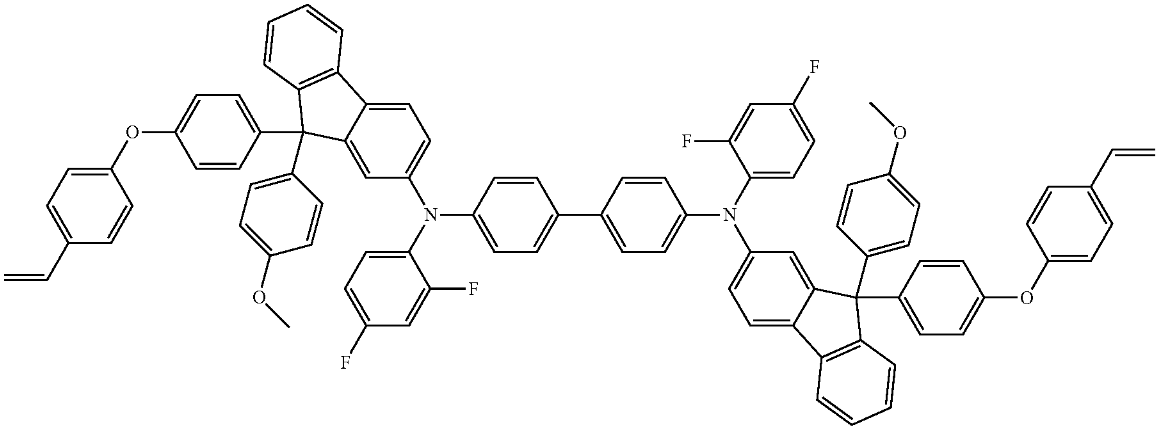
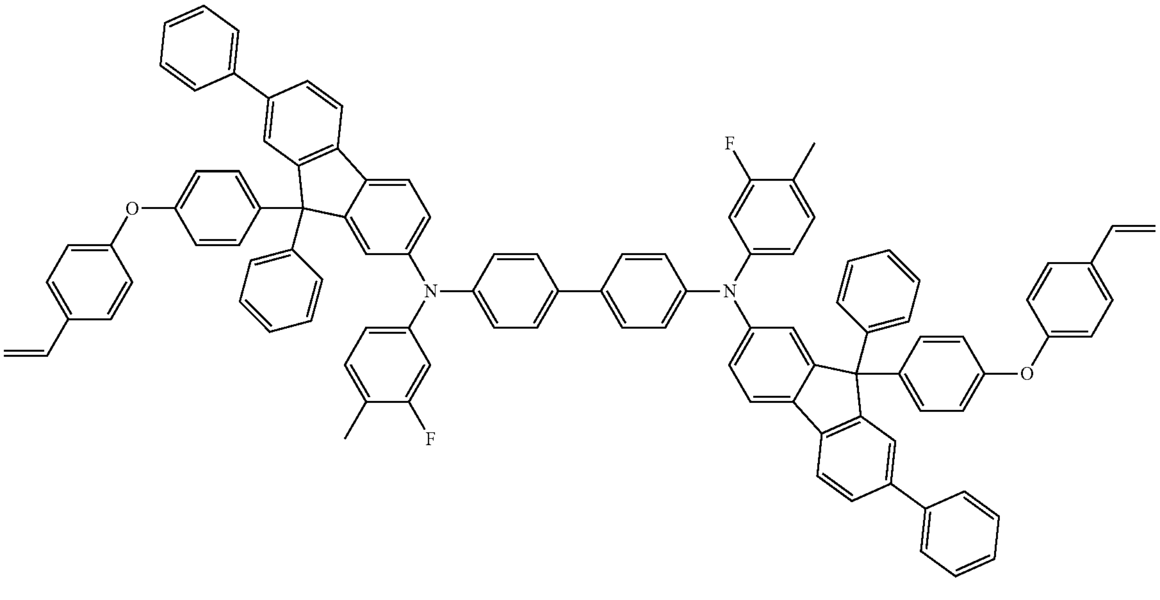

-continued
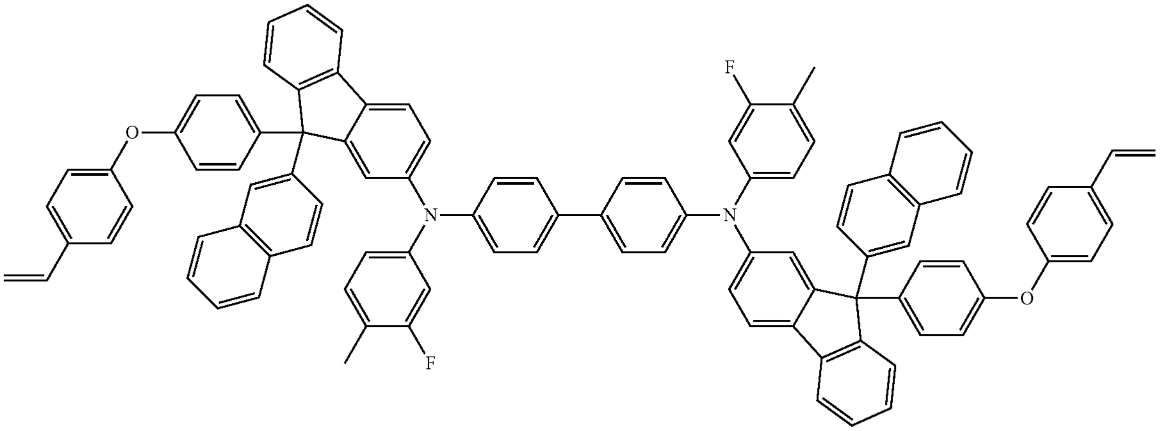
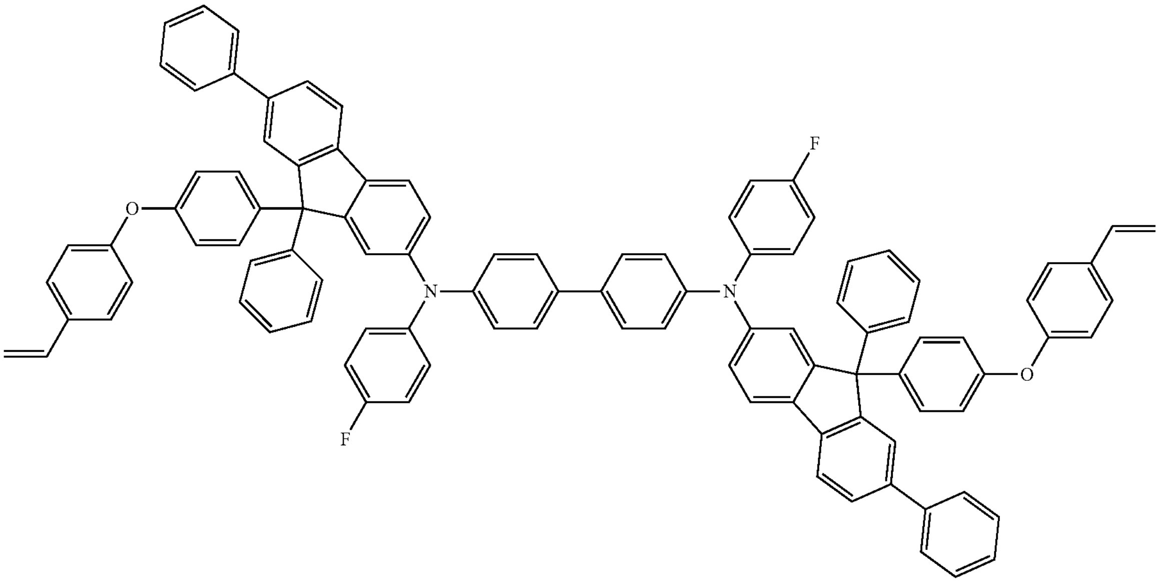
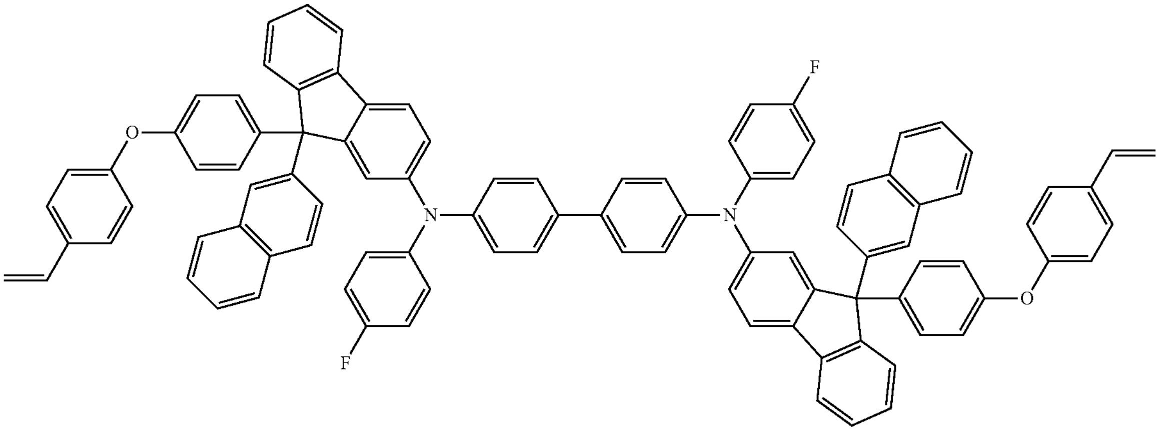

-continued
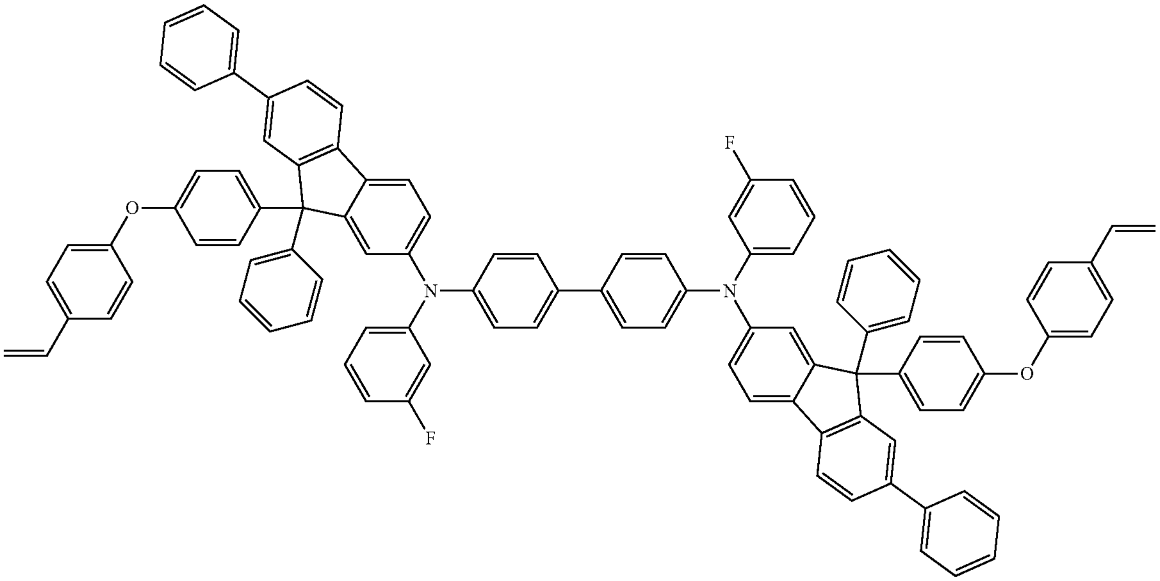
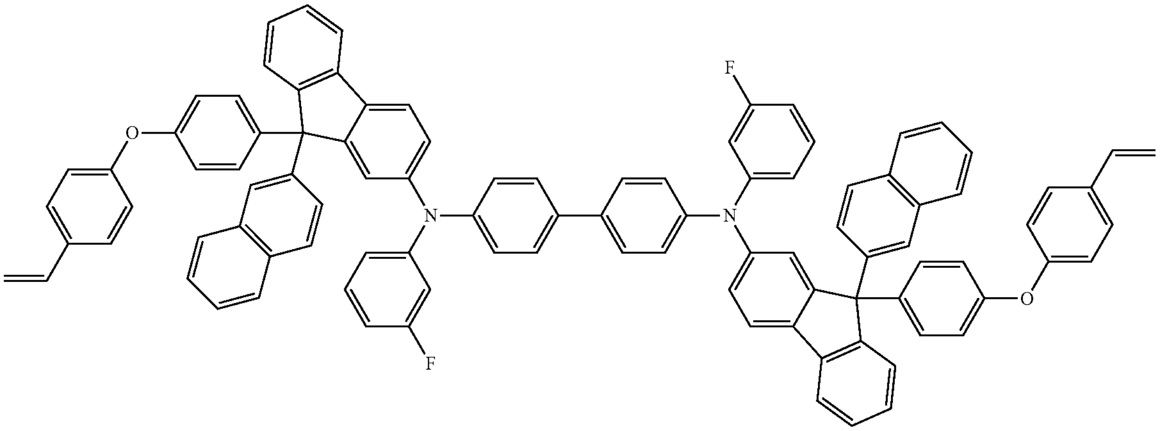
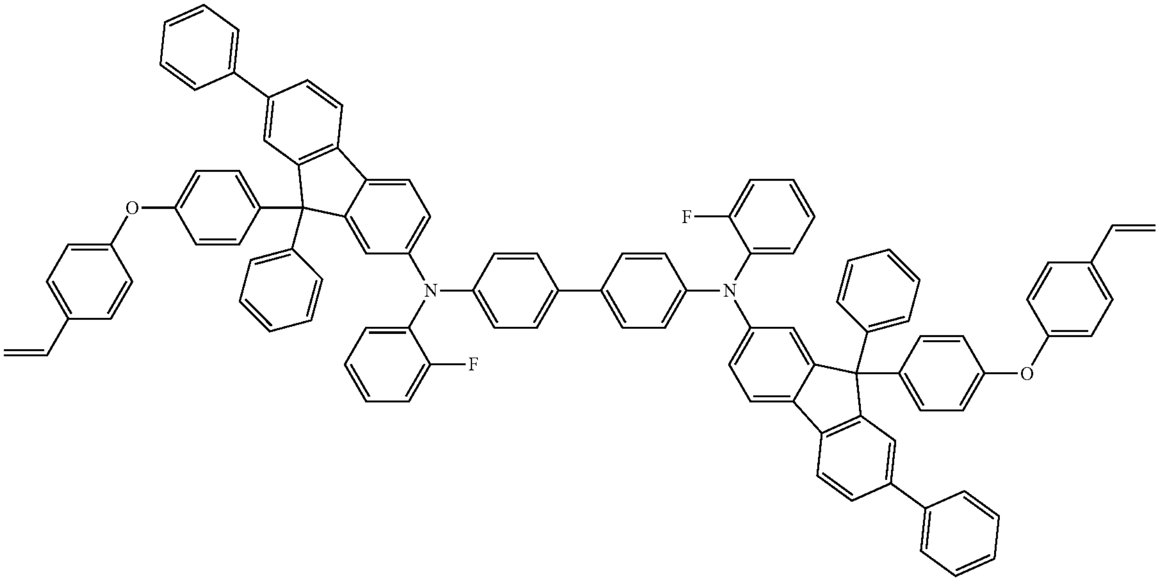

-continued
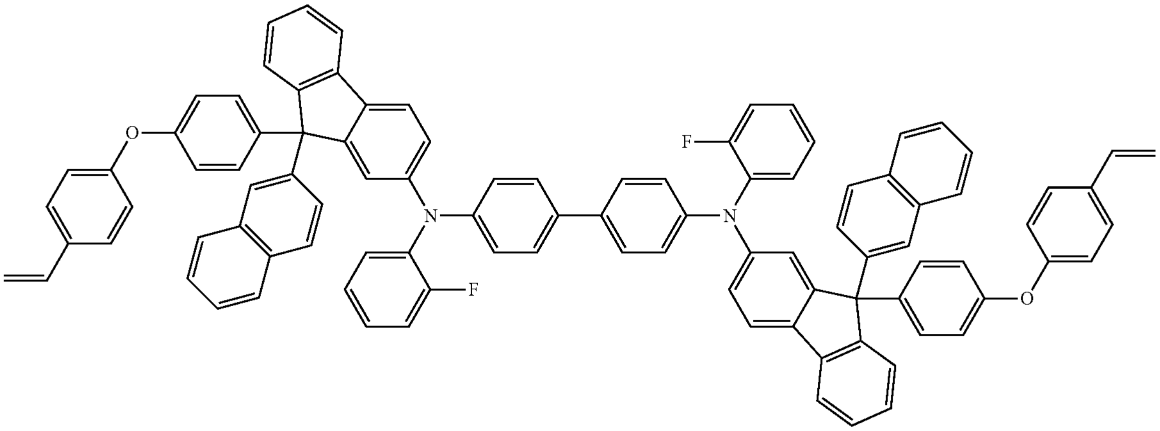
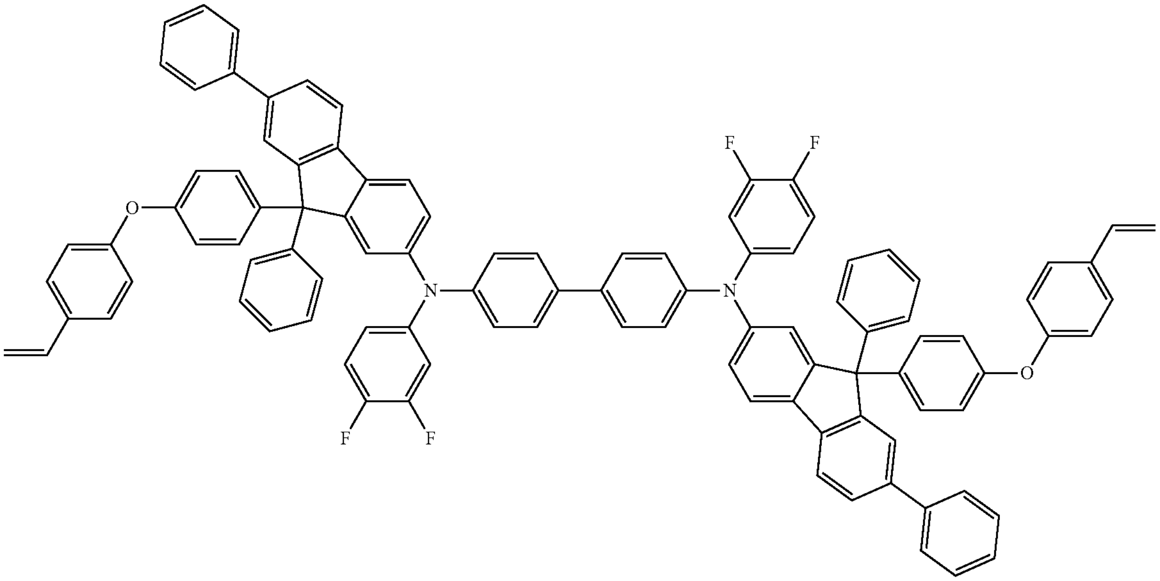
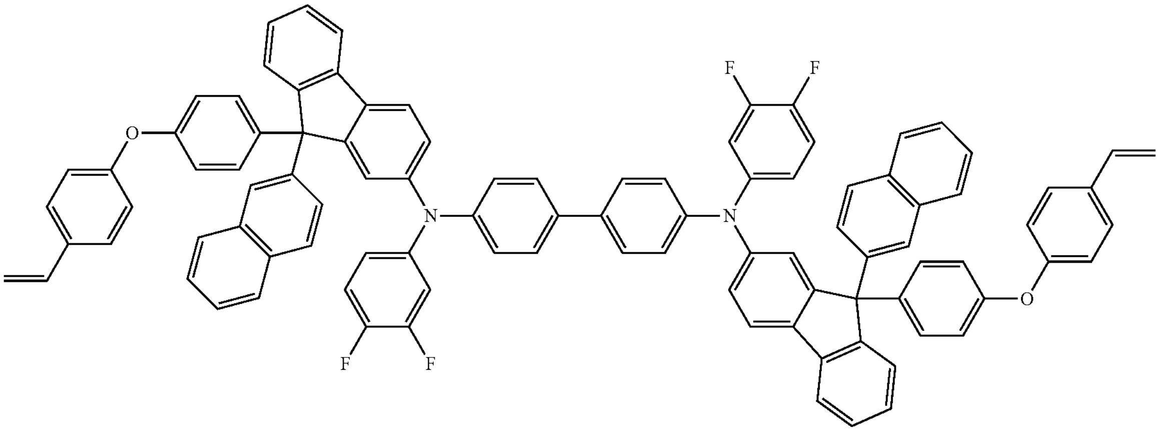

-continued
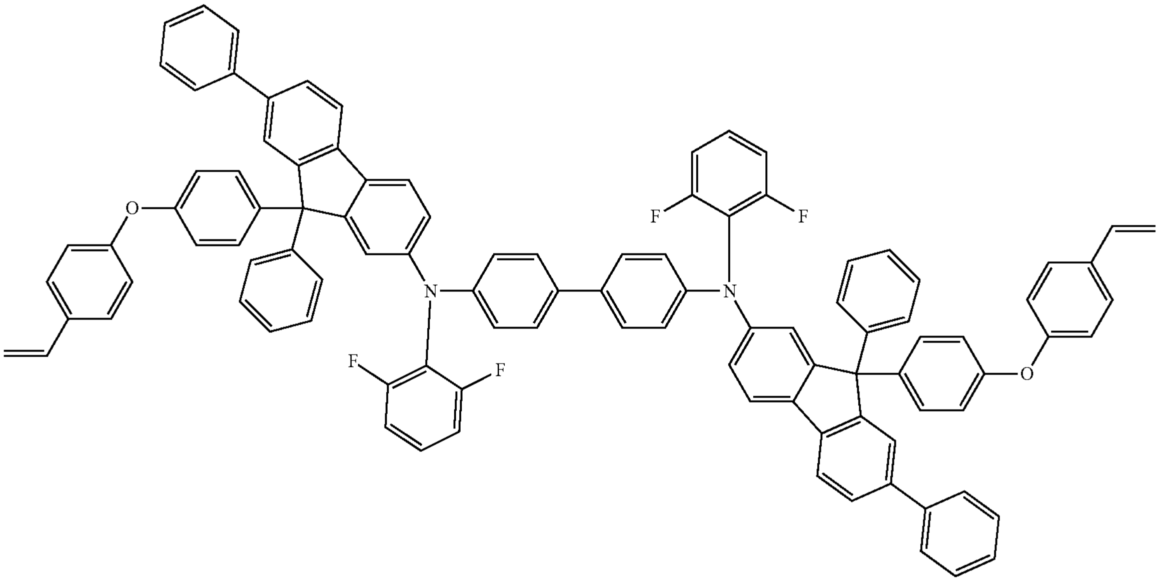
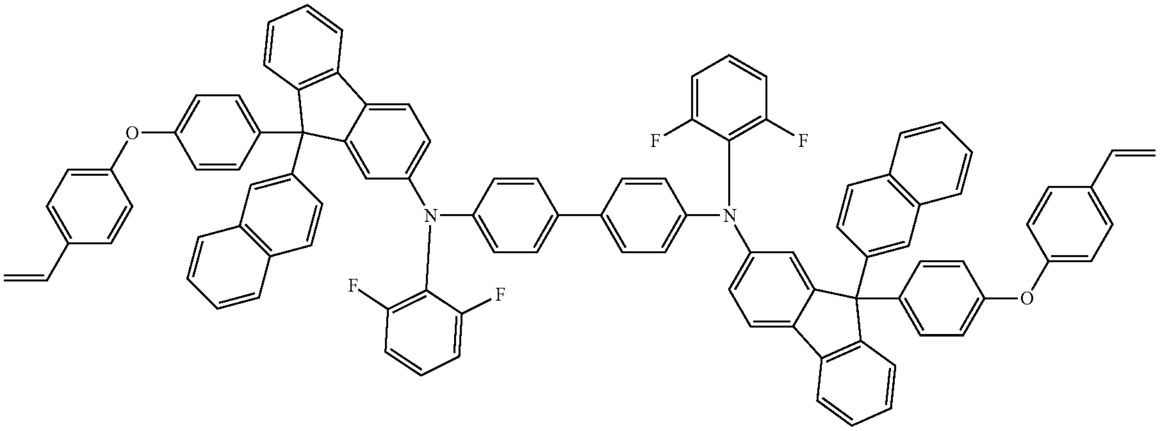
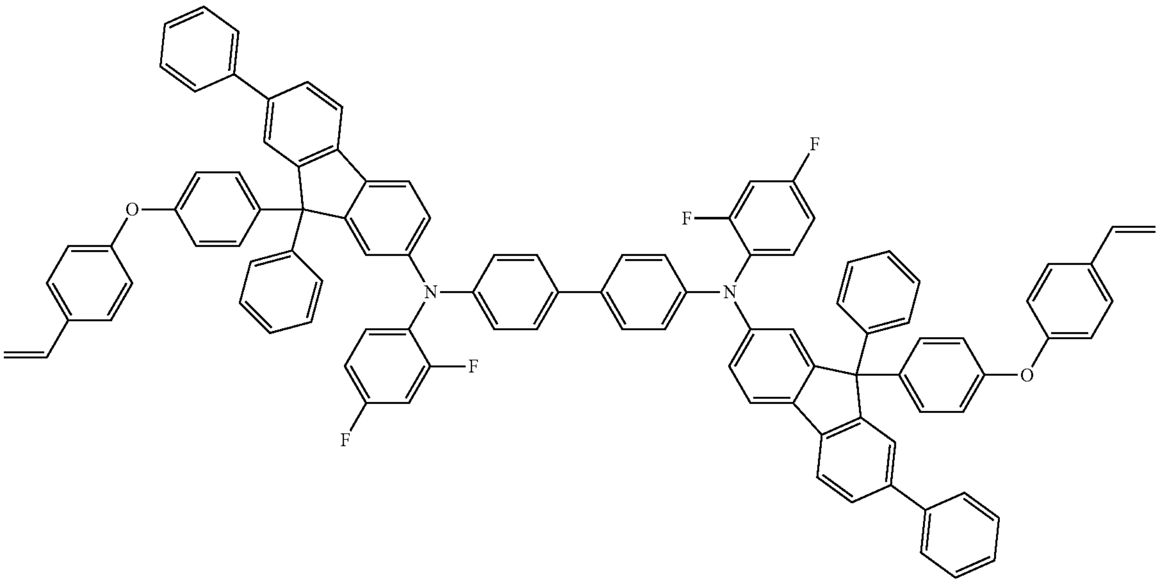

-continued
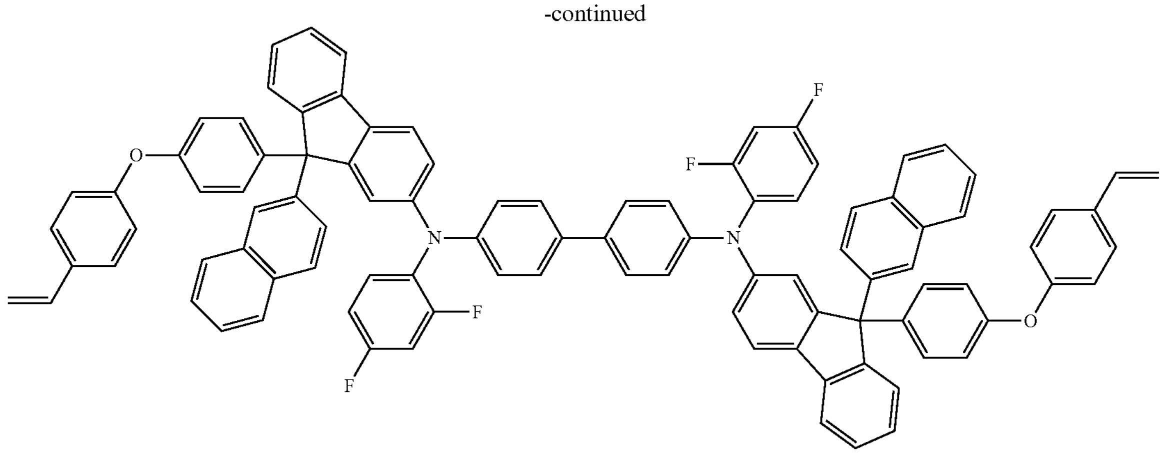
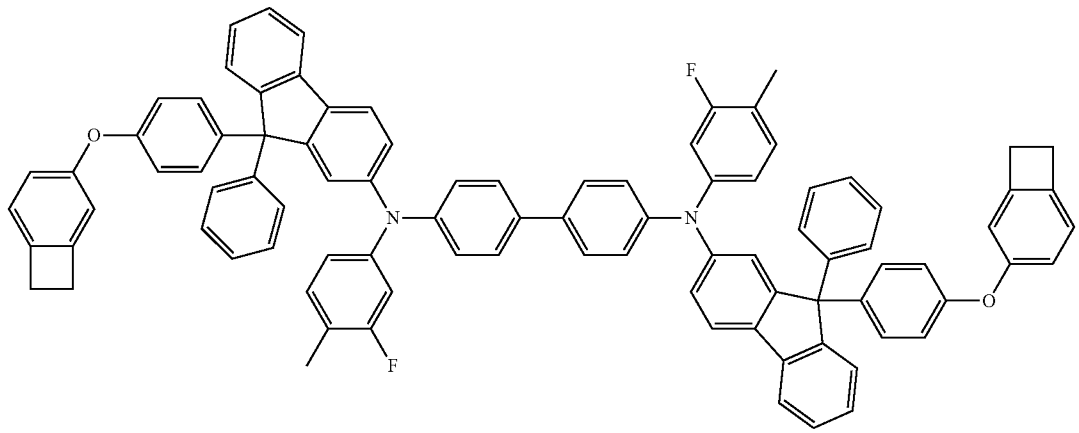
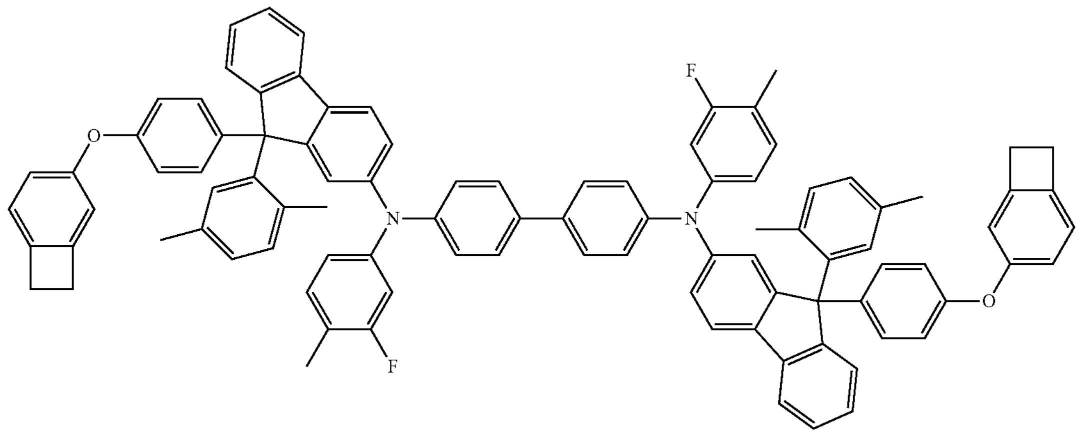
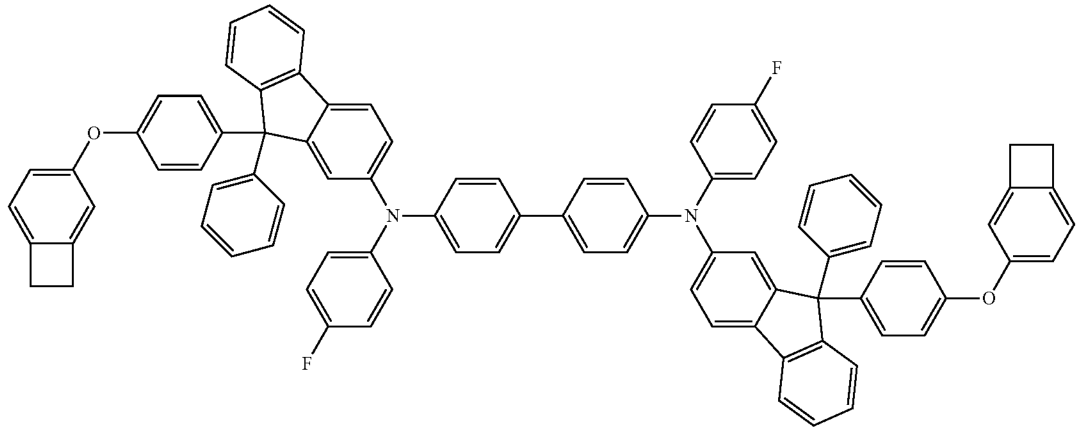

-continued
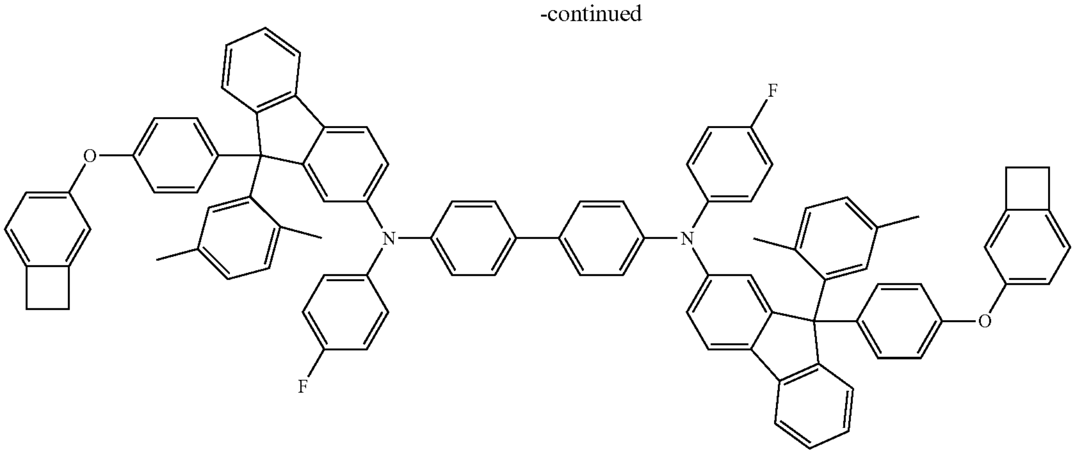
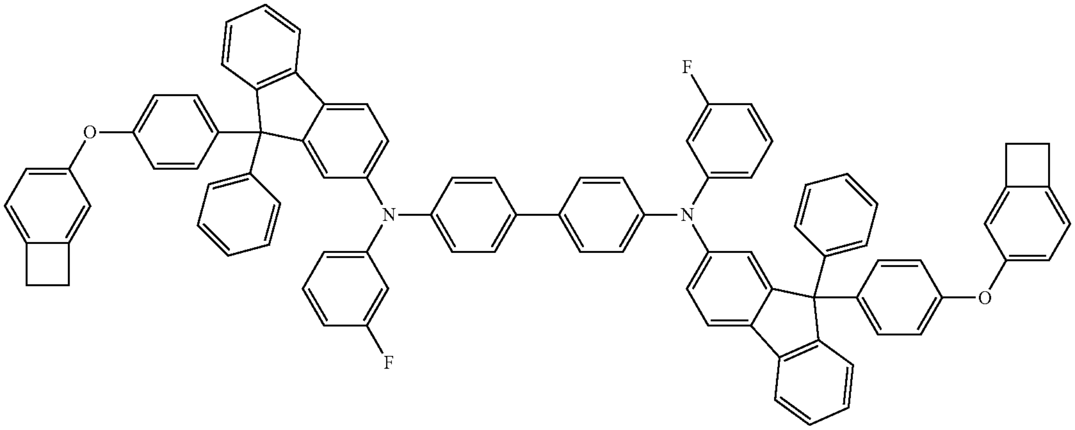
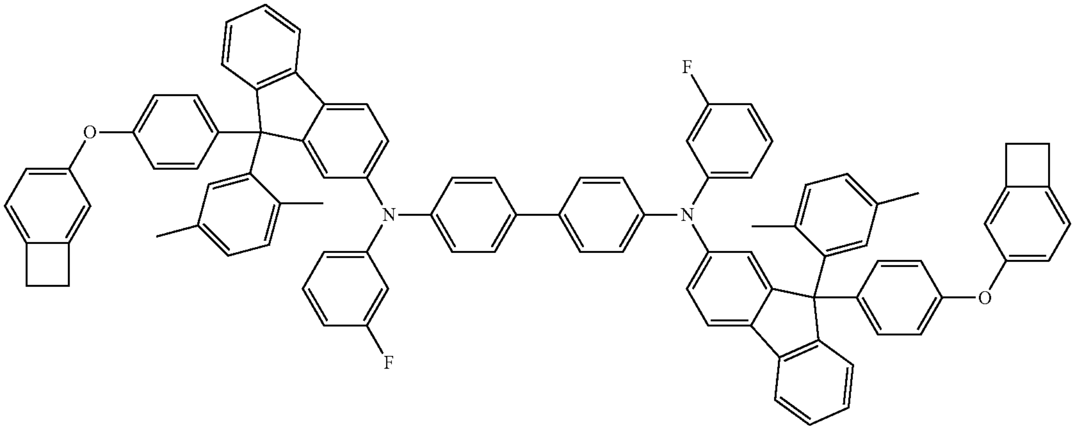
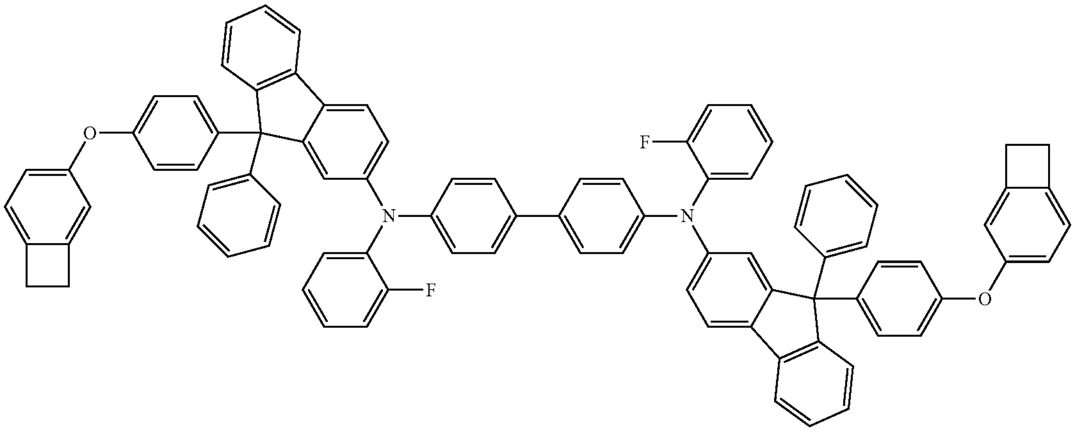

-continued
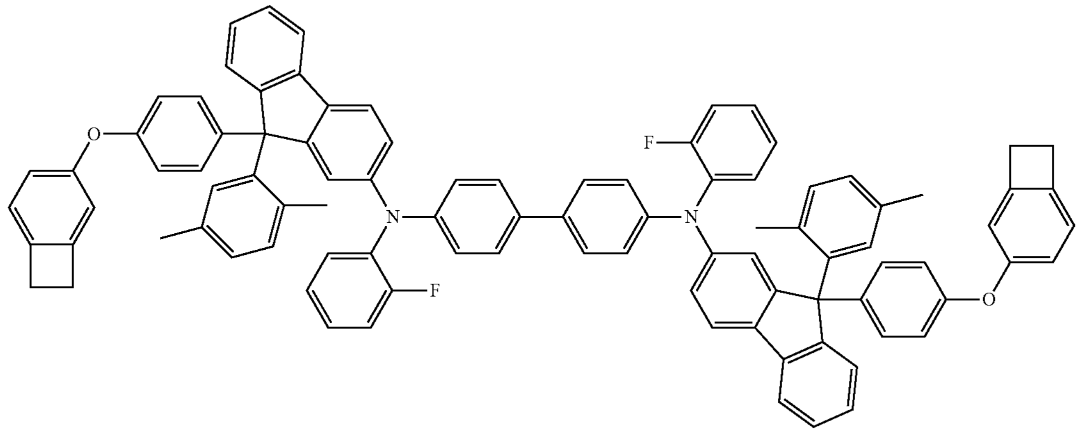
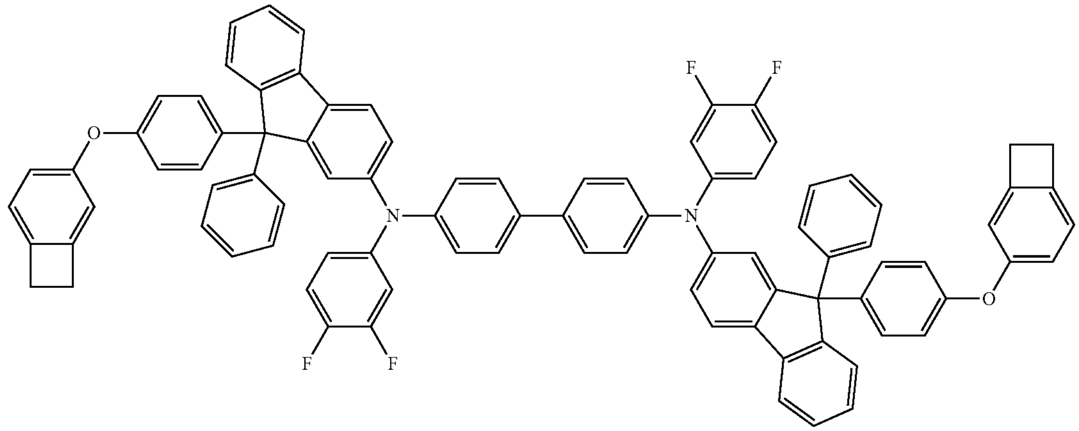
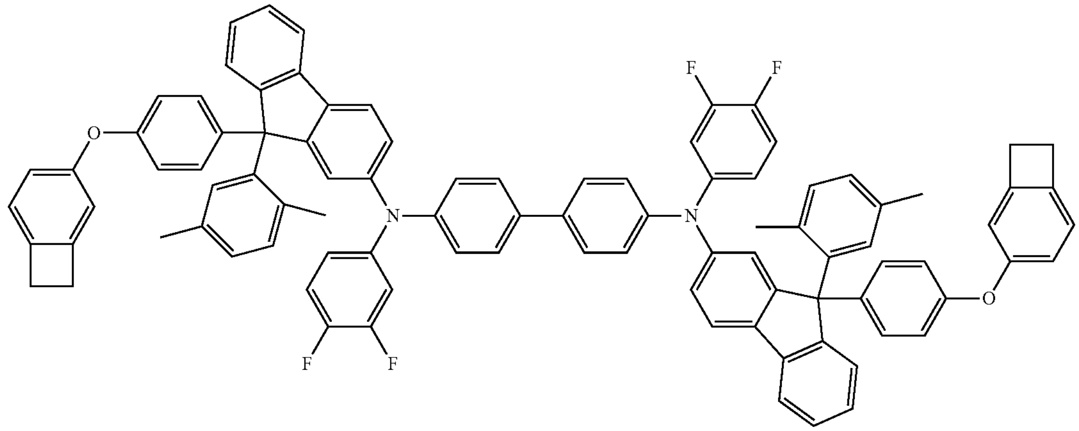
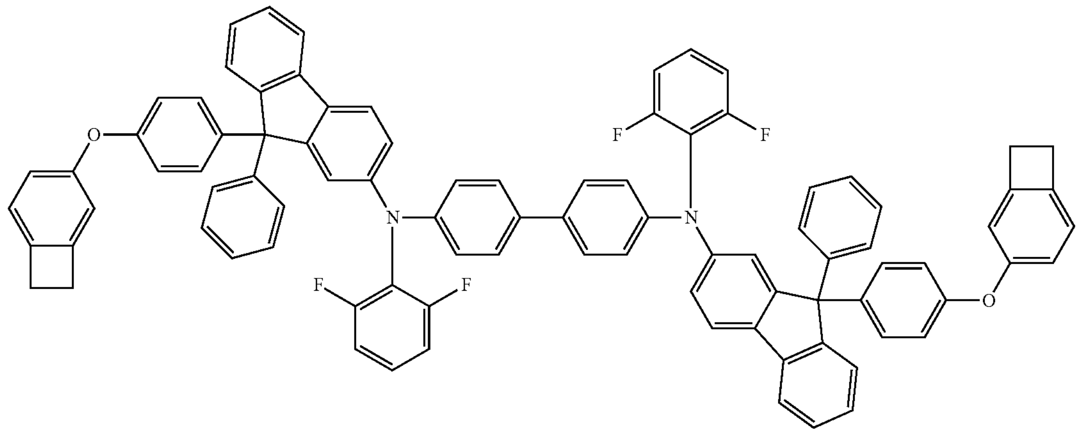

-continued
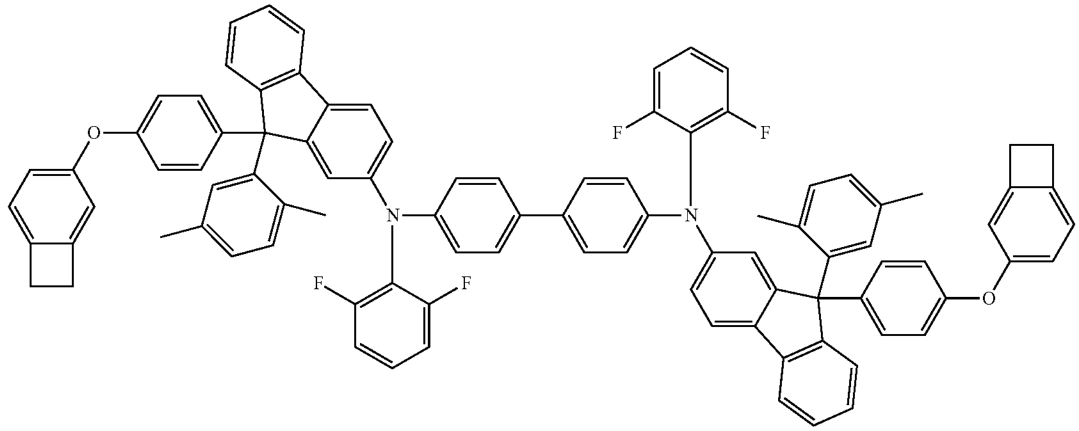
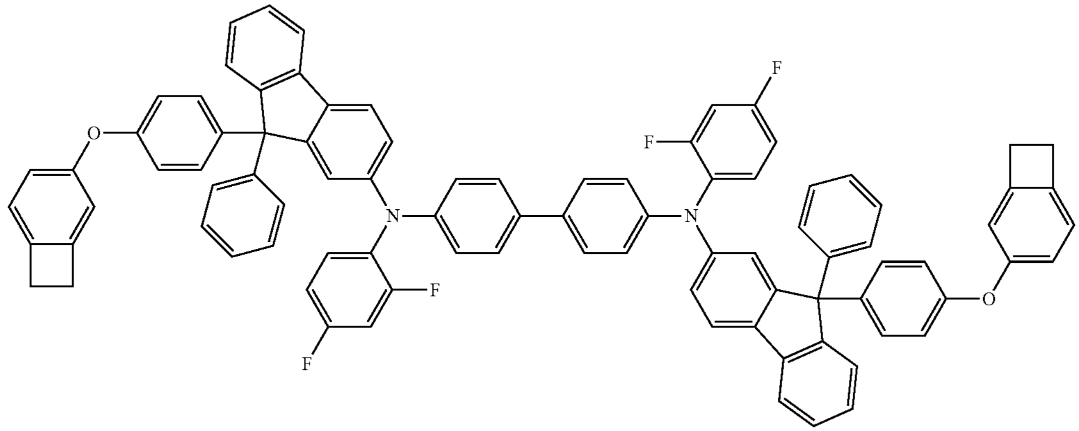
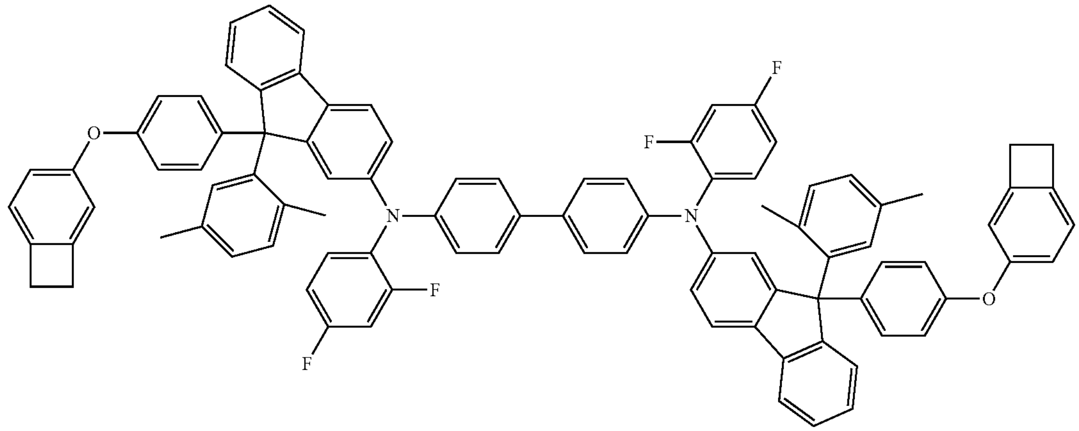
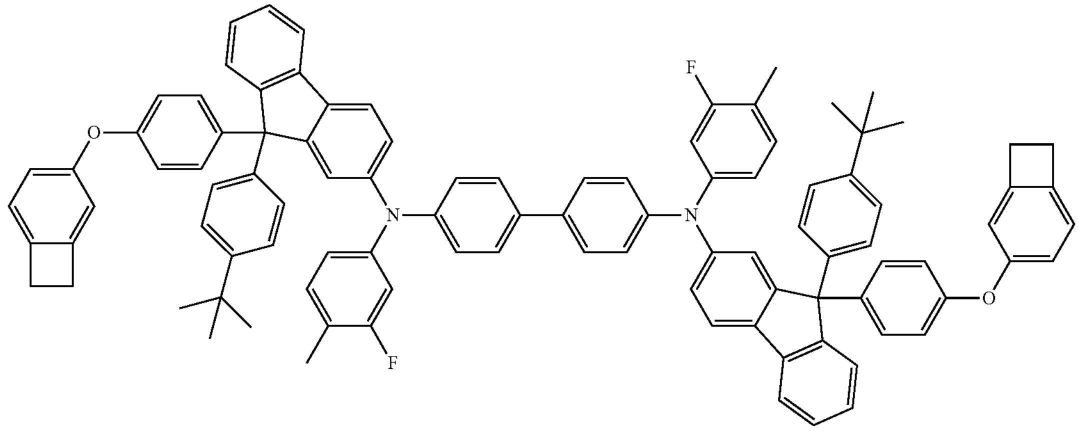

-continued
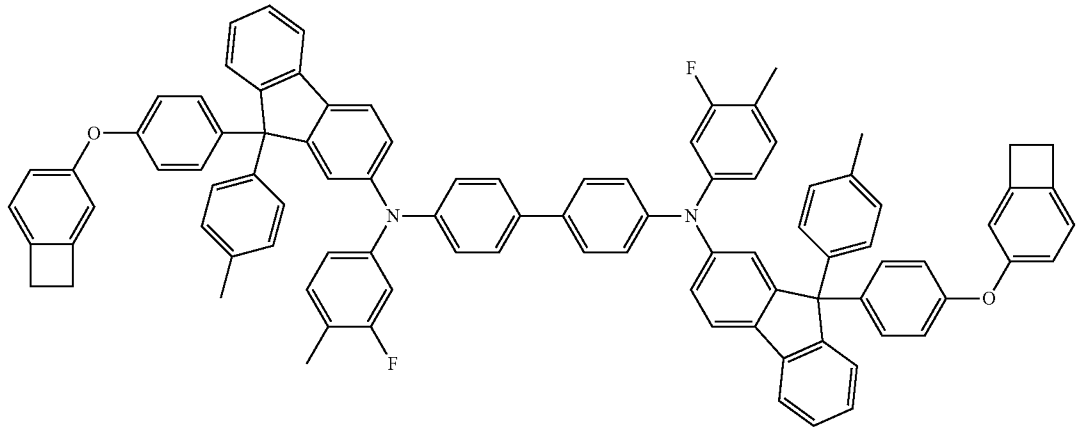
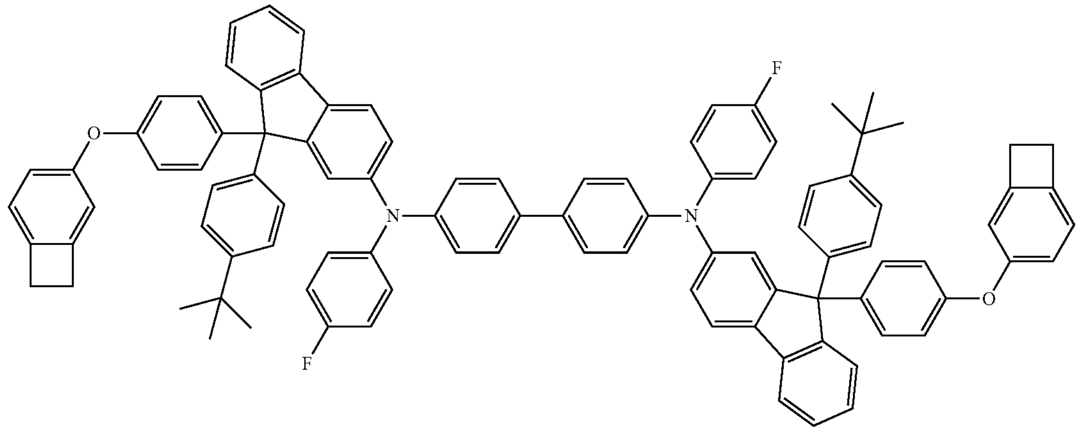
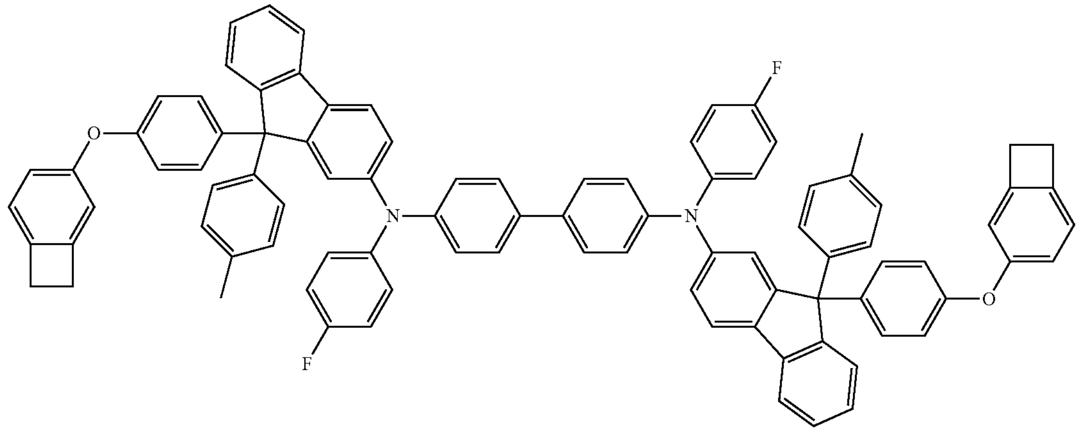
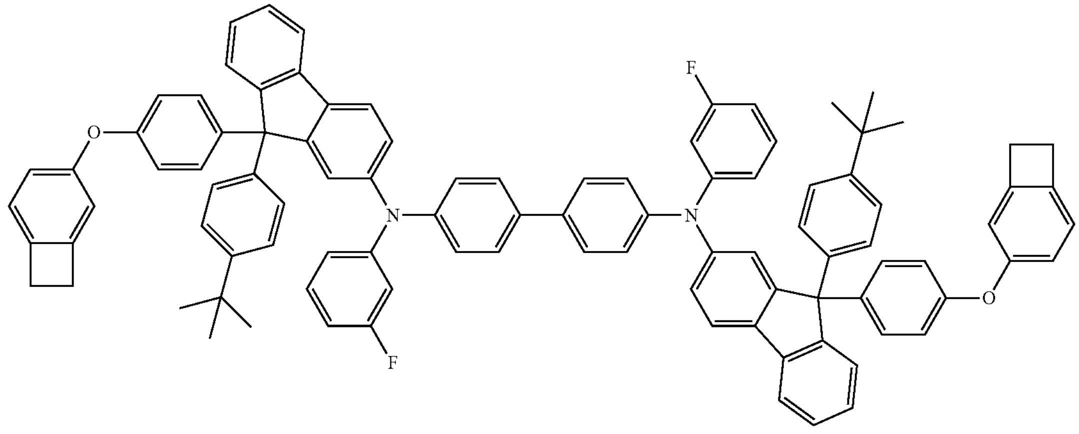

-continued
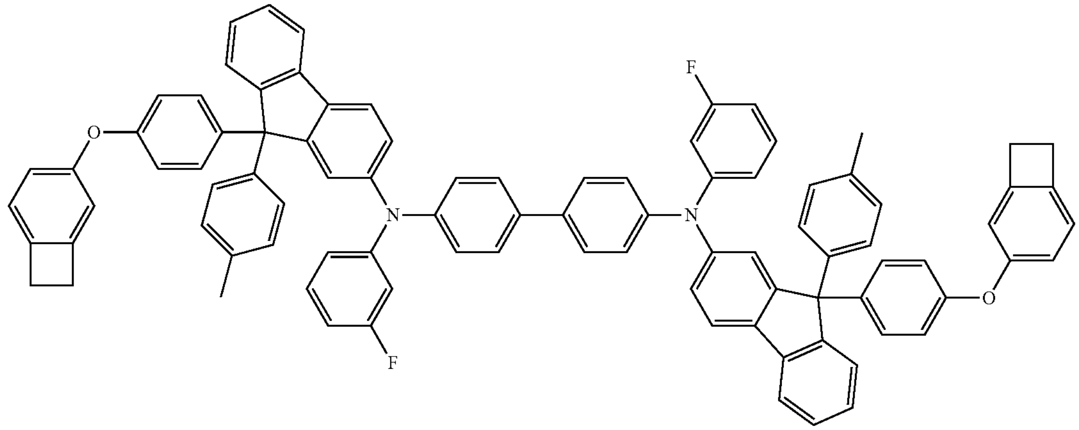
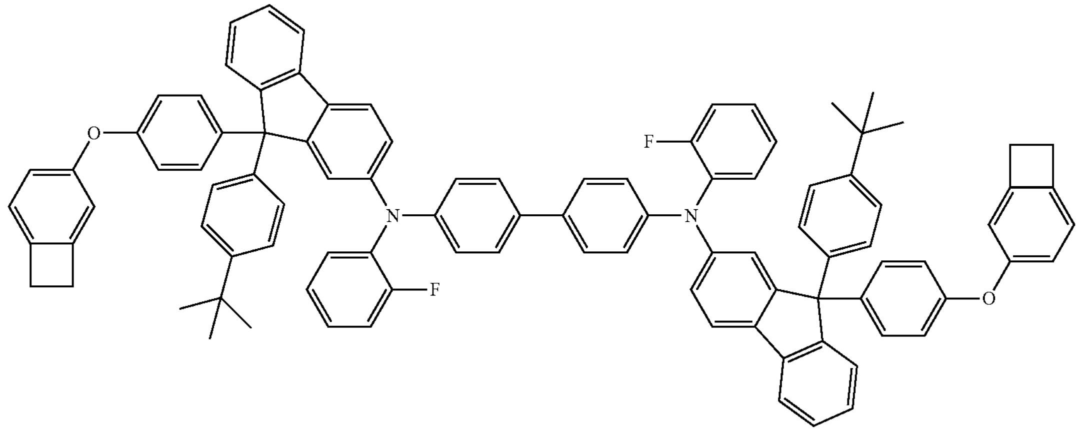
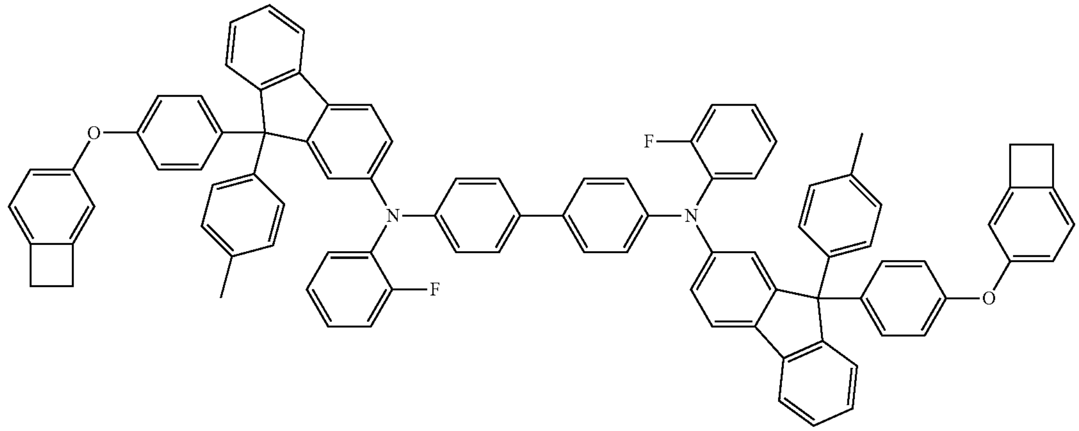
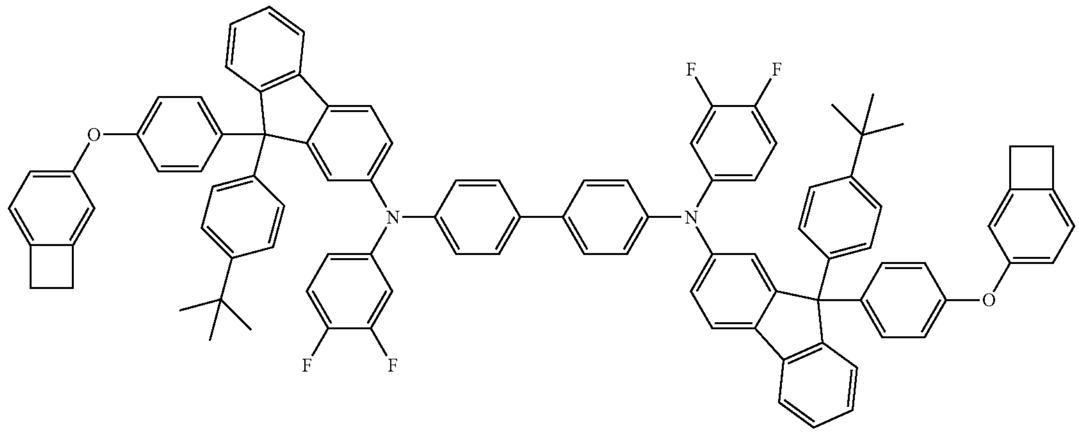

-continued
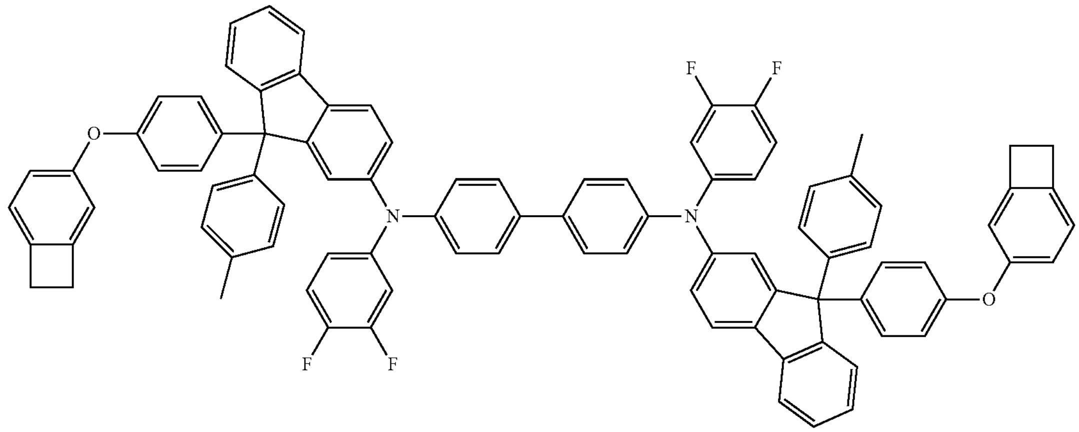
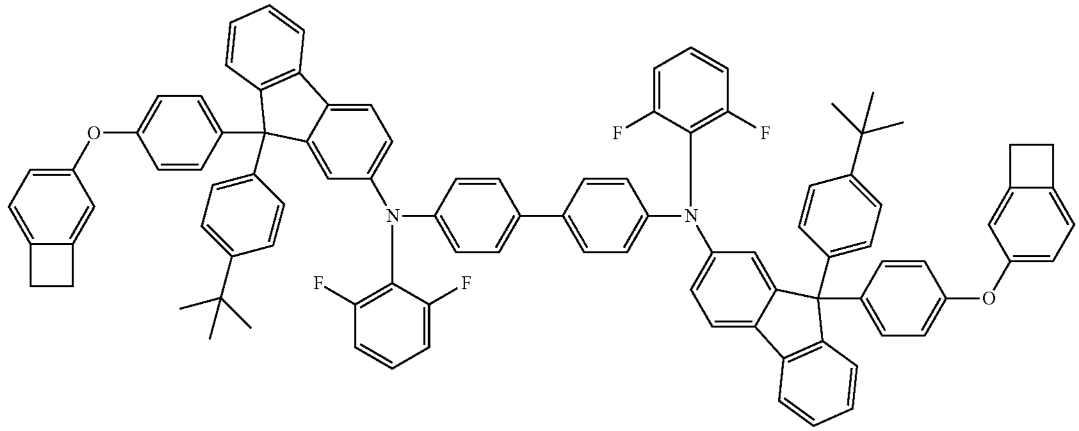
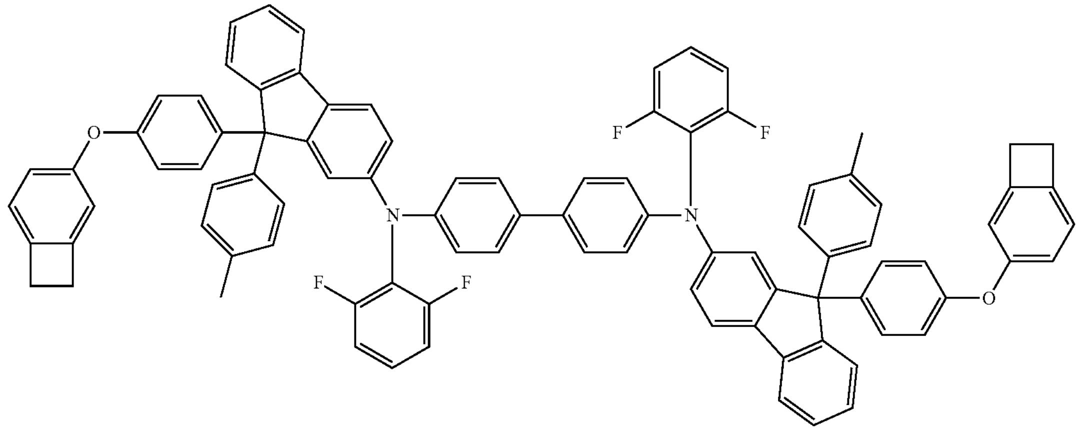
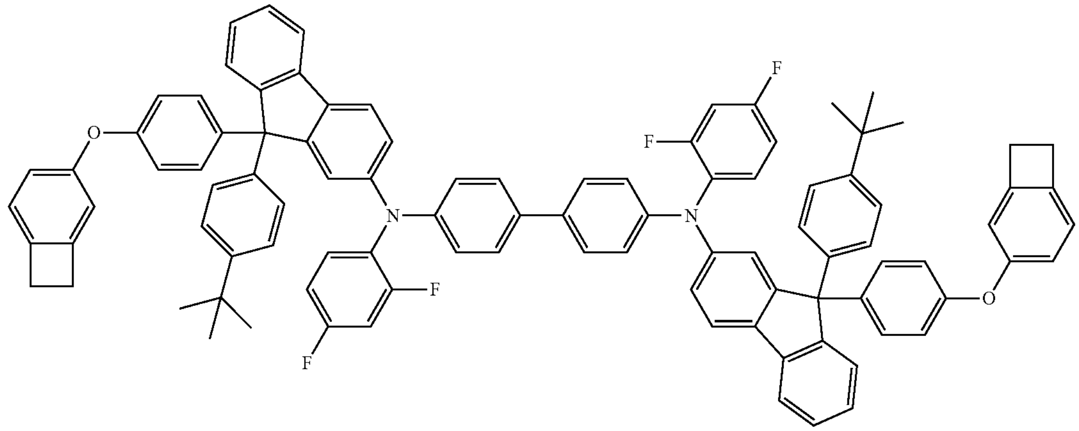

-continued
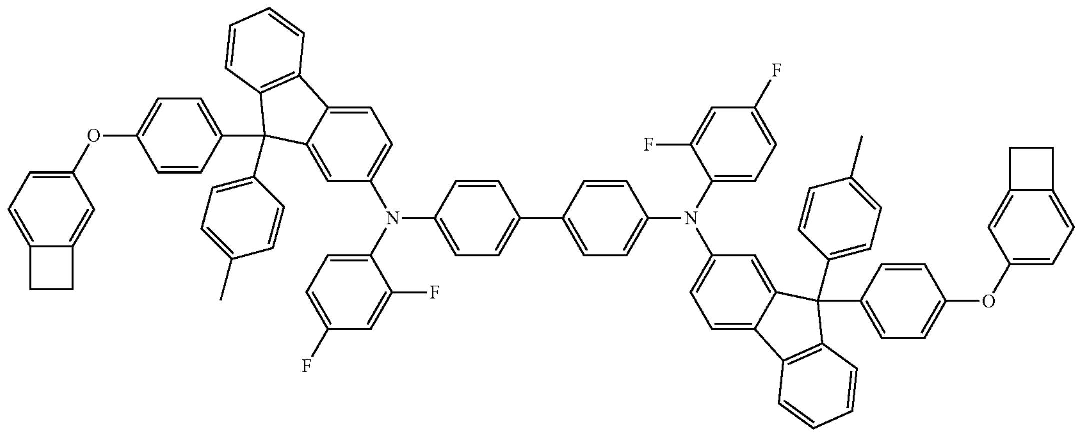
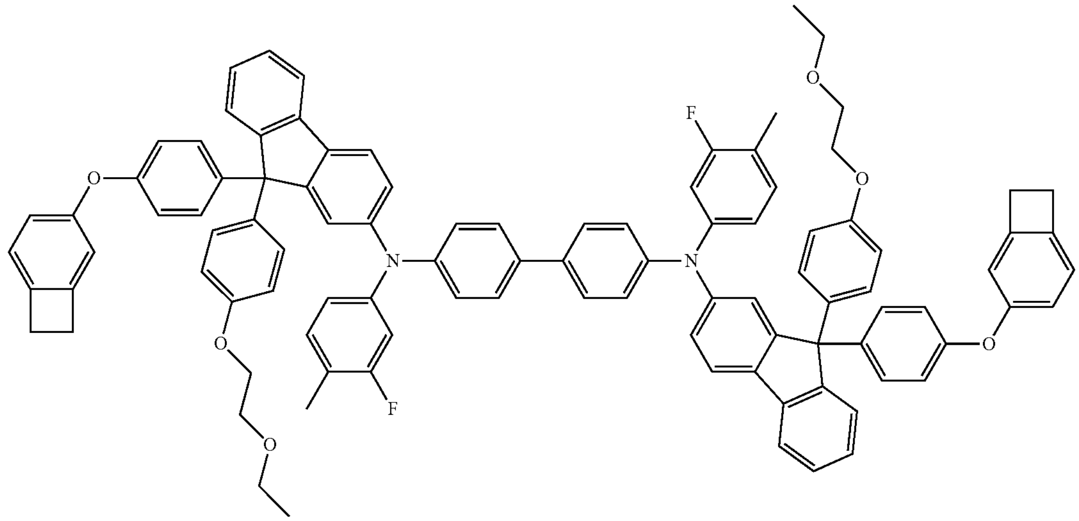
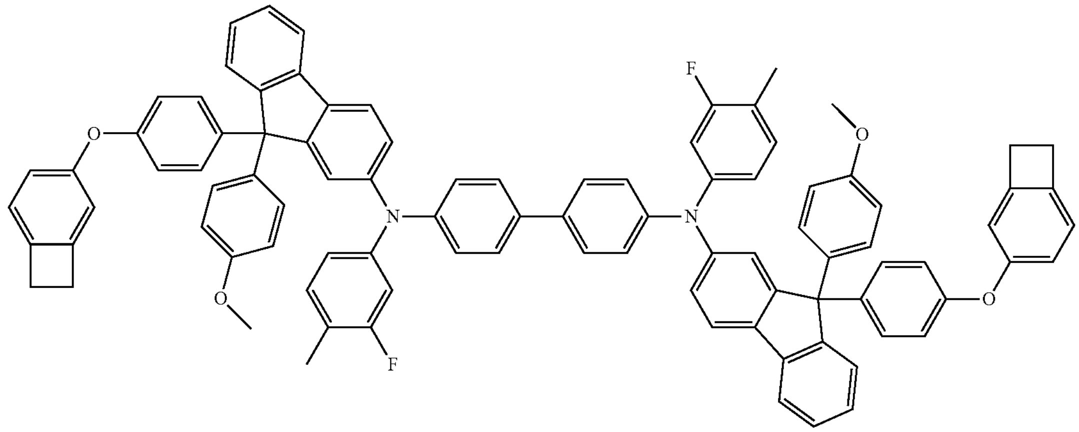

-continued
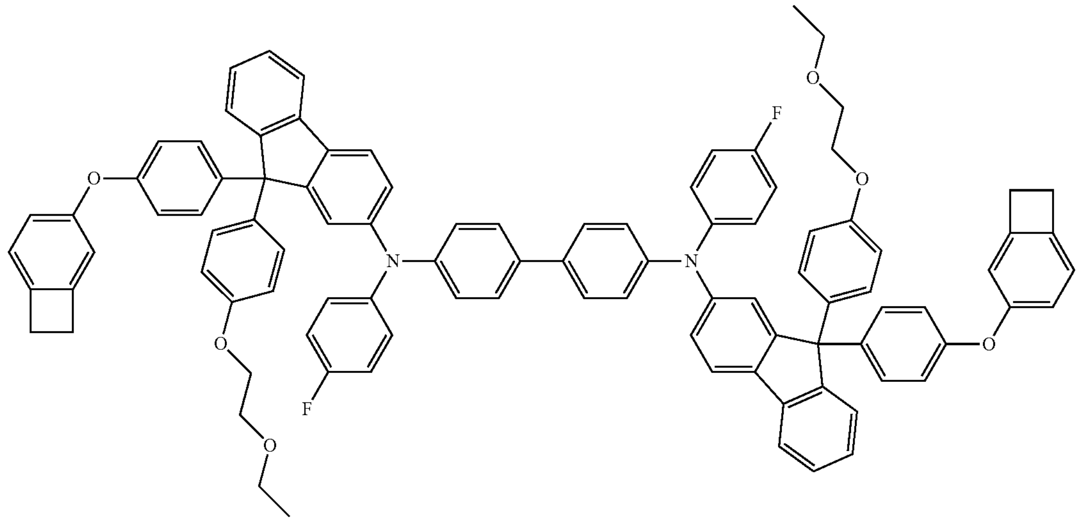
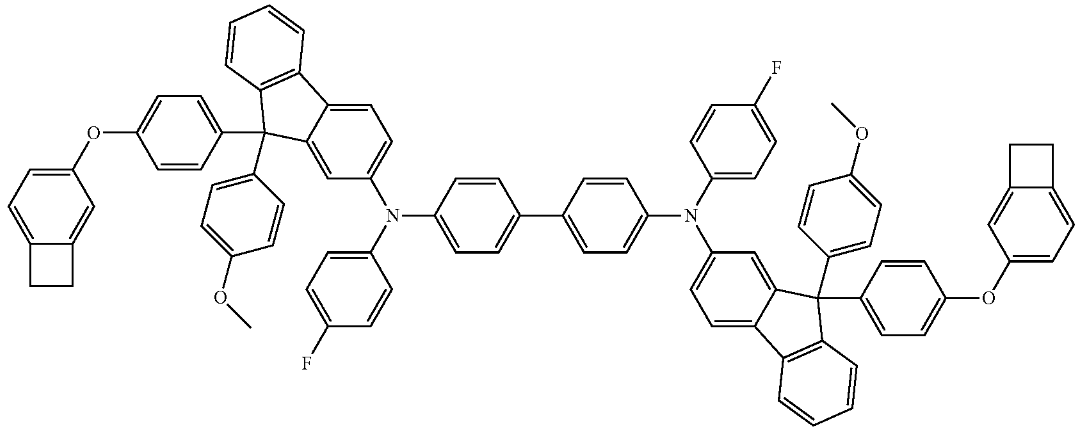
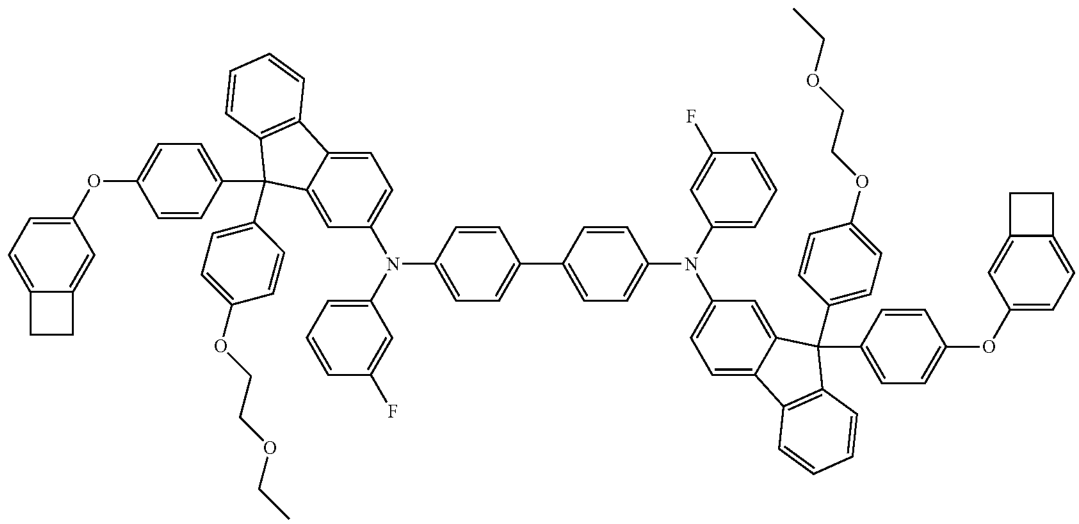

-continued
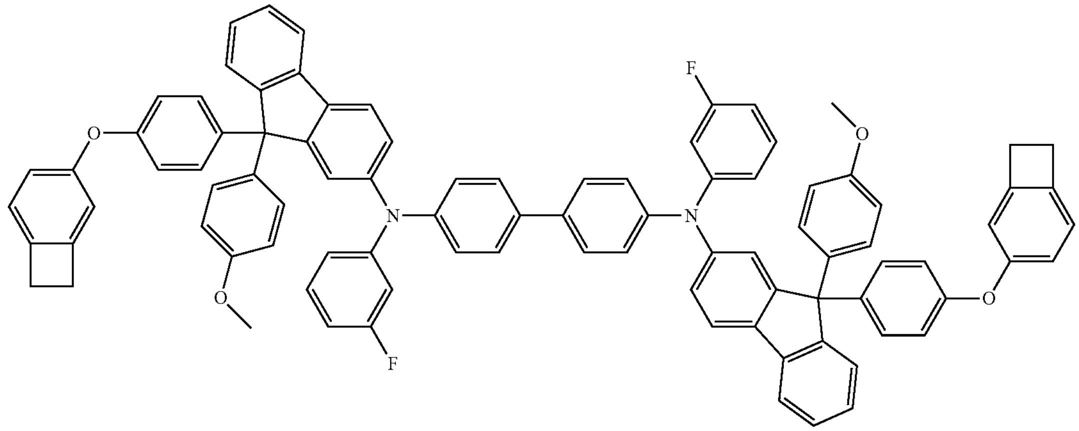
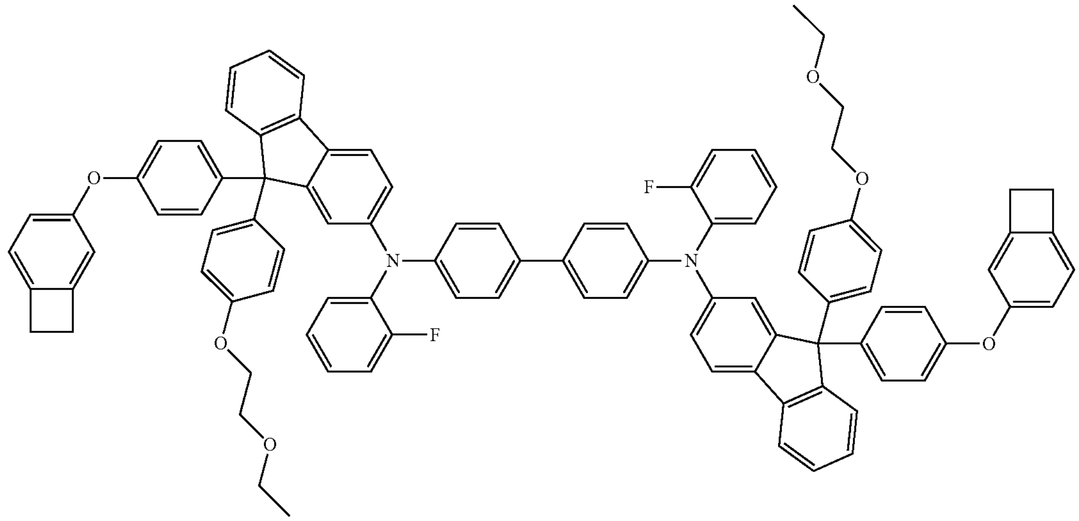
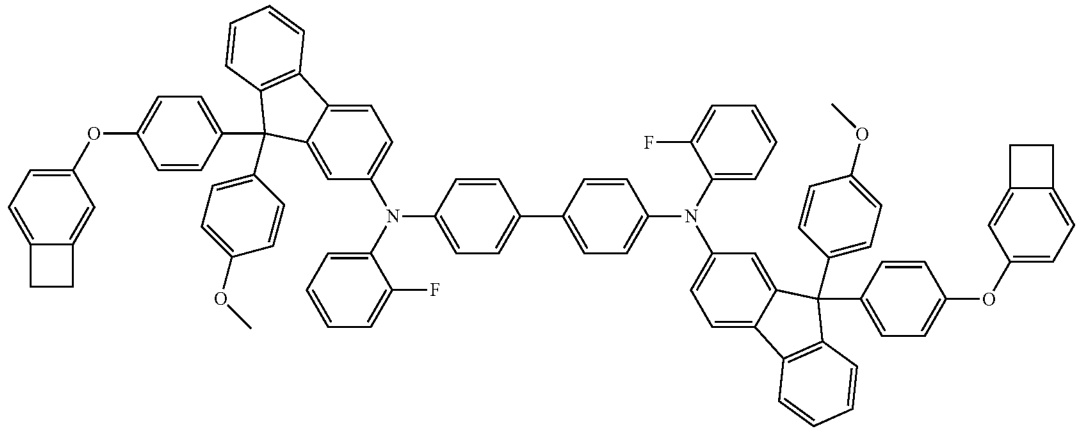

-continued
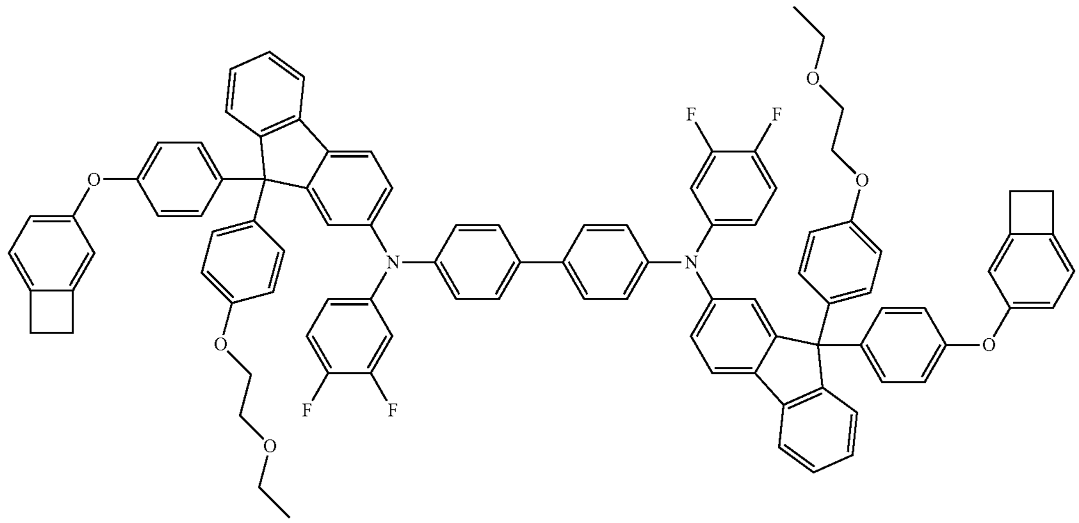
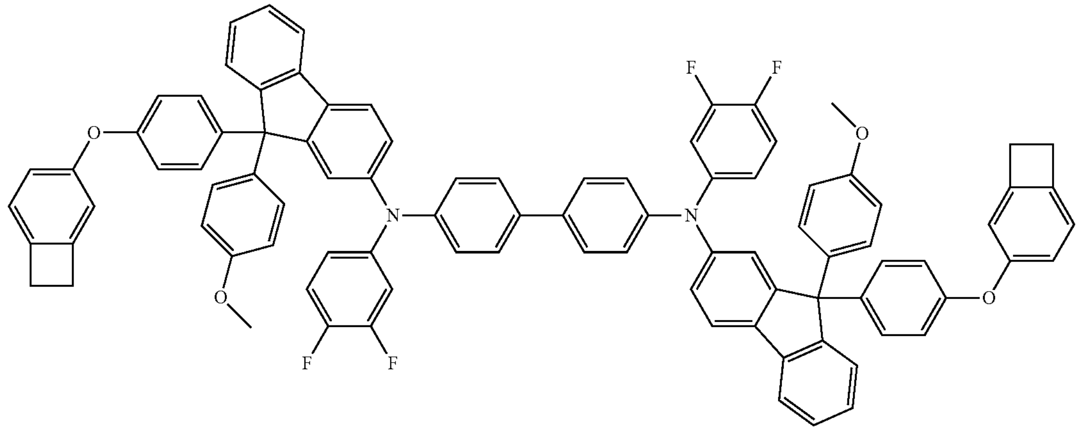
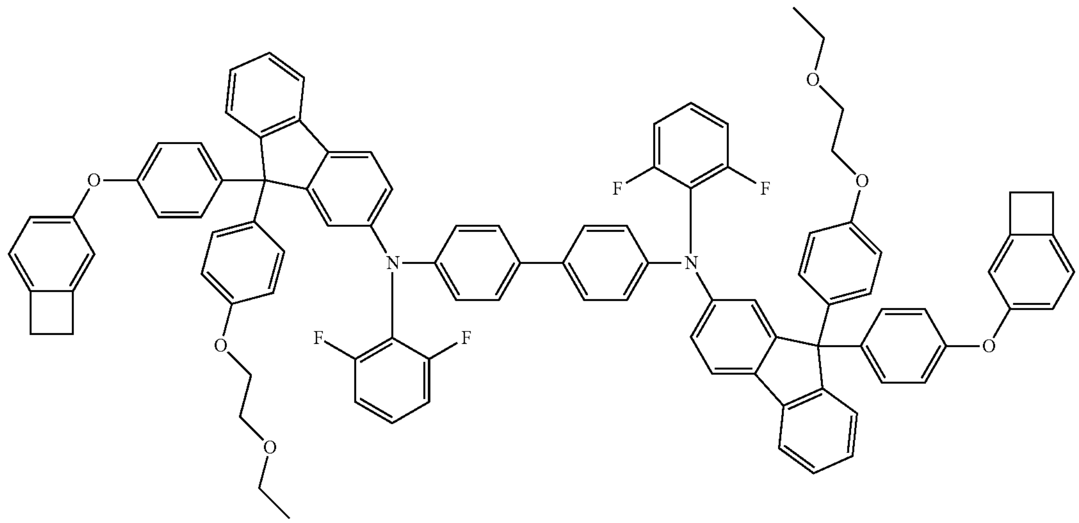

-continued
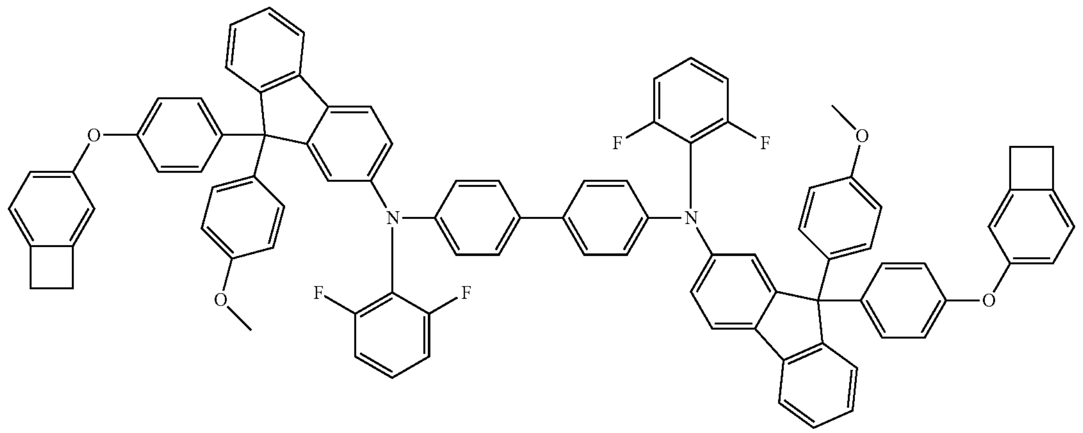
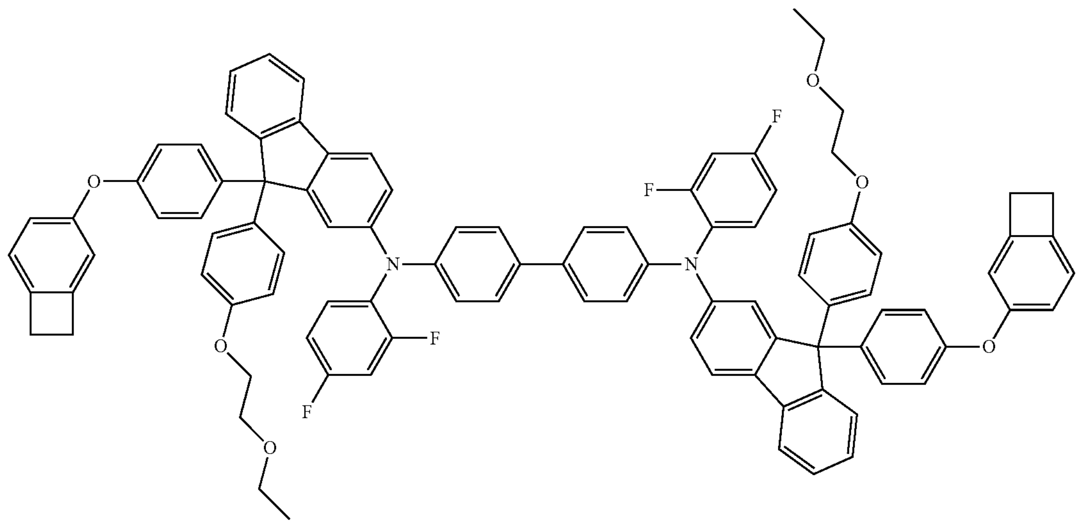
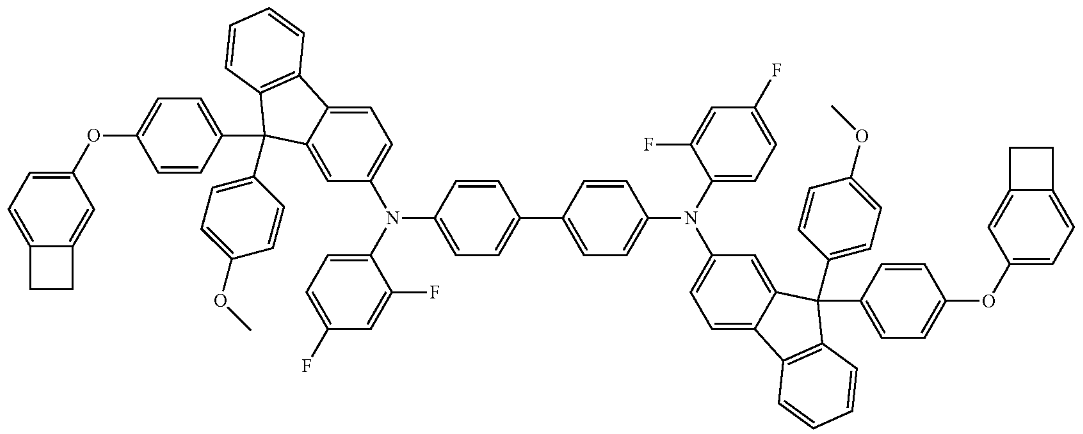

-continued
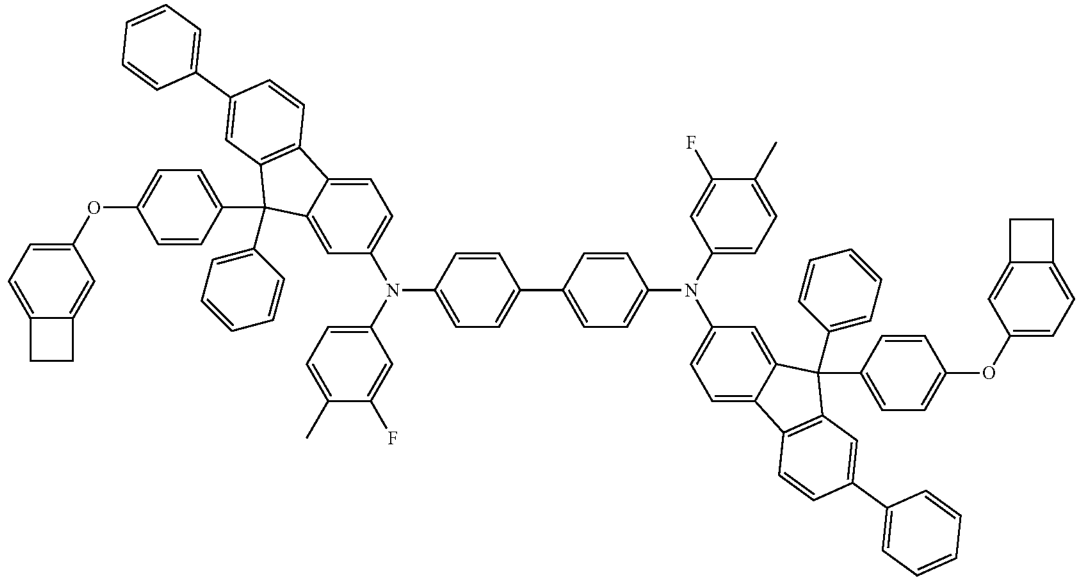
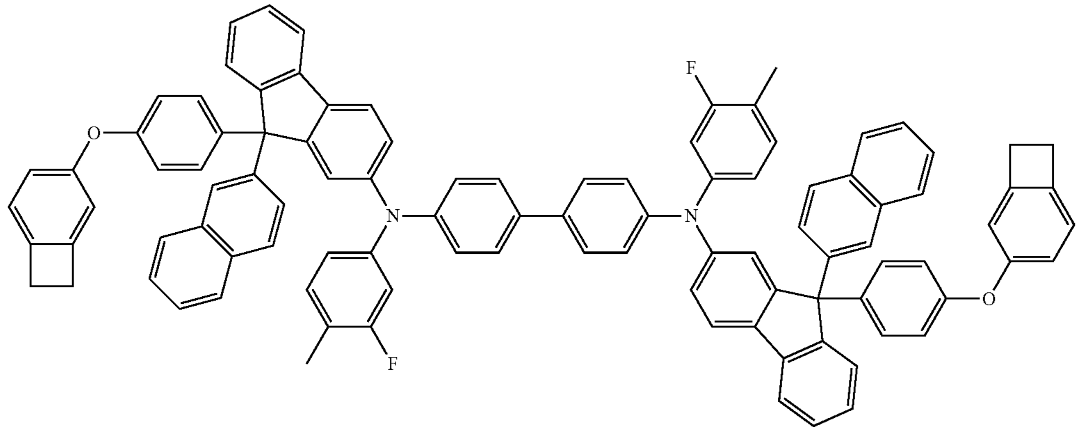
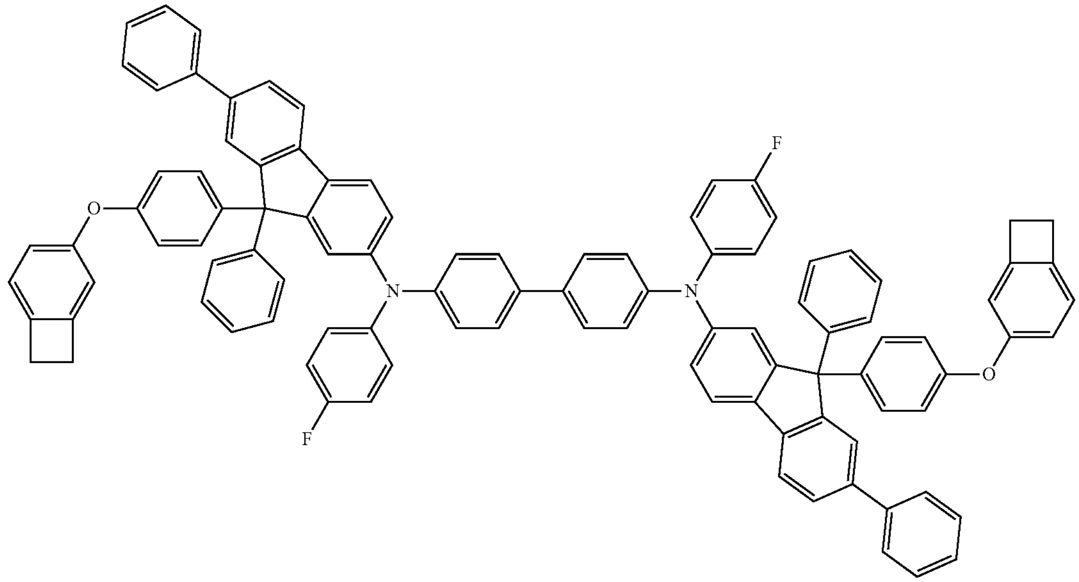

-continued
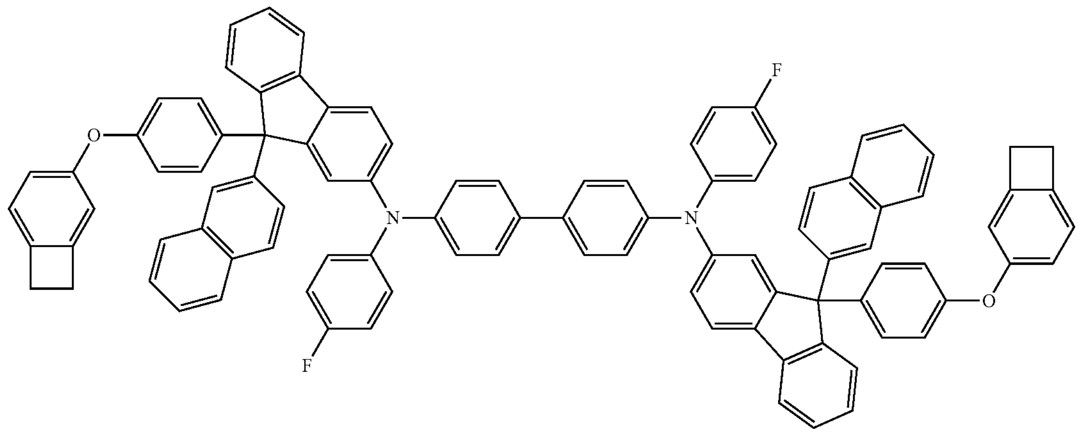
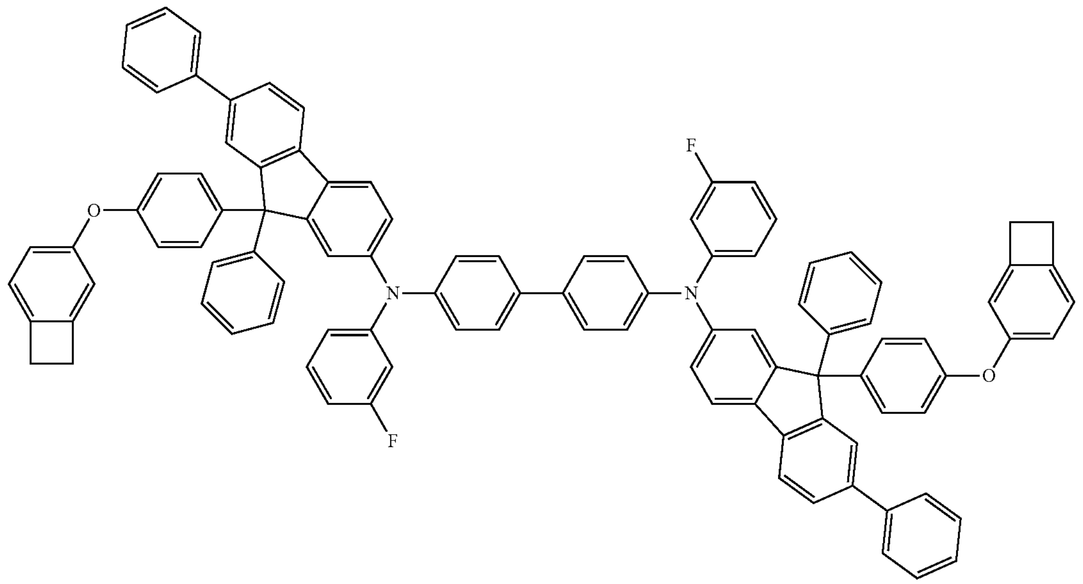
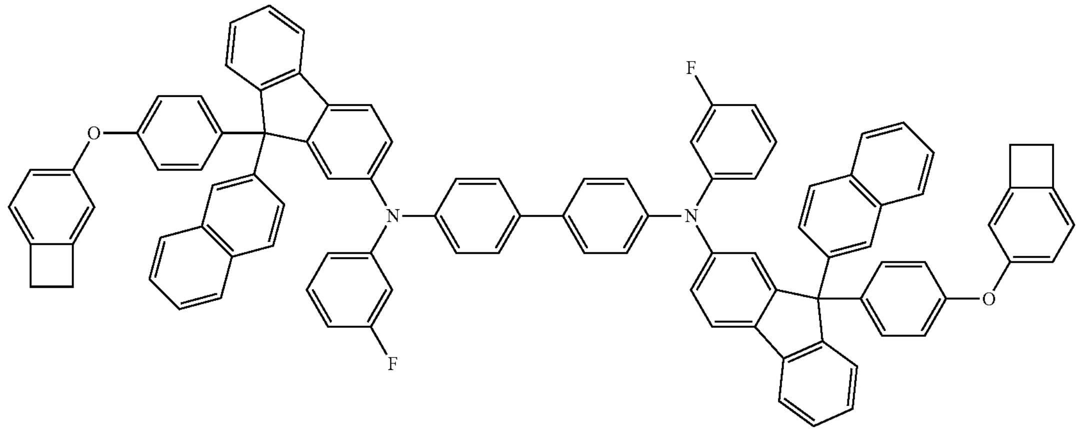

-continued
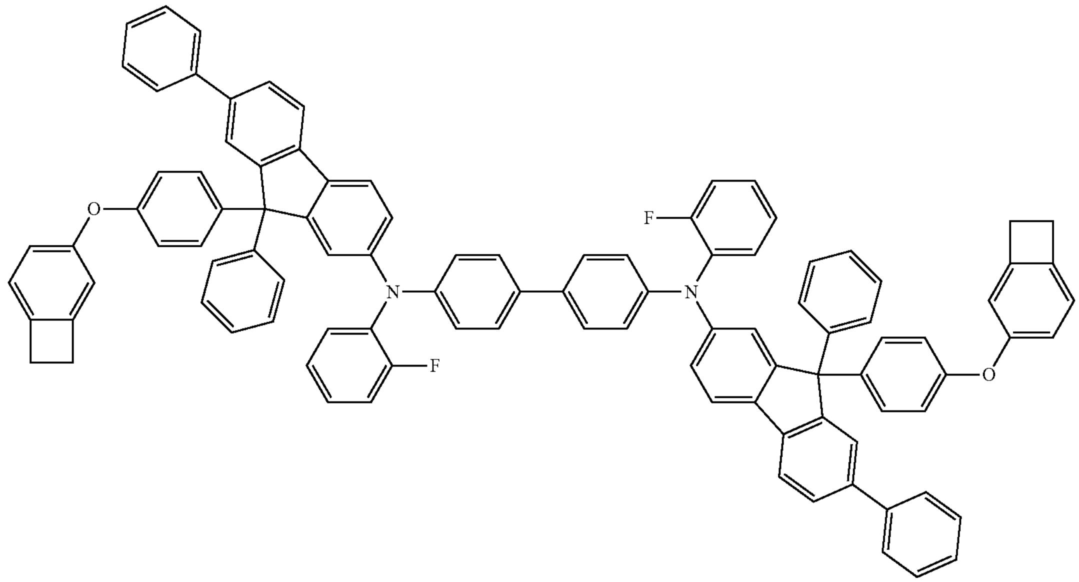
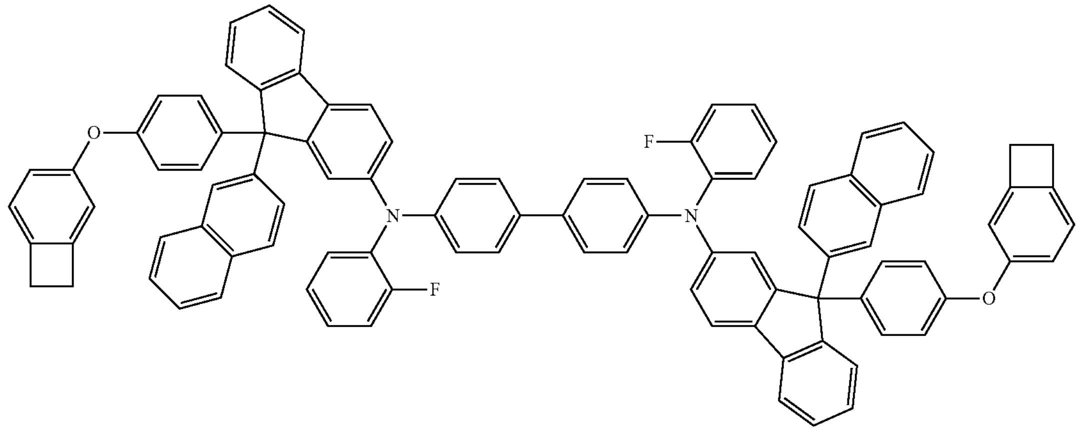
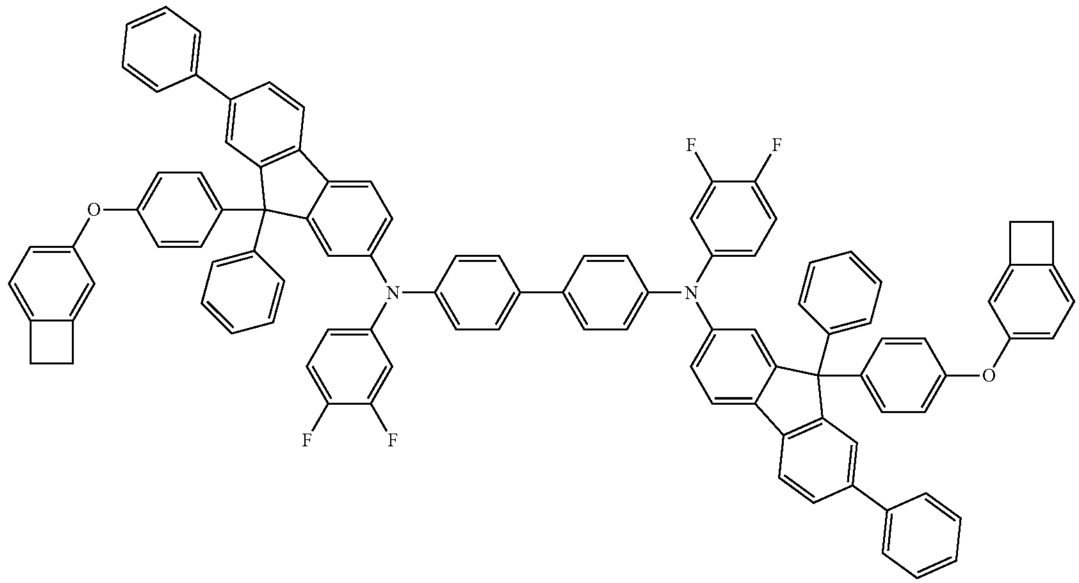

-continued
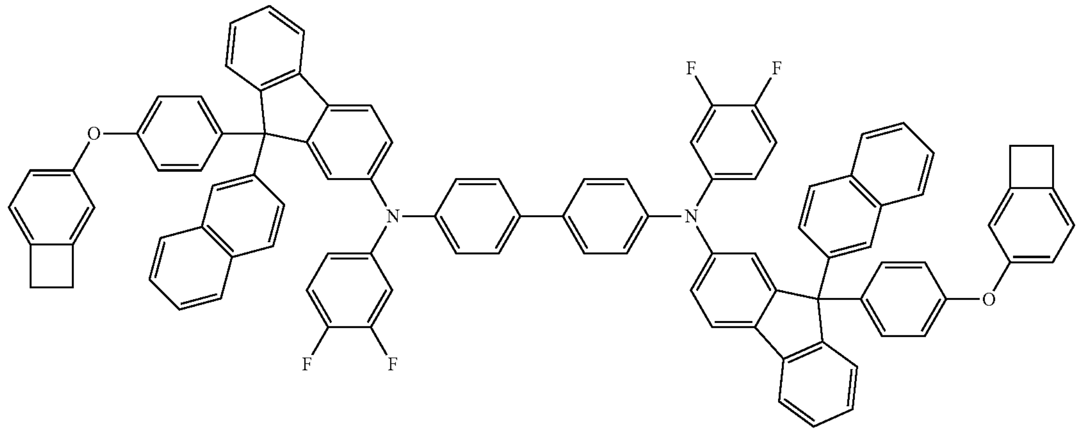
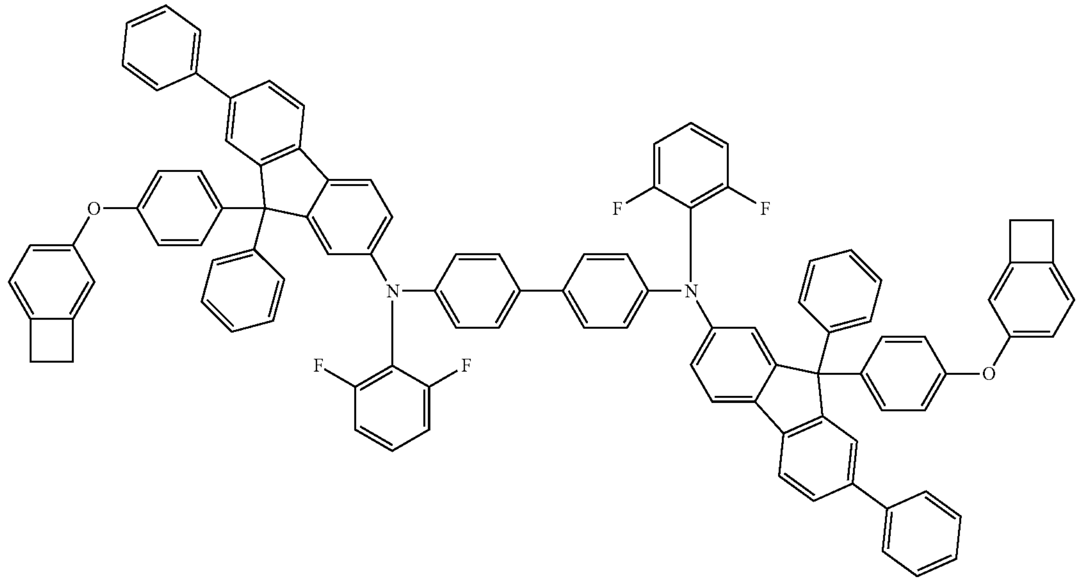
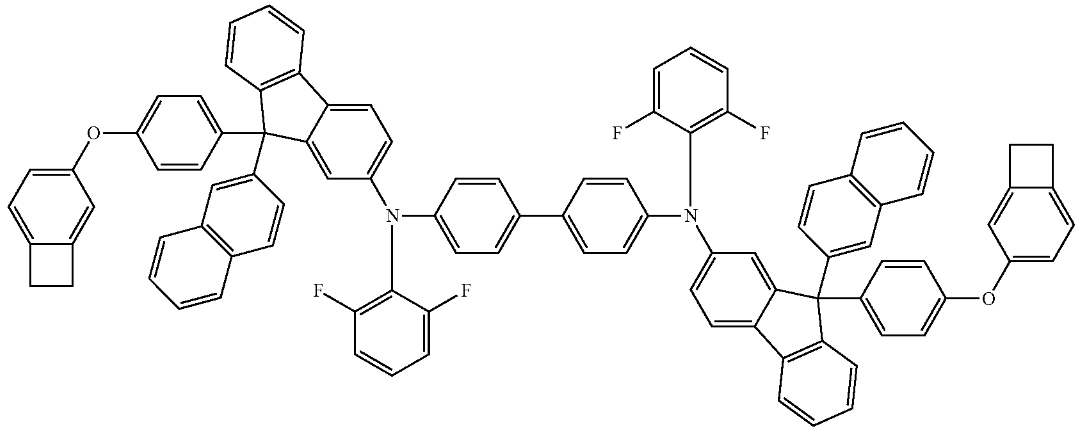

-continued
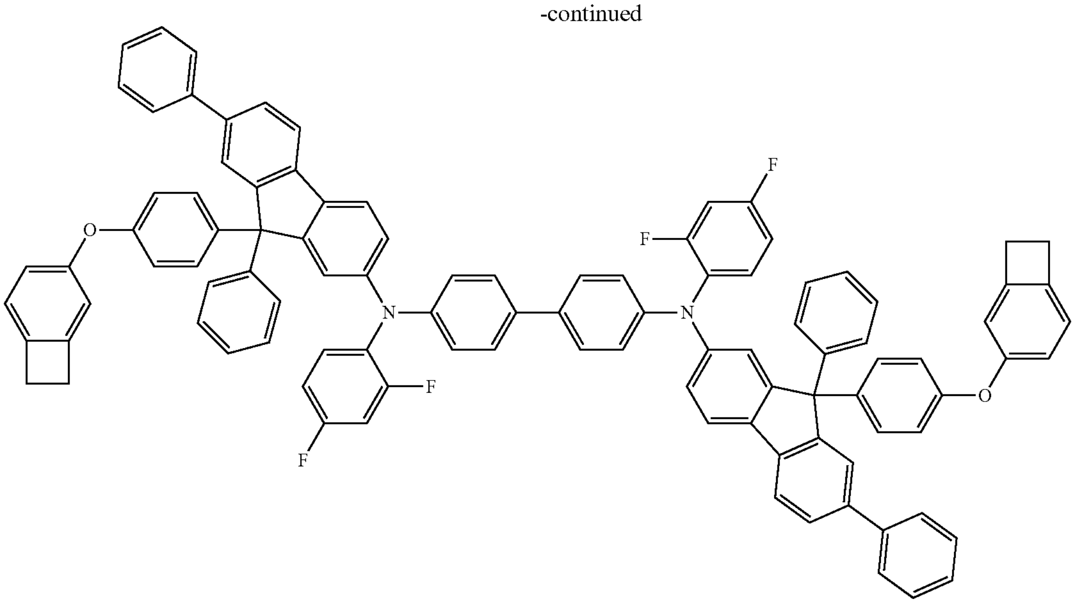
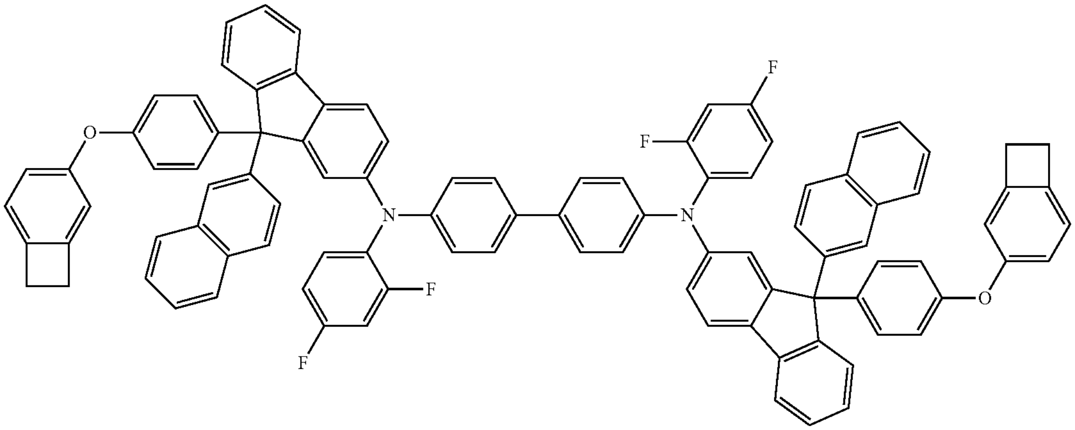
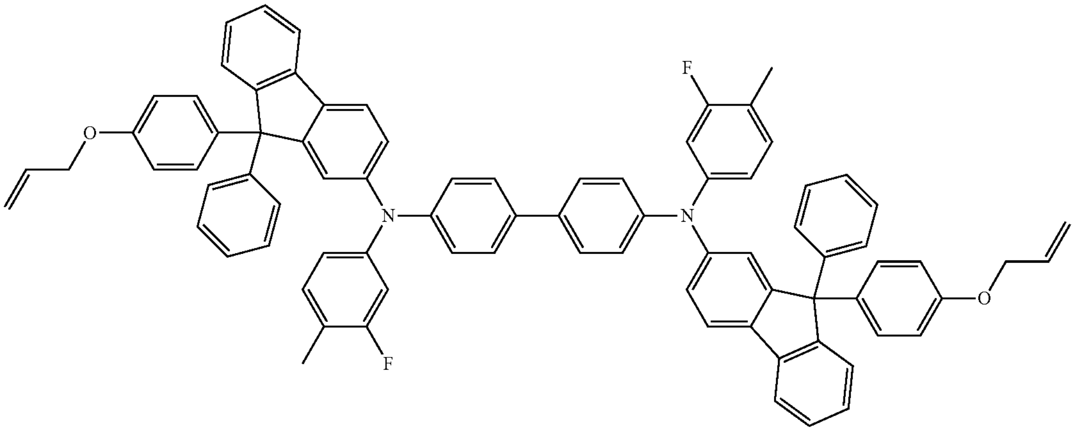

-continued
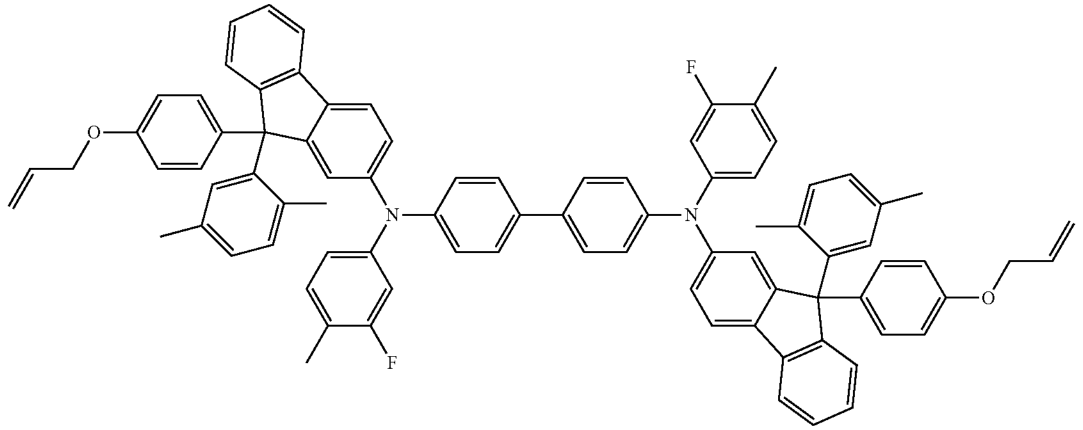
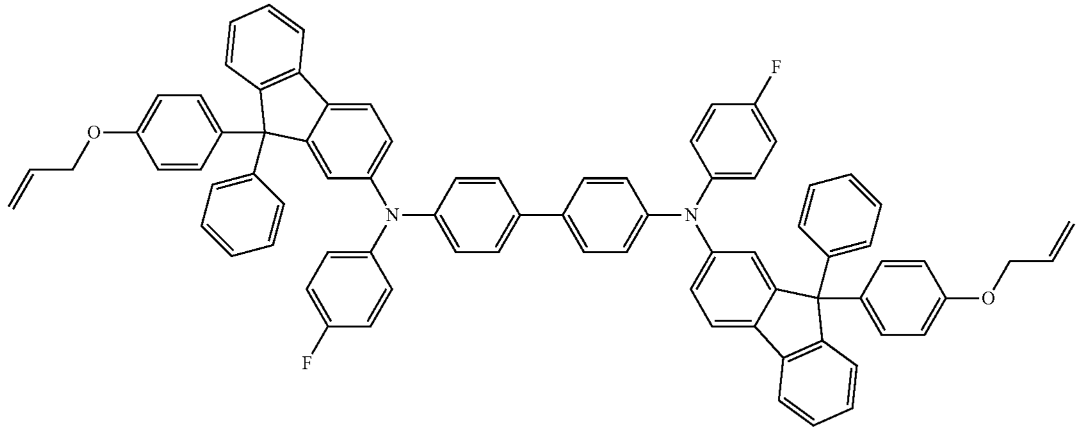
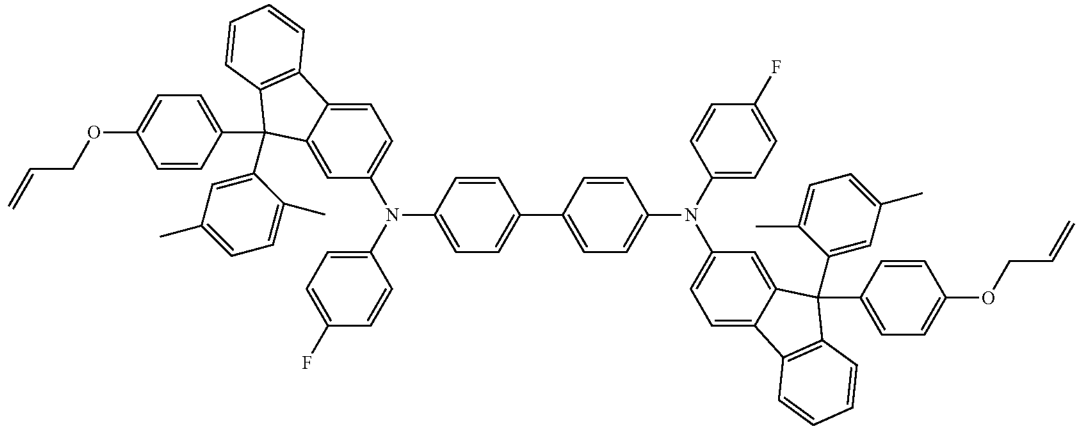
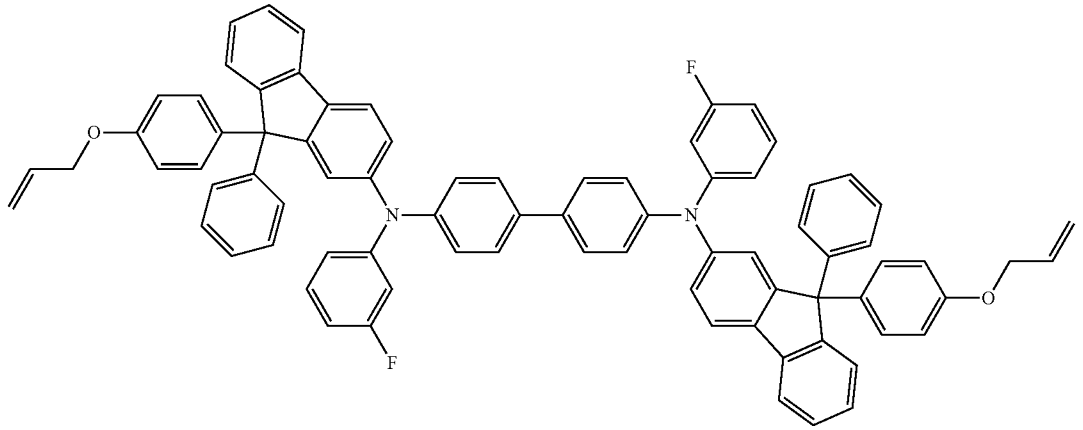

-continued
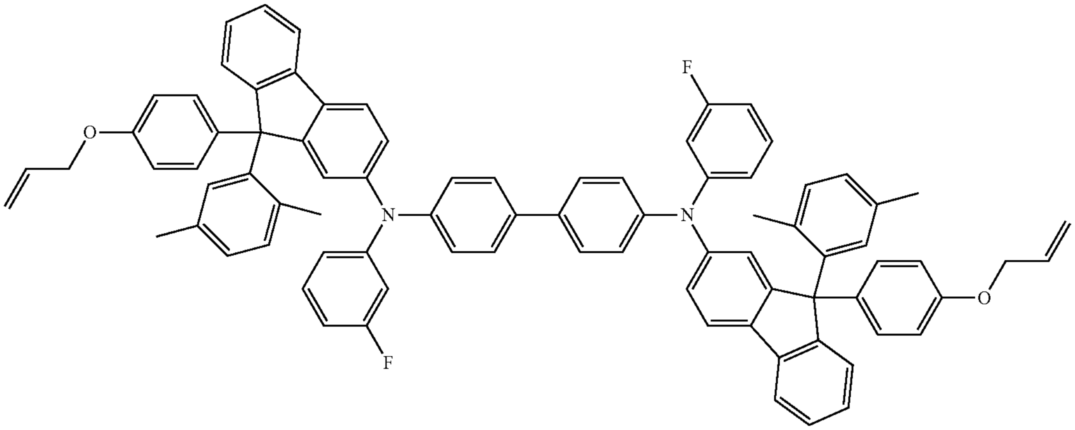
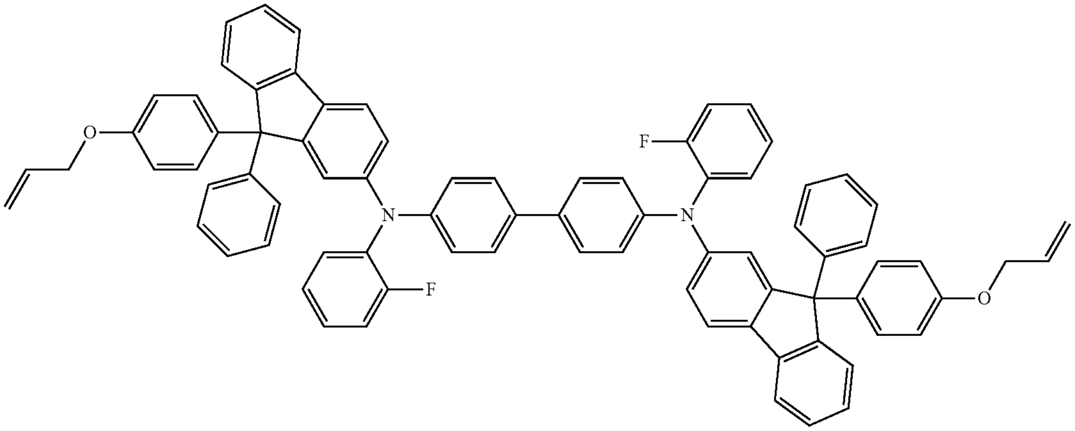
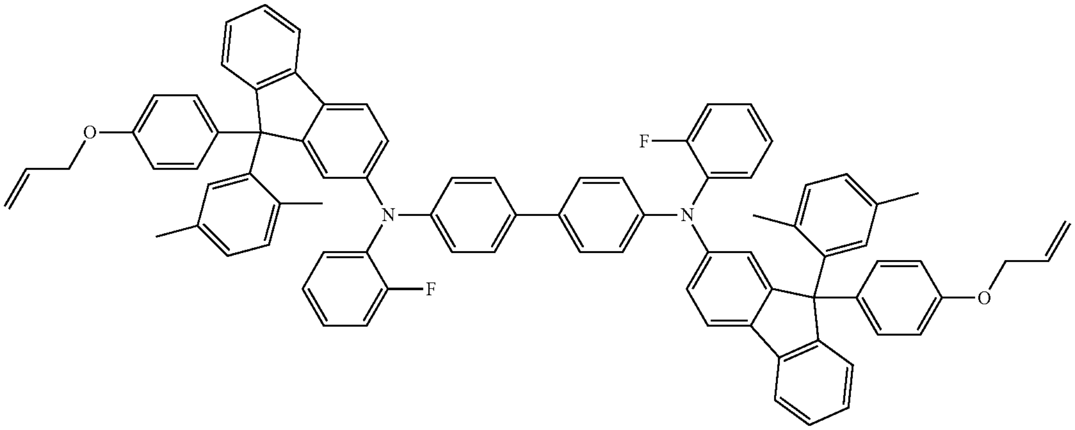
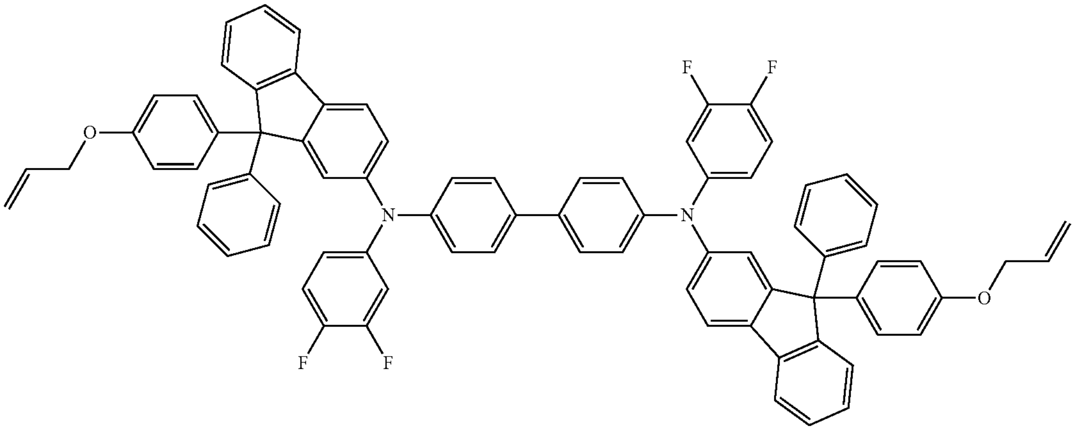

-continued
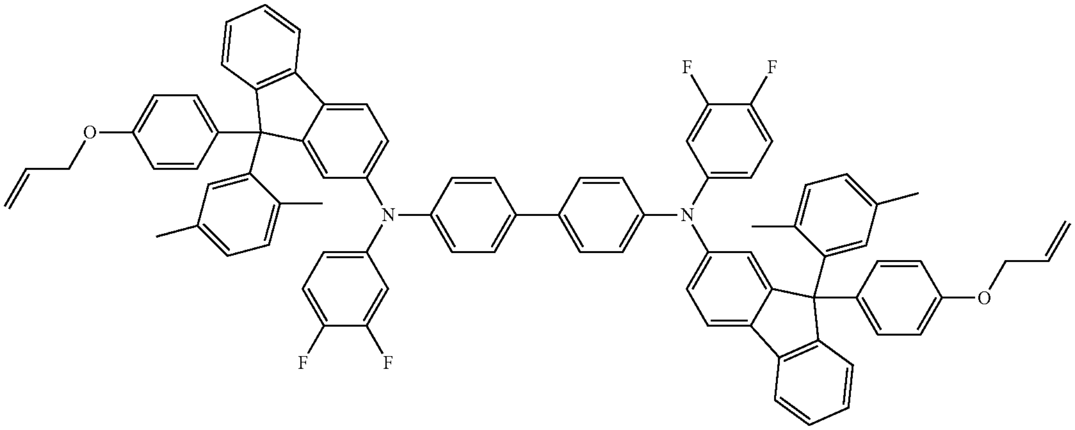
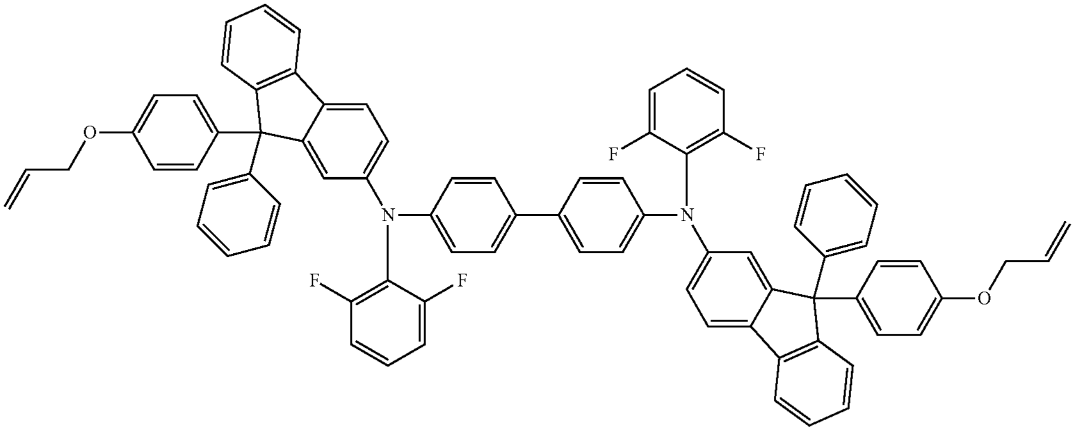
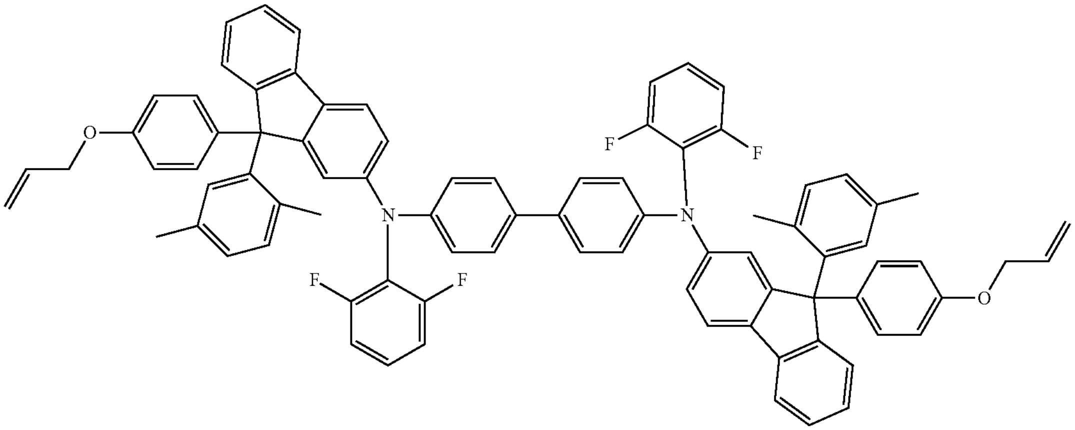
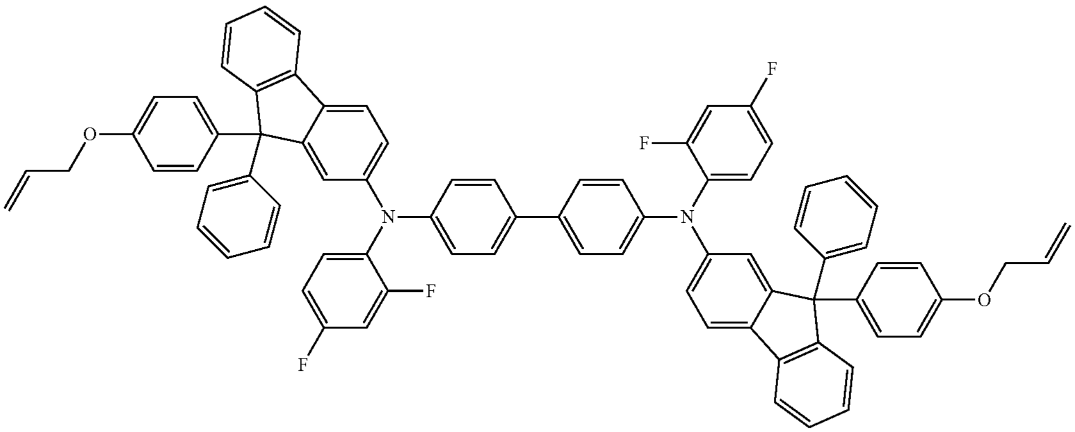

-continued
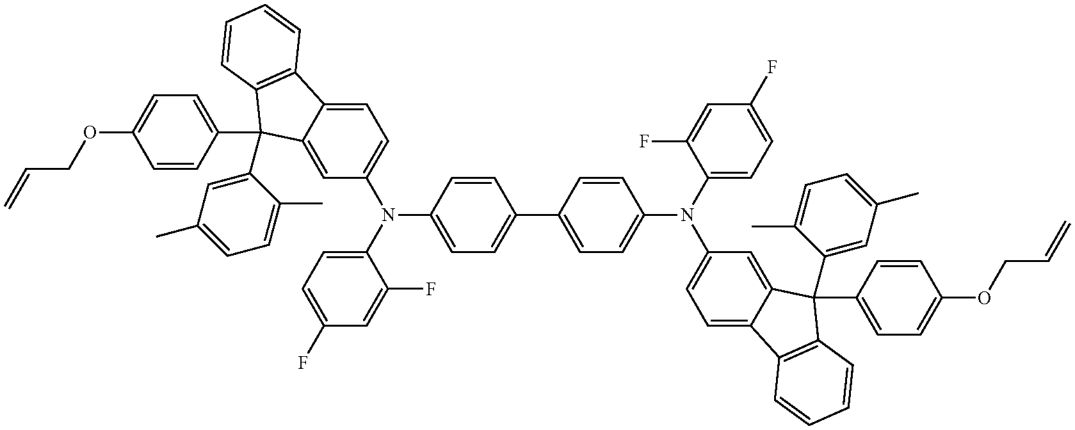
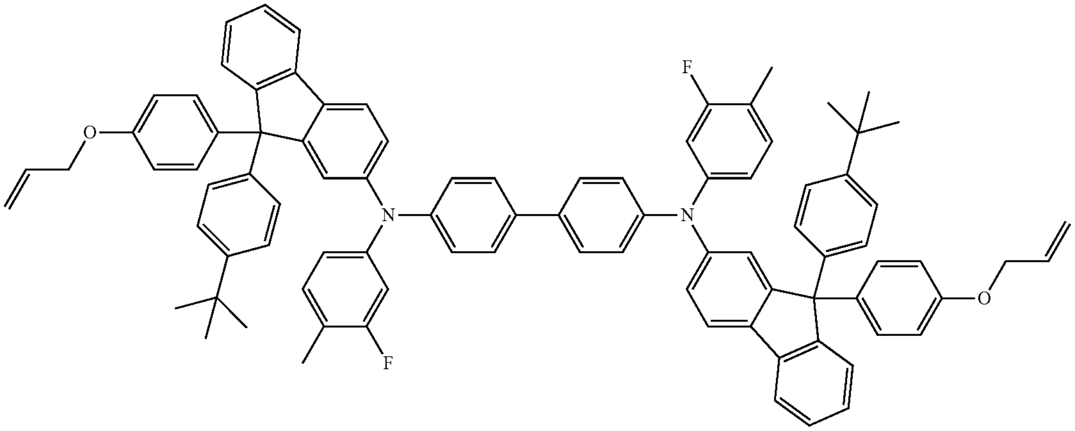
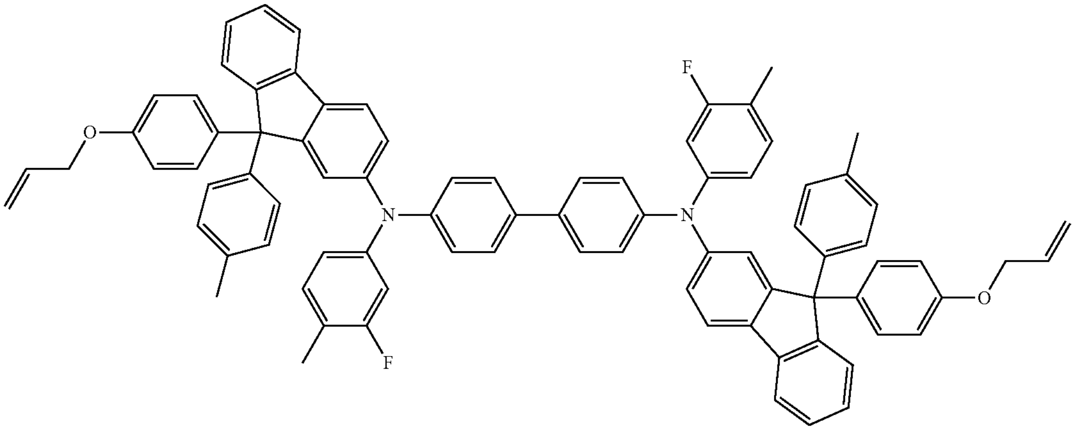
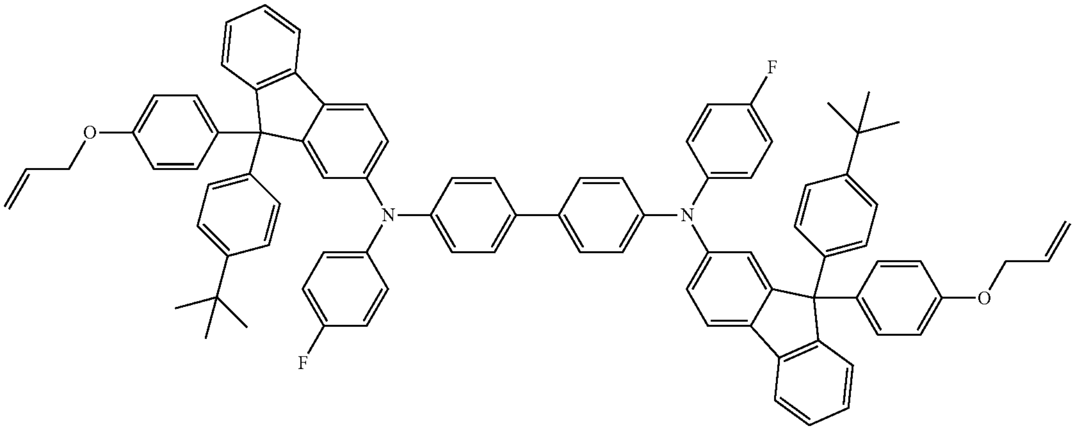

-continued
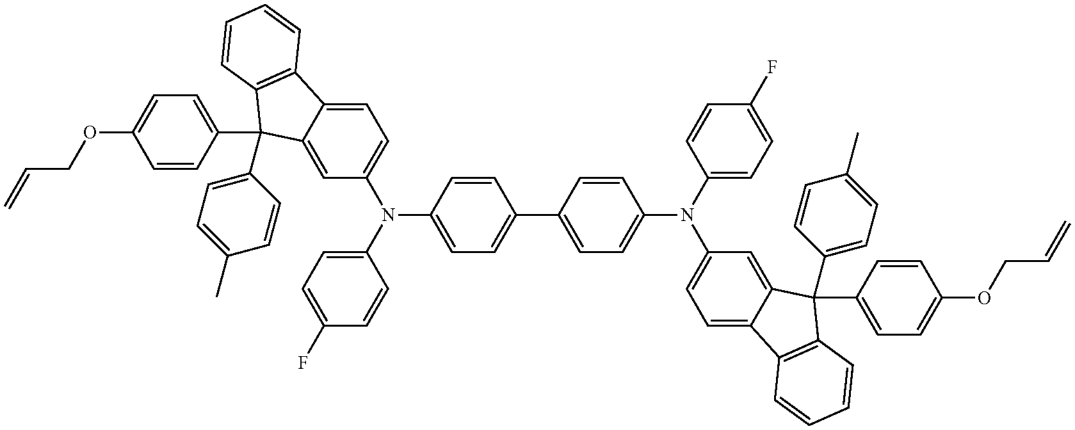
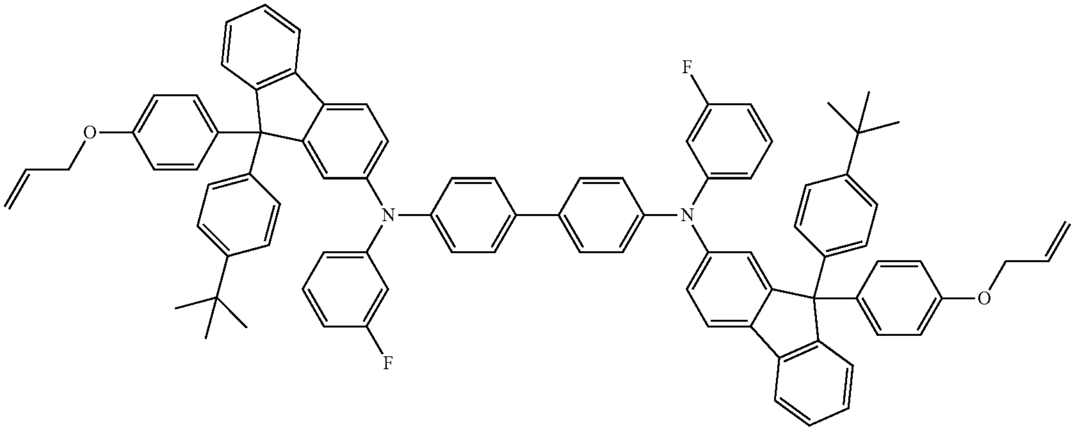
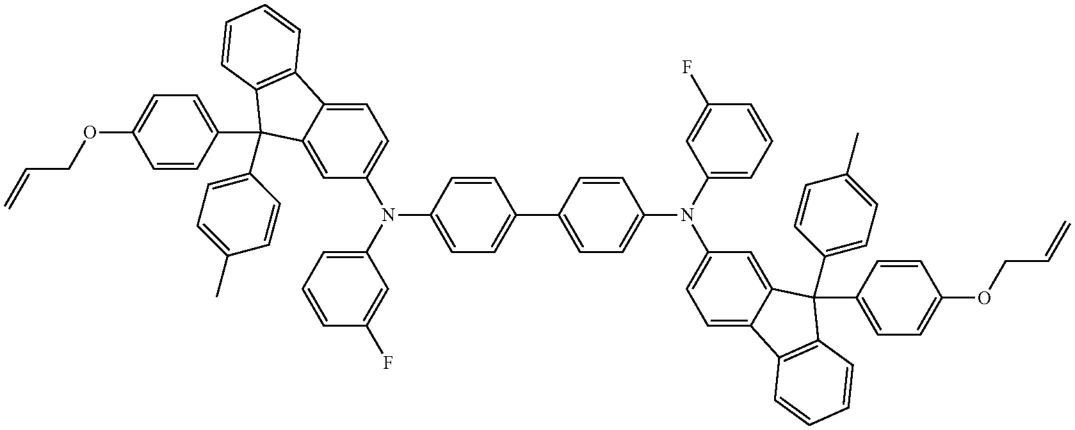
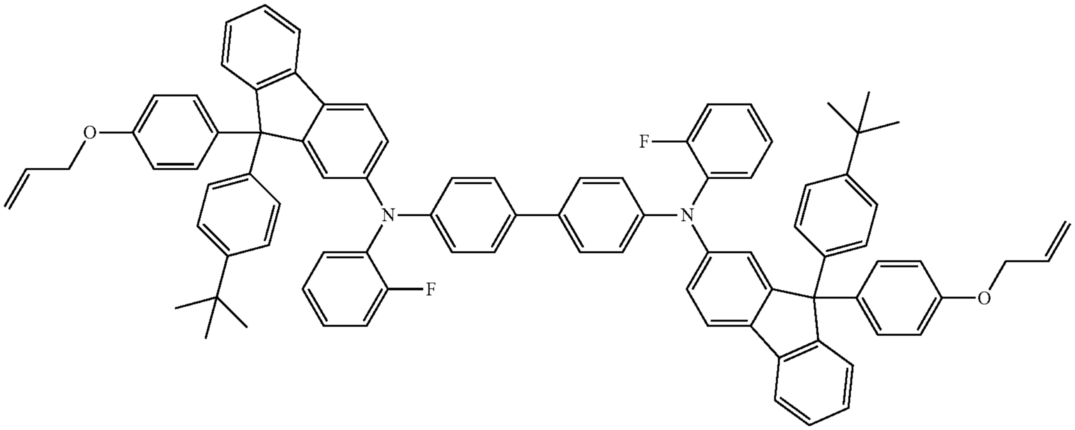

-continued
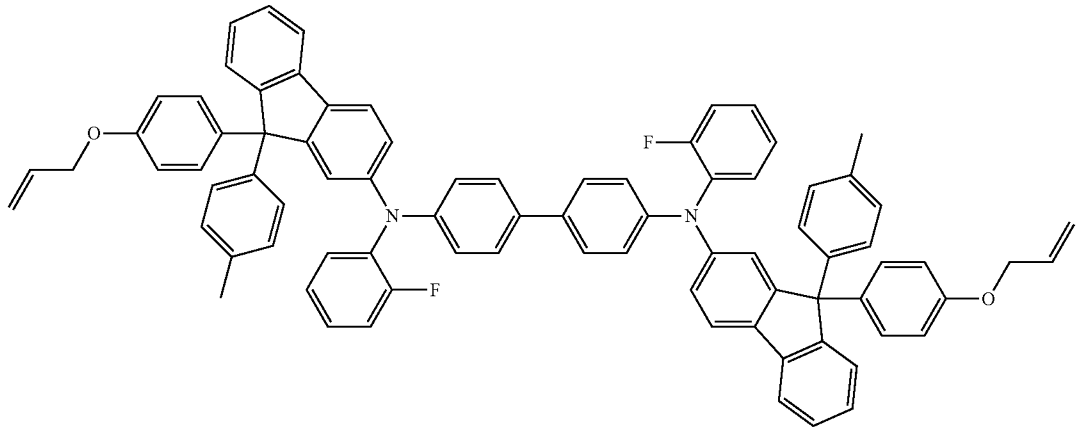
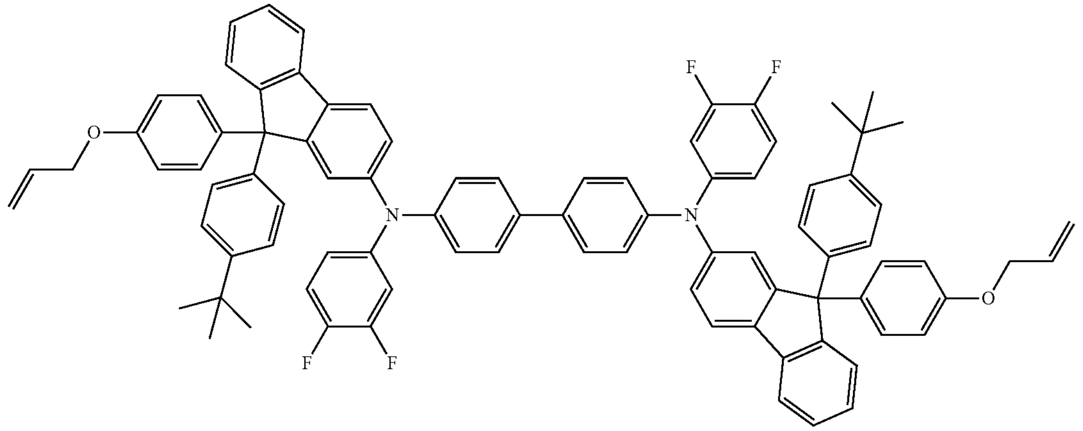
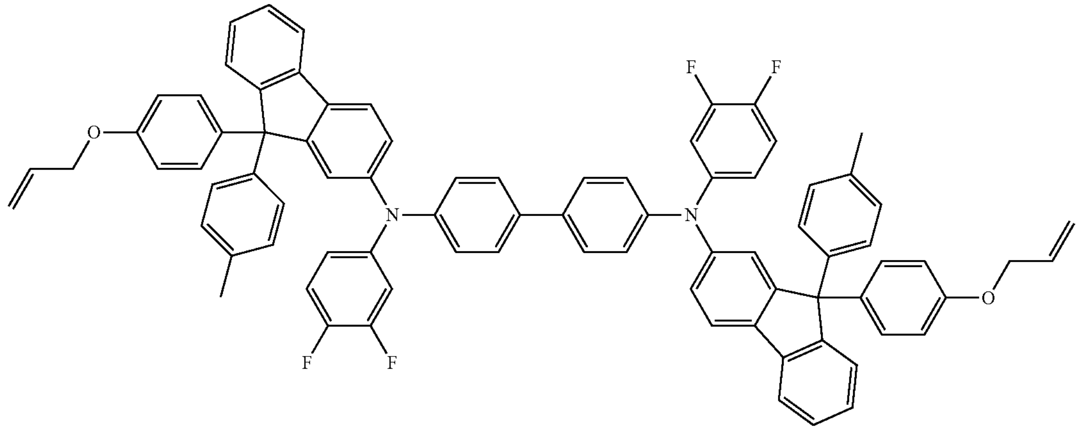
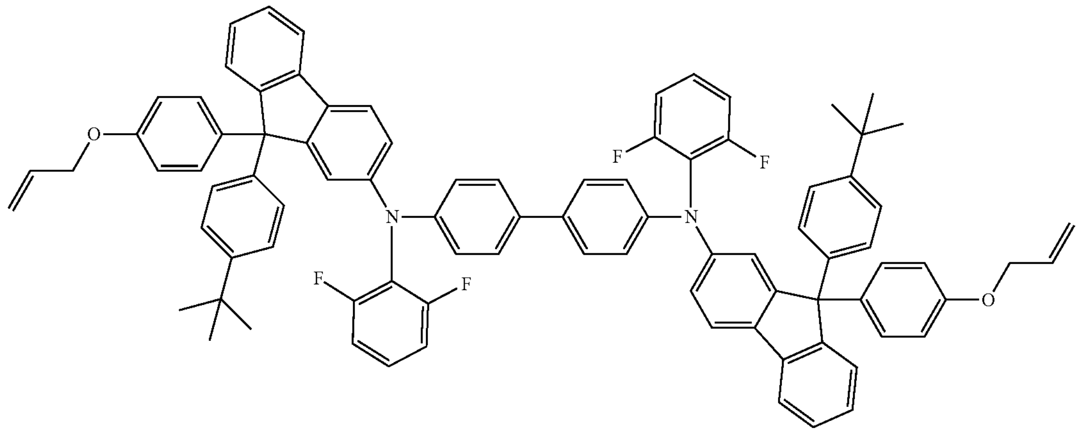

-continued
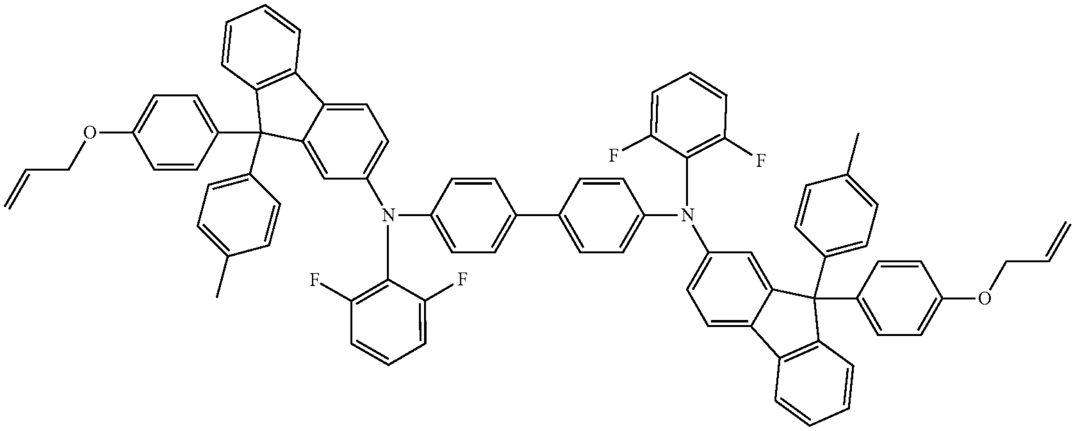
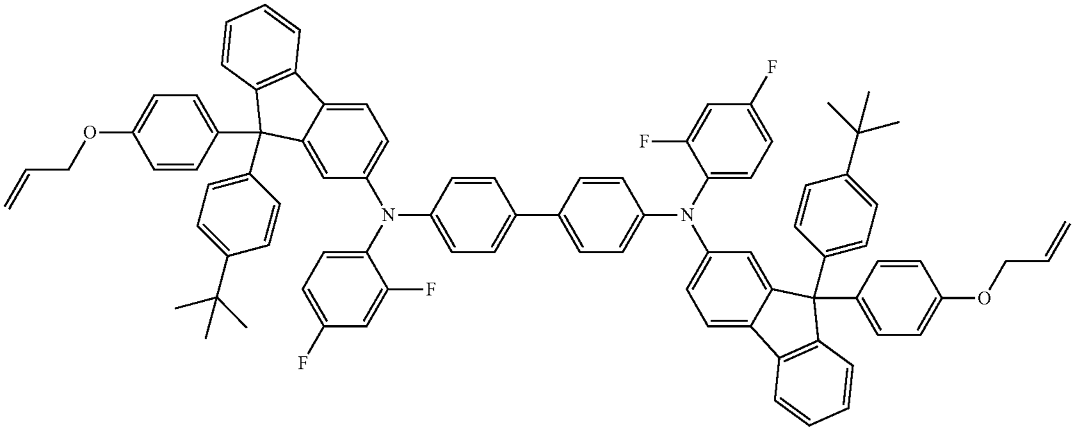
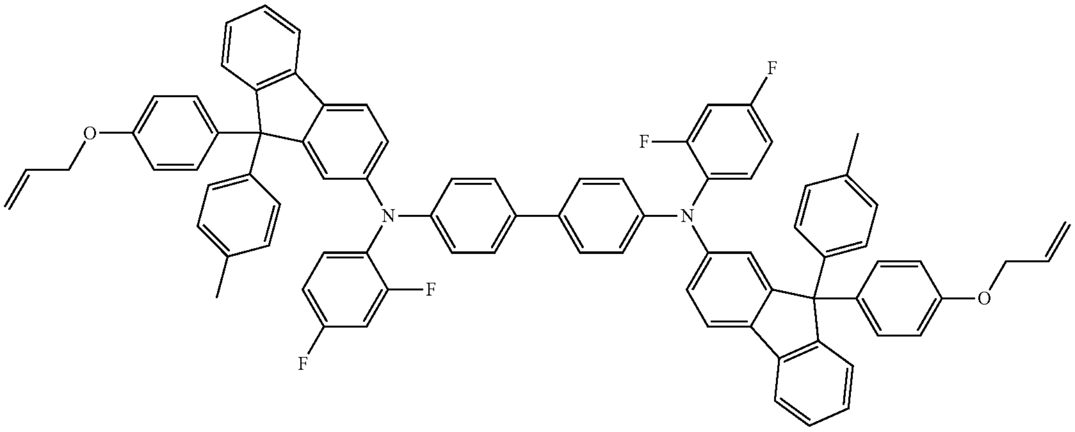

-continued
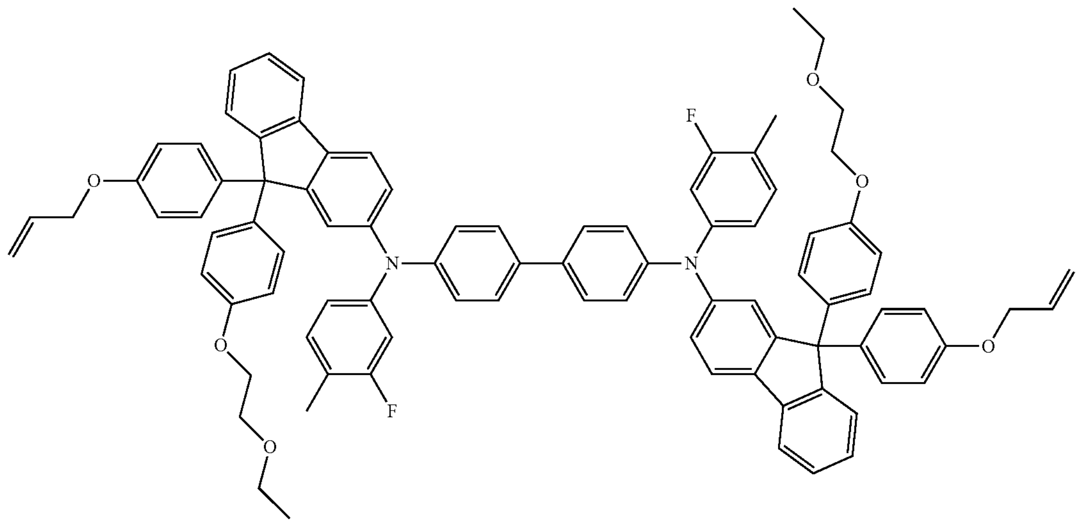
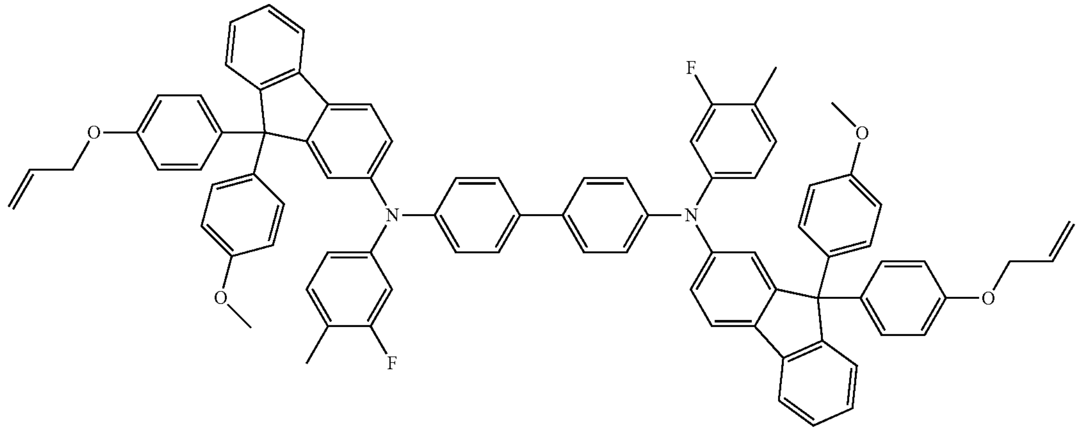
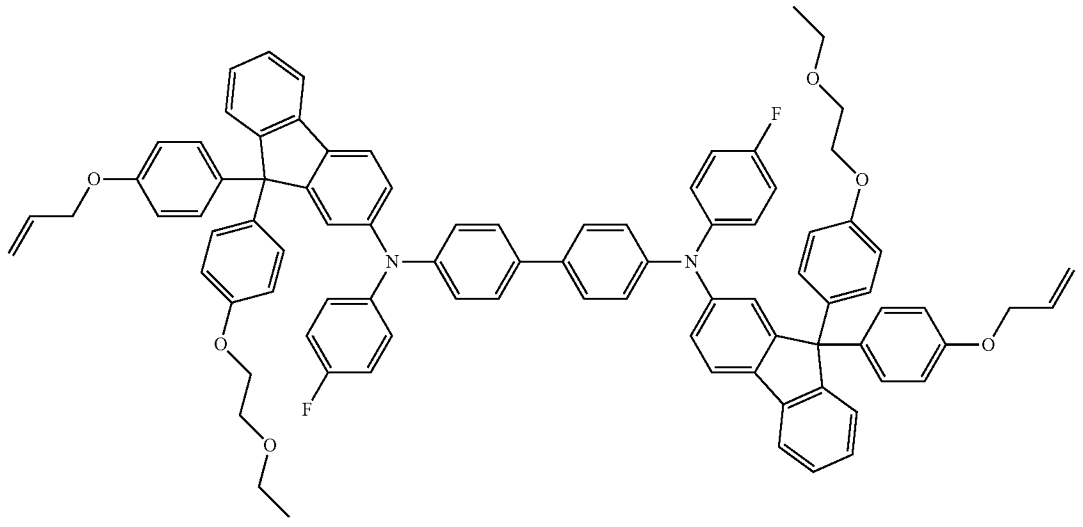

-continued
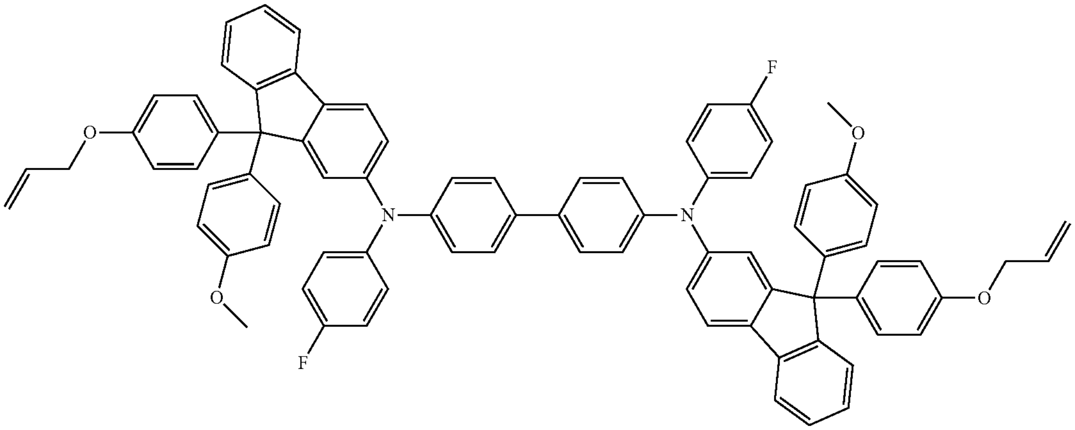
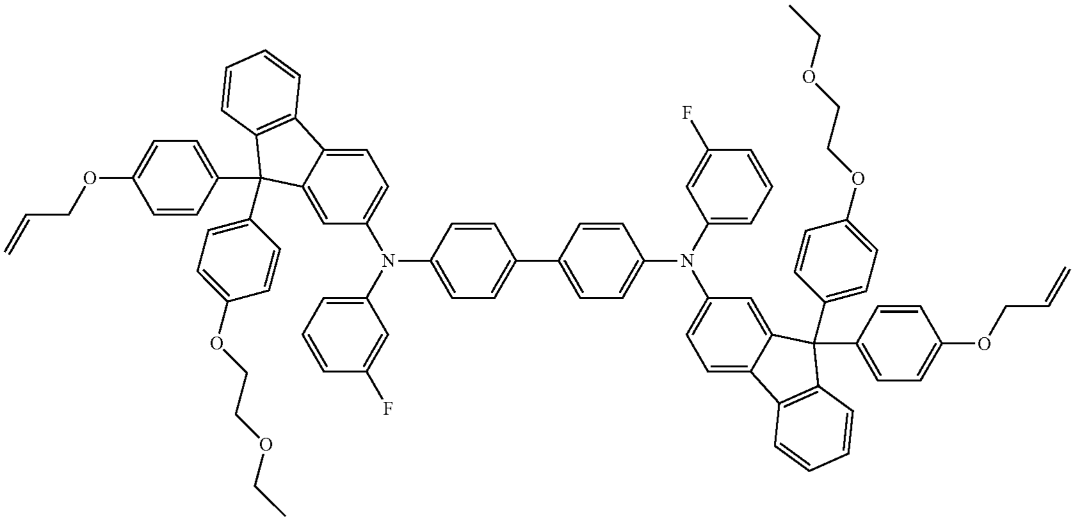
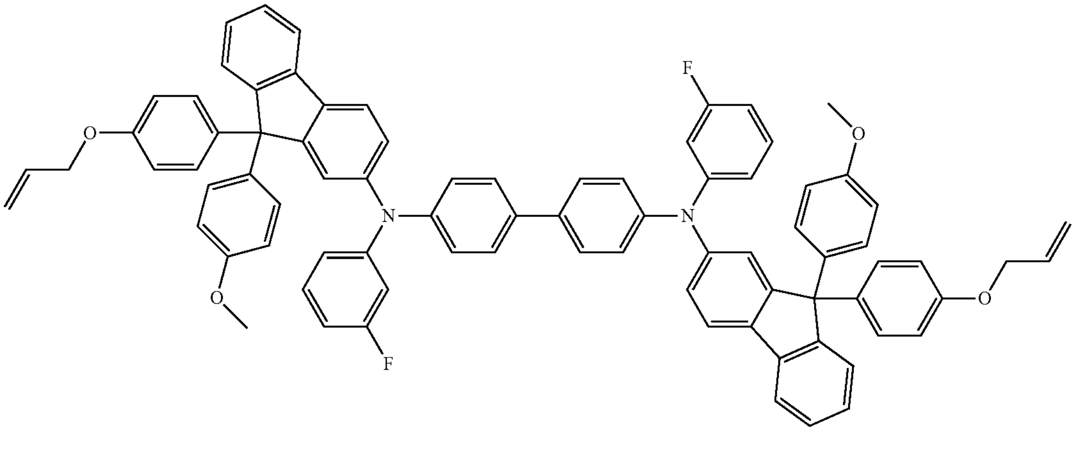

-continued
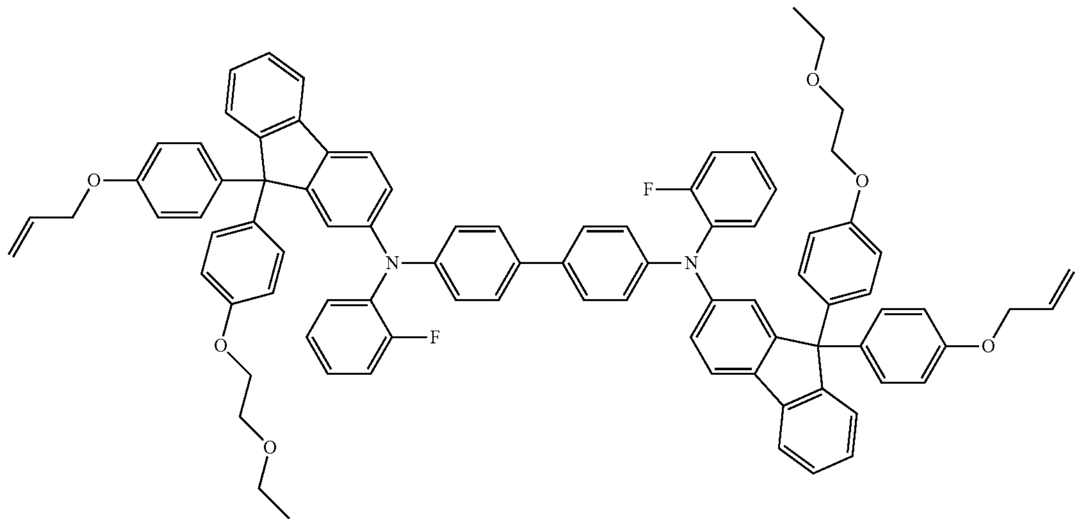
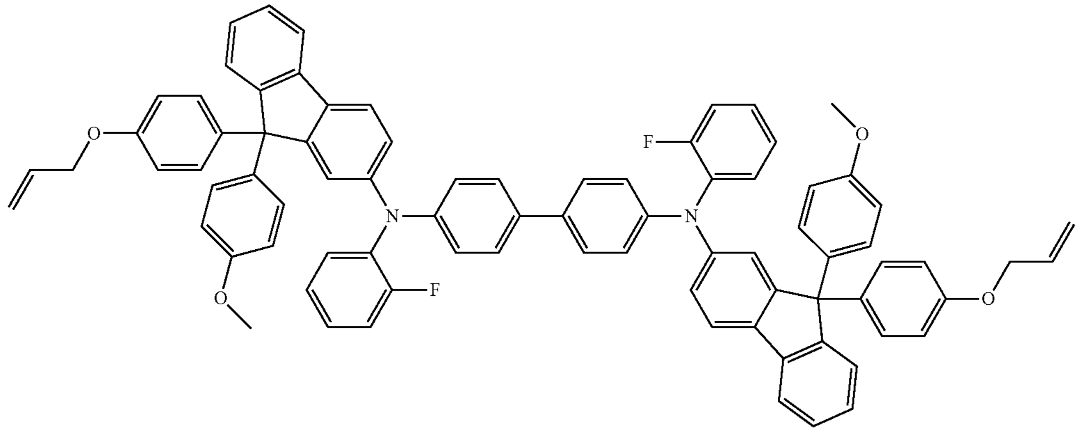
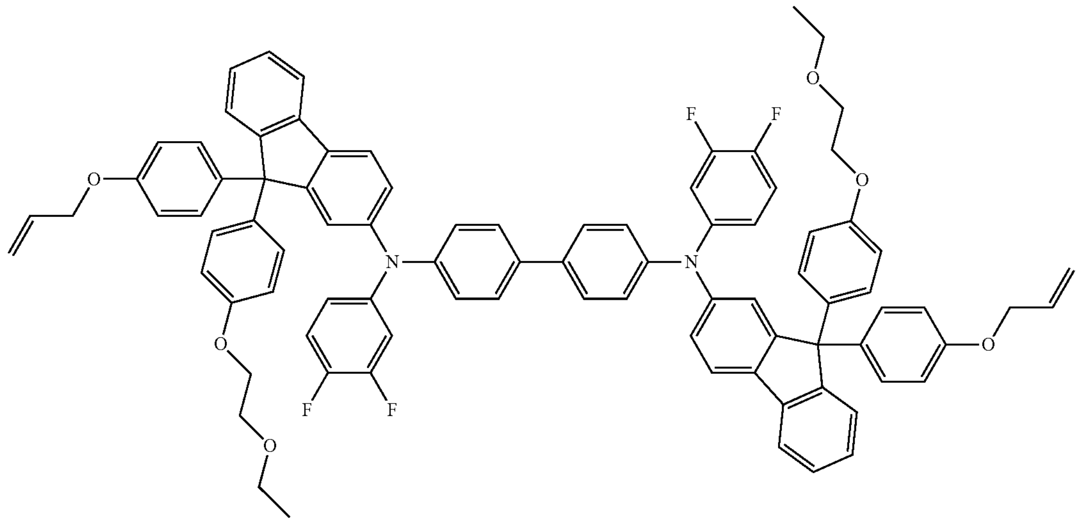

-continued
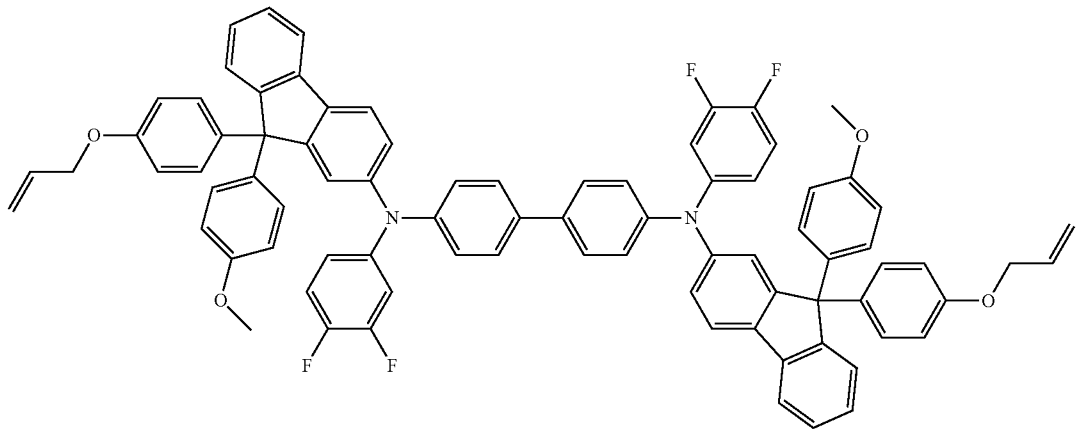
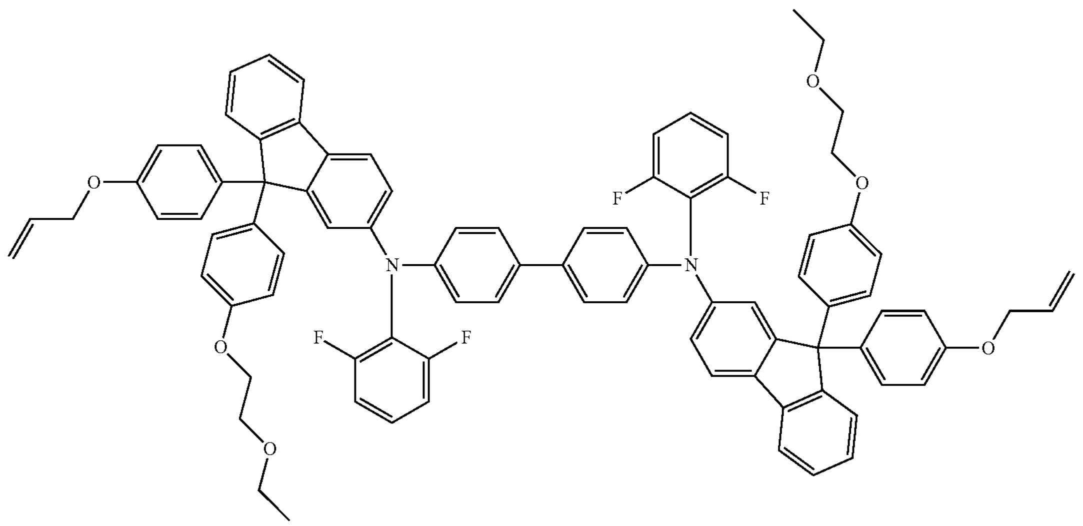
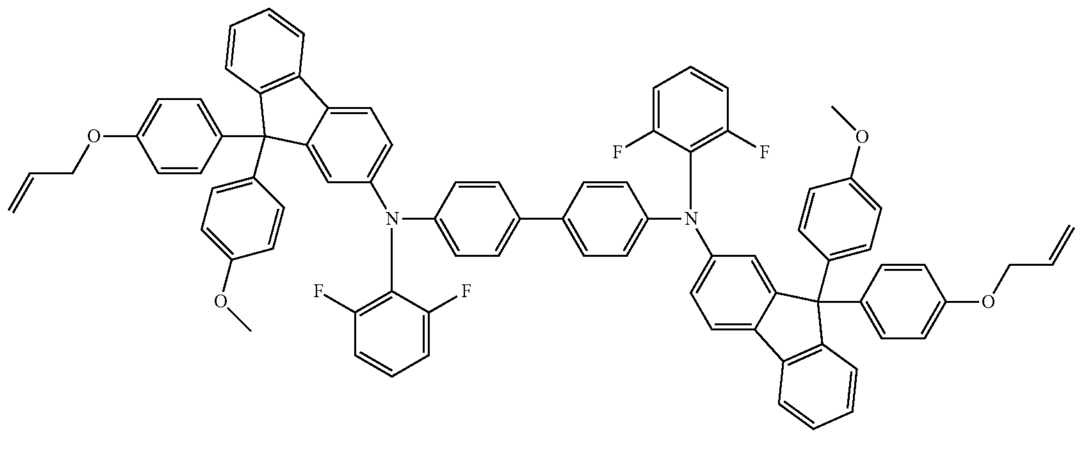

-continued
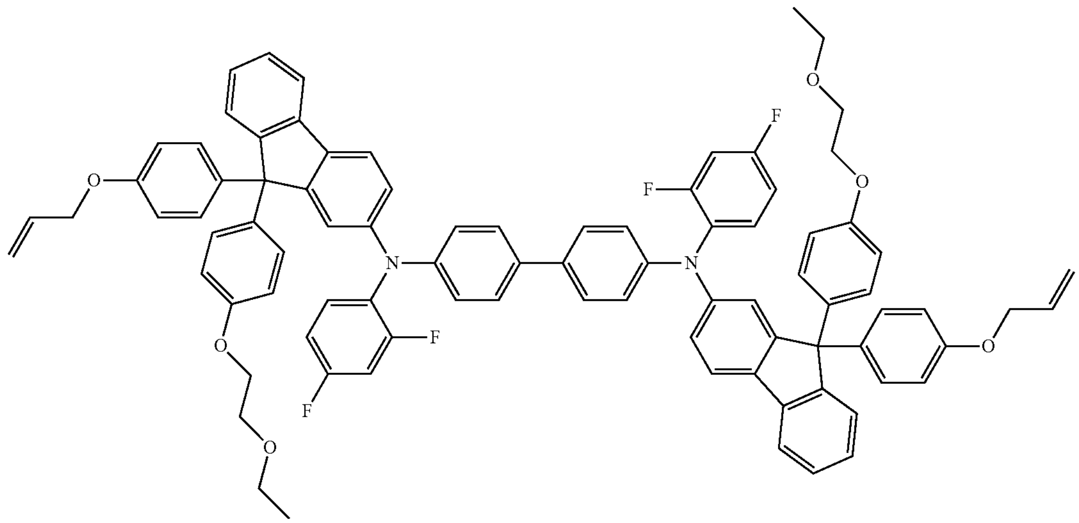
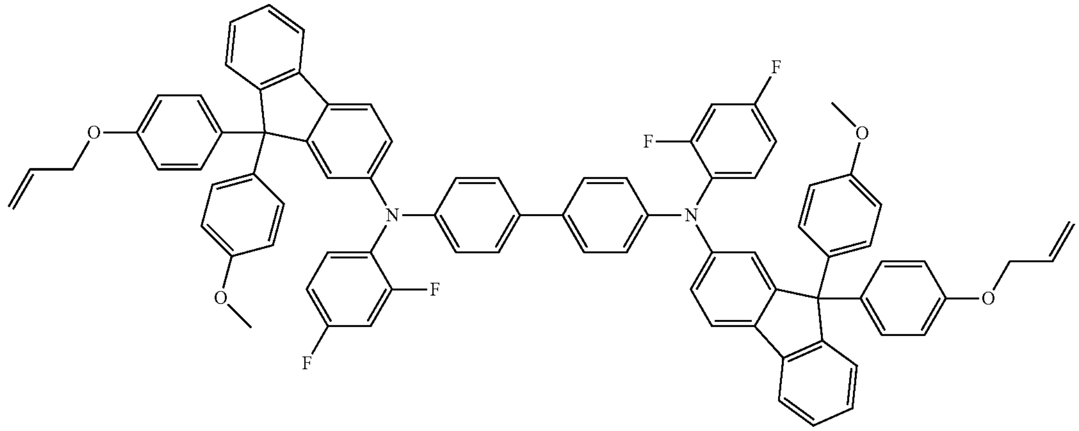
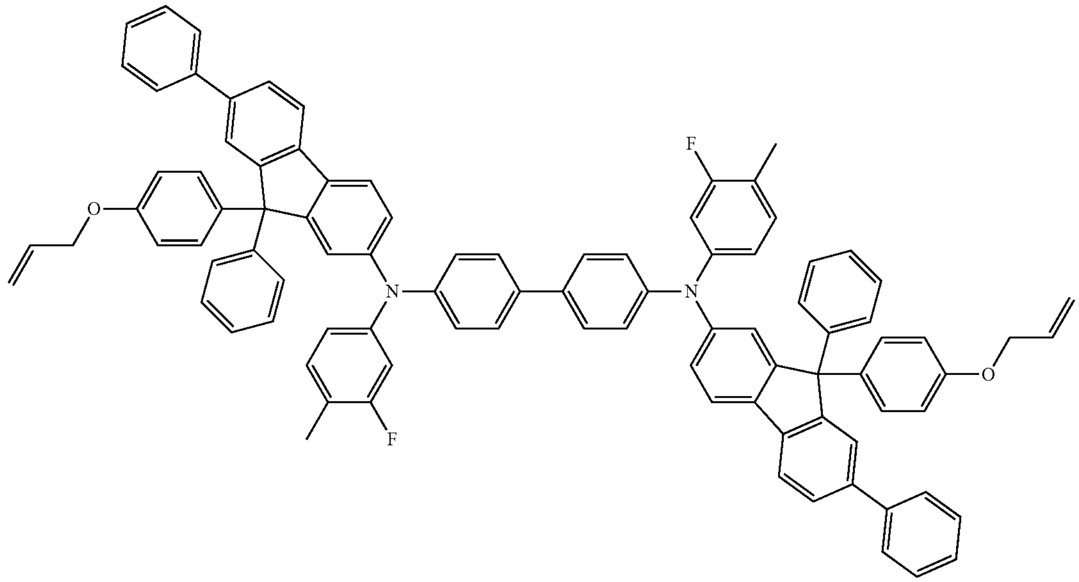

-continued
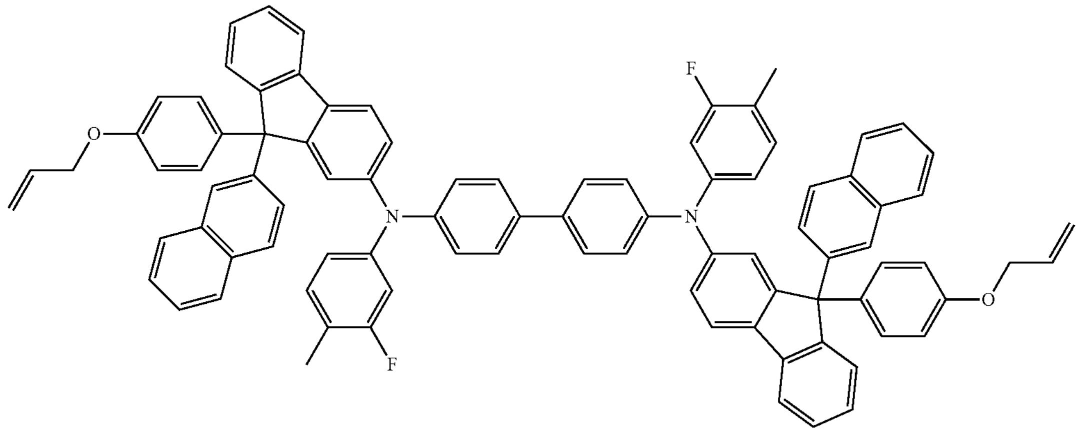
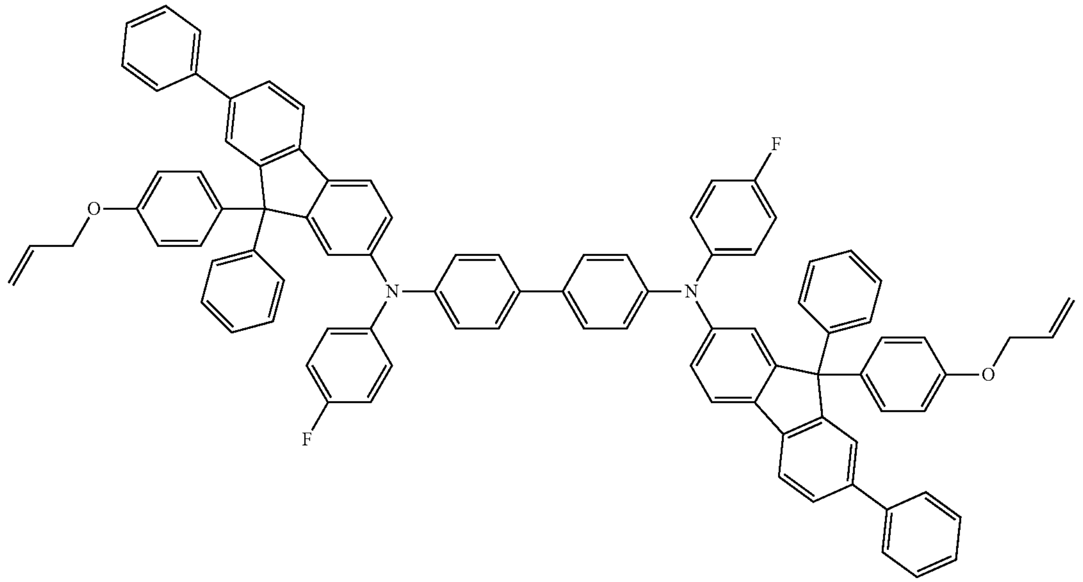
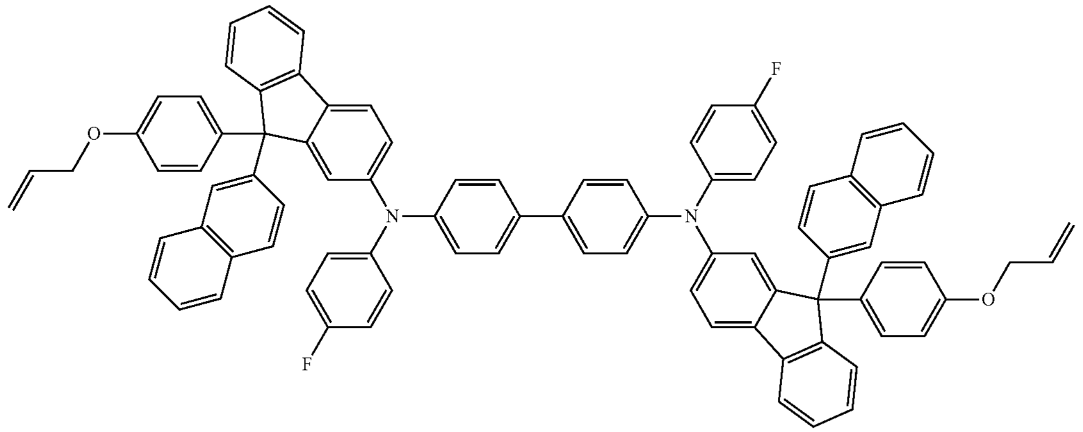

-continued
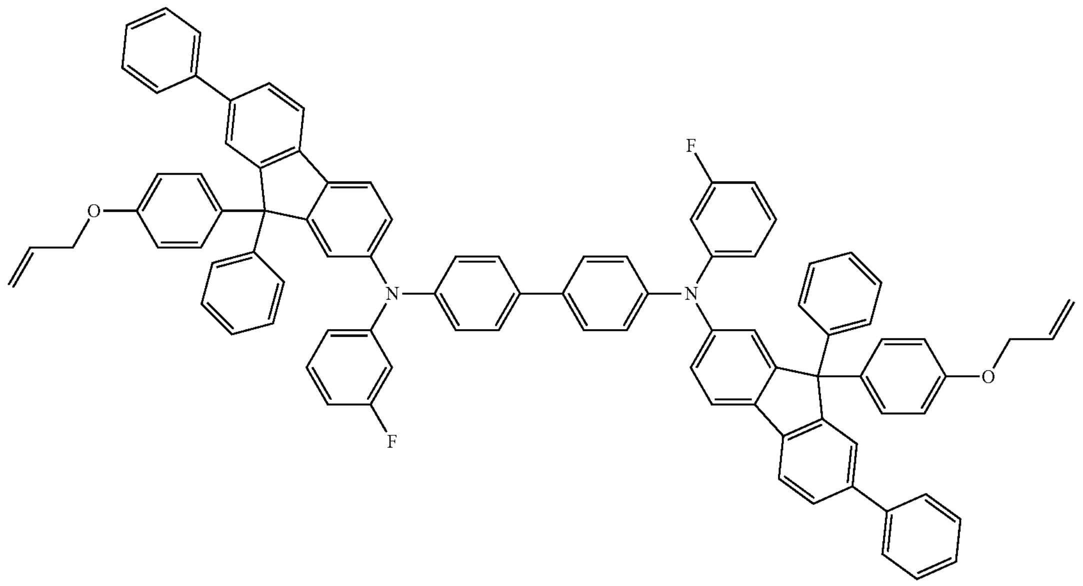
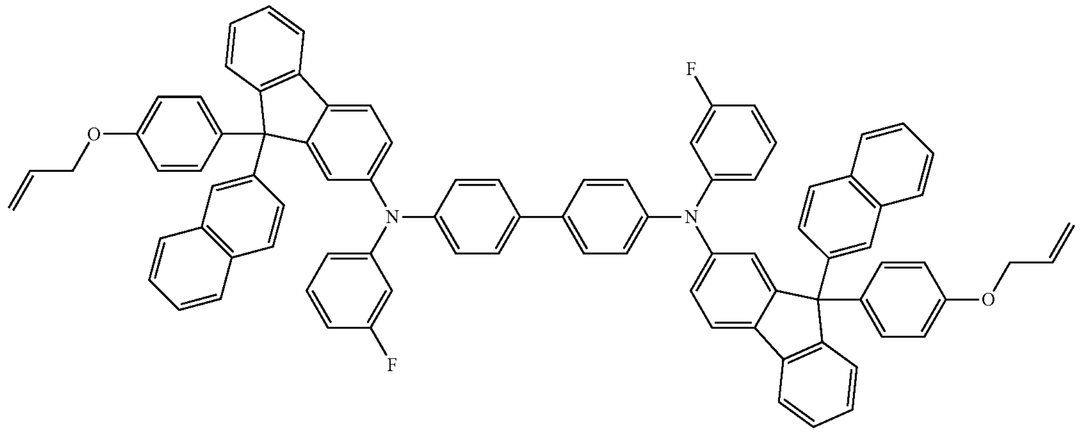
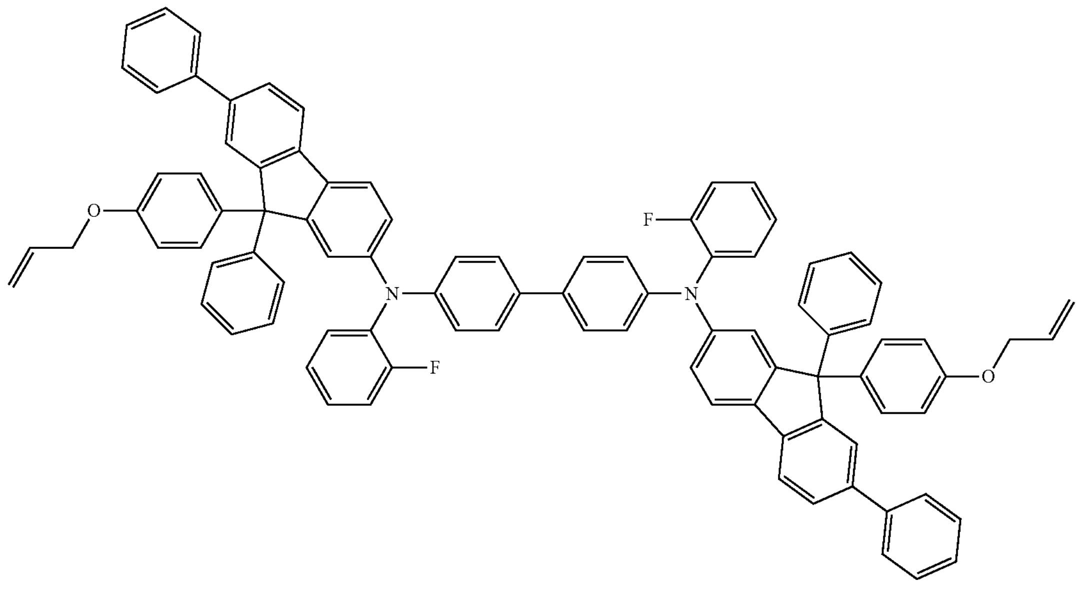

-continued
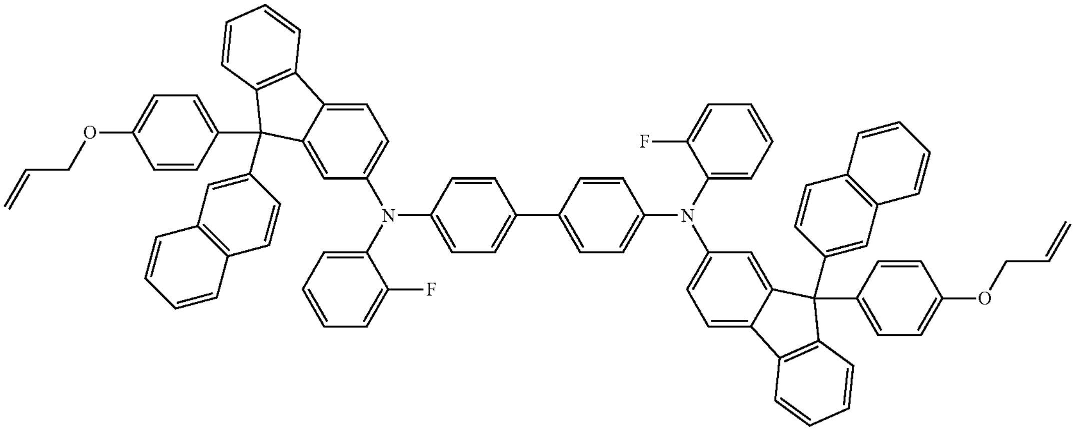
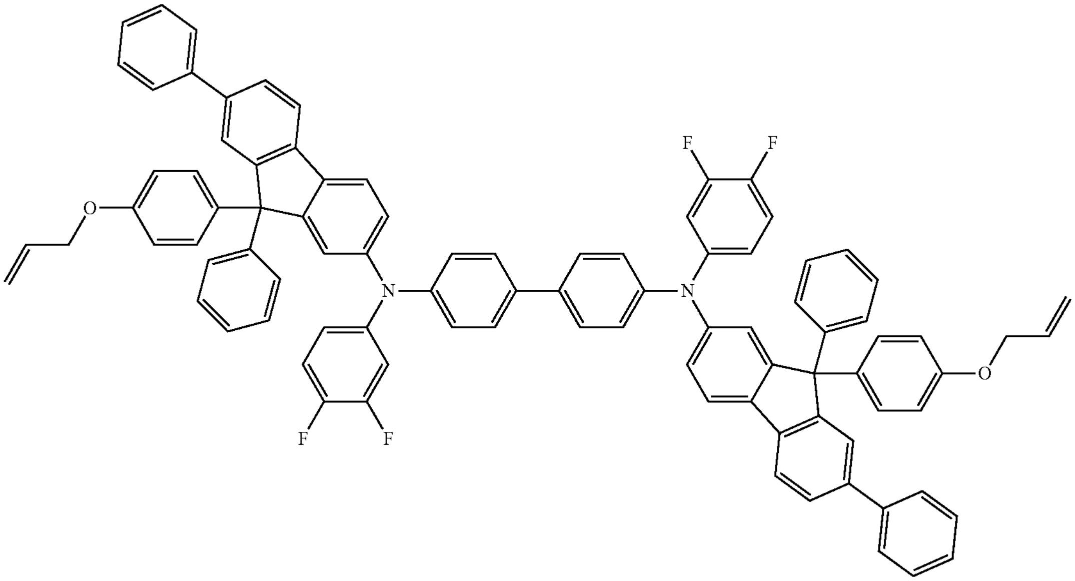
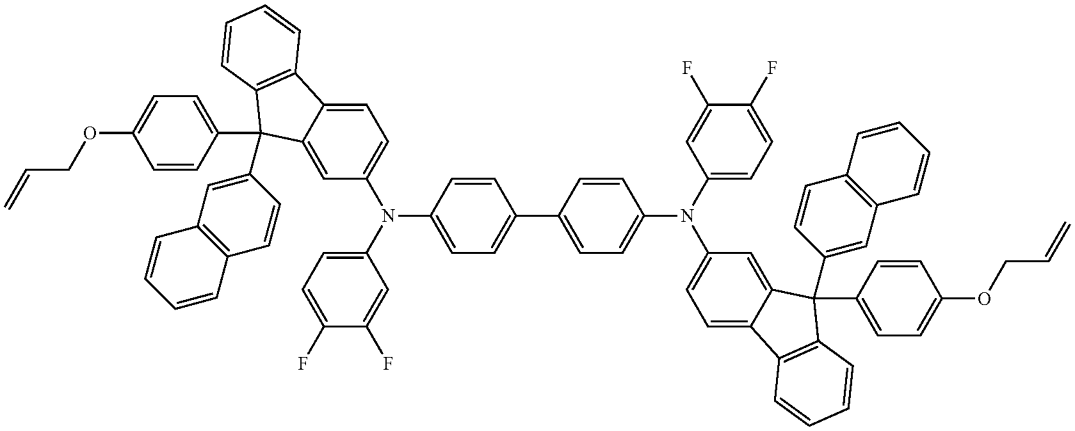

-continued
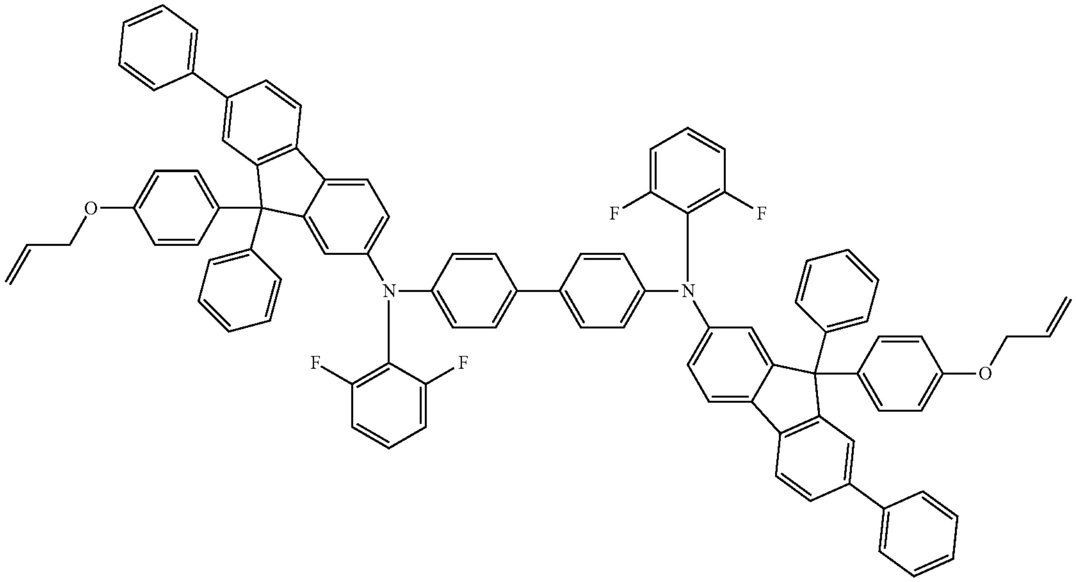
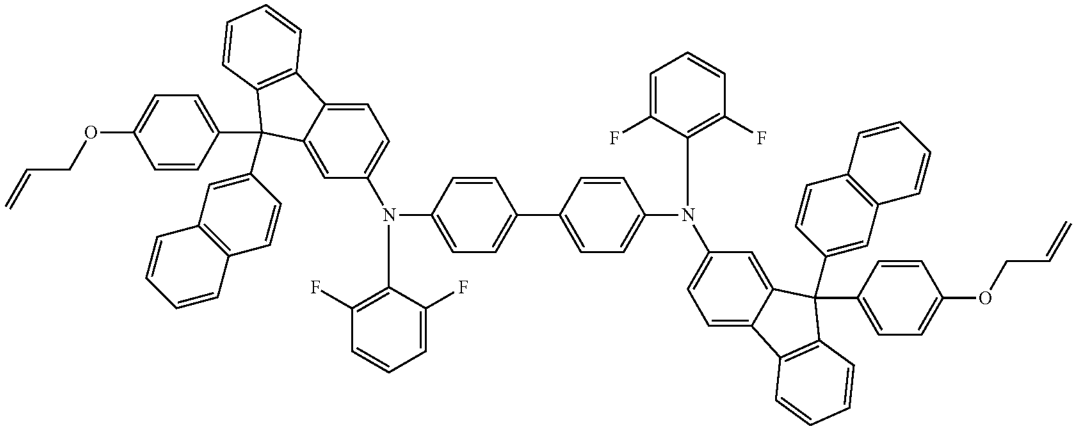
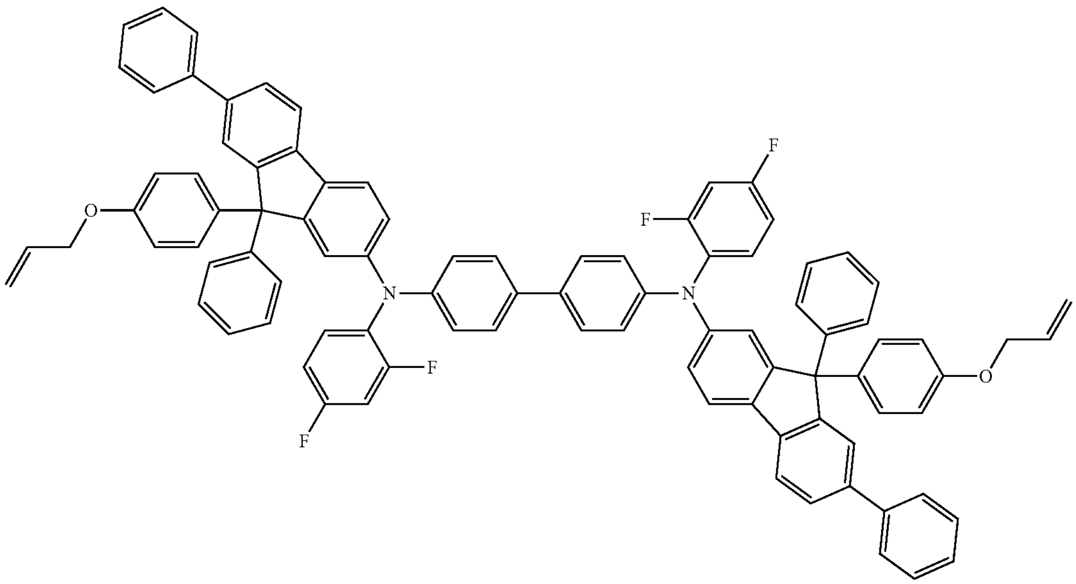

-continued
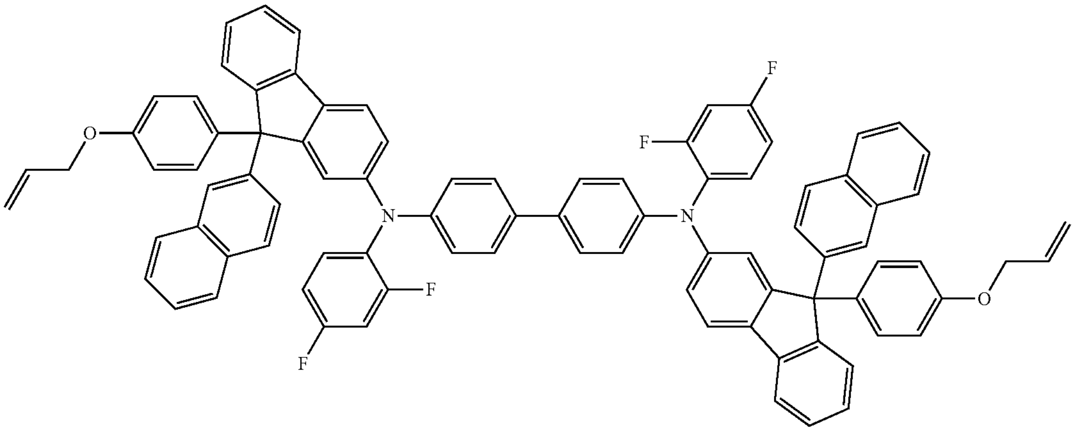
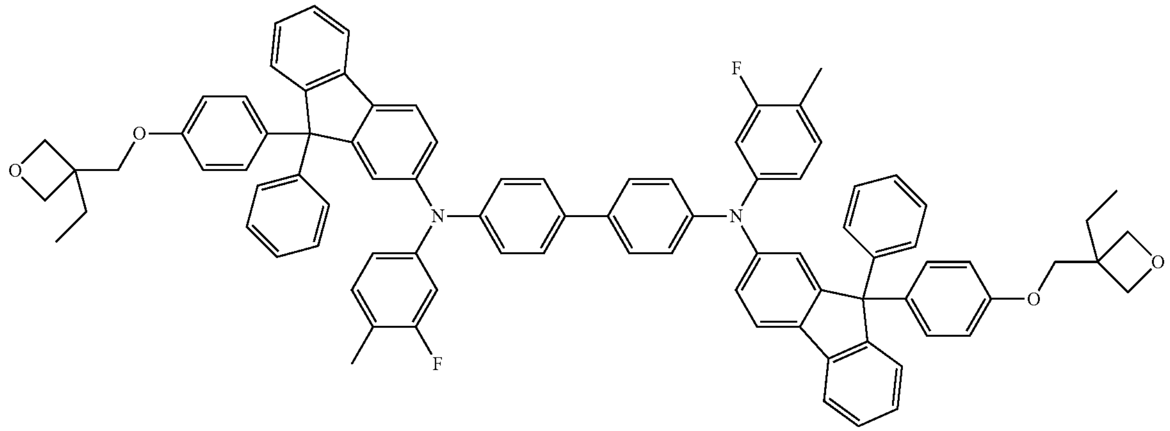
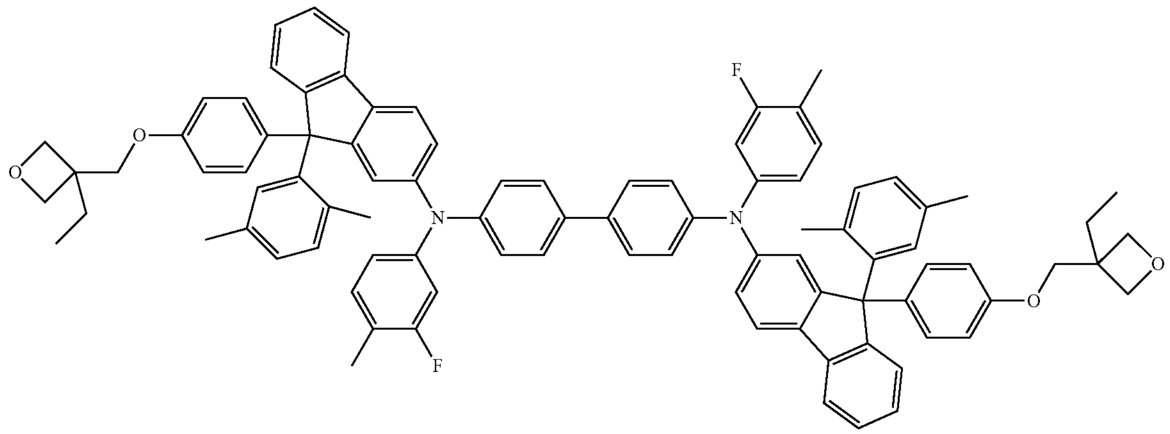
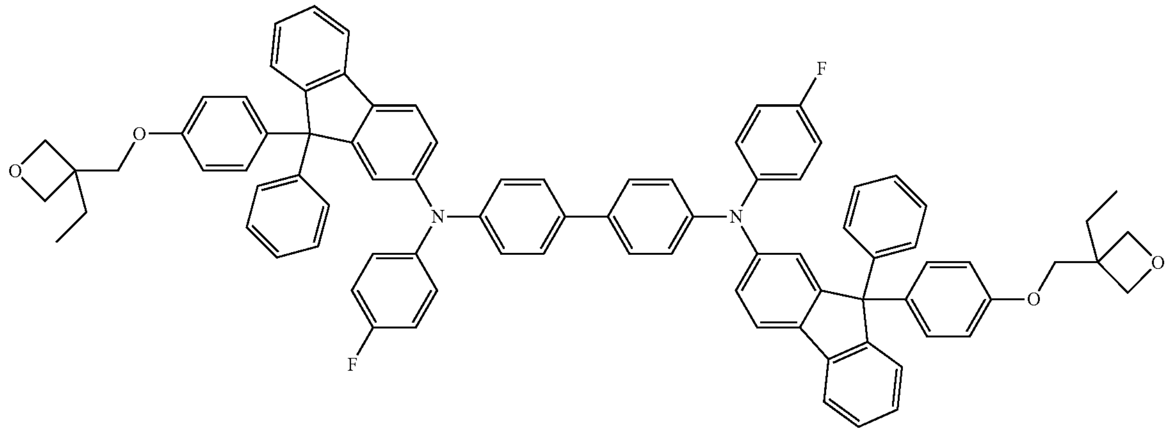

-continued
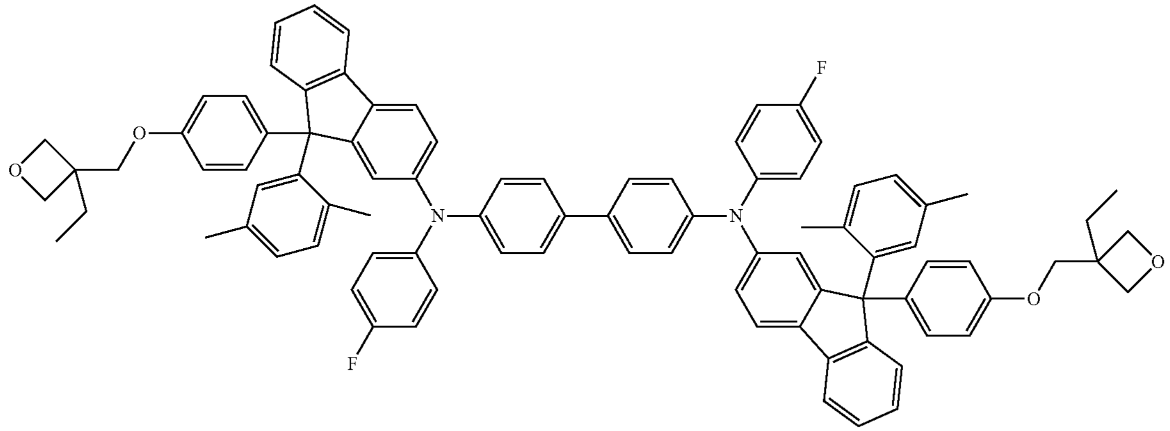
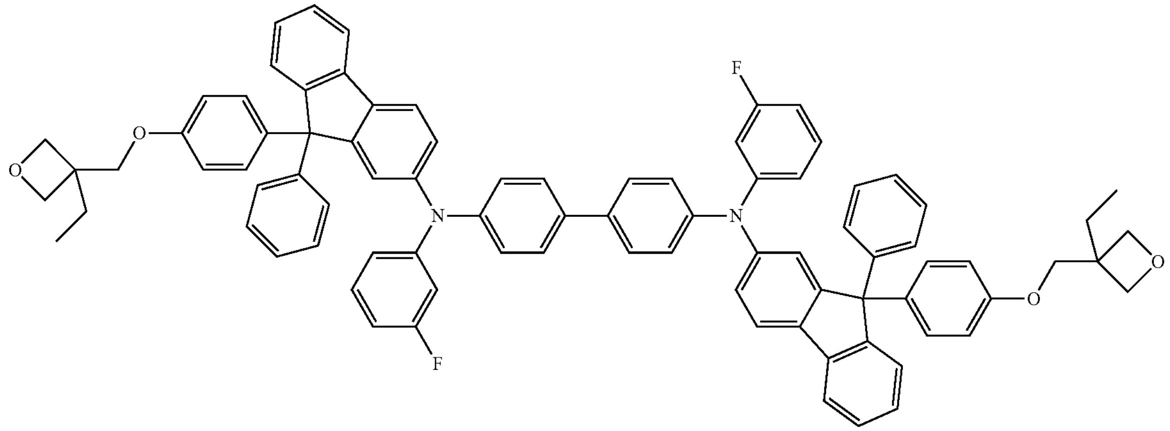
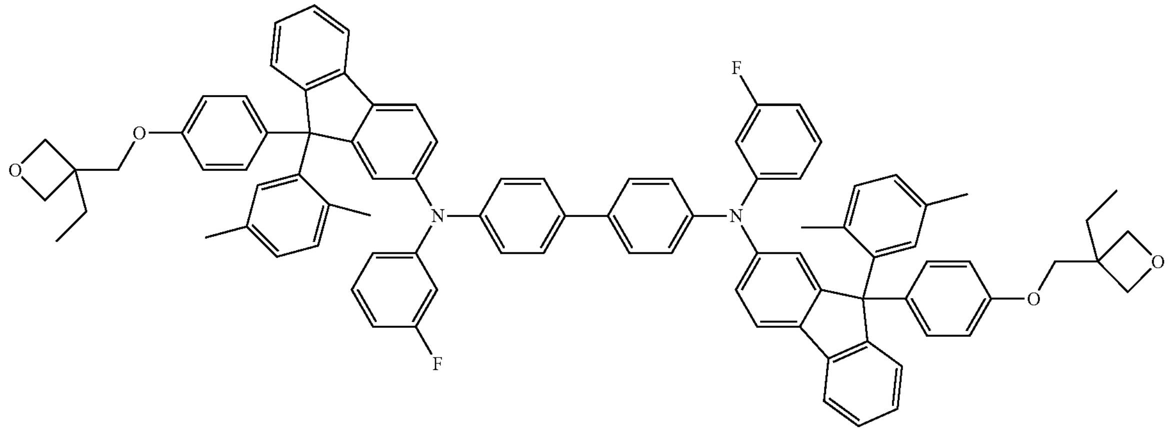
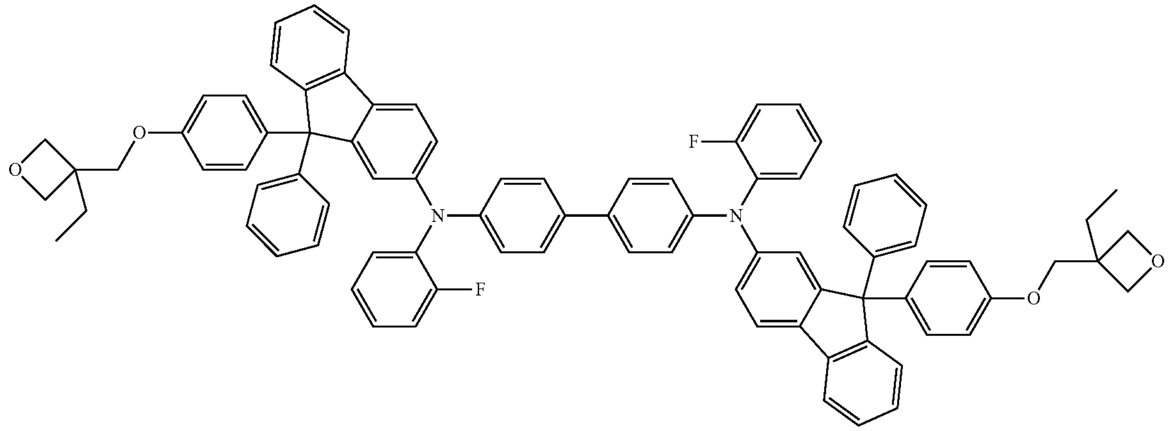

-continued
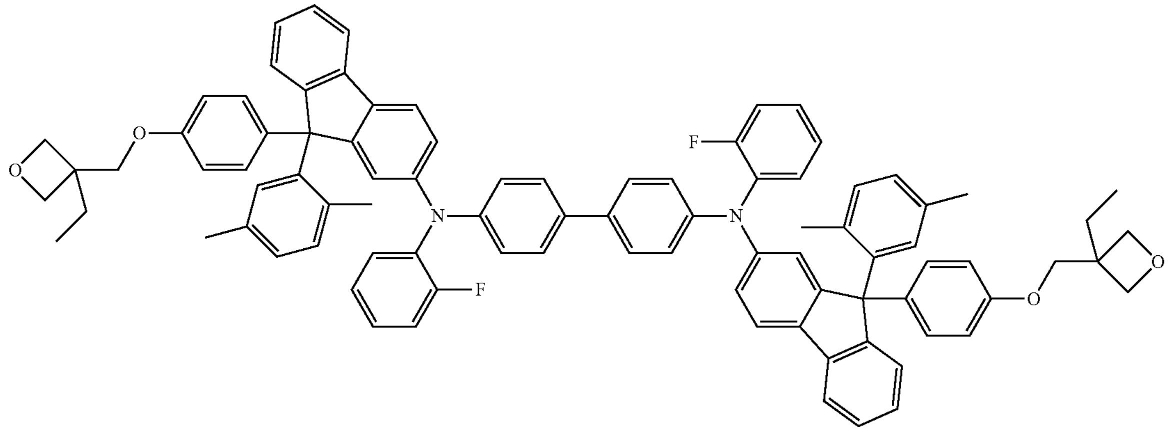
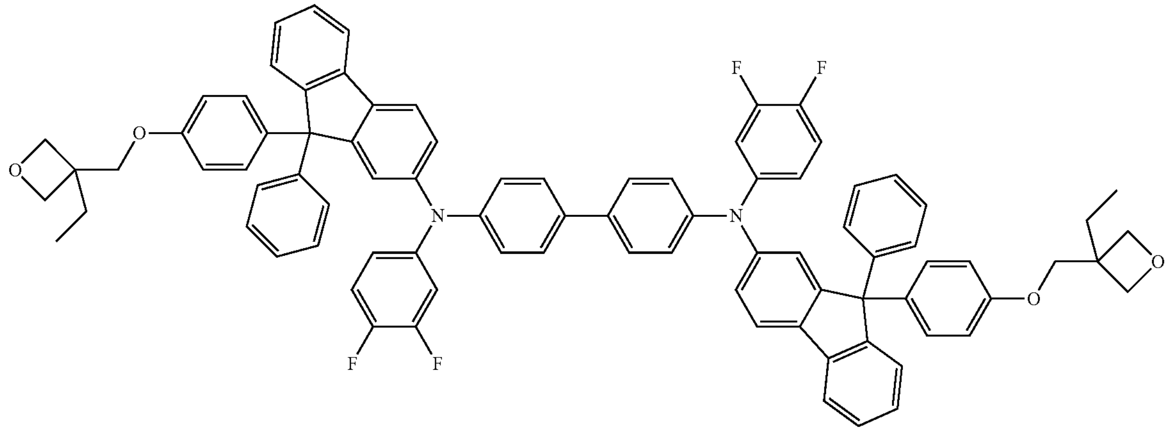
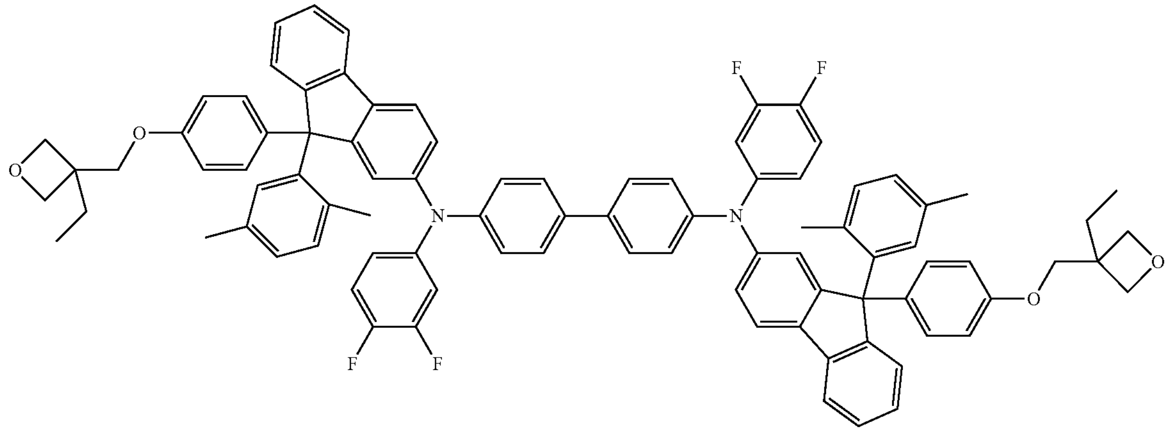
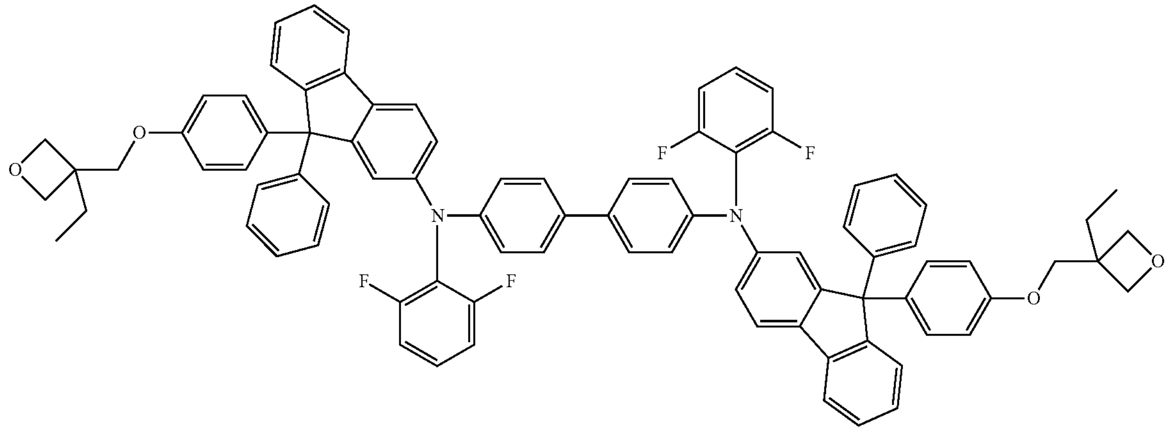

-continued
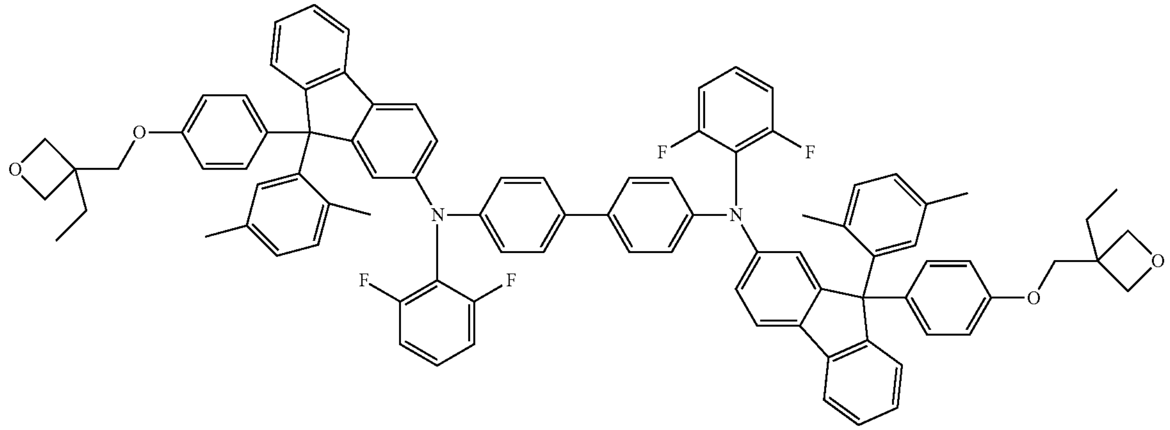
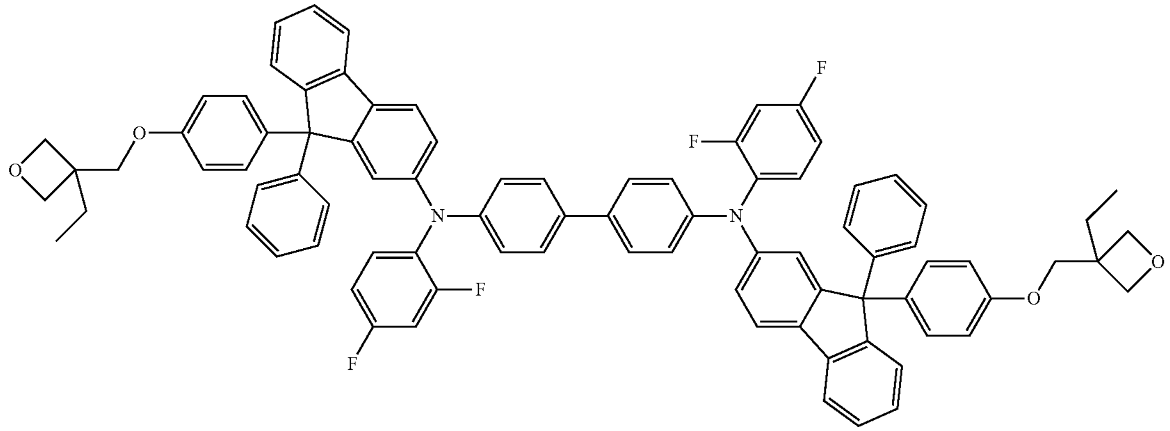
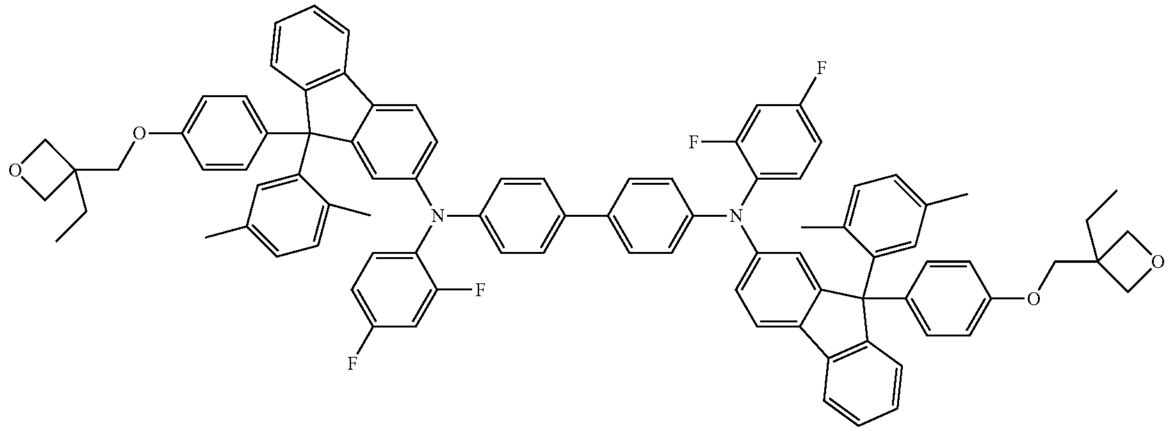
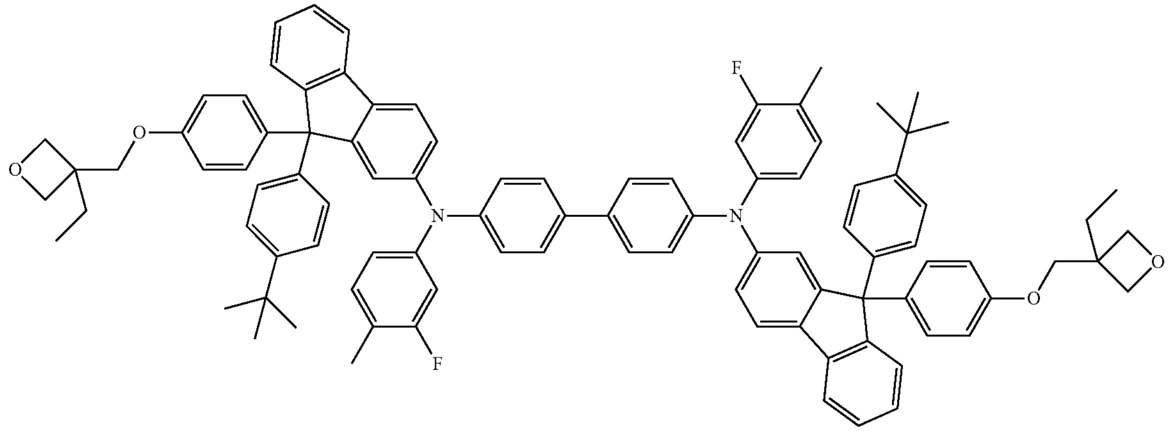

-continued
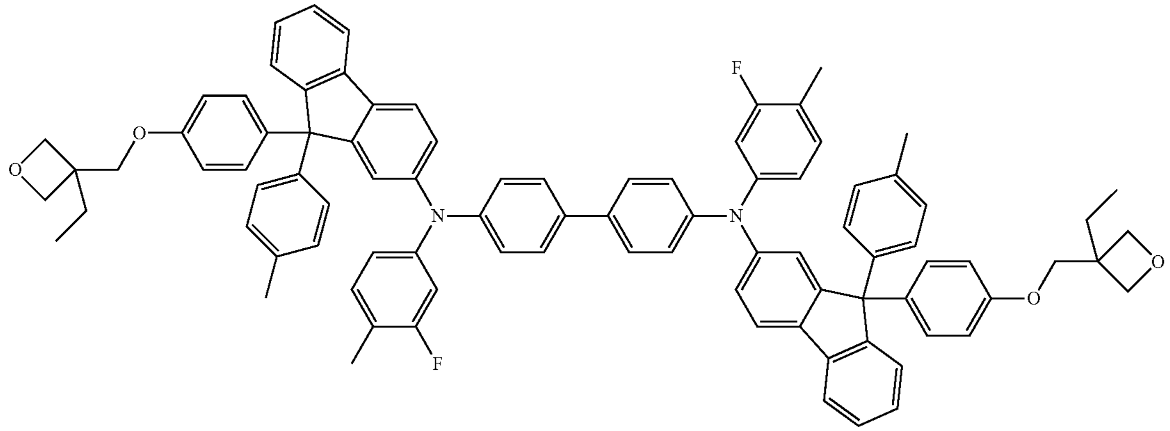
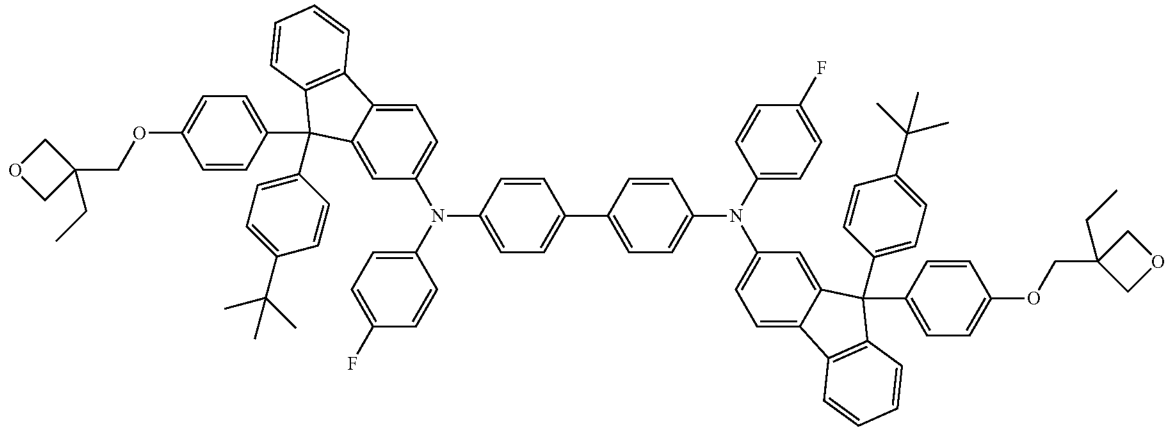
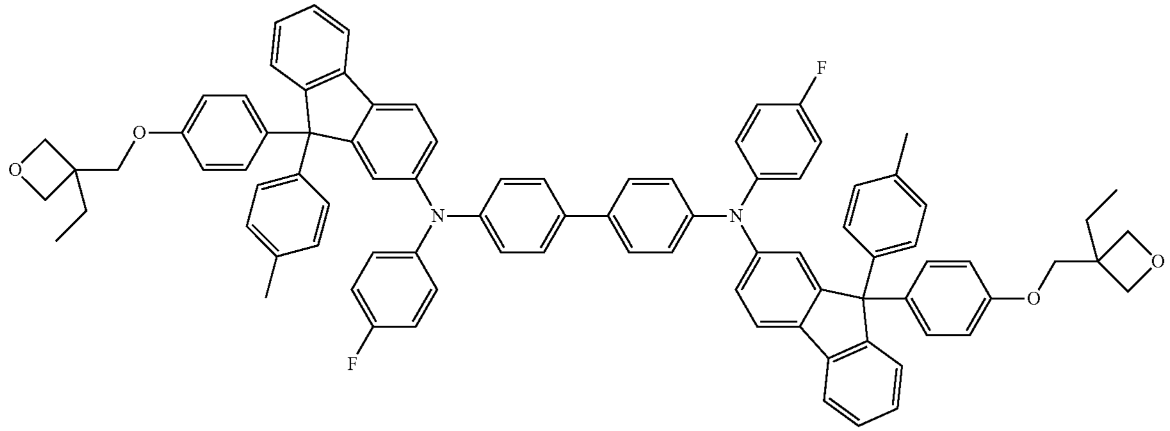
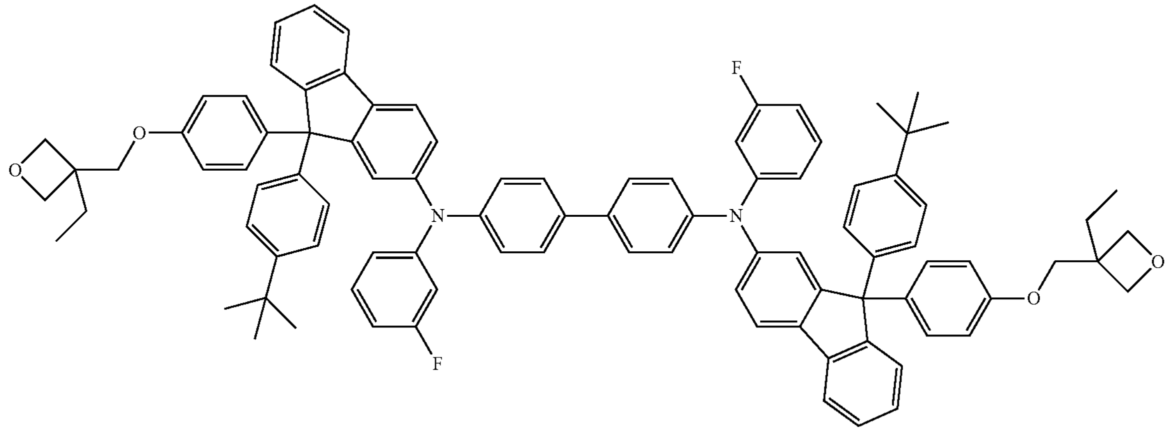

-continued
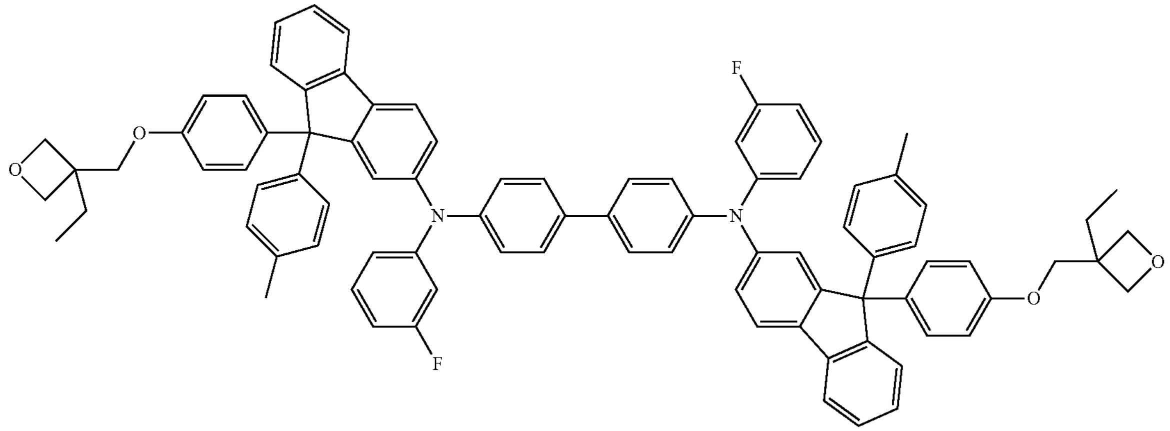
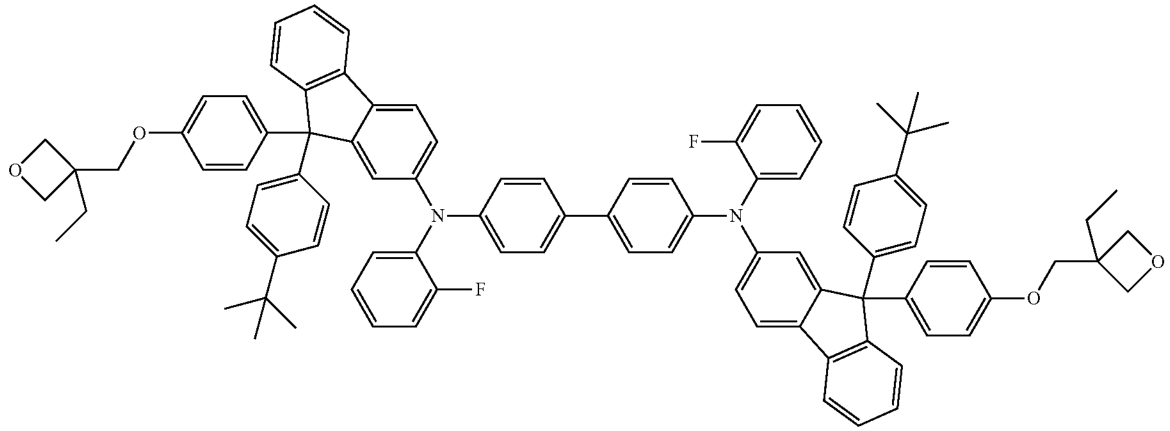
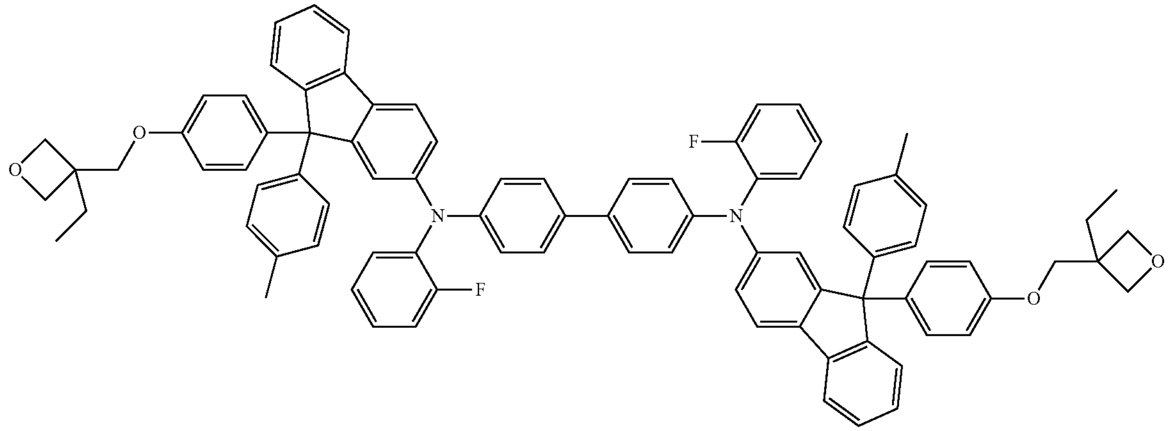
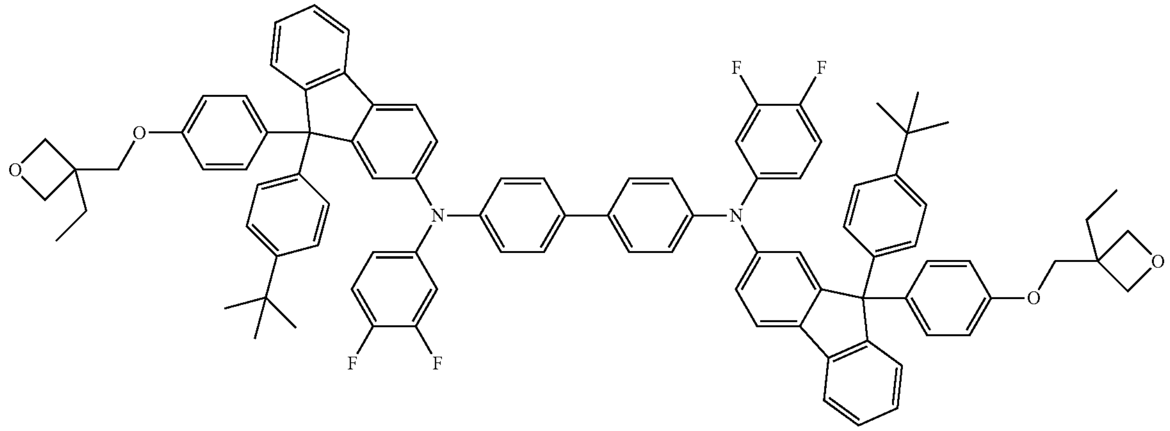

-continued
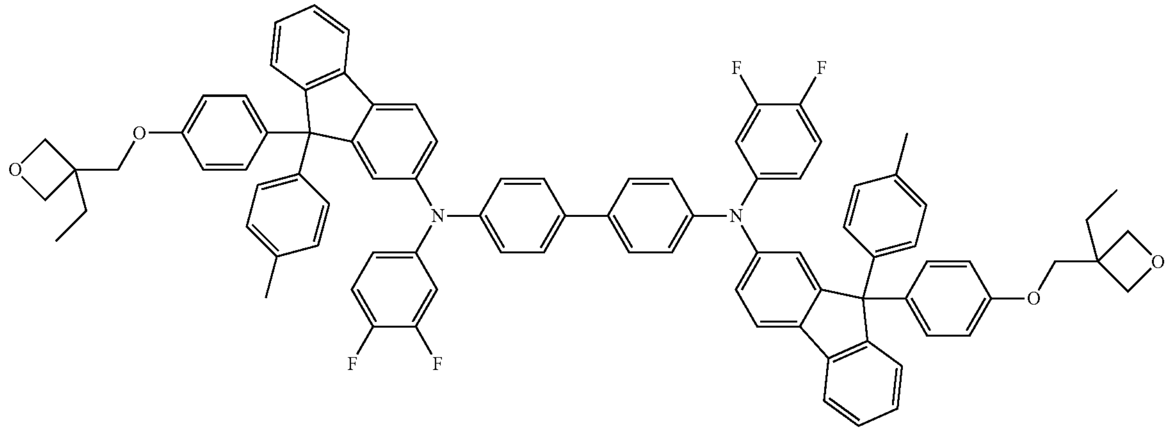
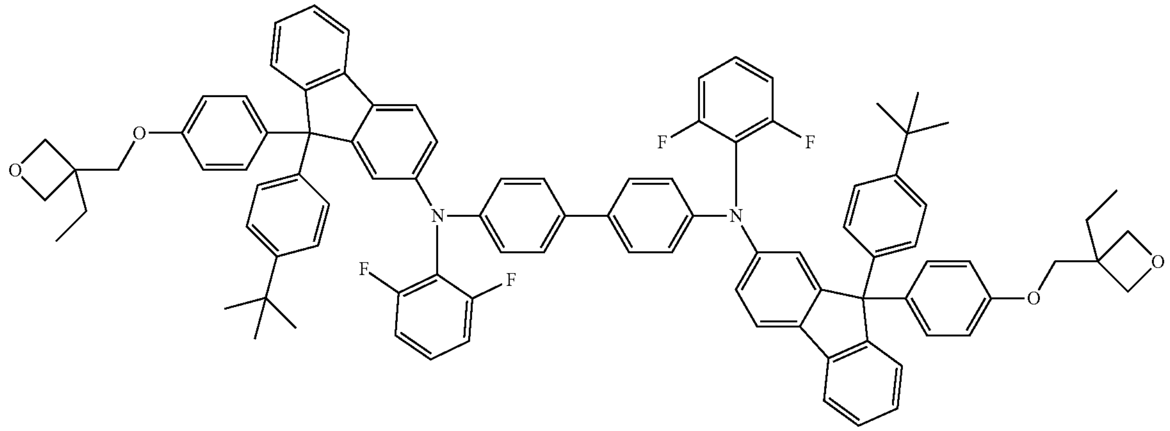
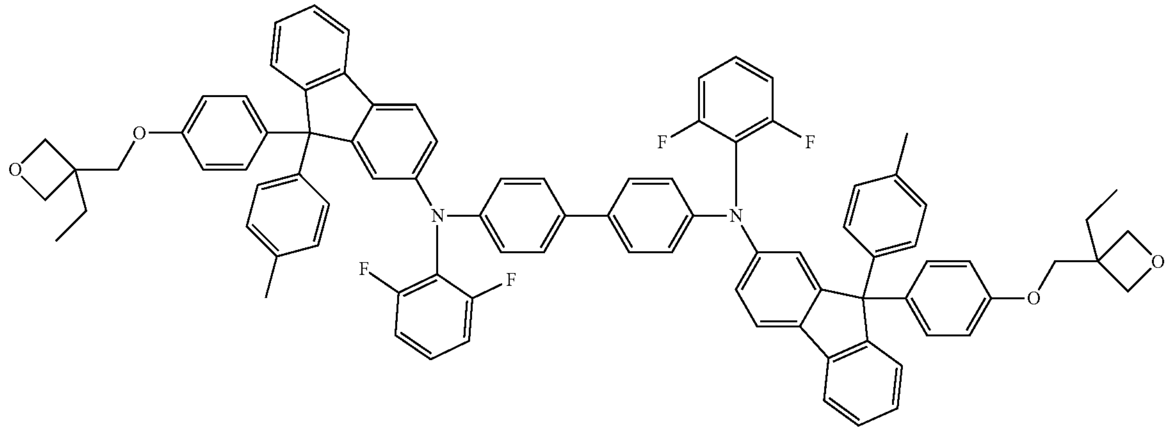
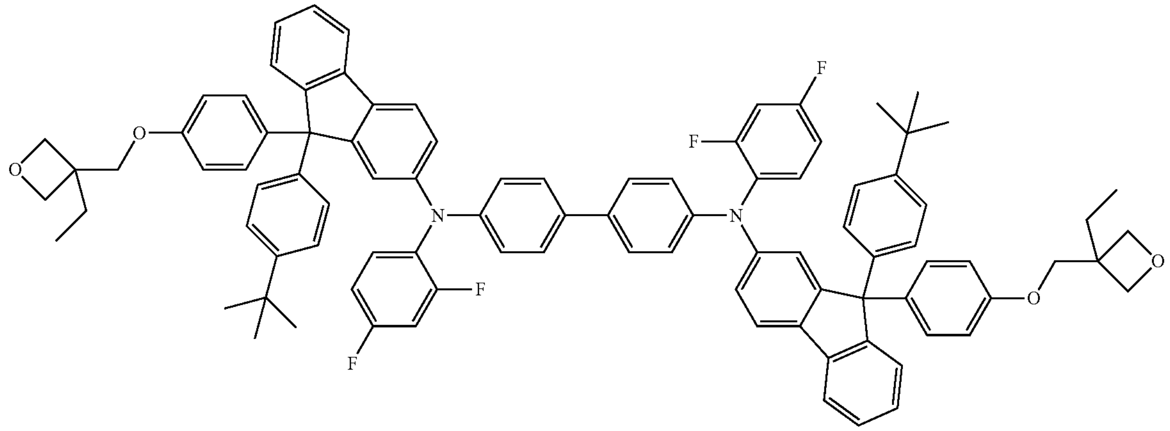

-continued
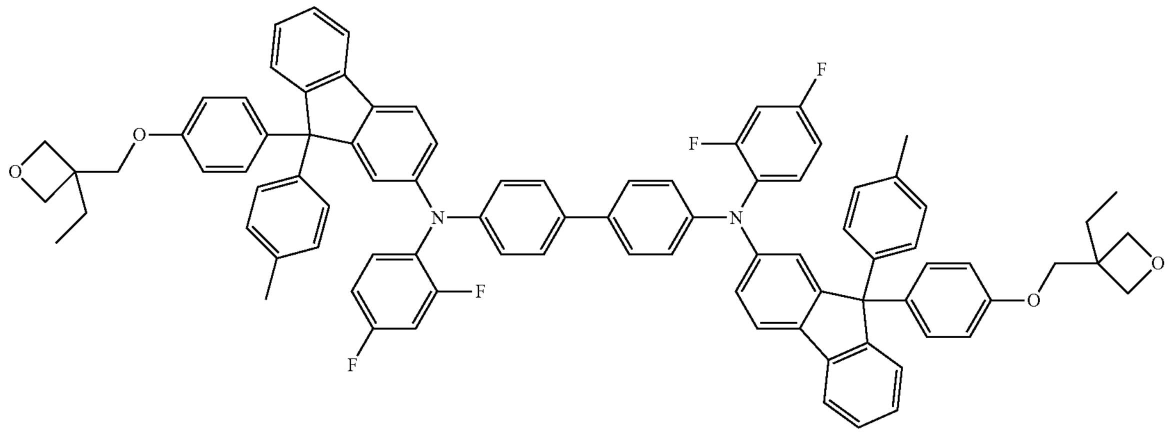
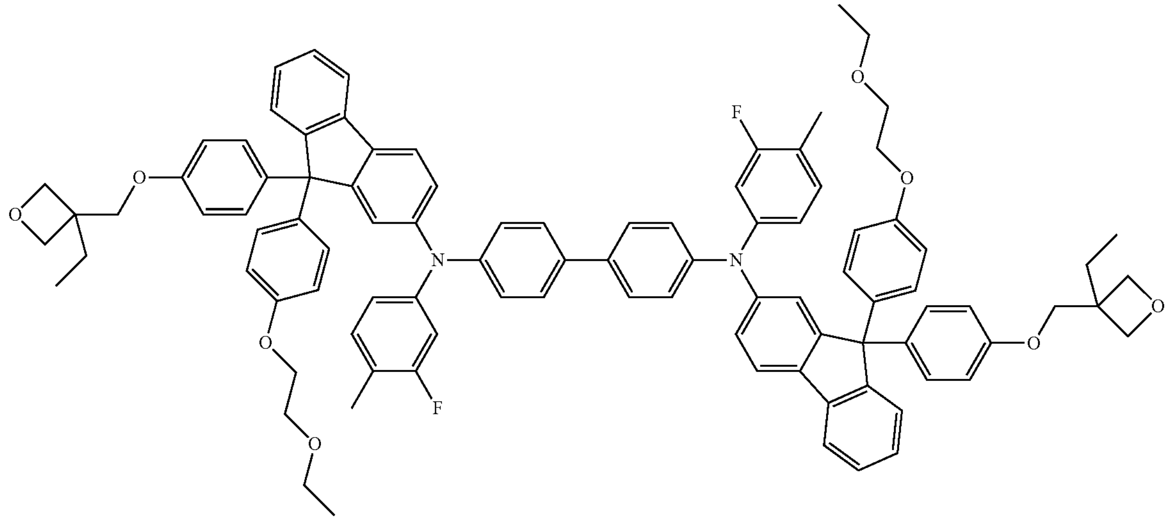
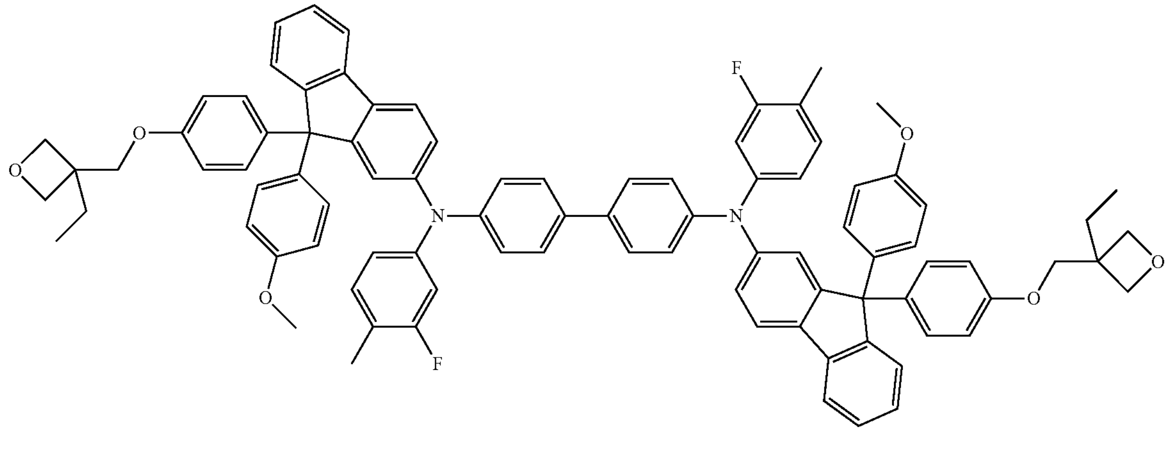

-continued
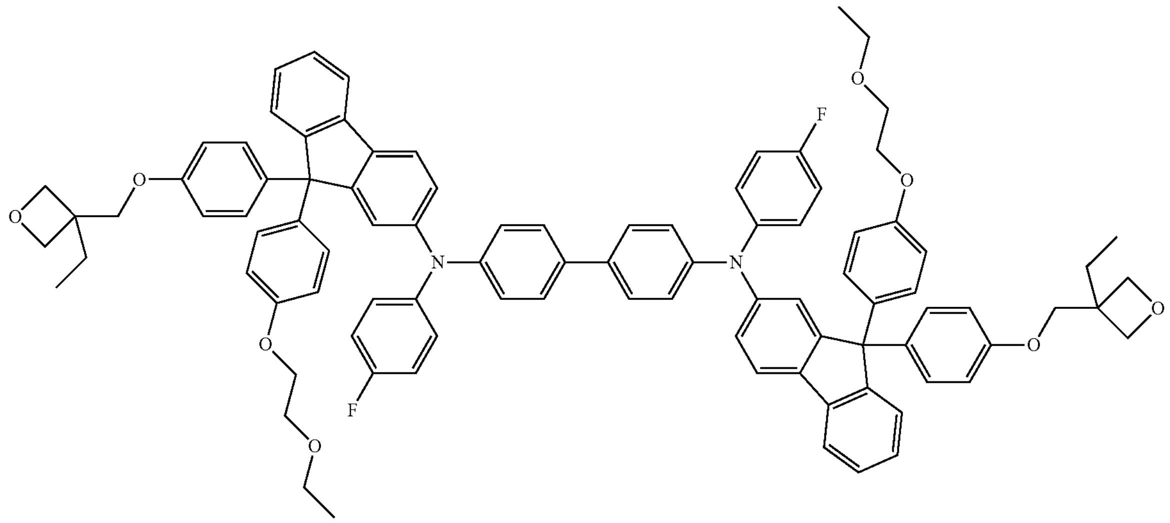
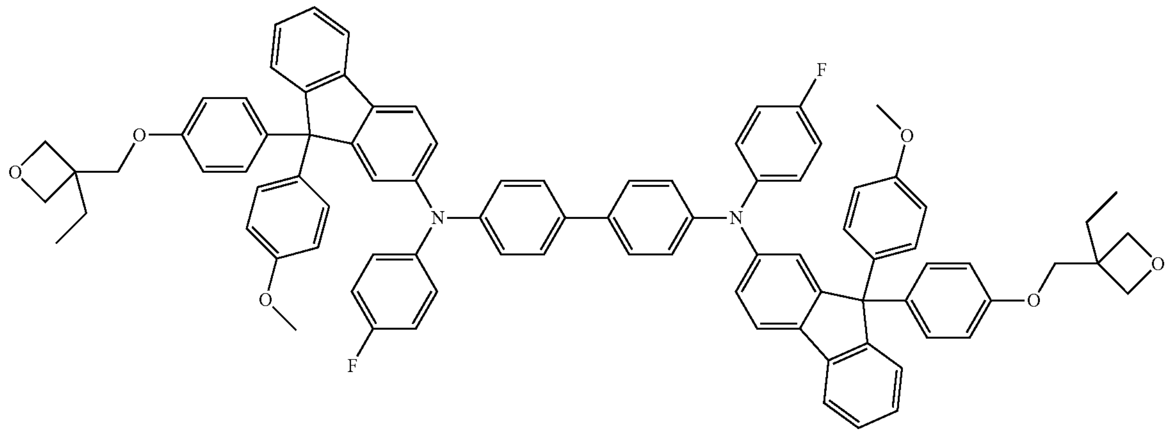
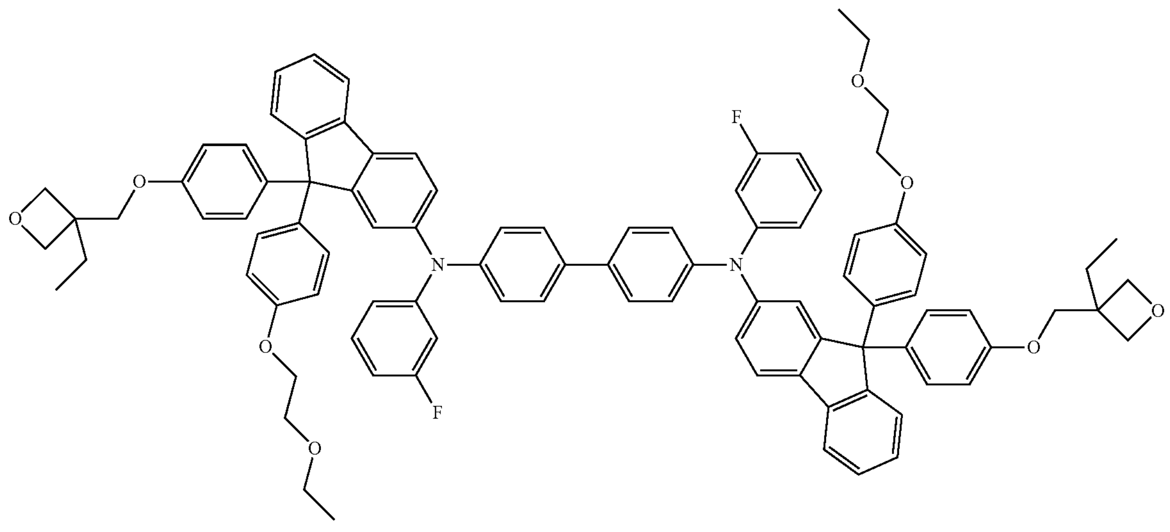

-continued
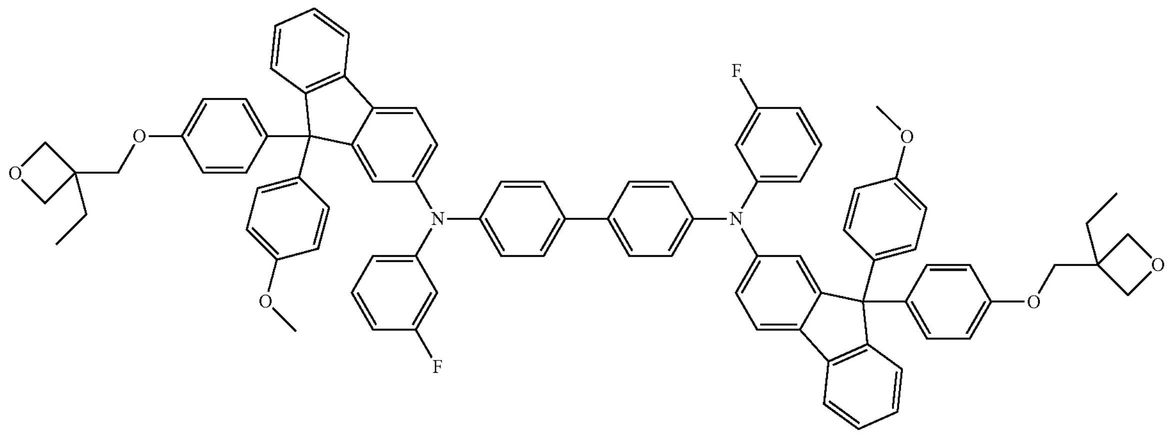
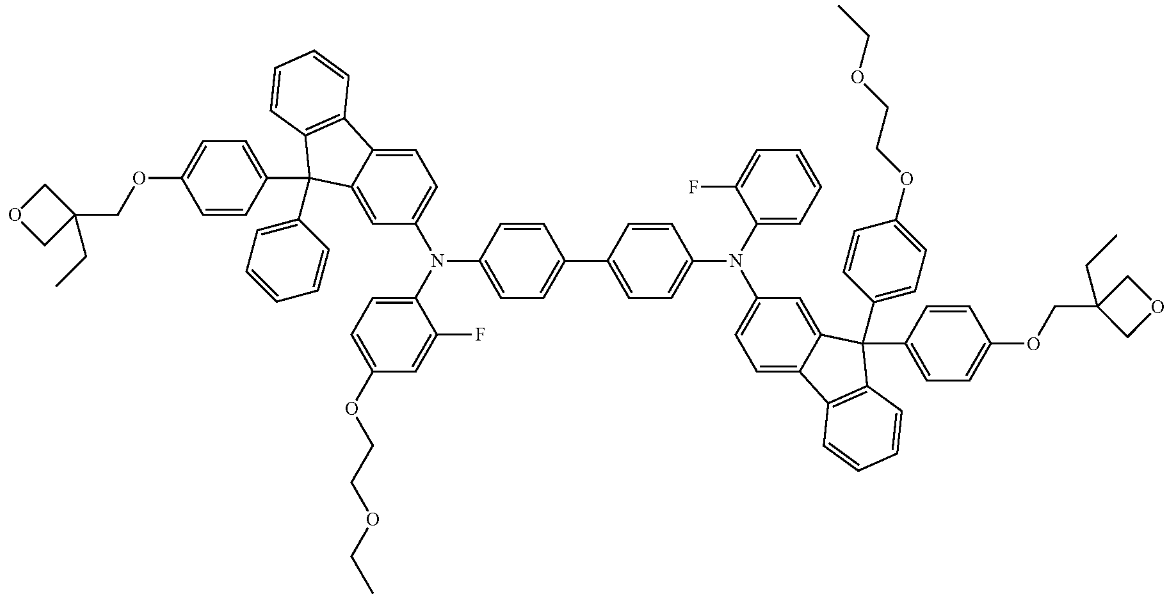
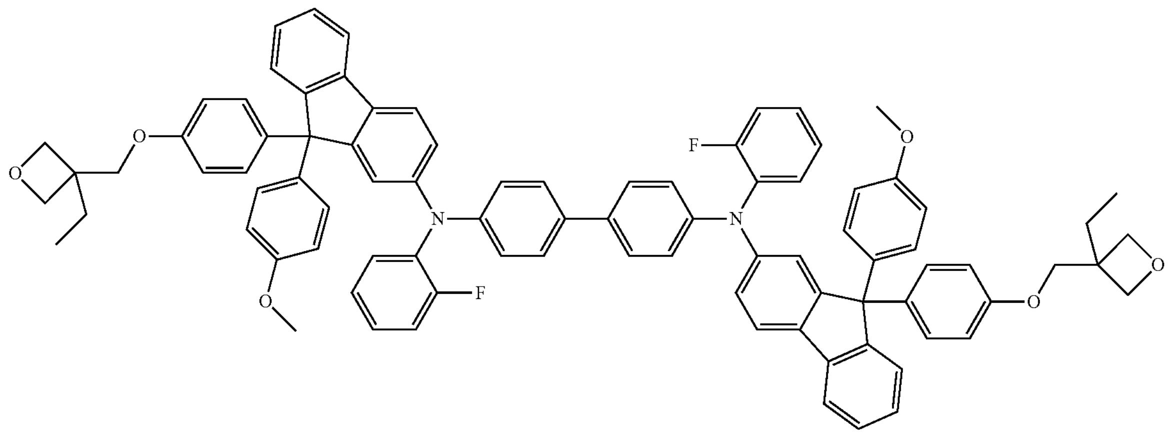

-continued
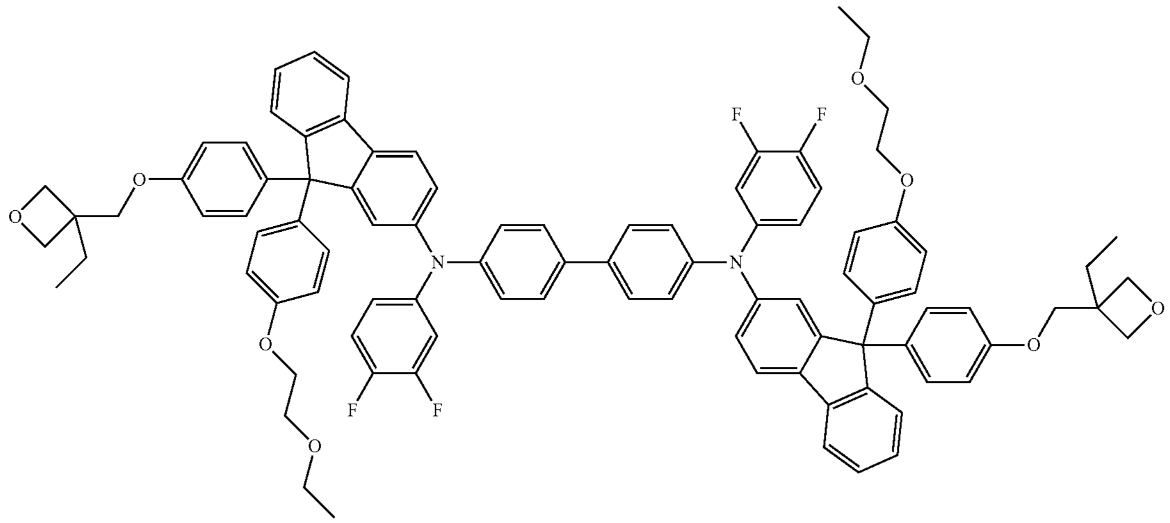
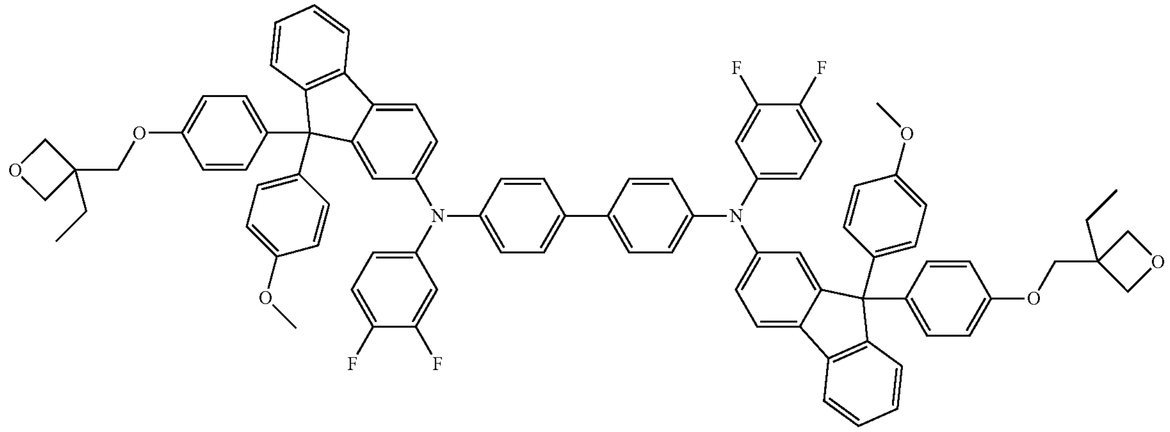
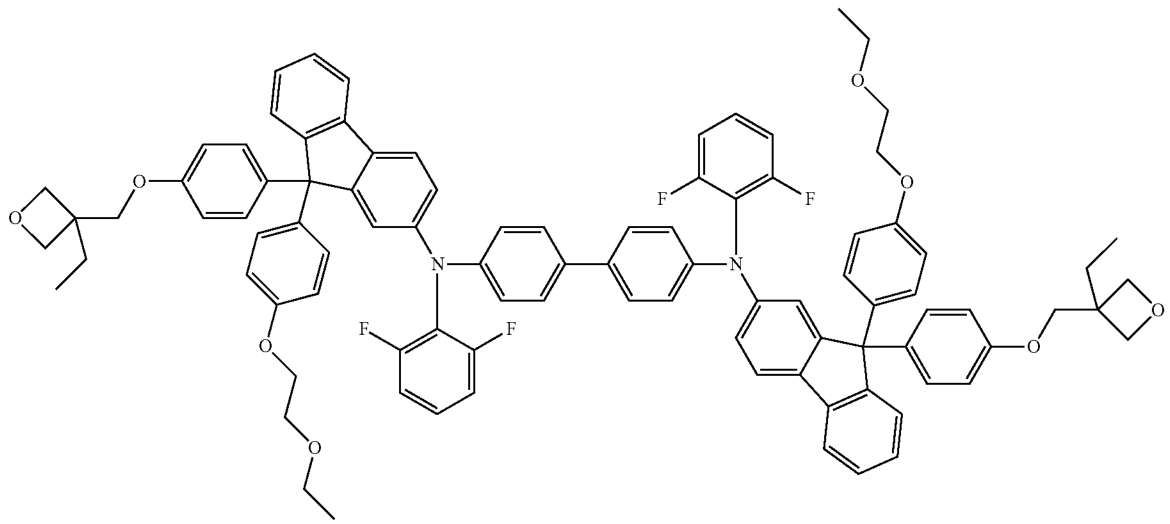

-continued
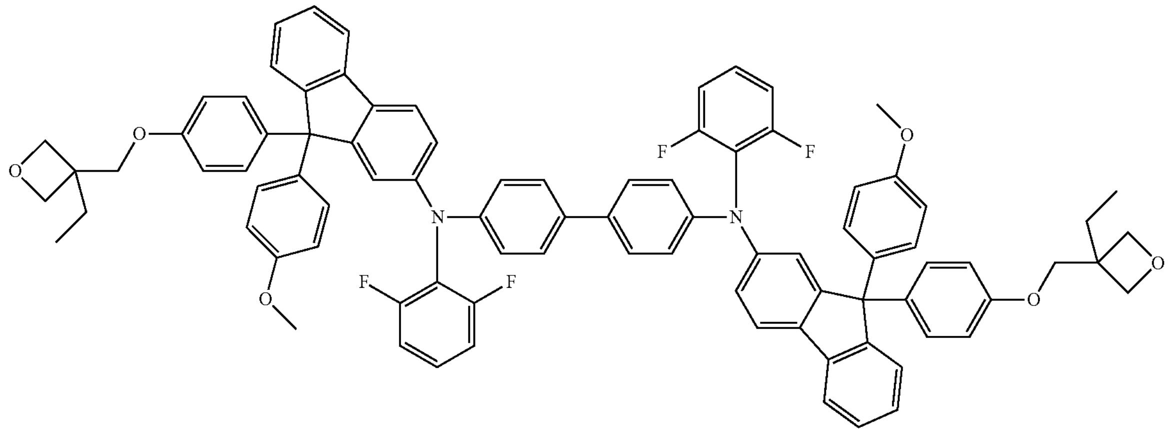
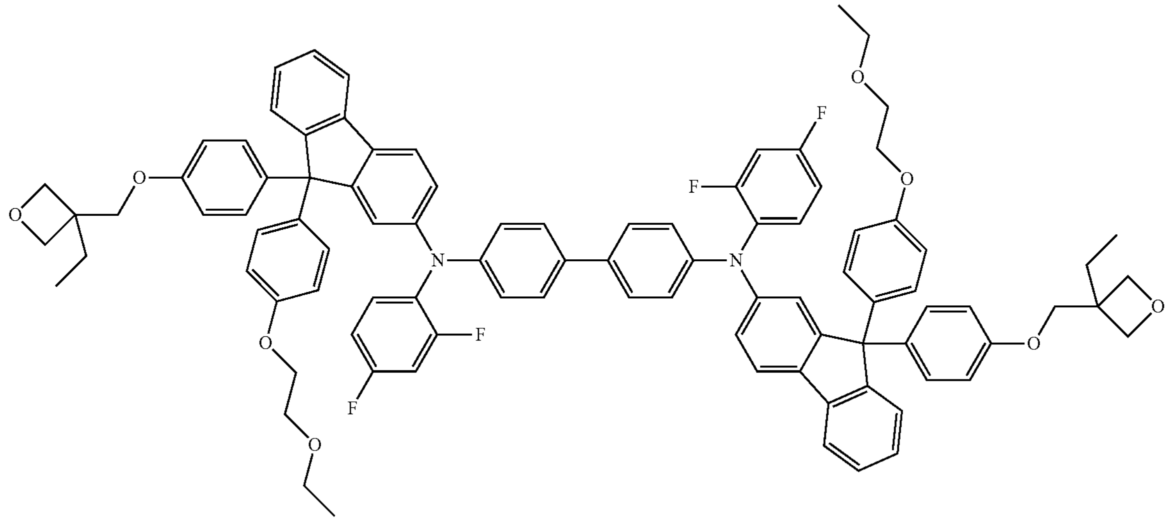
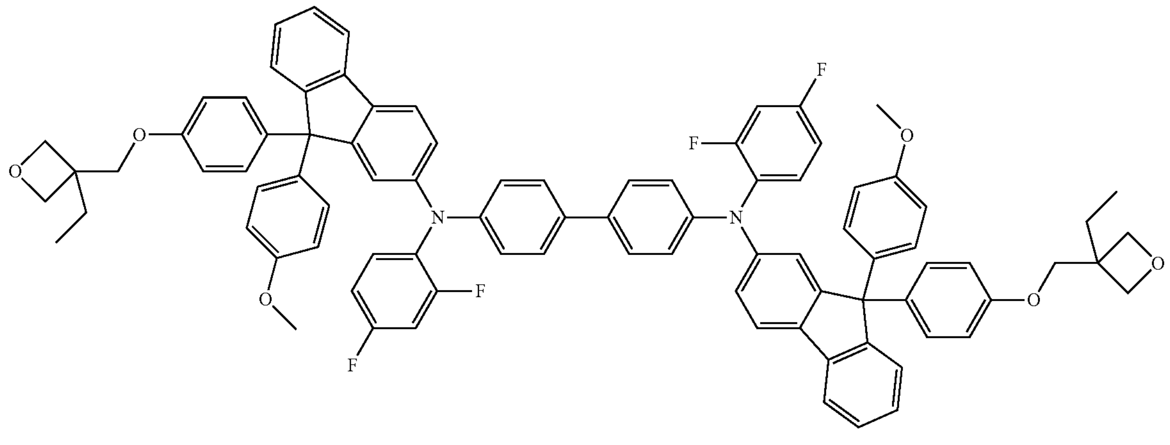

-continued
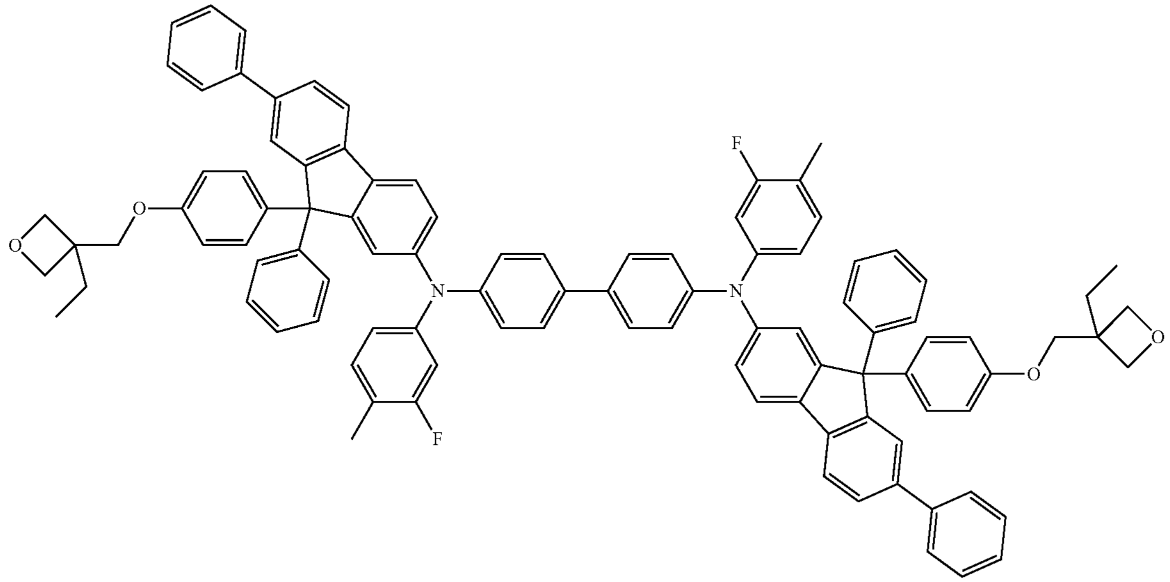
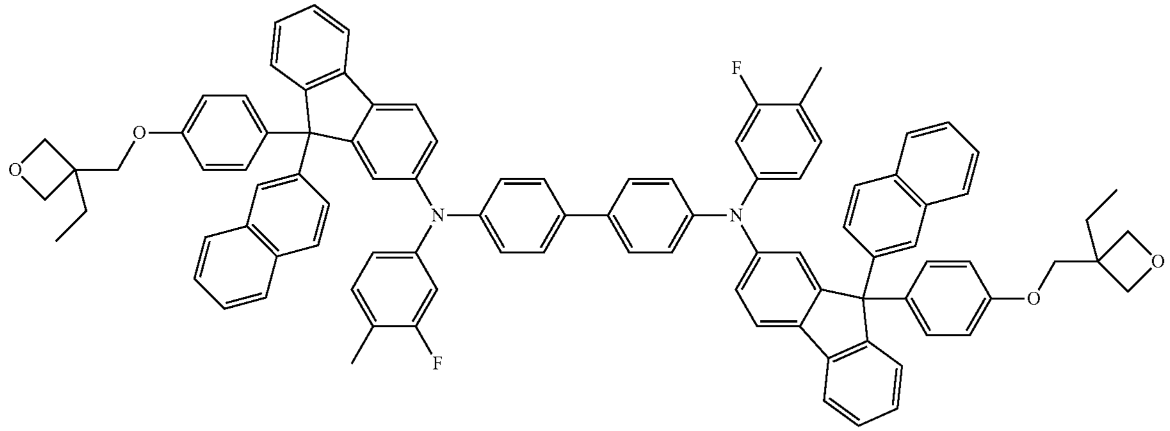
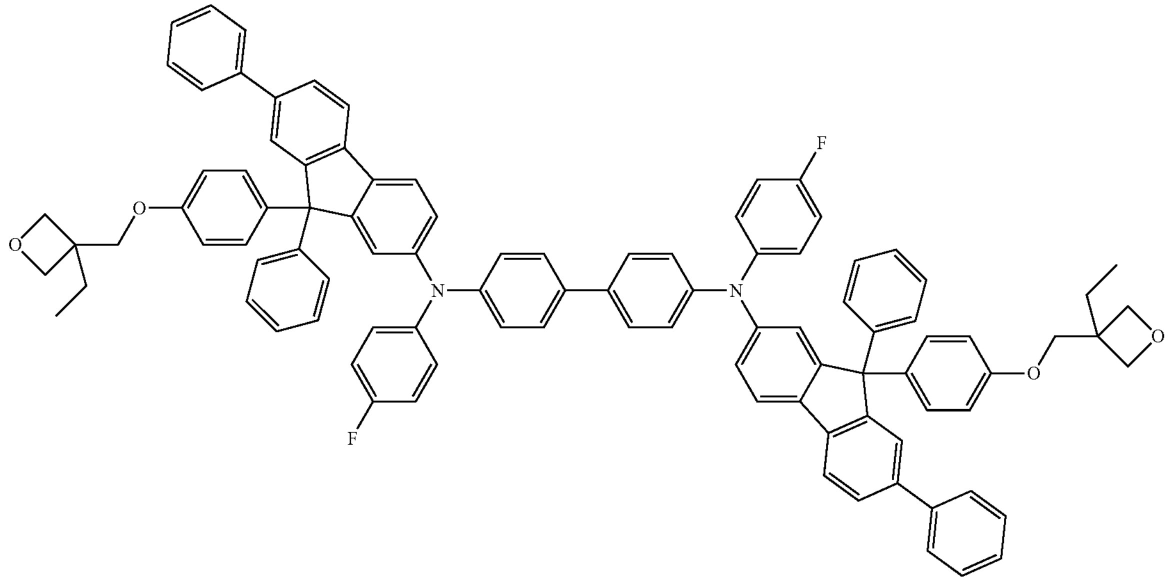

-continued
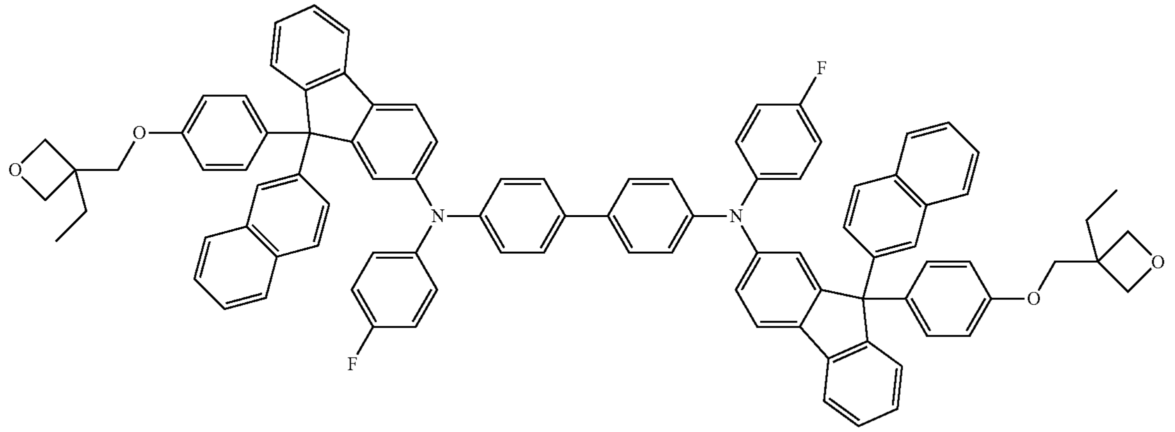
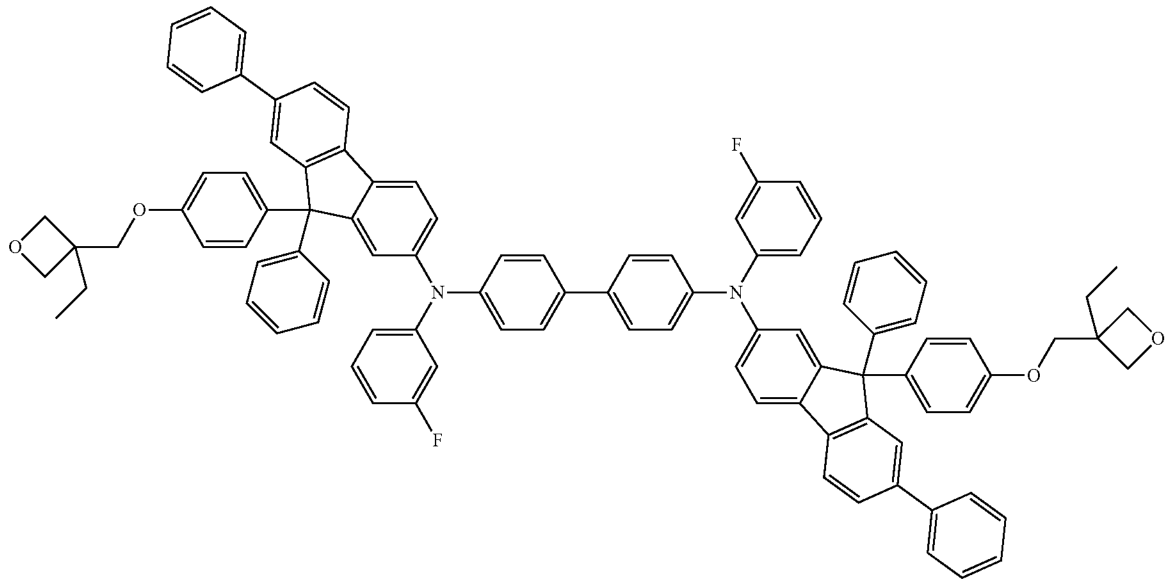
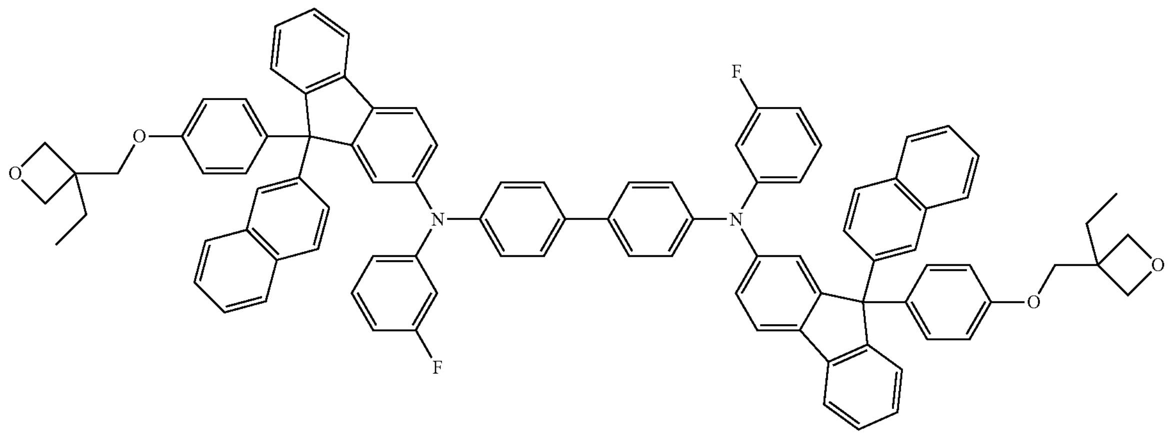

-continued
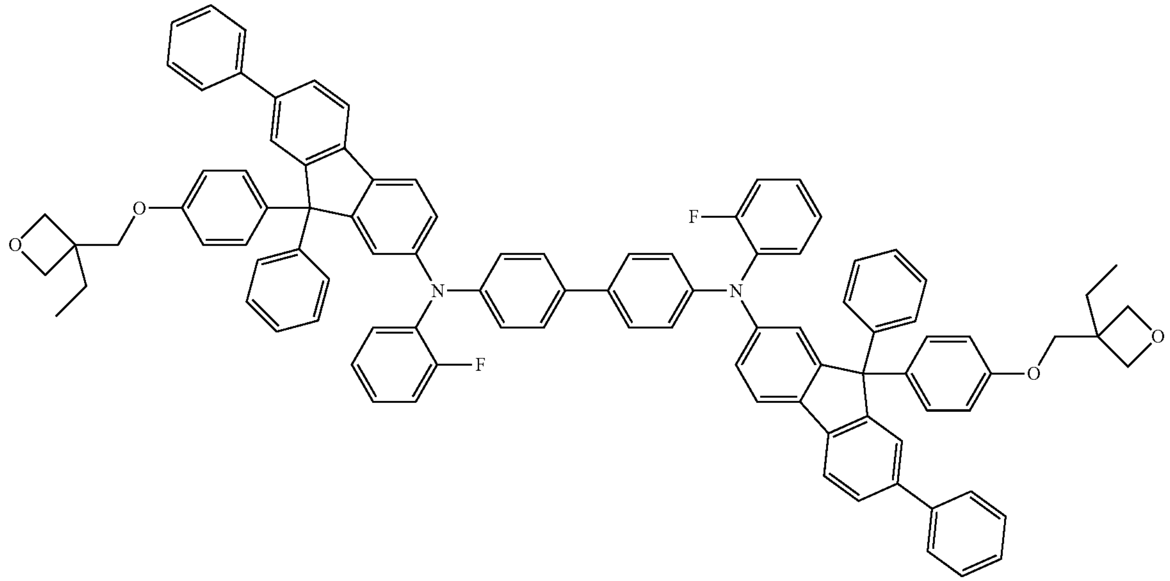
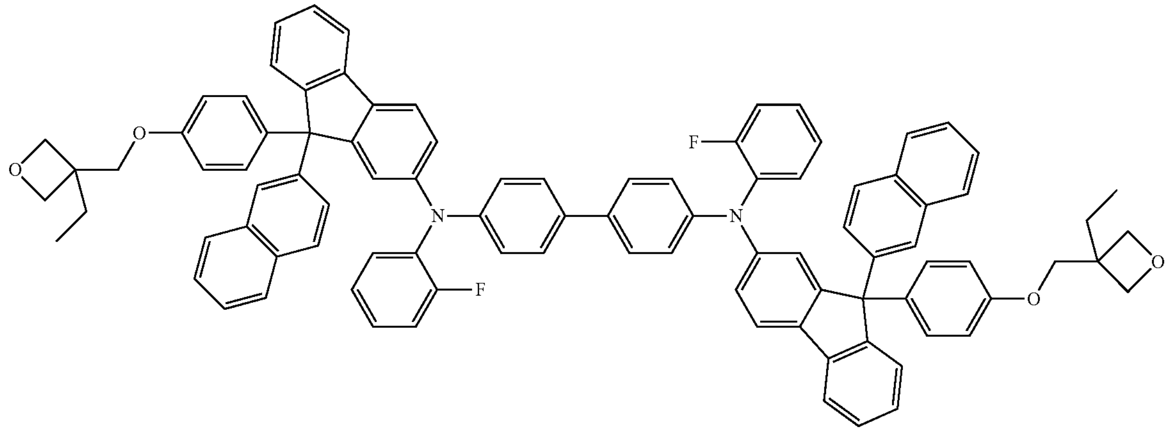
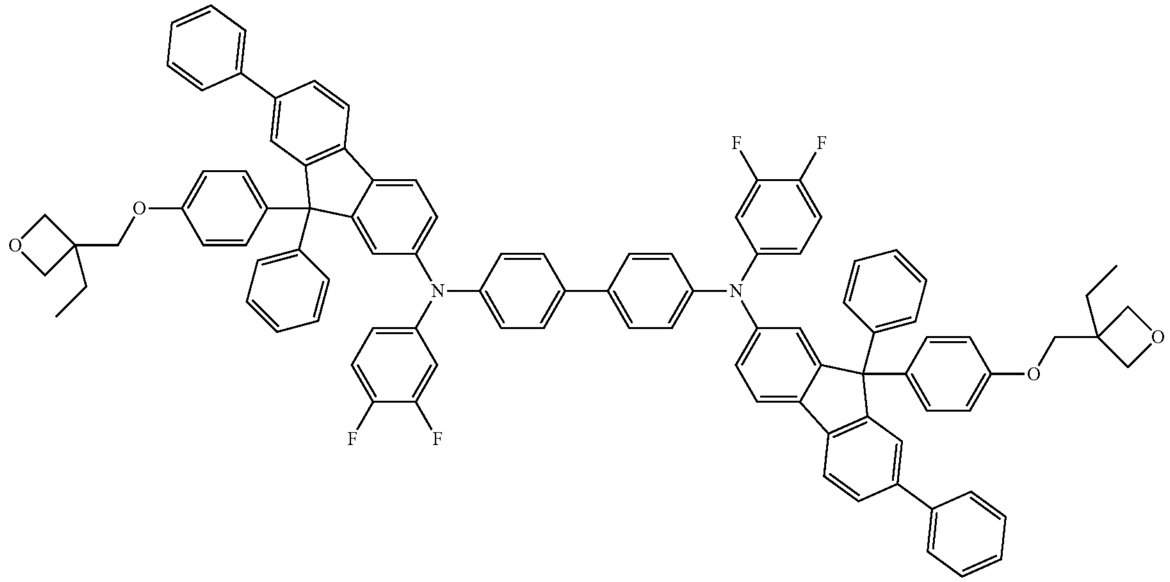

-continued
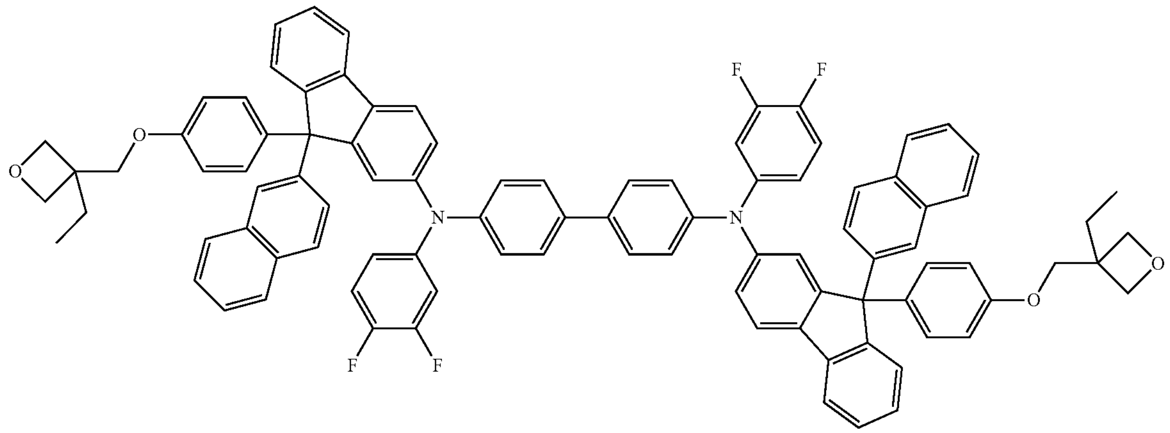
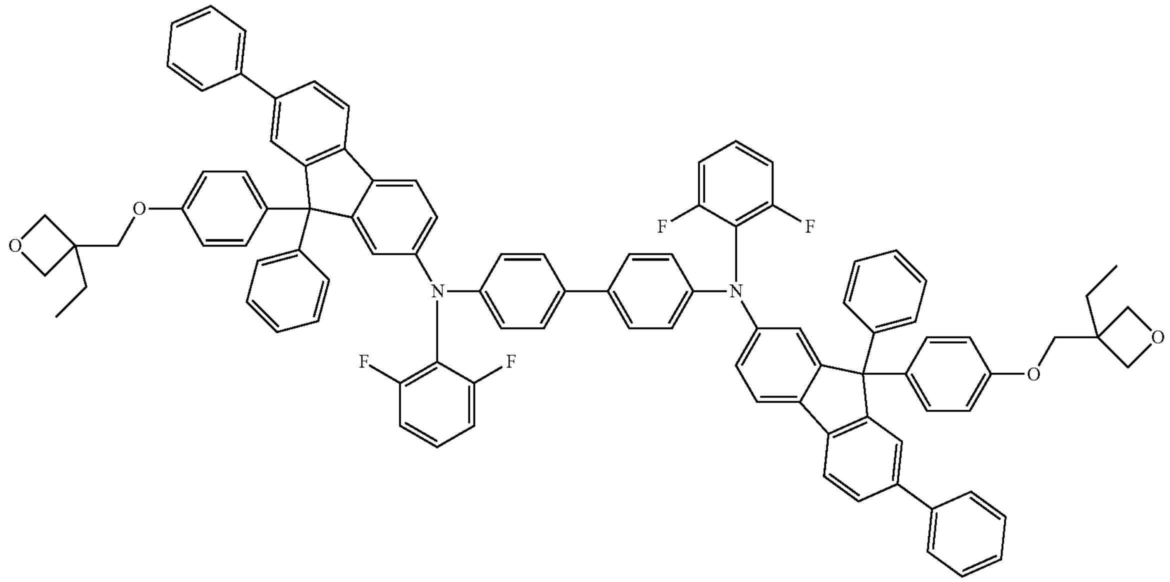
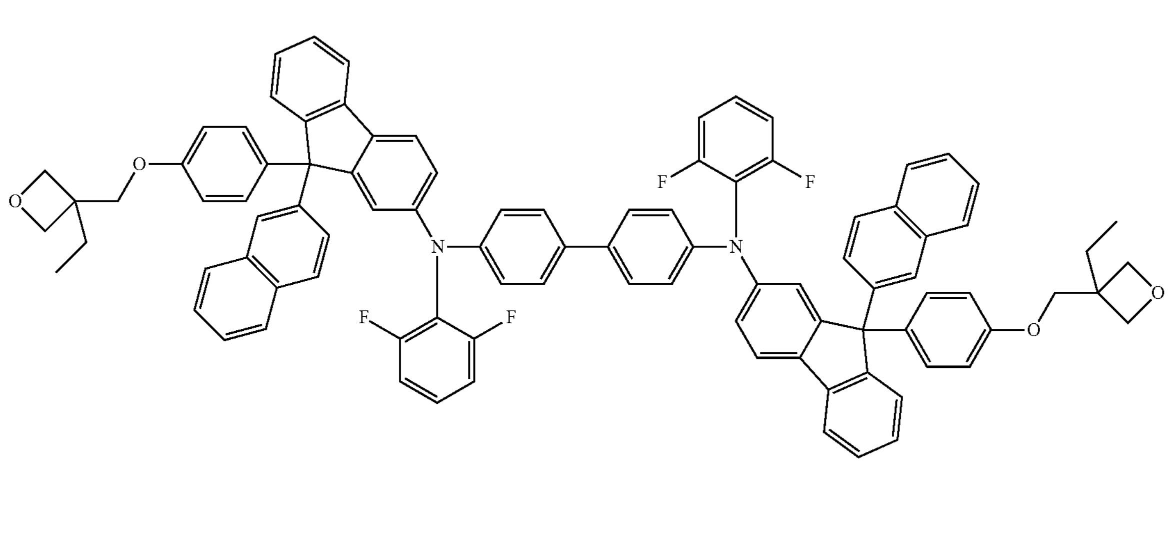

-continued

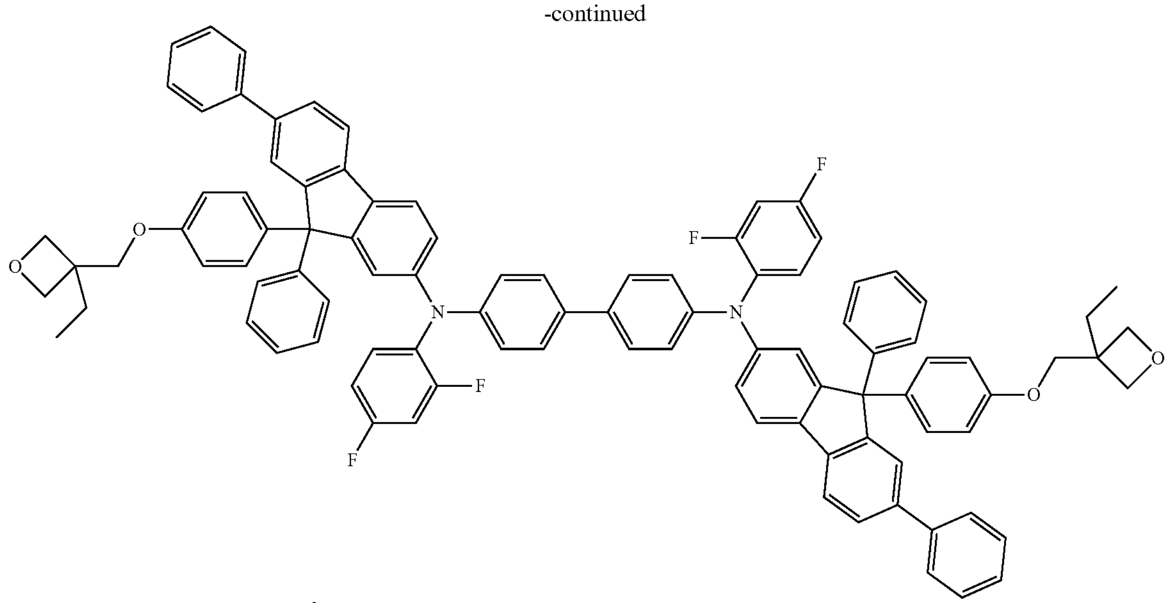

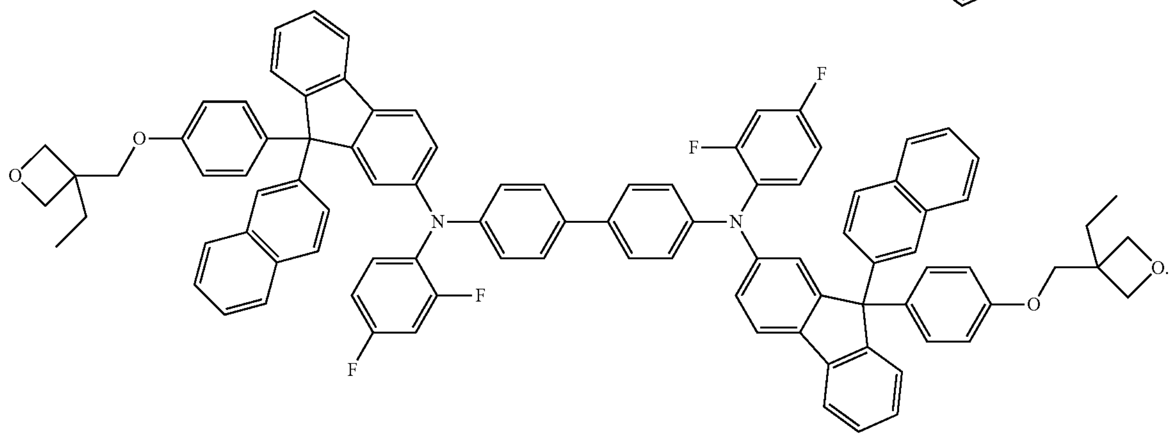

8. A coating composition comprising the compound of claim 1.

9. The coating composition of claim 8, further comprising a p-doping material.

10. An organic light emitting device comprising:

a first electrode;

a second electrode; and an organic material layer having one or more layers provided between the first electrode and the second electrode, wherein the one or more layers of the organic material layer comprise the coating composition of claim 8 or a cured product thereof.

11. The organic light emitting device of claim 10, wherein the organic material layer comprising the coating composition or the cured product thereof is a hole transport layer or a hole injection layer.

12. A method of manufacturing an organic light emitting device, the method comprising:

preparing a substrate;

forming a first electrode on the substrate;

forming an organic material layer having one or more layers on the first electrode; and forming a second electrode on the organic material layer, wherein the forming of the organic material layer comprises forming an organic material layer having one or more layers by using the coating composition of claim 8.

13. The method of claim 12, wherein the forming of the organic material layer having one or more layers by using the coating composition is performed by a spin coating method.

14. The method of claim 12, wherein the forming of the organic material layer having one or more layers by using the coating composition comprises:

coating the first electrode or the organic material layer having one or more layers with the coating composition; and heat-treating or light-treating the coated coating composition.

* * * * *